United States Patent
Joung et al.

(10) Patent No.: US 11,591,589 B2
(45) Date of Patent: Feb. 28, 2023

(54) VARIANTS OF CPF1 (CAS12A) WITH ALTERED PAM SPECIFICITY

(71) Applicant: The General Hospital Corporation, Boston, MA (US)

(72) Inventors: J. Keith Joung, Winchester, MA (US); Benjamin Kleinstiver, Medford, MA (US); Alexander Sousa, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 674 days.

(21) Appl. No.: 15/960,271

(22) Filed: Apr. 23, 2018

(65) Prior Publication Data

US 2019/0010481 A1    Jan. 10, 2019

Related U.S. Application Data

(60) Provisional application No. 62/488,426, filed on Apr. 21, 2017, provisional application No. 62/616,066, filed on Jan. 11, 2018.

(51) Int. Cl.
| | | |
|---|---|---|
| *C12N 9/88* | (2006.01) | |
| *C12N 9/22* | (2006.01) | |
| *C12N 9/52* | (2006.01) | |
| *C12N 15/62* | (2006.01) | |
| *C12Q 1/6813* | (2018.01) | |

(52) U.S. Cl.
CPC ............... *C12N 9/88* (2013.01); *C12N 9/22* (2013.01); *C12N 9/52* (2013.01); *C12N 15/62* (2013.01); *C12N 2310/20* (2017.05); *C12Q 1/6813* (2013.01); *C12Y 401/99013* (2013.01)

(58) Field of Classification Search
CPC ... C12N 9/88; C12N 9/22; C12N 9/52; C12N 15/62; C12N 2310/20; C12Q 1/6813; C12Y 401/99013
See application file for complete search history.

(56) References Cited

U.S. PATENT DOCUMENTS

| | | |
|---|---|---|
| 2011/0136895 A1 | 6/2011 | Gregory et al. |
| 2014/0068797 A1 | 3/2014 | Doudna et al. |
| 2014/0273226 A1 | 9/2014 | Wu |
| 2014/0315985 A1 | 10/2014 | May et al. |
| 2016/0208243 A1 | 7/2016 | Zhang et al. |

(Continued)

FOREIGN PATENT DOCUMENTS

| | | |
|---|---|---|
| CN | 105543195 | 5/2016 |
| WO | WO 2015/089364 | 6/2015 |

(Continued)

OTHER PUBLICATIONS

'www.biorxiv.org' [online], "Engineered Cpf1 Enzymes with Altered PAM Specificities," Dec. 4, 2016, retrieved from the Internet: URL https://www.biorxiv.org/content/biorxiv/early/2016/12/04/091611.full.pdf, 17 pages.

(Continued)

*Primary Examiner* — Marsha Tsay
(74) *Attorney, Agent, or Firm* — Fish & Richardson P.C.

(57) ABSTRACT

Engineered CRISPR from *Prevotella* and *Francisella* 1 (Cpf1) nucleases with improved targeting range and enhanced on-target activity, and their use in genomic engineering, epigenomic engineering, base editing, genome targeting, genome editing, and in vitro diagnostics.

Figure 1:
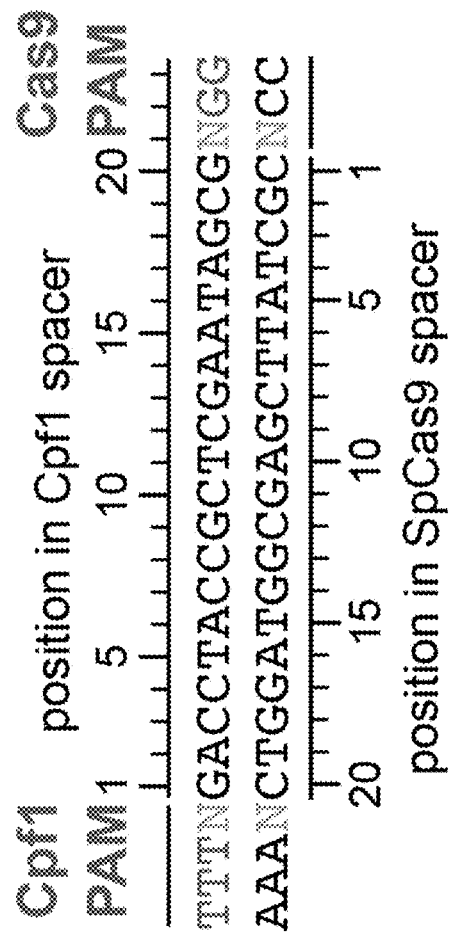

36 Claims, 96 Drawing Sheets
Specification includes a Sequence Listing.

(56) References Cited

U.S. PATENT DOCUMENTS

| | | |
|---|---|---|
| 2017/0233756 A1 | 8/2017 | Begemann et al. |
| 2017/0362644 A1 | 12/2017 | Doudna et al. |
| 2018/0100148 A1 | 4/2018 | Vakulskas et al. |
| 2018/0282714 A1 | 10/2018 | Joung et al. |
| 2019/0106687 A1 | 4/2019 | Joung et al. |
| 2019/0382775 A1 | 12/2019 | Tan et al. |

FOREIGN PATENT DOCUMENTS

| | | |
|---|---|---|
| WO | WO 2016/115179 | 7/2016 |
| WO | WO 2016/115355 | 7/2016 |
| WO | WO 2016/141224 | 9/2016 |
| WO | WO 2017/015015 | 1/2017 |
| WO | WO 2017/040348 | 3/2017 |
| WO | WO 2017/070633 | 4/2017 |
| WO | WO 2017/127807 | 7/2017 |
| WO | WO 2017/184768 | 10/2017 |
| WO | WO 2017/219027 | 12/2017 |
| WO | WO 2018/022634 | 2/2018 |
| WO | WO 2018/226855 | 12/2018 |
| WO | WO 2019/040650 | 2/2019 |
| WO | WO 2019/126762 | 6/2019 |
| WO | WO 2021/151073 | 7/2021 |
| WO | WO 2021/151085 | 7/2021 |

OTHER PUBLICATIONS

'www.biorxiv.org' [online]. "Enhanced proofreading governs CRISPR-Cas9 targeting accuracy," Jul. 6, 2017, retrieved from the Internet: URL https://www.biorxiv.org/content/biorxiv/early/2017/07/06/160036.full.pdf. 22 pages.

'www.biorxiv.org' [online], "Inducible, tunable and multiplex human gene regulation using CRISPR-Cpf1-based transcription factors," Jun. 15, 2017, retrieved from the Internet: URL https://www.biorxiv.org/content/biorxiv/early/2017/06/15/150656.full.pdf 21 pages.

Bae et al., "Cas-OFFinder: a fast and versatile algorithm that searches for potential off-target sites of Cas9 RNA-guided endonucleases," Bioinformatics, 2014, 30:1473-1475.

Bolukbasi et al., "DNA-binding-domain fusions enhance the targeting range and precision of Cas9," Nat Methods, 2015, 12:1150-1156.

Chavez et al., "Highly-efficient Cas9-mediated transcriptional programming," Nat Methods., 2015, 12:326-8.

Chen et al., "CRISPR-Cas12a target binding unleashes indiscriminate single-stranded DNase activity," Science, 2018, 8 pages.

Chen et al., "Supplementary Materials for CRISPR-Cas12a target binding unleashes indiscriminate single-stranded DNase activity," Science, 2018, 28 pages.

Cong et al., "Multiplex genome engineering using CRISPR/Cas systems," Science, 2013, 339:819-823.

Deltcheva et al., "CRISPR RNA maturation by trans-encoded small RNA and host factor RNase III," Nature, 2011, 471:602-607.

Dong et al., "The crystal structure of Cpf1 in complex with CRISPR RNA," Nature, 2016, 532(7600):522-6.

Doudna and Charpentier, "Genome editing. The new frontier of genome engineering with CRISPR-Cas9," Science, 2014, 346:1258096.

East-Seletsky et al., "Two Distinct RNase Activities of CRISPR-C2c2 Enable Guide RNA Processing and RNA Detection," Nature, 2016, 538(7624): 270-273.

Fagerlund et al., "The Cpf1 CRISPR-Cas protein expands genome-editing tools," Genome Biol, 2015, 16:251.

Fonfara et al., "The CRISPR-associated DNA-cleaving enzyme Cpf1 also processes precursor CRISPR RNA," Nature, 2016, 532(7600):517-21.

Friedland et al., "Characterization of Staphylococcus aureus Cas9: a smaller Cas9 for all-in-one adeno-associated virus delivery and paired nickase applications," Genome Biol, 2015, 16:257.

Frock et al., "Genome-wide detection of DNA double-stranded breaks induced by engineered nucleases," Nat Biotechnol, 2015, 33:179-186.

Fu et al., "Improving CRISPR-Cas nuclease specificity using truncated guide RNAs," Nat Biotechnol, 2014, 32:279-284.

Gaudelli et al., "Programmable base editing of A•T to G•C in genomic DNA without DNA cleavage," Nature. 2017, 551(7681):464-471.

Gootenberg et al., "Multiplexed and portable nucleic acid detection platform with Cas13, Cas12a, and Csm6," Science, 2018, 10 pages.

Gootenberg et al., "Nucleic acid detection with CRISPR-Cas13a/C2c2," Science, 2017, 356: 438-442.

Gootenberg et al., "Supplementary Materials for Nucleic acid detection with CRISPR-Cas13a/C2c2," Science, 2017, 45 pages.

Gootenberg et al., "Supplementary Materials for Multiplexed and portable nucleic acid detection platform with Cas13, Cas12a, and Csm6," Science, 2018, 85 pages.

Hsu et al., "Development and applications of CRISPR-Cas9 for genome engineering," Cell, 2014, 157:1262-1278.

International Search Report and Written Opinion in International Application No. PCT/US18/28919, dated Oct. 1, 2018, 17 pages.

Invitation to Pay Additional Fees And, Where Applicable, Protest Fee in Application No. PCT/US18/28919, dated Aug. 7, 2018.

Jinek et al., "A programmable dual-RNA-guided DNA endonuclease in adaptive bacterial immunity," Science, 2012, 337:816-821.

Jinek et al., "RNA-programmed genome editing in human cells," Elife, 2013, 2:e00471.

Kim et al., "Digenome-seq: genome-wide profiling of CRISPR-Cas9 off-target effects in human cells," Nat Methods, 2015, 12:237-243. 231. page following 243.

Kim et al., "Erratum: Genome-wide analysis reveals specificities of Cpf1 endonucleases in human cells," Nat Biotechnol. 2016, 34(8): 888.

Kim et al., "Genome-wide analysis reveals specificities of Cpf1 endonucleases in human cells," Nat Biotechnol. 2016, 34(8):863-8.

Kim et al., "Increasing the genome-targeting scope and precision of base editing with engineered Cas9-cytidine deaminase fusions," Nat Biotechnol, 2017, 35(4):371-376.

Kleinstiver et al., "Broadening the targeting range of Staphylococcus aureus CRISPR-Cas9 by modifying PAM recognition," Nat Biotechnol, 2015, 33: 1293-1298.

Kleinstiver et al., "Engineered CRISPR-Cas9 nucleases with altered specificities," Nature, 2015, 523:481-485.

Kleinstiver et al., "Genome-wide specificities of CRISPR-Cas Cpf1 nucleases in human cells," Nat Biotechnol, 2016, 34(8):869-74.

Kleinstiver et al., "High-fidelity CRISPR-Cas9 nucleases with no detectable genome-wide off-target effects," Nature, 2016, 529:490-495.

Komor et al., "Improved base excision repair inhibition and bacteriophage Mu Gam protein yields C:G-to-T:A base editors with higher efficiency and product purity," Sci Adv, 2017, 3(8):eaao4774.

Komor et al., "Programmable editing of a target base in genomic DNA without double-stranded DNA cleavage," Nature, 2016, 33(7603):420-4.

Maeder and Gersbach, "Genome-editing Technologies for Gene and Cell Therapy," Mol Ther, 2016, 24: 430-446.

Makarova et al., "An updated evolutionary classification of CRISPR-Cas systems," Nat Rev Microbiol, 2015, 13:722-736.

Mali et al., "RNA-guided human genome engineering via Cas9," Science, 2013, 339:823-826.

Moreno-Mateos et al., "CRISPR-Cpf1 mediates efficient homology-directed repair and temperature-controlled genome editing," Nat Commun., 2017, 8:2024.

Nishida et al., "Targeted nucleotide editing using hybrid prokaryotic and vertebrate adaptive immune systems," Science. 2016, 353(6305).

Reyon et al., "FLASH assembly of TALENs for high-throughput genome editing," Nat Biotechnol, 2012, 30:460-465.

Rohland and Reich, "Cost-effective, high-throughput DNA sequencing libraries for multiplexed target capture," Genome Res, 2012, 22:939-46.

Sander and Joung, "CRISPR-Cas systems for editing, regulating and targeting genomes," Nat Biotechnol, 2014, 32:347-355.

Schunder et al., "First indication for a functional CRISPR/Cas system in Francisella tularensis," Int J Med Microbiol, 2013, 303:51-60.

(56) References Cited

OTHER PUBLICATIONS

Shmakov et al., "Discovery and Functional Characterization of Diverse Class 2 CRISPR-Cas Systems," Mol Cell, 2015, 60(3):385-97.
Slaymaker et al., "Rationally engineered Cas9 nucleases with improved specificity," Science, 2016, 351:84-88.
Tak et al., "Inducible and multiplex gene regulation using CRISPR-Cpf1-based transcription factors," Nat Methods, 2017, 14:1163-1166.
Tsai et al., "Dimeric CRISPR RNA-guided FokI nucleases for highly specific genome editing," Nat Biotechnol, 2014, 32:569-576.
Tsai et al., "GUIDE-seq enables genome-wide profiling of off-target cleavage by CRISPR-Cas nucleases," Nat Biotechnol, 2015, 33:187-197.
Tsai et al., "Open-source guideseq software for analysis of GUIDE-seq data," Nat Biotechnol, 2016, 34:483.
Wang et al., "Unbiased detection of off-target cleavage by CRISPR-Cas9 and TALENs using integrase-defective lentiviral vectors," Nat Biotechnol, 2015, 33:175-178.
Wright et al., "Biology and Applications of CRISPR Systems: Harnessing Nature's Toolbox for Genome Engineering," Cell, 2016, 164:29-44.
Yamano et al., "Crystal Structure of Cpf1 in Complex with Guide RNA and Target DNA," Cell, 2016, 165(4):949-62.
Yin et al., "Therapeutic genome editing by combined viral and non-viral delivery of CRISPR system components in vivo," Nat Biotechnol, 2016.
Zetsche et al., "Cpf1 Is a Single RNA-Guided Endonuclease of a Class 2 CRISPR-Cas System," Cell, 2015, 163:759-771.
Zetsche et al., "Multiplex gene editing by CRISPR-Cpf1 through autonomous processing of a single crRNA array," Nat Biotechnol., 2017, 35:31-34.
International Preliminary Report on Patentability in International Appln. No. PCT/US2018/028919, dated Oct. 22, 2019.
EP Extended European Search Report in European Appln. No. 18788179.2, dated Nov. 27, 2020, 10 pages.
Anders et al., "Structural basis of PAM-dependent target DNA recognition by the Cas9 endonuclease," Nature, Sep. 2014, 513(7519):569-573.
Chen et al., "Enhanced proofreading governs CRISPR-Cas9 targeting accuracy," Nature, Oct. 2017, 550(7676):407-410.
CL Office Action in Chilean Appln. No. 201903004, dated Jun. 7, 2021, 34 pages (with English translation).
EP Partial Supplementary European Search Report in European Appln. No. 17835126.8, dated Jan. 2, 2020, 12 pages.
EP Partial Supplementary European Search Report in European Appln. No. 17835126.8, dated Apr. 2, 2020, 9 pages.
GenBank Accession No. EOS46485.1, "The Genome Sequence of Lachnospiraceae bacterium COEI," May 29, 2013, retrieved on Nov. 7, 2017, retrieved from URL <https://www.ncbi.nlm.nih.gov/protein/EOS46485>, 2 pages.
International Preliminary Report on Patentability in International Appln. No. PCT/US2017/043753, dated Feb. 7, 2019, 10 pages.
International Search Report and Written Opinion in International Appln. No. PCT/US2017/043753, dated Dec. 28, 2017, 18 pages.
International Search Report and Written Opinion in International Appln. No. PCT/US2016/020756, dated Jul. 26, 2016, 12 pages.
International Search Report and Written Opinion in International Appln. No. PCT/US2016/049147, dated on Dec. 23, 2016, 12 pages.
International Search Report and Written Opinion in International Appln. No. PCT/US2018/036293, dated Nov. 8, 2018, 12 pages.
International Search Report and Written Opinion in International Appln. No. PCT/US2018/047577, dated Jan. 29, 2019, 12 pages.
International Search Report and Written Opinion in International Appln. No. PCT/US2021/014900, dated Jul. 21, 2021, 12 pages.
International Search Report and Written Opinion in International Appln. No. PCT/US2021/014933, dated Jul. 20, 2021, 12 pages.
Invitation To Pay Additional Fees in International Appln. No. PCT/US2017/043753, dated Oct. 24, 2017, 2 pages.
Nishamasu et al., "Engineered CRISPR-Cas9 nuclease with expanded targeting space," Science, Aug. 2018, 361(6408):1259-1262.
Protein Data Bank (PDB) [online], "4UN3-Crystal structure of Cas9 bound to PAM-containing DNA target," Sequence Display for the Entities in Pdb 4UN3, Jul. 23, 2014, retrieved May 6, 2015, retrieved from URL <http://www.rcsb.org/pdb/explore/explore.do?structureid=4UN3>, 2 pages.
Office Action in Australian Appln. No. 2018254619, dated Oct. 29, 2021, 5 pages.
Office Action in Chilean Appln. No. 201903004, dated Dec. 6, 2021, 26 pages (with English machine translation).
Office Action in European Appln. No. 18788179.2, dated Apr. 11, 2022, 5 pages.
Notice of Acceptance in Australian Appln. No. 2018254619, dated Jul. 12, 2022, 4 pages.

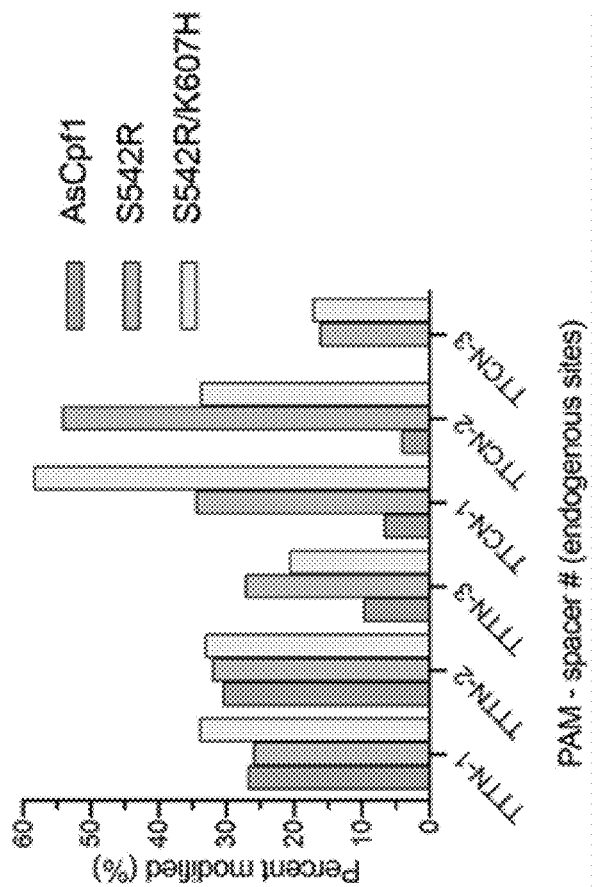
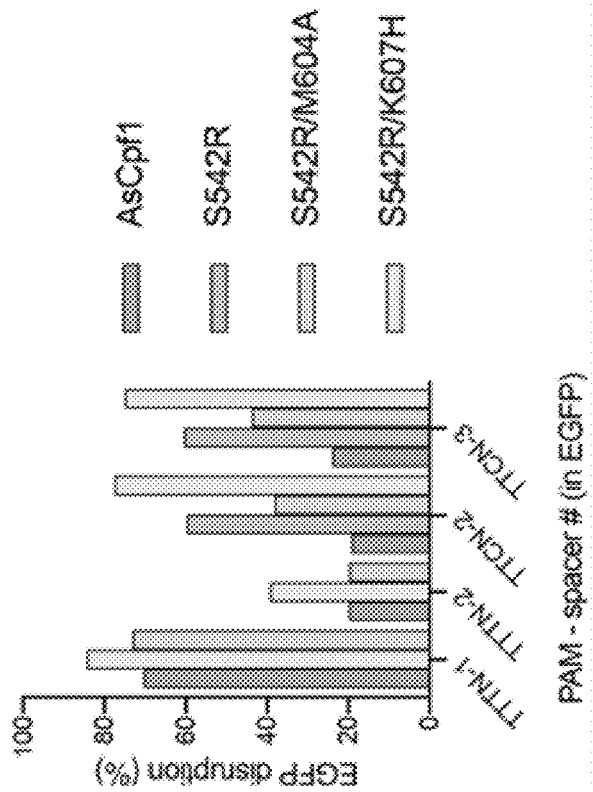
FIG. 5G
FIG. 5H

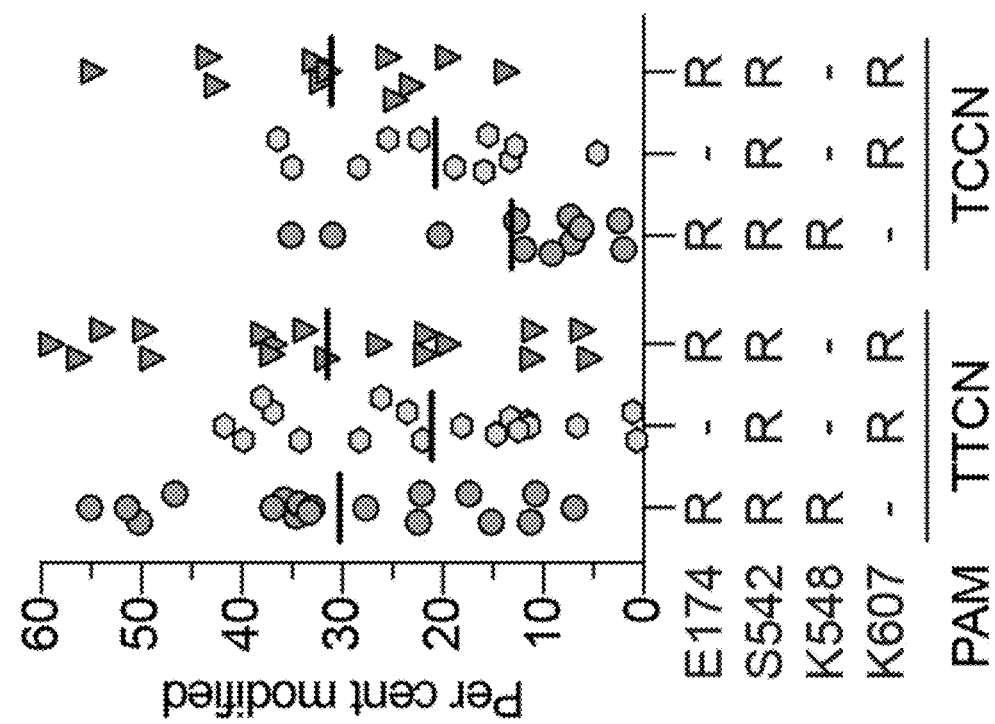
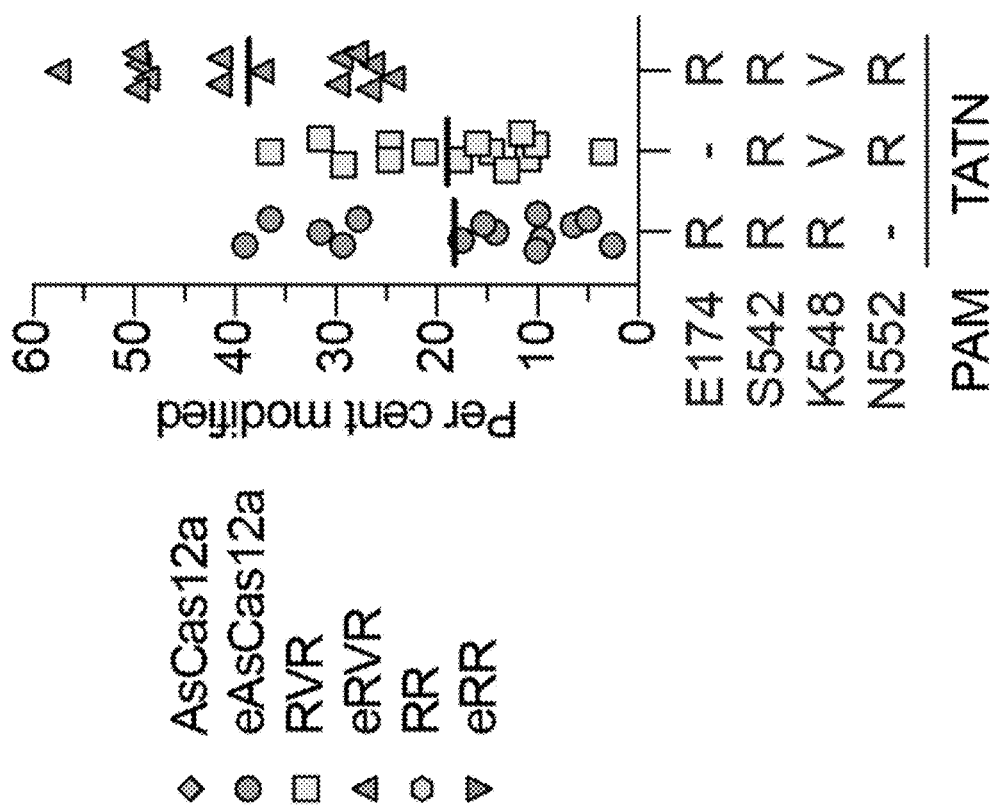
FIGs. 16C-D

FIG. 17A

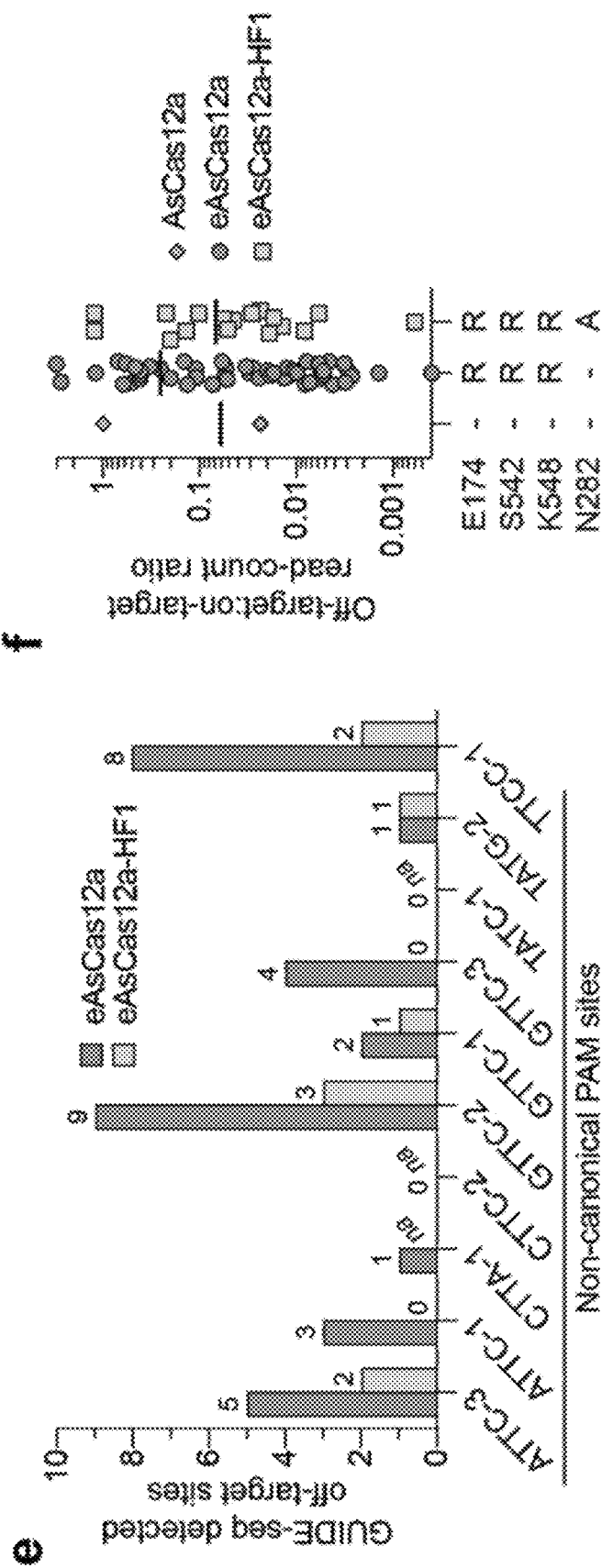
FIGs. 17E-F

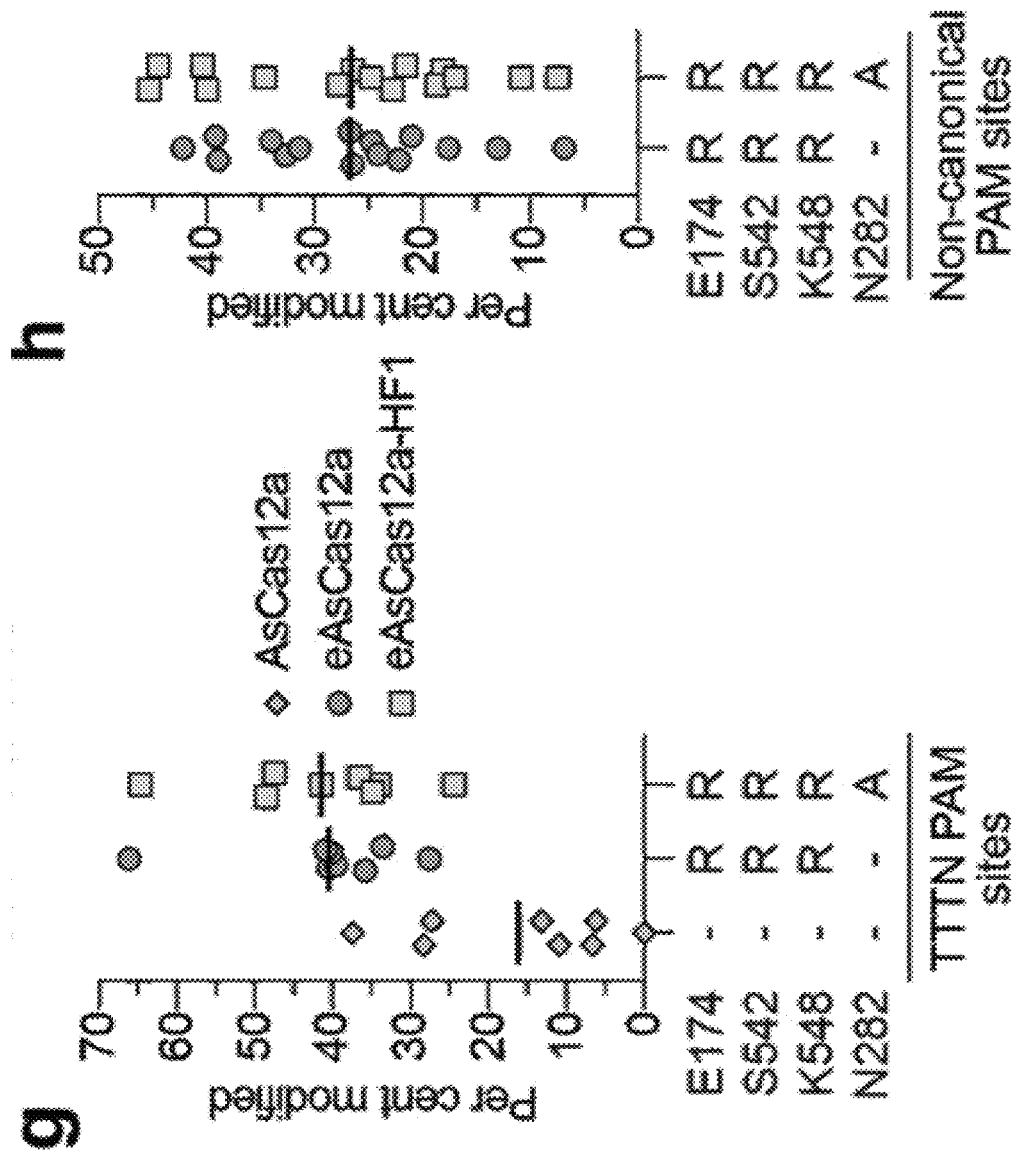
FIGs. 17G-H

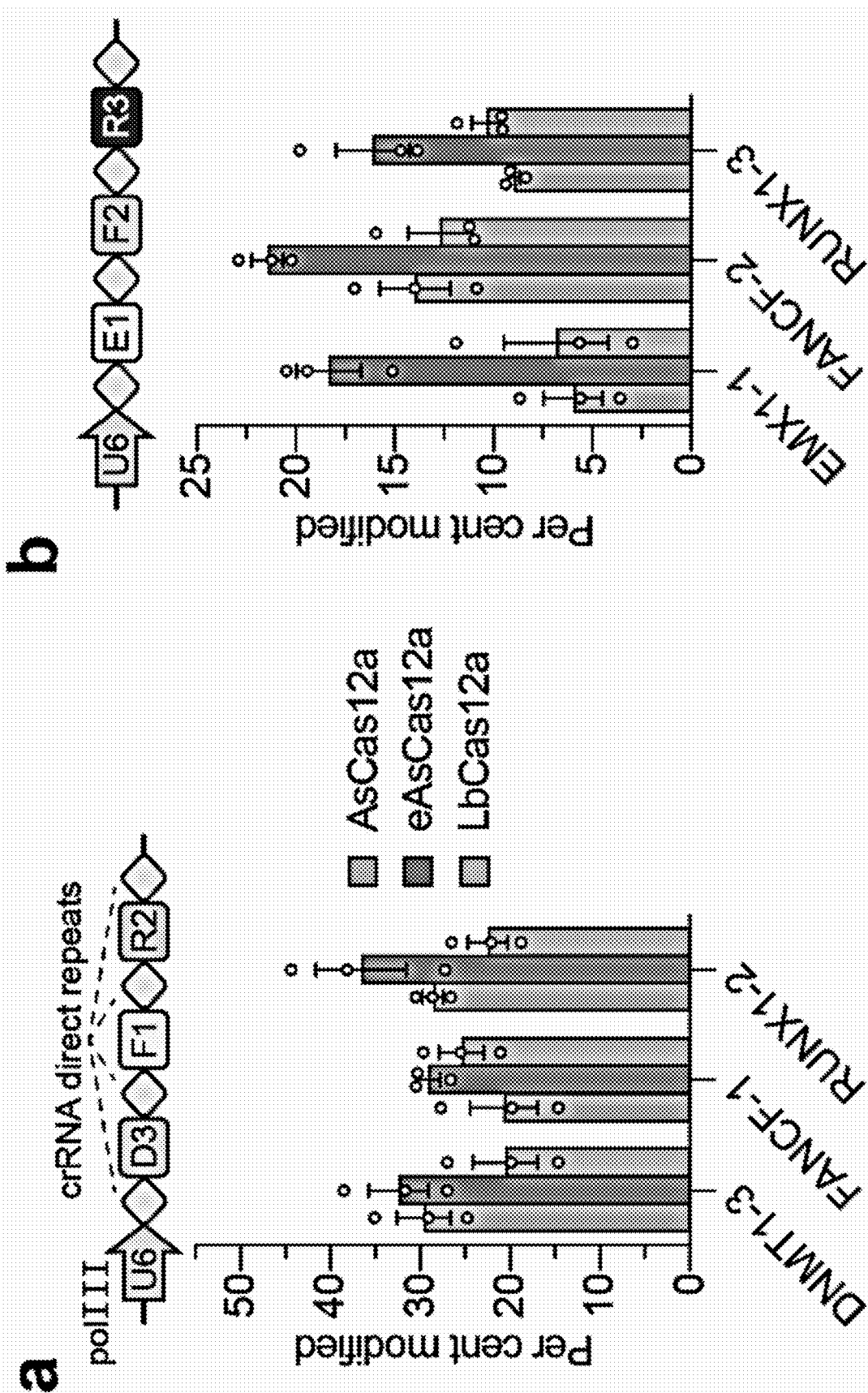
FIGs. 18A-B

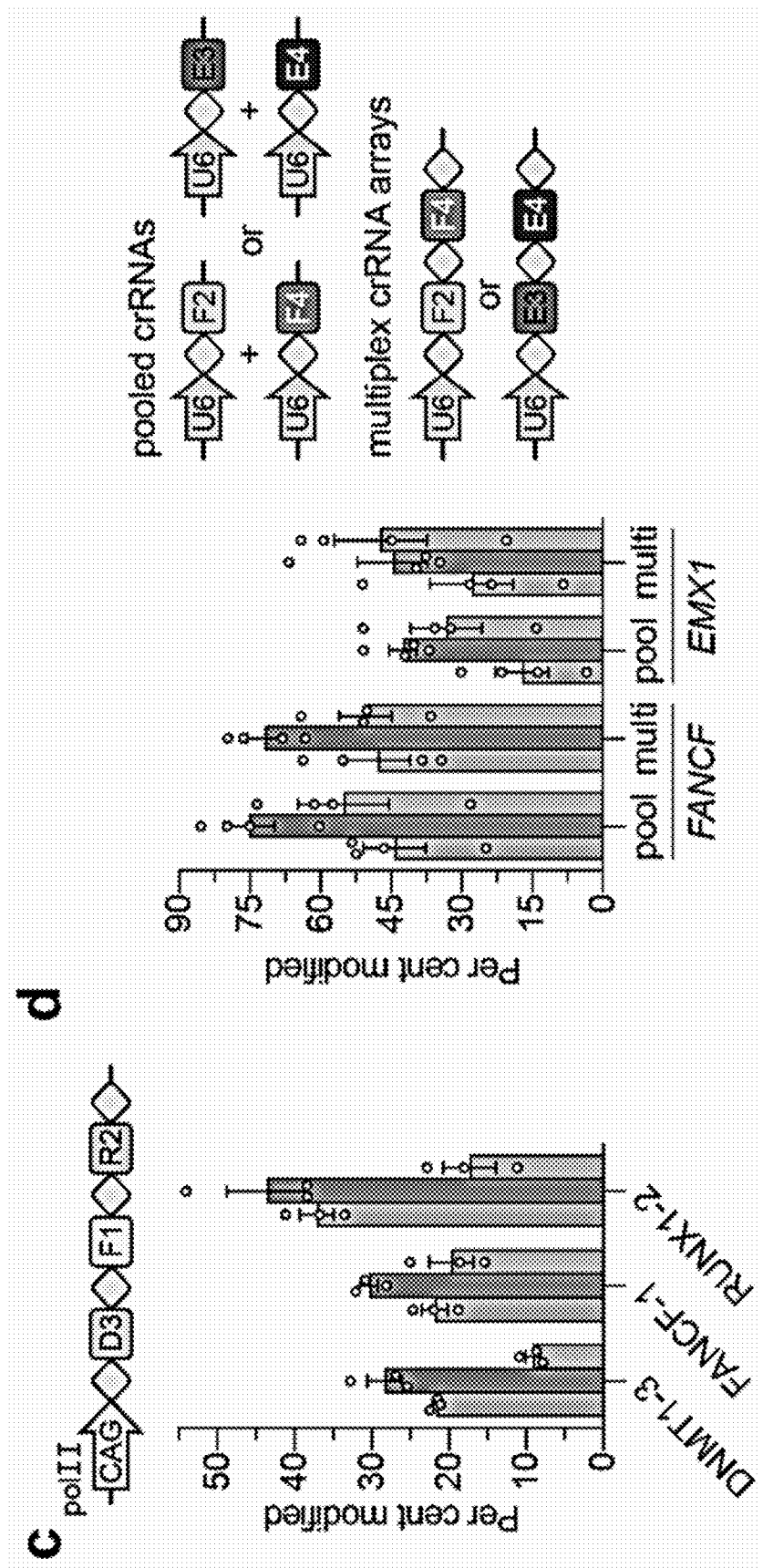
FIGs. 18C-D

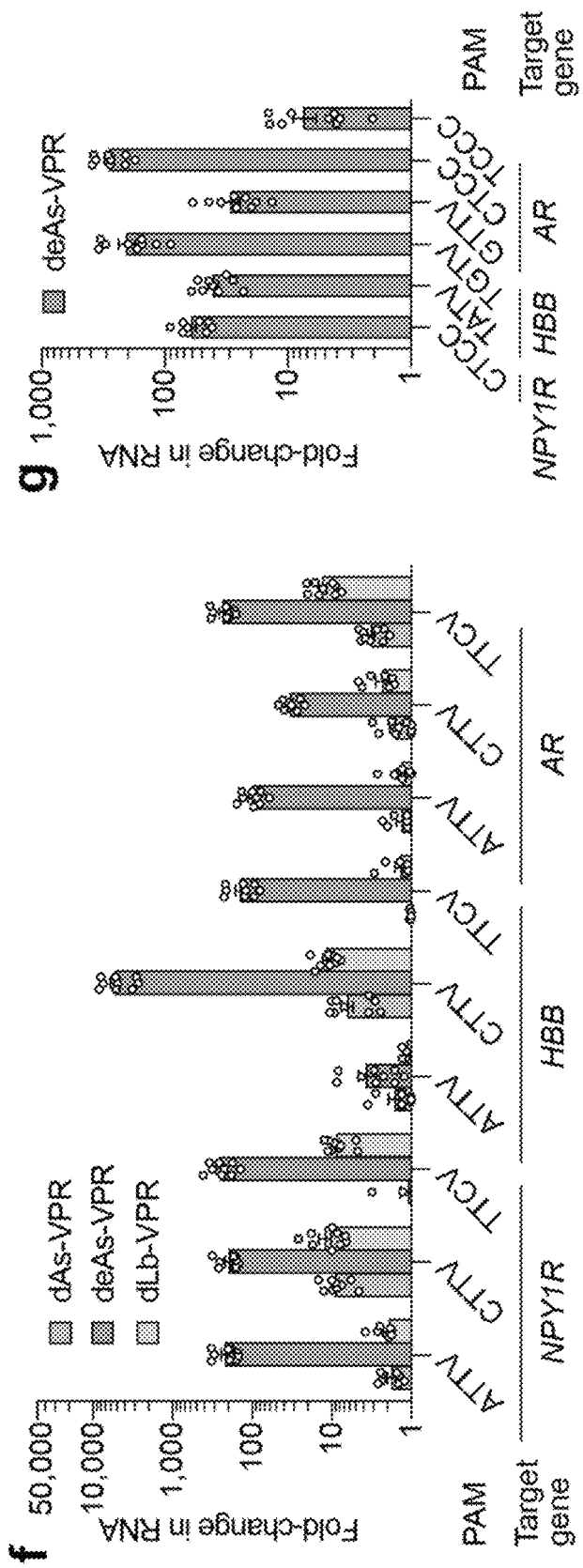
FIGs. 18F-G

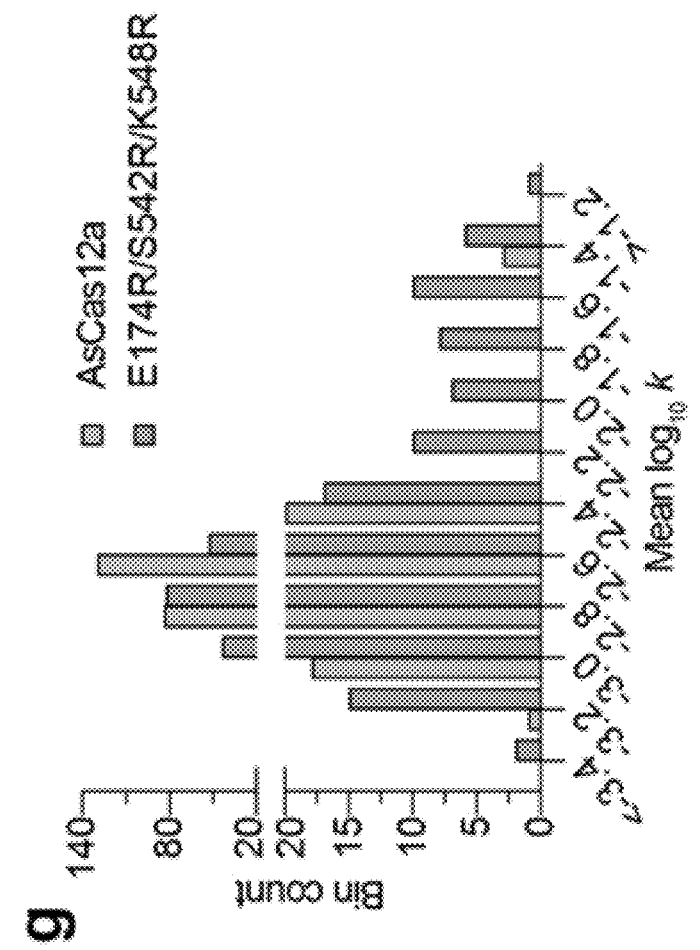
FIGs. 21F-G

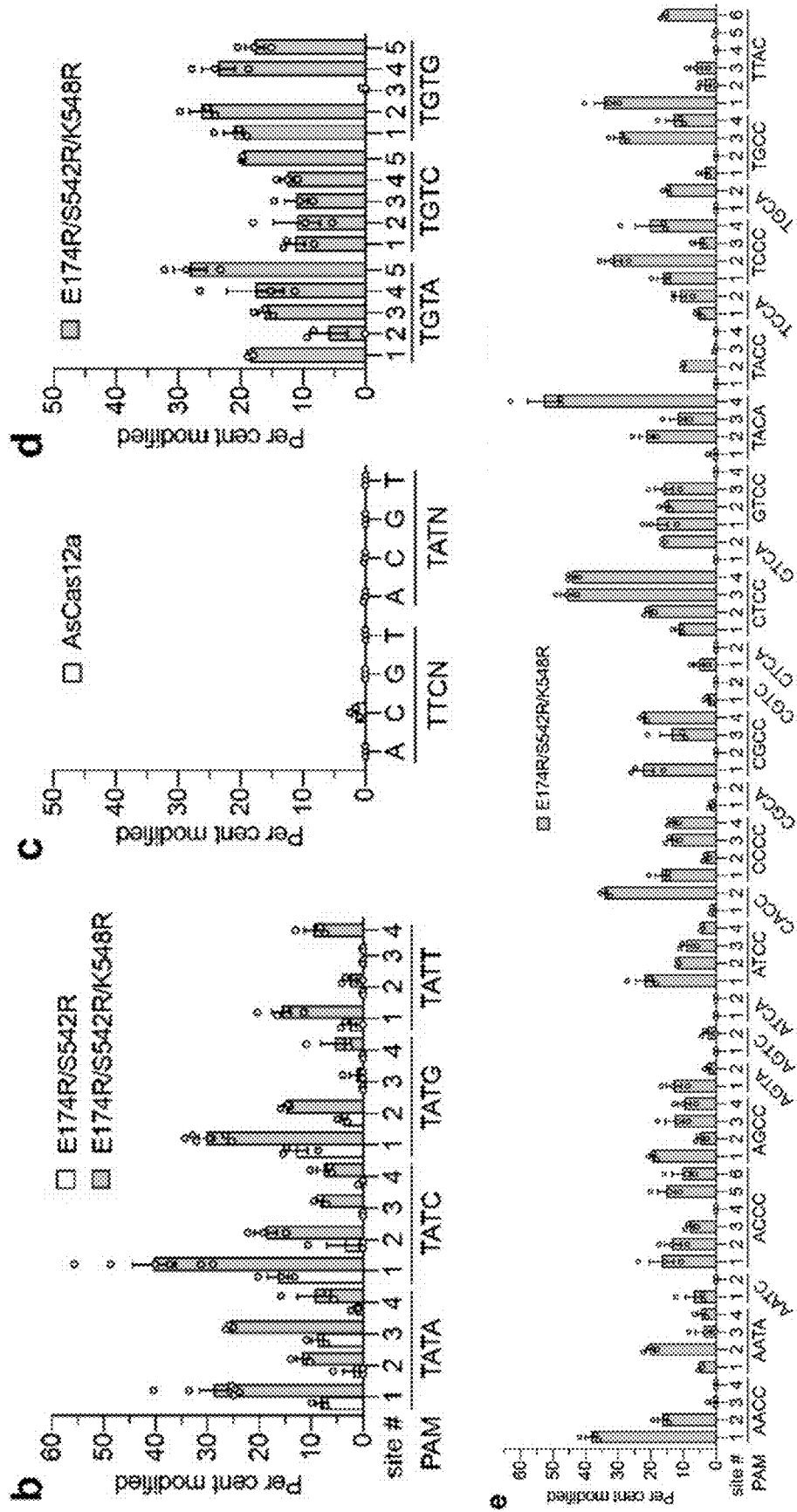
FIGs. 23B-E

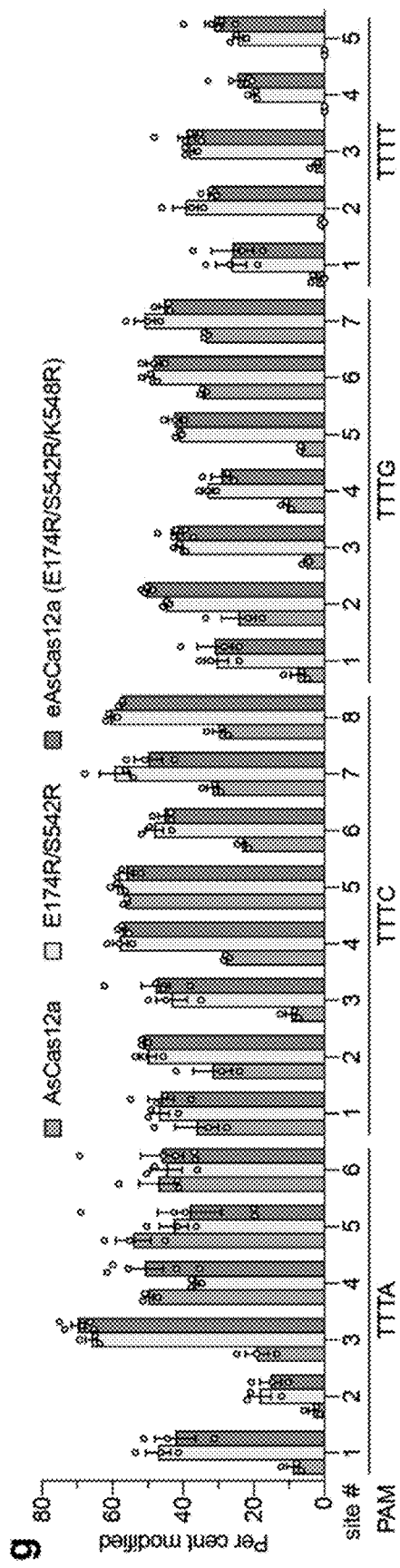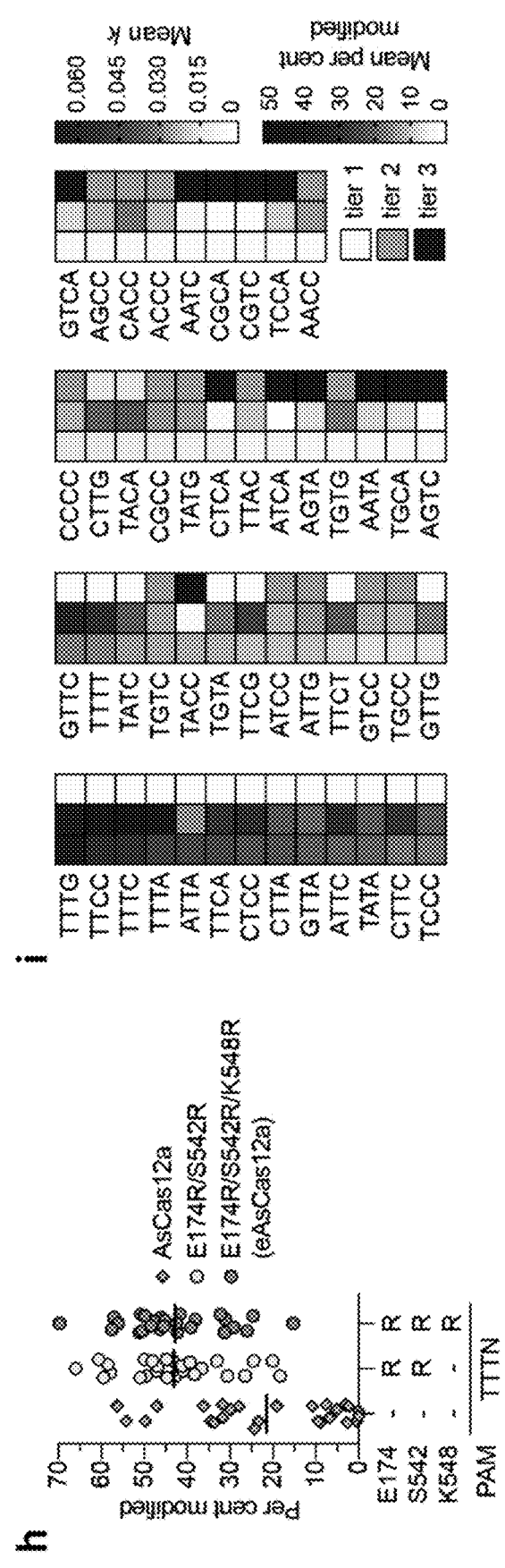
FIGs. 23G-I

Figure 25D:
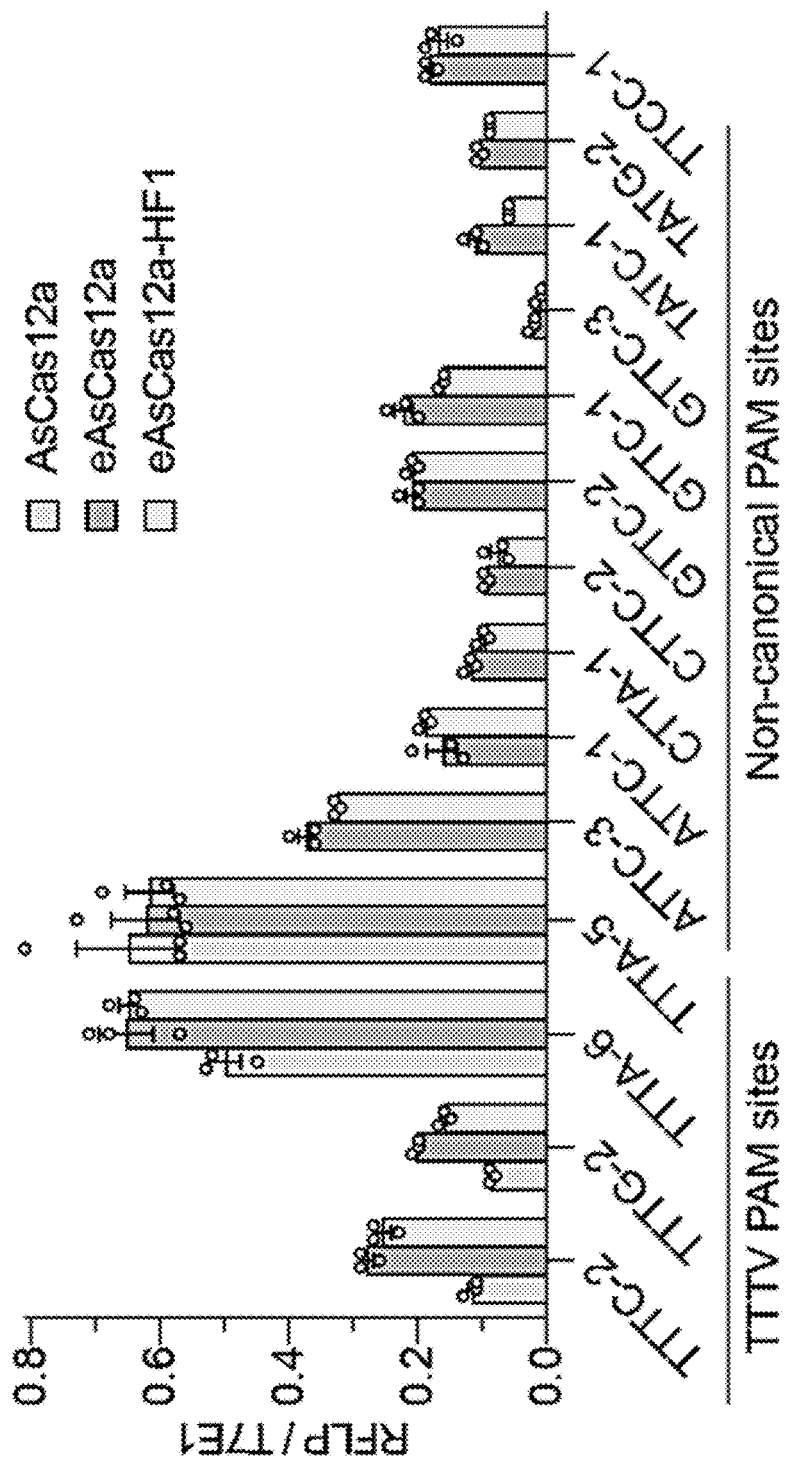

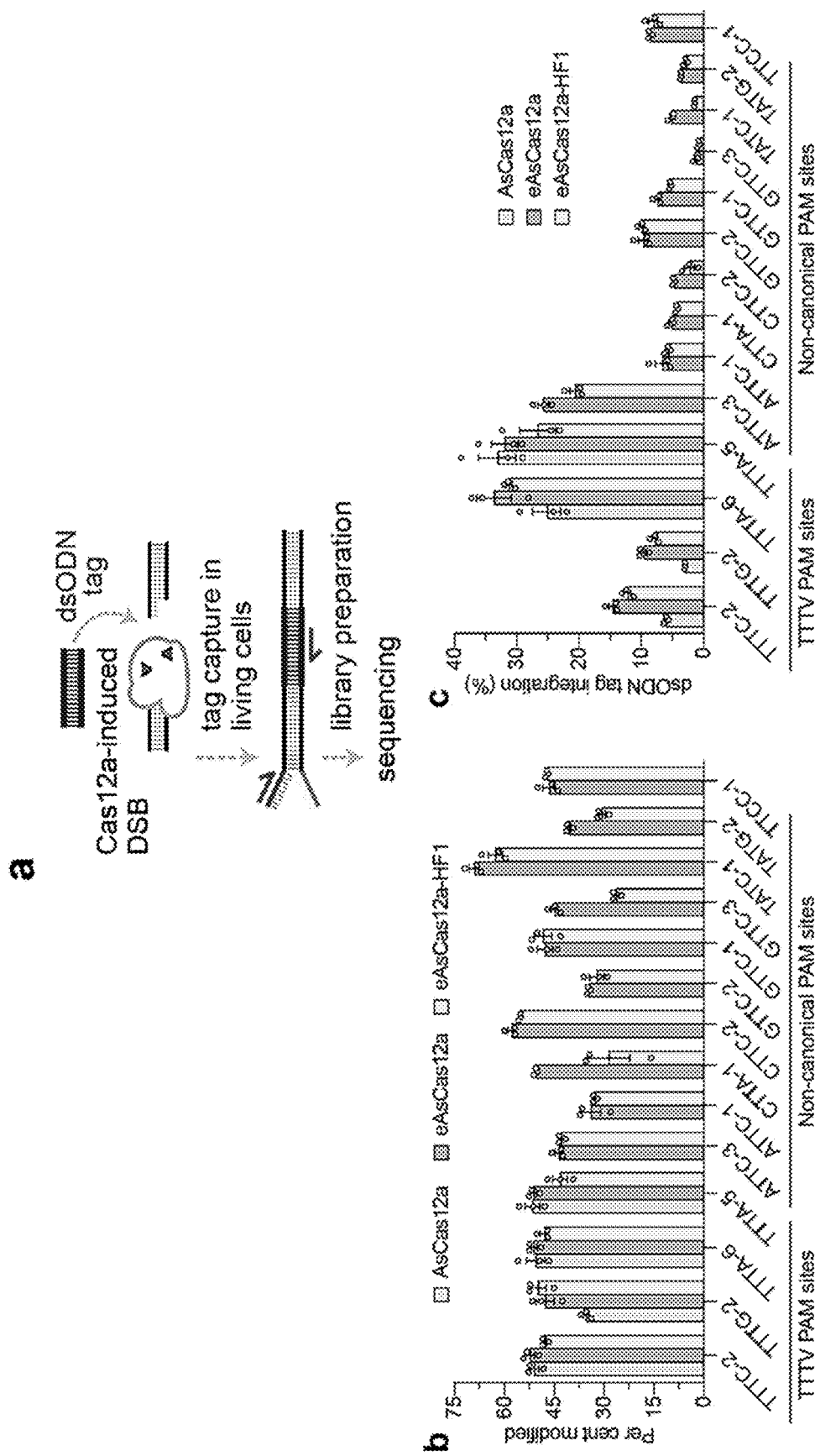
FIGs. 25A-C

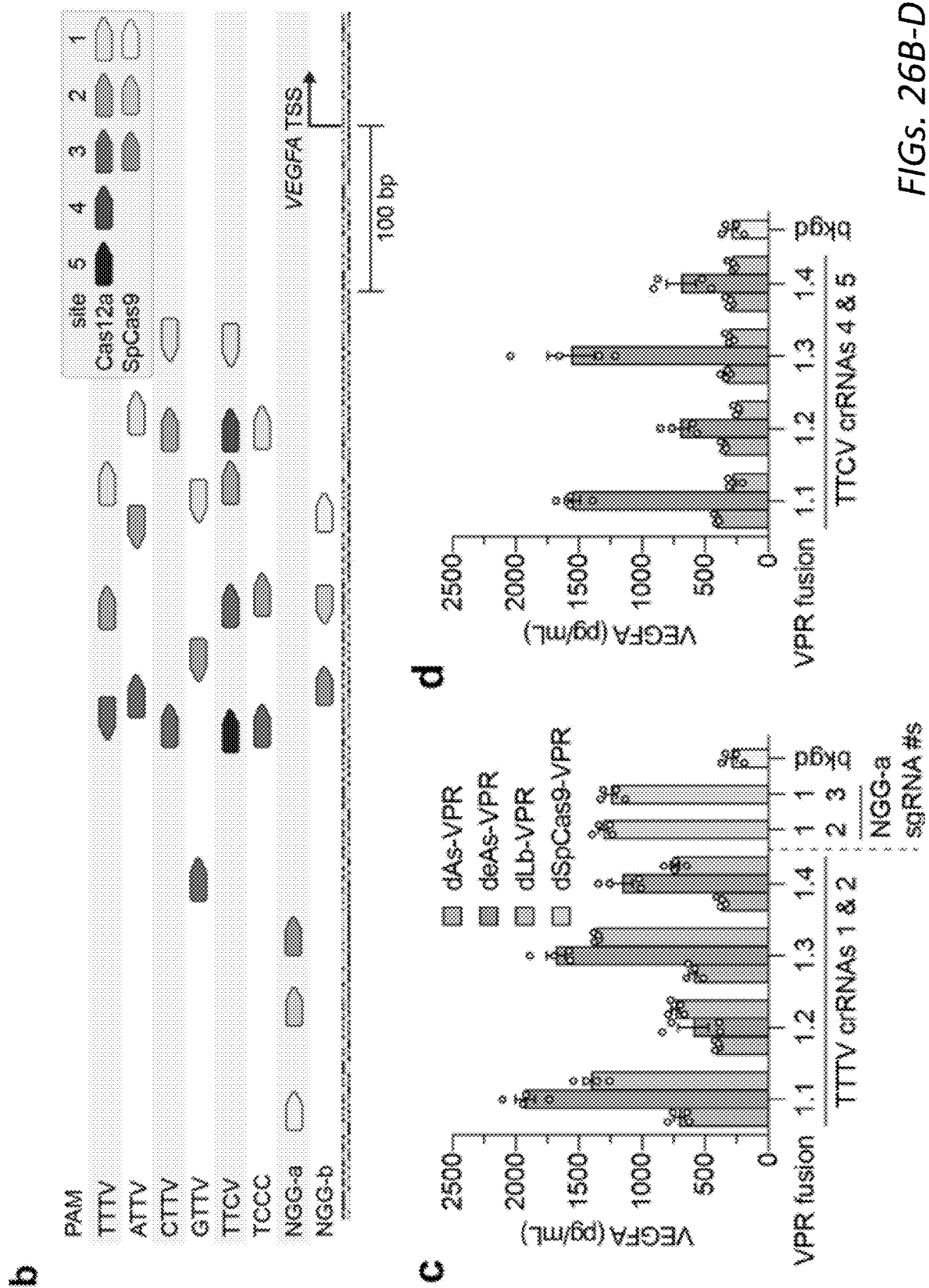
FIGs. 26B-D

US 11,591,589 B2

VARIANTS OF CPF1 (CAS12A) WITH ALTERED PAM SPECIFICITY

CLAIM OF PRIORITY

This application claims the benefit of U.S. Patent Application Ser. No. 62/488,426, filed on Apr. 21, 2017, and 62/616,066, filed on Jan. 11, 2018. The entire contents of the foregoing are hereby incorporated by reference.

FEDERALLY SPONSORED RESEARCH OR DEVELOPMENT

This invention was made with Government support under Grant No. GM105378, HG009490, and GM118158 awarded by the National Institutes of Health. The Government has certain rights in the invention.

TECHNICAL FIELD

The present invention relates, at least in part, to engineered CRISPR from Prevotella and Francisella 1 (Cpf1) nucleases with altered and improved target specificities and their use in genomic engineering, epigenomic engineering, genome targeting, genome editing, and in vitro diagnostics.

BACKGROUND

CRISPR-Cas Cpf1 nucleases (also referred to as Cas12a nucleases) have recently been described as an alternative to Cas9 nucleases for genome editing applications (Zetsche et al. *Cell* 163, 759-771 (2015); Shmakov et al., *Mol Cell.* 2015 Nov. 5; 60(3): 385-97; Kleinstiver et al., *Nat Biotechnol.* 2016 August; 34(8): 869-74; Kim et al., *Nat Biotechnol.* 2016 August; 34(8):863-8). Cpf1 nucleases possess a number of potentially advantageous properties that include, but are not limited to: recognition of T-rich protospacer-adjacent motif (PAM) sequences, relatively greater genome-wide specificities in human cells than wild-type *Streptococcus pyogenes* Cas9 (SpCas9), an endoribonuclease activity to process pre-crRNAs that simplifies the simultaneous targeting of multiple sites (multiplexing), DNA endonuclease activity that generates a 5' DNA overhang (rather than a blunt double-strand break as observed with SpCas9), and cleavage of the protospacer DNA sequence on the end most distal from the PAM (compared with cleavage at the PAM proximal end of the protospacer as is observed with SpCas9 and SaCas9). To date, Cpf1 orthologues from *Acidaminococcus* sp. BV3L6, *Lachnospiraceae bacterium* ND2006, and *Francisella tularensis* subsp. *novicida* U112 (AsCpf1, LbCpf1, and FnCpf1 respectively), are the only orthologues that have been described to robustly function in human cells. Despite these capabilities, Cpf1 nucleases have been adopted less rapidly for genome editing compared to SpCas9. One potential reason could be the requirement for a longer PAM that constrains targeting to roughly once in every 43 bps of random DNA sequence, compared to once in every 8 bps for SpCas9.

Here we addressed this targeting range limitation by utilizing a structure-guided engineering approach to generate AsCpf1 variants with not only greatly expanded targeting range, but also substantially improved on-target activities. In addition to improved potency and versatility as nucleases for genome editing, we demonstrate that these variants can be leveraged for other applications including multiplex nuclease targeting, epigenome editing, C-to-T base-editing, and Cpf1-mediated DNA detection, all at levels not previously possible with wild-type AsCpf1.

SUMMARY

Described herein are a series of AsCpf1, FnCpf1, and LbCpf1 variants that recognize a broader range of PAMs than their wild-type counterparts, thereby increasing the range of sites that can be targeted by this class of RNA-guided nucleases. In addition, these variants perform better than wild-type Cpf1 nucleases at recognizing and modifying target sites harboring canonical TTTN PAMs. The enhanced activities of the variants described herein improve the activities of AsCpf1 for genome editing, epigenome editing, base editing, and in vitro DNA detection.

Thus, provided herein are isolated CRISPR from *Prevotella* and *Francisella* 1 (Cpf1) proteins from *Acidaminococcus* sp. BV3L6 (AsCpf1), comprising a sequence that is at least 80% identical to the amino acid sequence of SEQ ID NO:2 with mutations at one or more of the following positions: E174, S170, K548, N551, T167, T539, N552, M604, and/or K607 of SEQ ID NO:2.

In some embodiments, the isolated Cpf1 proteins include a mutation at E174R, optionally with one or more additional mutations at S170R, K548, N551, T167, T539, S542, N552, M604, and/or K607. In some embodiments, the isolated Cpf1 proteins include a mutation at S170R, optionally with one or more additional mutations at E174R, K548, N551, T167, T539, S542, N552, M604, and/or K607.

In some embodiments, the isolated Cpf1 proteins include a mutation at S542.

In some embodiments, the isolated Cpf1 proteins include mutations S542Q, S542K, or S542R.

In some embodiments, the isolated Cpf1 proteins include a sequence that is at least 95% identical to the amino acid sequence of SEQ ID NO:2.

In some embodiments, the isolated Cpf1 proteins include one or more of the following mutations: E174R, S170R, K548R, S170K, E174K, T167A, T539K, T539R, K548V, N551R, N552R, M604A, K607Q, K607R, K607S, and/or K607H.

In some embodiments, the isolated Cpf1 proteins include the following mutations: S170R/E174R, E174R/K548R, S170R/K548R, E174R/S542R, S170R/S542R, E174R/S542R/K548R, E174R/N551R, S170R/N551R, S542R/K548R, S542R/N551R, S542R/N552R, K548R/N551R, S170R/S542R/K607R, E174R/S542R/K607R, E174R/S542R/K607H, E174R/S542R/K548R/N551R, S170R/S542R/K548V/N552R, E174R/S542R/K548V/N552R, S170R/S542R/K607R, or E174R/S542R/K607R of SEQ ID NO:2.

In some embodiments, the isolated Cpf1 proteins include one or more mutations that decrease nuclease activity, e.g., selected from the group consisting of mutations at D908, E993, R1226, D1235, and/or D1263, preferably D908A, E993A, R1226A, D1235A, and/or D1263A.

In some embodiments, the isolated Cpf1 proteins include a mutation at one or more of N282, N178, S186, N278, R301, T315, S376, N515, K523, K524, K603, K965, Q1013, Q1014, and/or K1054, preferably at N282, T315, N515, or N278, preferably wherein the mutation increases specificity of the protein. In some embodiments, the isolated Cpf1 proteins include a mutation selected from the group consisting of N282A, T315A, N515A, or N278A Also provided herein are isolated CRISPR from *Prevotella* and *Francisella* 1 (Cpf1) proteins from *Lachnospiraceae bacterium* ND2006 (LbCpf1), comprising a sequence that is at least 80% identical to SEQ ID NO:11, with one or more of the following positions: T152, D156, G532, and/or K538 of SEQ ID NO:11.

In some embodiments, the isolated Cpf1 proteins include a sequence that is at least 95% identical to the amino acid sequence of SEQ ID NO:11.

In some embodiments, the isolated Cpf1 proteins include one or more of the following mutations: T152R, T152K, D156R, D156K, G532R, and/or K538R.

In some embodiments, the isolated Cpf1 proteins include the following mutations: D156R/G532R/K538R.

In some embodiments, the isolated Cpf1 proteins include one or more mutations that decrease nuclease activity, e.g., selected from the group consisting of mutations at D832, E925, R1138, D1148, and/or D1180, preferably D832A, E925A, R1138A, D1148A, and/or D1180A.

In some embodiments, the isolated Cpf1 proteins include mutations at one or more of S202, N274, N278, K290, K367, K532, K609, K915, Q962, K963, K966, K1002 and/or S1003, preferably wherein the mutation increases specificity of the protein. In some embodiments, the isolated Cpf1 proteins include one or more of the following mutations: S202A, N274A, N278A, K290A, K367A, K532A, K609A, K915A, Q962A, K963A, K966A, K1002A and/or S1003A.

Also provided herein are isolated CRISPR from *Prevotella* and *Francisella* 1 (Cpf1) proteins from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4.

In some embodiments, the isolated Cpf1 proteins include a sequence that is at least 95% identical to the amino acid sequence of SEQ ID NO:4.

In some embodiments, the isolated Cpf1 proteins include one or more of the following mutations: K180R, E184R, N607R, K613R, K613V, D616R, N617R, K671H, and K671R.

In some embodiments, the isolated Cpf1 proteins include the following mutations: N607R/K613R, N607R/K613V, N607R/K613V/D616R, or N607R/K613R/D616R.

In some embodiments, the isolated Cpf1 proteins include one or more mutations that decrease nuclease activity, e.g., selected from the group consisting of mutations at D917, E1006, R1218, D1227, and/or D1255, preferably D917A, E1006A, R1218A, D1227A, and/or D1255A.

Also provided herein are fusion proteins comprising the Cpf1 proteins described herein, fused to a heterologous functional domain, with an optional intervening linker, wherein the linker does not interfere with activity of the fusion protein.

In some embodiments, the heterologous functional domain is a transcriptional activation domain, e.g., the tetrameric VP16 fusion termed VP64, Rta, NF-κB p65, or VPR (a VP64, p65, Rta fusion protein).

In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1).

In some embodiments, the heterologous functional domain is an enzyme that modifies the methylation state of DNA, e.g., a DNA methyltransferase (DNMT) or a TET protein, e.g., TET1.

In some embodiments, the heterologous functional domain is an enzyme that modifies a histone subunit, e.g., a histone acetyltransferase (HAT), histone deacetylase (HDAC), histone methyltransferase (HMT), or histone demethylase.

In some embodiments, the heterologous functional domain is a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, APOBEC4, activation-induced cytidine deaminase (AID), cytosine deaminase 1 (CDA1), and CDA2, and cytosine deaminase acting on tRNA (CDAT).

In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA).

In some embodiments, the heterologous functional domain is an enzyme, domain, or peptide that inhibits or enhances endogenous DNA repair or base excision repair (BER) pathways, e.g., uracil DNA glycosylase inhibitor (UGI) that inhibits uracil DNA glycosylase (UDG, also known as uracil N-glycosylase, or UNG) mediated excision of uracil to initiate BER; or DNA end-binding proteins such as Gam from the bacteriophage Mu.

In some embodiments, the heterologous functional domain is a biological tether, e.g., MS2, Csy4 or lambda N protein.

In some embodiments, the heterologous functional domain is FokI.

Also provided herein are isolated nucleic acids encoding the Cpf1 variant proteins and fusion proteins described herein.

In addition, provided herein are vectors comprising the nucleic acids. In some embodiments, the isolated nucleic acid encodes an isolated CRISPR from *Prevotella* and *Francisella* 1 (Cpf1) protein from *Acidaminococcus* sp. BV3L6 (AsCpf1), with mutations at one or more of the following positions: T167, S170, E174, T539, K548, N551, N552, M604, and/or K607 of SEQ ID NO:2 and is operably linked to one or more regulatory domains for expressing an isolated CRISPR from *Prevotella* and *Francisella* 1 (Cpf1) protein from *Acidaminococcus* sp. BV3L6 (AsCpf1), with mutations at one or more of the following positions: T167, S170, E174, T539, K548, N551, N552, M604, and/or K607 of SEQ ID NO:2.

In some embodiments, the isolated nucleic acid encodes an isolated CRISPR from *Prevotella* and *Francisella* 1 (Cpf1) protein from *Lachnospiraceae bacterium* ND2006 (LbCpf1), with mutations at one or more of the following positions: T152, D156, G532, and/or K538 of SEQ ID NO:11 and is operably linked to one or more regulatory domains for expressing an isolated CRISPR from *Prevotella* and *Francisella* 1 (Cpf1) protein from *Lachnospiraceae bacterium* ND2006 (LbCpf1), with mutations at one or more of the following positions: T152, D156, G532, and/or K538 of SEQ ID NO:11.

In some embodiments, the isolated nucleic acid encodes an isolated CRISPR CRISPR from *Prevotella* and *Francisella* 1 (Cpf1) protein from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4 and is operably linked to one or more regulatory domains for expressing an isolated CRISPR CRISPR from *Prevotella* and *Francisella* 1 (Cpf1) protein from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4.

Also provided herein are host cells, preferably mammalian host cells, comprising the nucleic acids described herein, and optionally expressing a protein or fusion protein described herein.

In addition, provided herein are method for altering the genome of a cell, the method comprising expressing in the cell, or contacting the cell with, an isolated protein or fusion protein as described herein, and at least one guide RNA having a region complementary to a selected portion of the genome of the cell, i.e., wherein the complementary region is adjacent to a PAM sequence that corresponds to the protein or fusion protein, e.g., as shown in Table B. In some embodiments, the isolated protein or fusion protein comprises one or more of a nuclear localization sequence, cell penetrating peptide sequence, and/or affinity tag. In some embodiments, the cell is a stem cell. In some embodiments, the cell is an embryonic stem cell, mesenchymal stem cell, or induced pluripotent stem cell; is in a living animal; or is in an embryo.

Also provided are methods of altering a double stranded DNA (dsDNA) molecule, the method comprising contacting the dsDNA molecule with an isolated protein or fusion protein as described herein, and a guide RNA having a region complementary to a selected portion of the dsDNA molecule, i.e., wherein the complementary region is adjacent to a PAM sequence that corresponds to the protein or fusion protein, e.g., as shown in Table B. In some embodiments, the dsDNA molecule is in vitro.

Also provided are methods for detecting a target ssDNA or dsDNA in vitro in a sample. The methods include contacting the sample with (i) the isolated protein or fusion protein as described above, (ii) a guide RNA having a region complementary to a selected portion of the target ssDNA or dsDNA molecule, and (iii) a labeled detector DNA, wherein the isolated protein or fusion protein cleaves the detector DNA upon binding to the target ssDNA or dsDNA; and measuring a detectable signal produced by cleavage of the labeled detector DNA, thereby detecting the target ssDNA or dsDNA.

In some embodiments, measuring the labeled detector DNA comprises detecting one or more of a gold nanoparticle, a fluorophore, fluorescence polarization, colloid phase transition/dispersion, electrochemical signals, and semiconductor-based signals.

In some embodiments, the labeled detector DNA produces an amount of detectable signal prior to being cleaved, and the amount of detectable signal is reduced when the labeled detector DNA is cleaved. In some embodiments, the labeled detector DNA produces a first detectable signal prior to being cleaved and a second detectable signal when the labeled detector DNA is cleaved.

In some embodiments, the labeled detector DNA comprises a quencher/fluor pair or a FRET pair.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1: Representative target sites for Cpf1 and SpCas9 nucleases. AsCpf1 and LbCpf1 recognize a TTTN PAM sequence at the 5' end of the target site spacer, whereas SpCas9 recognizes an NGG PAM at the 3' end of the spacer. Sense sequence: SEQ ID NO:1.

FIG. 2: PAM recognition profiles of wild-type AsCpf1 and LbCpf1 nucleases. The abilities of wild-type AsCpf1 and LbCpf1 to recognize target sites in the human cell-based EGFP disruption assay were determined using crRNAs targeted to sites with either a canonical TTTN PAM, or sites with non-canonical PAMs bearing single base differences. Three sites for each non-canonical PAM were examined, with the exception of ATTN and TTAN due to lack of target sites in the EGFP reporter gene.

FIG. 3: PAM recognition profiles of wild-type AsCpf1 for sites with canonical PAMs and non-canonical PAMs bearing double and triple base differences. The ability of AsCpf1 to recognize and disrupt target sites in the human cell-based EGFP disruption assay was determined using crRNAs targeted to sites with the indicated PAM. Where possible, three sites for each non-canonical PAM were examined, with the exception of ATTN and TTAN due to the lack of target sites in the EGFP reporter gene. Error bars, s.e.m. for n=3, otherwise n=1.

FIG. 4: PAM recognition profiles of AsCpf1 and LbCpf1 for canonical and non-canonical (single base difference) PAM sites. The abilities of wild-type AsCpf1 and LbCpf1 to recognize and disrupt endogenous target sites in U2OS human cells was determined by T7E1 assay using crRNAs targeted to sites with either a canonical TTTN PAM or with a non-canonical PAM bearing a single base difference. Where possible, three sites for each non-canonical PAM were examined. Error bars, s.e.m. for n=2 or 3, otherwise n=1.

FIGS. 5A-5H: Alteration of AsCpf1 PAM recognition specificity by rational mutation of residues physically proximal to PAM DNA bases. The activities of wild-type AsCpf1 and variants bearing single or double mutations were assessed with crRNAs targeted to sites bearing canonical TTTN or non-canonical PAM sites using either the human cell EGFP disruption assay or by quantifying indel mutation frequencies induced at endogenous gene sites in human U2OS cells. Wild-type AsCpf1 was compared to: (A) T167/T539 variants using crRNAs targeted to sites in EGFP; (B) S170 and E174 variants using crRNAs targeted to sites in EGFP; (C and D) S542 variants using crRNAs targeted to sites in EGFP (panel C) or endogenous human gene sites (panel D); (E) N551 and N552 variants using crRNAs targeted to sites in EGFP; (F) K607 variants using crRNAs targeted to sites in EGFP; (G and H) S542/K607 variants using crRNAs targeted to sites in EGFP (panel G) and endogenous human gene sites (panel H).

FIGS. 6A-6B: PAM recognition profiles of wild-type AsCpf1 and the AsCpf1-S542R variant. The activities of these nucleases in the human cell-based EGFP disruption assay were determined with crRNAs targeted to sites bearing either a canonical TTTN PAM or a non-canonical PAM with a single base difference (panel A) or double or triple base differences (panel B). Where possible, three sites for each non-canonical PAM were examined, with the exception of ATTN and TTAN due to lack of sufficient target sites in the EGFP reporter gene. n=1.

Figure 7A:
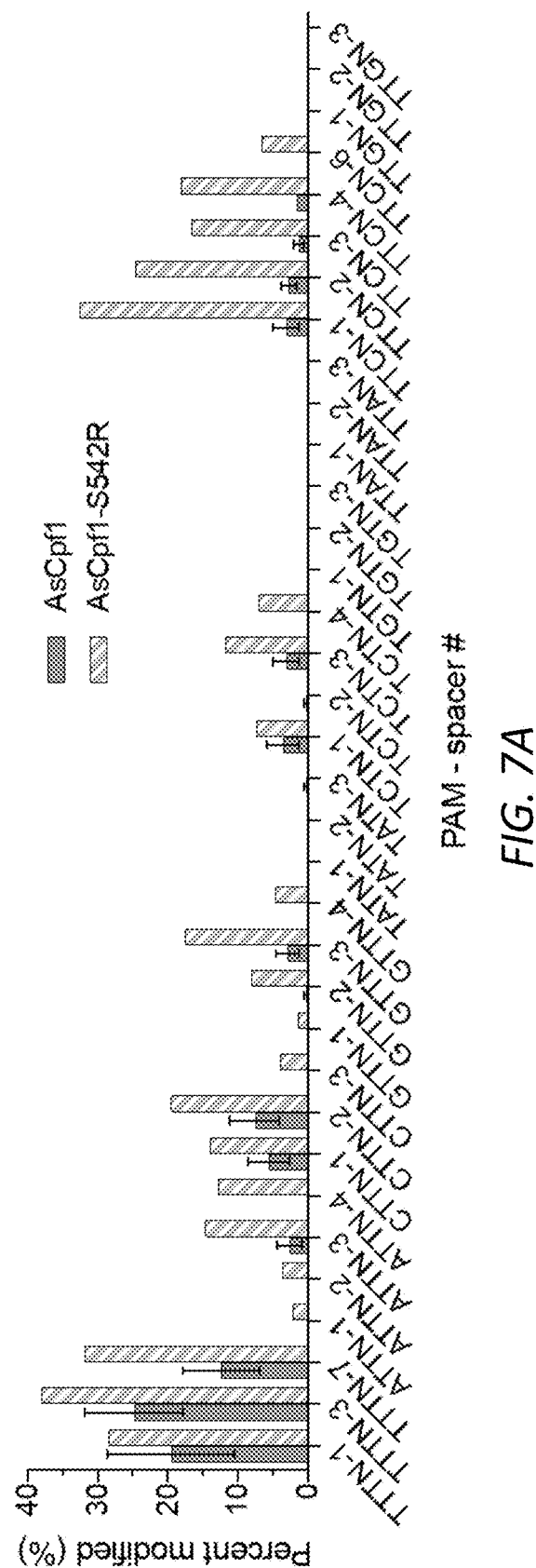
Figure 7B:
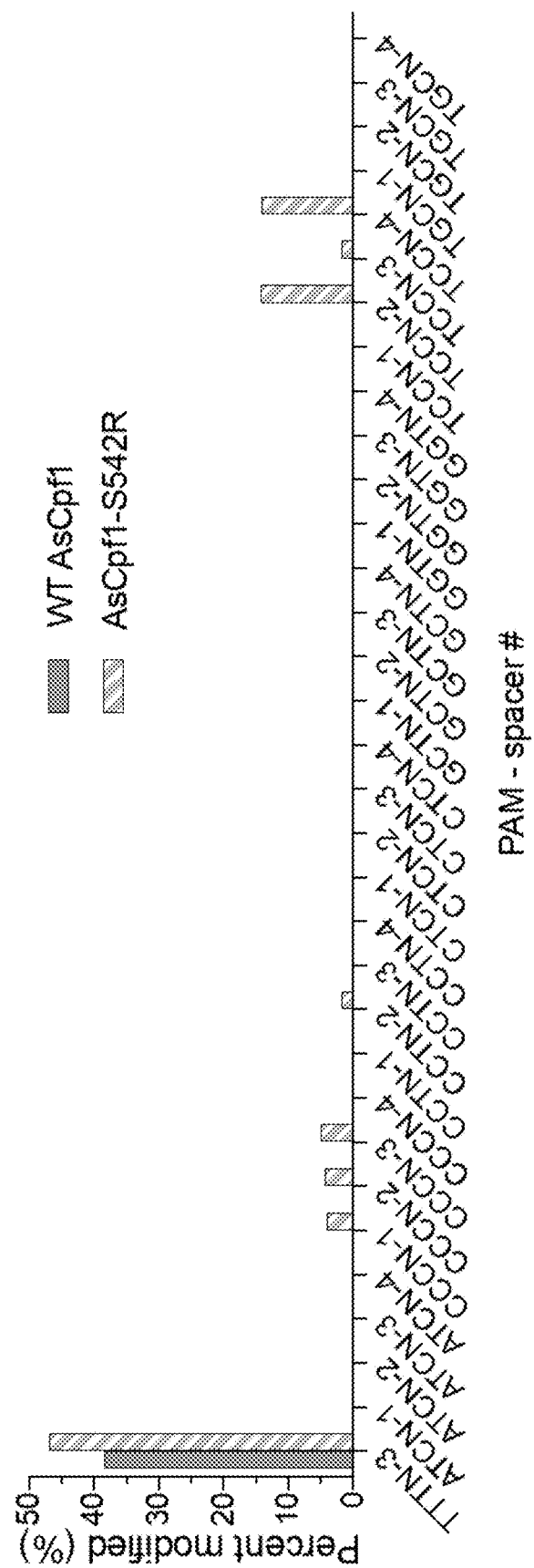

FIGS. 7A-7B: PAM recognition profiles of wild-type AsCpf1 and the AsCpf1-S542R variant on endogenous human gene target sites. Nucleases were assessed for their abilities to mutagenize endogenous gene target sites in human U2OS cells using crRNAs targeted to sites bearing either a canonical TTTN PAM or a non-canonical PAM with a single base difference (panel A) or double or triple base differences (panel B). Where possible, three sites for each non-canonical PAM were examined.

Figure 8A:
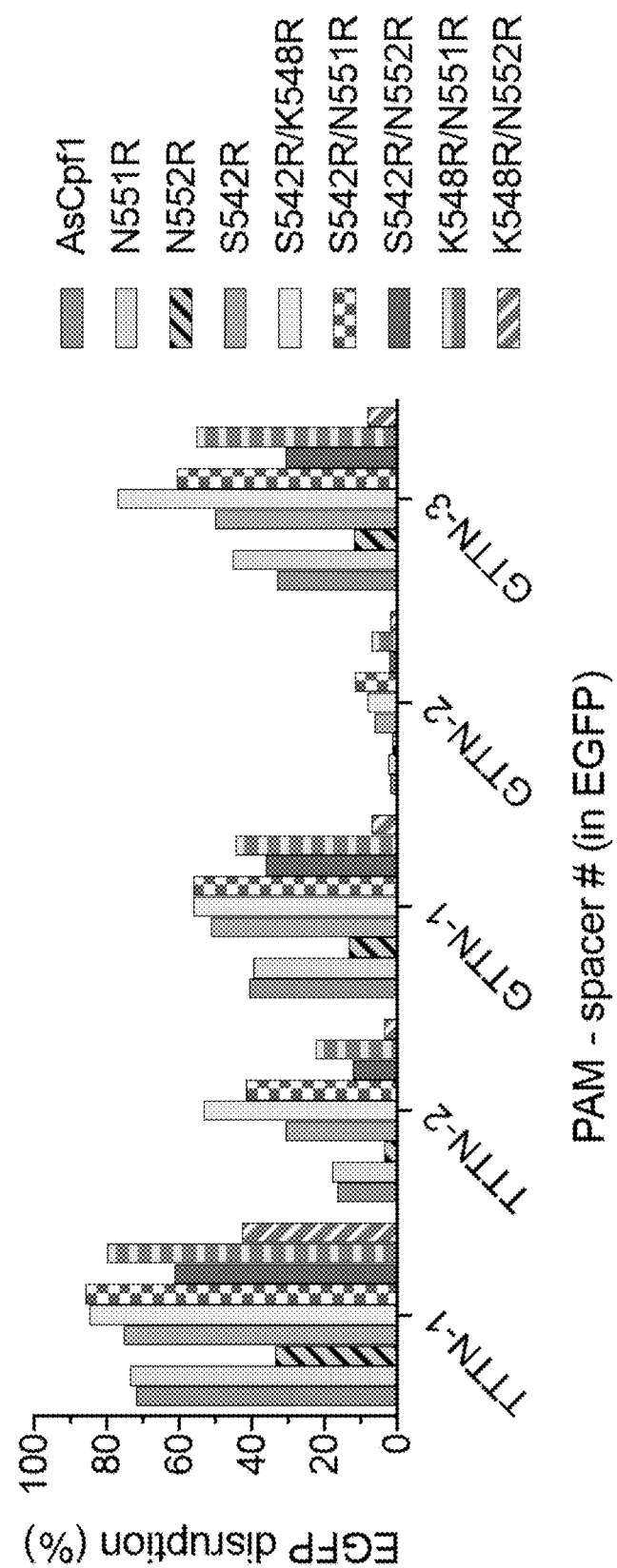
Figure 8B:
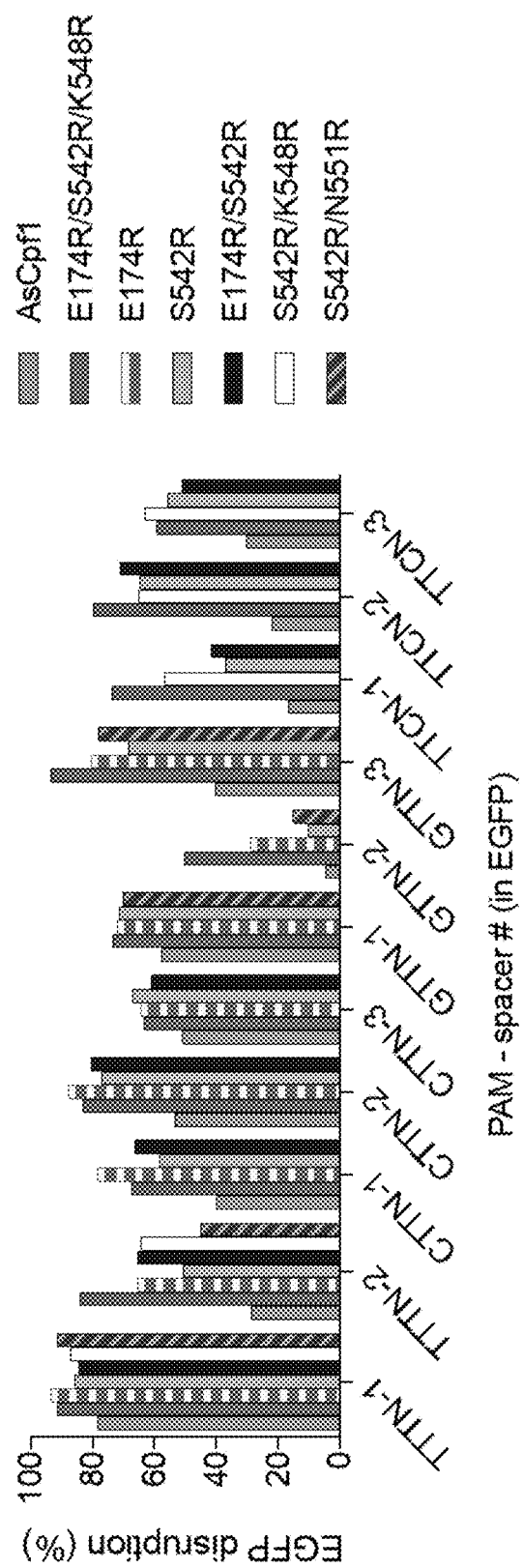
Figure 8C:
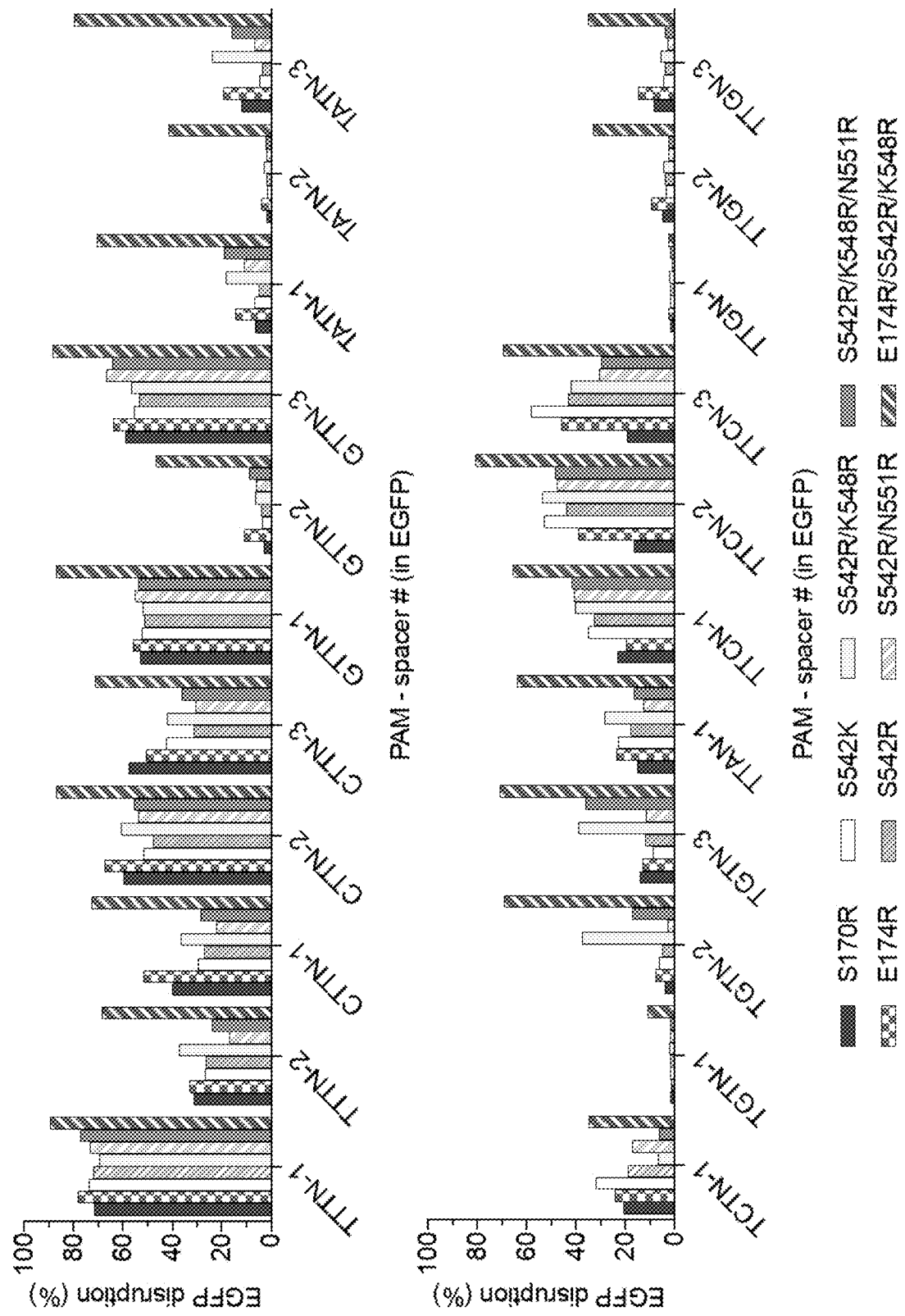

FIGS. 8A-8C: PAM recognition profiles of rationally designed AsCpf1 variants bearing additional mutations at residues positioned near PAM DNA bases. In separate experiments shown in panels A, B, and C, single amino acid substitutions and double or triple combinations of amino acid substitutions were tested using the human cell-based EGFP reporter assay to assess their abilities to recognize target sites bearing canonical TTTN or non-canonical PAM sites.

Figure 9A:
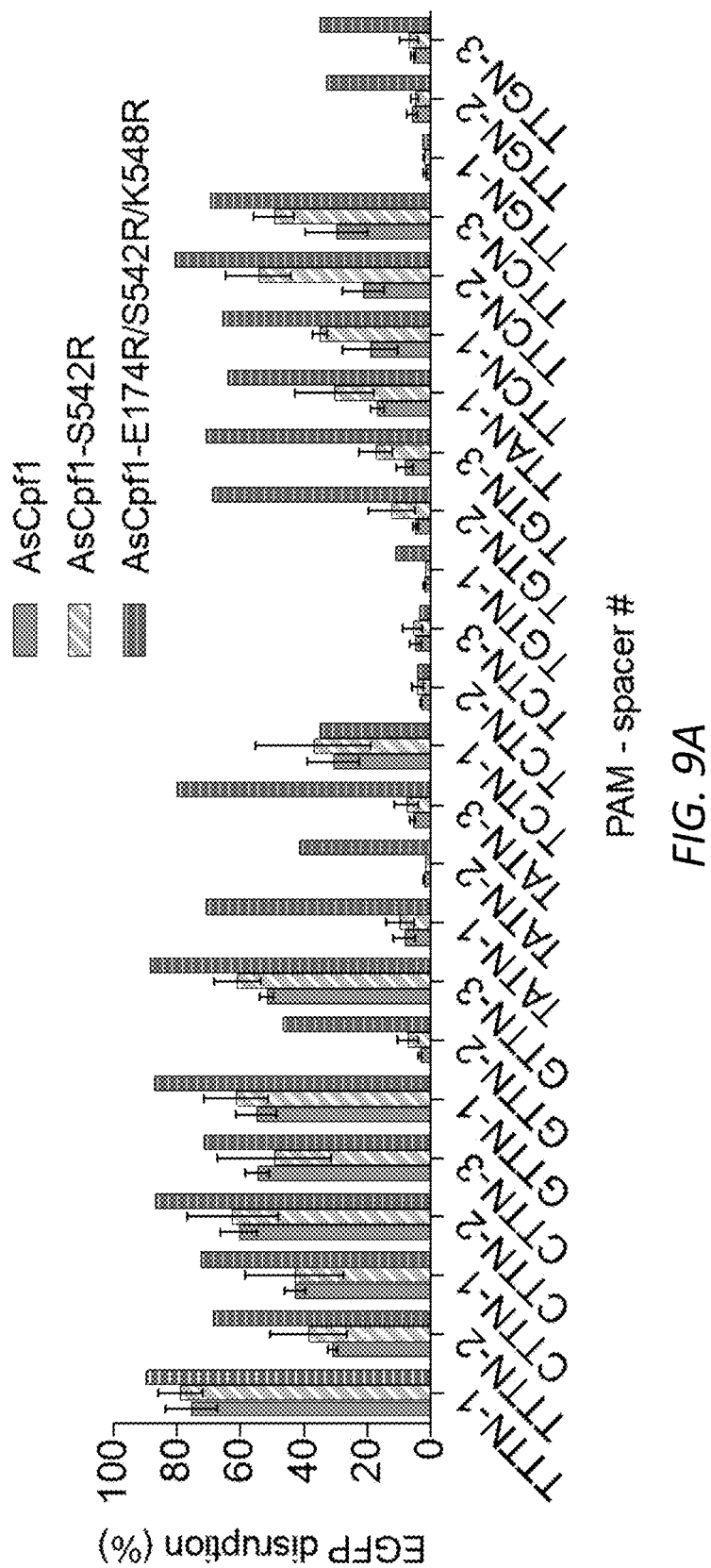
Figure 9B:
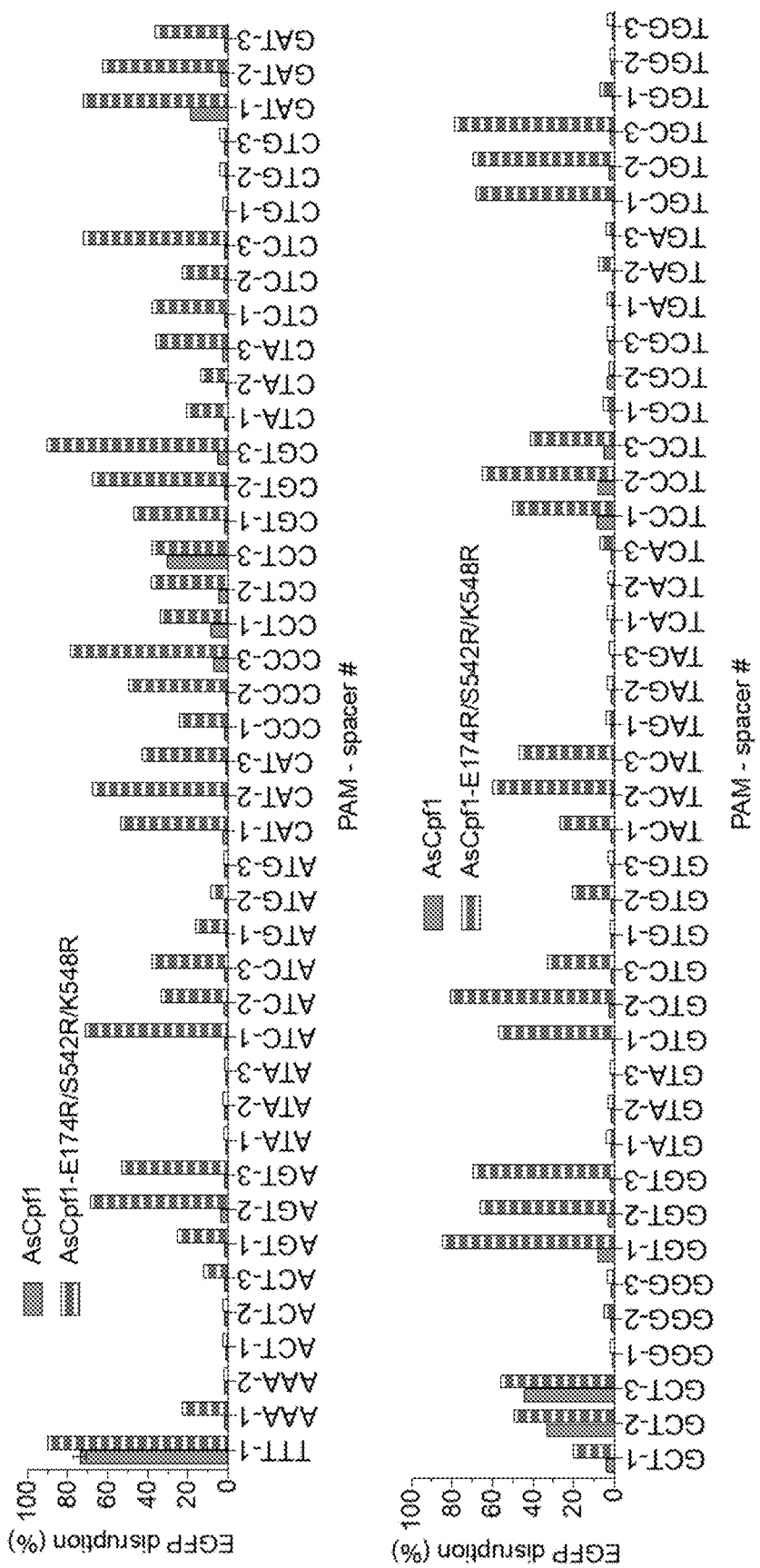

FIGS. 9A-9B: PAM of wild-type AsCpf1 and AsCpf1 variants. (A) The activity of wild-type AsCpf1 was compared to the activities of variants bearing a single S542R substitution or a combination of the E174R, S542R, and K548R substitutions. Activities of these nucleases were tested using human cell-based EGFP disruption assay using crRNAs targeted to sites bearing either a canonical TTTN PAM or PAMs with single base differences. (B) The activity of wild-type AsCpf1 was also compared to the E174R/S542R/K548R variant using the human cell-based EGFP reporter assay with crRNAs targeting sites with a canonical TTTN PAM or PAM bearing double or triple base differences. Where possible, three sites for each non-canonical PAM were examined. Error bars, s.e.m. for n=2 or 3, otherwise n=1.

Figure 10A:
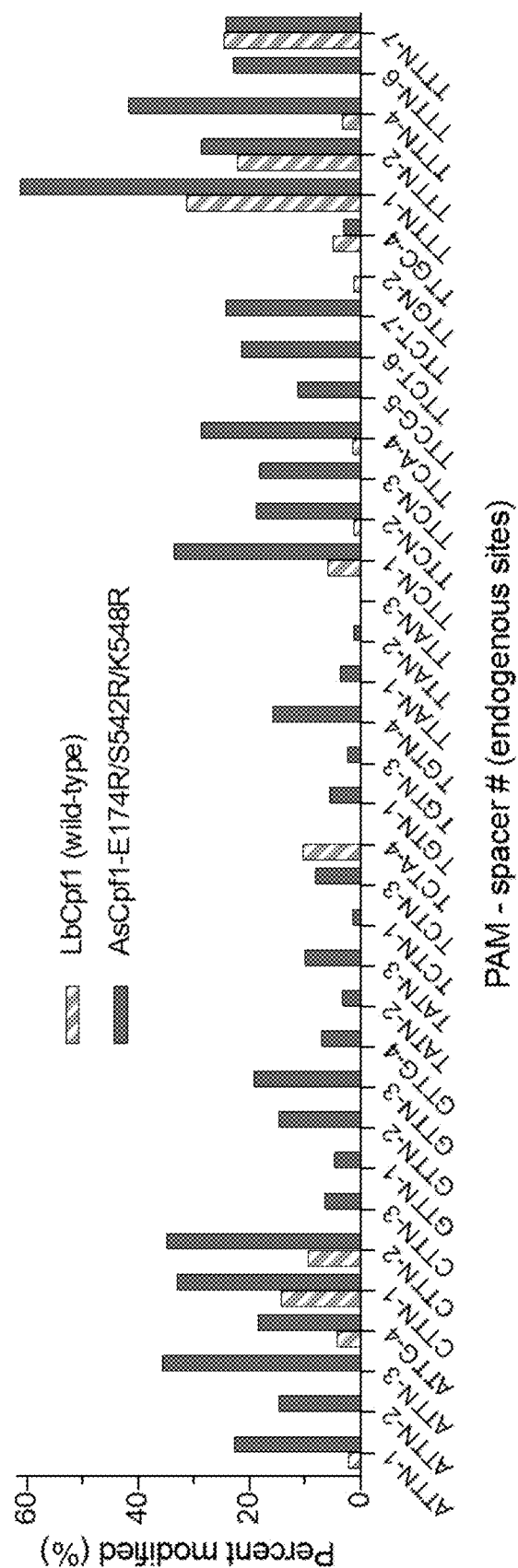
Figure 10B:
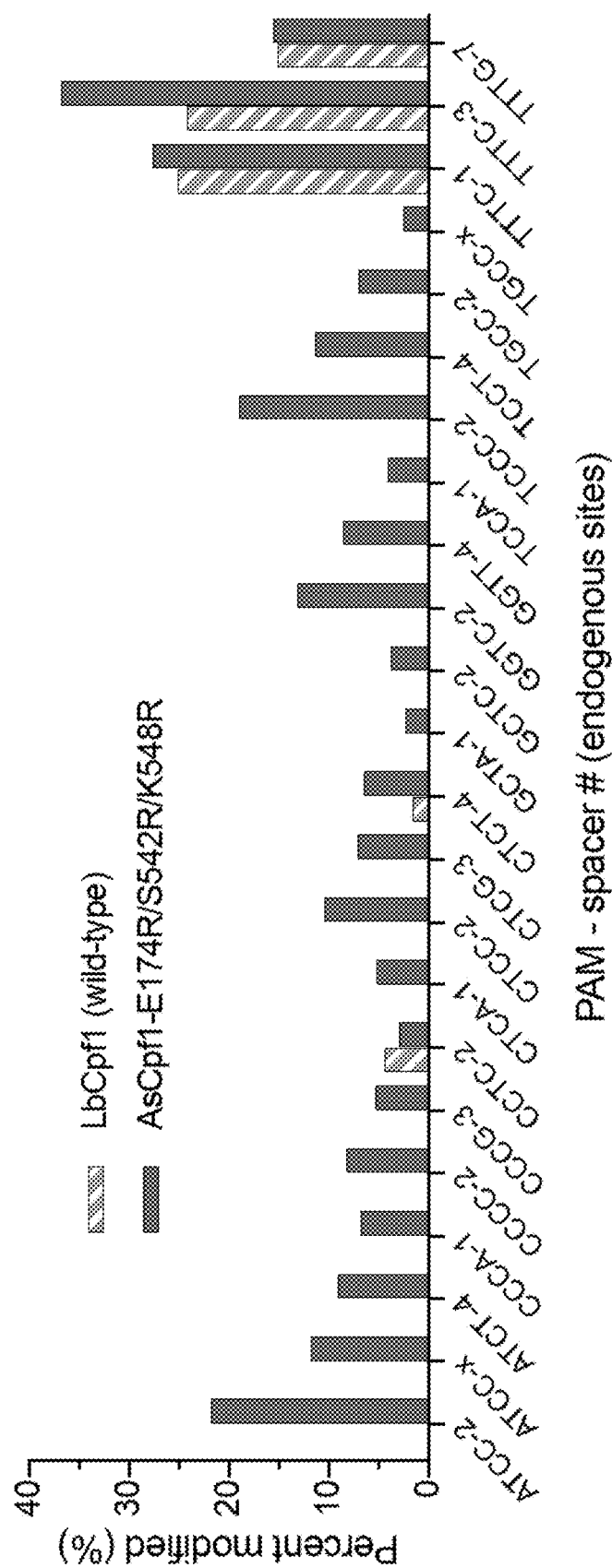

FIGS. 10A-10B: Comparison of the PAM recognition profiles of wild-type LbCpf1 and AsCpf1 variants. The ability of wild-type LbCpf1 to modify endogenous human gene target sites was compared to that of the AsCpf1 E174R/S542R/K548R variant. This experiment used crRNAs targeted to sites bearing either canonical TTTN PAMs and PAMs with single base differences (panel A), or PAMs with double or triple base differences (panel B).

Figure 11A:
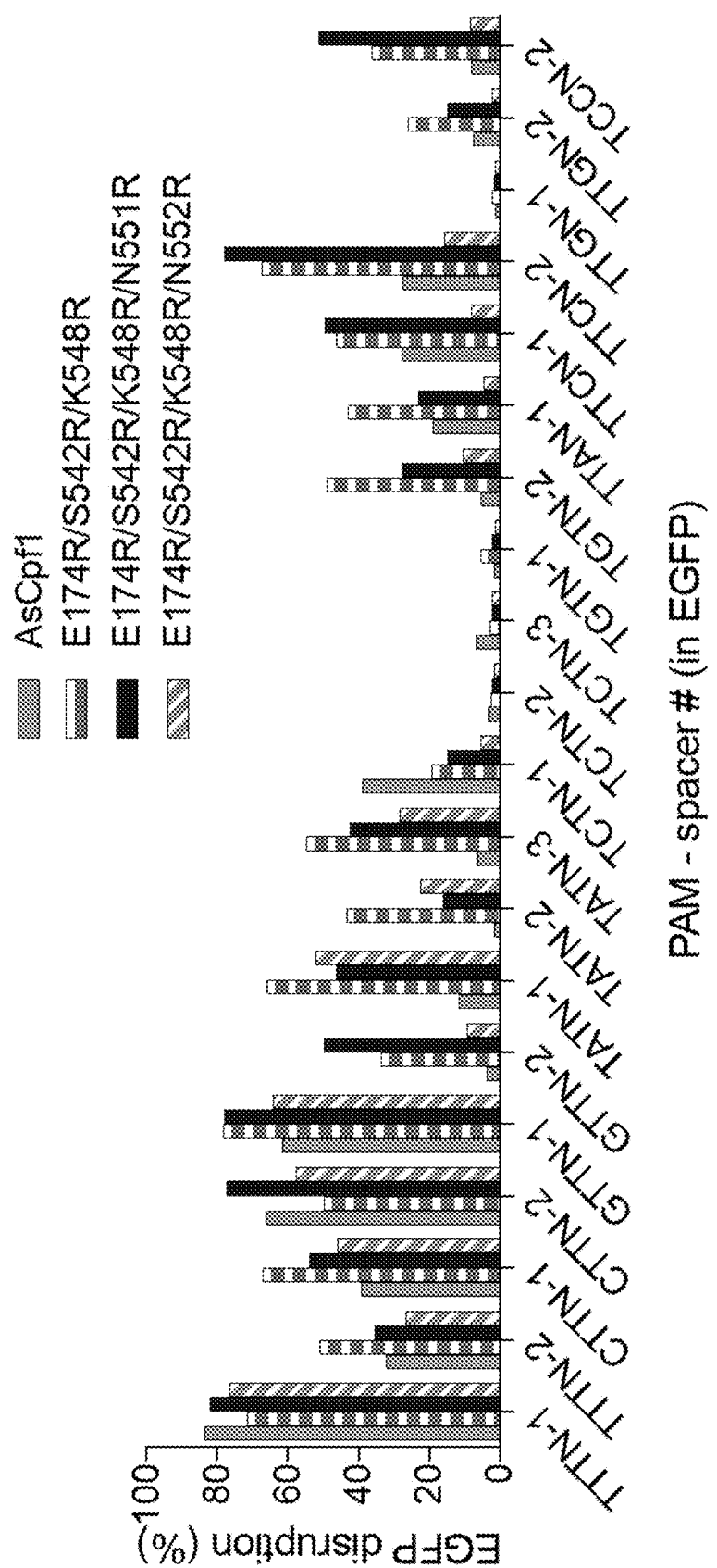
Figure 11B:
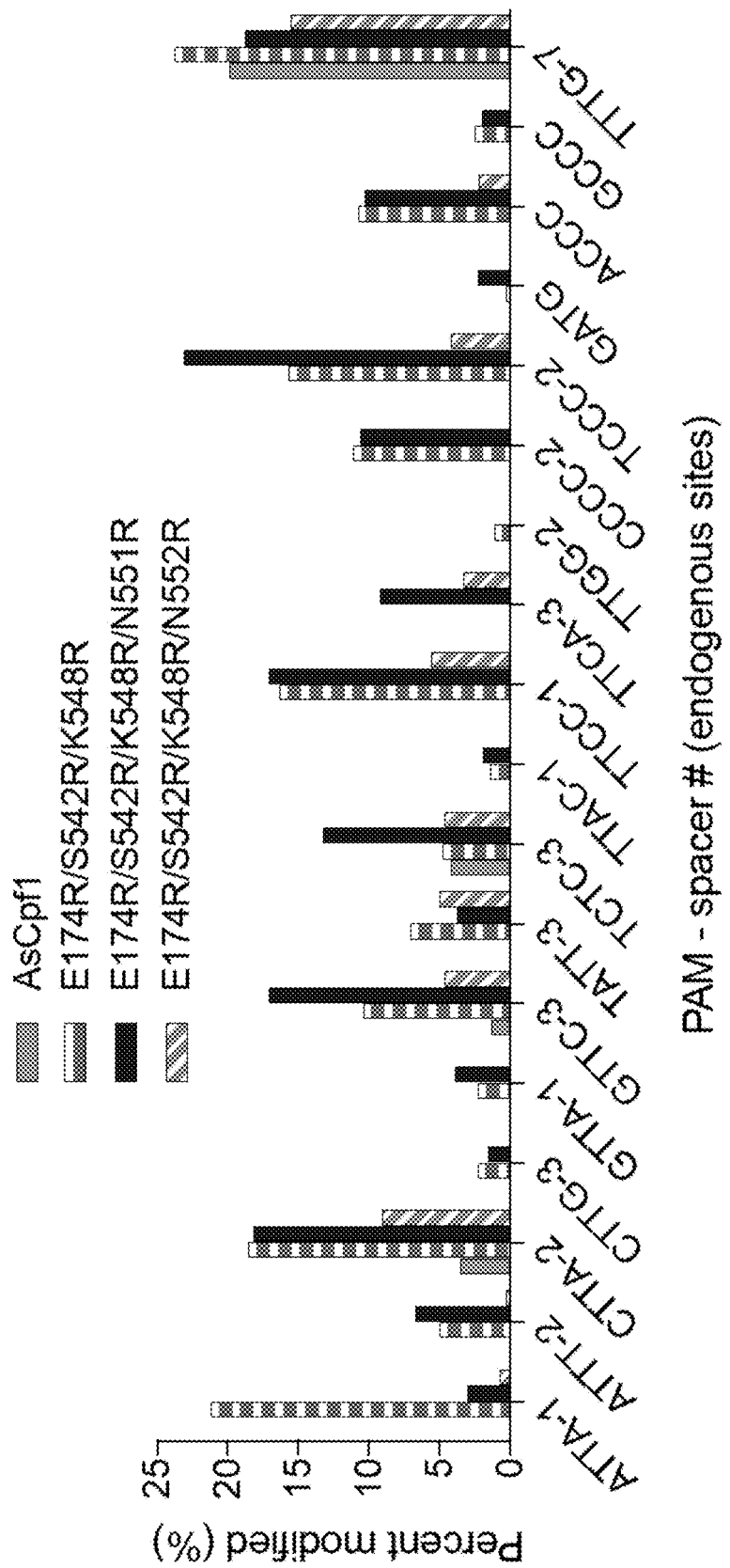
Figure 11C:
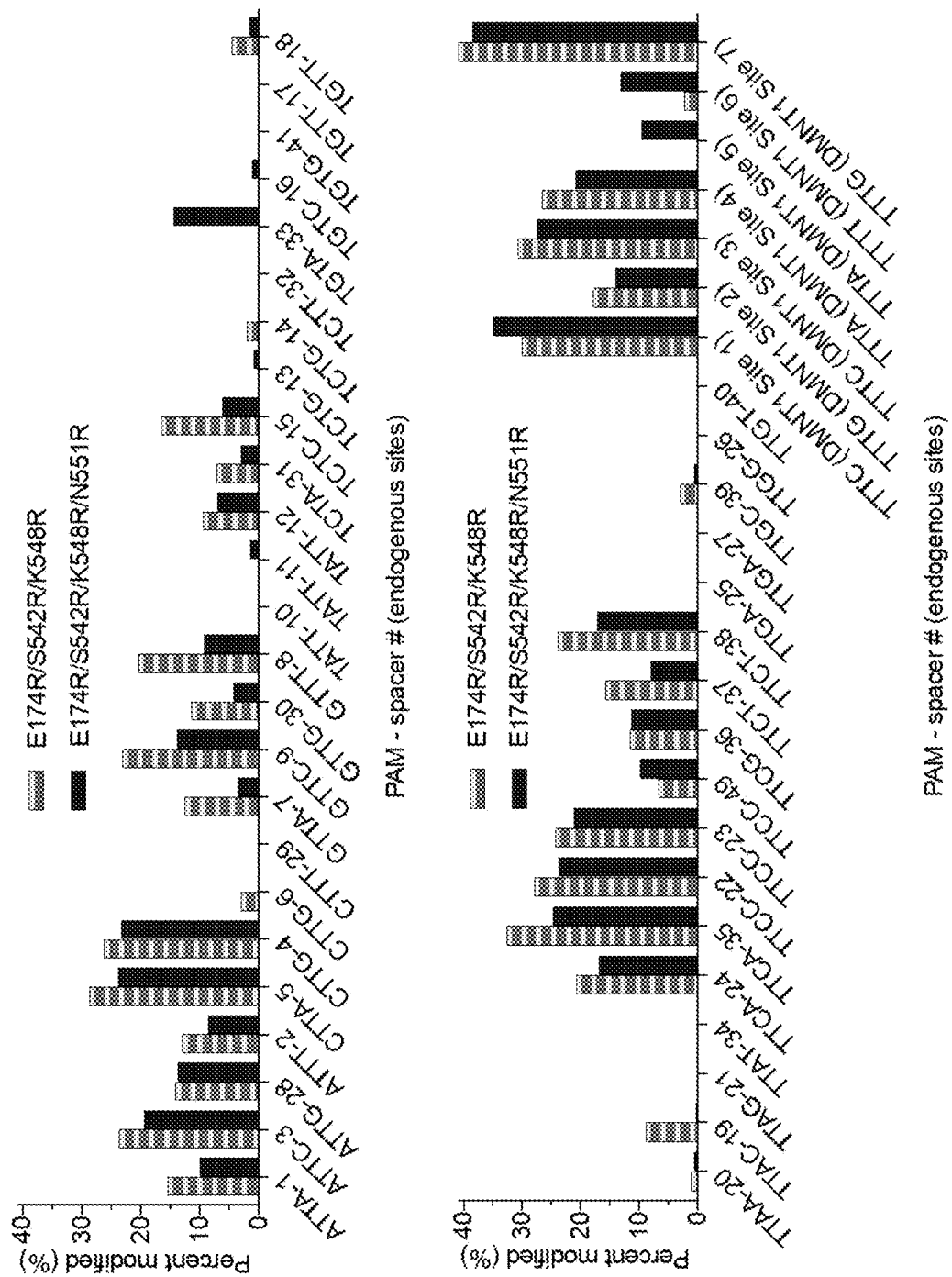

FIGS. 11A-11C: PAM recognition profiles of wild-type AsCpf1 and various engineered AsCpf1 variants. The activity of wild-type AsCpf1 was compared to the activities of AsCpf1 PAM variants using crRNAs targeted to sites bearing either canonical TTTN PAMs or PAMs with single, double, or triple base differences. Comparisons were performed (A) with the human cell-based EGFP disruption assay or (B) by assessing mutation frequencies (as judged by T7EI endonuclease assay) at endogenous human gene target sites. (C) The mutational activities of two AsCpf1 PAM variants were compared using crRNAs targeted to endogenous human gene sites bearing either canonical TTTN PAMs or PAMs bearing single, double, or triple base differences.

Figure 12A:
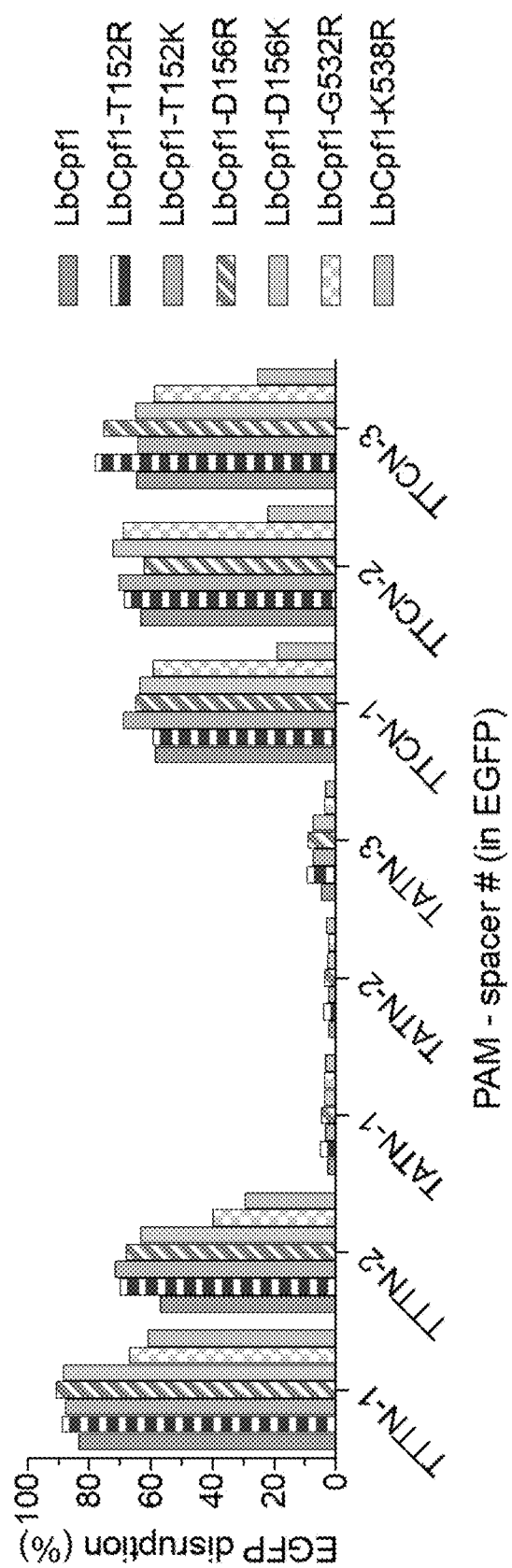
Figure 12B:
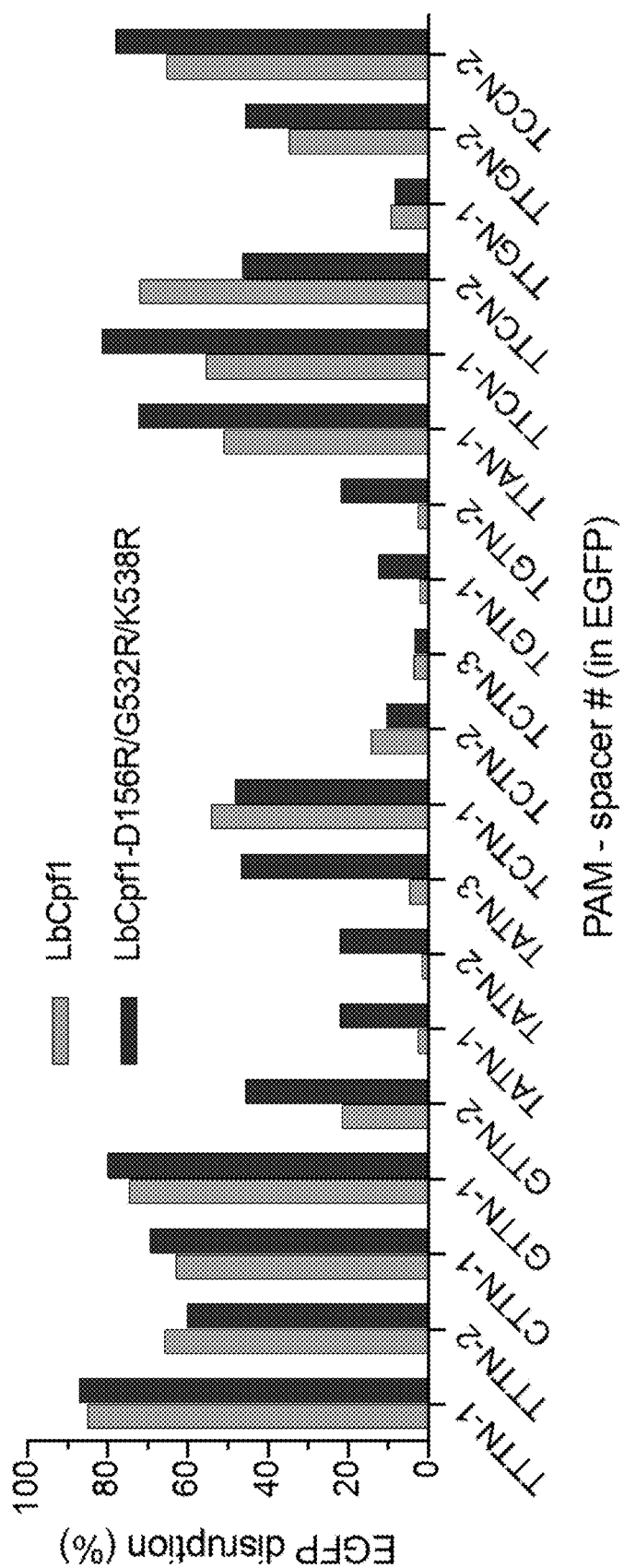

FIGS. 12A-12B: PAM recognition profiles of wild-type LbCpf1 and engineered LbCpf1 variants. (A) The activity of wild-type LbCpf1 and variants bearing various single amino acid substitutions were using the human cell-based EGFP disruption assay with crRNAs targeted to sites bearing either a canonical TTTN PAM or a PAM with a single base difference. (B) The activity of wild-type LbCpf1 was also compared to the LbCpf1-D156R/G532R/K538R variant using the human cell-based EGFP disruption assay with crRNAs targeted to sites bearing either a canonical TTTN PAM or a PAM with a single base difference. n=1.

Figure 13A:
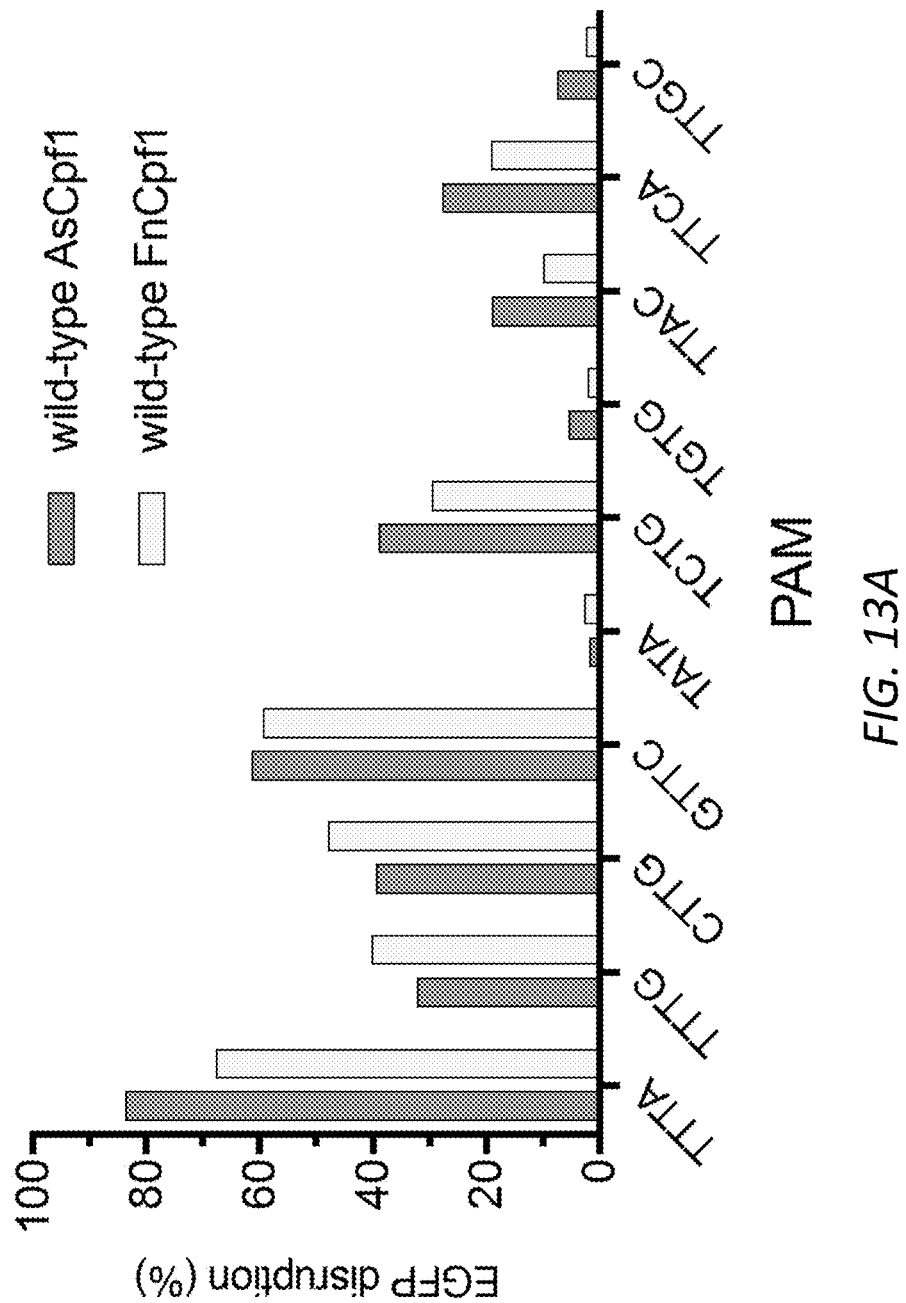
Figure 13B:
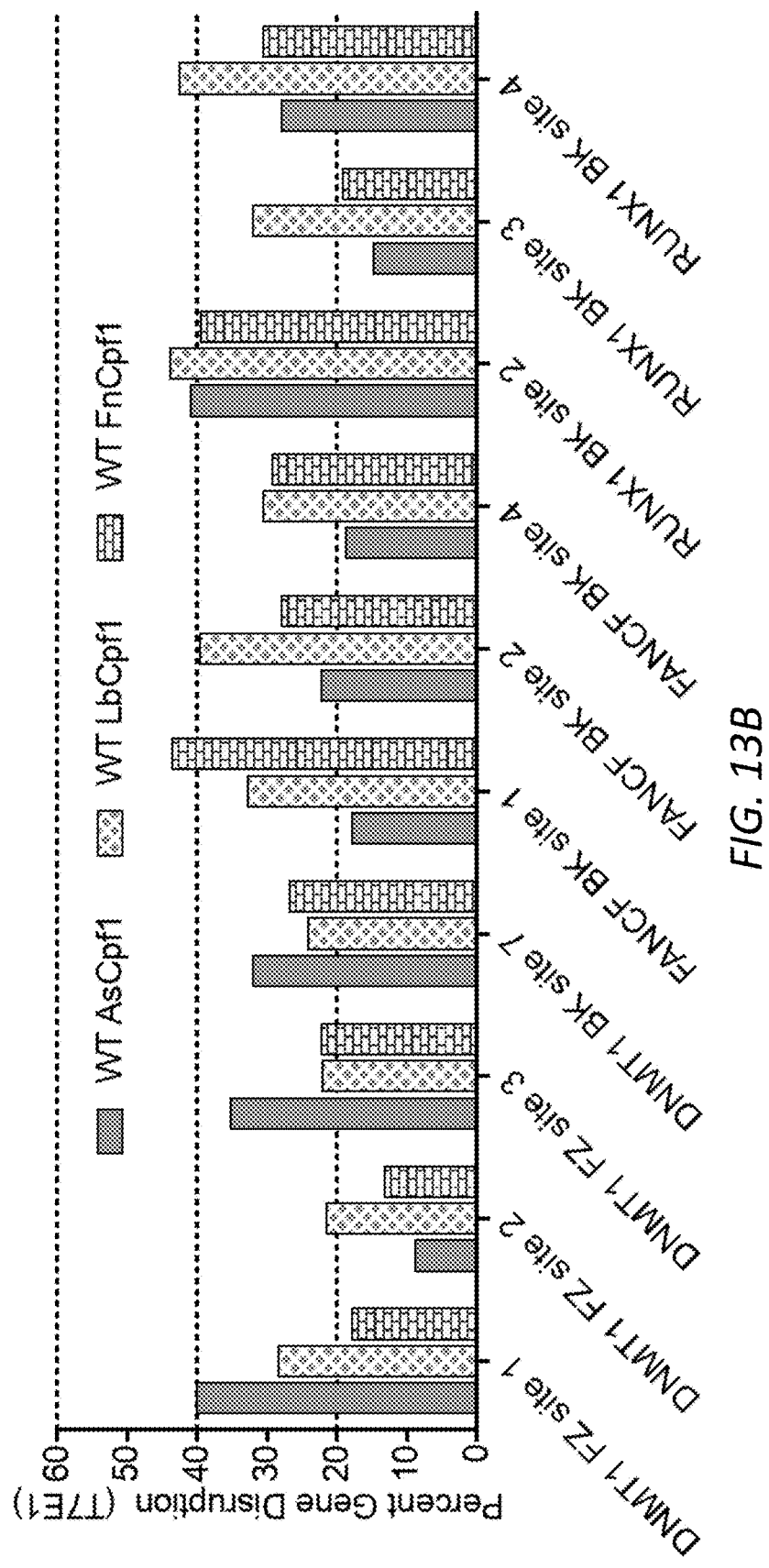
Figure 13C:
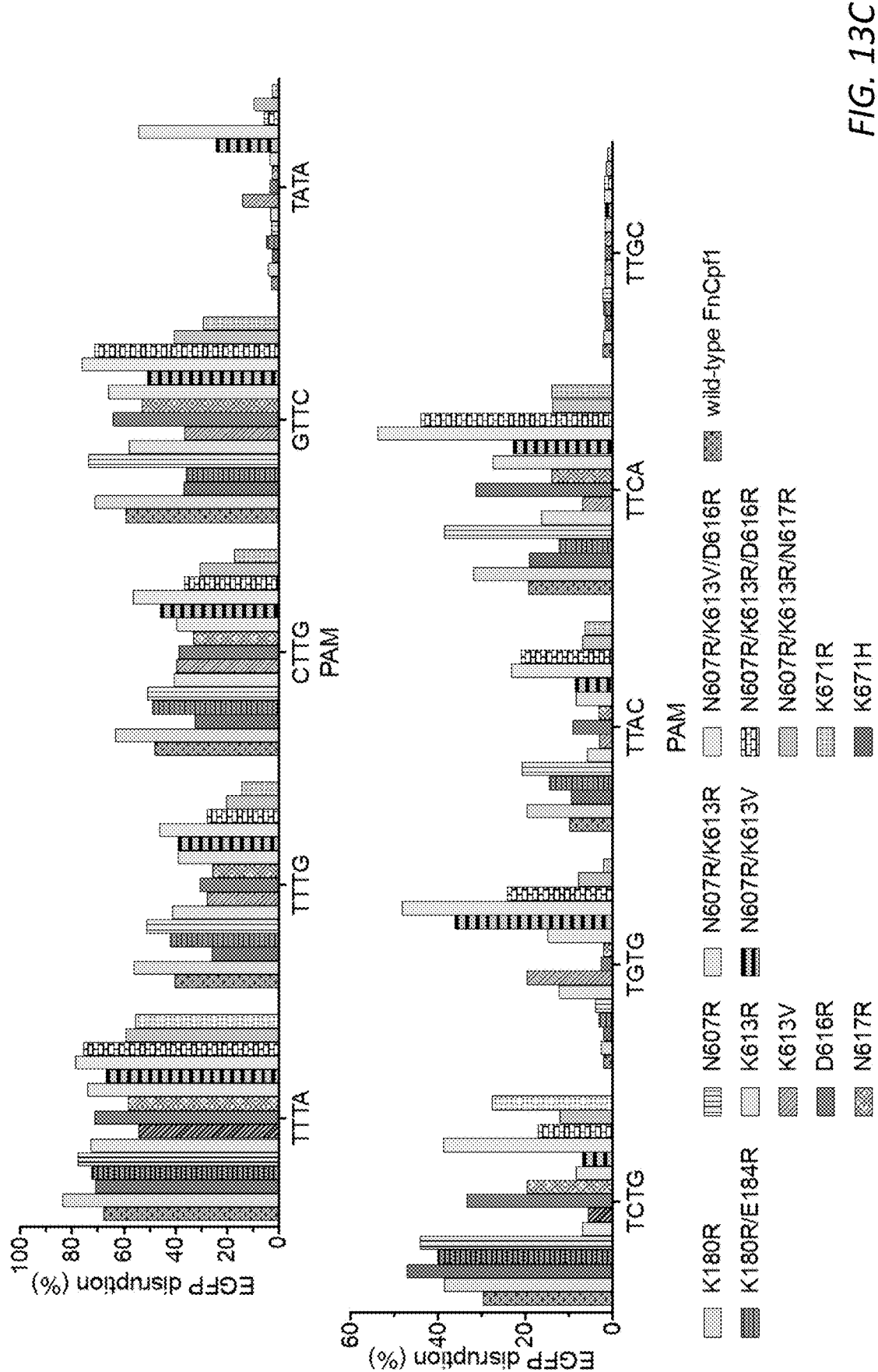

FIGS. 13A-13C: PAM recognition profiles of wild-type FnCpf1 and engineered LbCpf1 variants. (A) The activity of wild-type FnCpf1 using the human cell-based EGFP disruption assay with crRNAs targeted to sites bearing either a canonical TTN PAM or a PAM with a single base difference. (B) The activity of wild-type FnCpf1, AsCpf1, and LbCpf1 against endogenous human cell target sites with crRNAs targeted to sites bearing TTTN PAMs. (C) Comparison of the activity of wild-type FnCpf1 to engineered FnCpf1 PAM variants using the human cell-based EGFP disruption assay with crRNAs targeted to sites bearing either a canonical TTTN PAM or a PAM with a single base difference. n=1.

Figure 14A:
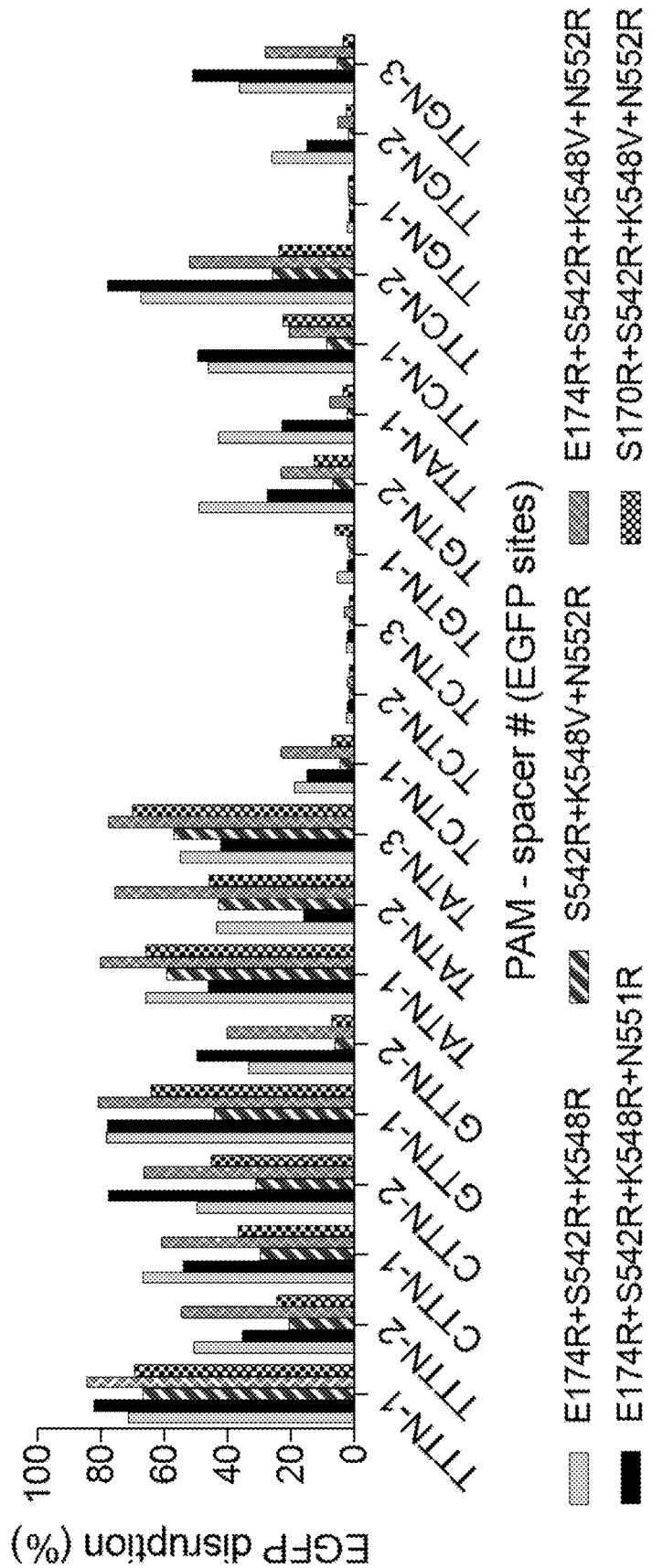
Figure 14B:
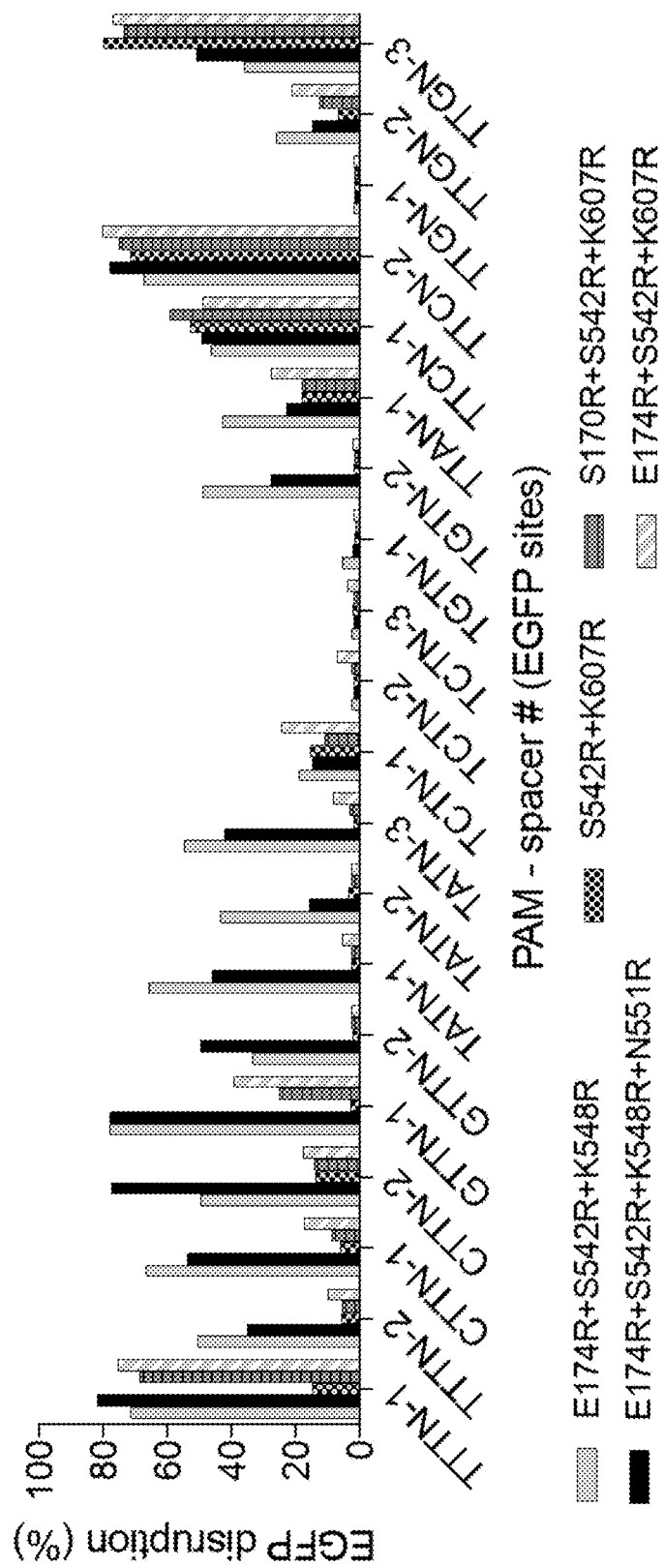
Figure 14C:
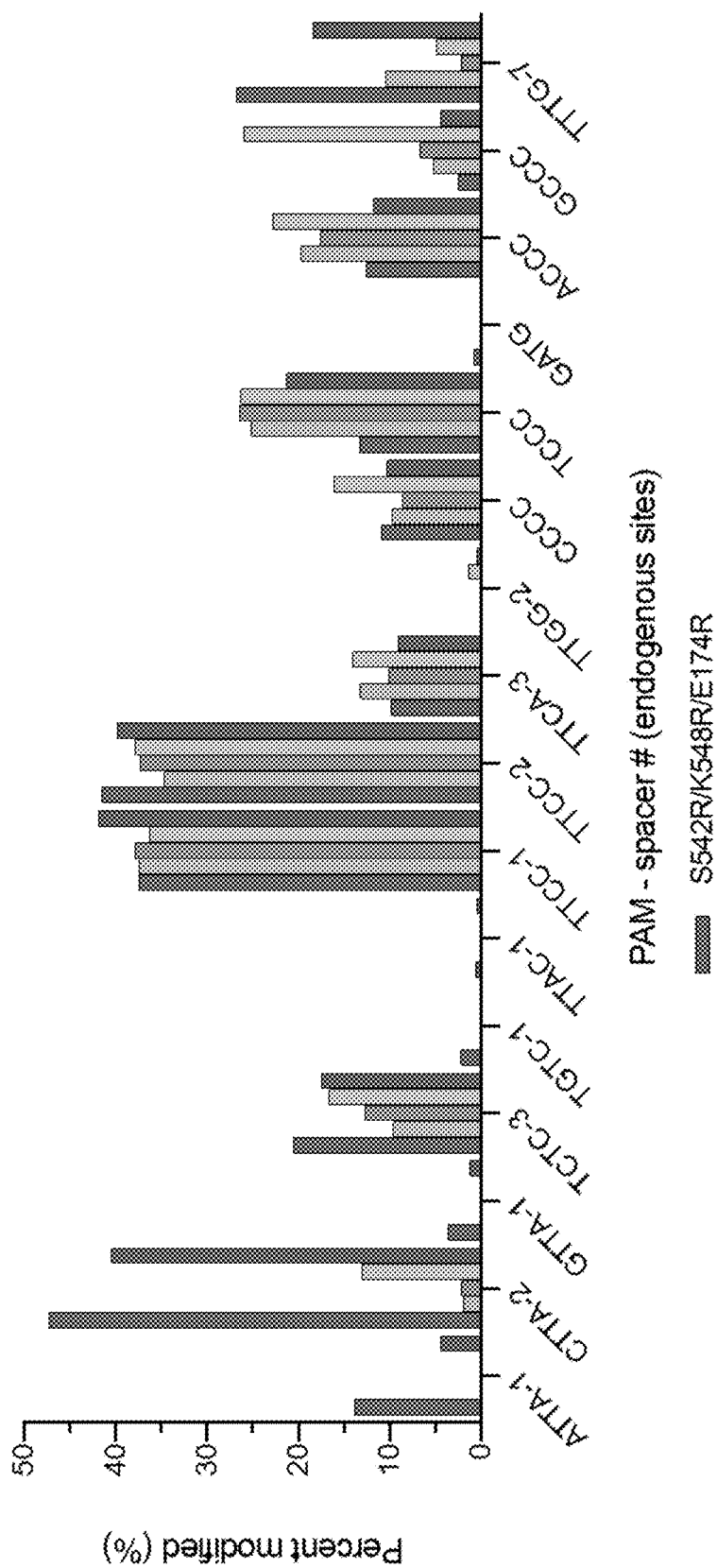

FIGS. 14A-14C: Comparison of PAM recognition profiles of AsCpf1 variants described in this application with different AsCpf1 variants disclosed in other work. (A, B) The activities of a number of our engineered AsCpf1 PAM recognition variants were compared to the S542R/K548V/N552R (panel A) and S542R/K607R (panel B) PAM recognition variants using the human cell-based EGFP disruption assay with crRNAs targeted to sites bearing either canonical TTTN PAMs or PAMs with single or double base differences. (C) Additional comparisons of our AsCpf1 variants to the S542R/K607R variant were performed by examining the abilities of these nucleases to mutagenize endogenous human gene sites with crRNAs targeted to sites with either canonical TTTN PAMs or PAMs with single, double, or triple base differences.

FIGS. 15A-15G: Engineering and characterization of an AsCas12a variant with expanded target range. (A), Modification of endogenous sites in human cells by AsCas12a variants bearing amino acid substitutions. Activities assessed by T7E1 assay; mean, s.e.m., and individual data points shown for n≥3. (B), PAM preference profiles for wild-type AsCas12a and the E174R/S542R/K548R variant, evaluated by the PAM determination assay (PAMDA). The $\log_{10}$ rate constants (k) are the mean of four replicates, two each against two distinct spacer sequences (see FIG. 21D). (C), Mean activity plots for E174R/S542R and E174R/S542R/K548R AsCas12a on non-canonical PAMs, where the black line represents the mean of 12 to 20 sites (dots) for each PAM class (see also FIGS. 23A, 23B and 23D). (D), Summary of the activities of wild-type, E174R/S542R, and E174R/S542R/K548R AsCas12a across 20 sites encoding non-canonical PAMs, one for each PAM of the VTTN, TTCN, and TATN classes (see also FIGS. 19A, 23A, and 23B; all sites numbered '1'). (E), Mean activity plots for AsCas12a, the E174R/S542R variant, and eAsCas12a on TTTN PAMs, where the black line represents the mean of 5 to 8 sites (dots) for each PAM class (see FIG. 23G). (F), Superimposition of the summaries of the human cell activities and PAMDA rate constants (k) for various targetable and non-targetable PAMs with eAsCas12a (E174R/S542R/K548R). Box and whisker plots shown for human cell activities determined by T7E1 assay. Tier 1 PAMs exhibit greater than 20% mean targeting in human cells and a PAMDA k greater than 0.01, and PAMs that meet a modest threshold of greater than 10% mean targeting in cells and a PAMDA k greater than 0.005 are considered tier 2 PAMs. (G), Calculation of the improvements in targeting range enabled by AsCas12a variants compared to wild-type AsCas12a, determined by enumerating complete PAM sequences within the indicated sequence feature and normalizing for element size. TSS, transcription start site; PAM sequences targetable by each AsCas12a variant are: wild-type, TTTV; eAsCas12a, see panel F and Extended Data FIG. 23I for PAM tiers; RVR, TATV; RR, TYCV.

Figure 24A:
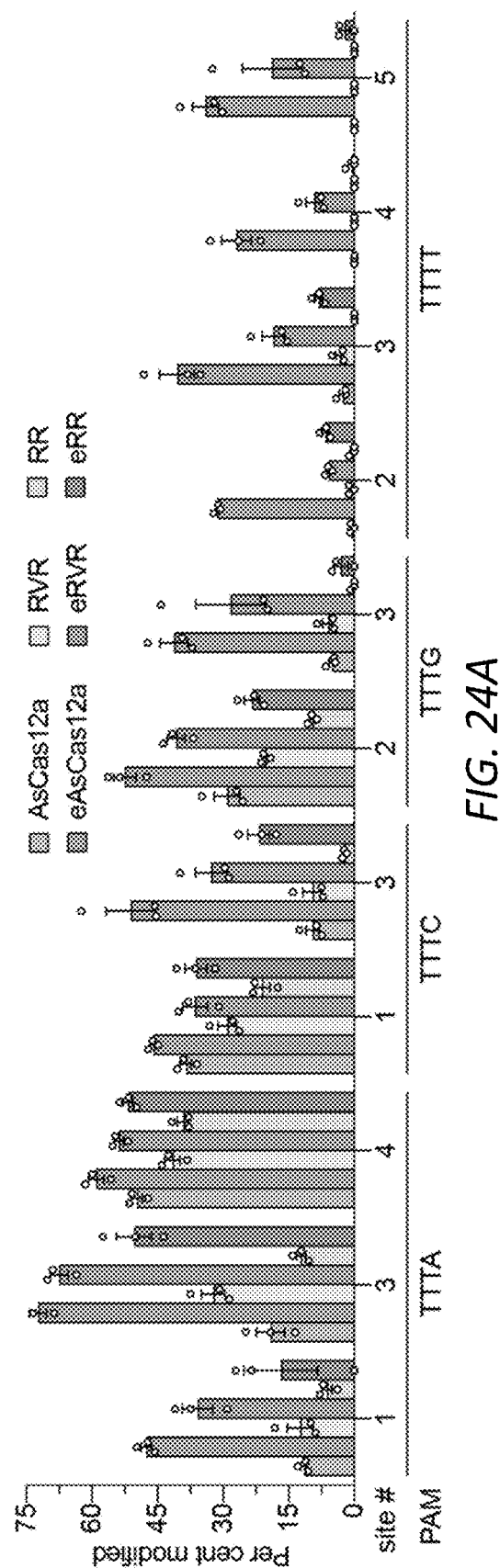
Figure 24B:
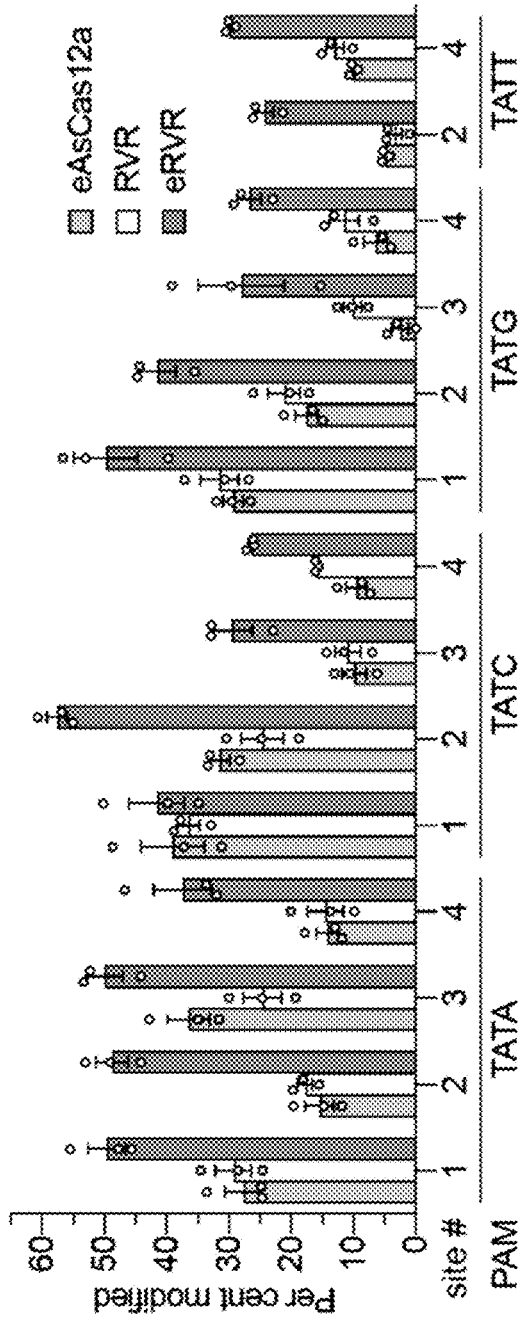
Figure 24C:
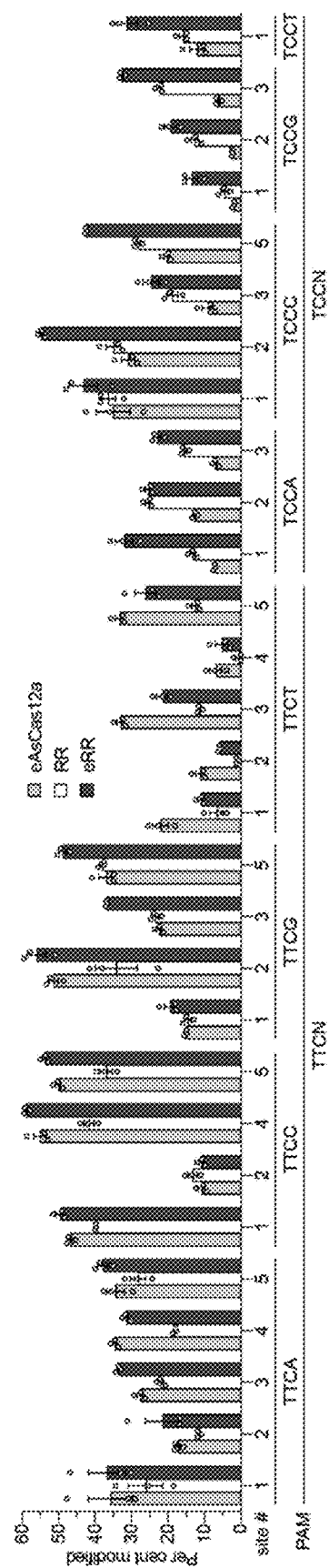

FIGS. 16A-16E: Enhanced activities of AsCas12a variants. (A), Quantification of time-course in vitro cleavage reactions of Cas12a orthologs and variants on linearized plasmid substrates encoding PAMDA site 1 target, conducted at 37, 32, and 25° C. (left, middle, and right panels, respectively). Curves were fit using a one phase exponential decay equation; error bars represent s.e.m for n=3. (B-D), Summaries of the activities of wild-type and variant AsCas12a nucleases across sites encoding TTTN PAMs (panel B), TATN PAMs (panel C) and TYCN PAMs (panel D) (see also FIGS. 24A-C, respectively). (E), Scatterplots of the PAMDA determined rate constants for each NNNN PAM to compare the PAM preferences of AsCas12a variants (RVR to eRVR, left panel; RR to eRR, right panel). Variants encode the following substitutions: eAsCas12a, E174R/S542R/K548R; RVR, S542R/K548V/N552R; eRVR, E174R/S542R/K548V/N552R; RR, S542R/K607R; eRR, E174R/S542R/K607R.

Figure 17A:
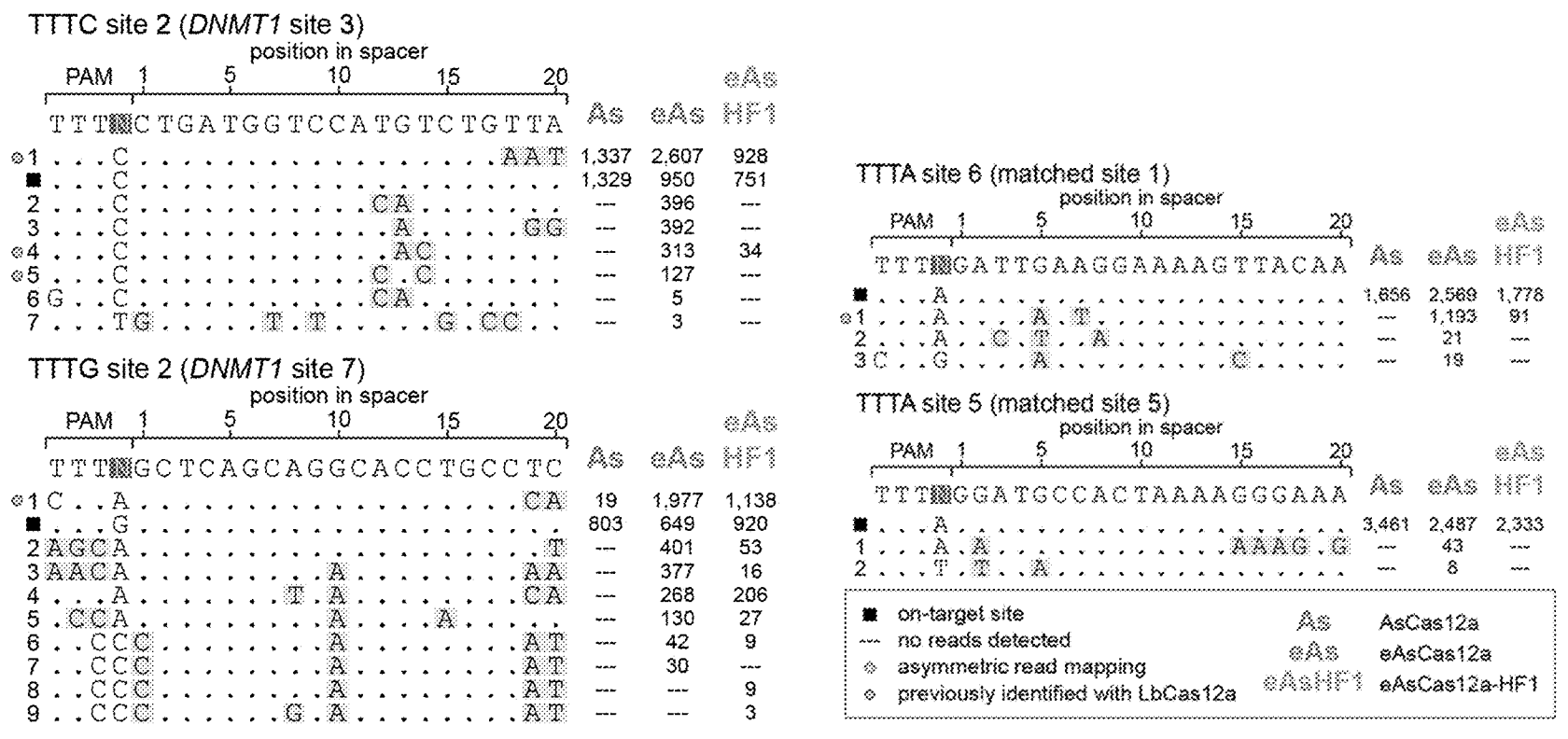

FIGS. 17A-17H: Characterization and improvement of eAsCas12a specificity. (A), GUIDE-seq genome-wide specificity profiles for AsCas12a, eAsCas12a, and eAsCas12a-HF1 each paired with crRNAs targeting sites with TTTV PAMs. Mismatched positions in off-target sites are highlighted; GUIDE-seq read counts are shown to the right of the sequences; yellow circles indicate off-target sites that are only supported by asymmetric GUIDE-seq reads; green circles indicate off-target sites previously identified for LbCas12a (Kleinstiver et al., Nat Biotechnol., 2016, 34:869-74); alternate nucleotides in non-canonical PAMs with mean PAMDA ks>0.005 for eAsCas12a are not coloured/highlighted as mismatches. SEQ ID NOs. 449-477, in order of appearance. (B), Histogram of the number of GUIDE-seq detected off-target sites for AsCas12a variants from the sites examined in panel A. (C), Scatterplot of the PAMDA determined rate constants for each NNNN PAM to compare the PAM preferences of eAsCas12a and eAsCas12a-HF1. (D), GUIDE-seq genome-wide specificity profiles for eAsCas12a and eAsCas12a-HF1 for crRNAs targeting sites with non-canonical PAMs. Illustrations as described for panel a; eAsCas12a-HF1 not assessed on CTTA-1, CTTC-2, or TATC-1. SEQ ID NOs. 478-530, in order of appearance. (E), Histogram of the number of GUIDE-seq detected off-target sites for eAsCas12a and eAsCas12a-HF1 from the sites examined in panel a; na, not assessed. (F), Off-target efficiency ratio calculated by normalizing off-target GUIDE-seq read counts against counts observed at the on-target site. (G, H), On-target activity summaries of wild-type, eAsCas12a, and eAsCas12a-HF1 across sites encoding TTTN PAMs (panel G) or non-canonical PAMs (panel H) (see FIGS. 25I and 25J, respectively).

FIGS. 18A-18K: Applications of eAsCas12a for multiplex targeting, gene activation, and base editing. (A-C), Comparison of the multiplex on-target modification efficiencies of AsCas12a, eAsCas12a, and LbCas12a, when programmed with TTTV PAM targeted crRNA arrays encoding 3 separate crRNAs expressed either from a polymerase III promoter (U6, panels A and B) or a polymerase II promoter (CAG, panel C). The activities at three separate loci were assessed by T7E1 assay using the same genomic DNA samples; mean, s.e.m., and individual data points shown for n=3. (D), Assessment of the editing efficiencies when using pooled crRNA plasmids or multiplex crRNA arrays expressing two crRNAs targeted to nearby (~100 bp) genomic loci. Activities assessed by T7E1 assay; mean, s.e.m., and individual data points shown for n=4. (E-G), Activation of endogenous human genes with dCas12a-VPR(1.1) fusions (see FIG. 26A) using pools of three crRNAs targeted to canonical PAM sites (panel E) and non-canonical PAM sites (panels F and G). Activities assessed by RT-qPCR and fold-changes in RNA were normalized to HPRT1 levels; mean, s.e.m., and individual data points shown for technical triplicates of three biological replicates (n=9). (H), Schematic of dCas12a base editor (BE) constructs with varying NLS and linker compositions. (I), Cytosine to thymine (C-to-T) conversion efficiencies directed by dCas12a-BEs across eight different target sites, assessed by targeted deep sequencing. The mean percent C-to-T editing of three biological replicates was examined within a −5 to +25 window; all Cs in this window are highlighted in green for each target site; the position of the C within the target site is indicated below the heat map. SEQ ID NOs. 531-538, in order of appearance. (J), Aggregate summary of C-to-T editing efficiency within the 20 nt target site spacer sequence with dCas12a-BEs across all eight target sites. (K), Summary of fold-change in the percent of sequencing reads that contain insertion or deletion mutations (indels) for each dCas12a-BE experiment (eight target sites and three replicates), normalized relative to the percent indels observed in the control sample (LbBE1.4 and an empty U6 plasmid). VPR, synthetic VP64-p65-Rta activation domain (Chavez et al., Nat Methods., 2015, 12:326-8); NLS(sv), SV40 nuclear localization signal; NLS(nuc), nucleoplasmin nuclear localization signal; rAPO1, rat APOBEC1; gs, glycine-serine peptide linker; UGI, uracil glycosylase inhibitor.

Figure 19A:
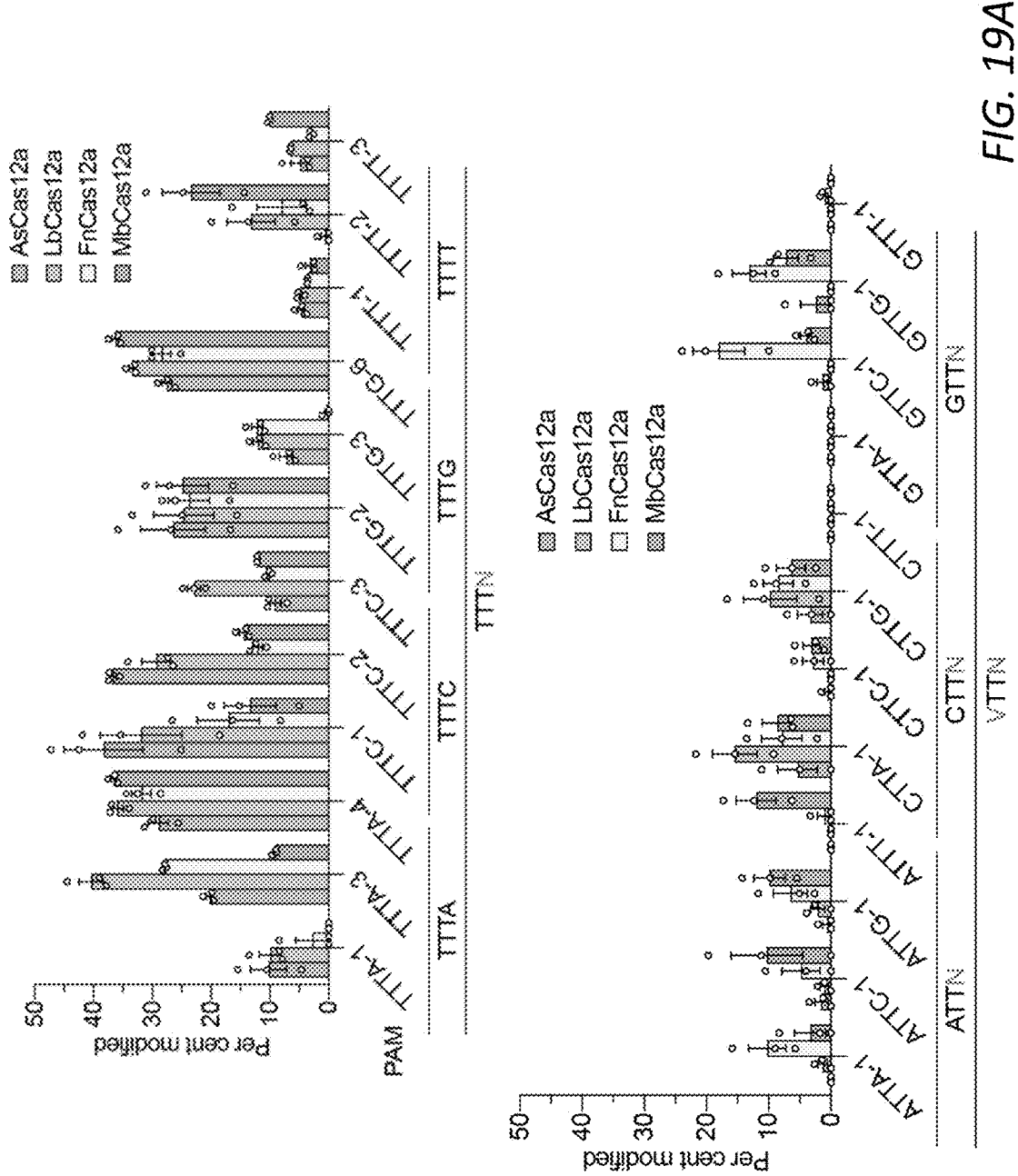
Figure 19B:
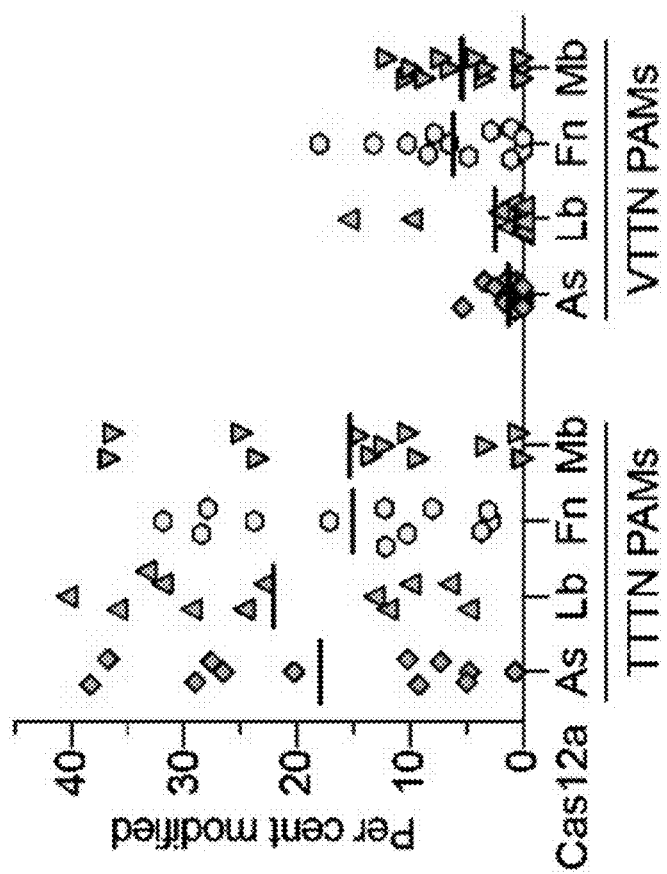

FIGS. 19A-19B: Activities of Cas12a orthologs in human cells. (A), Activities of Cas12a orthologs targeted to endogenous sites in human cells bearing TTTN or VTTN PAMs. Percent modification assessed by T7E1 assay; mean, s.e.m., and individual data points shown for n=3. (B), Summary of the activities of Cas12a orthologs against 24 sites with NTTN PAM sequences (mean activities from data in panel a shown).

FIGS. 20A-20D: Engineering and characterization of AsCas12a variants. (A), Schematic and structural representations of Cas12a paired with a crRNA, and interacting with a putative target site encoding a prototypical TTTV PAM. In structural representations, amino acid residues proximal to PAM DNA bases are highlighted in green; images generated from PDBID:5B43 (Yamano et al., Cell. 2016 May 5; 165(4):949-62) visualized in PyMOL (v 1.8.6.0). (B, C), Activities of AsCas12a variants bearing single amino acid substitutions when tested against endogenous sites in human cells bearing canonical (panel B) or non-canonical (panel C) PAMs. Percent modification assessed by T7E1 assay; mean, s.e.m., and individual data points shown for n=3. (D), Fold-change in the mean activities of AsCas12a variants compared to wild-type AsCas12a on sites bearing canonical and non-canonical PAMs. Fold-change compared to activity with wild-type AsCas12a calculated from the percent modification data from FIG. 15A.

FIGS. 21A-21H: Optimization of an in vitro PAM characterization assay. (A), Representative SDS-PAGE gel images of purified Cas12a orthologs and AsCas12a variants; s.m, size marker in kDa. (B), Schematic of linearized plasmid bearing combinations of PAMs and spacers used as substrates for in vitro cleavage reactions. SEQ ID NOs. 539-540. (C), Time-course in vitro cleavage reaction profiles of wild-type AsCas12a (left panel) and the E174R/S542R/

K548R variant (right panel) on the substrates illustrated in panel b. Curves were fit using a one phase exponential decay equation; error bars represent s.e.m for n=3. (D), Schematic of the PAM determination assay (PAMDA). Linearized plasmid libraries harboring 8 randomized nucleotides in place of the PAM were subjected to in vitro cleavage reactions with Cas12a ribonucleoprotein (RNP) complexes. Aliquots of the reaction were stopped at various time-points, and subsequently used as template for PCR. Substrates harboring incompletely targetable PAMs were amplified and sequenced to enable quantification of the rate of PAM depletion from the starting library over time. (E), Correlation between PAMDA rate constants (k) across replicates of wild-type AsCas12a (left panel) and the E174R/S542R/K548R variant (right panel). (F), Correlation between rate constants from mean PAMDA values across two spacer sequences. (G), Histogram of PAMDA rate constants for wild-type and E174R/S542R/K548R AsCas12a. (H), Depletion profiles of substrates encoding the indicated PAM sequences over time. Curves were fit using a one phase exponential decay equation; error bars represent s.e.m for n=4.

Figure 21A:
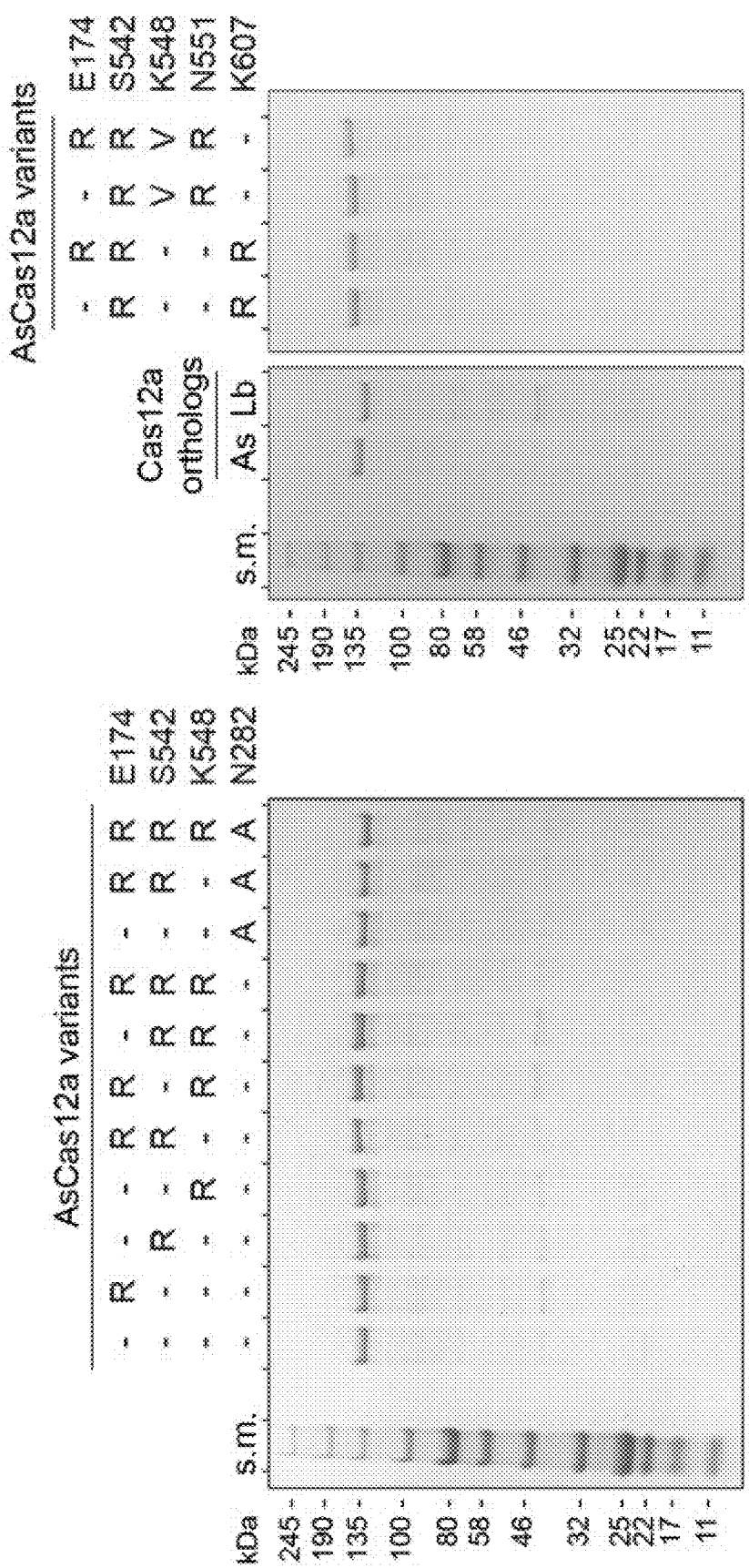
Figure 21B:
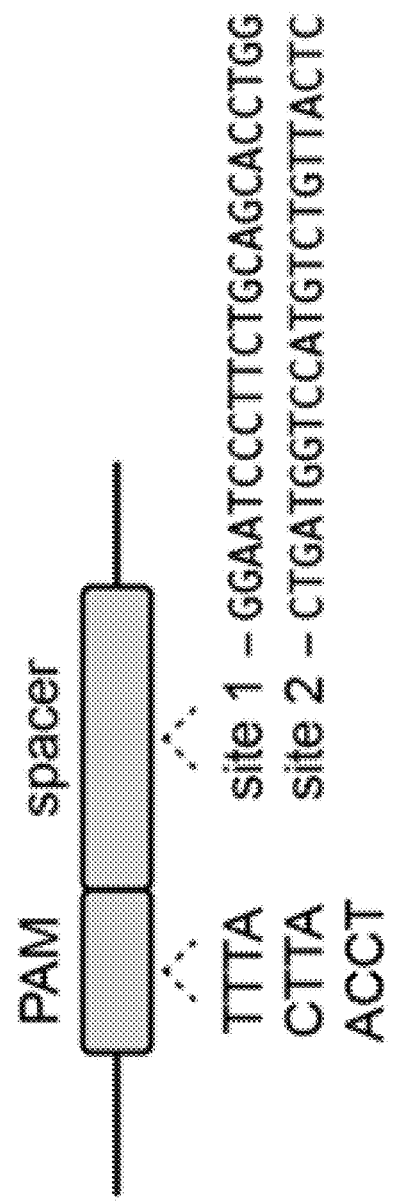
Figure 21C:
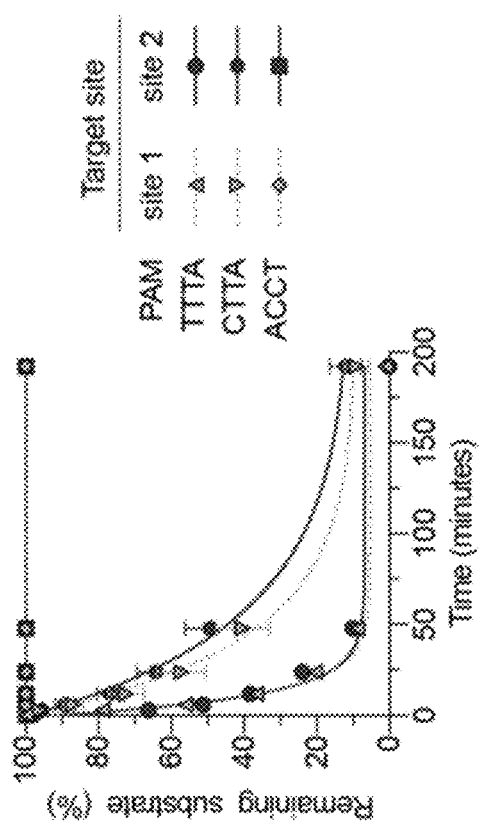
Figure 21C:
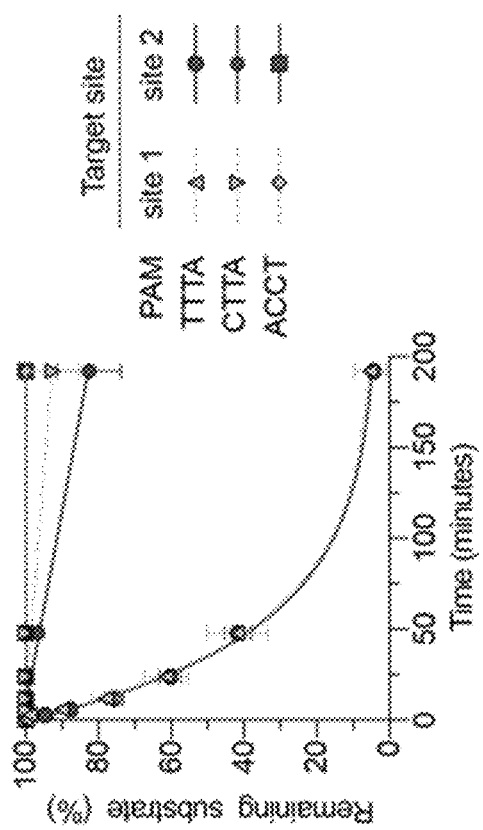
Figure 21D:
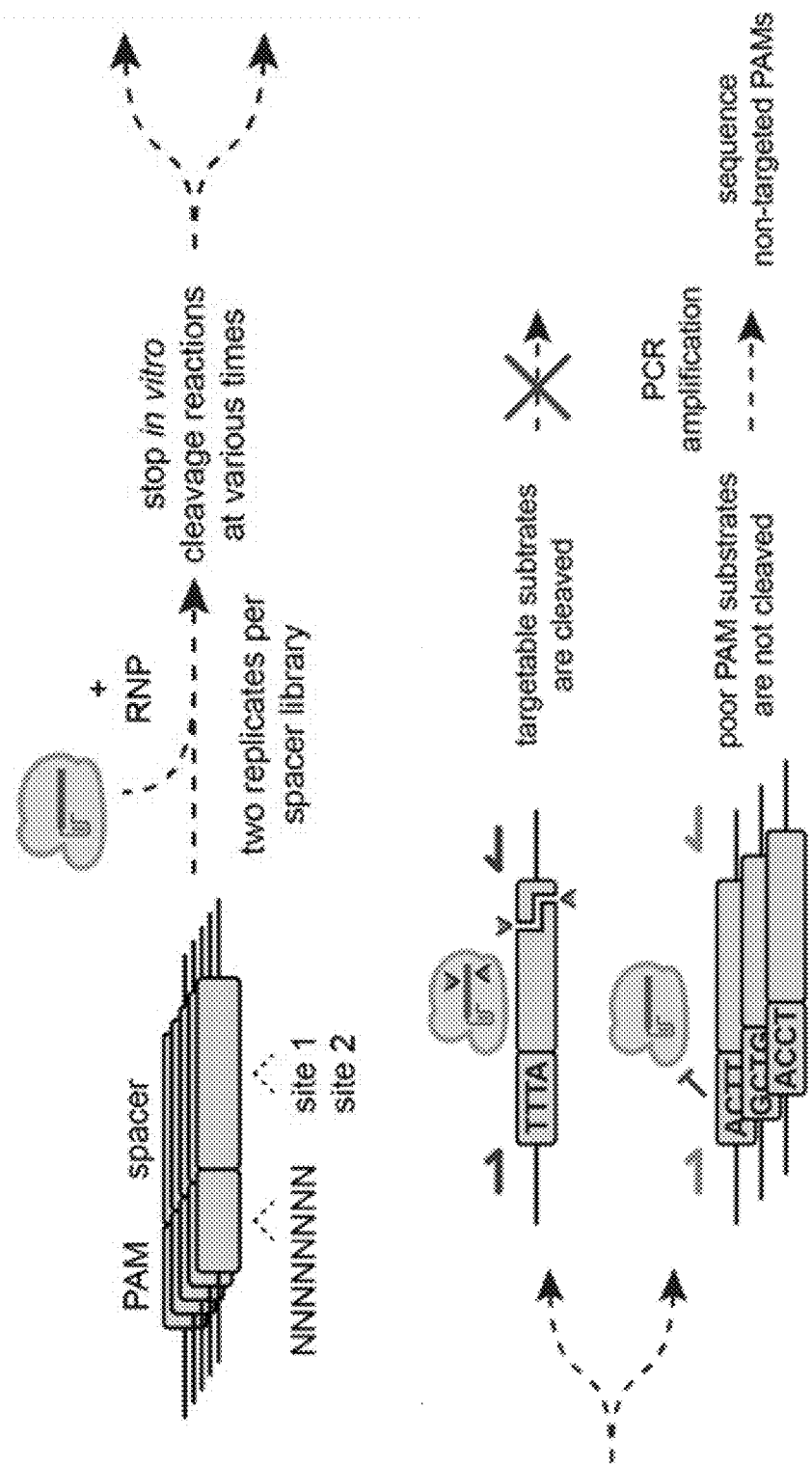
Figure 21E:
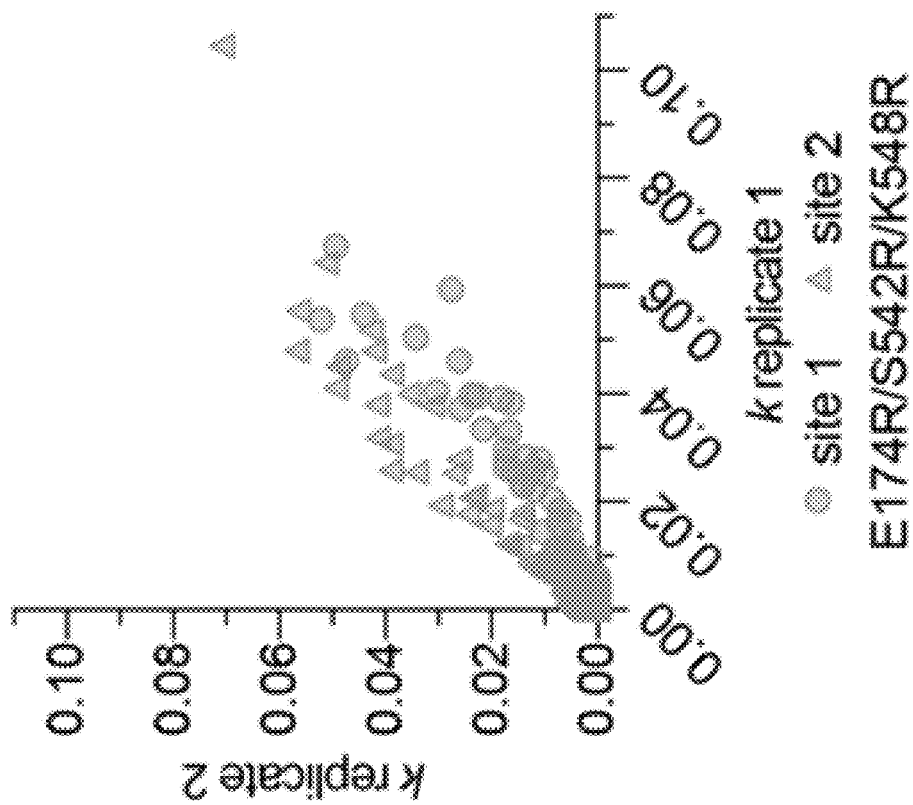
Figure 21E:
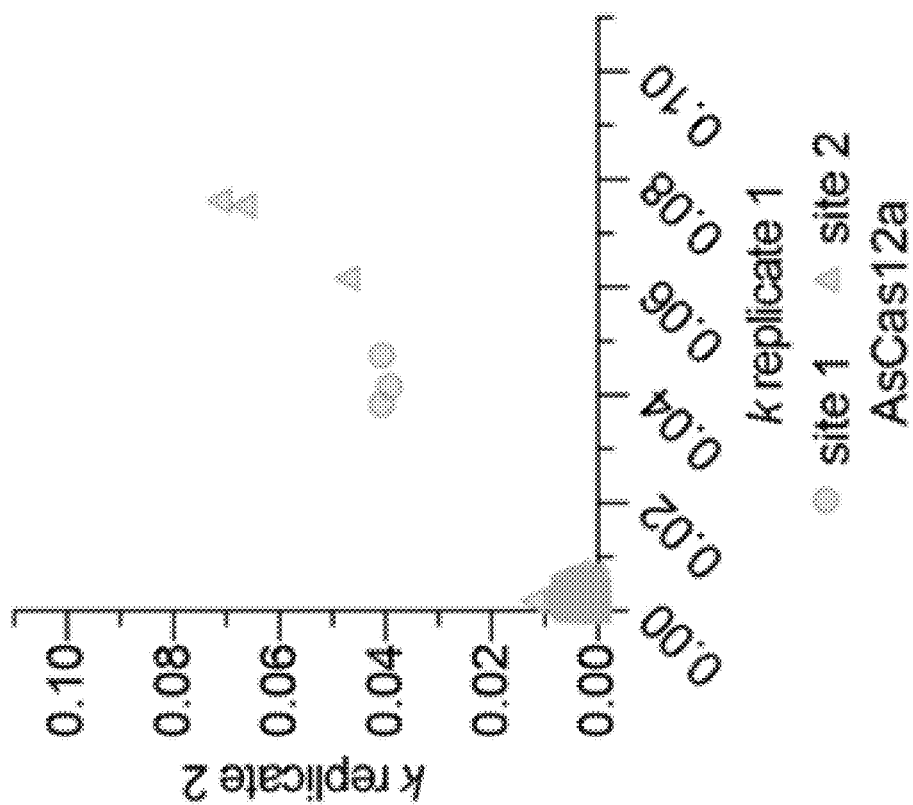
Figure 21H:
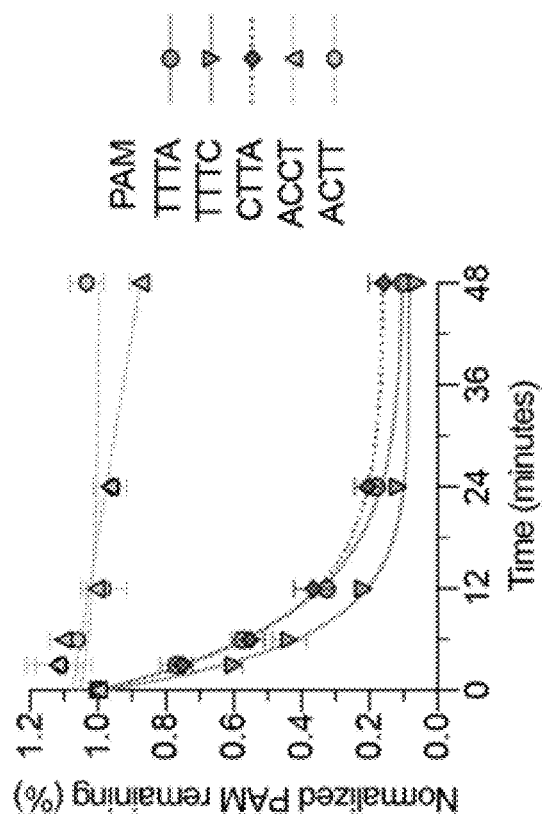
Figure 21H:
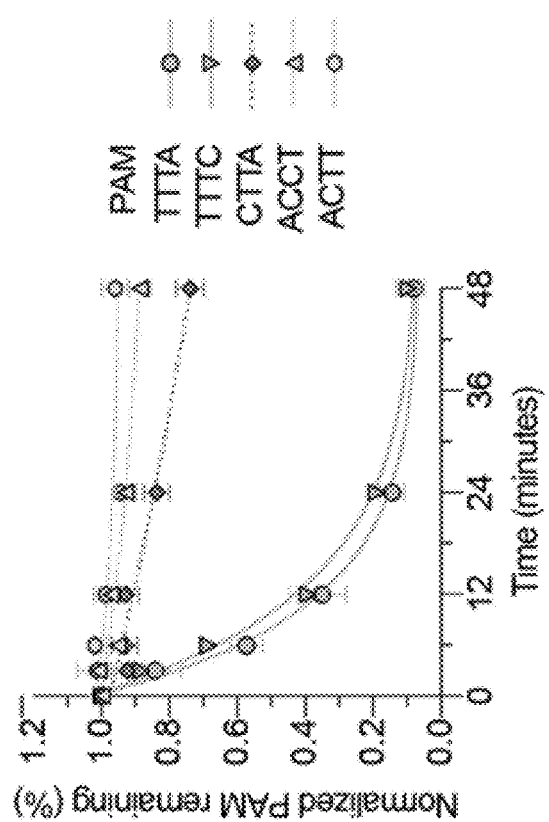
Figure 22A:
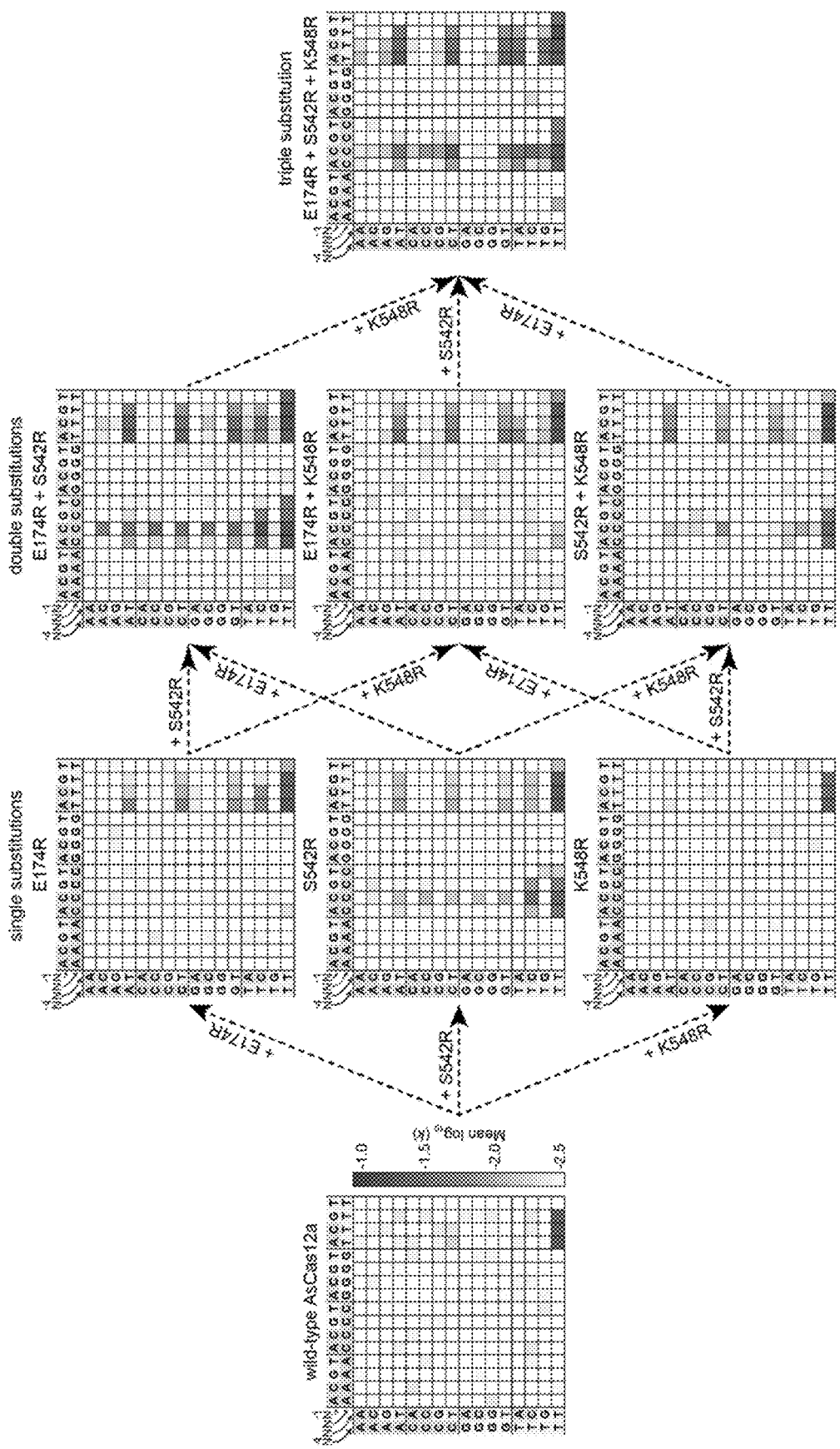
Figure 22B:
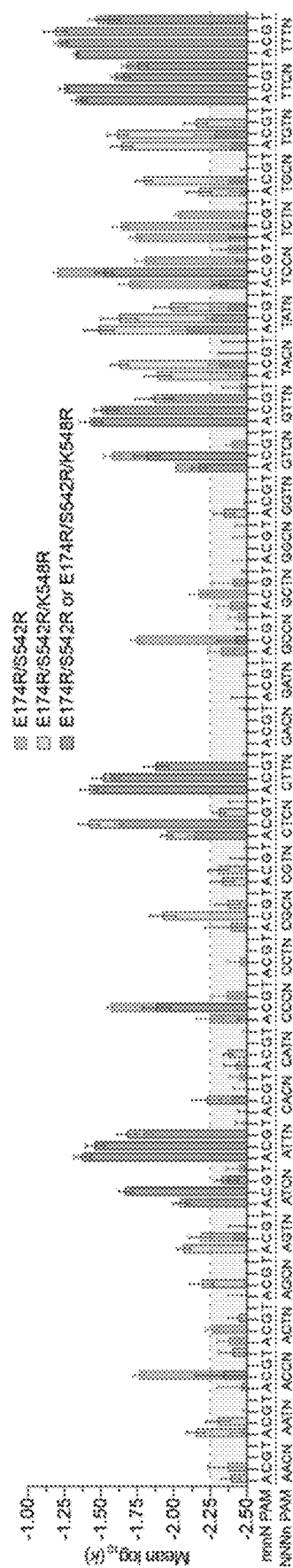
Figure 22C:
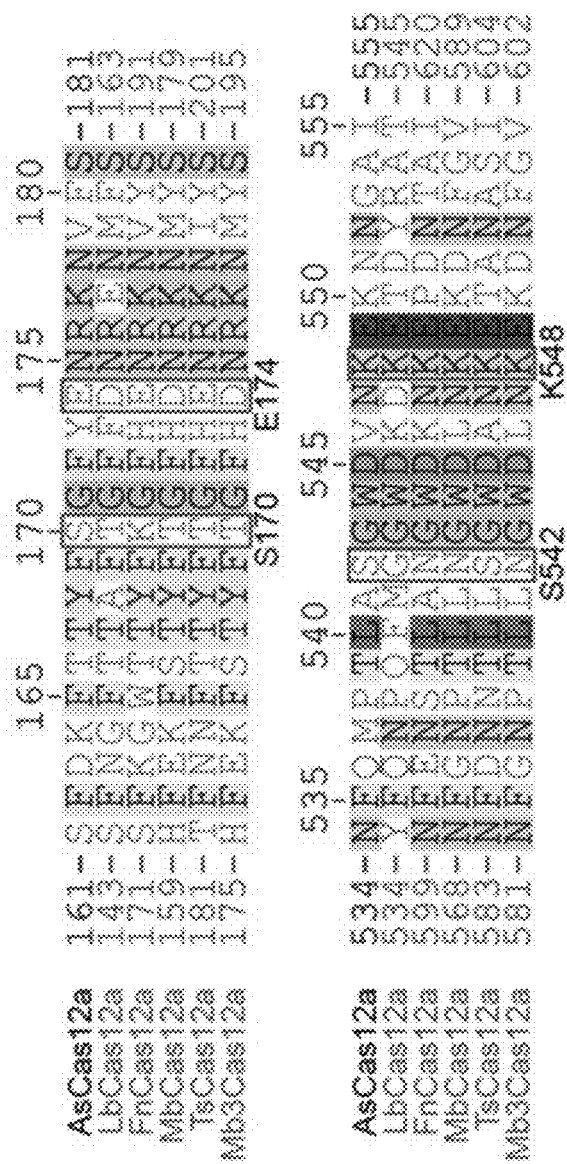

FIGS. 22A-22C: Deconvolution of the PAM specificities of eAsCas12a derivative variants. (A), PAM preference profiles for wild-type AsCas12a, the E174R/S542R/K548R variant, and all intermediate single and double substitution variants, assessed by PAMDA. The $\log_{10}$ rate constants (k) are the mean of four replicates, two each against two distinct spacer sequences (see FIG. 21A-21H). (B), Comparison of the PAM preference profiles of the E174R/S542R and E174R/S542R/K548R variants across all 128 NNYN PAMs. (C), Alignment of Cas12a orthologs with residues important for altering PAM preference in this study highlighted with a red border. (SEQ ID NOs.:541-552).

FIGS. 23A-23I: Assessment of the improved targeting range of eAsCas12a. (A, B), Comparison of the activities of E174R/S542R and E174R/S542R/K548R AsCas12a on endogenous sites in human cells bearing non-canonical VTTN and TTCN PAMs (panel a), or TATN PAMs (panel b). (C), Activity of wild-type AsCas12a on sites with TTCN or TATN PAMs. (D, E), Activity of the E174R/S542R/K548R variant against sites with TGTV PAMs (panel D) or additional sites with various non-canonical PAMs (panel E). (F), Correlation between the PAMDA rate constant and mean modification in human cells for the PAMs tested in panels A-E. The grey shaded box indicates an arbitrary PAMDA rate constant threshold of 0.005 (or $10^{-2.25}$) roughly predictive of activity in human cells. (G), Comparison of the activities of wild-type, E174R/S542R, and E174R/S542R/K548R AsCas12a on sites with TTTN PAMs. (H), Summary of the mean activities of AsCas12a, the E174R/S542R variant, and eAsCas12a across 26 sites encoding TTTN PAMs (see also FIG. 23G). (I), Summary of targetable PAMs for eAsCas12a. Tiers of PAMs: 1, high confidence PAM (mean k>0.01, mean percent modified>13%); 2, medium confidence PAM (mean k>0.005, mean percent modified>10%); 3, low activity or discrepant PAM (mean percent modified<10% or discrepancy between mean k and percent modified). For all panels, percent modification assessed by T7E1 assay; mean, s.e.m., and individual data points shown for n≥3.

FIGS. 24A-24E: Activities of enhanced Cas12a PAM variants. (A-C), Comparison of the endogenous site modification activities of AsCas12a variants on sites with TTTN PAMs (panel A), TATN PAMs (panel B), and TYCN PAMs (panel C). Percent modification assessed by T7E1 assay; mean, s.e.m., and individual data points shown for n=3. (D), PAM preference profiles for original and enhanced RVR and RR AsCas12a variants assessed by PAMDA. The $\log_{10}$ rate constants are the mean of four replicates, two each against two distinct spacer sequences (see FIG. 21A-21H). (E), Comparison of the PAM preference profiles of the RVR/eRVR (top panel) and RR/eRR (bottom panel) variants across all 128 NNYN PAMs. AsCas12a variants encode the following substitutions: eAsCas12a, E174R/S542R/K548R; RVR, S542R/K548V/N552R; eRVR, E174R/S542R/K548V/N552R; RR, S542R/K607R; eRR, E174R/S542R/K607R.

FIGS. 25A-25K: Assessment and improvement of AsCas12a and eAsCas12a specificities. (A), Schematic of the GUIDE-seq method. (B, C), Comparison of the on-target mutagenesis (panel b) and GUIDE-seq dsODN tag integration (panel c) activities of AsCas12a nucleases for GUIDE-seq samples. Percent modification and tag integration assessed by T7E1 and RFLP assays, respectively; mean, s.e.m., and individual data points shown for n=3. (D), Ratio of GUIDE-seq dsODN tag integration to overall mutagenesis for AsCas12a nucleases; data from panels b and c. (E), Activities of wild-type AsCas12a or variants bearing single substitutions when using crRNAs that perfectly match the on-target site, or that encode single nucleotide mismatches. Percent modification assessed by T7E1 assay; mean, s.e.m., and individual data points shown for n=3. SEQ ID NOs. 553-554. (F), Activities of eAsCas12a variants bearing single amino acid substitutions, assessed as in panel e. Percent modification assessed by T7E1 assay; mean, s.e.m., and individual data points shown for n=3. (G), PAM preference profiles of eAsCas12a and eAsCas12a-HF1 assessed by PAMDA. The $\log_{10}$ rate constants are the mean of four replicates, two each against two distinct spacer sequences (see FIG. 21A-21H). (H), Comparison of the PAM preference profiles of eAsCas12a and eAsCas12a-HF1 across all 128 NNYN PAMs. (I, J), Assessment of the on-target activities of AsCas12a, eAsCas12a, and eAsCas12a-HF1 on target sites harboring TTTN PAMs (panel i) or non-canonical VTTV, TATV, and TTCV PAMs (panel j). Percent modification assessed by T7E1 assay; mean, s.e.m., and individual data points shown for n=3. (K), Time-course in vitro cleavage reactions of Cas12a orthologs and variants on the PAMDA site 1 substrate, conducted at 37, 32, and 25° C. (left, middle, and right panels, respectively). Curves were fit using a one phase exponential decay equation; error bars represent s.e.m for n=3. AsCas12a variants encode the following substitutions: eAsCas12a, E174R/S542R/K548R; eAsCas12a-HF1, E174R/N282A/S542R/K548R.

FIGS. 26A-26F: Gene activation with Cas12a fusions. (A), Schematic of VPR activation domain fusions to DNase-inactive Cas12a (dCas12a) orthologs and variants. (B), Illustration of the sequence window encompassing roughly 700 bp upstream of the VEGFA transcription start site (TSS), with target sites for SpCas9 and Cas12a indicated. (C, D), Comparison of the activities of dCas12a-VPR and dSpCas9-VPR architectures (using pairs of crRNAs or sgRNAs, respectively) with crRNAs were targeted to sites with TTTV PAMs (panel C) or TTCV PAMs (panel D) in the VEGFA promoter. Activities assessed via changes in VEGFA production compared to a control transfection containing deAs-VPR(1.3) and a mock crRNA plasmid; mean, s.e.m., and individual data points shown for n=4. (E, F), VEGFA activation by dCas12a-VPR(1.1) or dSpCas9-VPR fusion proteins using pools of three or two (panels e and f, respectively) crRNAs or sgRNAs across a range of sites with canonical and non-canonical PAMs for the dCas12a-VPR fusions; mean, s.e.m., and individual data points shown for n≥3. VPR, synthetic VP64-p65-Rta activation domain (Chavez et al., Nat Methods., 2015, 12:326-8); NLS(sv), SV40 nuclear localization signal; NLS(nuc), nucleoplasmin nuclear localization signal; HA, Human influenza hemagglutinin tag; gs, glycine-serine peptide linker.

FIGS. 27A-D: Base editing with Cas12a. (A), Fold-change in C-to-T editing compared to the untreated control across all Cs in the 20 nt spacers of 8 target sites. (B), Influence of identity of the preceding (5') base on the conversion of cytosine to thymine (C-to-T). The C-to-T editing efficiency across eight target sites (see FIG. 18I) is plotted for all Cs in the window encompassing the −14 to +30 region of each target site (an additional 10 nt upstream of the 4 nt PAM and 10 nt downstream of the 20 nt spacer sequence). (C), Analysis of edit purity at six selected cytosines across five target sites. The fraction of each non-C identity is plotted over the sum of all non-C occurrences at that position for each BE construct. (D), Insertion or deletion mutation (indel) activities of Cas12a-BEs were calculated for each BE/crRNA pair by determining the percentage of alleles encoding an indel within the −14 to +30 window, not counting alleles with substitutions only.

Figure 28A:
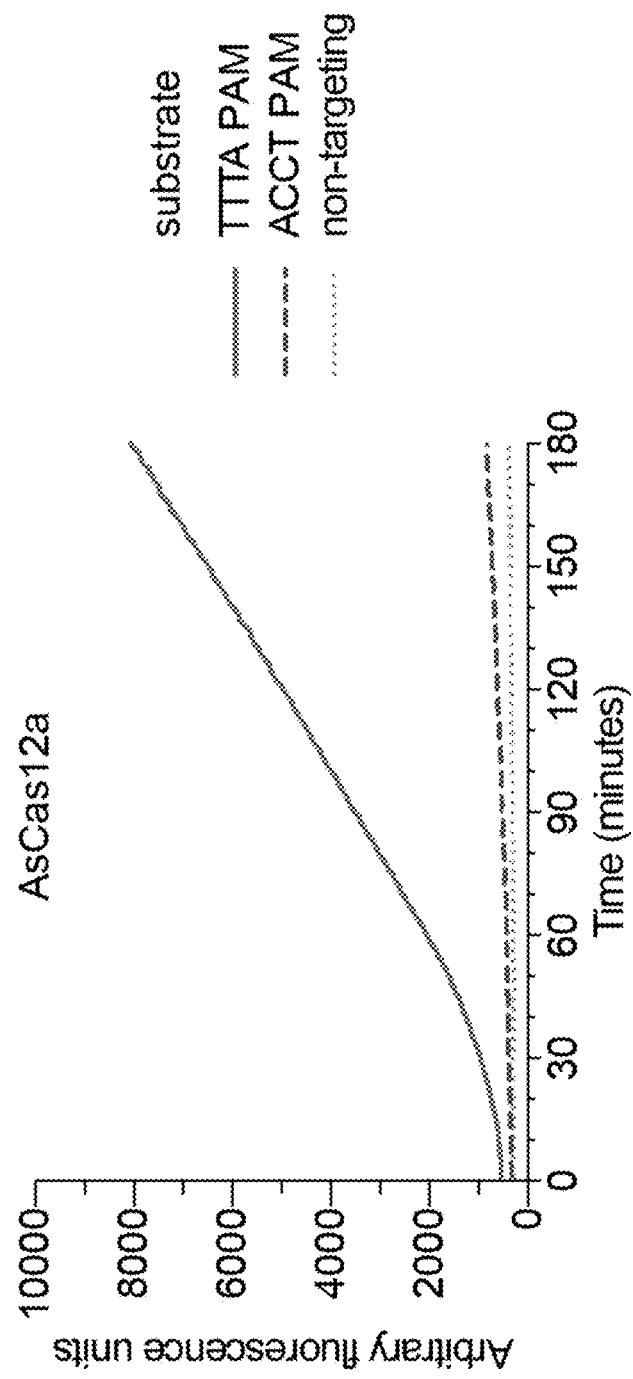
Figure 28B:
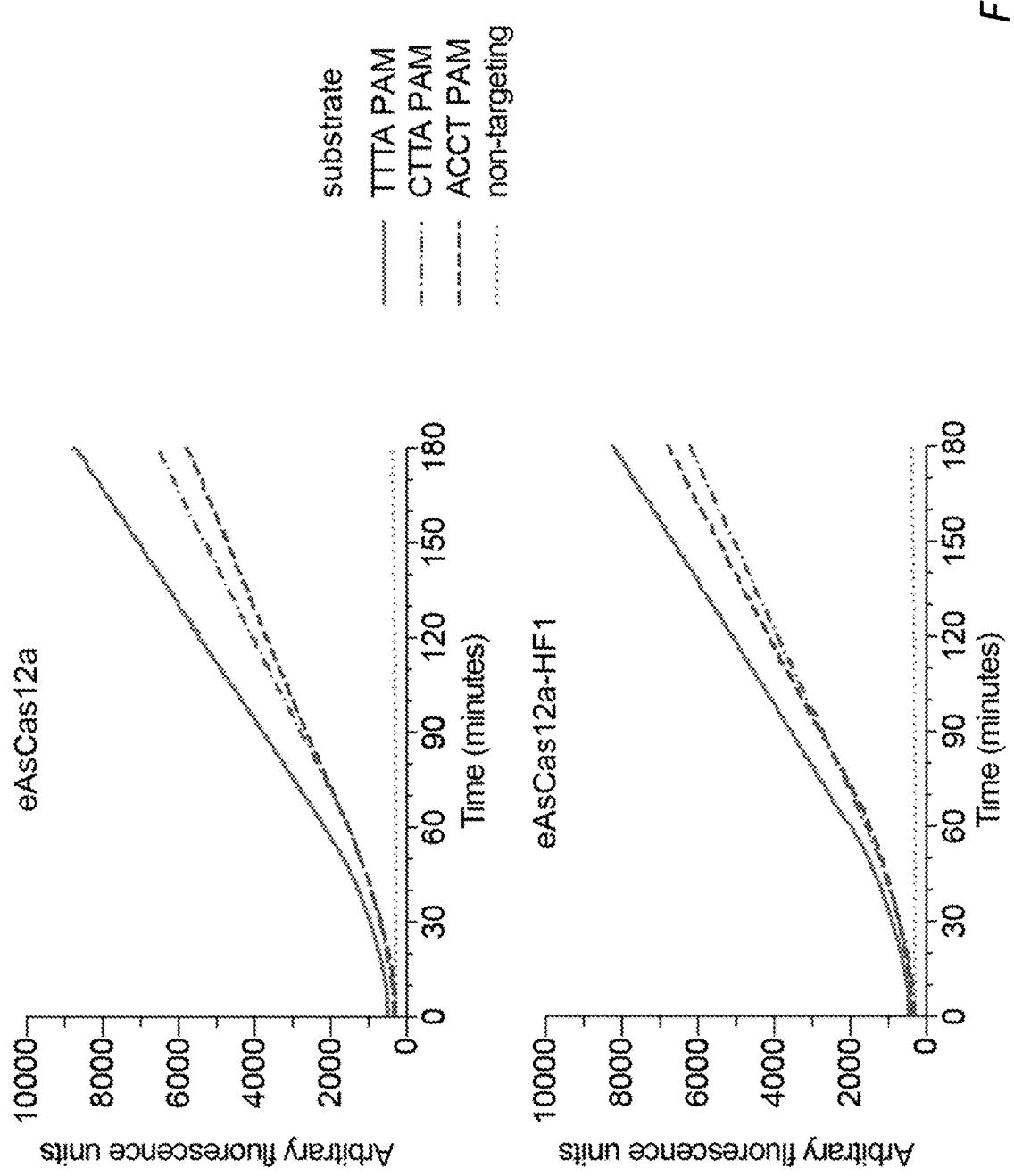

FIGS. 28A-28B: DNA detection with AsCas12 and eAsCas12a. (A), Time-course DNA-detection with wild-type AsCas12a via DNase-induced reporter molecule fluorescence. Activities assessed when programmed with different active and inactive substrates. (B), DNA-detection activities of eAsCas12a and eAsCas12a-HF1 (top and bottom panels, respectively) over time. Activities assessed when programmed with substrates bearing canonical PAM, non-canonical PAM, and non-targetable sequences. Measurements of fluorescence were taken every 60 seconds for three hours with with $\lambda_{ex}$=485 nm and $\lambda_{em}$=528 nm.

DETAILED DESCRIPTION

Cpf1 enzymes characterized to date recognize T-rich PAMs that are positioned 5' to the spacer sequence (FIG. 1). Both AsCpf1 and LbCpf1 have been reported to recognize a PAM of the form TTTN but strongly prefer TTTV (where V=A, C, or G). A TTTV PAM sequence is expected to occur roughly once in every 43 bases of random DNA, potentially limiting the targeting range (and utility) of AsCpf1 and LbCpf1 for genome editing. The targeting range of engineered nucleases is particularly important for applications that require precise targeting or placement of the DNA double-strand break (DSB), including but not limited to: 1) generation of insertion or deletion mutations (indels) in small genetic elements such as: short open reading frames (ORFs), transcription factor binding sites, micropeptides, miRNAs, etc.; 2) homology-directed repair (HDR), where proximity of the DSB to the desired sequence change can dramatically influence efficiency of repair, 3) allele-specific editing achieved by placing the SNP variation within the protospacer or PAM; 4) generating genomic deletions of defined length or translocations by introduction of pairs of DSBs; 5) performing saturation mutagenesis of genes or gene regulatory elements; and 6) use of engineered RNA-guided nucleases or nickases fused to DNA modifying enzymes for performing base editing. Given these clear advantages of an increased targeting range, we sought to alter or relax the PAM specificities of AsCpf1 and LbCpf1 to improve their capabilities to recognize a more diverse range of DNA sequences.

Herein we demonstrate that substitutions at or near PAM-proximal amino acid residues can alter the PAM preferences of both AsCpf1 and LbCpf1, generating variants of these nucleases that can recognize non-cognate PAM sequences, thereby increasing the targeting range of this platform. These engineered CRISPR-Cas12a variants have dramatically improved properties, exhibiting simultaneously broadened targeting range and enhanced targeting activity. To the best of our knowledge, this is the first description of amino acid substitutions that can improve the on-target activity of a CRISPR nuclease. The enhanced properties of eAsCas12a offer major advantages over currently available Cas12a orthologs and variants, exhibiting greater than an 8-fold improvement in targeting range, while also enabling more potent multiplex editing, gene activation, DNA detection, and base editing applications at efficiencies previously unachievable with wild-type AsCas12a. The development of eAsCas12a base editor technologies expands the scope of targetable bases in the genome and does so with little evidence of collateral indel mutations. Importantly, the targeting range of eAsCas12a is comparable to previously described engineered SpCas9 nucleases, providing greater target site density for Cas12a applications that require broadened PAM recognition (eg., for targeting within defined or small genomic windows, multiplex genome or epigenome editing, focused coding or non-coding crRNA-tiling screens, or when conceiving of complex combinatorial library screens). The improved properties of the variants described herein, including eAsCas12a, make them some of the most broadly targetable and active Cas12a enzymes described to-date.

Cpf1

Clustered, regularly interspaced, short palindromic repeat (CRISPR) systems encode RNA-guided endonucleases that are essential for bacterial adaptive immunity (Wright et al., Cell 164, 29-44 (2016)). CRISPR-associated (Cas) nucleases can be readily programmed to cleave target DNA sequences for genome editing in various organisms[2-5]. One class of these nucleases, referred to as Cas9 proteins, complex with two short RNAs: a crRNA and a trans-activating crRNA (tracrRNA)[7, 8]. The most commonly used Cas9 ortholog, SpCas9, uses a crRNA that has 20 nucleotides (nt) at its 5' end that are complementary to the "protospacer" region of the target DNA site. Efficient cleavage also requires that SpCas9 recognizes a protospacer adjacent motif (PAM). The crRNA and tracrRNA are usually combined into a single ~100-nt guide RNA (gRNA)[7, 9-11] that directs the DNA cleavage activity of SpCas9. The genome-wide specificities of SpCas9 nucleases paired with different gRNAs have been characterized using many different approaches[12-15]. SpCas9 variants with substantially improved genome-wide specificities have also been engineered[16, 17].

Recently, a Cas protein named Cpf1 has been identified that can also be programmed to cleave target DNA sequences[1, 18-20]. Unlike SpCas9, Cpf1 requires only a single 42-nt crRNA, which has 23 nt at its 3' end that are complementary to the protospacer of the target DNA sequence[1]. Furthermore, whereas SpCas9 recognizes an NGG PAM sequence that is 3' of the protospacer, AsCpf1 and LbCp1 recognize TTTN PAMs that are positioned 5' of the protospacer[1]. Early experiments with AsCpf1 and LbCpf1 showed that these nucleases can be programmed to edit target sites in human cells[1] but they were tested on only a small number of sites. Recent studies have demonstrated that both AsCpf1 and LbCpf1 possess robust on-target activities and high genome-wide specificities in human cells (see, e.g., Kleinstiver & Tsai et al., Nature Biotechnology 2016; and Kim et al., Nat Biotechnol. 2016). See also US20160208243.

The present findings provide support for engineered AsCpf1 and LbCpf1 variants, referred to collectively herein as "variants" or "the variants".

All of the variants described herein can be rapidly incorporated into existing and widely used vectors, e.g., by simple site-directed mutagenesis.

Thus, provided herein are AsCpf1 variants. The AsCpf1 wild type protein sequence is as follows:

AsCpf1-Type V CRISPR-associated protein Cpf1 [*Acidaminococ-cus* sp. BV3L6],
NCBI Reference Sequence: WP_021736722.1

(SEQ ID NO: 2)

```
   1  MTQFEGFTNL  YQVSKTLRFE  LIPQGKTLKH  IQEQGFIEED  KARNDHYKEL  KPIIDRIYKT

61  YADQCLQLVQ  LDWENLSAAI  DSYRKEKTEE  TRNALIEEQA  TYRNAIHDYF  IGRTDNLTDA

121  INKRHAEIYK  GLFKAELFNG  KVLKQLGTVT  TTEHENALLR  SFDKFTTYFS  GFYENRKNVF

181  SAEDISTAIP  HRIVQDNFPK  FKENCHIFTR  LITAVPSLRE  HFENVKKAIG  IFVSTSIEEV

241  FSFPFYNQLL  TQTQIDLYNQ  LLGGISREAG  TEKIKGLNEV  LNLAIQKNDE  TAHIIASLPH

301  RFIPLFKQIL  SDRNTLSFIL  EEFKSDEEVI  QSFCKYKTLL  RNENVLETAE  ALFNELNSID

361  LTHIFISHKK  LETISSALCD  HWDTLRNALY  ERRISELTGK  ITKSAKEKVQ  RSLKHEDINL

421  QEIISAAGKE  LSEAFKQKTS  EILSHAHAAL  DQPLPTTLKK  QEEKEILKSQ  LDSLLGLYHL

481  LDWFAVDESN  EVDPEFSARL  TGIKLEMEPS  LSFYNKARNY  ATKKPYSVEK  FKLNFQMPTL

541  ASGWDVNKEK  NNGAILFVKN  GLYYLGIMPK  QKGRYKALSF  EPTEKTSEGF  DKMYYDYFPD

601  AAKMIPKCST  QLKAVTAHFQ  THTTPILLSN  NFIEPLEITK  EIYDLNNPEK  EPKKFQTAYA

661  KKTGDQKGYR  EALCKWIDFT  RDFLSKYTKT  TSIDLSSLRP  SSQYKDLGEY  YAELNPLLYH

721  ISFQRIAEKE  IMDAVETGKL  YLFQIYNKDF  AKGHHGKPNL  HTLYWTGLFS  PENLAKTSIK

781  LNGQAELFYR  PKSRMKRMAH  RLGEKMLNKK  LKDQKTPIPD  TLYQELYDYV  NHRLSHDLSD

841  EARALLPNVI  TKEVSHEIIK  DRRFTSDKFF  FHVPITLNYQ  AANSPSKFNQ  RVNAYLKEHP

901  ETPIIGIDRG  ERNLIYITVI  DSTGKILEQR  SLNTIQQFDY  QKKLDNREKE  RVAARQAWSV

961  VGTIKDLKQG  YLSQVIHEIV  DLMIHYQAVV  VLENLNFGFK  SKRTGIAEKA  VYQQFEKMLI

1021  DKLNCLVLKD  YPAEKVGGVL  NPYQLTDQFT  SFAKMGTQSG  FLFYVPAPYT  SKIDPLTGFV

1081  DPFVWKTIKN  HESRKHFLEG  FDFLHYDVKT  GDFILHFKMN  RNLSFQRGLP  GFMPAWDIVF

1141  EKNETQFDAK  GTPFIAGKRI  VPVIENHRFT  GRYRDLYPAN  ELIALLEEKG  IVFRDGSNIL

1201  PKLLENDDSH  AIDTMVALIR  SVLQMRNSNA  ATGEDYINSP  VRDLNGVCFD  SRFQNPEWPM

1261  DADANGAYHI  ALKGQLLLNH  LKESKDLKLQ  NGISNQDWLA  YIQELRN
```

The AsCpf1 variants described herein can include the amino acid sequence of SEQ ID NO:2, e.g., at least comprising amino acids 1-1307 of SEQ ID NO:2, with mutations (i.e., replacement of the native amino acid with a different amino acid, e.g., alanine, glycine, or serine (except where the native amino acid is serine)), at one or more positions in Table 1, e.g., at the following positions: T167, S170, E174, T539, K548, N551, N552, M604, and/or K607 of SEQ ID NO:2 (or at positions analogous thereto, e.g., of SEQ ID NO:9). In some embodiments, the AsCpf1 variants are at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA).

Also provided herein are LbCpf1 variants. The LbCpf1 wild type protein sequence is as follows:

LbCpf1-TypeVCRISPR-associated protein Cpf1 [*Lachnospiraceae bacterium* ND2006], GenBank Acc No. WP_051666128.1

(SEQ ID NO: 3)

```
   1  MLKNVGIDRL  DVEKGRKNMS  KLEKFTNCYS  LSKTLRFKAI  PVGKTQENID  NKRLLVEDEK

61  RAEDYKGVKK  LLDRYYLSFI  NDVLHSIKLK  NLNNYISLFR  KKTRTEKENK  ELENLEINLR
```

```
121 KEIAKAFKGN EGYKSLFKKD IIETILPEFL DDKDEIALVN SFNGFTTAFT GFFDNRENMF

181 SEEAKSTSIA FRCINENLTR YISNMDIFEK VDAIFDKHEV QEIKEKILNS DYDVEDFFEG

241 EFFNFVLTQE GIDVYNAIIG GFVTESGEKI KGLNEYINLY NQKTKQKLPK FKPLYKQVLS

301 DRESLSFYGE GYTSDEEVLE VFRNTLNKNS EIFSSIKKLE KLFKNFDEYS SAGIFVKNGP

361 AISTISKDIF GEWNVIRDKW NAEYDDIHLK KKAVVTEKYE DDRRKSFKKI GSFSLEQLQE

421 YADADLSVVE KLKEIIIQKV DEIYKVYGSS EKLFDADFVL EKSLKKNDAV VAIMKDLLDS

481 VKSFENYIKA FFGEGKETNR DESFYGDFVL AYDILLKVDH IYDAIRNYVT QKPYSKDKFK

541 LYFQNPQFMG GWDKDKETDY RATILRYGSK YYLAIMDKKY AKCLQKIDKD DVNGNYEKIN

601 YKLLPGPNKM LPKVFFSKKW MAYYNPSEDI QKIYKNGTFK KGDMFNLNDC HKLIDFFKDS

661 ISRYPKWSNA YDFNFSETEK YKDIAGFYRE VEEQGYKVSF ESASKKEVDK LVEEGKLYMF

721 QIYNKDFSDK SHGTPNLHTM YFKLLFDENN HGQIRLSGGA ELFMRRASLK KEELVVHPAN

781 SPIANKNPDN PKKTTTLSYD VYKDKRFSED QYELHIPIAI NKCPKNIFKI NTEVRVLLKH

841 DDNPYVIGID RGERNLLYIV VVDGKGNIVE QYSLNEIINN FNGIRIKTDY HSLLDKKEKE

901 RFEARQNWTS IENIKELKAG YISQVVHKIC ELVEKYDAVI ALEDLNSGFK NSRVKVEKQV

961 YQKFEKMLID KLNYMVDKKS NPCATGGALK GYQITNKFES FKSMSTQNGF IFYIPAWLTS

1021 KIDPSTGFVN LLKTKYTSIA DSKKFISSFD RIMYVPEEDL FEFALDYKNF SRTDADYIKK

1081 WKLYSYGNRI RIFRNPKKNN VFDWEEVCLT SAYKELFNKY GINYQQGDIR ALLCEQSDKA

1141 FYSSFMALMS LMLQMRNSIT GRTDVDFLIS PVKNSDGIFY DSRNYEAQEN AILPKNADAN

1201 GAYNIARKVL WAIGQFKKAE DEKLDKVKIA ISNKEWLEYA QTSVKH
```

The LbCpf1 variants described herein can include the amino acid sequence of SEQ ID NO:3, e.g., at least comprising amino acids 23-1246 of SEQ ID NO:3, with mutations (i.e., replacement of the native amino acid with a different amino acid, e.g., alanine, glycine, or serine), at one or more of the following positions: T152, D156, G532, and/or K538 of SEQ ID NO:11 (or at positions analogous thereto, e.g., T170, D174, G550, and/or K556 of SEQ ID NO:3); amino acids 19-1246 of SEQ ID NO:3 are identical to amino acids 1-1228 of SEQ ID NO:11 (amino acids 1-1228 of SEQ ID NO:11 are also referred to herein as LbCPF1 (−18)). In some embodiments, the LbCpf1 variants are at least 80%, e.g., at least 85%, 90%, or 95% identical to the amino acid sequence of SEQ ID NO:3, e.g., have differences at up to 5%, 10%, 15%, or 20% of the residues of SEQ ID NO:3 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA). The version of LbCpf1 used in the present working examples starts at the MSKLEK motif, omitting the first 18 amino acids boxed above as described in Zetsche et al. Cell 163, 759-771 (2015).

Also provided herein are FnCpf1 variants. The FnCpf1 wild type protein sequence is as follows:

```
FnCpf1 - type V CRISPR-associated protein Cpf1
[Francisella tularensis], GenBank Acc No.
WP_003040289.1
                                  (SEQ ID NO: 4)
   1  MSIYQEFVNK YSLSKTLRFE LIPQGKTLEN IKARGLILDD

EKRAKDYKKA KQIIDKYHQF

61  FIEEILSSVC ISEDLLQNYS DVYFKLKKSD DDNLQKDFKS

AKDTIKKQIS EYIKDSEKFK

121  NLFNQNLIDA KKGQESDLIL WLKQSKDNGI ELFKANSDIT

DIDEALEIIK SFKGWTTYFK

181  GFHENRKNVY SSNDIPTSII YRIVDDNLPK FLENKAKYES

LKDKAPEAIN YEQIKKDLAE

241  ELTFDIDYKT SEVNQRVFSL DEVFEIANFN NYLNQSGITK

FNTIIGGKFV NGENTKRKGI

301  NEYINLYSQQ INDKTLKKYK MSVLFKQILS DTESKSFVID

KLEDDSDVVT TMQSFYEQIA

361  AFKTVEEKSI KETLSLLFDD LKAQKLDLSK IYFKNDKSLT

DLSQQVFDDY SVIGTAVLEY

421  ITQQIAPKNL DNPSKKEQEL IAKKTEKAKY LSLETIKLAL

EEFNKHRDID KQCRFEEILA

481  NFAAIPMIFD EIAQNKDNLA QISIKYQNQG KKDLLQASAE

DDVKAIKDLL DQTNNLLHKL

541  KIFHISQSED KANILDKDEH FYLVFEECYF ELANIVPLYN

KIRNYITQKP YSDEKFKLNF

601  ENSTLANGWD KNKEPDNTAI LFIKDDKYYL GVMNKKNNKI

FDDKAIKENK GEGYKKIVYK
```

```
 661  LLPGANKMLP  KVFFSAKSIK  FYNPSEDILR  IRNHSTHTKN

GSPQKGYEKF  EFNIEDCRKF

721  IDFYKQSISK  HPEWKDFGFR  FSDTQRYNSI  DEFYREVENQ

GYKLTFENIS  ESYIDSVVNQ

781  GKLYLFQIYN  KDFSAYSKGR  PNLHTLYWKA  LFDERNLQDV

VYKLNGEAEL  FYRKQSIPKK

841  ITHPAKEAIA  NKNKDNPKKE  SVFEYDLIKD  KRFTEDKFFF

HCPITINFKS  SGANKFNDEI

901  NLLLKEKAND  VHILSIDRGE  RHLAYYTLVD  GKGNIIKQDT

FNIIGNDRMK  TNYHDKLAAI

961  EKDRDSARKD  WKKINNIKEM  KEGYLSQVVH  EIAKLVIEYN

AIVVFEDLNF  GFKRGRFKVE

1021  KQVYQKLEKM  LIEKLNYLVF  KDNEFDKTGG  VLRAYQLTAP

FETFKKMGKQ  TGIIYYVPAG

1081  FTSKICPVTG  FVNQLYPKYE  SVSKSQEFFS  KFDKICYNLD

KGYFEFSFDY  KNFGDKAAKG

1141  KWTIASFGSR  LINFRNSDKN  HNWDTREVYP  TKELEKLLKD

YSIEYGHGEC  IKAAICGESD

1201  KKFFAKLTSV  LNTILQMRNS  KTGTELDYLI  SPVADVNGNF

FDSRQAPKNM  PQDADANGAY

1261  HIGLKGLMLL  GRIKNNQEGK  KLNLVIKNEE  YFEFVQNRNN
```

The FnCpf1 variants described herein can include the amino acid sequence of SEQ ID NO:4, with mutations (i.e., replacement of the native amino acid with a different amino acid, e.g., alanine, glycine, or serine), at one or more of the following positions: K180, E184, N607, K613, D616, N617, and/or K671 of SEQ ID NO:4. In some embodiments, the FnCpf1 variants are at least 80%, e.g., at least 85%, 90%, or 95% identical to the amino acid sequence of SEQ ID NO:4, e.g., have differences at up to 5%, 10%, 15%, or 20% of the residues of SEQ ID NO:4 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the mutants have alanine in place of the wild type amino acid. In some embodiments, the mutants have any amino acid other than arginine or lysine (or the native amino acid).

In some embodiments, the Cpf1 variants also include one of the following mutations listed in Table A, which reduce or destroy the nuclease activity of the Cpf1:

TABLE A

| | AsCpf1 | LbCpf1 (+18) | LbCpf1 | FnCpf1 |
|---|---|---|---|---|
| Residues involved in DNA and RNA catalysis | | | | |
| DNA targeting | D908 | D850 | D832 | D917 |
| | E911 | E853 | E835 | E920 |
| | N913 | N855 | N837 | H922 |
| | Y916 | Y858 | Y840 | Y925 |
| | E993 | E943 | E925 | E1006 |
| | R1226 | R1156 | R1138 | R1218 |
| | S1228 | S1158 | S1140 | S1220 |
| | D1235 | D1166 | D1148 | D1227 |
| | D1263 | D1198 | D1180 | D1255 |
| RNA processing | H800 | H777 | H759 | H843 |
| | K809 | K786 | K768 | K852 |
| | K860 | K803 | K785 | K869 |
| | F864 | F807 | F789 | F873 |
| Mutations that turn Cpf1 into a nickase | | | | |
| | R1226A | R1156A | R1138A | R1218A |

See, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71. Note that "LbCpf1 (+18)" refers to the full sequence of amino acids 1-1246 of SEQ ID NO:3, while the LbCpf1 refers to the sequence of LbCpf1 in Zetsche et al., also shown herein as amino acids 1-1228 of SEQ ID NO:11 and amino acids 19-1246 of SEQ ID NO:3.

Thus, in some embodiments, for AsCpf1, catalytic activity-destroying mutations are made at D908 and E993, e.g., D908A and E993A; and for LbCpf1 catalytic activity-destroying mutations at D832 and E925, e.g., D832A and E925A.

In some embodiments, the Cpf1 variants also include mutations that increase specificity (i.e., induce substantially fewer off target effects), e.g., as described in WO2018/022634. For example, LbCpf1 variant proteins can include one or more mutations at one, two, three, four, five, six or all seven of the following positions: S202, N274, N278, K290, K367, K532, K609, K915, Q962, K963, K966, K1002 and/or S1003, e.g., S202A, N274A, N278A, K290A, K367A, K532A, K609A, K915A, Q962A, K963A, K966A, K1002A and/or S1003A. AsCpf1 variant proteins can include one or more mutations at one, two, three, four, five, or six of the following positions: N178, N278, N282, R301, T315, S376, N515, K523, K524, K603, K965, Q1013, and/or K1054, e.g., N178A, N278A, N282A, R301A, T315A, S376A, N515A, K523A, K524A, K603A, K965A, Q1013A, and/or K1054A. In some embodiments, the AsCpf1 variants comprise mutations at N282A, T315A, N515A, or N278A.

Also provided herein are isolated nucleic acids encoding the Cpf1 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variants described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110226530; US20110217739; US20110002889; US20100076057; US20110189776; US20110223638; US20130130248; US20150050699; US20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The variant proteins described herein can be used in place of or in addition to any of the Cas9 or Cpf1 proteins described in the foregoing references, or in combination with analogous mutations described therein, with a guide RNA appropriate for the selected Cpf1, i.e., with guide RNAs that target sequences other than the wild type PAM, e.g., that have PAM sequences according to the following Table B.

TABLE B

| Variant protein | Stronger PAM | Weaker PAM |
| --- | --- | --- |
| AsCpf1 S170R | TTTN, CTTN, GTTN | TATN, TCTN, TTAN, TTCN, TTGN |
| AsCpf1 E174R | TTTN, CTTN, GTN, TTCN | TATN, TCTN, TTAN, TTGN |
| AsCpf1 S542K | TTTN, GTTN, TTCN | CTTN, TCTN, TTAN |
| AsCpf1 S542Q | TTTN | TTCN |
| AsCpf1 S542R | TTTN, ATTN, CTTN, GTTN, TCTN, TTCN, ATCN, CCCN, CCTN, GCTN, GGTN, TCCN | TGTN, TATN, CTCN, TGCN |
| AsCpf1 N551R | TTTN | GTTN |
| AsCpf1 N552R | | TTTN |
| AsCpf1 T167A/T539K | TTTN, GTTN | |
| AsCpf1 T167A/T539R | TTTN, GTTN | |
| AsCpf1 E174R/S542R | TTTN, CTTN, TTCN | |
| AsCpf1 S542R/K548R | TTTN, CTTN, GTTN, TTCN | TATN, TGTN, TTAN |
| AsCpf1 S542R/N551R | TTTN, GTN, TTCN | CTTN |
| AsCpf1 S542R/N552R | TTTN | GTTN |
| AsCpf1 K548R/N551R | TTTN, GTTN | |
| AsCpf1 K548R/N552R | | TTTN |
| AsCpf1 S542R/M604A | TTTN | TTCN |
| AsCpf1 S542R/K607H | TTTN, TTCN | |
| AsCpf1 E174R/S542R/K548R | TTTN, CTTN, GTTN, ATTN, TATN, TGTN, TTAN, TTCN, AGTN, CATN, CCCN, CGTN, CTCN, GATN, GCTN, GGTN, GTCN, TACN, TCCN, TGCN, ACCN | TCTN, TTGN, AAAN, ACTN, ATCN, CCTN, CTAN |

TABLE B-continued

| Variant protein | Stronger PAM | Weaker PAM |
|---|---|---|
| AsCpf1 S542R/K548R/N551R | TTTN, GTTN, TTCN | CTTN, TATN, TGTN, TTAN |
| AsCpf1 S170R/S542R/K607R | TTTN, TTCN, TCCN, TCTN, ACCN | GTTN, TTAN |
| AsCpf1 E174R/S542R/K607H | CTTN, TCTN, TTCN, TCCN, TTTN | CCCN, ACCN |
| AsCpf1 E174R/S542R/K607R | TTTN, TTCN, TCCN, CCCN, ACCN, GCCN | CTTN, GTTN, TCTN, TTAN, TTGN |
| AsCpf1 E174R/S542R/K548R/N551R | TTTN, CTTN, GTTN, TTCN, TCCN, CCCN, ACCN | TATN |
| AsCpf1 E174R/S542R/K548R/N552R | TTTN, CTTN, GTTN | TATN |
| AsCpf1 E174R/S542R/K548V/N552R | TTTN, CTTN, GTTN, TATN | TCTN, TGTN, TTCN, TCCN |
| AsCpf1 S170R/S542R/K548V/N552R | TTTN, GTTN, TATN, | CTTN, TGTN, TTCN |
| LbCpf1 T152R | TTTN, TTCN | |
| LbCpf1 T152K | TTTN, TTCN | |
| LbCpf1 D156R | TTTN, TTCN | |
| LbCpf1 D156K | TTTN, TTCN | |
| LbCpf1 G532R | TTTN, TTCN | |
| LbCpf1 K538R | TTTN | TTCN |
| LbCpf1 D156R/G532R/K538R | TTTN, CTTN, GTTN, TTAN, TTCN, TTGN, TCCN | TATN, TCTN |
| FnCpf1 K180R | TTTN, CTTN, GTTN, NTTN, TCTN | TTAN, TTCN |
| FnCpf1 N607R | TTTN, CTTN, GTTN, NTTN, TCTN, TTCN | TTAN |
| FnCpf1 K613R | TTTN, CTTN, GTTN, NTTN, | TTCN, TGTN |
| FnCpf1 K613V | TTTN, CTTN, GTTN, NTTN, | TATN, TGTN, TTCN |
| FnCpf1 D616R | TTTN, CTTN, GTTN, NTTN, TCTN, TTCN | TTAN |
| FnCpf1 N617R | TTTN, CTTN, GTTN, NTTN, TCTN | TTCN |
| FnCpf1 K671R | TTTN, TCTN | CTTN, GTTN, NTN, TTCN |
| FnCpf1 K671H | TTTN, CTTN, GTTN, TCTN, NTTN | TTCN |
| FnCpf1 K607R/K613V | TTTN, CTTN, GTTN, NTTN, TGTN, TTCN | TATN, TCTN, TTAN |
| FnCpf1 K607R/K613V/D616R | TTTN, CTTN, GTTN, GTTN, NTTN, TATN, TCTN, TGTN, TTAN, TTCN | |
| FnCpf1 K607R/K613R/D616R | TTTN, GTTN, GTTN, NTTN, TGTN, TTAN, TTCN | TCTN, |

The variants described herein can also be used in methods of detecting a target ssDNA or dsDNA in a sample in vitro, e.g., as described in US20170362644; East-Seletsky et al., Nature. 2016 Oct. 13; 538(7624): 270-273; Gootenberg et al., Science. 2017 Apr. 28; 356(6336): 438-442; Gootenberg et al., Science 10.1126/science.aaq0179 (2018); Chen et al., Science. 2018 Feb. 15. pii: eaar6245; Science. 2018 Feb. 15. pii: eaaq0179; and WO2017219027A1. In these methods, the binding of the variant to its target induces a non-specific DNase activity against other targets. The methods include contacting a sample known or suspected to include a target ssDNA or dsDNA with the fusion protein (or a plurality of fusion proteins), cognate guide RNAs that work with that fusion proteins, and labeled detector DNAs (e.g., a reporter ssDNA that is, eg., 3-30 nts, 3-20, 5-20, 5-15, or other suitable length). When a fusion protein binds its target the non-specific DNAse activity cleaves the detector DNAs, producing a signal. Methods for measuring the signal from the labeled detector DNA are known in the art, and can include, for example, detecting one or more of a gold nanoparticle, a fluorophore, fluorescence polarization, colloid phase transition/dispersion, electrochemical signals, and semiconductor-based signals. In some embodiments, the labeled detector DNA produces an amount of detectable signal prior to being cleaved, and the amount of detectable signal is reduced when the labeled detector DNA is cleaved. Alternatively, the labeled detector DNA can produce a first detectable signal prior to being cleaved and a second detectable signal when the labeled detector DNA is cleaved. In some embodiments, the labeled detector DNA comprises a quencher/fluor pair. In some embodiments, Csm6, an auxiliary CRISPR-associated enzyme, is also included.

In addition, the variants described herein can be used in fusion proteins in place of the wild-type Cas9 or other Cas9 mutations (such as the dCas9 or Cas9 nickase) as known in the art, e.g., a fusion protein with a heterologous functional domains as described in U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/124284. For example, the variants, preferably comprising one or more nuclease-reducing or killing mutation, can be fused on the N or C terminus of the Cpf1 to a transcriptional activation domain (e.g., a transcriptional activation domain from the VP16 domain form herpes simplex virus (Sadowski et al., 1988, Nature, 335:563-564) or VP64; the p65 domain from the cellular transcription factor NF-kappaB (Ruben et al., 1991, Science, 251:1490-93); or a tripartite effector fused to dCas9, composed of activators VP64, p65, and Rta (VPR) linked in tandem, Chavez et al., Nat Methods. 2015 April; 12(4):326-8) or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; base editors (enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary_material_DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a base editor, e.g., a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, APOBEC4 (see, e.g., Yang et al., J Genet Genomics. 2017 Sep. 20; 44(9):423-437); activation-induced cytidine deaminase (AID), e.g., activation induced cytidine deaminase (AICDA), cytosine deaminase 1 (CDA1), and CDA2, and cytosine deaminase acting on tRNA (CDAT). The following table provides exemplary sequences; other sequences can also be used.

| | GenBank Accession Nos. | |
|---|---|---|
| Deaminase | Nucleic Acid | Amino Acid |
| hAID/AICDA | NM_020661.3 isoform 1 | NP_065712.1 variant 1 |
| | NM_020661.3 isoform 2 | NP_065712.1 variant 2 |
| APOBEC1 | NM_001644.4 isoform 1 | NP_001635.2 variant 1 |
| | NM_005889.3 isoform b | NP_005880.2 variant 3 |
| APOBEC2 | NM_006789.3 | NP_006780.1 |
| APOBEC3A | NM_145699.3 isoform a | NP_663745.1 variant 1 |
| | NM_001270406.1 isoform b | NP_001257335.1 variant 2 |
| APOBEC3B | NM_004900.4 isoform a | NP_004891.4 variant 1 |
| | NM_001270411.1 isoform b | NP_001257340.1 variant 2 |
| APOBEC3C | NM_014508.2 | NP_055323.2 |
| APOBEC3D/E | NM_152426.3 | NP_689639.2 |
| APOBEC3F | NM_145298.5 isoform a | NP_660341.2 variant 1 |
| | NM_001006666.1 isoform b | NP_001006667.1 variant 2 |
| APOBEC3G | NM_021822.3 (isoform a) | NP_068594.1 (variant 1) |
| APOBEC3H | NM_001166003.2 | NP_001159475.2 (variant SV-200) |
| APOBEC4 | NM_203454.2 | NP_982279.1 |
| CDA1* | NM_127515.4 | NP_179547.1 |

*from *Saccharomyces cerevisiae* S288C

In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3 (see, e.g., Savva et al., Genome Biol. 2012 Dec. 28; 13(12):252); adenosine deaminase acting on tRNA 1 (ADAT1), ADAT2, ADAT3 (see Keegan et al., RNA. 2017 September; 23(9):1317-1328 and Schaub and Keller, Biochimie. 2002 August; 84(8):791-803); and naturally occurring or engineered tRNA-specific adenosine deaminase (TadA) (see, e.g., Gaudelli et al., Nature. 2017 Nov. 23; 551(7681):464-471) (NP_417054.2 (*Escherichia coli* str. K-12 substr. MG1655); See, e.g., Wolf et al., EMBO J. 2002 Jul. 15; 21(14):3841-51). The following table provides exemplary sequences; other sequences can also be used.

| | GenBank Accession Nos. | |
|---|---|---|
| Deaminase | Nucleic Acid | Amino Acid |
| ADA (ADA1) | NM_000022.3 variant 1 | NP_000013.2 isoform 1 |
| ADA2 | NM_001282225.1 | NP_001269154.1 |
| ADAR | NM_001111.4 | NP_001102.2 |
| ADAR2 (ADARB1) | NM_001112.3 variant 1 | NP_001103.1 isoform 1 |
| ADAR3 (ADARB2) | NM_018702.3 | NP_061172.1 |
| ADAT1 | NM_012091.4 variant 1 | NP_036223.2 isoform 1 |
| ADAT2 | NM_182503.2 variant 1 | NP_872309.2 isoform 1 |
| ADAT3 | NM_138422.3 variant 1 | NP_612431.2 isoform 1 |

In some embodiments, the heterologous functional domain is an enzyme, domain, or peptide that inhibits or enhances endogenous DNA repair or base excision repair (BER) pathways, e.g., thymine DNA glycosylase (TDG; GenBank Acc Nos. NM_003211.4 (nucleic acid) and NP_003202.3 (protein)) or uracil DNA glycosylase (UDG, also known as uracil N-glycosylase, or UNG; GenBank Acc Nos. NM_003362.3 (nucleic acid) and NP_003353.1 (protein)) or uracil DNA glycosylase inhibitor (UGI) that inhibits UNG mediated excision of uracil to initiate BER (see, e.g., Mol et al., Cell 82, 701-708 (1995); Komor et al., Nature. 2016 May 19; 533(7603)); or DNA end-binding proteins such as Gam, which is a protein from the bacteriophage Mu that binds free DNA ends, inhibiting DNA repair enzymes and leading to more precise editing (less unintended base edits; Komor et al., Sci Adv. 2017 Aug. 30; 3(8):eaao4774).

In some embodiments, all or part of the protein, e.g., at least a catalytic domain that retains the intended function of the enzyme, can be used.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCpf1 gRNA targeting sequences. For example, a dCpf1 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCpf1 variant binding site using the methods and compositions described herein. In some embodiments, the Csy4 is catalytically inactive. In some embodiments, the Cpf1 variant, preferably a dCpf1 variant, is fused to FokI as described in U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/204578.

In some embodiments, the fusion proteins include a linker between the Cpf1 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:12) or GGGGS (SEQ ID NO:13), e.g., two, three, four, or more repeats of the GGGS (SEQ ID NO:12) or GGGGS (SEQ ID NO:13) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15)00141-2.

In some embodiments, alternatively or in addition, the variant proteins can include a nuclear localization sequence, e.g., SV40 large T antigen NLS (PKKKRRV (SEQ ID NO:16)) and nucleoplasmin NLS (KRPAATKK-AGQAKKKK (SEQ ID NO:7)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences. Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the Cpf1 variants described herein, it may be desirable to express them from a nucleic acid that encodes them. This can be performed in a variety of ways. For example, the nucleic acid encoding the Cpf1 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cpf1 variant for production of the Cpf1 variant. The nucleic acid encoding the Cpf1 variant can also be cloned into an expression vector, for administration to a plant cell, animal cell, preferably a mammalian cell or a human cell, fungal cell, bacterial cell, or protozoan cell.

To obtain expression, a sequence encoding a Cpf1 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cpf1 variant is to be administered in vivo for gene regulation, either a constitutive or an inducible promoter can be used, depending on the particular use of the Cpf1 variant. In addition, a preferred promoter for administration of the Cpf1 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cpf1 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cpf1 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cpf1 variants can include RNA Pol III promoters to drive expression of the guide RNAs, e.g., the H1, U6 or 7SK promoters. These human promoters allow for expression of Cpf1 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cpf1 variant.

The present invention also includes the vectors and cells comprising the vectors. Also provided herein are compositions and kits comprising the variants described herein. In some embodiments, the kits include the fusion proteins and a cognate guide RNA (i.e., a guide RNA that binds to the protein and directs it to a target sequence appropriate for that protein). In some embodiments, the kits also include labeled detector DNA, e.g., for use in a method of detecting a target ssDNA or dsDNA. Labeled detector DNAs are known in the art, e.g., as described in US20170362644; East-Seletsky et al., Nature. 2016 Oct. 13; 538(7624): 270-273; Gootenberg et al., Science. 2017 Apr. 28; 356(6336): 438-442, and WO2017219027A1, and can include labeled detector DNAs comprising a fluorescence resonance energy transfer (FRET) pair or a quencher/fluor pair, or both. The kits can also include one or more additional reagents, e.g., additional enzymes (such as RNA polymerases) and buffers, e.g., for use in a method described herein.

EXAMPLES

The invention is further described in the following examples, which do not limit the scope of the invention described in the claims.

Methods

The following materials and methods were used in the Examples below, unless otherwise noted.

Plasmids and Oligonucleotides.

The target site sequences for crRNAs and oligonucleotide sequences used in Examples 1B, 4B, and 5-8 are available in Tables 2A-2D and 3A-3D respectively. Human expression plasmids for wild-type AsCas12a, LbCas12a, FnCas12a, and MbCas12a (SQT1659, SQT1665, AAS1472, AAS2134, respectively) were generated by sub-cloning the nuclease open-reading frames from plasmids pY010, pY016, pY004, and pY014, respectively (Addgene plasmids 69982, 69988, 69976, and 69986; gifts from Feng Zhang) into the NotI and AgeI sites of pCAG-CFP (Addgene plasmid 11179; a gift from Connie Cepko). Protein expression plasmids were generated by cloning the human codon-optimized open reading frames of As, Fn, and MbCas12a, and the bacterial codon-optimized LbCas12a open reading frame (from Addgene plasmid 79008; a gift from Jin Soo Kim) into the NcoI and FseI sites of pET28b-Cas9 (Addgene plasmid 47327; a gift from Alex Schier) to generate BPK3541, RTW656, RTW660, and RTW645, respectively. All Cas12a variants, activator constructs, and base editor fusions were generated via standard molecular cloning and isothermal assembly. Human cell expression plasmids for Cas12a crRNAs were generated by annealing and ligating oligonucleotides corresponding to spacer sequence duplexes into BsmBI-digested BPK3079, BPK3082, BPK4446, and BPK4449 for U6 promoter-driven transcription of As, Lb, Fn, and MbCas12a crRNAs, respectively. Substrate plasmids for in vitro cleavage reactions were generated by cloning target sites into the NheI and HindIII sites of pUC19. Plasmids for in vitro transcription of Cas12a crRNAs were generated by annealing and ligating oligonucleotides corresponding to spacer sequence duplexes into BsaI-digested MSP3491, MSP3495, RTW763, and RTW767 for T7 promoter-driven transcription of As, Lb, Fn, and MbCas12a crRNAs, respectively.

TABLE 2A

Cas12a crRNAs for nuclease experiments

| crRNA ID | gene name | 4 nt PAM | 20 nt Spacer | SEQ ID NO: |
|---|---|---|---|---|
| AACC-1 | FANCF | AACC | AGTGGAGGCAAGAGGGCGGC | 26. |
| AACC-2 | RUNX1 | AACC | AAGACAGGTCACTGTTTCAG | 27. |
| AACC-3 | EMX1 | AACC | ACACCTTCACCTGGGCCAGG | 28. |
| AACC-4 | EMX1 | AACC | GGTGGCGCATTGCCACGAAG | 29. |
| AATA-1 | FANCF | AATA | GCATTGCAGAGAGGCGTATC | 30. |
| AATA-2 | RUNX1 | AATA | TGCTGTCTGAAGCCATCGCT | 31. |
| AATA-3 | DNMT1 | AATA | AGTGGCAGAGTGCTAAGGGA | 32. |
| AATA-4 | EMX1 (amplicon 2) | AATA | TGGAGCCTGCTCCAGGTGGG | 33. |
| AATC-1 | FANCF | AATC | AGTACGCAGAGAGTCGCCGT | 34. |
| AATC-2 | CFTR | AATC | CTAACTGAGACCTTACACCG | 35. |
| AATG-1 | EMX1 | AATG | CGCCACCGGTTGATGTGATG | 36. |
| ACCC-1 | VEGFA | ACCC | CGGCTCTGGCTAAAGAGGGA | 37. |
| ACCC-2 | VEGFA | ACCC | CCTATTTCTGACCTCCCAAA | 38. |
| ACCC-3 | DNMT1 | ACCC | AGAGGCTCAAGTGAGCAGCT | 39. |
| ACCC-4 | EMX1 | ACCC | TAGTCATTGGAGGTGACATC | 40. |
| ACCC-5 | EMX1 | ACCC | ACGAGGGCAGAGTGCTGCTT | 41. |
| ACCC-6 | DNMT1 | ACCC | AATAAGTGGCAGAGTGCTAA | 42. |
| AGCC-1 | FANCF | AGCC | GCCCTCTTGCCTCCACTGGT | 43. |
| AGCC-2 | RUNX1 | AGCC | ATCGCTTCCTCCTGAAAATG | 44. |
| AGCC-3 | RUNX1 | AGCC | TCACCCCTCTAGCCCTACAT | 45. |
| AGCC-4 | EMX1 (amplicon 2) | AGCC | TGCTCCAGGTGGGGAATAAG | 46. |
| AGTA-1 | DNMT1 | AGTA | ACAGACATGGACCATCAGGA | 47. |
| AGTA-2 | CFTR | AGTA | CCAGATTCTGAGCAGGGAGA | 48. |
| AGTC-1 | DNMT1 | AGTC | TCCGTGAACGTTCCCTTAGC | 49. |
| AGTC-2 | CFTR | AGTC | TGTCCTGAACCTGATGACAC | 50. |
| ATCA-1 | DNMT1 | ATCA | GGAAACATTAACGTACTGAT | 51. |
| ATCA-2 | CFTR | ATCA | GAATCCTCTTCGATGCCATT | 52. |
| ATCC-1 | DNMT1 | ATCC | TCACAGCAGCCCCTTGAGAA | 53. |
| ATCC-2 | CFTR | ATCC | AATCAACTCTATACGAAAAT | 54. |
| ATCC-3 | DNMT1 | ATCC | CCAACATGCACTGATGTTGT | 55. |

TABLE 2A-continued

Cas12a crRNAs for nuclease experiments

| crRNA ID | gene name | 4 nt PAM | 20 nt Spacer | SEQ ID NO: |
|---|---|---|---|---|
| ATCC-4 | FANCF | ATCC | ATCGGCGCTTTGGTCGGCAT | 56. |
| ATTA-1 | DNMT1 | ATTA | ACGTACTGATGTTAACAGCT | 57. |
| ATTA-2 | EMX1 (amplicon 2) | ATTA | ACATTAACAAGAAGCATTTG | 58. |
| ATTA-3 | EMX1 (amplicon 2) | ATTA | TTCAAGTGGCGCAGATCTAG | 59. |
| ATTA-4 | CFTR | ATTA | GAAGGAGATGCTCCTGTCTC | 60. |
| ATTC-1 | DNMT1 | ATTC | ACCGAGCAGGAGTGAGGGAA | 61. |
| ATTC-2 | EMX1 (amplicon 2) | ATTC | CCCACCTGGAGCAGGCTCCA | 62. |
| ATTC-3 | CFTR | ATTC | TGATGAGCCTTTAGAGAGAA | 63. |
| ATTC-4 | VEGFA | ATTC | CCTCTTTAGCCAGAGCCGGG | 64. |
| ATTC-5 | FANCF | ATTC | GCACGGCTCTGGAGCGGCGG | 65. |
| ATTG-1 | DNMT1 | ATTG | GGTCAGCTGTTAACATCAGT | 66. |
| ATTG-2 | EMX1 (amplicon 2) | ATTG | TTATGAACCTGGGTGAAGTC | 67. |
| ATTG-3 | VEGFA | ATTG | GAATCCTGGAGTGACCCCTG | 68. |
| ATTG-4 | CFTR | ATTG | GATTGAGAATAGAATTCTTC | 69. |
| ATTG-5 | FANCF | ATTG | GAACATCCGCGAAATGATAC | 70. |
| ATTT-1 | DNMT1 | ATTT | GGCTCAGCAGGCACCTGCCT | 71. |
| ATTT-2 | EMX1 (amplicon 2) | ATTT | GCTTTCCACCCACCTTTCCC | 72. |
| ATTT-3 | VEGFA | ATTT | CTGACCTCCCAAACAGCTAC | 73. |
| ATTT-4 | CFTR | ATTT | CTTCTTTCTGCACTAAATTG | 74. |
| ATTT-5 | FANCF | ATTT | CGCGGATGTTCCAATCAGTA | 75. |
| CACC-1 | FANCF | CACC | GTGCGCCGGGCCTTGCAGTG | 76. |
| CACC-2 | RUNX1 | CACC | GAGGCATCTCTGCACCGAGG | 77. |
| CCCC-1 | FANCF | CCCC | GCCCAAAGCCGCCCTCTTGC | 78. |
| CCCC-2 | RUNX1 | CCCC | GCCTTCAGAAGAGGGTGCAT | 79. |
| CCCC-3 | DNMT1 | CCCC | AGAGGGTTCTAGACCCAGAG | 80. |
| CCCC-4 | DNMT1 | CCCC | AGGGCCAGCCCAGCAGCCAA | 81. |
| CGCA-1 | FANCF | CGCA | CGGCTCTGGAGCGGCGGCTG | 82. |
| CGCA-2 | EMX1 | CGCA | TTGCCACGAAGCAGGCCAAT | 83. |
| CGCC-1 | FANCF | CGCC | GCTCCAGAGCCGTGCGAATG | 84. |
| CGCC-2 | EMX1 | CGCC | ACCGGTTGATGTGATGGGAG | 85. |
| CGCC-3 | FANCF | CGCC | ACATCCATCGGCGCTTTGGT | 86. |
| CGCC-4 | FANCF | CGCC | GATGGATGTGGCGCAGGTAG | 87. |
| CGTC-1 | FANCF | CGTC | AGCACCTGGGACCCCGCCAC | 88. |
| CGTC-2 | FANCF | CGTC | TCCAAGGTGAAAGCGGAAGT | 89. |
| CTCA-1 | DNMT1 | CTCA | AACGGTCCCCAGAGGGTTCT | 90. |
| CTCA-2 | CFTR | CTCA | AAACTCATGGGATGTGATTC | 91. |
| CTCC-1 | DNMT1 | CTCC | GTGAACGTTCCCTTAGCACT | 92. |
| CTCC-2 | CFTR | CTCC | TTCTAATGAGAAACGGTGTA | 93. |

TABLE 2A-continued

Cas12a crRNAs for nuclease experiments

| crRNA ID | gene name | 4 nt PAM | 20 nt Spacer | SEQ ID NO: |
|---|---|---|---|---|
| CTCC-3 | FANCF | CTCC | ACTGGTTGTGCAGCCGCCGC | 94. |
| CTCC-4 | FANCF | CTCC | AGAGCCGTGCGAATGGGCC | 95. |
| CTCT-1 | DNMT1 | CTCT | GGGGAACACGCCCGGTGTCA | 96. |
| CTTA-1 | DNMT1 | CTTA | TTGGGTCAGCTGTTAACATC | 97. |
| CTTA-2 | EMX1 (amplicon 2) | CTTA | TTCCCCACCTGGAGCAGGCT | 98. |
| CTTA-3 | RUNX1 | CTTA | CTAATCAGATGGAAGCTCTT | 99. |
| CTTA-4 | CFTR | CTTA | CACCGTTTCTCATTAGAAGG | 100. |
| CTTC-1 | FANCF | CTTC | CGCTTTCACCTTGGAGACGG | 101. |
| CTTC-2 | EMX1 (amplicon 2) | CTTC | ACCCAGGTTCATAACAATGT | 102. |
| CTTC-3 | VEGFA | CTTC | TCCCCGCTCCAACGCCCTCA | 103. |
| CTTC-4 | CFTR | CTTC | TAATGAGAAACGGTGTAAGG | 104. |
| CTTC-5 | FANCF | CTTC | GCGCACCTCATGGAATCCCT | 105. |
| CTTG-1 | DNMT1 | CTTG | ACAGGCGAGTAACAGACATG | 106. |
| CTTG-2 | EMX1 (amplicon 2) | CTTG | TTAATGTTAATAACTTGCTT | 107. |
| CTTG-3 | CFTR | CTTG | GTTAACTGAGTGTGTCATCA | 108. |
| CTTG-4 | RUNX1 | CTTG | GGGAGTCCCAGAGGTATCCA | 109. |
| CTTT-1 | DNMT1 | CTTT | GGTCAGGTTGGCTGCTGGGC | 110. |
| CTTT-2 | EMX1 (amplicon 2) | CTTT | CCCTGGCCTACCTCACTGGC | 111. |
| CTTT-3 | VEGFA | CTTT | AGCCAGAGCCGGGGTGTGCA | 112. |
| CTTT-4 | CFTR | CTTT | AGAGAGAAGGCTGTCCTTAG | 113. |
| CTTT-5 | FANCF | CTTT | GGTCGGCATGGCCCCATTCG | 114. |
| GCCC-1 | DNMT1 | GCCC | GGTGTCACGCCACTTGACAG | 115. |
| GCCC-2 | CFTR | GCCC | CACGCTTCAGGCACGAAGGA | 116. |
| GTCA-1 | DNMT1 | GTCA | CGCCACTTGACAGGCGAGTA | 117. |
| GTCA-2 | CFTR | GTCA | TCAGGTTCAGGACAGACTGC | 118. |
| GTCC-1 | DNMT1 | GTCC | CCAGAGGGTTCTAGACCCAG | 119. |
| GTCC-2 | CFTR | GTCC | AGGAGACAGGAGCATCTCCT | 120. |
| GTCC-3 | FANCF | GTCC | CAGGTGCTGACGTAGGTAGT | 121. |
| GTCC-4 | EMX1 | GTCC | TCCCCATTGGCCTGCTTCGT | 122. |
| GTTA-1 | DNMT1 | GTTA | CTCGCCTGTCAAGTGGCGTG | 123. |
| GTTA-2 | EMX1 (amplicon 2) | GTTA | TGAACCTGGGTGAAGTCCCA | 124. |
| GTTA-3 | EMX1 (amplicon 2) | GTTA | ATGTTAATAACTTGCTTCAA | 125. |
| GTTA-4 | CFTR | GTTA | ACCAAGGTCAGAACATTCAC | 126. |
| GTTC-1 | DNMT1 | GTTC | CCTTAGCACTCTGCCACTTA | 127. |
| GTTC-2 | EMX1 (amplicon 2) | GTTC | ATTTGTCCAGAGGAAACCAC | 128. |
| GTTC-3 | RUNX1 | GTTC | CCTGTCTTGTTTGTGAGAGG | 129. |
| GTTC-4 | CFTR | GTTC | AGGACAGACTGCCTCCTTCG | 130. |
| GTTG-1 | DNMT1 | GTTG | GGGATTCCTGGTGCCAGAAA | 131. |

TABLE 2A-continued

Cas12a crRNAs for nuclease experiments

| crRNA ID | gene name | 4 nt PAM | 20 nt Spacer | SEQ ID NO: |
|---|---|---|---|---|
| GTTG-2 | EMX1 (amplicon 2) | GTTG | GGACTTCACCCAGGTTCATA | 132. |
| GTTG-3 | VEGFA | GTTG | AGGGCGTTGGAGCGGGGAGA | 133. |
| GTTG-4 | CFTR | GTTG | ATTGGATTGAGAATAGAATT | 134. |
| GTTG-5 | FANCF | GTTG | TGCAGCCGCCGCTCCAGAGC | 135. |
| GTTT-1 | DNMT1 | GTTT | CCTGATGGTCCATGTCTGTT | 136. |
| GTTT-2 | EMX1 (amplicon 2) | GTTT | GACTTGGGATAGTGGAATAG | 137. |
| GTTT-3 | VEGFA | GTTT | GGGAGGTCAGAAATAGGGGG | 138. |
| GTTT-4 | CFTR | GTTT | CTCATTAGAAGGAGATGCTC | 139. |
| GTTT-5 | RUNX1 | GTTT | CACCTCGGTGCAGAGATGCC | 140. |
| TACA-1 | RUNX1 | TACA | TCTCTCTTTCTTCTCCCCTC | 141. |
| TACA-2 | RUNX1 | TACA | GGCAAAGCTGAGCAAAAGTA | 142. |
| TACA-3 | EMX1 | TACA | AACGGCAGAAGCTGGAGGAG | 143. |
| TACA-4 | RUNX1 | TACA | AGACCAGCATGTACTCACCT | 144. |
| TACC-1 | DNMT1 | TACC | CACGTTCGTGGCCCCATCTT | 145. |
| TACC-2 | CFTR | TACC | AGATTCTGAGCAGGGAGAGG | 146. |
| TACC-3 | EMX1 (amplicon 2) | TACC | TCACTGGCCCCACCCCAGAG | 147. |
| TACC-4 | FANCF | TACC | TGCGCCACATCCATCGGCGC | 148. |
| TATA-1 | CFTR | TATA | GAGTTGATTGGATTGAGAAT | 149. |
| TATA-2 | CFTR | TATA | TTCAAGAAGGTTATCTCAAG | 150. |
| TATA-3 | CFTR | TATA | TATTCAAGAAGGTTATCTCA | 151. |
| TATA-4 | VEGFA (amplicon 2) | TATA | GACATGTCCCATTTGTGGGA | 152. |
| TATC-1 | CFTR | TATC | GCCTCTCCCTGCTCAGAATC | 153. |
| TATC-2 | CFTR | TATC | TCAAGAAACTGGCTTGGAAA | 154. |
| TATC-3 | CFTR | TATC | CAGTTCAGTCAAGTTTGCCT | 155. |
| TATC-4 | EMX1 (amplicon 2) | TATC | CCAAGTCAAACTTCTCTTCA | 156. |
| TATG-1 | VEGFA (amplicon 2) | TATG | TTCGGGTGCTGTGAACTTCC | 157. |
| TATG-2 | EMX1 (amplicon 2) | TATG | AACCTGGGTGAAGTCCCAAC | 158. |
| TATG-3 | VEGFA | TATG | TAGCTGTTTGGGAGGTCAGA | 159. |
| TATG-4 | CFTR | TATG | GGACATTTTCAGAACTCCAA | 160. |
| TATT-1 | DNMT1 | TATT | GGGTCAGCTGTTAACATCAG | 161. |
| TATT-2 | VEGFA | TATT | TCTGACCTCCCAAACAGCTA | 162. |
| TATT-3 | CFTR | TATT | CTCAATCCAATCAACTCTAT | 163. |
| TATT-4 | FANCF | TATT | GGTCGAAATGCATGTCAATC | 164. |
| TCCA-1 | DNMT1 | TCCA | TGTCTGTTACTCGCCTGTCA | 165. |
| TCCA-2 | CFTR | TCCA | GGAGACAGGAGCATCTCCTT | 166. |
| TCCA-3 | VEGFA | TCCA | GTCCCAAATATGTAGCTGTT | 167. |
| TCCC-1 | DNMT1 | TCCC | CAGAGGGTTCTAGACCCAGA | 168. |
| TCCC-2 | CFTR | TCCC | CAAACTCTCCAGTCTGTTTA | 169. |

TABLE 2A-continued

Cas12a crRNAs for nuclease experiments

| crRNA ID | gene name | 4 nt PAM | 20 nt Spacer | SEQ ID NO: |
|---|---|---|---|---|
| TCCC-3 | DNMT1 | TCCC | GTCACCCCTGTTTCTGGCAC | 170. |
| TCCC-4 | FANCF | TCCC | AGGTGCTGACGTAGGTAGTG | 171. |
| TCCC-5 | VEGFA | TCCC | TCTTTAGCCAGAGCCGGGGT | 172. |
| TCCG-1 | DNMT1 | TCCG | TGAACGTTCCCTTAGCACTC | 173. |
| TCCG-2 | FANCF | TCCG | AGCTTCTGGCGGTCTCAAGC | 174. |
| TCCG-3 | VEGFA | TCCG | CACGTAACCTCACTTTCCTG | 175. |
| TCCT-1 | DNMT1 | TCCT | GATGGTCCATGTCTGTTACT | 176. |
| TGCA-1 | DNMT1 | TGCA | CACAGCAGGCCTTTGGTCAG | 177. |
| TGCA-2 | CFTR | TGCA | GAAAGAAGAAATTCAATCCT | 178. |
| TGCC-1 | DNMT1 | TGCC | ACTTATTGGGTCAGCTGTTA | 179. |
| TGCC-2 | CFTR | TGCC | TCGCATCAGCGTGATCAGCA | 180. |
| TGCC-3 | FANCF | TGCC | TCCACTGGTTGTGCAGCCGC | 181. |
| TGCC-4 | FANCF | TGCC | GACCAAAGCGCCGATGGATG | 182. |
| TGTA-1 | RUNX1 | TGTA | ATGAAATGGCAGCTTGTTTC | 183. |
| TGTA-2 | EMX1 | TGTA | CTTTGTCCTCCGGTTCTGGA | 184. |
| TGTA-3 | Matched Site 5 | TGTA | CCTCACCACTGACATTAATT | 185. |
| TGTA-4 | Matched Site 5 | TGTA | ACCACAGTCAAGTAGTTAAT | 186. |
| TGTA-5 | CFTR | TGTA | AGGTCTCAGTTAGGATTGAA | 187. |
| TGTC-1 | FANCF | TGTC | AATCTCCCAGCGTCTTTATC | 188. |
| TGTC-2 | RUNX1 | TGTC | TTGTTTGTGAGAGGAATTCA | 189. |
| TGTC-3 | EMX1 (amplicon 2) | TGTC | CAGAGGAAACCACTGTTGGG | 190. |
| TGTC-4 | EMX1 (amplicon 2) | TGTC | TATTCCACTATCCCAAGTCA | 191. |
| TGTC-5 | EMX1 (amplicon 2) | TGTC | CCTCACCCATCTCCCTGTGA | 192. |
| TGTG-1 | FANCF | TGTG | CAGCCGCCGCTCCAGAGCCG | 193. |
| TGTG-2 | RUNX1 | TGTG | AGAGGAATTCAAACTGAGGC | 194. |
| TGTG-3 | FANCF | TGTG | GCGCAGGTAGCGCGCCCACT | 195. |
| TGTG-4 | EMX1 | TGTG | GTTCCAGAACCGGAGGACAA | 196. |
| TGTG-5 | EMX1 | TGTG | ATGGGAGCCCTTCTTCTTCT | 197. |
| TTAC-2 | RUNX1 | TTAC | AGGCAAAGCTGAGCAAAAGT | 198. |
| TTAC-3 | EMX1 (amplicon 2) | TTAC | TCATCTCTGCCAGACCACCT | 199. |
| TTAC-4 | Matched Site 5 | TTAC | TGATTCTGGGGTCAACATCT | 200. |
| TTAC-5 | CFTR | TTAC | AAATGAATGGCATCGAAGAG | 201. |
| TTAC-6 | CFTR | TTAC | ACCGTTTCTCATTAGAAGGA | 202. |
| TTAC-7 | Matched Site 5 | TTAC | TAGGGCAATAAGCAACACCT | 203. |
| TTCA-1 | DNMT1 | TTCA | GTCTCCGTGAACGTTCCCTT | 204. |
| TTCA-2 | EMX1 (amplicon 2) | TTCA | CCCAGGTTCATAACAATGTT | 205. |
| TTCA-3 | VEGFA | TTCA | CCCAGCTTCCCTGTGGTGGC | 206. |
| TTCA-4 | CFTR | TTCA | ATCCTAACTGAGACCTTACA | 207. |

TABLE 2A-continued

Cas12a crRNAs for nuclease experiments

| crRNA ID | gene name | 4 nt PAM | 20 nt Spacer | SEQ ID NO: |
|---|---|---|---|---|
| TTCA-5 | FANCF | TTCA | CCTTGGAGACGGCGACTCTC | 208. |
| TTCC-1 | DNMT1 | TTCC | TGATGGTCCATGTCTGTTAC | 209. |
| TTCC-2 | EMX1 (amplicon 2) | TTCC | CTGGCCTACCTCACTGGCCC | 210. |
| TTCC-3 | VEGFA | TTCC | AAAGCCCATTCCCTCTTTAG | 211. |
| TTCC-4 | CFTR | TTCC | ATTGTGCAAAAGACTCCCTT | 212. |
| TTCC-5 | FANCF | TTCC | GAGCTTCTGGCGGTCTCAAG | 213. |
| TTCG-1 | DNMT1 | TTCG | TGGCCCCATCTTTCTCAAGG | 214. |
| TTCG-2 | VEGFA | TTCG | AGAGTGAGGACGTGTGTGTC | 215. |
| TTCG-3 | RUNX1 | TTCG | GAGCGAAAACCAAGACAGGT | 216. |
| TTCG-4 | CFTR | TTCG | ACCAATTTAGTGCAGAAAGA | 217. |
| TTCG-5 | FANCF | TTCG | CACGGCTCTGGAGCGGCGGC | 218. |
| TTCT-1 | DNMT1 | TTCT | GCCCTCCCGTCACCCCTGTT | 219. |
| TTCT-2 | EMX1 (amplicon 2) | TTCT | GCCCTTTACTCATCTCTGCC | 220. |
| TTCT-3 | VEGFA | TTCT | GACCTCCCAAACAGCTACAT | 221. |
| TTCT-4 | CFTR | TTCT | TTCGACCAATTTAGTGCAGA | 222. |
| TTCT-5 | FANCF | TTCT | GGCGGTCTCAAGCACTACCT | 223. |
| TTTA-1 | DNMT1 | TTTA | TTTCCCTTCAGCTAAAATAA | 224. |
| TTTA-2 | DNMT1 | TTTA | TTTTAGCTGAAGGGAAATAA | 225. |
| TTTA-3 | FANCF | TTTA | TCCGTGTTCCTTGACTCTGG | 226. |
| TTTA-4 | RUNX1 | TTTA | CCTTCGGAGCGAAAACCAAG | 227. |
| TTTA-5 | Matched site 5 | TTTA | GGATGCCACTAAAAGGGAAA | 228. |
| TTTA-6 | Matched site 1 | TTTA | GATTGAAGGAAAAGTTACAA | 229. |
| TTTC-1 | DNMT1 | TTTC | CCTCACTCCTGCTCGGTGAA | 230. |
| TTTC-2 | DNMT1 | TTTC | CTGATGGTCCATGTCTGTTA | 231. |
| TTTC-3 | EMX1 | TTTC | TCATCTGTGCCCCTCCCTCC | 232. |
| TTTC-4 | FANCF | TTTC | ACCTTGGAGACGGCGACTCT | 233. |
| TTTC-5 | RUNX1 | TTTC | GCTCCGAAGGTAAAAGAAAT | 234. |
| TTTC-6 | RUNX1 | TTTC | AGCCTCACCCCTCTAGCCCT | 235. |
| TTTC-7 | RUNX1 | TTTC | TTCTCCCCTCTGCTGGATAC | 236. |
| TTTC-8 | FANCF | TTTC | CGAGCTTCTGGCGGTCTCAA | 237. |
| TTTG-1 | DNMT1 | TTTG | AGGAGTGTTCAGTCTCCGTG | 238. |
| TTTG-2 | DNMT1 | TTTG | GCTCAGCAGGCACCTGCCTC | 239. |
| TTTG-3 | EMX1 | TTTG | TCCTCCGGTTCTGGAACCAC | 240. |
| TTTG-4 | EMX1 | TTTG | TGGTTGCCCACCCTAGTCAT | 241. |
| TTTG-5 | EMX1 | TTTG | TACTTTGTCCTCCGGTTCTG | 242. |
| TTTG-6 | FANCF | TTTG | GGCGGGGTCCAGTTCCGGGA | 243. |
| TTTG-7 | FANCF | TTTG | GTCGGCATGGCCCCATTCGC | 244. |
| TTTT-1 | DNMT1 | TTTT | ATTTCCCTTCAGCTAAAATA | 245. |

TABLE 2A-continued

Cas12a crRNAs for nuclease experiments

| crRNA ID | gene name | 4 nt PAM | 20 nt Spacer | SEQ ID NO: |
|---|---|---|---|---|
| TTTT-2 | RUNX1 | TTTT | CAGGAGGAAGCGATGGCTTC | 246. |
| TTTT-3 | FANCF | TTTT | CCGAGCTTCTGGCGGTCTCA | 247. |
| TTTT-4 | CFTR | TTTT | CGTATAGAGTTGATTGGATT | 248. |
| TTTT-5 | CFTR | TTTT | GAGCTAAAGTCTGGCTGTAG | 249. |

TABLE 2B

Cas12a crRNAs for gene activation experiments

| crRNA ID | gene name | 4 nt PAM | 20 nt Spacer | SEQ ID NO: | Distance from TSS (bp) | Strand |
|---|---|---|---|---|---|---|
| AR-TTTV-a-1 | AR | TTTG | AGAGTCTGGATGAGAAATGC | 250. | 639 | C |
| AR-TTTV-a-2 | AR | TTTC | TACCCTCTTCTCTGCCTTTC | 251. | 588 | T |
| AR-TTTV-a-3 | AR | TTTG | CTCTAGGAACCCTCAGCCCC | 252. | 550 | T |
| AR-TTTV-b-1 | AR | TTTC | TCCAAAGCCACTAGGCAGGC | 253. | 141 | C |
| AR-TTTV-b-2 | AR | TTTA | GGAAAGCAGGAGCTATTCAG | 254. | 231 | C |
| AR-TTTV-b-3 | AR | TTTG | GAACCAAATTTGGTGAGTGC | 255. | 296 | C |
| AR-ATTV-1 | AR | ATTC | AGGAAGCAGGGGTCCTCCAG | 256. | 142 | C |
| AR-ATTV-2 | AR | ATTG | GGCTTTGGAACCAAATTTGG | 257. | 303 | C |
| AR-ATTV-3 | AR | ATTC | CGTCATAGGGATAGATCGGG | 258. | 508 | T |
| AR-CTTV-1 | AR | CTTG | TTTCTCCAAAGCCACTAGGC | 259. | 145 | C |
| AR-CTTV-2 | AR | CTTC | CTGAATAGCTCCTGCTTTCC | 260. | 227 | T |
| AR-CTTV-3 | AR | CTTA | TCAGTCCTGAAAAGAACCCC | 261. | 398 | C |
| AR-GTTV-1 | AR | GTTG | CATTTGCTCTCCACCTCCCA | 262. | 9 | C |
| AR-GTTV-2 | AR | GTTA | GCGCGCGGTGAGGGGAGGGG | 263. | 117 | C |
| AR-GTTV-3 | AR | GTTC | CAAAGCCCAATCTAAAAAAC | 264. | 312 | T |
| AR-TTCV-1 | AR | TTCA | GGAAGCAGGGGTCCTCCAGG | 265. | 212 | C |
| AR-TTCV-2 | AR | TTCC | TGGAGGCCAGCACTCACCAA | 266. | 283 | T |
| AR-TTCV-3 | AR | TTCA | GGACTGATAAGAGCGCGCAG | 267. | 407 | T |
| AR-CTCC-1 | AR | CTCC | AAAGCCACTAGGCAGGCGTT | 268. | 138 | C |
| AR-CTCC-2 | AR | CTCC | AGGAAATCTGGAGCCCTGGC | 269. | 268 | C |
| AR-CTCC-3 | AR | CTCC | CTCCCTCGCCTCCACCCTGT | 270. | 338 | C |
| AR-TCCC-1 | AR | TCCC | GCCCCCACCGGGCCGGCCTC | 271. | 48 | T |
| AR-TCCC-2 | AR | TCCC | CTCACCGCGCGCTAACGCCT | 272. | 121 | T |
| AR-TCCC-3 | AR | TCCC | TCGCCTCCACCCTGTTGGTT | 273. | 333 | C |
| HBB-TTTV-1 | NBB | TTTG | TACTGATGGTATGGGCCAA | 274. | 203 | C |
| HBB-TTTV-2 | NBB | TTTG | AAGTCCAACTCCTAAGCCAG | 275. | 150 | C |
| HBB-TTTV-3 | NBB | TTTG | CAAGTGTATTTACGTAATAT | 276. | 248 | T |
| HBB-ATTV-1 | NBB | ATTG | GCCAACCCTAGGGTGTGGCT | 277. | 71 | T |

TABLE 2B-continued

Cas12a crRNAs for gene activation experiments

| gene crRNA ID | name | 4 nt PAM | 20 nt Spacer | SEQ ID NO: | Distance from TSS (bp)1 | Strand |
|---|---|---|---|---|---|---|
| HBB-ATTV-2 | NBB | ATTG | CTACTAAAAACATCCTCCTT | 278. | 226 | T |
| HBB-ATTV-3 | NBB | ATTG | GGAAAACGATCTTCAATATG | 279. | 293 | T |
| HBB-CTTV-1 | NBB | CTTA | GACCTCACCCTGTGGAGCCA | 280. | 90 | C |
| HBB-CTTV-2 | NBB | CTTA | GGAGTTGGACTTCAAACCCT | 281. | 154 | T |
| HBB-CTTV-3 | NBB | CTTA | CCAAGCTGTGATTCCAAATA | 282. | 269 | C |
| HBB-TATV-1 | NBB | TATG | CCCAGCCCTGGCTCCTGCCC | 283. | 28 | T |
| HBB-TATV-2 | NBB | TATC | TCTTGGCCCCATACCATCAG | 284. | 197 | T |
| HBB-TATV-3 | NBB | TATC | CCAAAGCTGAATTATGGTAG | 285. | 369 | C |
| HBB-TGTV-1 | NBB | TGTC | ATCACTTAGACCTCACCCTG | 286. | 98 | C |
| HBB-TGTV-2 | NBB | TGTA | CTGATGGTATGGGGCCAAGA | 287. | 203 | C |
| HBB-TGTV-4 | NBB | TGTA | GATGGATCTCTTCCTGCGTC | 288. | 393 | T |
| HBB-TTCV-1 | NBB | TTCA | AACCCTCAGCCCTCCCTCTA | 289. | 167 | T |
| HBB-TTCV-2 | NBB | TTCC | AAATATTACGTAAATACACT | 290. | 254 | C |
| HBB-TTCV-3 | NBB | TTCA | GCTTTGGGATATGTAGATGG | 291. | 378 | T |
| HBB-CTCC-1 | NBB | CTCC | CTGCTCCTGGGAGTAGATTG | 292. | 51 | T |
| HBB-CTCC-2 | NBB | CTCC | CTCTAAGATATATCTCTTGG | 293. | 183 | T |
| HBB-CTCC-3 | NBB | CTCC | AGAATATGCAAAATACTTAC | 294. | 417 | T |
| HBB-TACC-1 | NBB | TACC | TGTCCTTGGCTCTTCTGGCA | 295. | 126 | T |
| HBB-TACC-2 | NBB | TACC | ATCAGTACAAATTGCTACTA | 296. | 212 | T |
| HBB-TACC-3 | NBB | TACC | ATAATTCAGCTTTGGGATAT | 297. | 370 | T |
| NPY1R-TTTV-1 | NPY1R | TTTC | AAGCCTCGGGAAACTGCCCT | 298. | 256 | C |
| NPY1R-TTTV-2 | NPY1R | TTTC | TTTGTTTGCAGGTCAGTGCC | 299. | 299 | T |
| NPY1R-TTTV-3 | NPY1R | TTTG | GGCTGGCGCTCGAGCTCTCC | 300. | 350 | C |
| NPY1R-ATTV-1 | NPY1R | ATTC | CTGGTTTGGGCTGGCGCTCG | 301. | 382 | C |
| NPY1R-ATTV-2 | NPY1R | ATTA | GTGCCATTATTGTGGCGAAT | 302. | 407 | C |
| NPY1R-ATTV-3 | NPY1R | ATTC | TCGGCACTGGCGTGAGAGTT | 303. | 464 | C |
| NPY1R-CTTV-1 | NPY1R | CTTC | CCCGGAGTCGAGGACTGTGG | 304. | 230 | C |
| NPY1R-CTTV-2 | NPY1R | CTTC | GGCCACAAGATGGCACTGAC | 305. | 314 | C |
| NPY1R-CTTV-3 | NPY1R | CTTA | TAAAGTGAGGAAAACAAATT | 306. | 485 | C |
| NPY1R-TTCV-1 | NPY1R | TTCC | CCGGAGTCGAGGACTGTGGG | 307. | 229 | C |
| NPY1R-TTCV-2 | NPY1R | TTCG | GCCACAAGATGGCACTGACC | 308. | 313 | C |
| NPY1R-TTCV-3 | NPY1R | TTCC | CAGCGAGCCTTGATTCCT | 309. | 376 | C |
| NPY1R-CTCC-1 | NPY1R | CTCC | GGGGAAGGCAGGGCATTC | 310. | 243 | T |
| NPY1R-CTCC-2 | NPY1R | CTCC | AGCCGGGTATGACTTCGGCC | 311. | 330 | C |
| NPY1R-CTCC-3 | NPY1R | CTCC | TTICTITGGCCCACTGAGAA | 312. | 554 | T |

TABLE 2B-continued

Cas12a crRNAs for gene activation experiments

| gene crRNA ID | name | 4 nt PAM | 20 nt Spacer | SEQ ID NO: | Distance from TSS (bp)[1] | Strand |
|---|---|---|---|---|---|---|
| VEGFA-TTTV-1 | VEGFA | TTTC | AGGCTGTGAACCTTGGTGGG | 313. | 200 | C |
| VEGFA-TTTV-2 | VEGFA | TTTC | CTGCTCCCTCCTCGCCAATG | 314. | 274 | C |
| VEGFA-TTTV-3 | VEGFA | TTTG | CTAGGAATATTGAAGGGGGC | 315. | 338 | T |
| VEGFA-ATTV-1 | VEGFA | ATTG | CGGCGGGCTGCGGGCCAGGC | 316. | 159 | C |
| VEGFA-ATTV-2 | VEGFA | ATTA | CCCATCCGCCCCCGGAAACT | 317. | 274 | T |
| VEGFA-ATTV-3 | VEGFA | ATTC | CTAGCAAAGAGGGAACGGCT | 318. | 326 | C |
| VEGFA-CTTV-1 | VEGFA | CTTC | CCCTTCATTGCGGCGGGCTG | 319. | 114 | T |
| VEGFA-CTTV-2 | VEGFA | CTTC | CCCTTCATTGCGGCGGGCTG | 320. | 169 | C |
| VEGFA-CTTV-3 | VEGFA | CTTC | CCCTGCCCCCTTCAATATTC | 321. | 346 | C |
| VEGFA-GTTV-1 | VEGFA | GTTC | ACAGCCTGAAAATTACCCAT | 322. | 209 | T |
| VEGFA-GTTV-2 | VEGFA | GTTA | CGTGCGGACAGGGCCTGAGA | 323. | 303 | T |
| VEGFA-GTTV-3 | VEGFA | GTTG | GAGCGGGGAGAAGGCCAGGG | 324. | 435 | C |
| VEGFA-TTCV-1 | VEGFA | TTCC | ACACGCGGCTCGGGCCCGGG | 325. | 115 | T |
| VEGFA-TTCV-2 | VEGFA | TTCA | GGCTGTGAACCTIGGIGGGG | 326. | 199 | C |
| VEGFA-TTCV-3 | VEGFA | TTCC | TGCTCCCTCCTCGCCAATGC | 327. | 213 | C |
| VEGFA-TTCV-4 | VEGFA | TTCC | CCTTCATTGCGGCGGGCTGC | 328. | 185 | C |
| VEGFA-TTCV-5 | VEGFA | TTCC | CCTGCCCCCTICAATATTCC | 329. | 362 | C |
| VEGFA-TCCC-1 | VEGFA | TCCC | CTTCATTGCGGCGGGCTGCG | 330. | 167 | C |
| VEGFA-TCCC-2 | VEGFA | TCCC | TCCTCGCCAATGCCCCGCGG | 331. | 266 | C |
| VEGFA-TCCC-3 | VEGFA | TCCC | CTGCCCCCTICAATATTCCT | 332. | 344 | C |
| VEGFA-CTCC-1 | VEGFA | CTCC | TCGCCAATGCCCCGCGGGCG | 333. | 263 | C |
| VEGFA-CTCC-2 | VEGFA | CTCC | CTCCTCGCCAATGCCCCGCG | 334. | 267 | C |
| VEGFA-CTCC-3 | VEGFA | CTCC | AGGATTCCAATAGATCTGTG | 335. | 407 | C |

C, Coding; T, template; [1], measured from the TSS to the -4 position of the PAM for template-strand guides or the 20th nt of the spacer for coding-strand guides

TABLE 2C

SpCas9 sgRNAs for VEGFA gene activation experiments

| guide ID | 3 nt PAM | 20 nt Spacer | SEQ ID NO: | Distance from TSS (bp)[1] | Strand |
|---|---|---|---|---|---|
| VEGFA-NGG-a-1 | AGG | GTGTGCAGACGGCAGTCACT | 336. | 571 | coding |
| VEGFA-NGG-a-2 | AGG | GAGCAGCGTCTTCGAGAGTG | 337. | 509 | coding |
| VEGFA-NGG-a-3 | TGG | GGTGAGTGAGTGTGTGCGTG | 338. | 469 | coding |
| VEGFA-NGG-b-4 | AGG | GGGGCGGATGGGTAATTTTC | 339. | 217 | coding |
| VEGFA-NGG-b-5 | AGG | GGCATTGGCGAGGAGGGAGC | 340. | 272 | template |
| VEGFA-NGG-b-6 | AGG | GCAAAGAGGGAACGGCTCTC | 341. | 320 | coding |

[1], measured from the TSS to the -3 position of the PAM for coding-strand guides or the 20th nt of the spacer for template-strand guides

TABLE 2D

Cas12a crRNAs for base editor experiments

| crRNA ID | gene name | 4 nt PAM | 20 nt Spacer | SEQ ID NO: |
|---|---|---|---|---|
| TTTA-3 | FANCF | TTTA | TCCGTGTTCCTTGACTCTGG | 342. |
| TTTC-1 | DNMT1 | TTTC | CCTCACTCCTGCTCGGTGAA | 343. |
| TTTC-3 | EMX1 | TTTC | TCATCTGTGCCCCTCCCTCC | 344. |
| TTTC-6 | RUNX1 | TTTC | AGCCTCACCCCTCTAGCCCT | 345. |
| TTTC-7 | RUNX1 | TTTC | TTCTCCCTCTGCTGGATAC | 346. |
| TTTC-8 | FANCF | TTTC | CGAGCTTCTGGCGGTCTCAA | 347. |
| TTTG-4 | EMX1 | TTTG | TGGTTGCCCACCCTAGTCAT | 348. |
| TTTG-7 | FANCF | TTTG | GTCGGCATGGCCCCATTCGC | 349. |

TABLE 3A

Oligonucleotides used in this study-For T7E1 and RFLP experiments

| description | sequence | SEQ ID NO: |
|---|---|---|
| forward PCR primer to amplify DNMT1 locus in human cells | CCAGAATGCACAAAGTACTGCAC | 350. |
| reverse PCR primer to amplify DNMT1 locus in human cells | GCCAAAGCCCGAGAGAGTGCC | 351. |
| forward PCR primer to amplify CFTR locus in human cells | GCTGTGTCTGTAAACTGATGGCTAACA | 352. |
| reverse PCR primer to amplify CFTR locus in human cells | TTGCATTCTACTCAATTGCATTCTGTGGG | 353. |
| forward PCR primer to amplify EMX1 locus in human cells | GGAGCAGCTGGTCAGAGGGG | 354. |
| reverse PCR primer to amplify EMX1 locus in human cells | CCATAGGGAAGGGGACACTGG | 355. |
| forward PCR primer to amplify EMX1 (amplicon 2) locus in human cells | CTGCCTCCTATTCATACACACTTACGGG | 356. |
| reverse PCR primer to amplify EMX1 (amplicon 2) locus in human cells | CTCTGTTGGTGGAAACTCCCTGACC | 357. |
| forward PCR primer to amplify FANCF locus in human cells | GGGCCGGGAAAGAGTTGCTG | 358. |
| reverse PCR primer to amplify FANCF locus in human cells | GCCCTACATCTGCTCTCCCTCC | 359. |
| forward PCR primer to amplify RUNX1 locus in human cells | CCAGCACAACTTACTCGCACTTGAC | 360. |
| reverse PCR primer to amplify RUNX1 locus in human cells | CATCACCAACCCACAGCCAAGG | 361. |
| forward PCR primer to amplify VEGFA locus in human cells | CAGCTCCACAAACTTGGTGCCAAATTC | 362. |
| reverse PCR primer to amplify VEGFA locus in human cells | CCGCAATGAAGGGGAAGCTCGAC | 363. |
| forward PCR primer to amplify VEGFA (amplicon 2) locus in human cells | CGCTGTTCAGGTCTCTGCTAGAAGTAGG | 364. |
| reverse PCR primer to amplify VEGFA (amplicon 2) locus in human cells | CCAGACCAGAGACCACTGGGAAG | 365. |
| forward PCR primer to amplify Matched Site 1 locus in human cells | GACAAATGTATCATGCTATTATAAGATGTTGAC | 366. |
| reverse PCR primer to amplify Matched Site 1 locus in human cells | CCATTTACTGAGAGTAATTATAATTGTGC | 367. |
| forward PCR primer to amplify Matched Site 5 locus in human cells | CCAAGGACAGGAATATCTTATACCCTCTGT | 368. |

TABLE 3A-continued

Oligonucleotides used in this study-For T7E1 and RFLP experiments

| description | sequence | SEQ ID NO: |
|---|---|---|
| reverse PCR primer to amplify Matched Site 5 locus in human cells | TGTCATTGTCCTTGTCCTTTAGCTACCG | 369. |

TABLE 3B

Oligonucleotides used in this study-For PAM determination assay (PAMDA) and other in vitro cleavage experiments

| description | sequence | SEQ ID NO: |
|---|---|---|
| reverse PCR primer for amplifying randomized PAM locus | CAAAACAGCCAAGCTTGCATGC | 370. |
| forward PCR primer for amplifying randomized PAM locus, adding CCAT barcode | AGCTGCCATCGGTATTTCACACCGCATACGTAC | 371. |
| forward PCR primer for amplifying randomized PAM locus, adding GCAA barcode | AGCTGGCAACGGTATTTCACACCGCATACGTAC | 372. |
| forward PCR primer for amplifying randomized PAM locus, adding ATGC barcode | AGCTGATGCCGGTATTTCACACCGCATACGTAC | 373. |
| forward PCR primer for amplifying randomized PAM locus, adding GATG barcode | AGCTGGATGCGGTATTTCACACCGCATACGTAC | 374. |
| forward PCR primer for amplifying randomized PAM locus, adding CGAT barcode | AGCTGCGATCGGTATTTCACACCGCATACGTAC | 375. |
| top strand oligo for NNNNNNNN PAM depletion library spacer 1 to be cloned into EcoRI/SphI of p11-lacY-wtx1 | AGACCGGAATTCNNNGTNNNNNNNNNNGGAATCCCTTCTGCAGCACCTGGGCGCAGGTCACGAGGCATG | 376. |
| top strand oligo for NNNNNNNN PAM depletion library spacer 2 to be cloned into EcoRI/SphI of p11-lacY-wtx1 | AGACCGGAATTCNNNGTNNNNNNNNNNCTGATGGTCCATGTCTGTTACTCGCGCAGGTCACGAGGCATG | 377. |
| reverse primer to fill in library oligos | /5Phos/CCTCGTGACCTGCGC | 378. |
| top strand for spacer 1 with TTTA PAM target to be cloned into EcoRI/SphI of p11-lacY-wtx1 | AATTCTTTAGGAATCCCTTCTGCAGCACCTGGGCATG | 379. |
| bottom strand for spacer 1 with TTTA PAM target to be cloned into EcoRI/SphI of p11-lacY-wtx1 | CCCAGGTGCTGCAGAAGGGATTCCTAAAG | 380. |
| top strand for spacer 1 with CTTA PAM target to be cloned into EcoRI/SphI of p11-lacY-wtx1 | AATTCCTTAGGAATCCCTTCTGCAGCACCTGGGCATG | 381. |
| bottom strand for spacer 1 with CTTA PAM target to be cloned into EcoRI/SphI of p11-lacY-wtx1 | CCCAGGTGCTGCAGAAGGGATTCCTAAGG | 382. |
| top strand for spacer 1 with ACCT PAM target to be cloned into EcoRI/SphI of p11-lacY-wtx1 | AATTCACCTGGAATCCCTTCTGCAGCACCTGGGCATG | 383. |
| bottom strand for spacer 1 with ACCT PAM target to be cloned into EcoRI/SphI of p11-lacY-wtx1 | CCCAGGTGCTGCAGAAGGGATTCCAGGTG | 384. |

TABLE 3B-continued

Oligonucleotides used in this study-For PAM determination assay (PAMDA) and other in vitro cleavage experiments

| description | sequence | SEQ ID NO: |
|---|---|---|
| top strand for spacer 2 with TTTA PAM target to be cloned into EcoRI/SphI of p11-lacY-wtx1 | AATTCTTTACTGATGGTCCATGTCTGTTAC TCGCATG | 385. |
| bottom strand for spacer 2 with TTTA PAM target to be cloned into EcoRI/SphI of p11-lacY-wtx1 | CGAGTAACAGACATGGACCATCAGTAAAG | 386. |
| top strand for spacer 2 with CTTA PAM target to be cloned into EcoRI/SphI of p11-lacY-wtx1 | AATTCCTTACTGATGGTCCATGTCTGTTAC TCGCATG | 387. |
| bottom strand for spacer 2 with CTTA PAM target to be cloned into EcoRI/SphI of p11-lacY-wtx1 | CGAGTAACAGACATGGACCATCAGTAAGG | 388. |
| top strand for spacer 2 with ACCT PAM target to be cloned into EcoRI/SphI of p11-lacY-wtx1 | AATTCACCTCTGATGGTCCATGTCTGTTAC TCGCATG | 389. |
| bottom strand for spacer 2 with ACCT PAM target to be cloned into EcoRI/SphI of p11-lacY-wtx1 | CGAGTAACAGACATGGACCATCAGAGGTG | 390. |

TABLE 3C

Oligonucleotides used in this study-For activator RT-qPCR experiments

| description | sequence | SEQ ID NO: |
|---|---|---|
| forward RT-qPCR primer for the human NPY1R gene | ATGGTGAGCAGAGTGCCCTATC | 391. |
| reverse RT-qPCR primer for the human NPY1R gene | ATGGTCCCTGGCAGTCTCCAAA | 392. |
| forward RT-qPCR primer for the human AR gene | CCATCGGACTCTCATAGGTTGTC | 393. |
| reverse RT-qPCR primer for the human AR gene | GACCTGTACTTATTGTCTCTCATC | 394. |
| forward RT-qPCR primer for the human HBB gene | GCACGTGGATCCTGAGAACT | 395. |
| reverse RT-qPCR primer for the human HBB gene | ATTGGACAGCAAGAAAGCGAG | 396. |
| forward RT-qPCR primer for the human HPRT1 gene | CATTATGCTGAGGATTTGGAAAGG | 397. |
| reverse RT-qPCR primer for the human HPRT1 gene | CTTGAGCACACAGAGGGCTACA | 398. |

TABLE 3D

Oligonucleotides used in this study-For base editor deep sequencing experiments

| description | sequence | SEQ ID NO: |
|---|---|---|
| forward PCR primer to amplify TTTA PAM site 3 in human cells | GCTCCAGAGCCGTGCGAATGG | 399. |
| reverse PCR primer to amplify TTTA PAM site 3 in human cells | GCCCTACATCTGCTCTCCCTCC | 400. |

TABLE 3D-continued

Oligonucleotides used in this study-For base editor deep sequencing experiments

| description | sequence | SEQ ID NO: |
|---|---|---|
| forward PCR primer to amplify TTTC PAM site 1 in human cells | CAGCTGACCCAATAAGTGGCAGAGTG | 401. |
| reverse PCR primer to amplify TTTC PAM site 1 in human cells | TCAGGTTGGCTGCTGGGCTGG | 402. |
| forward PCR primer to amplify TTTC PAM site 3 in human cells | CCCCAGTGGCTGCTCTGGG | 403. |
| reverse PCR primer to amplify TTTC PAM site 3 in human cells | CATCGATGTCCTCCCCATTGGC | 404. |
| forward PCR primer to amplify TTTC PAM site 6 in human cells | GCTGTCTGAAGCCATCGCTTCC | 405. |
| reverse PCR primer to amplify TTTC PAM site 6 in human cells | CAGAGGTATCCAGCAGAGGGGAG | 406. |
| forward PCR primer to amplify TTTC PAM site 7 in human cells | CCTTCGGAGCGAAAACCAAGACAG | 407. |
| reverse PCR primer to amplify TTTC PAM site 7 in human cells | CAGGCAGGACGAATCACACTGAATG | 408. |
| forward PCR primer to amplify TTTC PAM site 8 in human cells | GCTCCAGAGCCGTGCGAATGG | 409. |
| reverse PCR primer to amplify TTTC PAM site 8 in human cells | GCACCTCATGGAATCCCTTCTGC | 410. |
| forward PCR primer to amplify TTTG PAM site 4 in human cells | GAAGCTGGAGGAGGAAGGGC | 411. |
| reverse PCR primer to amplify TTTG PAM site 4 in human cells | CAGCAGCAAGCAGCACTCTGC | 412. |
| forward PCR primer to amplify TTTG PAM site 7 in human cells | GCCCTCTTGCCTCCACTGGTTG | 413. |
| reverse PCR primer to amplify TTTG PAM site 7 in human cells | CCAATAGCATTGCAGAGAGGCGT | 414. |

Cell Culture Conditions.

Human U2OS (from Toni Cathomen, Freiburg) and HEK293 cells (Invitrogen) were cultured in Advanced Dulbecco's Modified Eagle Medium (A-DMEM) and DMEM, respectively, supplemented with 10% heat-inactivated FBS, 1% and penicillin and streptomycin, and 2 mM GlutaMax (with the exception that HEK293 cells cultured for experiments analyzed by RT-qPCR use media containing 0.1% penicillin and streptomycin that lacked GlutaMax). All cell culture reagents were purchased from Life Technologies, and cells were grown at 37° C. in 5% $CO_2$. Media supernatant was analyzed biweekly for the presence of Mycoplasma, and cell line identities were confirmed by STR profiling (ATCC). Unless otherwise indicated, negative control transfections included Cas12a expression and U6-null plasmids.

Assessment of Gene and Base Editing by T7E1 or Deep-Sequencing.

For nuclease and base editor experiments, Cas12a and crRNA expression plasmids (500 ng and 250 ng, respectively) were electroporated into approximately $2 \times 10^5$ U2OS cells via the DN-100 program with the SE Cell Line Nucleofector Kit using a 4D-Nucleofector (Lonza). Genomic DNA (gDNA) was extracted approximately 72 or 120 hours post-nucleofection (for nuclease or base editing experiments, respectively) using the Agencourt DNAdvance Nucleic Acid Isolation Kit (Beckman Coulter), or by custom lysis and paramagnetic bead extraction. Paramagnetic beads prepared similar to as previously described (Rohland et al., Genome Res., 2012, 22:939-46)(GE Healthcare Sera-Mag SpeedBeads (Fisher Scientific) washed in 0.1× TE and suspended in 20% PEG-8000 (w/v), 1.5 M NaCl, 10 mM Tris-HCl pH 8, 1 mM EDTA pH 8, and 0.05% Tween20). For cell lysis, media supernatant was removed, a 500 µL PBS wash was performed, and the cells were treated with 200 µL lysis buffer (100 mM Tris HCl pH 8.0, 200 mM NaCl, 5 mM EDTA, 0.05% SDS, 1.4 mg/mL Proteinase K (NEB), and 12.5 mM DTT) for 12-20 hours at 55° C. To extract gDNA, the lysate was combined with 165 µL paramagnetic beads, mixed thoroughly, incubated for 5 minutes, separated on a magnetic plate and washed 3 times with 70% EtOH, allowed to dry for 5 minutes, and eluted in 65 µL elution buffer (1.2 mM Tris-HCl pH 8.0). Genomic loci were amplified by PCR with Phusion Hot Start Flex DNA Polymerase (New England Biolabs; NEB) using 100 ng of gDNA as a template and the primers listed in Table 3. Following analysis on a QIAxcel capillary electrophoresis machine (Qiagen), PCR products were purified with using paramagnetic beads.

For nuclease experiments, the percent modification of endogenous human target sites was determined by T7 Endonuclease I (T7EI) assays, similar to as previously described (Reyon et al., Nat Biotechnol., 2012, 30:460-5). Briefly, 200 ng of purified PCR products were denatured, annealed, and digested with 10 U T7EI (NEB) at 37° C. for 25 minutes. Digests were purified with paramagnetic beads and analyzed using a QIAxcel to estimate target site modification.

For base editing experiments, targeted deep sequencing was performed essentially as previously described (Kleinstiver et al., Nature, 2016, 529:490-5). Dual-indexed Tru-seq libraries were generated from purified and pooled PCR products using a KAPA HTP Library Preparation Kit (KAPA BioSystems) and sequenced on an Illumina MiSeq Sequencer. Samples were sequenced to an average read count of 55,000 and a minimum of 8,500 reads. Nucleotide substitutions and insertion or deletion mutations (indels) were analyzed using a modified version of CRISPResso (Pinello et al., Nat Biotechnol., 2016, 34:695-7), with an additional custom analysis performed to examine indel percentages (defined as [modified reads—substitution only reads]/total reads*100), in a 44 nt window encompassing the −14 to +30 region of each target site (an additional 10 nt upstream of the 4 nt PAM and 10 nt downstream of the 20 nt spacer sequence).

GUIDE-seq.

GUIDE-seq experiments were performed as previously described (Tsai et al., Nat Biotechnol., 2015, 33:187-197). Briefly, U2OS cells were electroporated as described above but including 100 pmol of the double-stranded oligodeoxynucleotide (dsODN) GUIDE-seq tag. Restriction-fragment length polymorphisms (RFLP) assays (performed as previously described; Kleinstiver et al., Nature, 2015, 523:481-5) and T7E1 assays (as described above) were performed to assess GUIDE-seq tag integration and on-target modification percentages, respectively. GUIDE-seq libraries were sequenced using an Illumina MiSeq sequencer, and data was analyzed using guideseq (Tsai et al., Nat Biotechnol., 2016, 34:483) v1.1 with a 75 bp window and allowing up to 9 mismatches prior to downstream data processing. High-confidence, cell-type-specific, single-nucleotide polymorphisms (SNPs) were identified using SAMTools.

Gene Activation Experiments.

For experiments with crRNAs or sgRNAs targeting the VEGFA promoter, $1.6 \times 10^5$ HEK293 cells per well were seeded in 24-well plates roughly 24 hours prior to transfection with plasmids encoding Cas12a or Cas9 activators and pools of crRNAs or sgRNAs (750 ng and 250 ng, respectively), 1.5 µL TransIT-LT1 (Mirus), and Opti-MEM to a total volume of 50 µL. The cell culture media was changed 22 hours post-transfection, and aliquots of the media supernatant were collected 44 hours post-transfection to determine VEGFA concentration using a Human VEGF Quantikine ELISA Kit (R&D Systems).

For experiments with crRNAs targeting the AR, HBB, or NPY1R promoters, $8.6 \times 10^4$ HEK293 cells per well were seeded in 12-well plates roughly 24 hours prior to transfection with 750 ng Cas12a activator expression plasmid, 250 ng crRNA plasmid pools, 3 µL TransIT-LT1 (Mirus), and 100 µL Opti-MEM. Total RNA was extracted from the transfected cells 72 hours post-transfection using the NucleoSpin RNA Plus Kit (Clontech). cDNA synthesis using a High-Capacity RNA-to-cDNA kit (ThermoFisher) was performed with 250 ng of purified RNA, and 3 µL of 1:20 diluted cDNA was amplified by quantitative reverse transcription PCR (RT-qPCR) using Fast SYBR Green Master Mix (ThermoFisher) and the primers listed in Table 3. RT-qPCR reactions were performed on a LightCycler480 (Roche) with the following cycling program: initial denaturation at 95° C. for 20 seconds (s) followed by 45 cycles of 95° C. for 3 s and 60° C. for 30 s. If sample amplification did not reach the detection threshold after 35 cycles, Ct (Cycles to threshold) values are considered as 35 due to Ct fluctuations typical of transcripts expressed at very low levels. Gene expression levels over negative controls experiments (Cas12a activator and empty crRNA plasmids) were normalized to the expression of HPRT1.

Expression and Purification of Cas12a Proteins.

Plasmids encoding Cas12a-SV40NLS-6×His fusion proteins were transformed into Rosetta 2 (DE3) E. coli, and single colonies were inoculated into 25 mL LB medium cultures containing 50 mg/L kanamycin and 25 mg/L chloramphenicol (Kan/Cm) prior to growth at 25° C. for 16 hours. Starter cultures were then diluted 1:100 into 150 mL LB medium containing Kan/Cm and grown at 37° C. until the OD600 reached 0.4. Cultures were then induced with 0.2 mM isopropyl β-D-thiogalactopyranoside prior to shaking at 18° C. for 23 hours. Cell pellets from 50 mL of the culture were harvested by centrifugation at 1200 g for 15 minutes and suspended in 1 mL lysis buffer containing 20 mM Hepes pH 7.5, 100 mM KCl, 5 mM MgCl2, 5% glycerol, 1 mM DTT, Sigmafast protease inhibitor (Sigma-Aldrich), and 0.1% Triton X-100. The cell suspension was loaded into a 1 mL AFA fiber milliTUBE (Covaris) and was lysed using an E220evolution focused-ultrasonicator (Covaris) according to the following conditions: peak intensity power of 150 W, 200 cycles per burst, duty factor of 10%, and treatment for 20 minutes at 5° C. The cell lysate was centrifuged for 20 minutes at 21,000 g and 4° C., and the supernatant was mixed with an equal volume of binding buffer (lysis buffer+ 10 mM imidazole), added to 400 µL of HisPur Ni-NTA Resin (Thermo Fisher Scientific) that was pre-equilibrated in binding buffer, and rocked at 4° C. for 8 hours. The protein-bound resin was washed three times with 1 mL wash buffer (20 mM Hepes pH 7.5, 500 mM KCl, 5 mM MgCl2, 5% glycerol, 25 mM imidazole, and 0.1% Triton X-100), washed once with 1 mL binding buffer, and then three sequential elutions were performed with 500 µL elution buffer (20 mM Hepes pH 7.5, 100 mM KCl, 5 mM MgCl2, 10% glycerol, and 500 mM imidazole). Select elutions were pooled and dialyzed using Spectra/Por 4 Standard Cellulose Dialysis Tubing (Spectrum Chemical Manufacturing Corp) in three sequential 1:500 buffer exchanges, the first two into dialysis buffer (300 mM NaCl, 10 mM Tris-HCl pH 7.4, 0.1 mM EDTA, and 1 mM DTT) and the last into dialysis buffer containing 20% glycerol. Proteins were then concentrated with Amicon Ultra-0.5 mL Centrifugal Filter Units (Millipore Sigma), diluted with an equal volume of dialysis buffer with 80% glycerol, and stored at −20° C.

In Vitro Cleavage Reactions.

Cas12a crRNAs were in vitro transcribed from roughly 1 µg of HindIII linearized crRNA transcription plasmid using the T7 RiboMAX Express Large Scale RNA Production kit (Promega) at 37° C. for 16 hours. The DNA template was degraded by the addition of 1 µL RQ1 DNase at 37° C. for 15 minutes, and the RNA was subsequently purified with the miRNeasy Mini Kit (Qiagen). In vitro cleavage reactions consisted of 25 nM PvuI-linearized substrate plasmid, 300 nM crRNA, and 200 nM purified Cas12a protein in cleavage buffer (10 mM Hepes pH 7.5, 150 mM NaCl and 5 mM MgCl2), and were performed at 37° C. unless otherwise indicated. Plasmid substrates for temperature tolerance assays encoded the PAMDA site 2 spacer with a TTTA PAM. Cleavage reaction master-mixes were prepared and then aliquoted into 5 µL volumes for each time point, incubated in a thermal cycler, and halted by the addition of 10 µL of stop buffer (0.5% SDS, 50 mM EDTA). Stopped aliquots were purified with paramagnetic beads, and the percent cleavage was quantified by QIAxcel ScreenGel Software (v1.4).

PAM Determination Assay.

Plasmid libraries encoding target sites with randomized sequences were cloned using Klenoq(-exo) (NEB) to fill in the bottom strands of two separate oligos harboring 10 nt randomized sequences 5' of two distinct spacer sequences (Table 3). The double-stranded product was digested with EcoRI and ligated into EcoRI and SphI digested p11-lacY-wtx1 (Addgene plasmid 69056; a gift from Huimin Zhao). Ligations were transformed into electrocompetent XL1 Blue E. coli, recovered in 9 mL of SOC at 37° C. for 1 hour, and then grown for 16 hours in 150 mL of LB medium with 100 mg/L carbenicillin. The complexity of each library was estimated to be greater than $10^6$ based on the number of transformants observed.

Cleavage reactions of the randomized PAM plasmid libraries were performed as described above, with aliquots being stopped at 3, 6, 12, 24, and 48 minutes. Reactions were purified with magnetic beads and approximately 1-5 ng was used as template for PCR amplification of uncleaved molecules with Phusion Hot Start Flex DNA Polymerase (NEB) for 15 cycles. During the PCR reactions, a 4 nt unique molecular index (UMI) was added upstream of the PAM to enable demultiplexing of the time-point samples, and products were also generated from an undigested plasmid to determine initial PAM representation in the libraries. Purified PCR products were quantified with QuantiFluor dsDNA System (Promega), normalized, and pooled for library preparation with Illumina dual-indexed adapters using a KAPA HTP PCR-free Library Preparation Kit (KAPA Bio-Systems). Libraries were quantified using the Universal KAPA Illumina Library qPCR Quantification Kit (KAPA Biosystems) and sequenced on an Illumina MiSeq sequencer using a 300-cycle v2 kit (Illumina).

Sequencing reads were analyzed using a custom Python script to estimate cleavage rates on each PAM for a given protein. Paired-end reads were filtered by Phred score (≥Q30) and then merged with the requirement of perfect matches of time point UMIs, PAM, and spacer sequence. Counts were generated for every 4 and 5 nt PAM for all time points, protein, and spacer. PAM counts were then corrected for inter-sample differences in sequencing depth, converted to a fraction of the initial representation of that PAM in the original plasmid library (as determined by the undigested control), and then normalized to account for the increased fractional representation of uncleaved substrates over time due to depletion of cleaved substrates (by selecting the 5 PAMs with the highest average counts across all time points to represent the profile of uncleavable substrates). The depletion of each PAM over time was then fit to an exponential decay model ($y(t)=Ae^{(-kt)}$, where $y(t)$ is the normalized PAM count, t is the time (minutes), k is the rate constant, and A is a constant), by linear least squares regression.

Targeting Range Calculations.

The targeting ranges of wild-type and variant AsCas12a nucleases were assessed on various annotated genomic elements using GENCODE's Release 27 GTF file. Complete occurrences of targetable 4 nt PAMs were enumerated within regions encompassing 1 kb upstream of all transcription start sites (TSSs), within the first exon of all genes, and within all annotated miRNAs. Parameter value(s) for each element in the GTF file were: Exon1, feature-type exon, exon_number 1, gene_type protein_coding; TSS, feature-type transcript, gene_type protein_coding or miRNA; miRNA, feature-type gene, gene_type miRNA. For each element, PAM counts were normalized by length and were visualized through a boxplot. The PAM identification and enumeration script will be made available upon request. Targetable PAMs for Cas12a nucleases included: TTTV, for wild-type AsCas12a; TTYN, RTTC, CTTV, TATM, CTCC, TCCC, TACA (tier 1), and RTTS, TATA, TGTV, ANCC, CVCC, TGCC, GTCC, TTAC (tier 2) PAMs for eAsCas12a (see FIG. 1g and Extended Data FIG. 5h); TATV, AsCas12a-RVR; and TYCV for AsCas12a-RR.

DNA Detection Assays.

Cas12a-crRNA RNP complexes were formed by incubating 500 nM purified AsCas12a protein and 750 nM chemically synthesized crRNA (IDT) at 4° C. for 5 minutes. All reactions were carried out in 10 mM Hepes pH 7.5, 150 mM NaCl, and 5 mM $MgCl_2$. Next, RNPs were diluted to 100 nM and mixed with 250 nM linearized activating plasmid DNA harboring a matched target site with a canonical (TTTA) or non-canonical (CTTA or ACCT) PAM or an unrelated target site (negative control) in a total volume of 15 µL. Reactions were allowed to proceed at 37° C. for 30 minutes, prior to incubation at 4° C. For fluorescent detection, 10 µL of the RNP/target-DNA reaction was then mixed with an equal volume of 100 nM custom fluorescent-quenched reporter (IDT) in a low-volume 384-well black plate (Corning). Detection reactions were conducted at 37° C. for three hours with measurements taken every 60 seconds with $\lambda_{ex}=485$ nm and $\lambda_{em}=528$ nm, using a Synergy HTX Microplate Reader (BTX).

Sequences
The following constructs were used in the Examples below.
BPK3079: U6-AsCas12a-crRNA-BsmBIcassette
U6 promoter in black, AsCas12a crRNA in italics, guanine necessary for U6 transcription in bold, spacer entry cassette in lower case with BsmBI sites double underlined, U6 terminator (TTTTTTT) double underlined in bold (SEQ ID NO: 415)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCG*TAATTTCTACTCTTGTAGAT*ggagacgattaatgcgtctccTTTTTTT

-continued

BPK3082: U6-LbCas12a-crRNA-BsmBIcassette
U6 promoter in green, LbCas12a crRNA colored in italics, guanine necessary for U6 transcription
in bold, spacer entry cassette in lower case with BsmBI sites double underlined,, U6 terminator
(TTTTTTT) double underlined in bold (SEQ ID NO: 416)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCGAATTTCTACTAAGTGTAGATggagacgattaatgcgtctccTTTTTTT

BPK4446: U6-FnCas12a-crRNA-BsmBIcassette
U6 promoter in black, FnCas12a crRNA colored in italics, guanine necessary for U6 transcription in
bold, spacer entry cassette in lower case with BsmBI sites double underlined, U6 terminator
(TTTTTTT) double underlined in bold (SEQ ID NO: 417)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCGAATTTCTACTGTTGTAGATggagacgattaatgcgtctccTTTTTTT

BPK4449: U6-MbCas12a-crRNA-BsmBIcassette
U6 promoter in black, MbCas12a crRNA colored in italics, guanine necessary for U6 transcription
in bold, spacer entry cassette in lower case with BsmBI sites double underlined, U6 terminator
(TTTTTTT) double underlined in bold (SEQ ID NO: 418)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCGAATTTCTACTGTTTGTAGATggagacgattaatgcgtctccTTTTTTT

MSP3491: T7-AsCas12a-crRNA-Bsalcassette
l7 promoter in black, guanine necessary for l7 transcription in bold, AsCas12a crRNA in italics,
spacer entry cassette in lower case with BsaI sites double underlined, restriction sites for DraI
(tttaaa) in lower case bold and HindIII (AAGCTT) double underlined in bold for linearization (SEQ ID NO: 419)

TAATACGACTCACTATAGTAATTTCTACTCTTGTAGATggagacccatgccatagcgttgttcggaatatgaattt ttgaacagattcaccaacacctagtggtctcctttaaaAAGCTT MSP3495: T7-LbCas12a-crRNA-Bsalcassette
T7 promoter in black, guanine necessary for T7 transcription in bold, LbCas12a crRNA in italics,
spacer entry cassette in lower case with BsaI sites double underlined, restriction sites for DraI
(tttaaa) in lower case bold and HindIII (AAGCTT) double underlined in bold for linearization:

(SEQ ID NO: 420)

TAATACGACTCACTATAGAATTTCTACTAAGTGTAGATggagacccatgccatagcgttgttcggaatatgaattt ttgaacagattcaccaacacctagtggtctcctttaaaAAGCTT Nucleotide sequence of pCAG-humanAsCpf1-NLS-3xHA
Human codon optimized AsCpf1 in normal font (NTs 1-3921), NLS in lower case
(aaaaggccggcggccacgaaaaaggccggccaggcaaaaaagaaaaag, SEQ ID NO: 21), 3xHA tag
(TACCCATACGATGTTCCAGATTACGCTTATCCCTACGACGTGCCTGATTATGCATACCCATAT
GATGTCCCCGACTATGCC, SEQ ID NO: 5) in bold (SEQ ID NO: 6)

ATGACACAGTTCGAGGGCTTTACCAACCTGTATCAGGTGAGCAAGACACTGCGGTTT

GAGCTGATCCCACAGGGCAAGACCCTGAAGCACATCCAGGAGCAGGGCTTCATCGAGGAGG

ACAAGGCCCGCAATGATCACTACAAGGAGCTGAAGCCCATCATCGATCGGATCTACAAGACC

-continued

```
TATGCCGACCAGTGCCTGCAGCTGGTGCAGCTGGATTGGGAGAACCTGAGCGCCGCCATCG

ACTCCTATAGAAAGGAGAAAACCGAGGAGACAAGGAACGCCCTGATCGAGGAGCAGGCCACA

TATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGCT

GAAGCAGCTGGGCACCGTGACCACAACCGAGCACGAGAACGCCCTGCTGCGGAGCTTCGAC

AAGTTTACAACCTACTTCTCCGGCTTTTATGAGAACAGGAAGAACGTGTTCAGCGCCGAGGAT

ATCAGCACAGCCATCCCACACCGCATCGTGCAGGACAACTTCCCCAAGTTTAAGGAGAATTGT

CACATCTTCACACGCCTGATCACCGCCGTGCCCAGCCTGCGGGAGCACTTTGAGAACGTGAA

GAAGGCCATCGGCATCTTCGTGAGCACCTCCATCGAGGAGGTGTTTTCCTTCCCTTTTTATAA

CCAGCTGCTGACACAGACCCAGATCGACCTGTATAACCAGCTGCTGGGAGGAATCTCTCGGG

AGGCAGGCACCGAGAAGATCAAGGGCCTGAACGAGGTGCTGAATCTGGCCATCCAGAAGAAT

GATGAGACAGCCCACATCATCGCCTCCCTGCCACACAGATTCATCCCCCTGTTTAAGCAGATC

CTGTCCGATAGGAACACCCTGTCTTTCATCCTGGAGGAGTTTAAGAGCGACGAGGAAGTGAT

CCAGTCCTTCTGCAAGTACAAGACACTGCTGAGAAACGAGAACGTGCTGGAGACAGCCGAGG

CCCTGTTTAACGAGCTGAACAGCATCGACCTGACACACATCTTCATCAGCCACAAGAAGCTGG

AGACAATCAGCAGCGCCCTGTGCGACCACTGGGATACACTGAGGAATGCCCTGTATGAGCGG

AGAATCTCCGAGCTGACAGGCAAGATCACCAAGTCTGCCAAGGAGAAGGTGCAGCGCAGCCT

GAAGCACGAGGATATCAACCTGCAGGAGATCATCTCTGCCGCAGGCAAGGAGCTGAGCGAG

GCCTTCAAGCAGAAAACCAGCGAGATCCTGTCCCACGCACACGCCGCCCTGGATCAGCCACT

GCCTACAACCCTGAAGAAGCAGGAGGAGAAGGAGATCCTGAAGTCTCAGCTGGACAGCCTGC

TGGGCCTGTACCACCTGCTGGACTGGTTTGCCGTGGATGAGTCCAACGAGGTGGACCCCGA

GTTCTCTGCCCGGCTGACCGGCATCAAGCTGGAGATGGAGCCTTCTCTGAGCTTCTACAACA

AGGCCAGAAATTATGCCACCAAGAAGCCCTACTCCGTGGAGAAGTTCAAGCTGAACTTTCAGA

TGCCTACACTGGCCTCTGGCTGGGACGTGAATAAGGAGAAGAACAATGGCGCCATCCTGTTT

GTGAAGAACGGCCTGTACTATCTGGGCATCATGCCAAAGCAGAAGGGCAGGTATAAGGCCCT

GAGCTTCGAGCCCACAGAGAAAACCAGCGAGGGCTTTGATAAGATGTACTATGACTACTTCCC

TGATGCCGCCAAGATGATCCCAAAGTGCAGCACCCAGCTGAAGGCCGTGACAGCCCACTTTC

AGACCCACACAACCCCCATCCTGCTGTCCAACAATTTCATCGAGCCTCTGGAGATCACAAAGG

AGATCTACGACCTGAACAATCCTGAGAAGGAGCCAAAGAAGTTTCAGACAGCCTACGCCAAG

AAAACCGGCGACCAGAAGGGCTACAGAGAGGCCCTGTGCAAGTGGATCGACTTCACAAGGG

ATTTTCTGTCCAAGTATACCAAGACAACCTCTATCGATCTGTCTAGCCTGCGGCCATCCTCTCA

GTATAAGGACCTGGGCGAGTACTATGCCGAGCTGAATCCCCTGCTGTACCACATCAGCTTCC

AGAGAATCGCCGAGAAGGAGATCATGGATGCCGTGGAGACAGGCAAGCTGTACCTGTTCCAG

ATCTATAACAAGGACTTTGCCAAGGGCCACCACGGCAAGCCTAATCTGCACACACTGTATTGG

ACCGGCCTGTTTTCTCCAGAGAACCTGGCCAAGACAAGCATCAAGCTGAATGGCCAGGCCGA

GCTGTTCTACCGCCCTAAGTCCAGGATGAAGAGGATGGCACACCGGCTGGGAGAGAAGATG

CTGAACAAGAAGCTGAAGGATCAGAAAACCCCAATCCCCGACACCCTGTACCAGGAGCTGTA

CGACTATGTGAATCACAGACTGTCCCACGACCTGTCTGATGAGGCCAGGGCCCTGCTGCCCA

ACGTGATCACCAAGGAGGTGTCTCACGAGATCATCAAGGATAGGCGCTTTACCAGCGACAAG

TTCTTTTTTCCACGTGCCTATCACACTGAACTATCAGGCCGCCAATTCCCCATCTAAGTTCAACC

AGAGGGTGAATGCCTACCTGAAGGAGCACCCCGAGACACCTATCATCGGCATCGATCGGGG
```

-continued

```
CGAGAGAAACCTGATCTATATCACAGTGATCGACTCCACCGGCAAGATCCTGGAGCAGCGGA

GCCTGAACACCATCCAGCAGTTTGATTACCAGAAGAAGCTGGACAACAGGGAGAAGGAGAGG

GTGGCAGCAAGGCAGGCCTGGTCTGTGGTGGGCACAATCAAGGATCTGAAGCAGGGCTATC

TGAGCCAGGTCATCCACGAGATCGTGGACCTGATGATCCACTACCAGGCCGTGGTGGTGCTG

GAGAACCTGAATTTCGGCTTTAAGAGCAAGAGGACCGGCATCGCCGAGAAGGCCGTGTACCA

GCAGTTCGAGAAGATGCTGATCGATAAGCTGAATTGCCTGGTGCTGAAGGACTATCCAGCAG

AGAAAGTGGGAGGCGTGCTGAACCCATACCAGCTGACAGACCAGTTCACCTCCTTTGCCAAG

ATGGGCACCCAGTCTGGCTTCCTGTTTTACGTGCCTGCCCCATACACATCTAAGATCGATCCC

CTGACCGGCTTCGTGGACCCCTTCGTGTGGAAAACCATCAAGAATCACGAGAGCCGCAAGCA

CTTCCTGGAGGGCTTCGACTTTCTGCACTACGACGTGAAAACCGGCGACTTCATCCTGCACTT

TAAGATGAACAGAAATCTGTCCTTCCAGAGGGGCCTGCCCGGCTTTATGCCTGCATGGGATAT

CGTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGCC

AACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACCATGGTGGCCCTGATCCGCA

GCGTGCTGCAGATGCGGAACTCCAATGCCGCCACAGGCGAGGACTATATCAACAGCCCCGT

GCGCGATCTGAATGGCGTGTGCTTCGACTCCCGGTTTCAGAACCCAGAGTGGCCCATGGACG

CCGATGCCAATGGCGCCTACCACATCGCCCTGAAGGGCCAGCTGCTGCTGAATCACCTGAAG

GAGAGCAAGGATCTGAAGCTGCAGAACGGCATCTCCAATCAGGACTGGCTGGCCTACATCCA

GGAGCTGCGCAACaaaaggccggcggccacgaaaaaggccggccaggcaaaaaagaaaaagGGATCCTACCC

ATACGATGTTCCAGATTACGCTTATCCCTACGACGTGCCTGATTATGCATACCCATATGATGT

CCCCGACTATGCCTAA
```

Amino acid sequence of AsCpf1-NLS-3xHA
AsCpf1 in normal font (AAs 1-1306), NLS (krpaatkkagqakkkk, SEQ ID NO: 7) in lowercase,
3xHA tag (YPYDVPDYAYPYDVPDYAYPYDVPDYA, SEQ ID NO: 8) in bold (SEQ ID NO: 9)

```
MTQFEGFTNLYQVSKTLRFELIPQGKTLKHIQEQGFIEEDKARNDHYKELKPIIDRIYKTYAD

QCLQLVQLDWENLSAAIDSYRKEKTEETRNALIEEQATYRNAIHDYFIGRTDNLTDAINKRHAEIYK

GLFKAELFNGKVLKQLGTVTTTEHENALLRSFDKFTTYFSGFYENRKNVFSAEDISTAIPHRIVQDN

FPKFKENCHIFTRLITAVPSLREHFENVKKAIGIFVSTSIEEVFSFPFYNQLLTQTQIDLYNQLLGGISR

EAGTEKIKGLNEVLNLAIQKNDETAHIIASLPHRFIPLFKQILSDRNTLSFILEEFKSDEEVIQSFCKYK

TLLRNENVLETAEALFNELNSIDLTHIFISHKKLETISSALCDHWDTLRNALYERRISELTGKITKSAKE

KVQRSLKHEDINLQEIISAAGKELSEAFKQKTSEILSHAHAALDQPLPTTLKKQEEKEILKSQLDSLL

GLYHLLDWFAVDESNEVDPEFSARLTGIKLEMEPSLSFYNKARNYATKKPYSVEKFKLNFQMPTLA

SGWDVNKEKNNGAILFVKNGLYYLGIMPKQKGRYKALSFEPTEKTSEGFDKMYYDYFPDAAKMIP

KCSTQLKAVTAHFQTHTTPILLSNNFIEPLEITKEIYDLNNPEKEPKKFQTAYAKKTGDQKGYREALC

KWIDFTRDFLSKYTKTTSIDLSSLRPSSQYKDLGEYYAELNPLLYHISFQRIAEKEIMDAVETGKLYL

FQIYNKDFAKGHHGKPNLHTLYVVTGLFSPENLAKTSIKLNGQAELFYRPKSRMKRMAHRLGEKML

NKKLKDQKTPIPDTLYQELYDYVNHRLSHDLSDEARALLPNVITKEVSHEIIKDRRFTSDKFFFHVPI

TLNYQAANSPSKFNQRVNAYLKEHPETPIIGIDRGERNLIYITVIDSTGKILEQRSLNTIQQFDYQKKL

DNREKERVAARQAWSVVGTIKDLKQGYLSQVIHEIVDLMIHYQAVVVLENLNFGFKSKRTGIAEKA

VYQQFEKMLIDKLNCLVLKDYPAEKVGGVLNPYQLTDQFTSFAKMGTQSGFLFYVPAPYTSKIDPL

TGFVDPFVWKTIKNHESRKHFLEGFDFLHYDVKTGDFILHFKMNRNLSFQRGLPGFMPAWDIVFE
```

-continued

KNETQFDAKGTPFIAGKRIVPVIENHRFTGRYRDLYPANELIALLEEKGIVFRDGSNILPKLLENDDS

HAIDTMVALIRSVLQMRNSNAATGEDYINSPVRDLNGVCFDSRFQNPEWPMDADANGAYHIALKG

QLLLNHLKESKDLKLQNGISNQDWLAYIQELRNkrpaatkkagqakkkkGSYPYDVPDYAYPYDVPDYA

YPYDVPDYA

SQT1659: pCAG-hAsCas12a-NLS-3xHA
Human codon optimized *Acidaminococcus sp. BV3L6* Cas12a (AsCas12a) in
black, nucleoplasmin NLS (aaaaggccggcggccacgaaaaaggccggccaggcaaaaaagaaaaag, SEQ
ID NO: 21) in lower case, linker sequences in italics, 3xHA tag
(TACCCATACGATGITCCAGATTACGCTTATCCCTACGACGTGCCTGATTATGCATACCCATA
TGATGTCCCCGACTATGCC, SEQ ID NO: 5) in BOLD (SEQ ID NO: 421)

ATGACACAGTTCGAGGGCTTTACCAACCTGTATCAGGTGAGCAAGACACTGCGGTTT

GAGCTGATCCCACAGGGCAAGACCCTGAAGCACATCCAGGAGCAGGGCTTCATCGAGGAGGA

CAAGGCCCGCAATGATCACTACAAGGAGCTGAAGCCCATCATCGATCGGATCTACAAGACCT

ATGCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAATA

AGAGACACGCCGAGATCTACAAGGGCCTGTTCAAGGCCGAGCTGTTTAATGGCAAGGTGCTG

AAGCAGCTGGGCACCGTGACCACAACCGAGCACGAGAACGCCCTGCTGCGGAGCTTCGACAA

GTTTACAACCTACTTCTCCGGCTTTTATGAGAACAGGAAGAACGTGTTCAGCGCCGAGGATAT

CAGCACAGCCATCCCACACCGCATCGTGCAGGACAACTTCCCCAAGTTTAAGGAGAATTGTCA

CATCTTCACACGCCTGATCACCGCCGTGCCCAGCCTGCGGGAGCACTTTGAGAACGTGAAGAA

GGCCATCGGCATCTTCGTGAGCACCTCCATCGAGGAGGTGTTTTCCTTCCCTTTTTATAACCAG

CTGCTGACACAGACCCAGATCGACCTGTATAACCAGCTGCTGGGAGGAATCTCTCGGGAGGC

AGGCACCGAGAAGATCAAGGGCCTGAACGAGGTGCTGAATCTGGCCATCCAGAAGAATGATG

AGACAGCCCACATCATCGCCTCCCTGCCACACAGATTCATCCCCCTGTTTAAGCAGATCCTGT

CCGATAGGAACACCCTGTCTTTCATCCTGGAGGAGTTTAAGAGCGACGAGGAAGTGATCCAGT

CCTTCTGCAAGTACAAGACACTGCTGAGAAACGAGAACGTGCTGGAGACAGCCGAGGCCCTG

TTTAACGAGCTGAACAGCATCGACCTGACACACATCTTCATCAGCCACAAGAAGCTGGAGAC

AATCAGCAGCGCCCTGTGCGACCACTGGGATACACTGAGGAATGCCCTGTATGAGCGGAGAA

TCTCCGAGCTGACAGGCAAGATCACCAAGTCTGCCAAGGAGAAGGTGCAGCGCAGCCTGAAG

CACGAGGATATCAACCTGCAGGAGATCATCTCTGCCGCAGGCAAGGAGCTGAGCGAGGCCTT

CAAGCAGAAAACCAGCGAGATCCTGTCCCACGCACACGCCGCCCTGGATCAGCCACTGCCTA

CAACCCTGAAGAAGCAGGAGGAGAAGGAGATCCTGAAGTCTCAGCTGGACAGCCTGCTGGGC

CTGTACCACCTGCTGGACTGGTTTGCCGTGGATGAGTCCAACGAGGTGGACCCCGAGTTCTCT

GCCCGGCTGACCGGCATCAAGCTGGAGATGGAGCCTTCTCTGAGCTTCTACAACAAGGCCAG

AAATTATGCCACCAAGAAGCCCTACTCCGTGGAGAAGTTCAAGCTGAACTTTCAGATGCCTAC

ACTGGCCTCTGGCTGGGACGTGAATAAGGAGAAGAACAATGGCGCCATCCTGTTTGTGAAGA

ACGGCCTGTACTATCTGGGCATCATGCCAAAGCAGAAGGGCAGGTATAAGGCCCTGAGCTTC

GAGCCCACAGAGAAAACCAGCGAGGGCTTTGATAAGATGTACTATGACTACTTCCCTGATGCC

GCCAAGATGATCCCAAAGTGCAGCACCCAGCTGAAGGCCGTGACAGCCCACTTTCAGACCCA

CACAACCCCCATCCTGCTGTCCAACAATTTCATCGAGCCTCTGGAGATCACAAAGGAGATCTA

CGACCTGAACAATCCTGAGAAGGAGCCAAAGAAGTTTCAGACAGCCTACGCCAAGAAAACCG

GCGACCAGAAGGGCTACAGAGAGGCCCTGTGCAAGTGGATCGACTTCACAAGGGGATTTTCTG

```
TCCAAGTATACCAAGACAACCTCTATCGATCTGTCTAGCCTGCGGCCATCCTCTCAGTATAAG

GACCTGGGCGAGTACTATGCCGAGCTGAATCCCCTGCTGTACCACATCAGCTTCCAGAGAATC

GCCGAGAAGGAGATCATGGATGCCGTGGAGACAGGCAAGCTGTACCTGTTCCAGATCTATAA

CAAGGACTTTGCCAAGGGCCACCACGGCAAGCCTAATCTGCACACACTGTATTGGACCGGCCT

GTTTTCTCCAGAGAACCTGGCCAAGACAAGCATCAAGCTGAATGGCCAGGCCGAGCTGTTCTA

CCGCCCTAAGTCCAGGATGAAGAGGATGGCACACCGGCTGGGAGAGAAGATGCTGAACAAG

AAGCTGAAGGATCAGAAAACCCCAATCCCCGACACCCTGTACCAGGAGCTGTACGACTATGT

GAATCACAGACTGTCCCACGACCTGTCTGATGAGGCCAGGGCCCTGCTGCCCAACGTGATCAC

CAAGGAGGTGTCTCACGAGATCATCAAGGATAGGCGCTTTACCAGCGACAAGTTCTTTTTCCA

CGTGCCTATCACACTGAACTATCAGGCCGCCAATTCCCCATCTAAGTTCAACCAGAGGGTGAA

TGCCTACCTGAAGGAGCACCCCGAGACACCTATCATCGGCATCGATCGGGGCGAGAGAAACC

TGATCTATATCACAGTGATCGACTCCACCGGCAAGATCCTGGAGCAGCGGAGCCTGAACACC

ATCCAGCAGTTTGATTACCAGAAGAAGCTGGACAACAGGGAGAAGGAGAGGGTGGCAGCAA

GGCAGGCCTGGTCTGTGGTGGGCACAATCAAGGATCTGAAGCAGGGCTATCTGAGCCAGGTC

ATCCACGAGATCGTGGACCTGATGATCCACTACCAGGCCGTGGTGGTGCTGGAGAACCTGAAT

TTCGGCTTTAAGAGCAAGAGGACCGGCATCGCCGAGAAGGCCGTGTACCAGCAGTTCGAGAA

GATGCTGATCGATAAGCTGAATTGCCTGGTGCTGAAGGACTATCCAGCAGAGAAGTGGGAG

GCGTGCTGAACCCATACCAGCTGACAGACCAGTTCACCTCCTTTGCCAAGATGGGCACCCAGT

CTGGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGCT

TCGACTTTCTGCACTACGACGTGAAAACCGGCGACTTCATCCTGCACTTTAAGATGAACAGAA

ATCTGTCCTTCCAGAGGGGCCTGCCCGGCTTTATGCCTGCATGGGATATCGTGTTCGAGAAGA

ACGAGACACAGTTTGACGCCAAGGGCACCCCTTTCATCGCCGGCAAGAGAATCGTGCCAGTG

ATCGAGAATCACAGATTCACCGGCAGATACCGGGACCTGTATCCTGCCAACGAGCTGATCGCC

CTGCTGGAGGAGAAGGGCATCGTGTTCAGGGATGGCTCCAACATCCTGCCAAAGCTGCTGGA

GAATGACGATTCTCACGCCATCGACACCATGGTGGCCCTGATCCGCAGCGTGCTGCAGATGCG

GAACTCCAATGCCGCCACAGGCGAGGACTATATCAACAGCCCCGTGCGCGATCTGAATGGCG

TGTGCTTCGACTCCCGGTTTCAGAACCCAGAGTGGCCCATGGACGCCGATGCCAATGGCGCCT

ACCACATCGCCCTGAAGGGCCAGCTGCTGCTGAATCACCTGAAGGAGAGCAAGGATCTGAAG

CTGCAGAACGGCATCTCCAATCAGGACTGGCTGGCCTACATCCAGGAGCTGCGCAACaaaaggcc ggcggccacgaaaaaggccggccaggcaaaaaagaaaaag*GGATCC*TACCCATACGATGTTCCAGATTACGCTTA

TCCCTACGACGTGCCTGATTATGCATACCCATATGATGTCCCCGACTATGCCTAA
```

AAS826: pCAG-hAsCas12a(E174R/S542R)-NLS-3xHA
Human codon optimized *Acidaminococcus* sp. *BV3L6* Cas12a (AsCas12a) in black, modified
codons (E174R/S542R) double underlined, nucleoplasmin NLS
(aaaaggccggcggccacgaaaaaggccggccaggcaaaaaagaaaaag, SEQ ID NO: 21) in lower case, linker
sequences in italics, 3xHA tag
(TACCCATACGATGITCCAGATTACGCTTATCCCTACGACGTGCCTGATTATGCATACCCATA
TGATGTCCCCGACTATGCC, SEQ ID NO: 5) in BOLD (SEQ ID NO: 422)

```
ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT
```

-continued

```
ATCGCAATGCCATCCACGACTACTTCATCGGCCGGACAGACAACCTGACCGATGCCATCAAT
AAGAGACACGCCGAGATCTACAAGGGCCTGTTCAAGGCCGAGCTGTTTAATGGCAAGGTGC
TGAAGCAGCTGGGCACCGTGACCACAACCGAGCACGAGAACGCCCTGCTGCGGAGCTTCG
ACAAGTTTACAACCTACTTCTCCGGCTTTTATAGAAACAGGAAGAACGTGTTCAGCGCCGAG
GATATCAGCACAGCCATCCCACACCGCATCGTGCAGGACAACTTCCCCAAGTTTAAGGAGA
ATTGTCACATCTTCACACGCCTGATCACCGCCGTGCCCAGCCTGCGGGAGCACTTTGAGAA
CGTGAAGAAGGCCATCGGCATCTTCGTGAGCACCTCCATCGAGGAGGTGTTTTCCTTCCCTT
TTTATAACCAGCTGCTGACACAGACCCAGATCGACCTGTATAACCAGCTGCTGGGAGGAATC
TCTCGGGAGGCAGGCACCGAGAAGATCAAGGGCCTGAACGAGGTGCTGAATCTGGCCATC
CAGAAGAATGATGAGACAGCCCACATCATCGCCTCCCTGCCACACAGATTCATCCCCCTGTT
TAAGCAGATCCTGTCCGATAGGAACACCCTGTCTTTCATCCTGGAGGAGTTTAAGAGCGACG
AGGAAGTGATCCAGTCCTTCTGCAAGTACAAGACACTGCTGAGAAACGAGAACGTGCTGGA
GACAGCCGAGGCCCTGTTTAACGAGCTGAACAGCATCGACCTGACACACATCTTCATCAGC
CACAAGAAGCTGGAGACAATCAGCAGCGCCCTGTGCGACCACTGGGATACACTGAGGAATG
CCCTGTATGAGCGGAGAATCTCCGAGCTGACAGGCAAGATCACCAAGTCTGCCAAGGAGAA
GGTGCAGCGCAGCCTGAAGCACGAGGATATCAACCTGCAGGAGATCATCTCTGCCGCAGG
CAAGGAGCTGAGCGAGGCCTTCAAGCAGAAAACCAGCGAGATCCTGTCCCACGCACACGC
CGCCCTGGATCAGCCACTGCCTACAACCCTGAAGAAGCAGGAGGAGAAGGAGATCCTGAA
GTCTCAGCTGGACAGCCTGCTGGGCCTGTACCACCTGCTGGACTGGTTTGCCGTGGATGAG
TCCAACGAGGTGGACCCCGAGTTCTCTGCCCGGCTGACCGGCATCAAGCTGGAGATGGAG
CCTTCTCTGAGCTTCTACAACAAGGCCAGAAATTATGCCACCAAGAAGCCCTACTCCGTGGA
GAAGTTCAAGCTGAACTTTCAGATGCCTACACTGGCCAGAGGCTGGGACGTGAATAAGGAG
AAGAACAATGGCGCCATCCTGTTTGTGAAGAACGGCCTGTACTATCTGGGCATCATGCCAAA
GCAGAAGGGCAGGTATAAGGCCCTGAGCTTCGAGCCCACAGAGAAAACCAGCGAGGGCTT
TGATAAGATGTACTATGACTACTTCCCTGATGCCGCCAAGATGATCCCAAAGTGCAGCACCC
AGCTGAAGGCCGTGACAGCCCACTTTCAGACCCACACAACCCCCATCCTGCTGTCCAACAA
TTTCATCGAGCCTCTGGAGATCACAAAGGAGATCTACGACCTGAACAATCCTGAGAAGGAGC
CAAAGAAGTTTCAGACAGCCTACGCCAAGAAAACCGGCGACCAGAAGGGCTACAGAGAGGC
CCTGTGCAAGTGGATCGACTTCACAAGGGATTTTCTGTCCAAGTATACCAAGACAACCTCTA
TCGATCTGTCTAGCCTGCGGCCATCCTCTCAGTATAAGGACCTGGGCGAGTACTATGCCGA
GCTGAATCCCCTGCTGTACCACATCAGCTTCCAGAGAATCGCCGAGAAGGAGATCATGGAT
GCCGTGGAGACAGGCAAGCTGTACCTGTTCCAGATCTATAACAAGGACTTTGCCAAGGGCC
ACCACGGCAAGCCTAATCTGCACACACTGTATTGGACCGGCCTGTTTTCTCCAGAGAACCTG
GCCAAGACAAGCATCAAGCTGAATGGCCAGGCCGAGCTGTTCTACCGCCCTAAGTCCAGGA
TGAAGAGGATGGCACACCGGCTGGGAGAGAAGATGCTGAACAAGAAGCTGAAGGATCAGA
AAACCCCAATCCCCGACACCCTGTACCAGGAGCTGTACGACTATGTGAATCACAGACTGTCC
CACGACCTGTCTGATGAGGCCAGGGCCCTGCTGCCCAACGTGATCACCAAGGAGGTGTCTC
ACGAGATCATCAAGGATAGGCGCTTTACCAGCGACAAGTTCTTTTTCCACGTGCCTATCACA
CTGAACTATCAGGCCGCCAATTCCCCATCTAAGTTCAACCAGAGGGTGAATGCCTACCTGAA
GGAGCACCCCGAGACACCTATCATCGGCATCGATCGGGGCGAGAGAAACCTGATCTATATC
ACAGTGATCGACTCCACCGGCAAGATCCTGGAGCAGCGGAGCCTGAACACCATCCAGCAGT
```

-continued

```
TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

AAGAACGAGACACAGTTTGACGCCAAGGGCACCCCTTTCATCGCCGGCAAGAGAATCGTGC

CAGTGATCGAGAATACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

AGCTGCGCAACaaaaggccggcggccacgaaaaaggccggccaggcaaaaaagaaaaag*GGATCC*TACCCA

TACGATGTTCCAGATTACGCTTATCCCTACGACGTGCCTGATTATGCATACCCATATGATGT

CCCCGACTATGCCTAA
```

AAS848: pCAG-heAsCas12a(E174R/S542R/K548R)-NLS-3xHA
Human codon optimized *Acidaminococcus sp. BV3L6* Cas12a (AsCas12a) in
black, modified codons for eAsCas12a (E174R/S542R/K548R) double underlined,
nucleoplasmin NLS (aaaaggccggcggccacgaaaaaggccggccaggcaaaaaagaaaaag, SEQ ID
NO: 21) in lower case, linker sequences in italics, 3xHA tag
(TACCCATACGATGITCCAGATTACGCTTATCCCTACGACGTGCCTGATTATGCATACCCATA
TGATGTCCCCGACTATGCC, SEQ ID NO: 5) in BOLD (SEQ ID NO: 423)

```
ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

ACAAGTTTACAACCTACTTCTCCGGCTTTTATGAGAAACAGGAAGAACGTGTTCAGCGCCGAG

GATATCAGCACAGCCATCCCACACCGCATCGTGCAGGACAACTTCCCCAAGTTTAAGGAGA

ATTGTCACATCTTCACACGCCTGATCACCGCCGTGCCCAGCCTGCGGGAGCACTTTGAGAA

CGTGAAGAAGGCCATCGGCATCTTCGTGAGCACCTCCATCGAGGAGGTGTTTTCCTTCCCTT

TTTATAACCAGCTGCTGACACAGACCCAGATCGACCTGTATAACCAGCTGCTGGGAGGAATC

TCTCGGGAGGCAGGCACCGAGAAGATCAAGGGCCTGAACGAGGTGCTGAATCTGGCCATC

CAGAAGAATGATGAGACAGCCCACATCATCGCCTCCCTGCCACACAGATTCATCCCCCTGTT

TAAGCAGATCCTGTCCGATAGGAACACCCTGTCTTTCATCCTGGAGGAGTTTAAGAGCGACG
```

```
AGGAAGTGATCCAGTCCTTCTGCAAGTACAAGACACTGCTGAGAAACGAGAACGTGCTGGA

GACAGCCGAGGCCCTGTTTAACGAGCTGAACAGCATCGACCTGACACACATCTTCATCAGC

CACAAGAAGCTGGAGACAATCAGCAGCGCCCTGTGCGACCACTGGGATACACTGAGGAATG

CCCTGTATGAGCGGAGAATCTCCGAGCTGACAGGCAAGATCACCAAGTCTGCCAAGGAGAA

GGTGCAGCGCAGCCTGAAGCACGAGGATATCAACCTGCAGGAGATCATCTCTGCCGCAGG

CAAGGAGCTGAGCGAGGCCTTCAAGCAGAAAACCAGCGAGATCCTGTCCCACGCACACGC

CGCCCTGGATCAGCCACTGCCTACAACCCTGAAGAAGCAGGAGGAGAAGGAGATCCTGAA

GTCTCAGCTGGACAGCCTGCTGGGCCTGTACCACCTGCTGGACTGGTTTGCCGTGGATGAG

TCCAACGAGGTGGACCCCGAGTTCTCTGCCCGGCTGACCGGCATCAAGCTGGAGATGGAG

CCTTCTCTGAGCTTCTACAACAAGGCCAGAAATTATGCCACCAAGAAGCCCTACTCCGTGGA

GAAGTTCAAGCTGAACTTTCAGATGCCTACACTGGCCAGAGGCTGGGACGTGAATAGAGAG

AAGAACAATGGCGCCATCCTGTTTGTGAAGAACGGCCTGTACTATCTGGGCATCATGCCAAA

GCAGAAGGGCAGGTATAAGGCCCTGAGCTTCGAGCCCACAGAGAAAACCAGCGAGGGCTT

TGATAAGATGTACTATGACTACTTCCCTGATGCCGCCAAGATGATCCCAAAGTGCAGCACCC

AGCTGAAGGCCGTGACAGCCCACTTTCAGACCCACACAACCCCCATCCTGCTGTCCAACAA

TTTCATCGAGCCTCTGGAGATCACAAAGGAGATCTACGACCTGAACAATCCTGAGAAGGAGC

CAAAGAAGTTTCAGACAGCCTACGCCAAGAAAACCGGCGACCAGAAGGGCTACAGAGAGGC

CCTGTGCAAGTGGATCGACTTCACAAGGGATTTTCTGTCCAAGTATACCAAGACAACCTCTA

TCGATCTGTCTAGCCTGCGGCCATCCTCTCAGTATAAGGACCTGGGCGAGTACTATGCCGA

GCTGAATCCCCTGCTGTACCACATCAGCTTCCAGAGAATCGCCGAGAAGGAGATCATGGAT

GCCGTGGAGACAGGCAAGCTGTACCTGTTCCAGATCTATAACAAGGACTTTGCCAAGGGCC

ACCACGGCAAGCCTAATCTGCACACACTGTATTGGACCGGCCTGTTTTCTCCAGAGAACCTG

GCCAAGACAAGCATCAAGCTGAATGGCCAGGCCGAGCTGTTCTACCGCCCTAAGTCCAGGA

TGAAGAGGATGGCACACCGGCTGGGAGAGAAGATGCTGAACAAGAAGCTGAAGGATCAGA

AAACCCCAATCCCCGACACCCTGTACCAGGAGCTGTACGACTATGTGAATCACAGACTGTCC

CACGACCTGTCTGATGAGGCCAGGGCCCTGCTGCCCAACGTGATCACCAAGGAGGTGTCTC

ACGAGATCATCAAGGATAGGCGCTTTACCAGCGACAAGTTCTTTTTCCACGTGCCTATCACA

CTGAACTATCAGGCCGCCAATTCCCCATCTAAGTTCAACCAGAGGGTGAATGCCTACCTGAA

GGAGCACCCCGAGACACCTATCATCGGCATCGATCGGGGCGAGAGAAACCTGATCTATATC

ACAGTGATCGACTCCACCGGCAAGATCCTGGAGCAGCGGAGCCTGAACACCATCCAGCAGT

TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

AAGAACGAGACACAGTTTGACGCCAAGGGCACCCCTTTCATCGCCGGCAAGAGAATCGTGC
```

-continued

CAGTGATCGAGAATCACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

AGCTGCGCAACaaaaggccggcggccacgaaaaaggccggccaggcaaaaaagaaaaag*GGATCC*TACCCA

TACGATGTTCCAGATTACGCTTATCCCTACGACGTGCCTGATTATGCATACCCATATGATGT

CCCCGACTATGCCTAA

AAS1815: pCAG-heAsCas12a-HF1(E174R/N282A/S542R/K548R)-NLS-3xHA
Human codon optimized *Acidaminococcus* sp. *BV3L6* Cas12a (AsCas12a) in black, modified
codons (E174R/N282A/S542R/K548R) in double underlined, nucleoplasmin NLS
(aaaaggccggcggccacgaaaaaggccggccaggcaaaaaagaaaaag, SEQ ID NO: 21) in lower case,
linker sequences in italics, 3xHA tag
(TACCCATACGATGITCCAGATTACGCTTATCCCTACGACGTGCCTGATTATGCATACCCATA
TGATGTCCCCGACTATGCC, SEQ ID NO: 5) in BOLD (SEQ ID NO: 424)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

ACAAGTTTACAACCTACTTCTCCGGCTTTTAT<u>AGA</u>AACAGGAAGAACGTGTTCAGCGCCGAG

GATATCAGCACAGCCATCCCACACCGCATCGTGCAGGACAACTTCCCCAAGTTTAAGGAGA

ATTGTCACATCTTCACACGCCTGATCACCGCCGTGCCCAGCCTGCGGGAGCACTTTGAGAA

CGTGAAGAAGGCCATCGGCATCTTCGTGAGCACCTCCATCGAGGAGGTGTTTTCCTTCCCTT

TTTATAACCAGCTGCTGACACAGACCCAGATCGACCTGTATAACCAGCTGCTGGGAGGAATC

TCTCGGGAGGCAGGCACCGAGAAGATCAAGGGCCTGAACGAGGTGCTG<u>GCC</u>CTGGCCATC

CAGAAGAATGATGAGACAGCCCACATCATCGCCTCCCTGCCACACAGATTCATCCCCCTGTT

TAAGCAGATCCTGTCCGATAGGAACACCCTGTCTTTCATCCTGGAGGAGTTTAAGAGCGACG

AGGAAGTGATCCAGTCCTTCTGCAAGTACAAGACACTGCTGAGAAACGAGAACGTGCTGGA

GACAGCCGAGGCCCTGTTTAACGAGCTGAACAGCATCGACCTGACACACATCTTCATCAGC

CACAAGAAGCTGGAGACAATCAGCAGCGCCCTGTGCGACCACTGGGATACACTGAGGAATG

CCCTGTATGAGCGGAGAATCTCCGAGCTGACAGGCAAGATCACCAAGTCTGCCAAGGAGAA

GGTGCAGCGCAGCCTGAAGCACGAGGATATCAACCTGCAGGAGATCATCTCTGCCGCAGG

CAAGGAGCTGAGCGAGGCCTTCAAGCAGAAAACCAGCGAGATCCTGTCCCACGCACACGC

CGCCCTGGATCAGCCACTGCCTACAACCCTGAAGAAGCAGGAGGAGAAGGAGATCCTGAA

GTCTCAGCTGGACAGCCTGCTGGGCCTGTACCACCTGCTGGACTGGTTTGCCGTGGATGAG

TCCAACGAGGTGGACCCCGAGTTCTCTGCCCGGCTGACCGGCATCAAGCTGGAGATGGAG

CCTTCTCTGAGCTTCTACAACAAGGCCAGAAATTATGCCACCAAGAAGCCCTACTCCGTGGA

GAAGTTCAAGCTGAACTTTCAGATGCCTACACTGGCC<u>AGA</u>GGCTGGGACGTGAAT<u>AGA</u>GAG

-continued

AAGAACAATGGCGCCATCCTGTTTGTGAAGAACGGCCTGTACTATCTGGGCATCATGCCAAA

GCAGAAGGGCAGGTATAAGGCCCTGAGCTTCGAGCCCACAGAGAAAACCAGCGAGGGCTT

TGATAAGATGTACTATGACTACTTCCCTGATGCCGCCAAGATGATCCCAAAGTGCAGCACCC

AGCTGAAGGCCGTGACAGCCCACTTTCAGACCCACACAACCCCCATCCTGCTGTCCAACAA

TTTCATCGAGCCTCTGGAGATCACAAAGGAGATCTACGACCTGAACAATCCTGAGAAGGAGC

CAAAGAAGTTTCAGACAGCCTACGCCAAGAAAACCGGCGACCAGAAGGGCTACAGAGAGGC

CCTGTGCAAGTGGATCGACTTCACAAGGGATTTTCTGTCCAAGTATACCAAGACAACCTCTA

TCGATCTGTCTAGCCTGCGGCCATCCTCTCAGTATAAGGACCTGGGCGAGTACTATGCCGA

GCTGAATCCCCTGCTGTACCACATCAGCTTCCAGAGAATCGCCGAGAAGGAGATCATGGAT

GCCGTGGAGACAGGCAAGCTGTACCTGTTCCAGATCTATAACAAGGACTTTGCCAAGGGCC

ACCACGGCAAGCCTAATCTGCACACACTGTATTGGACCGGCCTGTTTTCTCCAGAGAACCTG

GCCAAGACAAGCATCAAGCTGAATGGCCAGGCCGAGCTGTTCTACCGCCCTAAGTCCAGGA

TGAAGAGGATGGCACACCGGCTGGGAGAGAAGATGCTGAACAAGAAGCTGAAGGATCAGA

AAACCCCAATCCCCGACACCCTGTACCAGGAGCTGTACGACTATGTGAATCACAGACTGTCC

CACGACCTGTCTGATGAGGCCAGGGCCCTGCTGCCCAACGTGATCACCAAGGAGGTGTCTC

ACGAGATCATCAAGGATAGGCGCTTTACCAGCGACAAGTTCTTTTTCCACGTGCCTATCACA

CTGAACTATCAGGCCGCCAATTCCCCATCTAAGTTCAACCAGAGGGTGAATGCCTACCTGAA

GGAGCACCCCGAGACACCTATCATCGGCATCGATCGGGGCGAGAGAAACCTGATCTATATC

ACAGTGATCGACTCCACCGGCAAGATCCTGGAGCAGCGGAGCCTGAACACCATCCAGCAGT

TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

AAGAACGAGACACAGTTTGACGCCAAGGGCACCCCTTTCATCGCCGGCAAGAGAATCGTGC

CAGTGATCGAGAATCACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

AGCTGCGCAACaaaaggccggcggccacgaaaaaggccggccaggcaaaaaagaaaaag*GGATCC*TACCC

ATACGATGTTCCAGATTACGCTTATCCCTACGACGTGCCTGATTATGCATACCCATATGA

TGTCCCCGACTATGCCTAA

-continued

BPK3541: pET-28b-hAsCas12a-NLS-6xHis
Human codon optimized *Acidaminococcus* sp. *BV3L6* Cas12a (AsCas12a) in
black, codons with silent mutations to remove NcoI sites double underlined,
inserted glycine dash-underlined, nucleoplasmin NLS
(aaaaggccggcggccacgaaaaaggccggccaggcaaaaaagaaaaag, SEQ ID NO: 21) in lower case,
linker sequences in italics, 6xHis in bold (SEQ ID NO: 425)

ATGGGGACACAGTTCGAGGGCTTTACCAACCTGTATCAGGTGAGCAAGACACTGCGGTTTG

AGCTGATCCCACAGGGCAAGACCCTGAAGCACATCCAGGAGCAGGGCTTCATCGAGGAGG

ACAAGGCCCGCAATGATCACTACAAGGAGCTGAAGCCCATCATCGATCGGATCTACAAGAC

CTATGCCGACCAGTGCCTGCAGCTGGTGCAGCTGGATTGGGAGAACCTGAGCGCCGCCAT

CGACTCCTATAGAAAGGAGAAAACCGAGGAGACAAGGAACGCCCTGATCGAGGAGCAGGC

CACATATCGCAATGCCATCCACGACTACTTCATCGGCCGGACAGACAACCTGACCGATGCC

ATCAATAAGAGACACGCCGAGATCTACAAGGGCCTGTTCAAGGCCGAGCTGTTTAATGGCA

AGGTGCTGAAGCAGCTGGGCACCGTGACCACAACCGAGCACGAGAACGCCCTGCTGCGGA

GCTTCGACAAGTTTACAACCTACTTCTCCGGCTTTTATGAGAACAGGAAGAACGTGTTCAGC

GCCGAGGATATCAGCACAGCCATCCCACACCGCATCGTGCAGGACAACTTCCCCAAGTTTA

AGGAGAATTGTCACATCTTCACACGCCTGATCACCGCCGTGCCCAGCCTGCGGGAGCACTT

TGAGAACGTGAAGAAGGCCATCGGCATCTTCGTGAGCACCTCCATCGAGGAGGTGTTTTCC

TTCCCTTTTTATAACCAGCTGCTGACACAGACCCAGATCGACCTGTATAACCAGCTGCTGGG

AGGAATCTCTCGGGAGGCAGGCACCGAGAAGATCAAGGGCCTGAACGAGGTGCTGAATCT

GGCCATCCAGAAGAATGATGAGACAGCCCACATCATCGCCTCCCTGCCACACAGATTCATC

CCCCTGTTTAAGCAGATCCTGTCCGATAGGAACACCCTGTCTTTCATCCTGGAGGAGTTTAA

GAGCGACGAGGAAGTGATCCAGTCCTTCTGCAAGTACAAGACACTGCTGAGAAACGAGAAC

GTGCTGGAGACAGCCGAGGCCCTGTTTAACGAGCTGAACAGCATCGACCTGACACACATCT

TCATCAGCCACAAGAAGCTGGAGACAATCAGCAGCGCCCTGTGCGACCACTGGGATACACT

GAGGAATGCCCTGTATGAGCGGAGAATCTCCGAGCTGACAGGCAAGATCACCAAGTCTGCC

AAGGAGAAGGTGCAGCGCAGCCTGAAGCACGAGGATATCAACCTGCAGGAGATCATCTCTG

CCGCAGGCAAGGAGCTGAGCGAGGCCTTCAAGCAGAAAACCAGCGAGATCCTGTCCCACG

CACACGCCGCCCTGGATCAGCCACTGCCTACAACCCTGAAGAAGCAGGAGGAGAAGGAGA

TCCTGAAGTCTCAGCTGGACAGCCTGCTGGGCCTGTACCACCTGCTGGACTGGTTTGCCGT

GGATGAGTCCAACGAGGTGGACCCCGAGTTCTCTGCCCGGCTGACCGGCATCAAGCTGGA

GATGGAGCCTTCTCTGAGCTTCTACAACAAGGCCAGAAATTATGCCACCAAGAAGCCCTACT

CCGTGGAGAAGTTCAAGCTGAACTTTCAGATGCCTACACTGGCCTCTGGCTGGGACGTGAA

TAAGGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

-continued

```
GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACGATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGGCCAATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAACaaaaaggccggcggccacgaaaaaggccggccaggcaaaaaagaaaaagGGAGC

GGCCGCACTCGAGCACCACCACCACCACCACTGA
```

RTW645: pET-28b-bLbCas12a-NLS-6xHis
Bacterial codon optimized *Lachnospiraceae bacterium* ND2006 Cas12a
(LbCas12a) in black, inserted glycine dash-underlined, nucleoplasmin NLS
(aaaaggccggcggccacgaaaaaggccggccaggcaaaaaagaaaaag, SEQ ID NO: 21) in lower case,
linker sequences in italics, 6xHis in bold (SEQ ID NO: 426)

```
ATGGGGAGCAAACTGGAAAAATTTACGAATTGTTATAGCCTGTCCAAGACCCTGCGTTTCAA

AGCCATCCCCGTTGGCAAAACCCAGGAGAATATTGATAATAAACGTCTGCTGGTTGAGGATG

AAAAAAGAGCAGAAGACTATAAGGGAGTCAAAAAACTGCTGGATCGGTACTACCTGAGCTTT

ATAAATGACGTGCTGCATAGCATTAAACTGAAAAATCTGAATAACTATATTAGTCTGTTCCGC

AAGAAAACCCGAACAGAGAAAGAAAATAAAGAGCTGGAAAACCTGGAGATCAATCTGCGTAA

AGAGATCGCAAAAGCTTTTAAAGGAAATGAAGGTTATAAAAGCCTGTTCAAAAAAGACATTAT

TGAAACCATCCTGCCGGAATTTCTGGATGATAAAGACGAGATAGCGCTCGTGAACAGCTTCA

ACGGGTTCACGACCGCCTTCACGGGCTTTTTCGATAACAGGGAAAATATGTTTTCAGAGGAA
```

-continued

```
GCCAAAAGCACCTCGATAGCGTTCCGTTGCATTAATGAAAATTTGACAAGATATATCAGCAAC
ATGGATATTTTCGAGAAAGTTGATGCGATCTTTGACAAACATGAAGTGCAGGAGATTAAGGA
AAAAATTCTGAACAGCGATTATGATGTTGAGGATTTTTTCGAGGGGGAATTTTTTAACTTTGT
ACTGACACAGGAAGGTATAGATGTGTATAATGCTATTATCGGCGGGTTCGTTACCGAATCCG
GCGAGAAAATTAAGGGTCTGAATGAGTACATCAATCTGTATAACCAAAAGACCAAACAGAAA
CTGCCAAAATTCAAACCGCTGTACAAGCAAGTCCTGAGCGATCGGGAAAGCTTGAGCTTTTA
CGGTGAAGGTTATACCAGCGACGAGGAGGTACTGGAGGTCTTTCGCAATACCCTGAACAAG
AACAGCGAAATTTTCAGCTCCATTAAAAAGCTGGAGAAACTGTTTAAGAATTTTGACGAGTAC
AGCAGCGCAGGTATTTTTGTGAAGAACGGACCTGCCATAAGCACCATTAGCAAGGATATTTT
TGGAGAGTGGAATGTTATCCGTGATAAATGGAACGCGGAATATGATGACATACACCTGAAAA
AGAAGGCTGTGGTAACTGAGAAATATGAAGACGATCGCCGCAAAAGCTTTAAAAAAATCGGC
AGCTTTAGCCTGGAGCAGCTGCAGGAATATGCGGACGCCGACCTGAGCGTGGTCGAGAAA
CTGAAGGAAATTATTATCCAAAAAGTGGATGAGATTTACAAGGTATATGGTAGCAGCGAAAAA
CTGTTTGATGCGGACTTCGTTCTGGAAAAAAGCCTGAAAAAAAATGATGCTGTTGTTGCGAT
CATGAAAGACCTGCTCGATAGCGTTAAGAGCTTTGAAAATTACATTAAAGCATTCTTTGGCGA
GGGCAAAGAAACAAACAGAGACGAAAGCTTTTATGGCGACTTCGTCCTGGCTTATGACATCC
TGTTGAAGGTAGATCATATATATGATGCAATTCGTAATTACGTAACCCAAAAGCCGTACAGCA
AAGATAAGTTCAAACTGTATTTCCAGAACCCGCAGTTTATGGGTGGCTGGGACAAAGACAAG
GAGACAGACTATCGCGCCACTATTCTGCGTTACGGCAGCAAGTACTATCTCGCCATCATGGA
CAAAAAATATGCAAAGTGTCTGCAGAAAATCGATAAAGACGACGTGAACGGAAATTACGAAA
AGATTAATTATAAGCTGCTGCCAGGGCCCAACAAGATGTTACCGAAAGTATTTTTTTCCAAAA
AATGGATGGCATACTATAACCCGAGCGAGGATATACAGAAGATTTACAAAAATGGGACCTTC
AAAAAGGGGGATATGTTCAATCTGAATGACTGCCACAAACTGATCGATTTTTTTAAAGATAGC
ATCAGCCGTTATCCTAAATGGTCAAACGCGTATGATTTTAATTTCTCCGAAACGGAGAAATAT
AAAGACATTGCTGGTTTCTATCGCGAAGTCGAAGAACAGGGTTATAAAGTTAGCTTTGAATC
GGCCAGCAAGAAAGAGGTTGATAAACTGGTGGAGGAGGGTAAGCTGTATATGTTTCAGATTT
ATAACAAAGACTTTAGCGACAAAAGCCACGGTACTCCTAATCTGCATACGATGTACTTTAAAC
TGCTGTTTGATGAGAATAACCACGGCCAAATCCGTCTCTCCGGTGGAGCAGAACTTTTTATG
CGGCGTGCGAGCCTAAAAAAGGAAGAACTGGTGGTGCATCCCGCCAACAGCCCGATTGCTA
ACAAAAATCCAGATAATCCTAAGAAGACCACCACACTGTCGTACGATGTCTATAAGGATAAAC
GTTTCTCGGAAGACCAGTATGAATTGCATATACCGATAGCAATTAATAAATGCCCAAAAAACA
TTTTCAAAATCAACACTGAAGTTCGTGTGCTGCTGAAACATGATGATAATCCGTATGTGATCG
GAATTGACCGTGGGGAGAGAAATCTGCTGTATATTGTAGTCGTTGATGGCAAGGGCAACATC
GTTGAGCAGTATAGCCTGAATGAAATAATTAATAATTTTAACGGTATACGTATTAAAACCGAC
TATCATAGCCTGCTGGATAAAAAGGAGAAAGAGCGTTTTGAGGCACGCCAAAATTGGACGA
GCATCGAAAACATCAAGGAACTGAAGGCAGGATATATCAGCCAAGTAGTCCATAAAATCTGT
GAACTGGTGGAGAAGTACGACGCTGTCATTGCCCTGGAAGACCTCAATAGCGGCTTTAAAA
ACAGCCGGGTGAAGGTGGAGAAACAGGTATACCAAAAGTTTGAAAAGATGCTCATTGATAAG
CTGAACTATATGGTTGATAAAAAGAGCAACCCGTGCGCCACTGGCGGTGCACTGAAAGGGT
ACCAAATTACCAATAAATTTGAAAGCTTTAAAAGCATGAGCACGCAGAATGGGTTTATTTTTA
TATACCAGCATGGCTGACGAGCAAGATTGACCCCAGCACTGGTTTTGTCAATCTGCTGAAAA
```

-continued

CCAAATACACAAGCATTGCGGATAGCAAAAAATTTATTTCGAGCTTCGACCGTATTATGTATG

TTCCGGAGGAAGATCTGTTTGAATTTGCCCTGGATTATAAAAACTTCAGCCGCACCGATGCA

GATTATATCAAAAAATGGAAGCTGTACAGTTATGGTAATCGTATACGTATCTTCCGTAATCCG

AAGAAAAACAATGTGTTCGATTGGGAAGAGGTCTGTCTGACCAGCGCGTATAAAGAACTGTT

CAACAAGTACGGAATAAATTATCAGCAAGGTGACATTCGCGCACTGCTGTGTGAACAGTCAG

ATAAAGCATTTTATAGCAGCTTTATGGCGCTGATGAGCCTGATGCTCCAGATGCGCAACAGC

ATAACCGGTCGCACAGATGTTGACTTTCTGATCAGCCCTGTGAAGAATAGCGACGGCATCTT

CTACGATTCCAGGAACTATGAAGCACAGGAAAACGCTATTCTGCCTAAAAATGCCGATGCCA

ACGGCGCCTATAATATTGCACGGAAGGTTCTGTGGGCGATTGGACAGTTCAAGAAAGCGGA

AGATGAGAAGCTGGATAAGGTAAAAATTGCTATTAGCAATAAGGAATGGCTGGAGTACGCAC

AGACATCGGTTAAAC*ACGGTAGT*aaaaggccggcggccacgaaaaaggccggccaggcaaaaaagaaaaag*G*

*GAGCGGCCGCACTCGAG*CACCACCACCACCACCACTGA

AAS1885: pET-28b-heAsCas12a(E174R/S542R/K548R)-NLS-6xHis
Human codon optimized *Acidaminococcus* sp. *BV3L6* Cas12a (AsCas12a) in black, modified
codons for eAsCas12a (E174R/S542R/K548R) in double underlined lower case, codons
with silent mutations to remove NcoI sites double underlined UPPER CASE,
inserted glycine dash-underlined, nucleoplasmin NLS
(aaaaggccggcggccacgaaaaaggccggccaggcaaaaaagaaaaag, SEQ ID NO: 21) in lower case,
linker sequences in italics, 6xHis in bold

SEQ ID NO: 427)

ATG<u>GGG</u>ACACAGTTCGAGGGCTTTACCAACCTGTATCAGGTGAGCAAGACACTGCG

GTTTGAGCTGATCCCACAGGGCAAGACCCTGAAGCACATCCAGGAGCAGGGCTTCATCGAG

GAGGACAAGGCCCGCAATGATCACTACAAGGAGCTGAAGCCCATCATCGATCGGATCTACA

AGACCTATGCCGACCAGTGCCTGCAGCTGGTGCAGCTGGATTGGGAGAACCTGAGCGCCG

CCATCGACTCCTATAGAAAGGAGAAAACCGAGGAGACAAGGAACGCCCTGATCGAGGAGCA

GGCCACATATCGCAATGCCATCCACGACTACTTCATCGGCCGGACAGACAACCTGACCGAT

GCCATCAATAAGAGACACGCCGAGATCTACAAGGGCCTGTTCAAGGCCGAGCTGTTTAATG

GCAAGGTGCTGAAGCAGCTGGGCACCGTGACCACAACCGAGCACGAGAACGCCCTGCTGC

GGAGCTTCGACAAGTTTACAACCTACTTCTCCGGCTTTTAT<u>aga</u>AACAGGAAGAACGTGTTCA

GCGCCGAGGATATCAGCACAGCCATCCCACACACCGCATCGTGCAGGACAACTTCCCCAAGTT

TAAGGAGAATTGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAGGAGGTGTTTT

CCTTCCCTTTTTATAACCAGCTGCTGACACAGACCCAGATCGACCTGTATAACCAGCTGCTG

GGAGGAATCTCTCGGGAGGCAGGCACCGAGAAGATCAAGGGCCTGAACGAGGTGCTGAAT

CTGGCCATCCAGAAGAATGATGAGACAGCCCACATCATCGCCTCCCTGCCACACACAGATTCAT

CCCCCTGTTTAAGCAGATCCTGTCCGATAGGAACACCCTGTCTTTCATCCTGGAGGAGTTTA

AGAGCGACGAGGAAGTGATCCAGTCCTTCTGCAAGTACAAGACACTGCTGAGAAACGAGAA

CGTGCTGGAGACAGCCGAGGCCCTGTTTAACGAGCTGAACAGCATCGACCTGACACACATC

TTCATCAGCCACAAGAAGCTGGAGACAATCAGCAGCGCCCTGTGCGACCACTGGGATACAC

TGAGGAATGCCCTGTATGAGCGGAGAATCTCCGAGCTGACAGGCAAGATCACCAAGTCTGC

CAAGGAGAAGGTGCAGCGCAGCCTGAAGCACGAGGATATCAACCTGCAGGAGATCATCTCT

GCCGCAGGCAAGGAGCTGAGCGAGGCCTTCAAGCAGAAAACCAGCGAGATCCTGTCCCAC

GCACACGCCGCCCTGGATCAGCCACTGCCTACAACCCTGAAGAAGCAGGAGGAGAAGGAG

ATCCTGAAGTCTCAGCTGGACAGCCTGCTGGGCCTGTACCACCTGCTGGACTGGTTTGCCG

-continued

TGGATGAGTCCAACGAGGTGGACCCCGAGTTCTCTGCCCGGCTGACCGGCATCAAGCTGG

AGATGGAGCCTTCTCTGAGCTTCTACAACAAGGCCAGAAATTATGCCACCAAGAAGCCCTAC

TCCGTGGAGAAGTTCAAGCTGAACTTTCAGATGCCTACACTGGCC<u>aga</u>GGCTGGGACGTGAA

T<u>aga</u>GAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACGATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGGCCAATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

-continued
ATCCAGGAGCTGCGCAACaaaaggccggcggccacgaaaaaggccggccaggcaaaaaagaaaaag*GGAGC*

*GGCCGCACTCGAG*CACCACCACCACCACCACTGA

AAS1880: pET-28b-hAsCas12a(E174R/S542R)-NLS-6xHis
Human codon optimized *Acidaminococcus* sp. *BV3L6* Cas12a (AsCas12a) in black, modified codons (E174R/S542R) in double underlined lower case, codons with silent mutations to remove NcoI sites double underlined UPPER CASE, inserted glycine dash-underlined, nucleoplasmin NLS (aaaaggccggcggccacgaaaaaggccggccaggcaaaaaagaaaaag, SEQ ID NO: 21) in lower case, linker sequences in italics, 6xHis in bold

SEQ ID NO: 428)

ATGGGGACACAGTTCGAGGGCTTTACCAACCTGTATCAGGTGAGCAAGACACTGCG

GTTTGAGCTGATCCCACAGGGCAAGACCCTGAAGCACATCCAGGAGCAGGGCTTCATCGAG

GAGGACAAGGCCCGCAATGATCACTACAAGGAGCTGAAGCCCATCATCGATCGGATCTACA

AGACCTATGCCGACCAGTGCCTGCAGCTGGTGCAGCTGGATTGGGAGAACCTGAGCGCCG

CCATCGACTCCTATAGAAAGGAGAAAACCGAGGAGACAAGGAACGCCCTGATCGAGGAGCA

GGCCACATATCGCAATGCCATCCACGACTACTTCATCGGCCGGACAGACAACCTGACCGAT

GCCATCAATAAGAGACACGCCGAGATCTACAAGGGCCTGTTCAAGGCCGAGCTGTTTAATG

GCAAGGTGCTGAAGCAGCTGGGCACCGTGACCACAACCGAGCACGAGAACGCCCTGCTGC

GGAGCTTCGACAAGTTTACAACCTACTTCTCCGGCTTTTATagaAACAGGAAGAACGTGTTCA

GCGCCGAGGATATCAGCACAGCCATCCCACACCGCATCGTGCAGGACAACTTCCCCAAGTT

TAAGGAGAATTGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAGGAGGTGTTTT

CCTTCCCTTTTTATAACCAGCTGCTGACACAGACCCAGATCGACCTGTATAACCAGCTGCTG

GGAGGAATCTCTCGGGAGGCAGGCACCGAGAAGATCAAGGGCCTGAACGAGGTGCTGAAT

CTGGCCATCCAGAAGAATGATGAGACAGCCCACATCATCGCCTCCCTGCCACACAGATTCAT

CCCCCTGTTTAAGCAGATCCTGTCCGATAGGAACACCCTGTCTTTCATCCTGGAGGAGTTTA

AGAGCGACGAGGAAGTGATCCAGTCCTTCTGCAAGTACAAGACACTGCTGAGAAACGAGAA

CGTGCTGGAGACAGCCGAGGCCCTGTTTAACGAGCTGAACAGCATCGACCTGACACACATC

TTCATCAGCCACAAGAAGCTGGAGACAATCAGCAGCGCCCTGTGCGACCACTGGGATACAC

TGAGGAATGCCCTGTATGAGCGGAGAATCTCCGAGCTGACAGGCAAGATCACCAAGTCTGC

CAAGGAGAAGGTGCAGCGCAGCCTGAAGCACGAGGATATCAACCTGCAGGAGATCATCTCT

GCCGCAGGCAAGGAGCTGAGCGAGGCCTTCAAGCAGAAAACCAGCGAGATCCTGTCCCAC

GCACACGCCGCCCTGGATCAGCCACTGCCTACAACCCTGAAGAAGCAGGAGGAGAAGGAG

ATCCTGAAGTCTCAGCTGGACAGCCTGCTGGGCCTGTACCACCTGCTGGACTGGTTTGCCG

TGGATGAGTCCAACGAGGTGGACCCCGAGTTCTCTGCCCGGCTGACCGGCATCAAGCTGG

AGATGGAGCCTTCTCTGAGCTTCTACAACAAGGCCAGAAATTATGCCACCAAGAAGCCCTAC

TCCGTGGAGAAGTTCAAGCTGAACTTTCAGATGCCTACACTGGCCagaGGCTGGGACGTGAA

TAAGGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

-continued

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGAC<u>ACG</u>ATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGG<u>CC</u>AATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAAC*aaaaggccggcggccacgaaaaaggccggccaggcaaaaaagaaaaag*GGAGC

GGCCGCACTCGAGCACCACCACCACCACCACTGA

AAS1935: pET-28b-heAsCas12a-HF1(E174R/N282A/S542R/K548R)-NLS-6xHis
Human codon optimized Acidaminococcus sp. BV3L6 Cas12a (AsCas12a) in black, modified
codons for eAsCas12a-HF1 (E174R/N282A/S542R/K548R) in double underlined lower
case, codons with silent mutations to remove NcoI sites double underlined
UPPER CASE, inserted glycine dash-underlined, nucleoplasmin NLS
(aaaaggccggcggccacgaaaaaggccggccaggcaaaaaagaaaaag, SEQ ID NO: 21) in lower case,
linker sequences in italics, 6xHis in bold (SEQ ID NO: 429)

ATG<u>GGG</u>ACACAGTTCGAGGGCTTTACCAACCTGTATCAGGTGAGCAAGACACTGCG

GTTTGAGCTGATCCCACAGGGCAAGACCCTGAAGCACATCCAGGAGCAGGGCTTCATCGAG

GAGGACAAGGCCCGCAATGATCACTACAAGGAGCTGAAGCCCATCATCGATCGGATCTACA

AGACCTATGCCGACCAGTGCCTGCAGCTGGTGCAGCTGGATTGGGAGAACCTGAGCGCCG

CCATCGACTCCTATAGAAAGGAGAAAACCGAGGAGACAAGGAACGCCCTGATCGAGGAGCA

-continued

```
GGCCACATATCGCAATGCCATCCACGACTACTTCATCGGCCGGACAGACAACCTGACCGAT

GCCATCAATAAGAGACACGCCGAGATCTACAAGGGCCTGTTCAAGGCCGAGCTGTTTAATG

GCAAGGTGCTGAAGCAGCTGGGCACCGTGACCACAACCGAGCACGAGAACGCCCTGCTGC

GGAGCTTCGACAAGTTTACAACCTACTTCTCCGGCTTTTATagaAACAGGAAGAACGTGTTCA

GCGCCGAGGATATCAGCACAGCCATCCCACACCGCATCGTGCAGGACAACTTCCCCAAGTT

TAAGGAGAATTGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAGGAGGTGTTTT

CCTTCCCTTTTTATAACCAGCTGCTGACACAGACCCAGATCGACCTGTATAACCAGCTGCTG

GGAGGAATCTCTCGGGAGGCAGGCACCGAGAAGATCAAGGGCCTGAACGAGGTGCTGgccC

TGGCCATCCAGAAGAATGATGAGACAGCCCACATCATCGCCTCCCTGCCACACAGATTCATC

CCCCTGTTTAAGCAGATCCTGTCCGATAGGAACACCCTGTCTTTCATCCTGGAGGAGTTTAA

GAGCGACGAGGAAGTGATCCAGTCCTTCTGCAAGTACAAGACACTGCTGAGAAACGAGAAC

GTGCTGGAGACAGCCGAGGCCCTGTTTAACGAGCTGAACAGCATCGACCTGACACACATCT

TCATCAGCCACAAGAAGCTGGAGACAATCAGCAGCGCCCTGTGCGACCACTGGGATACACT

GAGGAATGCCCTGTATGAGCGGAGAATCTCCGAGCTGACAGGCAAGATCACCAAGTCTGCC

AAGGAGAAGGTGCAGCGCAGCCTGAAGCACGAGGATATCAACCTGCAGGAGATCATCTCTG

CCGCAGGCAAGGAGCTGAGCGAGGCCTTCAAGCAGAAAACCAGCGAGATCCTGTCCCACG

CACACGCCGCCCTGGATCAGCCACTGCCTACAACCCTGAAGAAGCAGGAGGAGAAGGAGA

TCCTGAAGTCTCAGCTGGACAGCCTGCTGGGCCTGTACCACCTGCTGGACTGGTTTGCCGT

GGATGAGTCCAACGAGGTGGACCCCGAGTTCTCTGCCCGGCTGACCGGCATCAAGCTGGA

GATGGAGCCTTCTCTGAGCTTCTACAACAAGGCCAGAAATTATGCCACCAAGAAGCCCTACT

CCGTGGAGAAGTTCAAGCTGAACTTTCAGATGCCTACACTGGCCagaGGCTGGGACGTGAAT agaGAGAAGAACAATGGCGCCATCCTGTTTGTGAAGAACGGCCTGTACTATCTGGGCATCAT

GCCAAAGCAGAAGGGCAGGTATAAGGCCCTGAGCTTCGAGCCCACAGAGAAAACCAGCGA

GGGCTTTGATAAGATGTACTATGACTACTTCCCTGATGCCGCCAAGATGATCCCAAAGTGCA

GCACCCAGCTGAAGGCCGTGACAGCCCACTTTCAGACCCACACAACCCCCATCCTGCTGTC

CAACAATTTCATCGAGCCTCTGGAGATCACAAAGGAGATCTACGACCTGAACAATCCTGAGA

AGGAGCCAAAGAAGTTTCAGACAGCCTACGCCAAGAAAACCGGCGACCAGAAGGGCTACAG

AGAGGCCCTGTGCAAGTGGATCGACTTCACAAGGGATTTTCTGTCCAAGTATACCAAGACAA

CCTCTATCGATCTGTCTAGCCTGCGGCCATCCTCTCAGTATAAGGACCTGGGCGAGTACTAT

GCCGAGCTGAATCCCCTGCTGTACCACATCAGCTTCCAGAGAATCGCCGAGAAGGAGATCA

TGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC
```

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATOGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGAC<u>ACG</u>ATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGG<u>CC</u>AATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAAC*aaaaggccggcggccacgaaaaaggccggccaggcaaaaaagaaaaag**GGAGC*

*GGCCGCACTCGAG*CACCACCACCACCACCACTGA

Nucleotide sequence of SQT1665 pCAG-humanLbCpf1-NLS-3xHA
Human codon optimized LbCpf1 in normal font, nts 1-3684), NLS
(aaaaggccggcggccacgaaaaaggccggccaggcaaaaaagaaaaag, SEQ ID NO: 21) in lower case, 3xHA
tag
(TACCCATACGATGTTCCAGATTACGCTTATCCCTACGACGTGCCTGATTATGCATACCCATAT
GATGTCCCCGACTATGCC, SEQ ID NO: 5) in BOLD, linker sequence in italics (SEQ ID NO: 10)

ATGAGCAAGCTGGAGAAGTTTACAAACTGCTACTCCCTGTCTAAGACCCTGAGGTTCA

AGGCCATCCCTGTGGGCAAGACCCAGGAGAACATCGACAATAAGCGGCTGCTGGTGGAGGA

CGAGAAGAGAGCCGAGGATTATAAGGGCGTGAAGAAGCTGCTGGATCGCTACTATCTGTCTT

TTATCAACGACGTGCTGCACAGCATCAAGCTGAAGAATCTGAACAATTACATCAGCCTGTTCC

GGAAGAAAACCAGAACCGAGAAGGAGAATAAGGAGCTGGAGAACCTGGAGATCAATCTGCGG

AAGGAGATCGCCAAGGCCTTCAAGGGCAACGAGGGCTACAAGTCCCTGTTTAAGAAGGATAT

CATOGAGACAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTTTTCCGAGGA

GGCCAAGAGCACATCCATCGCCTTCAGGTGTATCAACGAGAATCTGACCCGCTACATCTCTAA

TATGGACATCTTCGAGAAGGTGGACGCCATCTTTGATAAGCACGAGGTGCAGGAGATCAAGG

AGAAGATCCTGAACAGCGACTATGATGTGGAGGATTTCTTTGAGGGCGAGTTCTTTAACTTTG

TGCTGACACAGGAGGGCATCGACGTGTATAACGCCATCATCGGCGGCTTCGTGACCGAGAGC

GGCGAGAAGATCAAGGGCCTGAACGAGTACATCAACCTGTATAATCAGAAAACCAAGCAGAA

GCTGCCTAAGTTTAAGCCACTGTATAAGCAGGTGCTGAGCGATCGGGAGTCTCTGAGCTTCTA

CGGCGAGGGCTATACATCCGATGAGGAGGTGCTGGAGGTGTTTAGAAACACCCTGAACAAGA

ACAGCGAGATCTTCAGCTCCATCAAGAAGCTGGAGAAGCTGTTCAAGAATTTTGACGAGTACT

CTAGCGCCGGCATCTTTGTGAAGAACGGCCCCGCCATCAGCACAATCTCCAAGGATATCTTC

-continued

```
GGCGAGTGGAACGTGATCCGGGACAAGTGGAATGCCGAGTATGACGATATCCACCTGAAGAA
GAAGGCCGTGGTGACCGAGAAGTACGAGGACGATCGGAGAAAGTCCTTCAAGAAGATCGGC
TCCTTTTCTCTGGAGCAGCTGCAGGAGTACGCCGACGCCGATCTGTCTGTGGTGGAGAAGCT
GAAGGAGATCATCATCCAGAAGGTGGATGAGATCTACAAGGTGTATGGCTCCTCTGAGAAGC
TGTTCGACGCCGATTTTGTGCTGGAGAAGAGCCTGAAGAAGAACGACGCCGTGGTGGCCATC
ATGAAGGACCTGCTGGATTCTGTGAAGAGCTTCGAGAATTACATCAAGGCCTTCTTTGGCGAG
GGCAAGGAGACAAACAGGGACGAGTCCTTCTATGGCGATTTTGTGCTGGCCTACGACATCCT
GCTGAAGGTGGACCACATCTACGATGCCATCCGCAATTATGTGACCCAGAAGCCCTACTCTAA
GGATAAGTTCAAGCTGTATTTTCAGAACCCTCAGTTCATGGGCGGCTGGGACAAGGATAAGGA
GACAGACTATCGGGCCACCATCCTGAGATACGGCTCCAAGTACTATCTGGCCATCATGGATAA
GAAGTACGCCAAGTGCCTGCAGAAGATCGACAAGGACGATGTGAACGGCAATTACGAGAAGA
TCAACTATAAGCTGCTGCCCGGCCCTAATAAGATGCTGCCAAAGGTGTTCTTTTCTAAGAAGT
GGATGGCCTACTATAACCCCAGCGAGGACATCCAGAAGATCTACAAGAATGGCACATTCAAGA
AGGGCGATATGTTTAACCTGAATGACTGTCACAAGCTGATCGACTTCTTTAAGGATAGCATCTC
CCGGTATCCAAAGTGGTCCAATGCCTACGATTTCAACTTTTCTGAGACAGAGAAGTATAAGGA
CATCGCCGGCTTTTACAGAGAGGTGGAGGAGCAGGGCTATAAGGTGAGCTTCGAGTCTGCCA
GCAAGAAGGAGGTGGATAAGCTGGTGGAGGAGGGCAAGCTGTATATGTTCCAGATCTATAAC
AAGGACTTTTCCGATAAGTCTCACGGCACACCCAATCTGCACACCATGTACTTCAAGCTGCTG
TTTGACGAGAACAATCACGGACAGATCAGGCTGAGCGGAGGAGCAGAGCTGTTCATGAGGCG
CGCCTCCCTGAAGAAGGAGGAGCTGGTGGTGCACCCAGCCAACTCCCCTATCGCCAACAAGA
ATCCAGATAATCCCAAGAAAACCACAACCCTGTCCTACGACGTGTATAAGGATAAGAGGTTTT
CTGAGGACCAGTACGAGCTGCACATCCCAATCGCCATCAATAAGTGCCCCAAGAACATCTTCA
AGATCAATACAGAGGTGCGCGTGCTGCTGAAGCACGACGATAACCCCTATGTGATCGGCATC
GATAGGGGCGAGCGCAATCTGCTGTATATCGTGGTGGTGGACGGCAAGGGCAACATCGTGG
AGCAGTATTCCCTGAACGAGATCATCAACAACTTCAACGGCATCAGGATCAAGACAGATTACC
ACTCTCTGCTGGACAAGAAGGAGAAGGAGAGGTTCGAGGCCCGCCAGAACTGGACCTCCATC
GAGAATATCAAGGAGCTGAAGGCCGGCTATATCTCTCAGGTGGTGCACAAGATCTGCGAGCT
GGTGGAGAAGTACGATGCCGTGATCGCCCTGGAGGACCTGAACTCTGGCTTTAAGAATAGCC
GCGTGAAGGTGGAGAAGCAGGTGTATCAGAAGTTCGAGAAGATGCTGATCGATAAGCTGAAC
TACATGGTGGACAAGAAGTCTAATCCTTGTGCAACAGGCGGCGCCCTGAAGGGCTATCAGAT
CACCAATAAGTTCGAGAGCTTTAAGTCCATGTCTACCCAGAACGGCTTCATCTTTTACATCCCT
GCCTGGCTGACATCCAAGATCGATCCATCTACCGGCTTTGTGAACCTGCTGAAAACCAAGTAT
ACCAGCATCGCCGATTCCAAGAAGTTCATCAGCTCCTTTGACAGGATCATGTACGTGCCCGAG
GAGGATCTGTTCGAGTTTGCCCTGGACTATAAGAACTTCTCTCGCACAGACGCCGATTACATC
AAGAAGTGGAAGCTGTACTCCTACGGCAACCGGATCAGAATCTTCCGGAATCCTAAGAAGAAC
AACGTGTTCGACTGGGAGGAGGTGTGCCTGACCAGCGCCTATAAGGAGCTGTTCAACAAGTA
CGGCATCAATTATCAGCAGGGCGATATCAGAGCCCTGCTGTGCGAGCAGTCCGACAAGGCCT
TCTACTCTAGCTTTATGGCCCTGATGAGCCTGATGCTGCAGATGCGGAACAGCATCACAGGC
CGCACCGACGTGGATTTTCTGATCAGCCCTGTGAAGAACTCCGACGGCATCTTCTACGATAGC
CGGAACTATGAGGCCCAGGAGAATGCCATCCTGCCAAAGAACGCCGACGCCAATGGCGCCT
ATAACATCGCCAGAAAGGTGCTGTGGGCCATCGGCCAGTTCAAGAAGGCCGAGGACGAGAA
```

```
GCTGGATAAGGTGAAGATCGCCATCTCTAACAAGGAGTGGCTGGAGTACGCCCAGACCAGCG

TGAAGCACaaaaggccggcggccacgaaaaaggccggccaggcaaaaaagaaaaagGGATCCTACCCATACGA

TGTTCCAGATTACGCTTATCCCTACGACGTGCCTGATTATGCATACCCATATGATGTCCCCG

ACTATGCCTAA
```

Amino acid sequence of LbCpf1-NLS-3xHA
LbCpf1 in normal text (AAs 1-1228), NLS (krpaatkkagqakkkk, SEQ ID NO: 7) in lower case,
3xHA tag (YPYDVPDYAYPYDVPDYAYPYDVPDYA, SEQ ID NO: 8) in bold (SEQ ID NO: 11)

```
MSKLEKFTNCYSLSKTLRFKAIPVGKTQENIDNKRLLVEDEKRAEDYKGVKKLLDRYYLSFI

NDVLHSIKLKNLNNYISLFRKKTRTEKENKELENLEINLRKEIAKAFKGNEGYKSLFKKDIIETILPEFL

DDKDEIALVNSFNGFTTAFTGFFDNRENMFSEEAKSTSIAFRCINENLTRYISNMDIFEKVDAIFDKH

EVQEIKEKILNSDYDVEDFFEGEFFNFVLTQEGIDVYNAIIGGFVTESGEKIKGLNEYINLYNQKTKQ

KLPKFKPLYKQVLSDRESLSFYGEGYTSDEEVLEVFRNTLNKNSEIFSSIKKLEKLFKNFDEYSSAGI

FVKNGPAISTISKDIFGEWNVIRDKWNAEYDDIHLKKKAVVTEKYEDDRRKSFKKIGSFSLEQLQEY

ADADLSVVEKLKEIIIQKVDEIYKVYGSSEKLFDADFVLEKSLKKNDAVVAIMKDLLDSVKSFENYIKA

FFGEGKETNRDESFYGDFVLAYDILLKVDHIYDAIRNYVTQKPYSKDKFKLYFQNPQFMGGWDKD

KETDYRATILRYGSKYYLAIMDKKYAKCLQKIDKDDVNGNYEKINYKLLPGPNKMLPKVFFSKKWM

AYYNPSEDIQKIYKNGTFKKGDMFNLNDCHKLIDFFKDSISRYPKWSNAYDFNFSETEKYKDIAGFY

REVEEQGYKVSFESASKKEVDKLVEEGKLYMFQIYNKDFSDKSHGTPNLHTMYFKLLFDENNHGQ

IRLSGGAELFMRRASLKKEELVVHPANSPIANKNPDNPKKTTTLSYDVYKDKRFSEDQYELHIPIAIN

KCPKNIFKINTEVRVLLKHDDNPYVIGIDRGERNLLYIVVVDGKGNIVEQYSLNEIINNFNGIRIKTDYH

SLLDKKEKERFEARQNVVTSIENIKELKAGYISQVVHKICELVEKYDAVIALEDLNSGFKNSRVKVEK

QVYQKFEKMLIDKLNYMVDKKSNPCATGGALKGYQITNKFESFKSMSTQNGFIFYIPAWLTSKIDPS

TGFVNLLKTKYTSIADSKKFISSFDRIMYVPEEDLFEFALDYKNFSRTDADYIKKWKLYSYGNRIRIF

RNPKKNNVFDWEEVCLTSAYKELFNKYGINYQQGDIRALLCEQSDKAFYSSFMALMSLMLQMRNS

ITGRTDVDFLISPVKNSDGIFYDSRNYEAQENAILPKNADANGAYNIARKVLWAIGQFKKAEDEKLD

KVKIAISNKEWLEYAQTSVKHkrpaatkkagqakkkkGSYPYDVPDYAYPYDVPDYAYPYDVPDYA
```

Nucleotide sequence of AAS1472 pCAG-humanFnCpf1-NLS-3xHA
Human codon optimized FnCpf1 in normal font, nts 1-3900), NLS
(aaaaggccggcggccacgaaaaaggccggccaggcaaaaaagaaaaag, SEQ ID NO: 21) in lower case, 3xHA
tag
(TACCCATACGATGTTCCAGATTACGCTTATCCCTACGACGTGCCTGATTATGCATACCCATAT
GATGTCCCCGACTATGCC, SEQ ID NO: 5) in BOLD (SEQ ID NO: 17)

```
ATGAGCATCTACCAGGAGTTCGTCAACAAGTATTCACTGAGTAAGACACTGCGGTTCG

AGCTGATCCCACAGGGCAAGACACTGGAGAACATCAAGGCCCGAGGCCTGATTCTGGACGAT

GAGAAGCGGGCAAAAGACTATAAGAAAGCCAAGCAGATCATTGATAAATACCACCAGTTCTTT

ATCGAGGAAATTCTGAGCTCCGTGTGCATCAGTGAGGATCTGCTGCAGAATTACTCAGACGTG

TACTTCAAGCTGAAGAAGAGCGACGATGACAACCTGCAGAAGGACTTCAAGTCCGCCAAGGA

CACCATCAAGAAACAGATTAGCGAGTACATCAAGGACTCCGAAAAGTTTAAAAATCTGTTCAAC

CAGAATCTGATCGATGCTAAGAAAGGCCAGGAGTCCGACCTGATCCTGTGGCTGAAACAGTC

TAAGGACAATGGGATTGAACTGTTCAAGGCTAACTCCGATATCACTGATATTGACGAGGCACT

GGAAATCATCAAGAGCTTCAAGGGATGGACCACATACTTTAAAGGCTTCCACGAGAACCGCAA

GAACGTGTACTCCAGCAACGACATTCCTACCTCCATCATCTACCGAATCGTCGATGACAATCT

GCCAAAGTTCCTGGAGAACAAGGCCAAATATGAATCTCTGAAGGACAAAGCTCCCGAGGCAA

TTAATTACGAACAGATCAAGAAAGATCTGGCTGAGGAACTGACATTCGATATCGACTATAAGAC
```

-continued

```
TAGCGAGGTGAACCAGAGGGTCTTTTCCCTGGACGAGGTGTTTGAAATCGCCAATTTCAACAA

TTACCTGAACCAGTCCGGCATTACTAAATTCAATACCATCATTGGCGGGAAGTTTGTGAACGG

GGAGAATACCAAGCGCAAGGGAATTAACGAATACATCAATCTGTATAGCCAGCAGATCAACGA

CAAAACTCTGAAGAAATACAAGATGTCTGTGCTGTTCAAACAGATCCTGAGTGATACCGAGTC

CAAGTCTTTTGTCATTGATAAACTGGAAGATGACTCAGACGTGGTCACTACCATGCAGAGCTTT

TATGAGCAGATCGCCGCTTTCAAGACAGTGGAGGAAAAATCTATTAAGGAAACTCTGAGTCTG

CTGTTCGATGACCTGAAAGCCCAGAAGCTGGACCTGAGTAAGATCTACTTCAAAAACGATAAG

AGTCTGACAGACCTGTCACAGCAGGTGTTTGATGACTATTCCGTGATTGGGACCGCCGTCCT

GGAGTACATTACACAGCAGATCGCTCCAAAGAACCTGGATAATCCCTCTAAGAAAGAGCAGGA

ACTGATCGCTAAGAAAACCGAGAAGGCAAAATATCTGAGTCTGGAAACAATTAAGCTGGCACT

GGAGGAGTTCAACAAGCACAGGGATATTGACAAACAGTGCCGCTTTGAGGAAATCCTGGCCA

ACTTCGCAGCCATCCCCATGATTTTTGATGAGATCGCCCAGAACAAAGACAATCTGGCTCAGA

TCAGTATTAAGTACCAGAACCAGGGCAAGAAAGACCTGCTGCAGGCTTCAGCAGAAGATGAC

GTGAAAGCCATCAAGGATCTGCTGGACCAGACCAACAATCTGCTGCACAAGCTGAAAATCTTC

CATATTAGTCAGTCAGAGGATAAGGCTAATATCCTGGATAAAGACGAACACTTCTACCTGGTG

TTCGAGGAATGTTACTTCGAGCTGGCAAACATTGTCCCCCTGTATAACAAGATTAGGAACTAC

ATCACACAGAAGCCTTACTCTGACGAGAAGTTTAAACTGAACTTCGAAAATAGTACCCTGGCC

AACGGGTGGGATAAGAACAAGGAGCCTGACAACACAGCTATCCTGTTCATCAAGGATGACAA

GTACTATCTGGGAGTGATGAATAAGAAAAACAATAAGATCTTCGATGACAAAGCCATTAAGGA

GAACAAAGGGGAAGGATACAAGAAAATCGTGTATAAGCTGCTGCCCGGCGCAAATAAGATGC

TGCCTAAGGTGTTCTTCAGCGCCAAGAGTATCAAATTCTACAACCCATCCGAGGACATCCTGC

GGATTAGAAATCACTCAACACATACTAAGAACGGGAGCCCCAGAAGGGATATGAGAAATTTG

AGTTCAACATCGAGGATTGCAGGAAGTTTATTGACTTCTACAAGCAGAGCATCTCCAAACACC

CTGAATGGAAGGATTTTGGCTTCCGGTTTTCCGACACACAGAGATATAACTCTATCGACGAGT

TCTACCGCGAGGTGGAAAATCAGGGGTATAAGCTGACTTTTGAGAACATTTCTGAAAGTTACA

TCGACAGCGTGGTCAATCAGGGAAAGCTGTACCTGTTCCAGATCTATAACAAAGATTTTTCAG

CATACAGCAAGGGCAGACCAAACCTGCATACACTGTACTGGAAGGCCCTGTTCGATGAGAGG

AATCTGCAGGACGTGGTCTATAAACTGAACGGAGAGGCCGAACTGTTTTACCGGAAGCAGTC

TATTCCTAAGAAAATCACTCACCCAGCTAAGGAGGCCATCGCTAACAAGAACAAGGACAATCC

TAAGAAAGAGAGCGTGTTCGAATACGATCTGATTAAGGACAAGCGGTTCACCGAAGATAAGTT

CTTTTTCCATTGTCCAATCACCATTAACTTCAAGTCAAGCGGCGCTAACAAGTTCAACGACGAG

ATCAATCTGCTGCTGAAGGAAAAAGCAAACGATGTGCACATCCTGAGCATTGACCGAGGAGA

GCGGCATCTGGCCTACTATACCCTGGTGGATGGCAAAGGGAATATCATTAAGCAGGATACATT

CAACATCATTGGCAATGACCGGATGAAAACCAACTACCACGATAAACTGGCTGCAATCGAGAA

GGATAGAGACTCAGCTAGGAAGGACTGGAAGAAAATCAACAACATTAAGGAGATGAAGGAAG

GCTATCTGAGCCAGGTGGTCCATGAGATTGCAAAGCTGGTCATCGAATACAATGCCATTGTGG

TGTTCGAGGATCTGAACTTCGGCTTTAAGAGGGGCGCTTTAAGGTGGAAAAACAGGTCTATC

AGAAGCTGGAGAAAATGCTGATCGAAAAGCTGAATTACCTGGTGTTTAAAGATAACGAGTTCG

ACAAGACCGGAGGCGTCCTGAGAGCCTACCAGCTGACAGCTCCCTTTGAAACTTTCAAGAAA

ATGGGAAAACAGACAGGCATCATCTACTATGTGCCAGCCGGATTCACTTCCAAGATCTGCCCC

GTGACCGGCTTTGTCAACCAGCTGTACCCTAAATATGAGTCAGTGAGCAAGTCCCAGGAATTT
```

-continued

```
TTCAGCAAGTTCGATAAGATCTGTTATAATCTGGACAAGGGGTACTTCGAGTTTTCCTTCGATT

ACAAGAACTTCGGCGACAAGGCCGCTAAGGGGAAATGGACCATTGCCTCCTTCGGATCTCGC

CTGATCAACTTTCGAAATTCCGATAAAAACCACAATTGGGACACTAGGGAGGTGTACCCAACC

AAGGAGCTGGAAAAGCTGCTGAAAGACTACTCTATCGAGTATGGACATGGCGAATGCATCAA

GGCAGCCATCTGTGGCGAGAGTGATAAGAAATTTTTCGCCAAGCTGACCTCAGTGCTGAATAC

AATCCTGCAGATGCGGAACTCAAAGACCGGGACAGAACTGGACTATCTGATTAGCCCCGTGG

CTGATGTCAACGGAAACTTCTTCGACAGCAGACAGGCACCCAAAAATATGCCTCAGGATGCAG

ACGCCAACGGGGCCTACCACATCGGGCTGAAGGGACTGATGCTGCTGGGCCGGATCAAGAA

CAATCAGGAGGGGAAGAAGCTGAACCTGGTCATTAAGAACGAGGAATACTTCGAGTTTGTCCA

GAATAGAAATAACaaaaggccggcggccacgaaaaaggccggccaggcaaaaaagaaaaagGGATCCTACCCA

TACGATGTTCCAGATTACGCTTATCCCTACGACGTGCCTGATTATGCATACCCATATGATGTC

CCCGACTATGCCTAA
```

Amino acid sequence of FnCpf1-NLS-3xHA
FnCpf1 in normal text (AAs 1-1300), NLS (krpaatkkagqakkkk, SEQ ID NO: 7) in lowercase,
3xHA tag (YPYDVPDYAYPYDVPDYAYPYDVPDYA, SEQ ID NO: 8) in bold (SEQ ID NO: 18)

```
MSIYQEFVNKYSLSKTLRFELIPQGKTLENIKARGLILDDEKRAKDYKKAKQIIDKYHQFFI

EEILSSVCISEDLLQNYSDVYFKLKKSDDDNLQKDFKSAKDTIKKQISEYIKDSEKFKNLFNQNLID

AKKGQESDLILWLKQSKIDNGIELFKANSDITDIDEALEIIKSFKGVVTTYFKGFHENRKNVYSSNDIP

TSIIYRIVDDNLPKFLENKAKYESLKDKAPEAINYEQIKKDLAEELTFDIDYKTSEVNQRVFSLDEVF

EIANFNNYLNQSGITKFNTIIGGKFVNGENTKRKGINEYINLYSQQINDKTLKKYKMSVLFKQILSDT

ESKSFVIDKLEDDSDVVTTMQSFYEQIAAFKTVEEKSIKETLSLLFDDLKAQKLDLSKIYFKNDKSL

TDLSQQVFDDYSVIGTAVLEYITQQIAPKNLDNPSKKEQELIAKKTEKAKYLSLETIKLALEEFNKH

RDIDKQCRFEEILANFAAIPMIFDEIAQNKDNLAQISIKYQNQGKKDLLQASAEDDVKAIKDLLDQT

NNLLHKLKIFHISQSEDKANILDKDEHFYLVFEECYFELANIVPLYNKIRNYITQKPYSDEKFKLNFE

NSTLANGWDKNKEPDNTAILFIKDDKYYLGVMNKKNNKIFDDKAIKENKGEGYKKIVYKLLPGANK

MLPKVFFSAKSIKFYNPSEDILRIRNHSTHTKNGSPQKGYEKFEFNIEDCRKFIDFYKQSISKHPE

WKDFGFRFSDTQRYNSIDEFYREVENQGYKLTFENISESYIDSVVNQGKLYLFQIYNKDFSAYSK

GRPNLHTLYWKALFDERNLQDVVYKLNGEAELFYRKQSIPKKITHPAKEAIANKNKDNPKKESVF

EYDLIKDKRFTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQVVHEIAKLVIE

YNAIVVFEDLNFGFKRGRFKVEKQVYQKLEKMLIEKLNYLVFKDNEFDKTGGVLRAYQLTAPFET

FKKMGKQTGIIYYVPAGFTSKICPVTGFVNQLYPKYESVSKSQEFFSKFDKICYNLDKGYFEFSFD

YKNFGDKAAKGKVVTIASFGSRLINFRNSDKNHNWDTREVYPTKELEKLLKDYSIEYGHGECIKAA

ICGESDKKFFAKLTSVLNTILQMRNSKTGTELDYLISPVADVNGNFFDSRQAPKNMPQDADANGA

YHIGLKGLMLLGRIKNNQEGKKLNLVIKNEEYFEFVQNRNNkrpaatkkagqakkkkGSYPYDVPDYAY

PYDVPDYAYPYDVPDYA
```

AAS2134: pCAG-hMbCas12a-NLS-3xHA
Human codon optimized *Moraxella bovoculi* 237 Cas12a (MbCas12a) in black,
nucleoplasmin nucleoplasmin NLS
(aaaaggccggcggccacgaaaaaggccggccaggcaaaaaagaaaaag, SEQ ID NO: 21) in lower case,
linker sequences in italics, 3xHA tag
(TACCCATACGATGITCCAGATTACGCTTATCCCTACGACGTGCCTGATTATGCATACCCATA
TGATGTCCCCGACTATGCC, SEQ ID NO: 5) in BOLD (SEQ ID NO: 430)

```
ATGCTGTTCCAGGACTTTACCCACCTGTATCCACTGTCCAAGACAGTGAGATTTGAG

CTGAAGCCCATCGATAGGACCCTGGAGCACATCCACGCCAAGAACTTCCTGTCTCAGGACG
```

```
-continued
AGACAATGGCCGATATGCACCAGAAGGTGAAAGTGATCCTGGACGATTACCACCGCGACTT

CATCGCCGATATGATGGGCGAGGTGAAGCTGACCAAGCTGGCCGAGTTCTATGACGTGTAC

CTGAAGTTTCGGAAGAACCCAAAGGACGATGAGCTGCAGAAGCAGCTGAAGGATCTGCAGG

CCGTGCTGAGAAAGGAGATCGTGAAGCCCATCGGCAATGGCGGCAAGTATAAGGCCGGCT

ACGACAGGCTGTTCGGCGCCAAGCTGTTTAAGGACGGCAAGGAGCTGGGCGATCTGGCCA

AGTTCGTGATCGCACAGGAGGGAGAGAGCTCCCCAAAGCTGGCCCACCTGGCCCACTTCG

AGAAGTTTTCCACCTATTTCACAGGCTTTCACGATAACCGGAAGAATATGTATTCTGACGAGG

ATAAGCACACCGCCATCGCCTACCGCCTGATCCACGAGAACCTGCCCCGGTTTATCGACAA

TCTGCAGATCCTGACCACAATCAAGCAGAAGCACTCTGCCCTGTACGATCAGATCATCAACG

AGCTGACCGCCAGCGGCCTGGACGTGTCTCTGGCCAGCCACCTGGATGGCTATCACAAGC

TGCTGACACAGGAGGGCATCACCGCCTACAATACACTGCTGGGAGGAATCTCCGGAGAGG

CAGGCTCTCCTAAGATCCAGGGCATCAACGAGCTGATCAATTCTCACCACAACCAGCACTGC

CACAAGAGCGAGAGAATCGCCAAGCTGAGGCCACTGCACAAGCAGATCCTGTCCGACGGC

ATGAGCGTGTCCTTCCTGCCCTCTAAGTTTGCCGACGATAGCGAGATGTGCCAGGCCGTGA

ACGAGTTCTATCGCCACTACGCCGACGTGTTCGCCAAGGTGCAGAGCCTGTTCGACGGCTT

TGACGATCACCAGAAGGATGGCATCTACGTGGAGCACAAGAACCTGAATGAGCTGTCCAAG

CAGGCCTTCGGCGACTTTGCACTGCTGGGACGCGTGCTGGACGGATACTATGTGGATGTGG

TGAATCCAGAGTTCAACGAGCGGTTTGCCAAGGCCAAGACCGACAATGCCAAGGCCAAGCT

GACAAAGGAGAAGGATAAGTTCATCAAGGGCGTGCACTCCCTGGCCTCTCTGGAGCAGGCC

ATCGAGCACTATACCGCAAGGCACGACGATGAGAGCGTGCAGGCAGGCAAGCTGGGACAG

TACTTCAAGCACGGCCTGGCCGGAGTGGACAACCCCATCCAGAAGATCCACAACAATCACA

GCACCATCAAGGGCTTTCTGGAGAGGGAGCGCCCTGCAGGAGAGAGAGCCCTGCCAAAGA

TCAAGTCCGGCAAGAATCCTGAGATGACACAGCTGAGGCAGCTGAAGGAGCTGCTGGATAA

CGCCCTGAATGTGGCCCACTTCGCCAAGCTGCTGACCACAAAGACCACACTGGACAATCAG

GATGGCAACTTCTATGGCGAGTTTGGCGTGCTGTACGACGAGCTGGCCAAGATCCCCACCC

TGTATAACAAGGTGAGAGATTACCTGAGCCAGAAGCCTTTCTCCACCGAGAAGTACAAGCTG

AACTTTGGCAATCCAACACTGCTGAATGGCTGGGACCTGAACAAGGAGAAGGATAATTTCGG

CGTGATCCTGCAGAAGGACGGCTGCTACTATCTGGCCCTGCTGGACAAGGCCCACAAGAAG

GTGTTTGATAACGCCCCTAATACAGGCAAGAGCATCTATCAGAAGATGATCTATAAGTACCT

GGAGGTGAGGAAGCAGTTCCCCAAGGTGTTCTTTTCCAAGGAGGCCATCGCCATCAACTAC

CACCCTTCTAAGGAGCTGGTGGAGATCAAGGACAAGGGCCGGCAGAGATCCGACGATGAG

CGCCTGAAGCTGTATCGGTTTATCCTGGAGTGTCTGAAGATCCACCCTAAGTACGATAAGAA

GTTCGAGGGCGCCATCGGCGACATCCAGCTGTTTAAGAAGGATAAGAAGGGCAGAGAGGT

GCCAATCAGCGAGAAGGACCTGTTCGATAAGATCAACGGCATCTTTTCTAGCAAGCCTAAGC

TGGAGATGGAGGACTTCTTTATCGGCGAGTTCAAGAGGTATAACCCAAGCCAGGACCTGGT

GGATCAGTATAATATCTACAAGAAGATCGACTCCAACGATAATCGCAAGAAGGAGAATTTCTA

CAACAATCACCCCAAGTTTAAGAAGGATCTGGTGCGGTACTATTACGAGTCTATGTGCAAGC

ACGAGGAGTGGGAGGAGAGCTTCGAGTTTTCCAAGAAGCTGCAGGACATCGGCTGTTACGT

GGATGTGAACGAGCTGTTTACCGAGATCGAGACACGGAGACTGAATTATAAGATCTCCTTCT

GCAACATCAATGCCGACTACATCGATGAGCTGGTGGAGCAGGGCCAGCTGTATCTGTTCCA

GATCTACAACAAGGACTTTTCCCCAAAGGCCCACGGCAAGCCCAATCTGCACACCCTGTACT
```

-continued

```
TCAAGGCCCTGTTTTCTGAGGACAACCTGGCCGATCCTATCTATAAGCTGAATGGCGAGGC

CCAGATCTTCTACAGAAAGGCCTCCCTGGACATGAACGAGACAACAATCCACAGGGCCGGC

GAGGTGCTGGAGAACAAGAATCCCGATAATCCTAAGAAGAGACAGTTCGTGTACGACATCAT

CAAGGATAAGAGGTACACACAGGACAAGTTCATGCTGCACGTGCCAATCACCATGAACTTTG

GCGTGCAGGGCATGACAATCAAGGAGTTCAATAAGAAGGTGAACCAGTCTATCCAGCAGTA

TGACGAGGTGAACGTGATCGGCATCGATCGGGGCGAGAGACACCTGCTGTACCTGACCGT

GATCAATAGCAAGGGCGAGATCCTGGAGCAGTGTTCCCTGAACGACATCACCACAGCCTCT

GCCAATGGCACACAGATGACCACACCTTACCACAAGATCCTGGATAAGAGGGAGATCGAGC

GCCTGAACGCCCGGGTGGGATGGGGCGAGATCGAGACAATCAAGGAGCTGAAGTCTGGCT

ATCTGAGCCACGTGGTGCACCAGATCAGCCAGCTGATGCTGAAGTACAACGCCATCGTGGT

GCTGGAGGACCTGAATTTCGGCTTTAAGAGGGGCCGCTTTAAGGTGGAGAAGCAGATCTAT

CAGAACTTCGAGAATGCCCTGATCAAGAAGCTGAACCACCTGGTGCTGAAGGACAAGGCCG

ACGATGAGATCGGCTCTTACAAGAATGCCCTGCAGCTGACCAACAATTTCACAGATCTGAAG

AGCATCGGCAAGCAGACCGGCTTCCTGTTTTATGTGCCCGCCTGGAACACCTCTAAGATCG

ACCCTGAGACAGGCTTTGTGGATCTGCTGAAGCCAAGATACGAGAACATCGCCCAGAGCCA

GGCCTTCTTTGGCAAGTTCGACAAGATCTGCTATAATGCCGACAAGGATTACTTCGAGTTTC

ACATCGACTACGCCAAGTTTACCGATAAGGCCAAGAATAGCCGCCAGATCTGGACAATCTGT

TCCCACGGCGACAAGCGGTACGTGTACGATAAGACAGCCAACCAGAATAAGGGCGCCGCC

AAGGGCATCAACGTGAATGATGAGCTGAAGTCCCTGTTCGCCCGCCACCACATCAACGAGA

AGCAGCCCAACCTGGTCATGGACATCTGCCAGAACAATGATAAGGAGTTTCACAAGTCTCTG

ATGTACCTGCTGAAAACCCTGCTGGCCCTGCGGTACAGCAACGCCTCCTCTGACGAGGATT

TCATCCTGTCCCCCGTGGCAAACGACGAGGGCGTGTTCTTTAATAGCGCCCTGGCCGACGA

TACACAGCCTCAGAATGCCGATGCCAACGGCGCCTACCACATCGCCCTGAAGGGCCTGTGG

CTGCTGAATGAGCTGAAGAACTCCGACGATCTGAACAAGGTGAAGCTGGCCATCGACAATC

AGACCTGGCTGAATTTCGCCCAGAACAGGaaaaggccggcggccacgaaaaaggccggccaggcaaaaaa gaaaaagGGATCCTACCCATACGATGTTCCAGATTACGCTTATCCCTACGACGTGCCTGAT

TATGCATACCCATATGATGTCCCCGACTATGCCTAA
```

Nucleotide sequence of (RTW876) pCAG-human-dAsCpf1(D908A)-NLS(nucleoplasmin)-
3xHA-VPR
Human codon optimized dAsCpf1(D908A) in normal font (NTs 1-3921), Nucleoplasmin
NLS in lower case (aaaaggccggcggccacgaaaaaggccggccaggcaaaaaagaaaaag, SEQ ID NO: 21),
3xHA tag
(TACCCATACGATGTTCCAGATTACGCTTATCCCTACGACGTGCCTGATTATGCATACCCATAT
GATGTCCCCGACTATGCC, SEQ ID NO: 5) in bold, and VPR double underlined

SEQ ID NO: 431)

```
ATGACACAGTTCGAGGGCTTTACCAACCTGTATCAGGTGAGCAAGACACTGCGGTT

TGAGCTGATCCCACAGGGCAAGACCCTGAAGCACATCCAGGAGCAGGGCTTCATCGAGGA

GGACAAGGCCCGCAATGATCACTACAAGGAGCTGAAGCCCATCATCGATCGGATCTACAAG

ACCTATGCCGACCAGTGCCTGCAGCTGGTGCAGCTGGATTGGGAGAACCTGAGCGCCGCC

ATCGACTCCTATAGAAAGGAGAAAACCGAGGAGACAAGGAACGCCCTGATCGAGGAGCAGG

CCACATATCGCAATGCCATCCACGACTACTTCATCGGCCGGACAGACAACCTGACCGATGC

CATCAATAAGAGACACGCCGAGATCTACAAGGGCCTGTTCAAGGCCGAGCTGTTTAATGGC

AAGGTGCTGAAGCAGCTGGGCACCGTGACCACAACCGAGCACGAGAACGCCCTGCTGCGG

AGCTTCGACAAGTTTACAACCTACTTCTCCGGCTTTTATGAGAACAGGAAGAACGTGTTCAG

CGCCGAGGATATCAGCACAGCCATCCCACACCGCATCGTGCAGGACAACTTCCCCAAGTTT
```

-continued

```
AAGGAGAATTGTCACATCTTCACACGCCTGATCACCGCCGTGCCCAGCCTGCGGGAGCACT
TTGAGAACGTGAAGAAGGCCATCGGCATCTTCGTGAGCACCTCCATCGAGGAGGTGTTTTC
CTTCCCTTTTTATAACCAGCTGCTGACACAGACCCAGATCGACCTGTATAACCAGCTGCTGG
GAGGAATCTCTCGGGAGGCAGGCACCGAGAAGATCAAGGGCCTGAACGAGGTGCTGAATC
TGGCCATCCAGAAGAATGATGAGACAGCCCACATCATCGCCTCCCTGCCACACAGATTCATC
CCCCTGTTTAAGCAGATCCTGTCCGATAGGAACACCCTGTCTTTCATCCTGGAGGAGTTTAA
GAGCGACGAGGAAGTGATCCAGTCCTTCTGCAAGTACAAGACACTGCTGAGAAACGAGAAC
GTGCTGGAGACAGCCGAGGCCCTGTTTAACGAGCTGAACAGCATCGACCTGACACACATCT
TCATCAGCCACAAGAAGCTGGAGACAATCAGCAGCGCCCTGTGCGACCACTGGGATACACT
GAGGAATGCCCTGTATGAGCGGAGAATCTCCGAGCTGACAGGCAAGATCACCAAGTCTGCC
AAGGAGAAGGTGCAGCGCAGCCTGAAGCACGAGGATATCAACCTGCAGGAGATCATCTCTG
CCGCAGGCAAGGAGCTGAGCGAGGCCTTCAAGCAGAAAACCAGCGAGATCCTGTCCCACG
CACACGCCGCCCTGGATCAGCCACTGCCTACAACCCTGAAGAAGCAGGAGGAGAAGGAGA
TCCTGAAGTCTCAGCTGGACAGCCTGCTGGGCCTGTACCACCTGCTGGACTGGTTTGCCGT
GGATGAGTCCAACGAGGTGGACCCCGAGTTCTCTGCCCGGCTGACCGGCATCAAGCTGGA
GATGGAGCCTTCTCTGAGCTTCTACAACAAGGCCAGAAATTATGCCACCAAGAAGCCCTACT
CCGTGGAGAAGTTCAAGCTGAACTTTCAGATGCCTACACTGGCCTCTGGCTGGGACGTGAA
TAAGGAGAAGAACAATGGCGCCATCCTGTTTGTGAAGAACGGCCTGTACTATCTGGGCATCA
TGCCAAAGCAGAAGGGCAGGTATAAGGCCCTGAGCTTCGAGCCCACAGAGAAACCAGCG
AGGGCTTTGATAAGATGTACTATGACTACTTCCCTGATGCCGCCAAGATGATCCCAAAGTGC
AGCACCCAGCTGAAGGCCGTGACAGCCCACTTTCAGACCCACACAACCCCCATCCTGCTGT
CCAACAATTTCATCGAGCCTCTGGAGATCACAAAGGAGATCTACGACCTGAACAATCCTGAG
AAGGAGCCAAAGAAGTTTCAGACAGCCTACGCCAAGAAAACCGGCGACCAGAAGGGCTACA
GAGAGGCCCTGTGCAAGTGGATCGACTTCACAAGGGATTTTCTGTCCAAGTATACCAAGACA
ACCTCTATCGATCTGTCTAGCCTGCGGCCATCCTCTCAGTATAAGGACCTGGGCGAGTACTA
TGCCGAGCTGAATCCCCTGCTGTACCACATCAGCTTCCAGAGAATCGCCGAGAAGGAGATC
ATGGATGCCGTGGAGACAGGCAAGCTGTACCTGTTCCAGATCTATAACAAGGACTTTGCCAA
GGGCCACCACGGCAAGCCTAATCTGCACACACTGTATTGGACCGGCCTGTTTTCTCCAGAG
AACCTGGCCAAGACAAGCATCAAGCTGAATGGCCAGGCCGAGCTGTTCTACCGCCCTAAGT
CCAGGATGAAGAGGATGGCACACCGGCTGGGAGAGAAGATGCTGAACAAGAAGCTGAAGG
ATCAGAAAACCCCAATCCCCGACACCCTGTACCAGGAGCTGTACGACTATGTGAATCACAGA
CTGTCCCACGACCTGTCTGATGAGGCCAGGGCCCTGCTGCCCAACGTGATCACCAAGGAG
GTGTCTCACGAGATCATCAAGGATAGGCGCTTTACCAGCGACAAGTTCTTTTTCCACGTGCC
TATCACACTGAACTATCAGGCCGCCAATTCCCCATCTAAGTTCAACCAGAGGGTGAATGCCT
ACCTGAAGGAGCACCCCGAGACACCTATCATCGGCATCGCCCGGGGCGAGAGAAACCTGA
TCTATATCACAGTGATCGACTCCACCGGCAAGATCCTGGAGCAGCGGAGCCTGAACACCAT
CCAGCAGTTTGATTACCAGAAGAAGCTGGACAACAGGGAGAAGGAGAGGGTGGCAGCAAG
GCAGGCCTGGTCTGTGGTGGGCACAATCAAGGATCTGAAGCAGGGCTATCTGAGCCAGGT
CATCCACGAGATCGTGGACCTGATGATCCACTACCAGGCCGTGGTGGTGCTGGAGAACCTG
AATTTCGGCTTTAAGAGCAAGAGGACCGGCATCGCCGAGAAGGCCGTGTACCAGCAGTTCG
AGAAGATGCTGATCGATAAGCTGAATTGCCTGGTGCTGAAGGACTATCCAGCAGAGAAAGT
```

-continued

```
GGGAGGCGTGCTGAACCCATACCAGCTGACAGACCAGTTCACCTCCTTTGCCAAGATGGGC

ACCCAGTCTGGCTTCCTGTTTTACGTGCCTGCCCCATATACATCTAAGATCGATCCCCTGAC

CGGCTTCGTGGACCCCTTCGTGTGGAAAACCATCAAGAATCACGAGAGCCGCAAGCACTTC

CTGGAGGGCTTCGACTTTCTGCACTACGACGTGAAAACCGGCGACTTCATCCTGCACTTTAA

GATGAACAGAAATCTGTCCTTCCAGAGGGGCCTGCCCGGCTTTATGCCTGCATGGGATATC

GTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGC

CAACGAGCTGATCGCCCTGCTGGAGGAGAAGGGCATCGTGTTCAGGGATGGCTCCAACATC

CTGCCAAAGCTGCTGGAGAATGACGATTCTCACGCCATCGACACCATGGTGGCCCTGATCC

GCAGCGTGCTGCAGATGCGGAACTCCAATGCCGCCACAGGCGAGGACTATATCAACAGCC

CCGTGCGCGATCTGAATGGCGTGTGCTTCGACTCCCGGTTTCAGAACCCAGAGTGGCCCAT

GGACGCCGATGCCAATGGCGCCTACCACATCGCCCTGAAGGGCCAGCTGCTGCTGAATCA

CCTGAAGGAGAGCAAGGATCTGAAGCTGCAGAACGGCATCTCCAATCAGGACTGGCTGGCC

TACATCCAGGAGCTGCGCAACaaaaggccggcggccacgaaaaaggccggccaggcaaaaaagaaaaagGGA

TCCTACCCATACGATGTTCCAGATTACGCTTATCCCTACGACGTGCCTGATTATGCATACC

CATATGATGTCCCCGACTATGCCGGAAGCGAGGCCAGCGGTTCCGGACGGGCTGACGCAT

TGGACGATTTTGATCTGGATATGCTGGGAAGTGACGCCCTCGATGATTTTGACCTTGACATG

CTTGGTTCGGATGCCCTTGATGACTTTGACCTCGACATGCTCGGCAGTGACGCCCTTGATGA

TTTCGACCTGGACATGCTGATTAACTCTAGAAGTTCCGGATCTCCGAAAAAGAAACGCAAAG

TTGGTAGCCAGTACCTGCCCGACACCGACGACCGGCACCGGATCGAGGAAAAGCGGAAGC

GGACCTACGAGACATTCAAGAGCATCATGAAGAAGTCCCCCTTCAGCGGCCCCACCGACCC

TAGACCTCCACCTAGAAGAATCGCCGTGCCCAGCAGATCCAGCGCCAGCGTGCCAAAACCT

GCCCCCAGCCTTACCCCTTCACCAGCAGCCTGAGCACCATCAACTACGACGAGTTCCCTA

CCATGGTGTTCCCCAGCGGCCAGATCTCTCAGGCCTCTGCTCTGGCTCCAGCCCTCCTCA

GGTGCTGCCTCAGGCTCCTGCTCCTGCACCAGCTCCAGCCATGGTGTCTGCACTGGCTCAG

GCACCAGCACCCGTGCCTGTGCTGGCTCCTGGACCTCCACAGGCTGTGGCTCCACCAGCC

CCTAAACCTACACAGGCCGGCGAGGGCACACTGTCTGAAGCTCTGCTGCAGCTGCAGTTCG

ACGACGAGGATCTGGGAGCCCTGCTGGGAAACAGCACCGATCCTGCCGTGTTCACCGACC

TGGCCAGCGTGGACAACAGCGAGTTCCAGCAGCTGCTGAACCAGGGCATCCCTGTGGCCC

CTCACACCACCGAGCCCATGCTGATGGAATACCCCGAGGCCATCACCCGGCTCGTGACAG

GCGCTCAGAGGCCTCCTGATCCAGCTCCTGCCCCTCTGGGAGCACCAGGCCTGCCTAATG

GACTGCTGTCTGGCGACGAGGACTTCAGCTCTATCGCCGATATGGATTTCTCAGCCTTGCTG

GGCTCTGGCAGCGGCAGCCGGGATTCCAGGGAAGGGATGTTTTTGCCGAAGCCTGAGGCC

GGCTCCGCTATTAGTGACGTGTTTGAGGGCCGCGAGGTGTGCCAGCCAAAACGAATCCGG

CCATTTCATCCTCCAGGAAGTCCATGGGCCAACCGCCCACTCCCCGCCAGCCTCGCACCAA

CACCAACCGGTCCAGTACATGAGCCAGTCGGGTCACTGACCCCGGCACCAGTCCCTCAGC

CACTGGATCCAGCGCCCGCAGTGACTCCCGAGGCCAGTCACCTGTTGGAGGATCCCGATG

AAGAGACGAGCCAGGCTGTCAAAGCCCTTCGGGAGATGGCCGATACTGTGATTCCCCAGAA

GGAAGAGGCTGCAATCTGTGGCCAAATGGACCTTTCCCATCCGCCCCAAGGGGCCATCTG

GATGAGCTGACAACCACACTTGAGTCCATGACCGAGGATCTGAACCTGGACTCACCCCTGA
```

-continued

<u>CCCCGGAATTGAACGAGATTCTGGATACCTTCCTGAACGACGAGTGCCTCTTGCATGCCATG</u>

<u>CATATCAGCACAGGACTGTCCATCTTCGACACATCTCTGTTTTAA</u>

Amino acid sequence of dAsCpf1(D908A)-NLS(nucleoplasmin)-3xHA-VPR
AsCpf1 in normal font (AAs 1-1306), NLS(nucleoplasmin) (krpaatkkagqakkkk, SEQ ID
NO: 7) in lower case, 3xHA tag (YPYDVPDYAYPYDVPDYAYPYDVPDYA, SEQ ID NO: 8) in bold,
and VPR double underlined

SEQ ID NO: 432)

MTQFEGFTNLYQVSKTLRFELIPQGKTLKHIQEQGFIEEDKARNDHYKELKPIIDRIYKTYA

DQCLQLVQLDWENLSAAIDSYRKEKTEETRNALIEEQATYRNAIHDYFIGRTDNLTDAINKRHAEI

YKGLFKAELFNGKVLKQLGTVTTTEHENALLRSFDKFTTYFSGFYENRKNVFSAEDISTAIPHRIV

QDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQ

SFCKYKTLLRNENVLETAEALFNELNSIDLTHIFISHKKLETISSALCDHWDTLRNALYERRISELTG

KITKSAKEKVQRSLKHEDINLQEIISAAGKELSEAFKQKTSEILSHAHAALDQPLPTTLKKQEEKEIL

KSQLDSLLGLYHLLDWFAVDESNEVDPEFSARLTGIKLEMEPSLSFYNKARNYATKKPYSVEKFK

LNFQMPTLASGWDVNKEKNNGAILFVKNGLWLGIMPKQKGRYKALSFEPTEKTSEGFDKMYYD

YFPDAAKMIPKCSTQLKAVTAHFQTHTTPILLSNNFIEPLEITKEIYDLNNPEKEPKKFQTAYAKKT

GDQKGYREALCKWIDFIRDFLSKYTKITSIDLSSLRPSSQYKDLGEYYAELNPLLYHISFQRIAEK

EIMDAVETGKLYLFQIYNKDFAKGHHGKPNLHTLYVVTGLFSPENLAKTSIKLNGQAELFYRPKSR

MKRMAHRLGEKMLNKKLKDQKTPIPDTLYQELYDYVNHRLSHDLSDEARALLPNVITKEVSHEIIK

DRRFTSDKFFFHVPITLNYQAANSPSKFNQRVNAYLKEHPETPIIGIARGERNLIYITVIDSTGKILE

QRSLNTIQQFDYQKKLDNREKERVAARQAWSVVGTIKDLKQGYLSQVIHEIVDLMIHYQAVVVLE

NLNFGFKSKRTGIAEKAVYQQFEKMLIDKLNCLVLKDYPAEKVGGVLNPYQLTDQFTSFAKMGT

QSGFLFYVPAPYTSKIDPLIGFVDPFVWKTIKNHESRKHFLEGFDFLHYDVKTGDFILHFKMNRN

LSFQRGLPGFMPAWDIVFEKNETQFDAKGTPFIAGKRIVPVIENHRFTGRYRDLYPANELIALLEE

KGIVFRDGSNILPKLLENDDSHAIDTMVALIRSVLQMRNSNAATGEDYINSPVRDLNGVCFDSRF

QNPEWPMDADANGAYHIALKGQLLLNHLKESKDLKLQNGISNQDWLAYIQELRNkrpaatkkagqakk kkGSYPYDVPDYAYPYDVPDYAYPYDVPDYAGS<u>EASGSGRADALDDFDLDMLGSDALDDFDLD</u>

<u>MLGSDALDDFDLDMLGSDALDDFDLDMLINSRSSGSPKKKRKVGSQYLPDTDDRHRIEEKRKRT</u>

<u>YETFKSIMKKSPFSGPTDPRPPPRRIAVPSRSSASVPKPAPQPYPFTSSLSTINYDEFPTMVFPS</u>

<u>GQISQASALAPAPPQVLPQAPAPAPAPAMVSALAQAPAPVPVLAPGPPQAVAPPAPKPTQAGEG</u>

<u>TLSEALLQLQFDDEDLGALLGNSTDPAVFTDLASVDNSEFQQLLNQGIPVAPHTTEPMLMEYPEA</u>

<u>ITRLVTGAQRPPDPAPAPLGAPGLPNGLLSGDEDFSSIADMDFSALLGSGSGSRDSREGMFLPK</u>

<u>PEAGSAISDVFEGREVCQPKRIRPFHPPGSPWANRPLPASLAPTPTGPVHEPVGSLTPAPVPQP</u>

<u>LDPAPAVTPEASHLLEDPDEETSQAVKALREMADTVIPQKEEAAICGQMDLSHPPPRGHLDELTT</u>

<u>TLESMTEDLNLDSPLTPELNEILDTFLNDECLLHAMHISTGLSIFDTSLF</u>

Nucleotide sequence of (RTW776) pCAG-human-
dAsCpf1(D908A)triplevariant(E174R/S542R/K548R)-NLS(nucleoplasmin)-3xHA-VPR
Human codon optimized dAsCpf1 (D908A) in normal font (NTs 1-3921), Nucleoplasmin
NLS in lower case (aaaaggccggcggccacgaaaaaggccggccaggcaaaaaagaaaaag, SEQ ID NO: 21),
3xHA tag
(TACCCATACGATGITCCAGATTACGCTTATCCCTACGACGTGCCTGATTATGCATACCCATAT
GATGTCCCCGACTATGCC, SEQ ID NO: 5) in bold, and VPR double underlined

SEQ ID NO: 433)

ATGACACAGTTCGAGGGCTTTACCAACCTGTATCAGGTGAGCAAGACACTGCGGTT

TGAGCTGATCCCACAGGGCAAGACCCTGAAGCACATCCAGGAGCAGGGCTTCATCGAGGA

GGACAAGGCCCGCAATGATCACTACAAGGAGCTGAAGCCCATCATCGATCGGATCTACAAG

-continued

```
ACCTATGCCGACCAGTGCCTGCAGCTGGTGCAGCTGGATTGGGAGAACCTGAGCGCCGCC
ATCGACTCCTATAGAAAGGAGAAAACCGAGGAGACAAGGAACGCCCTGATCGAGGAGCAGG
CCACATATCGCAATGCCATCCACGACTACTTCATCGGCCGGACAGACAACCTGACCGATGC
CATCAATAAGAGACACGCCGAGATCTACAAGGGCCTGTTCAAGGCCGAGCTGTTTAATGGC
AAGGTGCTGAAGCAGCTGGGCACCGTGACCACAACCGAGCACGAGAACGCCCTGCTGCGG
AGCTTCGACAAGTTTACAACCTACTTCTCCGGCTTTTATAGAAACAGGAAGAACGTGTTCAG
CGCCGAGGATATCAGCACAGCCATCCCACACCGCATCGTGCAGGACAACTTCCCCAAGTTT
AAGGAGAATTGTCACATCTTCACACGCCTGATCACCGCCGTGCCCAGCCTGCGGGAGCACT
TTGAGAACGTGAAGAAGGCCATCGGCATCTTCGTGAGCACCTCCATCGAGGAGGTGTTTTC
CTTCCCTTTTTATAACCAGCTGCTGACACAGACCCAGATCGACCTGTATAACCAGCTGCTGG
GAGGAATCTCTCGGGAGGCAGGCACCGAGAAGATCAAGGGCCTGAACGAGGTGCTGAATC
TGGCCATCCAGAAGAATGATGAGACAGCCCACATCATCGCCTCCCTGCCACACAGATTCATC
CCCCTGTTTAAGCAGATCCTGTCCGATAGGAACACCCTGTCTTTCATCCTGGAGGAGTTTAA
GAGCGACGAGGAAGTGATCCAGTCCTTCTGCAAGTACAAGACACTGCTGAGAAACGAGAAC
GTGCTGGAGACAGCCGAGGCCCTGTTTAACGAGCTGAACAGCATCGACCTGACACACATCT
TCATCAGCCACAAGAAGCTGGAGACAATCAGCAGCGCCCTGTGCGACCACTGGGATACACT
GAGGAATGCCCTGTATGAGCGGAGAATCTCCGAGCTGACAGGCAAGATCACCAAGTCTGCC
AAGGAGAAGGTGCAGCGCAGCCTGAAGCACGAGGATATCAACCTGCAGGAGATCATCTCTG
CCGCAGGCAAGGAGCTGAGCGAGGCCTTCAAGCAGAAAACCAGCGAGATCCTGTCCCACG
CACACGCCGCCCTGGATCAGCCACTGCCTACAACCCTGAAGAAGCAGGAGGAGAAGGAGA
TCCTGAAGTCTCAGCTGGACAGCCTGCTGGGCCTGTACCACCTGCTGGACTGGTTTGCCGT
GGATGAGTCCAACGAGGTGGACCCCGAGTTCTCTGCCCGGCTGACCGGCATCAAGCTGGA
GATGGAGCCTTCTCTGAGCTTCTACAACAAGGCCAGAAATTATGCCACCAAGAAGCCCTACT
CCGTGGAGAAGTTCAAGCTGAACTTTCAGATGCCTACACTGGCCAGAGGCTGGGACGTGAA
TAGAGAGAAGAACAATGGCGCCATCCTGTTTGTGAAGAACGGCCTGTACTATCTGGGCATCA
TGCCAAAGCAGAAGGGCAGGTATAAGGCCCTGAGCTTCGAGCCCACAGAGAAAACCAGCG
AGGGCTTTGATAAGATGTACTATGACTACTTCCCTGATGCCGCCAAGATGATCCCAAAGTGC
AGCACCCAGCTGAAGGCCGTGACAGCCCACTTTCAGACCCACACAACCCCCATCCTGCTGT
CCAACAATTTCATCGAGCCTCTGGAGATCACAAAGGAGATCTACGACCTGAACAATCCTGAG
AAGGAGCCAAAGAAGTTTCAGACAGCCTACGCCAAGAAAACCGGCGACCAGAAGGGCTACA
GAGAGGCCCTGTGCAAGTGGATCGACTTCACAAGGGATTTTCTGTCCAAGTATACCAAGACA
ACCTCTATCGATCTGTCTAGCCTGCGGCCATCCTCTCAGTATAAGGACCTGGGCGAGTACTA
TGCCGAGCTGAATCCCCTGCTGTACCACATCAGCTTCCAGAGAATCGCCGAGAAGGAGATC
ATGGATGCCGTGGAGACAGGCAAGCTGTACCTGTTCCAGATCTATAACAAGGACTTTGCCAA
GGGCCACCACGGCAAGCCTAATCTGCACACACTGTATTGGACCGGCCTGTTTTCTCCAGAG
AACCTGGCCAAGACAAGCATCAAGCTGAATGGCCAGGCCGAGCTGTTCTACCGCCCTAAGT
CCAGGATGAAGAGGATGGCACACCGGCTGGGAGAAGATGCTGAACAAGAAGCTGAAGG
ATCAGAAACCCCAATCCCCGACACCCTGTACCAGGAGCTGTACGACTATGTGAATCACAGA
CTGTCCCACGACCTGTCTGATGAGGCCAGGGCCCTGCTGCCCAACGTGATCACCAAGGAG
GTGTCTCACGAGATCATCAAGGATAGGCGCTTTACCAGCGACAAGTTCTTTTTCCACGTGCC
TATCACACTGAACTATCAGGCCGCCAATTCCCCATCTAAGTTCAACCAGAGGGTGAATGCCT
```

```
ACCTGAAGGAGCACCCCGAGACACCTATCATCGGCATCGCCCGGGGCGAGAGAAACCTGA

TCTATATCACAGTGATCGACTCCACCGGCAAGATCCTGGAGCAGCGGAGCCTGAACACCAT

CCAGCAGTTTGATTACCAGAAGAAGCTGGACAACAGGGAGAAGGAGAGGGTGGCAGCAAG

GCAGGCCTGGTCTGTGGTGGGCACAATCAAGGATCTGAAGCAGGGCTATCTGAGCCAGGT

CATCCACGAGATCGTGGACCTGATGATCCACTACCAGGCCGTGGTGGTGCTGGAGAACCTG

AATTTCGGCTTTAAGAGCAAGAGGACCGGCATCGCCGAGAAGGCCGTGTACCAGCAGTTCG

AGAAGATGCTGATCGATAAGCTGAATTGCCTGGTGCTGAAGGACTATCCAGCAGAGAAGT

GGGAGGCGTGCTGAACCCATACCAGCTGACAGACCAGTTCACCTCCTTTGCCAAGATGGGC

ACCCAGTCTGGCTTCCTGTTTTACGTGCCTGCCCCATATACATCTAAGATCGATCCCCTGAC

CGGCTTCGTGGACCCCTTCGTGTGGAAAACCATCAAGAATCACGAGAGCCGCAAGCACTTC

CTGGAGGGCTTCGACTTTCTGCACTACGACGTGAAAACCGGCGACTTCATCCTGCACTTTAA

GATGAACAGAAATCTGTCCTTCCAGAGGGGCCTGCCCGGCTTTATGCCTGCATGGGATATC

GTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGC

CAACGAGCTGATCGCCCTGCTGGAGGAGAAGGGCATCGTGTTCAGGGATGGCTCCAACATC

CTGCCAAAGCTGCTGGAGAATGACGATTCTCACGCCATCGACACCATGGTGGCCCTGATCC

GCAGCGTGCTGCAGATGCGGAACTCCAATGCCGCCACAGGCGAGGACTATATCAACAGCC

CCGTGCGCGATCTGAATGGCGTGTGCTTCGACTCCCGGTTTCAGAACCCAGAGTGGCCCAT

GGACGCCGATGCCAATGGCGCCTACCACATCGCCCTGAAGGGCCAGCTGCTGCTGAATCA

CCTGAAGGAGAGCAAGGATCTGAAGCTGCAGAACGGCATCTCCAATCAGGACTGGCTGGCC

TACATCCAGGAGCTGCGCAACaaaaggccggcggccacgaaaaaggccggccaggcaaaaaagaaaaagGGA

TCCTACCCATACGATGTTCCAGATTACGCTTATCCCTACGACGTGCCTGATTATGCATACC

CATATGATGTCCCCGACTATGCCGGAAGCGAGGCCAGCGGTTCCGGACGGGCTGACGCAT

TGGACGATTTTGATCTGGATATGCTGGGAAGTGACGCCCTCGATGATTTTGACCTTGACATG

CTTGGTTCGGATGCCCTTGATGACTTTGACCTCGACATGCTCGGCAGTGACGCCCTTGATGA

TTTCGACCTGGACATGCTGATTAACTCTAGAAGTTCCGGATCTCCGAAAAAGAAACGCAAAG

TTGGTAGCCAGTACCTGCCCGACACCGACGACCGGCACCGGATCGAGGAAAAGCGGAAGC

GGACCTACGAGACATTCAAGAGCATCATGAAGAAGTCCCCCTTCAGCGGCCCCACCGACCC

TAGACCTCCACCTAGAAGAATCGCCGTGCCCAGCAGATCCAGCGCCAGCGTGCCAAAACCT

GCCCCCAGCCTTACCCCTTCACCAGCAGCCTGAGCACCATCAACTACGACGAGTTCCCTA

CCATGGTGTTCCCCAGCGGCCAGATCTCTCAGGCCTCTGCTCTGGCTCCAGCCCCTCCTCA

GGTGCTGCCTCAGGCTCCTGCTCCTGCACCAGCTCCAGCCATGGTGTCTGCACTGGCTCAG

GCACCAGCACCCGTGCCTGTGCTGGCTCCTGGACCTCCACAGGCTGTGGCTCCACCAGCC

CCTAAACCTACACAGGCCGGCGAGGGCACACTGTCTGAAGCTCTGCTGCAGCTGCAGTTCG

ACGACGAGGATCTGGGAGCCCTGCTGGGAAACAGCACCGATCCTGCCGTGTTCACCGACC

TGGCCAGCGTGGACAACAGCGAGTTCCAGCAGCTGCTGAACCAGGGCATCCCTGTGGCCC

CTCACACCACCGAGCCCATGCTGATGGAATACCCCGAGGCCATCACCCGGCTCGTGACAG

GCGCTCAGAGGCCTCCTGATCCAGCTCCTGCCCCTCTGGGAGCACCAGGCCTGCCTAATG

GACTGCTGTCTGGCGACGAGGACTTCAGCTCTATCGCCGATATGGATTTCTCAGCCTTGCTG

GGCTCTGGCAGCGGCAGCCGGGATTCCAGGGAAGGGATGTTTTTGCCGAAGCCTGAGGCC

GGCTCCGCTATTAGTGACGTGTTTGAGGGCCGCGAGGTGTGCCAGCCAAAACGAATCCGG
```

-continued

CCATTTCATCCTCCAGGAAGTCCATGGGCCAACCGCCCACTCCCCGCCAGCCTCGCACCAA

CACCAACCGGTCCAGTACATGAGCCAGTCGGGTCACTGACCCCGGCACCAGTCCCTCAGC

CACTGGATCCAGCGCCCGCAGTGACTCCCGAGGCCAGTCACCTGTTGGAGGATCCCGATG

AAGAGACGAGCCAGGCTGTCAAAGCCCTTCGGGAGATGGCCGATACTGTGATTCCCCAGAA

GGAAGAGGCTGCAATCTGTGGCCAAATGGACCTTTCCCATCCGCCCCCAAGGGGCCATCTG

GATGAGCTGACAACCACACTTGAGTCCATGACCGAGGATCTGAACCTGGACTCACCCCTGA

CCCCGGAATTGAACGAGATTCTGGATACCTTCCTGAACGACGAGTGCCTCTTGCATGCCATG

CATATCAGCACAGGACTGTCCATCTTCGACACATCTCTGTTT

Amino acid sequence of dAsCpf1(D908A)triplevariant(E174R/S542R/K548R)-
NLS(nucleoplasmin)-3xHA-VPR
AsCpf1 in normal font (AAs 1-1307), NLS(nucleoplasmin) (krpaatkkagqakkkk, SEQ ID
NO: 7) in lower case, 3xHA tag (YPYDVPDYAYPYDVPDYAYPYDVPDYA, SEQ ID NO: 8) in bold,
and VPR double underlined

SEQ ID NO: 434)

MTQFEGFTNLYQVSKTLRFELIPQGKTLKHIQEQGFIEEDKARNDHYKELKPIIDRIYKTYA

DQCLQLVQLDWENLSAAIDSYRKEKTEETRNALIEEQATYRNAIHDYFIGRTDNLTDAINKRHAEI

YKGLFKAELFNGKVLKQLGTVTTTEHENALLRSFDKFTTYFSGFYRNRKNVFSAEDISTAIPHRIV

QDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQ

SFCKYKTLLRNENVLETAEALFNELNSIDLTHIFISHKKLETISSALCDHWDTLRNALYERRISELTG

KITKSAKEKVQRSLKHEDINLQEIISAAGKELSEAFKQKTSEILSHAHAALDQPLPTTLKKQEEKEIL

KSQLDSLLGLYHLLDWFAVDESNEVDPEFSARLTGIKLEMEPSLSFYNKARNYATKKPYSVEKFK

LNFQMPTLARGWDVNKEKNNGAILFVKNGLYYLGIMPKQKGRYKALSFEPTEKTSEGFDKMYYD

YFPDAAKMIPKCSTQLKAVTAHFQTHTTPILLSNNFIEPLEITKEIYDLNNPEKEPKKFQTAYAKKT

GDQKGYREALCKWIDFIRDFLSKYTKITSIDLSSLRPSSQYKDLGEYYAELNPLLYHISFQRIAEK

EIMDAVETGKLYLFQIYNKDFAKGHHGKPNLHTLYVVTGLFSPENLAKTSIKLNGQAELFYRPKSR

MKRMAHRLGEKMLNKKLKDQKTPIPDTLYQELYDYVNHRLSHDLSDEARALLPNVITKEVSHEIIK

DRRFTSDKFFFHVPITLNYQAANSPSKFNQRVNAYLKEHPETPIIGIARGERNLIYITVIDSTGKILE

QRSLNTIQQFDYQKKLDNREKERVAARQAWSVVGTIKDLKQGYLSQVIHEIVDLMIHYQAVVLE

NLNFGFKSKRTGIAEKAVYQQFEKMLIDKLNCLVLKDYPAEKVGGVLNPYQLTDQFTSFAKMGT

QSGFLFYVPAPYTSKIDPLIGFVDPFVWKTIKNHESRKHFLEGFDFLHYDVKTGDFILHFKMNRN

LSFQRGLPGFMPAWDIVFEKNETQFDAKGTPFIAGKRIVPVIENHRFTGRYRDLYPANELIALLEE

KGIVFRDGSNILPKLLENDDSHAIDTMVALIRSVLQMRNSNAATGEDYINSPVRDLNGVCFDSRF

QNPEWPMDADANGAYHIALKGQLLLNHLKESKDLKLQNGISNQDWLAYIQELRNkrpaatkkagqakk kkGSYPYDVPDYAYPYDVPDYAYPYDVPDYAGS<ins>EASGSGRADALDDFDLDMLGSDALDDFDLD</ins>

<ins>MLGSDALDDFDLDMLGSDALDDFDLDMLINSRSSGSPKKKRKVGSQYLPDTDDRHRIEEKRKRT</ins>

<ins>YETFKSIMKKSPFSGPTDPRPPPRRIAVPSRSSASVPKPAPQPYPFTSSLSTINYDEFPTMVFPS</ins>

<ins>GQISQASALAPAPPQVLPQAPAPAPAPAMVSALAQAPAPVPVLAPGPPQAVAPPAPKPTQAGEG</ins>

<ins>TLSEALLQLQFDDEDLGALLGNSTDPAVFTDLASVDNSEFQQLLNQGIPVAPHTTEPMLMEYPEA</ins>

<ins>ITRLVTGAQRPPDPAPAPLGAPGLPNGLLSGDEDFSSIADMDFSALLGSGSGSRDSREGMFLPK</ins>

<ins>PEAGSAISDVFEGREVCQPKRIRPFHPPGSPWANRPLPASLAPTPTGPVHEPVGSLTPAPVPQP</ins>

<ins>LDPAPAVTPEASHLLEDPDEETSQAVKALREMADTVIPQKEEAAICGQMDLSHPPPRGHLDELTT</ins>

<ins>TLESMTEDLNLDSPLTPELNEILDTFLNDECLLHAMHISTGLSIFDTSLF</ins>

-continued

RTW1017: pCAG-2xNLS-hdeAsCas12a(E174R/S542R/K548R/D908A)-NLS-gs-3xHA-gs-VPR(deAs-VPR(1.2))
Human codon optimized *Acidaminococcus* sp. *BV3L6* Cas12a (AsCas12a) in black, modified codons for DNase inactive (D908A) eAsCas12a (E174R/S542R/K548R) in double underlined lower case, codons with silent mutations to remove NcoI sites double underlined UPPER CASE, inserted glycine dash-underlined nucleoplasmin NLS (aaaaggccggcggccacgaaaaaggccggccaggcaaaaaagaaaaag, SEQ ID NO: 21) in lower case, linker sequences in italics, 3xHA tag (YPYDVPDYAYPYDVPDYAYPYDVPDYA, SEQ ID NO: 8) in bold, SV40 NLS in lower case italics, VP64-p65-RTA (VPR) in double underlined italics (SEQ ID NO: 435)

ATGGGC*ccaaagaaaaagaggaaagtc*GGCAGTGGA*cctaaaaagaaacgaaaggtt*GGGTCAGGTACAC

AGTTCGAGGGCTTTACCAACCTGTATCAGGTGAGCAAGACACTGCGGTTTGAGCTGATCCC

ACAGGGCAAGACCCTGAAGCACATCCAGGAGCAGGGCTTCATCGAGGAGGACAAGGCCCG

CAATGATCACTACAAGGAGCTGAAGCCCATCATCGATCGGATCTACAAGACCTATGCCGACC

AGTGCCTGCAGCTGGTGCAGCTGGATTGGGAGAACCTGAGCGCCGCCATCGACTCCTATAG

AAAGGAGAAAACCGAGGAGACAAGGAACGCCCTGATCGAGGAGCAGGCCACATATCGCAAT

GCCATCCACGACTACTTCATCGGCCGGACAGACAACCTGACCGATGCCATCAATAAGAGAC

ACGCCGAGATCTACAAGGGCCTGTTCAAGGCCGAGCTGTTTAATGGCAAGGTGCTGAAGCA

GCTGGGCACCGTGACCACAACCGAGCACGAGAACGCCCTGCTGCGGAGCTTCGACAAGTT

TACAACCTACTTCTCCGGCTTTTATaga_AACAGGAAGAACGTGTTCAGCGCCGAGGATATCAG

CACAGCCATCCCACACCGCATCGTGCAGGACAACTTCCCCAAGTTTAAGGAGAATTGTCACA

TCTTCACACGCCTGATCACCGCCGTGCCCAGCCTGCGGGAGCACTTTGAGAACGTGAAGAA

GGCCATCGGCATCTTCGTGAGCACCTCCATCGAGGAGGTGTTTTCCTTCCCTTTTTATAACC

AGCTGCTGACACAGACCCAGATCGACCTGTATAACCAGCTGCTGGGAGGAATCTCTCGGGA

GGCAGGCACCGAGAAGATCAAGGGCCTGAACGAGGTGCTGAATCTGGCCATCCAGAAGAA

TGATGAGACAGCCCACATCATCGCCTCCCTGCCACACAGATTCATCCCCCTGTTTAAGCAGA

TCCTGTCCGATAGGAACACCCTGTCTTTCATCCTGGAGGAGTTTAAGAGCGACGAGGAAGT

GATCCAGTCCTTCTGCAAGTACAAGACACTGCTGAGAAACGAGAACGTGCTGGAGACAGCC

GAGGCCCTGTTTAACGAGCTGAACAGCATCGACCTGACACACATCTTCATCAGCCACAAGAA

GCTGGAGACAATCAGCAGCGCCCTGTGCGACCACTGGGATACACTGAGGAATGCCCTGTAT

GAGCGGAGAATCTCCGAGCTGACAGGCAAGATCACCAAGTCTGCCAAGGAGAAGGTGCAG

CGCAGCCTGAAGCACGAGGATATCAACCTGCAGGAGATCATCTCTGCCGCAGGCAAGGAG

CTGAGCGAGGCCTTCAAGCAGAAAACCAGCGAGATCCTGTCCCACGCACACGCCGCCCTG

GATCAGCCACTGCCTACAACCCTGAAGAAGCAGGAGGAGAAGGAGATCCTGAAGTCTCAGC

TGGACAGCCTGCTGGGCCTGTACCACCTGCTGGACTGGTTTGCCGTGGATGAGTCCAACGA

GGTGGACCCCGAGTTCTCTGCCCGGCTGACCGGCATCAAGCTGGAGATGGAGCCTTCTCT

GAGCTTCTACAACAAGGCCAGAAATTATGCCACCAAGAAGCCCTACTCCGTGGAGAAGTTCA

AGCTGAACTTTCAGATGCCTACACTGGCC*aga*GGCTGGGACGTGAAT*aga*GAGAAGAACAAT

GGCGCCATCCTGTTTGTGAAGAACGGCCTGTACTATCTGGGCATCATGCCAAAGCAGAAGG

GCAGGTATAAGGCCCTGAGCTTCGAGCCCACAGAGAAACCAGCGAGGGCTTTGATAAGAT

GTACTATGACTACTTCCCTGATGCCGCCAAGATGATCCCAAAGTGCAGCACCCAGCTGAAG

GCCGTGACAGCCCACTTTCAGACCCACACAACCCCCATCCTGCTGTCCAACAATTTCATCGA

GCCTCTGGAGATCACAAAGGAGATCTACGACCTGAACAATCCTGAGAAGGAGCCAAAGAAG

TTTCAGACAGCCTACGCCAAGAAAACCGGCGACCAGAAGGGCTACAGAGAGGCCCTGTGCA

AGTGGATCGACTTCACAAGGGATTTTCTGTCCAAGTATACCAAGACAACCTCTATCGATCTGT

```
CTAGCCTGCGGCCATCCTCTCAGTATAAGGACCTGGGCGAGTACTATGCCGAGCTGAATCC

CCTGCTGTACCACATCAGCTTCCAGAGAATCGCCGAGAAGGAGATCATGGATGCCGTGGAG

ACAGGCAAGCTGTACCTGTTCCAGATCTATAACAAGGACTTTGCCAAGGGCCACCACGGCA

AGCCTAATCTGCACACACTGTATTGGACCGGCCTGTTTTCTCCAGAGAACCTGGCCAAGACA

AGCATCAAGCTGAATGGCCAGGCCGAGCTGTTCTACCGCCCTAAGTCCAGGATGAAGAGGA

TGGCACACCGGCTGGGAGAGAAGATGCTGAACAAGAAGCTGAAGGATCAGAAAACCCCAAT

CCCCGACACCCTGTACCAGGAGCTGTACGACTATGTGAATCACAGACTGTCCCACGACCTG

TCTGATGAGGCCAGGGCCCTGCTGCCCAACGTGATCACCAAGGAGGTGTCTCACGAGATCA

TCAAGGATAGGCGCTTTACCAGCGACAAGTTCTTTTTCCACGTGCCTATCACACTGAACTAT

CAGGCCGCCAATTCCCCATCTAAGTTCAACCAGAGGGTGAATGCCTACCTGAAGGAGCACC

CCGAGACACCTATCATCGGCATCgccCGGGGCGAGAGAAACCTGATCTATATCACAGTGATC

GACTCCACCGGCAAGATCCTGGAGCAGCGGAGCCTGAACACCATCCAGCAGTTTGATTACC

AGAAGAAGCTGGACAACAGGGAGAAGGAGAGGGTGGCAGCAAGGCAGGCCTGGTCTGTGG

TGGGCACAATCAAGGATCTGAAGCAGGGCTATCTGAGCCAGGTCATCCACGAGATCGTGGA

CCTGATGATCCACTACCAGGCCGTGGTGGTGCTGGAGAACCTGAATTTCGGCTTTAAGAGC

AAGAGGACCGGCATCGCCGAGAAGGCCGTGTACCAGCAGTTCGAGAAGATGCTGATCGATA

AGCTGAATTGCCTGGTGCTGAAGGACTATCCAGCAGAGAAAGTGGGAGGCGTGCTGAACCC

ATACCAGCTGACAGACCAGTTCACCTCCTTTGCCAAGATGGGCACCCAGTCTGGCTTCCTGT

TTTACGTGCCTGCCCCATATACATCTAAGATCGATCCCCTGACCGGCTTCGTGGACCCCTTC

GTGTGGAAAACCATCAAGAATCACGAGAGCCGCAAGCACTTCCTGGAGGGCTTCGACTTTC

TGCACTACGACGTGAAAACCGGCGACTTCATCCTGCACTTTAAGATGAACAGAAATCTGTCC

TTCCAGAGGGGCCTGCCCGGCTTTATGCCTGCATGGGATATCGTGTTCGAGAAGAACGAGA

CACAGTTTGACGCCAAGGGCACCCCTTTCATCGCCGGCAAGAGAATCGTGCCAGTGATCGA

GAATCACAGATTCACCGGCAGATACCGGGACCTGTATCCTGCCAACGAGCTGATCGCCCTG

CTGGAGGAGAAGGGCATCGTGTTCAGGGATGGCTCCAACATCCTGCCAAAGCTGCTGGAGA

ATGACGATTCTCACGCCATCGACACGATGGTGGCCCTGATCCGCAGCGTGCTGCAGATGCG

GAACTCCAATGCCGCCACAGGCGAGGACTATATCAACAGCCCCGTGCGCGATCTGAATGGC

GTGTGCTTCGACTCCCGGTTTCAGAACCCAGAGTGGCCAATGGACGCCGATGCCAATGGCG

CCTACCACATCGCCCTGAAGGGCCAGCTGCTGCTGAATCACCTGAAGGAGAGCAAGGATCT

GAAGCTGCAGAACGGCATCTCCAATCAGGACTGGCTGGCCTACATCCAGGAGCTGCGCAAC aaaaggccggcggccacgaaaaaggccggccaggcaaaaaagaaaaag*GGATCC*TACCCATACGATGTTCCA

GATTACGCTTATCCCTACGACGTGCCTGATTATGCATACCCATATGATGTCCCCGACTATG

CC*GGAAGC*<u>GAGGCCAGCGGTTCCGGACGGGCTGACGCATTGGACGATTTTGATCTGGATAT</u>

<u>GCTGGGAAGTGACGCCCTCGATGATTTTGACCTTGACATGCTTGGTTCGGATGCCCTTGATG</u>

<u>ACTTTGACCTCGACATGCTCGGCAGTGACGCCCTTGATGATTTCGACCTGGACATGCTGATT</u>

<u>AACTCTAGAAGTFCCGGATCTCCGAAAAAGAAACGCAAAGTTGGTAGCCAGTACCTGCCCGA</u>

<u>CACCGACGACCGGCACCGGATCGAGGAAAAGCGGAAGCGGACCTACGAGACATTCAAGAG</u>

<u>CATCATGAAGAAGTCCCCCTTCAGCGGCCCCACCGACCCTAGACCTCCACCTAGAAGAATC</u>

<u>GCCGTGCCCAGCAGATCCAGCGCCAGCGTGCCAAAACCTGCCCCCCAGCCTTACCCCTTCA</u>

<u>CCAGCAGCCTGAGCACCATCAACTACGACGAGTTCCCTACCATGGTGTTCCCCAGCGGCCA</u>

<u>GATCTCTCAGGCCTCTGCTCTGGCTCCAGCCCCTCCTCAGGTGCTGCCTCAGGCTCCTGCT</u>
```

-continued

CCTGCACCAGCTCCAGCCATGGTGTCTGCACTGGCTCAGGCACCAGCACCCGTGCCTGTG

CTGGCTCCTGGACCTCCACAGGCTGTGGCTCCACCAGCCCCTAAACCTACACAGGCCGGC

GAGGGCACACTGTCTGAAGCTCTGCTGCAGCTGCAGTTCGACGACGAGGATCTGGGAGCC

CTGCTGGGAAACAGCACCGATCCTGCCGTGTTCACCGACCTGGCCAGCGTGGACAACAGC

GAGTTCCAGCAGCTGCTGAACCAGGGCATCCCTGTGGCCCCTCACACCACCGAGCCCATG

CTGATGGAATACCCCGAGGCCATCACCCGGCTCGTGACAGGCGCTCAGAGGCCTCCTGAT

CCAGCTCCTGCCCCTCTGGGAGCACCAGGCCTGCCTAATGGACTGCTGTCTGGCGACGAG

GACTTCAGCTCTATCGCCGATATGGATTTCTCAGCCTTGCTGGGCTCTGGCAGCGGCAGCC

GGGATTCCAGGGAAGGGATGTTTTTGCCGAAGCCTGAGGCCGGCTCCGCTATTAGTGACGT

GTTTGAGGGCCGCGAGGTGTGCCAGCCAAAACGAATCCGGCCATTTCATCCTCCAGGAAGT

CCATGGGCCAACCGCCCACTCCCCGCCAGCCTCGCACCAACACCAACCGGTCCAGTACAT

GAGCCAGTCGGGTCACTGACCCCGGCACCAGTCCCTCAGCCACTGGATCCAGCGCCCGCA

GTGACTCCCGAGGCCAGTCACCTGTTGGAGGATCCCGATGAAGAGACGAGCCAGGCTGTC

AAAGCCCTTCGGGAGATGGCCGATACTGTGATTCCCCAGAAGGAAGAGGCTGCAATCTGTG

GCCAAATGGACCTTTCCCATCCGCCCCAAGGGGCCATCTGGATGAGCTGACAACCACACT

TGAGTCCATGACCGAGGATCTGAACCTGGACTCACCCCTGACCCCGGAATTGAACGAGATT

CTGGATACCTTCCTGAACGACGAGTGCCTCTTGCATGCCATGCATATCAGCACAGGACTGTC

CATCTTCGACACATCTCTGTTTTAA

RTW1130: pCAG-hdeAsCas12a(E174R/S542R/K548R/D908A)-gs-NLS-gs-VPR(deAs-
VPR(1.3))Human codon optimized *Acidaminococcus* sp. *BV3L6* Cas12a (AsCas12a) in black,
modified codons for DNase inactive (D908A) eAsCas12a (E174R/S542R/K548R) in double
underlined lower case, codons with silent mutations to remove NcoI sites double underlined
UPPER CASE, linker sequences in italics, SV40 NLS in lower case italics, VP64-p65-RTA
(VPR) in double underlined italics (SEQ ID NO: 436)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

ACAAGTTTACAACCTACTTCTCCGGCTTTTAT<u>aga</u>AACAGGAAGAACGTGTTCAGCGCCGAGG

ATATCAGCACAGCCATCCCACACCGCATCGTGCAGGACAACTTCCCCAAGTTTAAGGAGAAT

TGTCACATCTTCACACGCCTGATCACCGCCGTGCCCAGCCTGCGGGAGCACTTTGAGAACG

TGAAGAAGGCCATCGGCATCTTCGTGAGCACCTCCATCGAGGAGGTGTTTTCCTTCCCTTTT

TATAACCAGCTGCTGACACAGACCCAGATCGACCTGTATAACCAGCTGCTGGGAGGAATCT

CTCGGGAGGCAGGCACCGAGAAGATCAAGGGCCTGAACGAGGTGCTGAATCTGGCCATCC

AGAAGAATGATGAGACAGCCCACATCATCGCCTCCCTGCCACACAGATTCATCCCCCTGTTT

AAGCAGATCCTGTCCGATAGGAACACCCTGTCTTTCATCCTGGAGGAGTTTAAGAGCGACGA

GGAAGTGATCCAGTCCTTCTGCAAGTACAAGACACTGCTGAGAAACGAGAACGTGCTGGAG

ACAGCCGAGGCCCTGTTTAACGAGCTGAACAGCATCGACCTGACACACATCTTCATCAGCC

ACAAGAAGCTGGAGACAATCAGCAGCGCCCTGTGCGACCACTGGGATACACTGAGGAATGC

-continued

```
CCTGTATGAGCGGAGAATCTCCGAGCTGACAGGCAAGATCACCAAGTCTGCCAAGGAGAAG

GTGCAGCGCAGCCTGAAGCACGAGGATATCAACCTGCAGGAGATCATCTCTGCCGCAGGCA

AGGAGCTGAGCGAGGCCTTCAAGCAGAAAACCAGCGAGATCCTGTCCCACGCACACGCCG

CCCTGGATCAGCCACTGCCTACAACCCTGAAGAAGCAGGAGGAGAAGGAGATCCTGAAGTC

TCAGCTGGACAGCCTGCTGGGCCTGTACCACCTGCTGGACTGGTTTGCCGTGGATGAGTCC

AACGAGGTGGACCCCGAGTTCTCTGCCCGGCTGACCGGCATCAAGCTGGAGATGGAGCCT

TCTCTGAGCTTCTACAACAAGGCCAGAAATTATGCCACCAAGAAGCCCTACTCCGTGGAGAA

GTTCAAGCTGAACTTTCAGATGCCTACACTGGCCagaGGCTGGGACGTGAATagaGAGAAGA

ACAATGGCGCCATCCTGTTTGTGAAGAACGGCCTGTACTATCTGGGCATCATGCCAAAGCA

GAAGGGCAGGTATAAGGCCCTGAGCTTCGAGCCCACAGAGAAAACCAGCGAGGGCTTTGAT

AAGATGTACTATGACTACTTCCCTGATGCCGCCAAGATGATCCCAAAGTGCAGCACCCAGCT

GAAGGCCGTGACAGCCCACTTTCAGACCCACACAACCCCCATCCTGCTGTCCAACAATTTCA

TCGAGCCTCTGGAGATCACAAAGGAGATCTACGACCTGAACAATCCTGAGAAGGAGCCAAA

GAAGTTTCAGACAGCCTACGCCAAGAAAACCGGCGACCAGAAGGGCTACAGAGAGGCCCT

GTGCAAGTGGATCGACTTCACAAGGGATTTTCTGTCCAAGTATACCAAGACAACCTCTATCG

ATCTGTCTAGCCTGCGGCCATCCTCTCAGTATAAGGACCTGGGCGAGTACTATGCCGAGCT

GAATCCCCTGCTGTACCACATCAGCTTCCAGAGAATCGCCGAGAAGGAGATCATGGATGCC

GTGGAGACAGGCAAGCTGTACCTGTTCCAGATCTATAACAAGGACTTTGCCAAGGGCCACC

ACGGCAAGCCTAATCTGCACACACTGTATTGGACCGGCCTGTTTTCTCCAGAGAACCTGGC

CAAGACAAGCATCAAGCTGAATGGCCAGGCCGAGCTGTTCTACCGCCCTAAGTCCAGGATG

AAGAGGATGGCACACCGGCTGGGAGAGAAGATGCTGAACAAGAAGCTGAAGGATCAGAAAA

CCCCAATCCCCGACACCCTGTACCAGGAGCTGTACGACTATGTGAATCACAGACTGTCCCA

CGACCTGTCTGATGAGGCCAGGGCCCTGCTGCCCAACGTGATCACCAAGGAGGTGTCTCAC

GAGATCATCAAGGATAGGCGCTTTACCAGCGACAAGTTCTTTTTCCACGTGCCTATCACACT

GAACTATCAGGCCGCCAATTCCCCATCTAAGTTCAACCAGAGGGTGAATGCCTACCTGAAG

GAGCACCCCGAGACACCTATCATCGGCATCgccCGGGGCGAGAGAAACCTGATCTATATCAC

AGTGATCGACTCCACCGGCAAGATCCTGGAGCAGCGGAGCCTGAACACCATCCAGCAGTTT

GATTACCAGAAGAAGCTGGACAACAGGGAGAAGGAGAGGGTGGCAGCAAGGCAGGCCTGG

TCTGTGGTGGGCACAATCAAGGATCTGAAGCAGGGCTATCTGAGCCAGGTCATCCACGAGA

TCGTGGACCTGATGATCCACTACCAGGCCGTGGTGGTGCTGGAGAACCTGAATTTCGGCTT

TAAGAGCAAGAGGACCGGCATCGCCGAGAAGGCCGTGTACCAGCAGTTCGAGAAGATGCT

GATCGATAAGCTGAATTGCCTGGTGCTGAAGGACTATCCAGCAGAGAAAGTGGGAGGCGTG

CTGAACCCATACCAGCTGACAGACCAGTTCACCTCCTTTGCCAAGATGGGCACCCAGTCTG

GCTTCCTGTTTTACGTGCCTGCCCCATATACATCTAAGATCGATCCCCTGACCGGCTTCGTG

GACCCCTTCGTGTGGAAAACCATCAAGAATCACGAGAGCCGCAAGCACTTCCTGGAGGGCT

TCGACTTTCTGCACTACGACGTGAAAACCGGCGACTTCATCCTGCACTTTAAGATGAACAGA

AATCTGTCCTTCCAGAGGGGCCTGCCCGGCTTTATGCCTGCATGGGATATCGTGTTCGAGA

AGAACGAGACACAGTTTGACGCCAAGGGCACCCCTTTCATCGCCGGCAAGAGAATCGTGCC

AGTGATCGAGAATCACAGATTCACCGGCAGATACCGGGACCTGTATCCTGCCAACGAGCTG

ATCGCCCTGCTGGAGGAGAAGGGCATCGTGTTCAGGGATGGCTCCAACATCCTGCCAAAGC

TGCTGGAGAATGACGATTCTCACGCCATCGACACGATGGTGGCCCTGATCCGCAGCGTGCT
```

-continued

```
GCAGATGCGGAACTCCAATGCCGCCACAGGCGAGGACTATATCAACAGCCCCGTGCGCGA

TCTGAATGGCGTGTGCTTCGACTCCCGGTTTCAGAACCCAGAGTGGCCAATGGACGCCGAT

GCCAATGGCGCCTACCACATCGCCCTGAAGGGCCAGCTGCTGCTGAATCACCTGAAGGAGA

GCAAGGATCTGAAGCTGCAGAACGGCATCTCCAATCAGGACTGGCTGGCCTACATCCAGGA

GCTGCGCAAC*GGTGGAAGCGGAGGGAGT*cccaagaagaagaggaaagtcGGGGGTTCCGGAGGAA

GCGAGGCCAGCGGTTCCGGACGGGCTGACGCATTGGACGATTTTGATCTGGATATGCTGG

GAAGTGACGCCCTCGATGATTTTGACCTTGACATGCTTGGTTCGGATGCCCTTGATGACTTT

GACCTCGACATGCTCGGCAGTGACGCCCTTGATGATTTCGACCTGGACATGCTGATTAACTC

TAGAAGTTCCGGATCTCCGAAAAAGAAACGCAAAGTTGGTAGCCAGTACCTGCCCGACACC

GACGACCGGCACCGGATCGAGGAAAAGCGGAAGCGGACCTACGAGACATTCAAGAGCATC

ATGAAGAAGTCCCCCTTCAGCGGCCCCACCGACCCTAGACCTCCACCTAGAAGAATCGCCG

TGCCCAGCAGATCCAGCGCCAGCGTGCCAAAACCTGCCCCCCAGCCTTACCCCTTCACCAG

CAGCCTGAGCACCATCAACTACGACGAGTTCCCTACCATGGTGTTCCCCAGCGGCCAGATC

TCTCAGGCCTCTGCTCTGGCTCCAGCCCCTCCTCAGGTGCTGCCTCAGGCTCCTGCTCCTG

CACCAGCTCCAGCCATGGTGTCTGCACTGGCTCAGGCACCAGCACCCGTGCCTGTGCTGG

CTCCTGGACCTCCACAGGCTGTGGCTCCACCAGCCCCTAAACCTACACAGGCCGGCGAGG

GCACACTGTCTGAAGCTCTGCTGCAGCTGCAGTTCGACGACGAGGATCTGGGAGCCCTGCT

GGGAAACAGCACCGATCCTGCCGTGTTCACCGACCTGGCCAGCGTGGACAACAGCGAGTT

CCAGCAGCTGCTGAACCAGGGCATCCCTGTGGCCCCTCACACCACCGAGCCCATGCTGAT

GGAATACCCCGAGGCCATCACCCGGCTCGTGACAGGCGCTCAGAGGCCTCCTGATCCAGC

TCCTGCCCCTCTGGGAGCACCAGGCCTGCCTAATGGACTGCTGTCTGGCGACGAGGACTTC

AGCTCTATCGCCGATATGGATTTCTCAGCCTTGCTGGGCTCTGGCAGCGGCAGCCGGGATT

CCAGGGAAGGGATGTTTTTGCCGAAGCCTGAGGCCGGCTCCGCTATTAGTGACGTGTTTGA

GGGCCGCGAGGTGTGCCAGCCAAAACGAATCCGGCCATTTCATCCTCCAGGAAGTCCATGG

GCCAACCGCCCACTCCCCGCCAGCCTCGCACCAACACCAACCGGTCCAGTACATGAGCCA

GTCGGGTCACTGACCCCGGCACCAGTCCCTCAGCCACTGGATCCAGCGCCCGCAGTGACT

CCCGAGGCCAGTCACCTGTTGGAGGATCCCGATGAAGAGACGAGCCAGGCTGTCAAAGCC

CTTCGGGAGATGGCCGATACTGTGATTCCCCAGAAGGAAGAGGCTGCAATCTGTGGCCAAA

TGGACCTTTCCCATCCGCCCCAAGGGGCCATCTGGATGAGCTGACAACCACACTTGAGTC

CATGACCGAGGATCTGAACCTGGACTCACCCCTGACCCCGGAATTGAACGAGATTCTGGAT

ACCTTCCTGAACGACGAGTGCCTCTTGCATGCCATGCATATCAGCACAGGACTGTCCATCTT

CGACACATCTCTGTTTTAA
```

RTW1319: pCAG-2xNLS-hdeAsCas12a(E174R/S542R/K548R/D908A)-gs-NLS-gs-VPR(deAs-VPR(1.4))
Human codon optimized *Acidaminococcus sp. BV3L6* Cas12a (AsCas12a) in black, modified codons for DNase inactive (D908A) eAsCas12a (E174R/S542R/K548R) in double underlined lower case, codons with silent mutations to remove NcoI sites double underlined UPPER CASE, inserted glycine dash-underlined linker sequences in italics, 3xHA tag (YPYDVPDYAYPYDVPDYAYPYDVPDYA, SEQ ID NO: 8) in bold, SV40 NLS in lower case italics, VP64-p65-RTA (VPR) in double underlined italics (SEQ ID NO: 437)

```
ATGGGCccaagaaaaagaggaaagtcGGCAGTGGAacctaaaaagaaacgaaaggttGGGTCAGGTACACA

GTTCGAGGGCTTTACCAACCTGTATCAGGTGAGCAAGACACTGCGGTTTGAGCTGATCCCA

CAGGGCAAGACCCTGAAGCACATCCAGGAGCAGGGCTTCATCGAGGAGGACAAGGCCCGC

AATGATCACTACAAGGAGCTGAAGCCCATCATCGATCGGATCTACAAGACCTATGCCGACCA
```

-continued

```
GTGCCTGCAGCTGGTGCAGCTGGATTGGGAGAACCTGAGCGCCGCCATCGACTCCTATAGA
AAGGAGAAAACCGAGGAGACAAGGAACGCCCTGATCGAGGAGCAGGCCACATATCGCAAT
GCCATCCACGACTACTTCATCGGCCGGACAGACAACCTGACCGATGCCATCAATAAGAGAC
ACGCCGAGATCTACAAGGGCCTGTTCAAGGCCGAGCTGTTTAATGGCAAGGTGCTGAAGCA
GCTGGGCACCGTGACCACAACCGAGCACGAGAACGCCCTGCTGCGGAGCTTCGACAAGTT
TACAACCTACTTCTCCGGCTTTTATagaAACAGGAAGAACGTGTTCAGCGCCGAGGATATCAG
CACAGCCATCCCACACCGCATCGTGCAGGACAACTTCCCCAAGTTTAAGGAGAATTGTCACA
TCTTCACACGCCTGATCACCGCCGTGCCCAGCCTGCGGGAGCACTTTGAGAACGTGAAGAA
GGCCATCGGCATCTTCGTGAGCACCTCCATCGAGGAGGTGTTTTCCTTCCCTTTTTATAACC
AGCTGCTGACACAGACCCAGATCGACCTGTATAACCAGCTGCTGGGAGGAATCTCTCGGGA
GGCAGGCACCGAGAAGATCAAGGGCCTGAACGAGGTGCTGAATCTGGCCATCCAGAAGAA
TGATGAGACAGCCCACATCATCGCCTCCCTGCCACACAGATTCATCCCCCTGTTTAAGCAGA
TCCTGTCCGATAGGAACACCCTGTCTTTCATCCTGGAGGAGTTTAAGAGCGACGAGGAAGT
GATCCAGTCCTTCTGCAAGTACAAGACACTGCTGAGAAACGAGAACGTGCTGGAGACAGCC
GAGGCCCTGTTTAACGAGCTGAACAGCATCGACCTGACACACATCTTCATCAGCCACAAGAA
GCTGGAGACAATCAGCAGCGCCCTGTGCGACCACTGGGATACACTGAGGAATGCCCTGTAT
GAGCGGAGAATCTCCGAGCTGACAGGCAAGATCACCAAGTCTGCCAAGGAGAAGGTGCAG
CGCAGCCTGAAGCACGAGGATATCAACCTGCAGGAGATCATCTCTGCCGCAGGCAAGGAG
CTGAGCGAGGCCTTCAAGCAGAAAACCAGCGAGATCCTGTCCCACGCACACGCCGCCCTG
GATCAGCCACTGCCTACAACCCTGAAGAAGCAGGAGGAGAAGGAGATCCTGAAGTCTCAGC
TGGACAGCCTGCTGGGCCTGTACCACCTGCTGGACTGGTTTGCCGTGGATGAGTCCAACGA
GGTGGACCCCGAGTTCTCTGCCCGGCTGACCGGCATCAAGCTGGAGATGGAGCCTTCTCT
GAGCTTCTACAACAAGGCCAGAAATTATGCCACCAAGAAGCCCTACTCCGTGGAGAAGTTCA
AGCTGAACTTTCAGATGCCTACACTGGCCagaGGCTGGGACGTGAATAGAGAGAAGAACAAT
GGCGCCATCCTGTTTGTGAAGAACGGCCTGTACTATCTGGGCATCATGCCAAAGCAGAAGG
GCAGGTATAAGGCCCTGAGCTTCGAGCCCACAGAGAAAACCAGCGAGGGCTTTGATAAGAT
GTACTATGACTACTTCCCTGATGCCGCCAAGATGATCCCAAAGTGCAGCACCCAGCTGAAG
GCCGTGACAGCCCACTTTCAGACCCACACAACCCCCATCCTGCTGTCCAACAATTTCATCGA
GCCTCTGGAGATCACAAAGGAGATCTACGACCTGAACAATCCTGAGAAGGAGCCAAAGAAG
TTTCAGACAGCCTACGCCAAGAAAACCGGCGACCAGAAGGGCTACAGAGAGGCCCTGTGCA
AGTGGATCGACTTCACAAGGGATTTTCTGTCCAAGTATACCAAGACAACCTCTATCGATCTGT
CTAGCCTGCGGCCATCCTCTCAGTATAAGGACCTGGGCGAGTACTATGCCGAGCTGAATCC
CCTGCTGTACCACATCAGCTTCCAGAGAATCGCCGAGAAGGAGATCATGGATGCCGTGGAG
ACAGGCAAGCTGTACCTGTTCCAGATCTATAACAAGGACTTTGCCAAGGGCCACCACGGCA
AGCCTAATCTGCACACACTGTATTGGACCGGCCTGTTTTCTCCAGAGAACCTGGCCAAGACA
AGCATCAAGCTGAATGGCCAGGCCGAGCTGTTCTACCGCCCTAAGTCCAGGATGAAGAGGA
TGGCACACCGGCTGGGAGAGAAGATGCTGAACAAGAAGCTGAAGGATCAGAAAACCCCAAT
CCCCGACACCCTGTACCAGGAGCTGTACGACTATGTGAATCACAGACTGTCCCACGACCTG
TCTGATGAGGCCAGGGCCCTGCTGCCCAACGTGATCACCAAGGAGGTGTCTCACGAGATCA
TCAAGGATAGGCGCTTTACCAGCGACAAGTTCTTTTTCCACGTGCCTATCACACTGAACTAT
CAGGCCGCCAATTCCCCATCTAAGTTCAACCAGAGGGTGAATGCCTACCTGAAGGAGCACC
```

-continued

CCGAGACACCTATCATCGGCATCgccCGGGGCGAGAGAAACCTGATCTATATCACAGTGATC

GACTCCACCGGCAAGATCCTGGAGCAGCGGAGCCTGAACACCATCCAGCAGTTTGATTACC

AGAAGAAGCTGGACAACAGGGAGAAGGAGAGGGTGGCAGCAAGGCAGGCCTGGTCTGTGG

TGGGCACAATCAAGGATCTGAAGCAGGGCTATCTGAGCCAGGTCATCCACGAGATCGTGGA

CCTGATGATCCACTACCAGGCCGTGGTGGTGCTGGAGAACCTGAATTTCGGCTTTAAGAGC

AAGAGGACCGGCATCGCCGAGAAGGCCGTGTACCAGCAGTTCGAGAAGATGCTGATCGATA

AGCTGAATTGCCTGGTGCTGAAGGACTATCCAGCAGAGAAGTGGGAGGCGTGCTGAACCC

ATACCAGCTGACAGACCAGTTCACCTCCTTTGCCAAGATGGGCACCCAGTCTGGCTTCCTGT

TTTACGTGCCTGCCCCATATACATCTAAGATCGATCCCCTGACCGGCTTCGTGGACCCCTTC

GTGTGGAAAACCATCAAGAATCACGAGAGCCGCAAGCACTTCCTGGAGGGCTTCGACTTTC

TGCACTACGACGTGAAAACCGGCGACTTCATCCTGCACTTTAAGATGAACAGAAATCTGTCC

TTCCAGAGGGGCCTGCCCGGCTTTATGCCTGCATGGGATATCGTGTTCGAGAAGAACGAGA

CACAGTTTGACGCCAAGGGCACCCCTTTCATCGCCGGCAAGAGAATCGTGCCAGTGATCGA

GAATCACAGATTCACCGGCAGATACCGGGACCTGTATCCTGCCAACGAGCTGATCGCCCTG

CTGGAGGAGAAGGGCATCGTGTTCAGGGATGGCTCCAACATCCTGCCAAAGCTGCTGGAGA

ATGACGATTCTCACGCCATCGACACGATGGTGGCCCTGATCCGCAGCGTGCTGCAGATGCG

GAACTCCAATGCCGCCACAGGCGAGGACTATATCAACAGCCCCGTGCGCGATCTGAATGGC

GTGTGCTTCGACTCCCGGTTTCAGAACCCAGAGTGGCCAATGGACGCCGATGCCAATGGCG

CCTACCACATCGCCCTGAAGGGCCAGCTGCTGCTGAATCACCTGAAGGAGAGCAAGGATCT

GAAGCTGCAGAACGGCATCTCCAATCAGGACTGGCTGGCCTACATCCAGGAGCTGCGCAAC

*GGTGGAAGCGGAGGGAGT*cccaagaagaagaggaaagtcGGGGGTTCCGGAGGAAGCGAGGCCA

GCGGTTCCGGACGGGCTGACGCATTGGACGATTTTGATCTGGATATGCTGGGAAGTGACGC

CCTCGATGATTTTGACCTTGACATGCTTGGTTCGGATGCCCTTGATGACTTTGACCTCGACA

TGCTCGGCAGTGACGCCCTTGATGATTTCGACCTGGACATGCTGATTAACTCTAGAAGTTCC

GGATCTCCGAAAAAGAAACGCAAAGTTGGTAGCCAGTACCTGCCCGACACCGACGACCGGC

ACCGGATCGAGGAAAAGCGGAAGCGGACCTACGAGACATTCAAGAGCATCATGAAGAAGTC

CCCCTTCAGCGGCCCCACCGACCCTAGACCTCCACCTAGAAGAATCGCCGTGCCCAGCAGA

TCCAGCGCCAGCGTGCCAAAACCTGCCCCCCAGCCTTACCCCTTCACCAGCAGCCTGAGCA

CCATCAACTACGACGAGTTCCCTACCATGGTGTTCCCCAGCGGCCAGATCTCTCAGGCCTC

TGCTCTGGCTCCAGCCCCTCCTCAGGTGCTGCCTCAGGCTCCTGCTCCTGCACCAGCTCCA

GCCATGGTGTCTGCACTGGCTCAGGCACCAGCACCCGTGCCTGTGCTGGCTCCTGGACCT

CCACAGGCTGTGGCTCCACCAGCCCCTAAACCTACACAGGCCGGCGAGGGCACACTGTCT

GAAGCTCTGCTGCAGCTGCAGTTCGACGACGAGGATCTGGGAGCCCTGCTGGGAAACAGC

ACCGATCCTGCCGTGTTCACCGACCTGGCCAGCGTGGACAACAGCGAGTTCCAGCAGCTG

CTGAACCAGGGCATCCCTGTGGCCCCTCACACCACCGAGCCCATGCTGATGGAATACCCCG

AGGCCATCACCCGGCTCGTGACAGGCGCTCAGAGGCCTCCTGATCCAGCTCCTGCCCCTCT

GGGAGCACCAGGCCTGCCTAATGGACTGCTGTCTGGCGACGAGGACTTCAGCTCTATCGCC

GATATGGATTTCTCAGCCTTGCTGGGCTCTGGCAGCGGCAGCCGGGATTCCAGGGAAGGG

ATGTTTTTGCCGAAGCCTGAGGCCGGCTCCGCTATTAGTGACGTGTTTGAGGGCCGCGAGG

TGTGCCAGCCAAAACGAATCCGGCCATTTCATCCTCCAGGAAGTCCATGGGCCAACCGCCC

ACTCCCCGCCAGCCTCGCACCAACACCAACCGGTCCAGTACATGAGCCAGTCGGGTCACTG

-continued

<u>ACCCCGGCACCAGTCCCTCAGCCACTGGATCCAGCGCCCGCAGTGACTCCCGAGGCCAGT</u>

<u>CACCTGTTGGAGGATCCCGATGAAGAGACGAGCCAGGCTGTCAAAGCCCTTCGGGAGATG</u>

<u>GCCGATACTGTGATTCCCCAGAAGGAAGAGGCTGCAATCTGTGGCCAAATGGACCTTTCCC</u>

<u>ATCCGCCCCAAGGGGCCATCTGGATGAGCTGACAACCACACTTGAGTCCATGACCGAGGA</u>

<u>TCTGAACCTGGACTCACCCCTGACCCCGGAATTGAACGAGATTCTGGATACCTTCCTGAACG</u>

<u>ACGAGTGCCTCTTGCATGCCATGCATATCAGCACAGGACTGTCCATCTTCGACACATCTCTG</u>

<u>TTTT</u>AA

RTW1351: pCAG-rAPOBEC1-gs-XTEN-gs-hdAsCas12a(D908A)-NLS-gs-UGI-NLS(AsBE1.1)
Rat APOBEC1 (rAPOBEC1) in bold upper case, inserted glycine dash-underlined
glycine/serine linkers in italics, XTEN linker in lower case italics, human codon optimized
*Acidaminococcus* sp. *BV3L6* Cas12a (AsCas12a) in black, modified codon for DNase inactive
(D908A) AsCas12a in double underlined lower case, codons with silent mutations to remove
NcoI sites double underlined UPPER CASE, nucleoplasmin NLS in lower case bold, UGI in
BOLD UPPER CASE WITH HYPHEN-UNDERLINING, SV40 NLS in double underlined italics (SEQ ID NO: 438)

ATGGGCAGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAATCTGGTGGTTCTTCTGGTGGTTCT*agcggcagcgagactcc*
*cgggacctcagagtccgccacacccgaaagt*TCCGGAGGGAGTAGCGGCGGGTCTACACAGTTCGAGGG <u>CTTTACCAACCTGTATCAGGTGAGCAAGACACTGCGGTTTGAGCTGATCCCACAGGGCAAG</u>

<u>ACCCTGAAGCACATCCAGGAGCAGGGCTTCATCGAGGAGGACAAGGCCCGCAATGATCACT</u>

<u>ACAAGGAGCTGAAGCCCATCATCGATCGGATCTACAAGACCTATGCCGACCAGTGCCTGCA</u>

<u>GCTGGTGCAGCTGGATTGGGAGAACCTGAGCGCCGCCATCGACTCCTATAGAAAGGAGAAA</u>

<u>ACCGAGGAGACAAGGAACGCCCTGATCGAGGAGCAGGCCACATATCGCAATGCCATCCAC</u>

<u>GACTACTTCATCGGCCGGACAGACAACCTGACCGATGCCATCAATAAGAGACACGCCGAGA</u>

<u>TCTACAAGGGCCTGTTCAAGGCCGAGCTGTTTAATGGCAAGGTGCTGAAGCAGCTGGGCAC</u>

<u>CGTGACCACAACCGAGCACGAGAACGCCCTGCTGCGGAGCTTCGACAAGTTTACAACCTAC</u>

<u>TTCTCCGGCTTTTATGAGAACAGGAAGAACGTGTTCAGCGCCGAGGATATCAGCACAGCCAT</u>

<u>CCCACACCGCATCGTGCAGGACAACTTCCCCAAGTTTAAGGAGAATTGTCACATCTTCACAC</u>

<u>GCCTGATCACCGCCGTGCCCAGCCTGCGGGAGCACTTTGAGAACGTGAAGAAGGCCATCG</u>

<u>GCATCTTCGTGAGCACCTCCATCGAGGAGGTGTTTTCCTTCCCTTTTTATAACCAGCTGCTG</u>

<u>ACACAGACCCAGATCGACCTGTATAACCAGCTGCTGGGAGGAATCTCTCGGGAGGCAGGCA</u>

<u>CCGAGAAGATCAAGGGCCTGAACGAGGTGCTGAATCTGGCCATCCAGAAGAATGATGAGAC</u>

<u>AGCCCACATCATCGCCTCCCTGCCACACAGATTCATCCCCCTGTTTAAGCAGATCCTGTCCG</u>

<u>ATAGGAACACCCTGTCTTTCATCCTGGAGGAGTTTAAGAGCGACGAGGAAGTGATCCAGTC</u>

```
-continued
CTTCTGCAAGTACAAGACACTGCTGAGAAACGAGAACGTGCTGGAGACAGCCGAGGCCCTG

TTTAACGAGCTGAACAGCATCGACCTGACACACATCTTCATCAGCCACAAGAAGCTGGAGAC

AATCAGCAGCGCCCTGTGCGACCACTGGGATACACTGAGGAATGCCCTGTATGAGCGGAGA

ATCTCCGAGCTGACAGGCAAGATCACCAAGTCTGCCAAGGAGAAGGTGCAGCGCAGCCTGA

AGCACGAGGATATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTGGATCAGCCACT

GCCTACAACCCTGAAGAAGCAGGAGGAGAAGGAGATCCTGAAGTCTCAGCTGGACAGCCTG

CTGGGCCTGTACCACCTGCTGGACTGGTTTGCCGTGGATGAGTCCAACGAGGTGGACCCC

GAGTTCTCTGCCCGGCTGACCGGCATCAAGCTGGAGATGGAGCCTTCTCTGAGCTTCTACA

ACAAGGCCAGAAATTATGCCACCAAGAAGCCCTACTCCGTGGAGAAGTTCAAGCTGAACTTT

CAGATGCCTACACTGGCCTCTGGCTGGGACGTGAATAAGGAGAAGAACAATGGCGCCATCC

TGTTTGTGAAGAACGGCCTGTACTATCTGGGCATCATGCCAAAGCAGAAGGGCAGGTATAA

GGCCCTGAGCTTCGAGCCCACAGAGAAAACCAGCGAGGGCTTTGATAAGATGTACTATGAC

TACTTCCCTGATGCCGCCAAGATGATCCCAAAGTGCAGCACCCAGCTGAAGGCCGTGACAG

CCCACTTTCAGACCCACACAACCCCCATCCTGCTGTCCAACAATTTCATCGAGCCTCTGGAG

ATCACAAAGGAGATCTACGACCTGAACAATCCTGAGAAGGAGCCAAAGAAGTTTCAGACAGC

CTACGCCAAGAAAACCGGCGACCAGAAGGGCTACAGAGAGGCCCTGTGCAAGTGGATCGA

CTTCACAAGGGATTTTCTGTCCAAGTATACCAAGACAACCTCTATCGATCTGTCTAGCCTGC

GGCCATCCTCTCAGTATAAGGACCTGGGCGAGTACTATGCCGAGCTGAATCCCCTGCTGTA

CCACATCAGCTTCCAGAGAATCGCCGAGAAGGAGATCATGGATGCCGTGGAGACAGGCAAG

CTGTACCTGTTCCAGATCTATAACAAGGACTTTGCCAAGGGCCACCACGGCAAGCCTAATCT

GCACACACTGTATTGGACCGGCCTGTTTTCTCCAGAGAACCTGGCCAAGACAAGCATCAAG

CTGAATGGCCAGGCCGAGCTGTTCTACCGCCCTAAGTCCAGGATGAAGAGGATGGCACACC

GGCTGGGAGAGAAGATGCTGAACAAGAAGCTGAAGGATCAGAAAACCCCAATCCCCGACAC

CCTGTACCAGGAGCTGTACGACTATGTGAATCACAGACTGTCCCACGACCTGTCTGATGAG

GCCAGGGCCCTGCTGCCCAACGTGATCACCAAGGAGGTGTCTCACGAGATCATCAAGGATA

GGCGCTTTACCAGCGACAAGTTCTTTTTCCACGTGCCTATCACACTGAACTATCAGGCCGCC

AATTCCCCATCTAAGTTCAACCAGAGGGTGAATGCCTACCTGAAGGAGCACCCCGAGACAC

CTATCATCGGCATCgccCGGGGCGAGAGAAACCTGATCTATATCACAGTGATCGACTCCACC

GGCAAGATCCTGGAGCAGCGGAGCCTGAACACCATCCAGCAGTTTGATTACCAGAAGAAGC

TGGACAACAGGGAGAAGGAGAGGGTGGCAGCAAGGCAGGCCTGGTCTGTGGTGGGCACAA

TCAAGGATCTGAAGCAGGGCTATCTGAGCCAGGTCATCCACGAGATCGTGGACCTGATGAT

CCACTACCAGGCCGTGGTGGTGCTGGAGAACCTGAATTTCGGCTTTAAGAGCAAGAGGACC

GGCATCGCCGAGAAGGCCGTGTACCAGCAGTTCGAGAAGATGCTGATCGATAAGCTGAATT

GCCTGGTGCTGAAGGACTATCCAGCAGAGAAAGTGGGAGGCGTGCTGAACCCATACCAGCT

GACAGACCAGTTCACCTCCTTTGCCAAGATGGGCACCCAGTCTGGCTTCCTGTTTTACGTGC

CTGCCCCATATACATCTAAGATCGATCCCCTGACCGGCTTCGTGGACCCCTTCGTGTGGAAA

ACCATCAAGAATCACGAGAGCCGCAAGCACTTCCTGGAGGGCTTCGACTTTCTGCACTACG

ACGTGAAAACCGGCGACTTCATCCTGCACTTTAAGATGAACAGAAATCTGTCCTTCCAGAGG

GGCCTGCCCGGCTTTATGCCTGCATGGGATATCGTGTTCGAGAAGAACGAGACACAGTTTG

ACGCCAAGGGCACCCCTTTCATCGCCGGCAAGAGAATCGTGCCAGTGATCGAGAATCACAG
```

```
ATTCACCGGCAGATACCGGGACCTGTATCCTGCCAACGAGCTGATCGCCCTGCTGGAGGAG

AAGGGCATCGTGTTCAGGGATGGCTCCAACATCCTGCCAAAGCTGCTGGAGAATGACGATT

CTCACGCCATCGACACGATGGTGGCCCTGATCCGCAGCGTGCTGCAGATGCGGAACTCCA

ATGCCGCCACAGGCGAGGACTATATCAACAGCCCCGTGCGCGATCTGAATGGCGTGTGCTT

CGACTCCCGGTTTCAGAACCCAGAGTGGCCAATGGACGCCGATGCCAATGGCGCCTACCA

CATCGCCCTGAAGGGCCAGCTGCTGCTGAATCACCTGAAGGAGAGCAAGGATCTGAAGCTG

CAGAACGGCATCTCCAATCAGGACTGGCTGGCCTACATCCAGGAGCTGCGCAACaaaaggcc ggcggccacgaaaaaggccggccaggcaaaaaagaaaaagGGATCCTCTGGTGGTTCTGGAGGATCTG

*GTGGTTCT*ACTAATCTGTCAGATATTATTGAAAAGGAGACCGGTAAGCAACTGGTTATCCA

GGAATCCATCCTCATGCTCCCAGAGGAGGTGGAAGAAGTCATTGGGAACAAGCCGGAAA

GCGATATACTCGTGCACACCGCCTACGACGAGAGCACCGACGAGAATGTCATGCTTCTGA

CTAGCGACGCCCCTGAATACAAGCCTTGGGCTCTGGTCATACAGGATAGCAACGGTGAGA

ACAAGATTAAGATGCTC*TCTGGTGGTTCTCCCAAGAAGAAGAGGAAAGTC*TAA
```

RTW1295: pCAG-rAPOBEC1-gs-XTEN-gs-hdLbCas12a(D832A)-NLS-gs-UGI-NLS(LbBE1.1)
Rat APOBEC1 (rAPOBEC1) in bold upper case, inserted glycine dash-underlined, glycine/serine linkers in italics, XTEN linker in lower case italics, human codon optimized *Lachnospiraceae bacterium* ND2006 Cas12a (LbCas12a) in black, modified codon for DNase inactive (D832A) LbCas12a in double underlined lower case, codons with silent mutations to remove NcoI sites in double underlined UPPER CASE, nucleoplasmin NLS lower case bold, UGI in BOLD UPPER CASE WITH HYPHEN-UNDERLINING, SV40 NLS in double underlined italics (SEQ ID NO: 439)

```
ATGGGCAGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCT*agcggcagcgagactcc cgggacctcagagtccgccacacccgaaagtTCCGGAGGGAGTAGCGGCGGGTCTAGCAAGCTGGAGAA

GTTTACAAACTGCTACTCCCTGTCTAAGACCCTGAGGTTCAAGGCCATCCCTGTGGGCAAGA

CCCAGGAGAACATCGACAATAAGCGGCTGCTGGTGGAGGACGAGAAGAGAGCCGAGGATT

ATAAGGGCGTGAAGAAGCTGCTGGATCGCTACTATCTGTCTTTTATCAACGACGTGCTGCAC

AGCATCAAGCTGAAGAATCTGAACAATTACATCAGCCTGTTCCGGAAGAAAACCAGAACCGA

GAAGGAGAATAAGGAGCTGGAGAACCTGGAGATCAATCTGCGGAAGGAGATCGCCAAGGC

CTTCAAGGGCAACGAGGGCTACAAGTCCCTGTTTAAGAAGGATATCATCGAGACAATCCTGC

CAGAGTTCCTGGACGATAAGGACGAGATCGCCCTGGTGAACAGCTTCAATGGCTTTACCAC

AGCCTTCACCGGCTTCTTTGATAACAGAGAGAATATGTTTTCCGAGGAGGCCAAGAGCACAT

CCATCGCCTTCAGGTGTATCAACGAGAATCTGACCCGCTACATCTCTAATATGGACATCTTC
```

-continued

```
GAGAAGGTGGACGCCATCTTTGATAAGCACGAGGTGCAGGAGATCAAGGAGAAGATCCTGA

ACAGCGACTATGATGTGGAGGATTTCTTTGAGGGCGAGTTCTTTAACTTTGTGCTGACACAG

GAGGGCATCGACGTGTATAACGCCATCATCGGCGGCTTCGTGACCGAGAGCGGCGAGAAG

ATCAAGGGCCTGAACGAGTACATCAACCTGTATAATCAGAAAACCAAGCAGAAGCTGCCTAA

GTTTAAGCCACTGTATAAGCAGGTGCTGAGCGATCGGGAGTCTCTGAGCTTCTACGGCGAG

GGCTATACATCCGATGAGGAGGTGCTGGAGGTGTTTAGAAACACCCTGAACAAGAACAGCG

AGATCTTCAGCTCCATCAAGAAGCTGGAGAAGCTGTTCAAGAATTTTGACGAGTACTCTAGC

GCCGGCATGTTTGTGAAGAACGGCCCCGCCATCAGCACAATCTCCAAGGATATCTTCGGCG

AGTGGAACGTGATCCGGGACAAGTGGAATGCCGAGTATGACGATATCCACCTGAAGAAGAA

GGCCGTGGTGACCGAGAAGTACGAGGACGATCGGAGAAAGTCCTTCAAGAAGATCGGCTC

CTTTTCTCTGGAGCAGCTGCAGGAGTACGCCGACGCCGATCTGTCTGTGGTGGAGAAGCTG

AAGGAGATCATCATCCAGAAGGTGGATGAGATCTACAAGGTGTATGGCTCCTCTGAGAAGCT

GTTCGACGCCGATTTTGTGCTGGAGAAGAGCCTGAAGAAGAACGACGCCGTGGTGGCCATC

ATGAAGGACCTGCTGGATTCTGTGAAGAGCTTCGAGAATTACATCAAGGCCTTCTTTGGCGA

GGGCAAGGAGACAAACAGGGACGAGTCCTTCTATGGCGATTTTGTGCTGGCCTACGACATC

CTGCTGAAGGTGGACCACATCTACGATGCCATCCGCAATTATGTGACCCAGAAGCCCTACTC

TAAGGATAAGTTCAAGCTGTATTTTCAGAACCCTCAGTTCATGGGCGGCTGGGACAAGGATA

AGGAGACAGACTATCGGGCCACCATCCTGAGATACGGCTCCAAGTACTATCTGGCCATCAT

GGATAAGAAGTACGCCAAGTGCCTGCAGAAGATCGACAAGGACGATGTGAACGGCAATTAC

GAGAAGATCAACTATAAGCTGCTGCCCGGCCCTAATAAGATGCTGCCAAAGGTGTTCTTTTC

TAAGAAGTGGATGGCCTACTATAACCCCAGCGAGGACATCCAGAAGATCTACAAGAATGGC

ACATTCAAGAAGGGCGATATGTTTAACCTGAATGACTGTCACAAGCTGATCGACTTCTTTAAG

GATAGCATCTCCCGGTATCCAAAGTGGTCCAATGCCTACGATTTCAACTTTTCTGAGACAGA

GAAGTATAAGGACATCGCCGGCTTTTACAGAGAGGTGGAGGAGCAGGGCTATAAGGTGAGC

TTCGAGTCTGCCAGCAAGAAGGAGGTGGATAAGCTGGTGGAGGAGGGCAAGCTGTATATGT

TCCAGATCTATAACAAGGACTTTTCCGATAAGTCTCACGGCACACCCAATCTGCACACCATG

TACTTCAAGCTGCTGTTTGACGAGAACAATCACGGACAGATCAGGCTGAGCGGAGGAGCAG

AGCTGTTCATGAGGCGCGCCTCCCTGAAGAAGGAGGAGCTGGTGGTGCACCCAGCCAACT

CCCCTATCGCCAACAAGAATCCAGATAATCCCAAGAAAACCACAACCCTGTCCTACGACGTG

TATAAGGATAAGAGGTTTTCTGAGGACCAGTACGAGCTGCACATCCCAATCGCCATCAATAA

GTGCCCCAAGAACATCTTCAAGATCAATACAGAGGTGCGCGTGCTGCTGAAGCACGACGAT

AACCCCTATGTGATCGGCATCgccAGGGGCGAGCGCAATCTGCTGTATATCGTGGTGGTGGA

CGGCAAGGGCAACATCGTGGAGCAGTATTCCCTGAACGAGATCATCAACAACTTCAACGGC

ATCAGGATCAAGACAGATTACCACTCTCTGCTGGACAAGAAGGAGAAGGAGAGGTTCGAGG

CCCGCCAGAACTGGACCTCCATCGAGAATATCAAGGAGCTGAAGGCCGGCTATATCTCTCA

GGTGGTGCACAAGATCTGCGAGCTGGTGGAGAAGTACGATGCCGTGATCGCCCTGGAGGA

CCTGAACTCTGGCTTTAAGAATAGCCGCGTGAAGGTGGAGAAGCAGGTGTATCAGAAGTTC

GAGAAGATGCTGATCGATAAGCTGAACTACATGGTGGACAAGAAGTCTAATCCTTGTGCAAC

AGGCGGCGCCCTGAAGGGCTATCAGATCACCAATAAGTTCGAGAGCTTTAAGTCCATGTCTA

CCCAGAACGGCTTCATCTTTTACATCCCTGCCTGGCTGACATCCAAGATCGATCCATCTACC

GGCTTTGTGAACCTGCTGAAAACCAAGTATACCAGCATCGCCGATTCCAAGAAGTTCATCAG
```

```
CTCCTTTGACAGGATCATGTACGTGCCCGAGGAGGATCTGTTCGAGTTTGCCCTGGACTATA

AGAACTTCTCTCGCACAGACGCCGATTACATCAAGAAGTGGAAGCTGTACTCCTACGGCAAC

CGGATCAGAATCTTCCGGAATCCTAAGAAGAACAACGTGTTCGACTGGGAGGAGGTGTGCC

TGACCAGCGCCTATAAGGAGCTGTTCAACAAGTACGGCATCAATTATCAGCAGGGCGATATC

AGAGCCCTGCTGTGCGAGCAGTCCGACAAGGCCTTCTACTCTAGCTTTATGGCCCTGATGA

GCCTGATGCTGCAGATGCGGAACAGCATCACAGGCCGCACCGACGTGGATTTTCTGATCAG

CCCTGTGAAGAACTCCGACGGCATCTTCTACGATAGCCGGAACTATGAGGCCCAGGAGAAT

GCCATCCTGCCAAAGAACGCCGACGCCAATGGCGCCTATAACATCGCCAGAAAGGTGCTGT

GGGCCATCGGCCAGTTCAAGAAGGCCGAGGACGAGAAGCTGGATAAGGTGAAGATCGCCA

TCTCTAACAAGGAGTGGCTGGAGTACGCCCAGACCAGCGTGAAGCACaaaaggccggcggccac gaaaaaggccggccaggcaaaaaagaaaaagGGATCCTCTGGTGGTTCTGGAGGATCTGGTGGTTCT

<u>ACTAATCTGTCAGATATTATTGAAAAGGAGACCGGTAAGCAACTGGTTATCCAGGAATCCA</u>

<u>TCCTCATGCTCCCAGAGGAGGTGGAAGAAGTCATTGGGAACAAGCCGGAAAGCGATATA</u>

<u>CTCGTGCACACCGCCTACGACGAGAGCACCGACGAGAATGTCATGCTTCTGACTAGCGAC</u>

<u>GCCCCTGAATACAAGCCTTGGGCTCTGGTCATACAGGATAGCAACGGTGAGAACAAGATT</u>

<u>AAGATGCTC</u>*TCTGGTGGTTCT*<u>CCCAAGAAGAAGAGGAAAGTC</u>TAA
```

RTW1352: pCAG-rAPOBEC1-gs-XTEN-gs-hdeAsCas12a(E174R/S542R/K548R/D908A)-NLS-
gs-UGI-NLS(eAsBE1.1)
Rat APOBEC1 (rAPOBEC1) in bold upper case, inserted glycine dash-underlined,
glycine/serine linkers in italics, XTEN linker in lower case italics, human codon optimized
*Acidaminococcus* sp. BV3L6 Cas12a (AsCas12a) in black, modified codons for DNase inactive
(D908A) eAsCas12a (E174R/S542R/K548R) in double underlined lower case, codons with
silent mutations to remove NcoI sites in double underlined UPPER CASE, nucleoplasmin NLS
lower case bold, UGI in BOLD UPPER CASE WITH HYPHEN-UNDERLINING, SV40 NLS in
double underlined italics (SEQ ID NO: 440)

```
ATG<u>GGC</u>AGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCT*agcggcagcgagactcc cgggacctcagagtccgccacacccgaaagtTCCGGAGGGAGTAGCGGCGGGTCTACACAGTTCGAGGG

CTTTACCAACCTGTATCAGGTGAGCAAGACACTGCGGTTTGAGCTGATCCCACAGGGCAAG

ACCCTGAAGCACATCCAGGAGCAGGGCTTCATCGAGGAGGACAAGGCCCGCAATGATCACT

ACAAGGAGCTGAAGCCCATCATCGATCGGATCTACAAGACCTATGCCGACCAGTGCCTGCA

GCTGGTGCAGCTGGATTGGGAGAACCTGAGCGCCGCCATCGACTCCTATAGAAAGGAGAAA

ACCGAGGAGACAAGGAACGCCCTGATCGAGGAGCAGGCCACATATCGCAATGCCATCCAC

GACTACTTCATCGGCCGGACAGACAACCTGACCGATGCCATCAATAAGAGACACGCCGAGA
```

-continued

```
TCTACAAGGGCCTGTTCAAGGCCGAGCTGTTTAATGGCAAGGTGCTGAAGCAGCTGGGCAC
CGTGACCACAACCGAGCACGAGAACGCCCTGCTGCGGAGCTTCGACAAGTTTACAACCTAC
TTCTCCGGCTTTTATagaAACAGGAAGAACGTGTTCAGCGCCGAGGATATCAGCACAGCCAT
CCCACACCGCATCGTGCAGGACAACTTCCCCAAGTTTAAGGAGAATTGTCACATCTTCACAC
GCCTGATCACCGCCGTGCCCAGCCTGCGGGAGCACTTTGAGAACGTGAAGAAGGCCATCG
GCATCTTCGTGAGCACCTCCATCGAGGAGGTGTTTTCCTTCCCTTTTTATAACCAGCTGCTG
ACACAGACCCAGATCGACCTGTATAACCAGCTGCTGGGAGGAATCTCTCGGGAGGCAGGCA
CCGAGAAGATCAAGGGCCTGAACGAGGTGCTGAATCTGGCCATCCAGAAGAATGATGAGAC
AGCCCACATCATCGCCTCCCTGCCACACAGATTCATCCCCCTGTTTAAGCAGATCCTGTCCG
ATAGGAACACCCTGTCTTTCATCCTGGAGGAGTTTAAGAGCGACGAGGAAGTGATCCAGTC
CTTCTGCAAGTACAAGACACTGCTGAGAAACGAGAACGTGCTGGAGACAGCCGAGGCCCTG
TTTAACGAGCTGAACAGCATCGACCTGACACACATCTTCATCAGCCACAAGAAGCTGGAGAC
AATCAGCAGCGCCCTGTGCGACCACTGGGATACACTGAGGAATGCCCTGTATGAGCGGAGA
ATCTCCGAGCTGACAGGCAAGATCACCAAGTCTGCCAAGGAGAAGGTGCAGCGCAGCCTGA
AGCACGAGGATATCAACCTGCAGGAGATCATCTCTGCCGCAGGCAAGGAGCTGAGCGAGG
CCTTCAAGCAGAAAACCAGCGAGATCCTGTCCCACGCACACGCCGCCCTGGATCAGCCACT
GCCTACAACCCTGAAGAAGCAGGAGGAGAAGGAGATCCTGAAGTCTCAGCTGGACAGCCTG
CTGGGCCTGTACCACCTGCTGGACTGGTTTGCCGTGGATGAGTCCAACGAGGTGGACCCC
GAGTTCTCTGCCCGGCTGACCGGCATCAAGCTGGAGATGGAGCCTTCTCTGAGCTTCTACA
ACAAGGCCAGAAATTATGCCACCAAGAAGCCCTACTCCGTGGAGAAGTTCAAGCTGAACTTT
CAGATGCCTACACTGGCCagaGGCTGGGACGTGAATagaGAGAAGAACAATGGCGCCATCCT
GTTTGTGAAGAACGGCCTGTACTATCTGGGCATCATGCCAAAGCAGAAGGGCAGGTATAAG
GCCCTGAGCTTCGAGCCCACAGAGAAAACCAGCGAGGGCTTTGATAAGATGTACTATGACT
ACTTCCCTGATGCCGCCAAGATGATCCCAAAGTGCAGCACCCAGCTGAAGGCCGTGACAGC
CCACTTTCAGACCCACACAACCCCCATCCTGCTGTCCAACAATTTCATCGAGCCTCTGGAGA
TCACAAAGGAGATCTACGACCTGAACAATCCTGAGAAGGAGCCAAAGAAGTTTCAGACAGC
CTACGCCAAGAAAACCGGCGACCAGAAGGGCTACAGAGAGGCCCTGTGCAAGTGGATCGA
CTTCACAAGGGATTTTCTGTCCAAGTATACCAAGACAACCTCTATCGATCTGTCTAGCCTGC
GGCCATCCTCTCAGTATAAGGACCTGGGCGAGTACTATGCCGAGCTGAATCCCCTGCTGTA
CCACATCAGCTTCCAGAGAATCGCCGAGAAGGAGATCATGGATGCCGTGGAGACAGGCAAG
CTGTACCTGTTCCAGATCTATAACAAGGACTTTGCCAAGGGCCACCACGGCAAGCCTAATCT
GCACACACTGTATTGGACCGGCCTGTTTTCTCCAGAGAACCTGGCCAAGACAAGCATCAAG
CTGAATGGCCAGGCCGAGCTGTTCTACCGCCCTAAGTCCAGGATGAAGAGGATGGCACACC
GGCTGGGAGAGAAGATGCTGAACAAGAAGCTGAAGGATCAGAAAACCCCAATCCCCGACAC
CCTGTACCAGGAGCTGTACGACTATGTGAATCACAGACTGTCCCACGACCTGTCTGATGAG
GCCAGGGCCCTGCTGCCCAACGTGATCACCAAGGAGGTGTCTCACGAGATCATCAAGGATA
GGCGCTTTACCAGCGACAAGTTCTTTTTCCACGTGCCTATCACACTGAACTATCAGGCCGCC
AATTCCCCATCTAAGTTCAACCAGAGGGTGAATGCCTACCTGAAGGAGCACCCCGAGACAC
CTATCATCGGCATCgccCGGGGCGAGAGAAACCTGATCTATATCACAGTGATCGACTCCACC
GGCAAGATCCTGGAGCAGCGGAGCCTGAACACCATCCAGCAGTTTGATTACCAGAAGAAGC
TGGACAACAGGGAGAAGGAGAGGGTGGCAGCAAGGCAGGCCTGGTCTGTGGTGGGCACAA
```

-continued

```
TCAAGGATCTGAAGCAGGGCTATCTGAGCCAGGTCATCCACGAGATCGTGGACCTGATGAT

CCACTACCAGGCCGTGGTGGTGCTGGAGAACCTGAATTTCGGCTTTAAGAGCAAGAGGACC

GGCATCGCCGAGAAGGCCGTGTACCAGCAGTTCGAGAAGATGCTGATCGATAAGCTGAATT

GCCTGGTGCTGAAGGACTATCCAGCAGAGAAAGTGGGAGGCGTGCTGAACCCATACCAGCT

GACAGACCAGTTCACCTCCTTTGCCAAGATGGGCACCCAGTCTGGCTTCCTGTTTTACGTGC

CTGCCCCATATACATCTAAGATCGATCCCCTGACCGGCTTCGTGGACCCCTTCGTGTGGAAA

ACCATCAAGAATCACGAGAGCCGCAAGCACTTCCTGGAGGGCTTCGACTTTCTGCACTACG

ACGTGAAAACCGGCGACTTCATCCTGCACTTTAAGATGAACAGAAATCTGTCCTTCCAGAGG

GGCCTGCCCGGCTTTATGCCTGCATGGGATATCGTGTTCGAGAAGAACGAGACACAGTTTG

ACGCCAAGGGCACCCCTTTCATCGCCGGCAAGAGAATCGTGCCAGTGATCGAGAATCACAG

ATTCACCGGCAGATACCGGGACCTGTATCCTGCCAACGAGCTGATCGCCCTGCTGGAGGAG

AAGGGCATCGTGTTCAGGGATGGCTCCAACATCCTGCCAAAGCTGCTGGAGAATGACGATT

CTCACGCCATCGACACGATGGTGGCCCTGATCCGCAGCGTGCTGCAGATGCGGAACTCCAA

TGCCGCCACAGGCGAGGACTATATCAACAGCCCCGTGCGCGATCTGAATGGCGTGTGCTTC

GACTCCCGGTTTCAGAACCCAGAGTGGCCAATGGACGCCGATGCCAATGGCGCCTACCACA

TCGCCCTGAAGGGCCAGCTGCTGCTGAATCACCTGAAGGAGAGCAAGGATCTGAAGCTGCA

GAACGGCATCTCCAATCAGGACTGGCTGGCCTACATCCAGGAGCTGCGCAACaaaaggccggc ggccacgaaaaaggccggccaggcaaaaaagaaaaagGGATCCTCTGGTGGTTCTGGAGGATCTGGTG

GTTCTACTAATCTGTCAGATATTATTGAAAAGGAGACCGGTAAGCAACTGGTTATCCAGGA

ATCCATCCTCATGCTCCCAGAGGAGGTGGAAGAAGTCATTGGGAACAAGCCGGAAAGCG

ATATACTCGTGCACACCGCCTACGACGAGAGCACCGACGAGAATGTCATGCTTCTGACTA

GCGACGCCCTGAATACAAGCCTTGGGCTCTGGTCATACAGGATAGCAACGGTGAGAACA

AGATTAAGATGCTCTCTGGTGGTTCTCCCAAGAAGAAGAGGAAAGTCTAA
```

RTW1348: pCAG-2xNLS-rAPOBEC1-gs-XTEN-gs-hdeAsCas12a(E174R/S542R/K548R/D908A)-NLS-gs-UGI-NLS (eAsBE1.2)
Rat APOBEC1 (rAPOBEC1) in bold upper case, inserted glycine dash-underlined SV40 NLS in double underlined italics, glycine/serine linkers in italics, XTEN linker in lower case italics, human codon optimized *Acidaminococcus* sp. *BV3L6* Cas12a (AsCas12a) in black, modified codons for DNase inactive (D908A) eAsCas12a (E174R/S542R/K548R) in double underlined lower case, codons with silent mutations to remove NcoI sites double underlined UPPER CASE, nucleoplasmin NLS lower case bold, UGI in BOLD UPPER CASE WITH HYPHEN-UNDERLINING, (SEQ ID NO: 441)

```
ATGGGCCCAAAGAAAAAGAGGAAAGTCGGCAGTGGACCTAAAAAGAAACGAAAGGTTGGGT

CAGGTAGCTCAGAGACTGGCCCAGTGGCTGTGGACCCCACATTGAGACGGCGGATCGAG

CCCCATGAGTTTGAGGTATTCTTCGATCCGAGAGAGCTCCGCAAGGAGACCTGCCTGCTTT

ACGAAATTAATTGGGGGGGCCGGCACTCCATTTGGCGACATACATCACAGAACACTAACA

AGCACGTCGAAGTCAACTTCATCGAGAAGTTCACGACAGAAAGATATTTCTGTCCGAACA

CAAGGTGCAGCATTACCTGGTTTCTCAGCTGGAGCCCATGCGGCGAATGTAGTAGGGCCA

TCACTGAATTCCTGTCAAGGTATCCCCACGTCACTCTGTTTATTTACATCGCAAGGCTGTAC

CACCACGCTGACCCCCGCAATCGACAAGGCCTGCGGGATTTGATCTCTTCAGGTGTGACT

ATCCAAATTATGACTGAGCAGGAGTCAGGATACTGCTGGAGAAACTTTGTGAATTATAGCC

CGAGTAATGAAGCCCACTGGCCTAGGTATCCCCATCTGTGGGTACGACTGTACGTTCTTGA

ACTGTACTGCATCATACTGGGCCTGCCTCCTTGTCTCAACATTCTGAGAAGGAAGCAGCCA

CAGCTGACATTCTTTACCATCGCTCTTCAGTCTTGTCATTACCAGCGACTGCCCCCACACA
```

-continued

TTCTCTGGGCCACCGGGTTGAAA*TCTGGTGGTTCTTCTGGTGGTTCT*agcggcagcgagactcccg ggacctcagagtccgccacacccgaaagtTCCGGAGGGAGTAGCGGCGGGTCTACACAGTTCGAGGGC

TTTACCAACCTGTATCAGGTGAGCAAGACACTGCGGTTTGAGCTGATCCCACAGGGCAAGA

CCCTGAAGCACATCCAGGAGCAGGGCTTCATCGAGGAGGACAAGGCCCGCAATGATCACTA

CAAGGAGCTGAAGCCCATCATCGATCGGATCTACAAGACCTATGCCGACCAGTGCCTGCAG

CTGGTGCAGCTGGATTGGGAGAACCTGAGCGCCGCCATCGACTCCTATAGAAAGGAGAAAA

CCGAGGAGACAAGGAACGCCCTGATCGAGGAGCAGGCCACATATCGCAATGCCATCCACG

ACTACTTCATCGGCCGGACAGACAACCTGACCGATGCCATCAATAAGAGACACGCCGAGAT

CTACAAGGGCCTGTTCAAGGCCGAGCTGTTTAATGGCAAGGTGCTGAAGCAGCTGGGCACC

GTGACCACAACCGAGCACGAGAACGCCCTGCTGCGGAGCTTCGACAAGTTTACAACCTACT

TCTCCGGCTTTTAT<u>AGA</u>ACAGGAAGAACGTGTTCAGCGCCGAGGATATCAGCACAGCCATC

CCACACCGCATCGTGCAGGACAACTTCCCCAAGTTTAAGGAGAATTGTCACATCTTCACACG

CCTGATCACCGCCGTGCCCAGCCTGCGGGAGCACTTTGAGAACGTGAAGAAGGCCATCGG

CATCTTCGTGAGCACCTCCATCGAGGAGGTGTTTTCCTTCCCTTTTTATAACCAGCTGCTGA

CACAGACCCAGATCGACCTGTATAACCAGCTGCTGGGAGGAATCTCTCGGGAGGCAGGCAC

CGAGAAGATCAAGGGCCTGAACGAGGTGCTGAATCTGGCCATCCAGAAGAATGATGAGACA

GCCCACATCATCGCCTCCCTGCCACACAGATTCATCCCCCTGTTTAAGCAGATCCTGTCCGA

TAGGAACACCCTGTCTTTCATCCTGGAGGAGTTTAAGAGCGACGAGGAAGTGATCCAGTCCT

TCTGCAAGTACAAGACACTGCTGAGAAACGAGAACGTGCTGGAGACAGCCGAGGCCCTGTT

TAACGAGCTGAACAGCATCGACCTGACACACATCTTCATCAGCCACAAGAAGCTGGAGACAA

TCAGCAGCGCCCTGTGCGACCACTGGGATACACTGAGGAATGCCCTGTATGAGCGGAGAAT

CTCCGAGCTGACAGGCAAGATCACCAAGTCTGCCAAGGAGAAGGTGCAGCGCAGCCTGAA

GCACGAGGATATCAACCTGCAGGAGATCATCTCTGCCGCAGGCAAGGAGCTGAGCGAGGC

CTTCAAGCAGAAAACCAGCGAGATCCTGTCCCACGCACACGCCGCCCTGGATCAGCCACTG

CCTACAACCCTGAAGAAGCAGGAGGAGAAGGAGATCCTGAAGTCTCAGCTGGACAGCCTGC

TGGGCCTGTACCACCTGCTGGACTGGTTTGCCGTGGATGAGTCCAACGAGGTGGACCCCG

AGTTCTCTGCCCGGCTGACCGGCATCAAGCTGGAGATGGAGCCTTCTCTGAGCTTCTACAA

CAAGGCCAGAAATTATGCCACCAAGAAGCCCTACTCCGTGGAGAAGTTCAAGCTGAACTTTC

AGATGCCTACACTGGCC<u>aga</u>GCTGGGACGTGAAT<u>aga</u>GAGAAGAACAATGGCGCCATCCTG

TTTGTGAAGAACGGCCTGTACTATCTGGGCATCATGCCAAAGCAGAAGGGCAGGTATAAGG

CCCTGAGCTTCGAGCCCACAGAGAAAACCAGCGAGGGCTTTGATAAGATGTACTATGACTA

CTTCCCTGATGCCGCCAAGATGATCCCAAAGTGCAGCACCCAGCTGAAGGCCGTGACAGCC

CACTTTCAGACCCACACAACCCCCATCCTGCTGTCCAACAATTTCATCGAGCCTCTGGAGAT

CACAAAGGAGATCTACGACCTGAACAATCCTGAGAAGGAGCCAAAGAAGTTTCAGACAGCC

TACGCCAAGAAAACCGGCGACCAGAAGGGCTACAGAGAGGCCCTGTGCAAGTGGATCGAC

TTCACAAGGGATTTTCTGTCCAAGTATACCAAGACAACCTCTATCGATCTGTCTAGCCTGCG

GCCATCCTCTCAGTATAAGGACCTGGGCGAGTACTATGCCGAGCTGAATCCCCTGCTGTAC

CACATCAGCTTCCAGAGAATCGCCGAGAAGGAGATCATGGATGCCGTGGAGACAGGCAAGC

TGTACCTGTTCCAGATCTATAACAAGGACTTTGCCAAGGGCCACCACGGCAAGCCTAATCTG

CACACACTGTATTGGACCGGCCTGTTTTCTCCAGAGAACCTGGCCAAGACAAGCATCAAGCT

GAATGGCCAGGCCGAGCTGTTCTACCGCCCTAAGTCCAGGATGAAGAGGATGGCACACCG

-continued

```
GCTGGGAGAGAAGATGCTGAACAAGAAGCTGAAGGATCAGAAAACCCCAATCCCCGACACC
CTGTACCAGGAGCTGTACGACTATGTGAATCACAGACTGTCCCACGACCTGTCTGATGAGG
CCAGGGCCCTGCTGCCCAACGTGATCACCAAGGAGGTGTCTCACGAGATCATCAAGGATAG
GCGCTTTACCAGCGACAAGTTCTTTTTCCACGTGCCTATCACACTGAACTATCAGGCCGCCA
ATTCCCCATCTAAGTTCAACCAGAGGGTGAATGCCTACCTGAAGGAGCACCCCGAGACACC
TATCATCGGCATCgccCGGGGCGAGAGAAACCTGATCTATATCACAGTGATCGACTCCACCG
GCAAGATCCTGGAGCAGCGGAGCCTGAACACCATCCAGCAGTTTGATTACCAGAAGAAGCT
GGACAACAGGGAGAAGGAGAGGGTGGCAGCAAGGCAGGCCTGGTCTGTGGTGGGCACAAT
CAAGGATCTGAAGCAGGGCTATCTGAGCCAGGTCATCCACGAGATCGTGGACCTGATGATC
CACTACCAGGCCGTGGTGGTGCTGGAGAACCTGAATTTCGGCTTTAAGAGCAAGAGGACCG
GCATCGCCGAGAAGGCCGTGTACCAGCAGTTCGAGAAGATGCTGATCGATAAGCTGAATTG
CCTGGTGCTGAAGGACTATCCAGCAGAGAAAGTGGGAGGCGTGCTGAACCCATACCAGCTG
ACAGACCAGTTCACCTCCTTTGCCAAGATGGGCACCCAGTCTGGCTTCCTGTTTTACGTGCC
TGCCCCATATACATCTAAGATCGATCCCCTGACCGGCTTCGTGGACCCCTTCGTGTGGAAAA
CCATCAAGAATCACGAGAGCCGCAAGCACTTCCTGGAGGGCTTCGACTTTCTGCACTACGA
CGTGAAAACCGGCGACTTCATCCTGCACTTTAAGATGAACAGAAATCTGTCCTTCCAGAGGG
GCCTGCCCGGCTTTATGCCTGCATGGGATATCGTGTTCGAGAAGAACGAGACACAGTTTGA
CGCCAAGGGCACCCCTTTCATCGCCGGCAAGAGAATCGTGCCAGTGATCGAGAATCACAGA
TTCACCGGCAGATACCGGGACCTGTATCCTGCCAACGAGCTGATCGCCCTGCTGAGGAGA
AGGGCATCGTGTTCAGGGATGGCTCCAACATCCTGCCAAAGCTGCTGGAGAATGACGATTC
TCACGCCATCGACACGATGGTGGCCCTGATCCGCAGCGTGCTGCAGATGCGGAACTCCAAT
GCCGCCACAGGCGAGGACTATATCAACAGCCCCGTGCGCGATCTGAATGGCGTGTGCTTC
GACTCCCGGTTTCAGAACCCAGAGTGGCCAATGGACGCCGATGCCAATGGCGCCTACCACA
TCGCCCTGAAGGGCCAGCTGCTGCTGAATCACCTGAAGGAGAGCAAGGATCTGAAGCTGCA
GAACGGCATCTCCAATCAGGACTGGCTGGCCTACATCCAGGAGCTGCGCAACaaaaggccggc
ggccacgaaaaaggccggccaggcaaaaaagaaaaag_GGATCCTCTGGTGGTTCTGGAGGATCTGGTG_
_GTTCT_<ins>ACTAATCTGTCAGATATTATTGAAAAGGAGACCGGTAAGCAACTGGTTATCCAGGA</ins>
<ins>ATCCATCCTCATGCTCCCAGAGGAGGTGGAAGAAGTCATTGGGAACAAGCCGGAAAGCG</ins>
<ins>ATATACTCGTGCACACCGCCTACGACGAGAGCACCGACGAGAATGTCATGCTTCTGACTA</ins>
<ins>GCGACGCCCCTGAATACAAGCCTTGGGCTCTGGTCATACAGGATAGCAACGGTGAGAACA</ins>
<ins>AGATTAAGATGCTC</ins>_TCTGGTGGTTCT_<ins>CCCAAGAAGAAGAGGAAAGTC</ins>TAA
```

RTW1296: pCAG-rAPOBEC1-gs-XTEN-gs-hdeAsCas12a(E174R/S542R/K548R/D908A)-gs-UGI-NLS(eAsBE1.3)
Rat APOBEC1 (rAPOBEC1) in bold upper case, inserted glycine dash-underlined, glycine/serine linkers in italics, XTEN linker lower case italics, human codon optimized *Acidaminococcus* sp. *BV3L6* Cas12a (AsCas12a) in black, modified codons for DNase inactive (D908A) eAsCas12a (E174R/S542R/K548R) in double underlined lower case, codons with silent mutations to remove NcoI sites in bold underlined black, UGI in BOLD UPPER CASE WITH HYPHEN-UNDERLINING SV40 NLS in double underlined italics (SEQ ID NO: 442)

ATG<ins>GGC</ins>AGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

-continued

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCT*AGCGGCAGCGAG

ACTCCCGGGACCTCAGAGTCCGCCACACCCGAAAGT*TCCGGAGGGAGTAGCGGCGGGTCT

ACACAGTTCGAGGGCTTTACCAACCTGTATCAGGTGAGCAAGACACTGCGGTTTGAGCTGAT

CCCACAGGGCAAGACCCTGAAGCACATCCAGGAGCAGGGCTTCATCGAGGAGGACAAGGC

CCGCAATGATCACTACAAGGAGCTGAAGCCCATCATCGATCGGATCTACAAGACCTATGCC

GACCAGTGCCTGCAGCTGGTGCAGCTGGATTGGGAGAACCTGAGCGCCGCCATCGACTCC

TATAGAAAGGAGAAAACCGAGGAGACAAGGAACGCCCTGATCGAGGAGCAGGCCACATATC

GCAATGCCATCCACGACTACTTCATCGGCCGGACAGACAACCTGACCGATGCCATCAATAA

GAGACACGCCGAGATCTACAAGGGCCTGTTCAAGGCCGAGCTGTTTAATGGCAAGGTGCTG

AAGCAGCTGGGCACCGTGACCACAACCGAGCACGAGAACGCCCTGCTGCGGAGCTTCGAC

AAGTTTACAACCTACTTCTCCGGCTTTTAT*aga*AACAGGAAGAACGTGTTCAGCGCCGAGGAT

ATCAGCACAGCCATCCCACACCGCATCGTGCAGGACAACTTCCCCAAGTTTAAGGAGAATTG

TCACATCTTCACACGCCTGATCACCGCCGTGCCCAGCCTGCGGGAGCACTTTGAGAACGTG

AAGAAGGCCATCGGCATCTTCGTGAGCACCTCCATCGAGGAGGTGTTTTCCTTCCCTTTTA

TAACCAGCTGCTGACACAGACCCAGATCGACCTGTATAACCAGCTGCTGGGAGGAATCTCT

CGGGAGGCAGGCACCGAGAAGATCAAGGGCCTGAACGAGGTGCTGAATCTGGCCATCCAG

AAGAATGATGAGACAGCCCACATCATCGCCTCCCTGCCACACAGATTCATCCCCCTGTTTAA

GCAGATCCTGTCCGATAGGAACACCCTGTCTTTCATCCTGGAGGAGTTTAAGAGCGACGAG

GAAGTGATCCAGTCCTTCTGCAAGTACAAGACACTGCTGAGAAACGAGAACGTGCTGGAGA

CAGCCGAGGCCCTGTTTAACGAGCTGAACAGCATCGACCTGACACACATCTTCATCAGCCA

CAAGAAGCTGGAGACAATCAGCAGCGCCCTGTGCGACCACTGGGATACACTGAGGAATGCC

CTGTATGAGCGGAGAATCTCCGAGCTGACAGGCAAGATCACCAAGTCTGCCAAGGAGAAGG

TGCAGCGCAGCCTGAAGCACGAGGATATCAACCTGCAGGAGATCATCTCTGCCGCAGGCAA

GGAGCTGAGCGAGGCCTTCAAGCAGAAAACCAGCGAGATCCTGTCCCACGCACACGCCGC

CCTGGATCAGCCACTGCCTACAACCCTGAAGAAGCAGGAGGAGAAGGAGATCCTGAAGTCT

CAGCTGGACAGCCTGCTGGGCCTGTACCACCTGCTGGACTGGTTTGCCGTGGATGAGTCCA

ACGAGGTGGACCCCGAGTTCTCTGCCCGGCTGACCGGCATCAAGCTGGAGATGGAGCCTT

CTCTGAGCTTCTACAACAAGGCCAGAAATTATGCCACCAAGAAGCCCTACTCCGTGGAGAAG

TTCAAGCTGAACTTTCAGATGCCTACACTGGCC*aga*GGCTGGGACGTGAAT*aga*GAGAAGAAC

AATGGCGCCATCCTGTTTGTGAAGAACGGCCTGTACTATCTGGGCATCATGCCAAAGCAGAA

GGGCAGGTATAAGGCCCTGAGCTTCGAGCCCACAGAGAAAACCAGCGAGGGCTTTGATAAG

ATGTACTATGACTACTTCCCTGATGCCGCCAAGATGATCCCAAAGTGCAGCACCCAGCTGAA

GGCCGTGACAGCCCACTTTCAGACCCACACAACCCCCATCCTGCTGTCCAACAATTTCATCG

AGCCTCTGGAGATCACAAAGGAGATCTACGACCTGAACAATCCTGAGAAGGAGCCAAAGAA

```
GTTTCAGACAGCCTACGCCAAGAAAACCGGCGACCAGAAGGGCTACAGAGAGGCCCTGTG

CAAGTGGATCGACTTCACAAGGGATTTTCTGTCCAAGTATACCAAGACAACCTCTATCGATCT

GTCTAGCCTGCGGCCATCCTCTCAGTATAAGGACCTGGGCGAGTACTATGCCGAGCTGAAT

CCCCTGCTGTACCACATCAGCTTCCAGAGAATCGCCGAGAAGGAGATCATGGATGCCGTGG

AGACAGGCAAGCTGTACCTGTTCCAGATCTATAACAAGGACTTTGCCAAGGGCCACCACGG

CAAGCCTAATCTGCACACACTGTATTGGACCGGCCTGTTTTCTCCAGAGAACCTGGCCAAGA

CAAGCATCAAGCTGAATGGCCAGGCCGAGCTGTTCTACCGCCCTAAGTCCAGGATGAAGAG

GATGGCACACCGGCTGGGAGAGAAGATGCTGAACAAGAAGCTGAAGGATCAGAAAACCCCA

ATCCCCGACACCCTGTACCAGGAGCTGTACGACTATGTGAATCACAGACTGTCCCACGACC

TGTCTGATGAGGCCAGGGCCCTGCTGCCCAACGTGATCACCAAGGAGGTGTCTCACGAGAT

CATCAAGGATAGGCGCTTTACCAGCGACAAGTTCTTTTTCCACGTGCCTATCACACTGAACT

ATCAGGCCGCCAATTCCCCATCTAAGTTCAACCAGAGGGTGAATGCCTACCTGAAGGAGCA

CCCCGAGACACCTATCATCGGCATCgccCGGGGCGAGAGAAACCTGATCTATATCACAGTGA

TCGACTCCACCGGCAAGATCCTGGAGCAGCGGAGCCTGAACACCATCCAGCAGTTTGATTA

CCAGAAGAAGCTGGACAACAGGGAGAAGGAGAGGGTGGCAGCAAGGCAGGCCTGGTCTGT

GGTGGGCACAATCAAGGATCTGAAGCAGGGCTATCTGAGCCAGGTCATCCACGAGATCGTG

GACCTGATGATCCACTACCAGGCCGTGGTGGTGCTGGAGAACCTGAATTTCGGCTTTAAGA

GCAAGAGGACCGGCATCGCCGAGAAGGCCGTGTACCAGCAGTTCGAGAAGATGCTGATCG

ATAAGCTGAATTGCCTGGTGCTGAAGGACTATCCAGCAGAGAAAGTGGGAGGCGTGCTGAA

CCCATACCAGCTGACAGACCAGTTCACCTCCTTTGCCAAGATGGGCACCCAGTCTGGCTTC

CTGTTTTACGTGCCTGCCCCATATACATCTAAGATCGATCCCCTGACCGGCTTCGTGGACCC

CTTCGTGTGGAAAACCATCAAGAATCACGAGAGCCGCAAGCACTTCCTGGAGGGCTTCGAC

TTTCTGCACTACGACGTGAAAACCGGCGACTTCATCCTGCACTTTAAGATGAACAGAAATCT

GTCCTTCCAGAGGGGCCTGCCCGGCTTTATGCCTGCATGGGATATCGTGTTCGAGAAGAAC

GAGACACAGTTTGACGCCAAGGGCACCCCTTTCATCGCCGGCAAGAGAATCGTGCCAGTGA

TCGAGAATCACAGATTCACCGGCAGATACCGGGACCTGTATCCTGCCAACGAGCTGATCGC

CCTGCTGGAGGAGAAGGGCATCGTGTTCAGGGATGGCTCCAACATCCTGCCAAAGCTGCTG

GAGAATGACGATTCTCACGCCATCGACACGATGGTGGCCCTGATCCGCAGCGTGCTGCAGA

TGCGGAACTCCAATGCCGCCACAGGCGAGGACTATATCAACAGCCCCGTGCGCGATCTGAA

TGGCGTGTGCTTCGACTCCCGGTTTCAGAACCCAGAGTGGCCAATGGACGCCGATGCCAAT

GGCGCCTACCACATCGCCCTGAAGGGCCAGCTGCTGCTGAATCACCTGAAGGAGAGCAAG

GATCTGAAGCTGCAGAACGGCATCTCCAATCAGGACTGGCTGGCCTACATCCAGGAGCTGC

GCAACTCTGGTGGTTCTGGAGGATCTGGTGGTTCTACTAATCTGTCAGATATTATTGAAAAG

GAGACCGGTAAGCAACTGGTTATCCAGGAATCCATCCTCATGCTCCCAGAGGAGGTGGAA

GAAGTCATTGGGAACAAGCCGGAAAGCGATATACTCGTGCACACCGCCTACGACGAGAG

CACCGACGAGAATGTCATGCTTCTGACTAGCGACGCCCCTGAATACAAGCCTTGGGCTCT

GGTCATACAGGATAGCAACGGTGAGAACAAGATTAAGATGCTCTCTGGTGGTTCTCCCAA

GAAGAAGAGGAAAGTCTAA
```

-continued

Nucleotide sequence of (JG1211) pCAG-human-dLbCpf1(D832A)-NLS(nucleoplasmin)-3xHA-VPR
Human codon optimized dLbCpf1(D832A) in normal font (NTs 1-3921), Nucleoplasmin
NLS in lower case (aaaaggccggcggccacgaaaaaggccggccaggcaaaaaagaaaaag, SEQ ID NO: 21),
3xHA tag
(TACCCATACGATGTTCCAGATTACGCTTATCCCTACGACGTGCCTGATTATGCATACCCATA
TGATGTCCCCGACTATGCC, SEQ ID NO: 5) in bold, and VPR double underlined

SEQ ID NO: 443)

ATGAGCAAGCTGGAGAAGTTTACAAACTGCTACTCCCTGTCTAAGACCCTGAGGTTC

AAGGCCATCCCTGTGGGCAAGACCCAGGAGAACATCGACAATAAGCGGCTGCTGGTGGAG

GACGAGAAGAGAGCCGAGGATTATAAGGGCGTGAAGAAGCTGCTGGATCGCTACTATCTGT

CTTTTATCAACGACGTGCTGCACAGCATCAAGCTGAAGAATCTGAACAATTACATCAGCCTG

TTCCGGAAGAAAACCAGAACCGAGAAGGAGAATAAGGAGCTGGAGAACCTGGAGATCAATC

TGCGGAAGGAGATCGCCAAGGCCTTCAAGGGCAACGAGGGCTACAAGTCCCTGTTTAAGAA

GGATATCATCGAGACAATCCTGCCAGAGTTCCTGGACGATAAGGACGAGATCGCCCTGGTG

AACAGCTTCAATGGCTTTACCACAGCCTTCACCGGCTTCTTTGATAACAGAGAGAATATGTTT

TCCGAGGAGGCCAAGAGCACATCCATCGCCTTCAGGTGTATCAACGAGAATCTGACCCGCT

ACATCTCTAATATGGACATCTTCGAGAAGGTGGACGCCATCTTTGATAAGCACGAGGTGCAG

GAGATCAAGGAGAAGATCCTGAACAGCGACTATGATGTGGAGGATTTCTTTGAGGGCGAGT

TCTTTAACTTTGTGCTGACACAGGAGGGCATCGACGTGTATAACGCCATCATCGGCGGCTTC

GTGACCGAGAGCGGCGAGAAGATCAAGGGCCTGAACGAGTACATCAACCTGTATAATCAGA

AAACCAAGCAGAAGCTGCCTAAGTTTAAGCCACTGTATAAGCAGGTGCTGAGCGATCGGGA

GTCTCTGAGCTTCTACGGCGAGGGCTATACATCCGATGAGGAGGTGCTGGAGGTGTTTAGA

AACACCCTGAACAAGAACAGCGAGATCTTCAGCTCCATCAAGAAGCTGGAGAAGCTGTTCAA

GAATTTTGACGAGTACTCTAGCGCCGGCATCTTTGTGAAGAACGGCCCCGCCATCAGCACA

ATCTCCAAGGATATCTTCGGCGAGTGGAACGTGATCCGGGACAAGTGGAATGCCGAGTATG

ACGATATCCACCTGAAGAAGAAGGCCGTGGTGACCGAGAAGTACGAGGACGATCGGAGAAA

GTCCTTCAAGAAGATCGGCTCCTTTTCTCTGGAGCAGCTGCAGGAGTACGCCGACGCCGAT

CTGTCTGTGGTGGAGAAGCTGAAGGAGATCATCATCCAGAAGGTGGATGAGATCTACAAGG

TGTATGGCTCCTCTGAGAAGCTGTTCGACGCCGATTTTGTGCTGGAGAAGAGCCTGAAGAA

GAACGACGCCGTGGTGGCCATCATGAAGGACCTGCTGGATTCTGTGAAGAGCTTCGAGAAT

TACATCAAGGCCTTCTTTGGCGAGGGCAAGGAGACAAACAGGGACGAGTCCTTCTATGGCG

ATTTTGTGCTGGCCTACGACATCCTGCTGAAGGTGGACCACATCTACGATGCCATCCGCAAT

TATGTGACCCAGAAGCCCTACTCTAAGGATAAGTTCAAGCTGTATTTTCAGAACCCTCAGTTC

ATGGGCGGCTGGGACAAGGATAAGGAGACAGACTATCGGGCCACCATCCTGAGATACGGC

TCCAAGTACTATCTGGCCATCATGGATAAGAAGTACGCCAAGTGCCTGCAGAAGATCGACAA

GGACGATGTGAACGGCAATTACGAGAAGATCAACTATAAGCTGCTGCCCGGCCCTAATAAG

ATGCTGCCAAAGGTGTTCTTTTCTAAGAAGTGGATGGCCTACTATAACCCCAGCGAGGACAT

CCAGAAGATCTACAAGAATGGCACATTCAAGAAGGGCGATATGTTTAACCTGAATGACTGTC

ACAAGCTGATCGACTTCTTTAAGGATAGCATCTCCCGGTATCCAAAGTGGTCCAATGCCTAC

GATTTCAACTTTTCTGAGACAGAGAAGTATAAGGACATCGCCGGCTTTTACAGAGAGGTGGA

GGAGCAGGGCTATAAGGTGAGCTTCGAGTCTGCCAGCAAGAAGGAGGTGGATAAGCTGGT

GGAGGAGGGCAAGCTGTATATGTTCCAGATCTATAACAAGGACTTTTCCGATAAGTCTCACG

GCACACCCAATCTGCACACCATGTACTTCAAGCTGCTGTTTGACGAGAACAATCACGGACAG

ATCAGGCTGAGCGGAGGAGCAGAGCTGTTCATGAGGCGCGCCTCCCTGAAGAAGGAGGAG

-continued

```
CTGGTGGTGCACCCAGCCAACTCCCCTATCGCCAACAAGAATCCAGATAATCCCAAGAAAAC

CACAACCCTGTCCTACGACGTGTATAAGGATAAGAGGTTTTCTGAGGACCAGTACGAGCTGC

ACATCCCAATCGCCATCAATAAGTGCCCCAAGAACATCTTCAAGATCAATACAGAGGTGCGC

GTGCTGCTGAAGCACGACGATAACCCCTATGTGATCGGCATCGCCAGGGGCGAGCGCAAT

CTGCTGTATATCGTGGTGGTGGACGGCAAGGGCAACATCGTGGAGCAGTATTCCCTGAACG

AGATCATCAACAACTTCAACGGCATCAGGATCAAGACAGATTACCACTCTCTGCTGGACAAG

AAGGAGAAGGAGAGGTTCGAGGCCCGCCAGAACTGGACCTCCATCGAGAATATCAAGGAG

CTGAAGGCCGGCTATATCTCTCAGGTGGTGCACAAGATCTGCGAGCTGGTGGAGAAGTACG

ATGCCGTGATCGCCCTGGAGGACCTGAACTCTGGCTTTAAGAATAGCCGCGTGAAGGTGGA

GAAGCAGGTGTATCAGAAGTTCGAGAAGATGCTGATCGATAAGCTGAACTACATGGTGGAC

AAGAAGTCTAATCCTTGTGCAACAGGCGGCGCCCTGAAGGGCTATCAGATCACCAATAAGTT

CGAGAGCTTTAAGTCCATGTCTACCCAGAACGGCTTCATCTTTTACATCCCTGCCTGGCTGA

CATCCAAGATCGATCCATCTACCGGCTTTGTGAACCTGCTGAAAACCAAGTATACCAGCATC

GCCGATTCCAAGAAGTTCATCAGCTCCTTTGACAGGATCATGTACGTGCCCGAGGAGGATCT

GTTCGAGTTTGCCCTGGACTATAAGAACTTCTCTCGCACAGACGCCGATTACATCAAGAAGT

GGAAGCTGTACTCCTACGGCAACCGGATCAGAATCTTCCGGAATCCTAAGAAGAACAACGT

GTTCGACTGGGAGGAGGTGTGCCTGACCAGCGCCTATAAGGAGCTGTTCAACAAGTACGGC

ATCAATTATCAGCAGGGCGATATCAGAGCCCTGCTGTGCGAGCAGTCCGACAAGGCCTTCT

ACTCTAGCTTTATGGCCCTGATGAGCCTGATGCTGCAGATGCGGAACAGCATCACAGGCCG

CACCGACGTGGATTTTCTGATCAGCCCTGTGAAGAACTCCGACGGCATCTTCTACGATAGCC

GGAACTATGAGGCCCAGGAGAATGCCATCCTGCCAAAGAACGCCGACGCCAATGGCGCCT

ATAACATCGCCAGAAAGGTGCTGTGGGCCATCGGCCAGTTCAAGAAGGCCGAGGACGAGA

AGCTGGATAAGGTGAAGATCGCCATCTCTAACAAGGAGTGGCTGGAGTACGCCCAGACCAG

CGTGAAGCACaaaaggccggcggccacgaaaaaggccggccaggcaaaaaagaaaaagGGATCCTACCCATA

CGATGTTCCAGATTACGCTTATCCCTACGACGTGCCTGATTATGCATACCCATATGATGTC

CCCGACTATGCCGGAAGCGAGGCCAGCGGTTCCGGACGGGCTGACGCATTGGACGATTTT

GATCTGGATATGCTGGGAAGTGACGCCCTCGATGATTTTGACCTTGACATGCTTGGTTCGGA

TGCCCTTGATGACTTTGACCTCGACATGCTCGGCAGTGACGCCCTTGATGATTTCGACCTGG

ACATGCTGATTAACTCTAGAAGTTCCGGATCTCCGAAAAAGAAACGCAAAGTTGGTAGCCAG

TACCTGCCCGACACCGACGACCGGCACCGGATCGAGGAAAAGCGGAAGCGGACCTACGAG

ACATTCAAGAGCATCATGAAGAAGTCCCCCTTCAGCGGCCCCACCGACCCCTAGACCTCCAC

CTAGAAGAATCGCCGTGCCCAGCAGATCCAGCGCCAGCGTGCCAAAACCTGCCCCCCAGC

CTTACCCCTTCACCAGCAGCCTGAGCACCATCAACTACGACGAGTTCCCTACCATGGTGTTC

CCCAGCGGCCAGATCTCTCAGGCCTCTGCTCTGGCTCCAGCCCCTCCTCAGGTGCTGCCTC

AGGCTCCTGCTCCTGCACCAGCTCCAGCCATGGTGTCTGCACTGGCTCAGGCACCAGCACC

CGTGCCTGTGCTGGCTCCTGGACCTCCACAGGCTGTGGCTCCACCAGCCCCTAAACCTACA

CAGGCCGGCGAGGGCACACTGTCTGAAGCTCTGCTGCAGCTGCAGTTCGACGACGAGGAT

CTGGGAGCCCTGCTGGGAAACAGCACCGATCCTGCCGTGTTCACCGACCTGGCCAGCGTG

GACAACAGCGAGTTCCAGCAGCTGCTGAACCAGGGCATCCCTGTGGCCCCTCACACCACC

GAGCCCATGCTGATGGAATACCCCGAGGCCATCACCCGGCTCGTGACAGGCGCTCAGAGG

CCTCCTGATCCAGCTCCTGCCCCTCTGGGAGCACCAGGCCTGCCTAATGGACTGCTGTCTG
```

-continued

GCGACGAGGACTTCAGCTCTATCGCCGATATGGATTTCTCAGCCTTGCTGGGCTCTGGCAG

CGGCAGCCGGGATTCCAGGGAAGGGATGTTTTTGCCGAAGCCTGAGGCCGGCTCCGCTAT

TAGTGACGTGTTTGAGGGCCGCGAGGTGTGCCAGCCAAAACGAATCCGGCCATTTCATCCT

CCAGGAAGTCCATGGGCCAACCGCCCACTCCCGCCAGCCTCGCACCAACACCAACCGGT

CCAGTACATGAGCCAGTCGGGTCACTGACCCCGGCACCAGTCCCTCAGCCACTGGATCCAG

CGCCCGCAGTGACTCCCGAGGCCAGTCACCTGTTGGAGGATCCCGATGAAGAGACGAGCC

AGGCTGTCAAAGCCCTTCGGGAGATGGCCGATACTGTGATTCCCCAGAAGGAAGAGGCTGC

AATCTGTGGCCAAATGGACCTTTCCCATCCGCCCCCAAGGGGCCATCTGGATGAGCTGACA

ACCACACTTGAGTCCATGACCGAGGATCTGAACCTGGACTCACCCCTGACCCCGGAATTGA

ACGAGATTCTGGATACCTTCCTGAACGACGAGTGCCTCTTGCATGCCATGCATATCAGCACA

GGACTGTCCATCTTCGACACATCTCTGTTTTAA

Amino acid sequence of dLbCpf1(D832A)-NLS(nucleoplasmin)-3xHA-VPR
LbCpf1 in normal font (AAs 1-1228), NLS(nucleoplasmin) (krpaatkkagqakkkk, SEQ ID
NO: 7) in lower case, 3xHA tag (YPYDVPDYAYPYDVPDYAYPYDVPDYA, SEQ ID NO: 8) in bold,
and VPR double underlined

SEQ ID NO: 444)

MSKLEKFTNCYSLSKTLRFKAIPVGKTQENIDNKRLLVEDEKRAEDYKGVKKLLDRYYLS

FINDVLHSIKLKNLNNYISLFRKKTRTEKENKELENLEINLRKEIAKAFKGNEGYKSLFKKDIIETILPE

FLDDKDEIALVNSFNGFTTAFTGFFDNRENMFSEEAKSTSIAFRCINENLTRYISNMDIFEKVDAIF

DKHEVQEIKEKILNSDYDVEDFFEGEFFNFVLTQEGIDVYNAIIGGFVTESGEKIKGLNEYINLYNQ

KTKQKLPKFKPLYKQVLSDRESLSFYGEGYTSDEEVLEVFRNTLNKNSEIFSSIKKLEKLFKNFDE

YSSAGIFVKNGPAISTISKDIFGEWNVIRDKWNAEYDDIHLKKKAVVTEKYEDDRRKSFKKIGSFSL

EQLQEYADADLSVVEKLKEIIIQKVDEIYKVYGSSEKLFDADFVLEKSLKKNDAVVAIMKDLLDSVK

SFENYIKAFFGEGKETNRDESFYGDFVLAYDILLKVDHIYDAIRNYVTQKPYSKDKFKLYFQNPQF

MGGWDKDKETDYRATILRYGSKYYLAIMDKKYAKCLQKIDKDDVNGNYEKINYKLLPGPNKMLP

KVFFSKKWMAYYNPSEDIQKIYKNGTFKKGDMFNLNDCHKLIDFFKDSISRYPKWSNAYDFNFSE

TEKYKDIAGFYREVEEQGYKVSFESASKKEVDKLVEEGKLYMFQIYNKDFSDKSHGTPNLHTMY

FKLLFDENNHGQIRLSGGAELFMRRASLKKEELVVHPANSPIANKNPDNPKKTTTLSYDVYKDKR

FSEDQYELHIPIAINKCPKNIFKINTEVRVLLKHDDNPYVIGIARGERNLLYIVVVDGKGNIVEQYSL

NEIINNFNGIRIKTDYHSLLDKKEKERFEARQNVVTSIENIKELKAGYISQVVHKICELVEKYDAVIAL

EDLNSGFKNSRVKVEKQVYQKFEKMLIDKLNYMVDKKSNPCATGGALKGYQITNKFESFKSMST

QNGFIFYIPAWLTSKIDPSTGFVNLLKTKYTSIADSKKFISSFDRIMYVPEEDLFEFALDYKNFSRTD

ADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYN

IARKVLWAIGQFKKAEDEKLDKVKIAISNKEWLEYAQTSVKHkrpaatkkagqakkkkGSYPYDVPDYA

YPYDVPDYAYPYDVPDYAGSEASGSGRADALDDFDLDMLGSDALDDFDLDMLGSDALDDFDLD

MLGSDALDDFDLDMLINSRSSGSPKKKRKVGSQYLPDTDDRHRIEEKRKRTYETFKSIMKKSPFS

GPTDPRPPPRRIAVPSRSSASVPKPAPQPYPFTSSLSTINYDEFPTMVFPSGQISQASALAPAPP

QVLPQAPAPAPAPAMVSALAQAPAPVPVLAPGPPQAVAPPAPKPTQAGEGTLSEALLQLQFDDE

DLGALLGNSTDPAVFTDLASVDNSEFQQLLNQGIPVAPHTTEPMLMEYPEAITRLVTGAQRPPDP

APAPLGAPGLPNGLLSGDEDFSSIADMDFSALLGSGSGSRDSREGMFLPKPEAGSAISDVFEGR

EVCQPKRIRPFHPPGSPWANRPLPASLAPTPTGPVHEPVGSLTPAPVPQPLDPAPAVTPEASHL

<u>LEDPDEETSQAVKALREMADTVIPQKEEAAICGQMDLSHPPPRGHLDELTTTLESMTEDLNLDSP</u>

<u>LTPELNEILDTFLNDECLLHAMHISTGLSIFDTSLF</u>

Nucleotide sequence of (RTW1008) pCAG-NLS(SV40)x2-rAPOBEC1-gsXTENgslinker-human-dAsCpf1(D908A)-NLS(nucleoplasmin)-GSlinker-UGI-NLS(SV40) Human codon optimized dAsCpf1 (D908A) in normal font (NTs 844-4764), rAPOBEC1 in bold (NTs 67-750), Nucleoplasmin NLS in lower case (aaaaggccggcggccacgaaaaaggccggccaggcaaaaaagaaaaag, SEQ ID NO: 21), SV40 NLS in lower case (ccaaagaaaaagaggaaagtc, cctaaaaagaaacgaaaggtt, or cccaagaagaagaggaaagtc, SEQ ID NOs: 19, 20, or 22, respectively), gsXTENgs linker (tctggtggttcttctggtggttctagcggcagcgagactcccgggacctcagagtccgccacacccgaaagttccggagggagtagcggcggg, SEQ ID NO: 23) in lower case, and UGI double underlined (SEQ ID NO: 445)

ATGGGCccaaagaaaaagaggaaagteGGCAGTGGAcctaaaaagaaacgaaaggttGGGTCAGGT

AGCTCAGAGACTGGCCCAGTGGCTGTGGACCCCACATTGAGACGGCGGATCGAGCCCCA

TGAGTTTGAGGTATTCTTCGATCCGAGAGAGCTCCGCAAGGAGACCTGCCTGCTTTACGA

AATTAATTGGGGGGCCGGCACTCCATTTGGCGACATACATCACAGAACACTAACAAGCA

CGTCGAAGTCAACTTCATCGAGAAGTTCACGACAGAAAGATATTTCTGTCCGAACACAAG

GTGCAGCATTACCTGGTTTCTCAGCTGGAGCCCATGCGGCGAATGTAGTAGGGCCATCAC

TGAATTCCTGTCAAGGTATCCCCACGTCACTCTGTTTATTTACATCGCAAGGCTGTACCAC

CACGCTGACCCCCGCAATCGACAAGGCCTGCGGGATTTGATCTCTTCAGGTGTGACTATC

CAAATTATGACTGAGCAGGAGTCAGGATACTGCTGGAGAAACTTTGTGAATTATAGCCCG

AGTAATGAAGCCCACTGGCCTAGGTATCCCCATCTGTGGGTACGACTGTACGTTCTTGAAC

TGTACTGCATCATACTGGGCCTGCCTCCTTGTCTCAACATTCTGAGAAGGAAGCAGCCACA

GCTGACATTCTTTACCATCGCTCTTCAGTCTTGTCATTACCAGCGACTGCCCCCACACATTC

TCTGGGCCACCGGGTTGAAAtctggtggttcttctggtggttctagcggcagcgagactcccgggacctcagagtccgcca cacccgaaagttccggagggagtagcggcgggTCTACACAGTTCGAGGGCTTTACCAACCTGTATCAGGT

GAGCAAGACACTGCGGTTTGAGCTGATCCCACAGGGCAAGACCCTGAAGCACATCCAGGAG

CAGGGCTTCATCGAGGAGGACAAGGCCCGCAATGATCACTACAAGGAGCTGAAGCCCATCA

TCGATCGGATCTACAAGACCTATGCCGACCAGTGCCTGCAGCTGGTGCAGCTGGATTGGGA

GAACCTGAGCGCCGCCATCGACTCCTATAGAAAGGAGAAAACCGAGGAGACAAGGAACGC

CCTGATCGAGGAGCAGGCCACATATCGCAATGCCATCCACGACTACTTCATCGGCCGGACA

GACAACCTGACCGATGCCATCAATAAGAGACACGCCGAGATCTACAAGGGCCTGTTCAAGG

CCGAGCTGTTTAATGGCAAGGTGCTGAAGCAGCTGGGCACCGTGACCACAACCGAGCACG

AGAACGCCCTGCTGCGGAGCTTCGACAAGTTTACAACCTACTTCTCCGGCTTTTATGAGAAC

AGGAAGAACGTGTTCAGCGCCGAGGATATCAGCACAGCCATCCCACACCGCATCGTGCAGG

ACAACTTCCCCAAGTTTAAGGAGAATTGTCACATCTTCACACGCCTGATCACCGCCGTGCCC

AGCCTGCGGGAGCACTTTGAGAACGTGAAGAAGGCCATCGGCATCTTCGTGAGCACCTCCA

TCGAGGAGGTGTTTTCCTTCCCTTTTTATAACCAGCTGCTGACACAGACCCAGATCGACCTG

TATAACCAGCTGCTGGGAGGAATCTCTCGGGAGGCAGGCACCGAGAAGATCAAGGGCCTG

AACGAGGTGCTGAATCTGGCCATCCAGAAGAATGATGAGACAGCCCACATCATCGCCTCCC

TGCCACACAGATTCATCCCCCTGTTTAAGCAGATCCTGTCCGATAGGAACACCCTGTCTTTC

ATCCTGGAGGAGTTTAAGAGCGACGAGGAAGTGATCCAGTCCTTCTGCAAGTACAAGACAC

TGCTGAGAAACGAGAACGTGCTGGAGACAGCCGAGGCCCTGTTTAACGAGCTGAACAGCAT

CGACCTGACACACATCTTCATCAGCCACAAGAAGCTGGAGACAATCAGCAGCGCCCTGTGC

GACCACTGGGATACACTGAGGAATGCCCTGTATGAGCGGAGAATCTCCGAGCTGACAGGCA

AGATCACCAAGTCTGCCAAGGAGAAGGTGCAGCGCAGCCTGAAGCACGAGGATATCAACCT

-continued

```
GCAGGAGATCATCTCTGCCGCAGGCAAGGAGCTGAGCGAGGCCTTCAAGCAGAAAACCAG
CGAGATCCTGTCCCACGCACACGCCGCCCTGGATCAGCCACTGCCTACAACCCTGAAGAAG
CAGGAGGAGAAGGAGATCCTGAAGTCTCAGCTGGACAGCCTGCTGGGCCTGTACCACCTG
CTGGACTGGTTTGCCGTGGATGAGTCCAACGAGGTGGACCCCGAGTTCTCTGCCCGGCTGA
CCGGCATCAAGCTGGAGATGGAGCCTTCTCTGAGCTTCTACAACAAGGCCAGAAATTATGC
CACCAAGAAGCCCTACTCCGTGGAGAAGTTCAAGCTGAACTTTCAGATGCCTACACTGGCCT
CTGGCTGGGACGTGAATAAGGAGAAGAACAATGGCGCCATCCTGTTTGTGAAGAACGGCCT
GTACTATCTGGGCATCATGCCAAAGCAGAAGGGCAGGTATAAGGCCCTGAGCTTCGAGCCC
ACAGAGAAAACCAGCGAGGGCTTTGATAAGATGTACTATGACTACTTCCCTGATGCCGCCAA
GATGATCCCAAAGTGCAGCACCCAGCTGAAGGCCGTGACAGCCCACTTTCAGACCCACACA
ACCCCCATCCTGCTGTCCAACAATTTCATCGAGCCTCTGGAGATCACAAAGGAGATCTACGA
CCTGAACAATCCTGAGAAGGAGCCAAAGAAGTTTCAGACAGCCTACGCCAAGAAAACCGGC
GACCAGAAGGGCTACAGAGAGGCCCTGTGCAAGTGGATCGACTTCACAAGGGATTTTCTGT
CCAAGTATACCAAGACAACCTCTATCGATCTGTCTAGCCTGCGGCCATCCTCTCAGTATAAG
GACCTGGGCGAGTACTATGCCGAGCTGAATCCCCTGCTGTACCACATCAGCTTCCAGAGAA
TCGCCGAGAAGGAGATCATGGATGCCGTGGAGACAGGCAAGCTGTACCTGTTCCAGATCTA
TAACAAGGACTTTGCCAAGGGCCACCACGGCAAGCCTAATCTGCACACACTGTATTGGACC
GGCCTGTTTTCTCCAGAGAACCTGGCCAAGACAAGCATCAAGCTGAATGGCCAGGCCGAGC
TGTTCTACCGCCCTAAGTCCAGGATGAAGAGGATGGCACACCGGCTGGGAGAGAAGATGCT
GAACAAGAAGCTGAAGGATCAGAAAACCCCAATCCCCGACACCCTGTACCAGGAGCTGTAC
GACTATGTGAATCACAGACTGTCCCACGACCTGTCTGATGAGGCCAGGGCCCTGCTGCCCA
ACGTGATCACCAAGGAGGTGTCTCACGAGATCATCAAGGATAGGCGCTTTACCAGCGACAA
GTTCTTTTTCCACGTGCCTATCACACTGAACTATCAGGCCGCCAATTCCCCATCTAAGTTCAA
CCAGAGGGTGAATGCCTACCTGAAGGAGCACCCCGAGACACCTATCATCGGCATCGCCCG
GGGCGAGAGAAACCTGATCTATATCACAGTGATCGACTCCACCGGCAAGATCCTGGAGCAG
CGGAGCCTGAACACCATCCAGCAGTTTGATTACCAGAAGAAGCTGGACAACAGGGAGAAGG
AGAGGGTGGCAGCAAGGCAGGCCTGGTCTGTGGTGGGCACAATCAAGGATCTGAAGCAGG
GCTATCTGAGCCAGGTCATCCACGAGATCGTGGACCTGATGATCCACTACCAGGCCGTGGT
GGTGCTGGAGAACCTGAATTTCGGCTTTAAGAGCAAGAGGACCGGCATCGCCGAGAAGGC
CGTGTACCAGCAGTTCGAGAAGATGCTGATCGATAAGCTGAATTGCCTGGTGCTGAAGGAC
TATCCAGCAGAGAAAGTGGGAGGCGTGCTGAACCCATACCAGCTGACAGACCAGTTCACCT
CCTTTGCCAAGATGGGCACCCAGTCTGGCTTCCTGTTTTACGTGCCTGCCCCATATACATCT
AAGATCGATCCCCTGACCGGCTTCGTGGACCCCTTCGTGTGGAAAACCATCAAGAATCACG
AGAGCCGCAAGCACTTCCTGGAGGGCTTCGACTTTCTGCACTACGACGTGAAAACCGGCGA
CTTCATCCTGCACTTTAAGATGAACAGAAATCTGTCCTTCCAGAGGGGCCTGCCCGGCTTTA
TGCCTGCATGGGATATCGTGTTCGAGAAGAACGAGACACAGTTTGACGCCAAGGGCACCCC
TTTCATCGCCGGCAAGAGAATCGTGCCAGTGATCGAGAATCACAGATTCACCGGCAGATAC
CGGGACCTGTATCCTGCCAACGAGCTGATCGCCCTGCTGGAGGAGAAGGGCATCGTGTTCA
GGGATGGCTCCAACATCCTGCCAAAGCTGCTGGAGAATGACGATTCTCACGCCATCGACAC
GATGGTGGCCCTGATCCGCAGCGTGCTGCAGATGCGGAACTCCAATGCCGCCACAGGCGA
GGACTATATCAACAGCCCCGTGCGCGATCTGAATGGCGTGTGCTTCGACTCCCGGTTTCAG
```

```
AACCCAGAGTGGCCAATGGACGCCGATGCCAATGGCGCCTACCACATCGCCCTGAAGGGC

CAGCTGCTGCTGAATCACCTGAAGGAGAGCAAGGATCTGAAGCTGCAGAACGGCATCTCCA

ATCAGGACTGGCTGGCCTACATCCAGGAGCTGCGCAACaaaaggccggcggccacgaaaaaggccggc caggcaaaaaagaaaaagGGATCCTCTGGTGGTTCTGGAGGATCTGGTGGTTCTACTAATCTGTCA

GATATTATTGAAAAGGAGACCGGTAAGCAACTGGTTATCCAGGAATCCATCCTCATGCTCCC

AGAGGAGGTGGAAGAAGTCATTGGGAACAAGCCGGAAAGCGATATACTCGTGCACACCGCC

TACGACGAGAGCACCGACGAGAATGTCATGCTTCTGACTAGCGACGCCCCTGAATACAAGC

CTTGGGCTCTGGTCATACAGGATAGCAACGGTGAGAACAAGATTAAGATGCTCTCTGGTGGT

TCTcccaagaagaagaggaaagtc

Amino acid sequence of NLS(SV40)x2-rAPOBEC1-gsXTENgslinker-human-
dAsCpf1(D908A)-NLS(nucleoplasmin)-GSlinker-UGI-NLS(SV40)
AsCpf1 in normal font (AAs x-xxxx), rAPOBEC1 in bold (AAs 23-250), NLS(nucleoplasmin)
(krpaatkkaggqakkkk, SEQ ID NO: 7) in lower case, SV40 NLS in lower case (pkkkrkv, SEQ ID
NO: 24), gsXTENgs linker (sggssggssgsetpgtsesatpessggssgg, SEQ ID NO: 25) in lower case, and
UGI double underlined
                                                                                                (SEQ ID NO: 446)
MGpkkkrkvGSGpkkkrkvGSGSSETGPVAVDPTLRRRIEPHEFEVFFDPRELRKETCLLYEI

NWGGRHSIWRHTSQNTNKHVEVNFIEKFTTERYFCPNTRCSITINFLSWSPCGECSRAITEFLSR

YPHVTLFIYIARLYHHADPRNRQGLRDLISSGVTIQIMTEQESGYCWRNFVNYSPSNEAHWPRY

PHLVVVRLYVLELYCIILGLPPCLNILRRKQPQLTFFTIALQSCHYQRLPPHILWATGLKsggssggss gsetpgtsesatpessggssggSTQFEGFTNLYQVSKTLRFELIPQGKTLKHIQEQGFIEEDKARNDHYKE

LKPIIDRIYKTYADQCLQLVQLDWENLSAAIDSYRKEKTEETRNALIEEQATYRNAIHDYFIGRTDN

LTDAINKRHAEIYKGLFKAELFNGKVLKQLGTVTTTEHENALLRSFDKFTTYFSGFYENRKNVFSA

EDISTAIPHRIVQDNFPKFKENCHIFTRLITAVPSLREHFENVKKAIGIFVSTSIEEVFSFPFYNQLLT

QTQIDLYNQLLGGISREAGTEKIKGLNEVLNLAIQKNDETAHIIASLPHRFIPLFKQILSDRNTLSFIL

EEFKSDEEVIQSFCKYKTLLRNENVLETAEALFNELNSIDLTHIFISHKKLETISSALCDHWDTLRNA

LYERRISELTGKITKSAKEKVQRSLKHEDINLQEIISAAGKELSEAFKQKTSEILSHAHAALDQPLPT

TLKKQEEKEILKSQLDSLLGLYHLLDWFAVDESNEVDPEFSARLTGIKLEMEPSLSFYNKARNYAT

KKPYSVEKFKLNFQMPTLASGWDVNKEKNNGAILFVKNGLYYLGIMPKQKGRYKALSFEPTEKT

SEGFDKMYYDYFPDAAKMIPKCSTQLKAVTAHFQTHTTPILLSNNFIEPLEITKEIYDLNNPEKEPK

KFQTAYAKKTGDQKGYREALCKWIDFTRDFLSKYTKTTSIDLSSLRPSSQYKDLGEYYAELNPLL

YHISFQRIAEKEIMDAVETGKLYLFQIYNKDFAKGHHGKPNLHTLYVVTGLFSPENLAKTSIKLNGQ

AELFYRPKSRMKRMAHRLGEKMLNKKLKDQKTPIPDTLYQELYDYVNHRLSHDLSDEARALLPN

VITKEVSHEIIKDRRFTSDKFFFHVPITLNYQAANSPSKFNQRVNAYLKEHPETPIIGIARGERNLIYI

TVIDSTGKILEQRSLNTIQQFDYQKKLDNREKERVAARQAWSVVGTIKDLKQGYLSQVIHEIVDLM

IHYQAVVVLENLNFGFKSKRTGIAEKAVYQQFEKMLIDKLNCLVLKDYPAEKVGGVLNPYQLTDQ

FTSFAKMGTQSGFLFYVPAPYTSKIDPLTGFVDPFVWKTIKNHESRKHFLEGFDFLHYDVKTGDFI

LHFKMNRNLSFQRGLPGFMPAWDIVFEKNETQFDAKGTPFIAGKRIVPVIENHRFTGRYRDLYPA

NELIALLEEKGIVFRDGSNILPKLLENDDSHAIDTMVALIRSVLQMRNSNAATGEDYINSPVRDLNG

VCFDSRFQNPEWPMDADANGAYHIALKGQLLLNHLKESKDLKLQNGISNQDWLAYIQELRNkrpa atkkaggakkkkGSSGGSGGSGGSTNLSDIIEKETGKQLVIQESILMLPEEVEEVIGNKPESDILVHTA YDESTDENVMLLTSDAPEYKPWALVIQDSNGENKIKMLSGGSpkkkrky
```

-continued

Nucleotide sequence of (RTW1028) pCAG-NLS(SV40)x2-rAPOBEC1-gsXTENgslinker-
human-dAsCpf1(D908A)triplevariant(E174R/S542R/K548R)-NLS(nucleoplasmin)-GSlinker-UGI-
NLS(SV40)
Human codon optimized dAsCpf1 (D908A) in normal font (NTs 844-4764), rAPOBEC1 in
bold (NTs 67-750), Nucleoplasmin NLS in lower case
(aaaaggccggcggccacgaaaaaggccggccaggcaaaaagaaaaag, SEQ ID NO: 21), SV40 NLS in lower
case (ccaaagaaaaagaggaaagtc, cctaaaaagaaacgaaaggtt, or cccaagaagaagaggaaagtc, SEQ ID
NOs: 19, 20, or 22, respectively), gsXTENgs linker
(tctggtggttcttctggtggttctagcggcagcgagactcccgggacctcagagtccgccacacccgaaagttccggagggagtagcgg
cggg, SEQ ID NO: 23) in lower case, and UGI double underlined (SEQ ID NO: 447)

ATGGGCccaaagaaaaagaggaaagteGGCAGTGGAcctaaaaagaaacgaaaggttGGGTCAGGT

AGCTCAGAGACTGGCCCAGTGGCTGTGGACCCCACATTGAGACGGCGGATCGAGCCCCA

TGAGTTTGAGGTATTCTTCGATCCGAGAGAGCTCCGCAAGGAGACCTGCCTGCTTTACGA

AATTAATTGGGGGGGCCGGCACTCCATTTGGCGACATACATCACAGAACACTAACAAGCA

CGTCGAAGTCAACTTCATCGAGAAGTTCACGACAGAAAGATATTTCTGTCCGAACACAAG

GTGCAGCATTACCTGGTTTCTCAGCTGGAGCCCATGCGGCGAATGTAGTAGGGCCATCAC

TGAATTCCTGTCAAGGTATCCCCACGTCACTCTGTTTATTTACATCGCAAGGCTGTACCAC

CACGCTGACCCCCGCAATCGACAAGGCCTGCGGGATTTGATCTCTTCAGGTGTGACTATC

CAAATTATGACTGAGCAGGAGTCAGGATACTGCTGGAGAAACTTTGTGAATTATAGCCCG

AGTAATGAAGCCCACTGGCCTAGGTATCCCCATCTGTGGGTACGACTGTACGTTCTTGAAC

TGTACTGCATCATACTGGGCCTGCCTCCTTGTCTCAACATTCTGAGAAGGAAGCAGCCACA

GCTGACATTCTTTACCATCGCTCTTCAGTCTTGTCATTACCAGCGACTGCCCCCACACATTC

TCTGGGCCACCGGGTTGAAAtctggtggttcttctggtggttctagcggcagcgagactcccgggacctcagagtccgcca cacccgaaagttccggagggagtagcggcgggTCTACACAGTTCGAGGGCTTTACCAACCTGTATCAGGT

GAGCAAGACACTGCGGTTTGAGCTGATCCCACAGGGCAAGACCCTGAAGCACATCCAGGAG

CAGGGCTTCATCGAGGAGGACAAGGCCCGCAATGATCACTACAAGGAGCTGAAGCCCATCA

TCGATCGGATCTACAAGACCTATGCCGACCAGTGCCTGCAGCTGGTGCAGCTGGATTGGGA

GAACCTGAGCGCCGCCATCGACTCCTATAGAAAGGAGAAAACCGAGGAGACAAGGAACGC

CCTGATCGAGGAGCAGGCCACATATCGCAATGCCATCCACGACTACTTCATCGGCCGGACA

GACAACCTGACCGATGCCATCAATAAGAGACACGCCGAGATCTACAAGGGCCTGTTCAAGG

CCGAGCTGTTTAATGGCAAGGTGCTGAAGCAGCTGGGCACCGTGACCACAACCGAGCACG

AGAACGCCCTGCTGCGGAGCTTCGACAAGTTTACAACCTACTTCTCCGGCTTTTATGCCAAC

AGGAAGAACGTGTTCAGCGCCGAGGATATCAGCACAGCCATCCCACACCGCATCGTGCAGG

ACAACTTCCCCAAGTTTAAGGAGAATTGTCACATCTTCACACGCCTGATCACCGCCGTGCCC

AGCCTGCGGGAGCACTTTGAGAACGTGAAGAAGGCCATCGGCATCTTCGTGAGCACCTCCA

TCGAGGAGGTGTTTTCCTTCCCTTTTTATAACCAGCTGCTGACACAGACCCAGATCGACCTG

TATAACCAGCTGCTGGGAGGAATCTCTCGGGAGGCAGGCACCGAGAAGATCAAGGGCCTG

AACGAGGTGCTGAATCTGGCCATCCAGAAGAATGATGAGACAGCCCACATCATCGCCTCCC

TGCCACACAGATTCATCCCCCTGTTTAAGCAGATCCTGTCCGATAGGAACACCCTGTCTTTC

ATCCTGGAGGAGTTTAAGAGCGACGAGGAAGTGATCCAGTCCTTCTGCAAGTACAAGACAC

TGCTGAGAAACGAGAACGTGCTGGAGACAGCCGAGGCCCTGTTTAACGAGCTGAACAGCAT

CGACCTGACACACATCTTCATCAGCCACAAGAAGCTGGAGACAATCAGCAGCGCCCTGTGC

GACCACTGGGATACACTGAGGAATGCCCTGTATGAGCGGAGAATCTCCGAGCTGACAGGCA

AGATCACCAAGTCTGCCAAGGAGAAGGTGCAGCGCAGCCTGAAGCACGAGGATATCAACCT

GCAGGAGATCATCTCTGCCGCAGGCAAGGAGCTGAGCGAGGCCTTCAAGCAGAAAACCAG

-continued

```
CGAGATCCTGTCCCACGCACACGCCGCCCTGGATCAGCCACTGCCTACAACCCTGAAGAAG

CAGGAGGAGAAGGAGATCCTGAAGTCTCAGCTGGACAGCCTGCTGGGCCTGTACCACCTG

CTGGACTGGTTTGCCGTGGATGAGTCCAACGAGGTGGACCCCGAGTTCTCTGCCCGGCTGA

CCGGCATCAAGCTGGAGATGGAGCCTTCTCTGAGCTTCTACAACAAGGCCAGAAATTATGC

CACCAAGAAGCCCTACTCCGTGGAGAAGTTCAAGCTGAACTTTCAGATGCCTACACTGGCC

GCCGGCTGGGACGTGAATAAGGCCAAGAACAATGGCGCCATCCTGTTTGTGAAGAACGGCC

TGTACTATCTGGGCATCATGCCAAAGCAGAAGGGCAGGTATAAGGCCCTGAGCTTCGAGCC

CACAGAGAAAACCAGCGAGGGCTTTGATAAGATGTACTATGACTACTTCCCTGATGCCGCCA

AGATGATCCCAAAGTGCAGCACCCAGCTGAAGGCCGTGACAGCCCACTTTCAGACCCACAC

AACCCCCATCCTGCTGTCCAACAATTTCATCGAGCCTCTGGAGATCACAAAGGAGATCTACG

ACCTGAACAATCCTGAGAAGGAGCCAAAGAAGTTTCAGACAGCCTACGCCAAGAAAACCGG

CGACCAGAAGGGCTACAGAGAGGCCCTGTGCAAGTGGATCGACTTCACAAGGGATTTTCTG

TCCAAGTATACCAAGACAACCTCTATCGATCTGTCTAGCCTGCGGCCATCCTCTCAGTATAA

GGACCTGGGCGAGTACTATGCCGAGCTGAATCCCCTGCTGTACCACATCAGCTTCCAGAGA

ATCGCCGAGAAGGAGATCATGGATGCCGTGGAGACAGGCAAGCTGTACCTGTTCCAGATCT

ATAACAAGGACTTTGCCAAGGGCCACCACGGCAAGCCTAATCTGCACACACTGTATTGGAC

CGGCCTGTTTTCTCCAGAGAACCTGGCCAAGACAAGCATCAAGCTGAATGGCCAGGCCGAG

CTGTTCTACCGCCCTAAGTCCAGGATGAAGAGGATGGCACACCGGCTGGGAGAGAAGATGC

TGAACAAGAAGCTGAAGGATCAGAAAACCCCAATCCCCGACACCCTGTACCAGGAGCTGTA

CGACTATGTGAATCACAGACTGTCCCACGACCTGTCTGATGAGGCCAGGGCCCTGCTGCCC

AACGTGATCACCAAGGAGGTGTCTCACGAGATCATCAAGGATAGGCGCTTTACCAGCGACA

AGTTCTTTTTCCACGTGCCTATCACACTGAACTATCAGGCCGCCAATTCCCCATCTAAGTTCA

ACCAGAGGGTGAATGCCTACCTGAAGGAGCACCCCGAGACACCTATCATCGGCATCGCCCG

GGGCGAGAGAAACCTGATCTATATCACAGTGATCGACTCCACCGGCAAGATCCTGGAGCAG

CGGAGCCTGAACACCATCCAGCAGTTTGATTACCAGAAGAAGCTGGACAACAGGGAGAAGG

AGAGGGTGGCAGCAAGGCAGGCCTGGTCTGTGGTGGGCACAATCAAGGATCTGAAGCAGG

GCTATCTGAGCCAGGTCATCCACGAGATCGTGGACCTGATGATCCACTACCAGGCCGTGGT

GGTGCTGGAGAACCTGAATTTCGGCTTTAAGAGCAAGAGGACCGGCATCGCCGAGAAGGC

CGTGTACCAGCAGTTCGAGAAGATGCTGATCGATAAGCTGAATTGCCTGGTGCTGAAGGAC

TATCCAGCAGAGAAAGTGGGAGGCGTGCTGAACCCATACCAGCTGACAGACCAGTTCACCT

CCTTTGCCAAGATGGGCACCCAGTCTGGCTTCCTGTTTTACGTGCCTGCCCCATATACATCT

AAGATCGATCCCCTGACCGGCTTCGTGGACCCCTTCGTGTGGAAAACCATCAAGAATCACG

AGAGCCGCAAGCACTTCCTGGAGGGCTTCGACTTTCTGCACTACGACGTGAAAACCGGCGA

CTTCATCCTGCACTTTAAGATGAACAGAAATCTGTCCTTCCAGAGGGGCCTGCCCGGCTTTA

TGCCTGCATGGGATATCGTGTTCGAGAAGAACGAGACACAGTTTGACGCCAAGGGCACCCC

TTTCATCGCCGGCAAGAGAATCGTGCCAGTGATCGAGAATCACAGATTCACCGGCAGATAC

CGGGACCTGTATCCTGCCAACGAGCTGATCGCCCTGCTGGAGGAGAAGGGCATCGTGTTCA

GGGATGGCTCCAACATCCTGCCAAAGCTGCTGGAGAATGACGATTCTCACGCCATCGACAC

GATGGTGGCCCTGATCCGCAGCGTGCTGCAGATGCGGAACTCCAATGCCGCCACAGGCGA

GGACTATATCAACAGCCCCGTGCGCGATCTGAATGGCGTGTGCTTCGACTCCCGGTTTCAG

AACCCAGAGTGGCCAATGGACGCCGATGCCAATGGCGCCTACCACATCGCCCTGAAGGGC
```

```
CAGCTGCTGCTGAATCACCTGAAGGAGAGCAAGGATCTGAAGCTGCAGAACGGCATCTCCA

ATCAGGACTGGCTGGCCTACATCCAGGAGCTGCGCAACaaaaaggccggcggccacgaaaaaggccggc caggcaaaaagaaaaagGGATCCTCTGGTGGTTCTGGAGGATCTGGTGGTTCTACTAATCTGTCA

GATATTATTGAAAAGGAGACCGGTAAGCAACTGGTTATCCAGGAATCCATCCTCATGCTCCC

AGAGGAGGTGGAAGAAGTCATTGGGAACAAGCCGGAAAGCGATATACTCGTGCACACCGCC

TACGACGAGAGCACCGACGAGAATGTCATGCTTCTGACTAGCGACGCCCCTGAATACAAGC

CTTGGGCTCTGGTCATACAGGATAGCAACGGTGAGAACAAGATTAAGATGCTCTCTGGTGGT

TCTcccaagaagaagaggaaagtc

Amino acid sequence of NLS(SV40)x2-rAPOBEC1-gsXTENgslinker-human-
dAsCpf1(D908A) triplevariant(E174R/S542R/K548R)-NLS(nucleoplasmin)-GSlinker-UGI-
NLS(SV40)
AsCpf1 in normal font (AAs x-xxxx), rAPOBEC1 in bold (AAs 23-250), NLS(nucleoplasmin)
(krpaatkkaggqakkkk, SEQ ID NO: 7) in lower case, SV40 NLS in lower case (pkkkrkv, SEQ ID
NO: 24), gsXTENgs linker (sggssggssgsetpgtsesatpessggssgg, SEQ ID NO: 25) in lower case, and
UGI double underlined
                                                                            (SEQ ID NO: 448)
MGpkkkrkvGSGpkkkrkvGSGSSETGPVAVDPTLRRRIEPHEFEVFFDPRELRKETCLLYEI

NWGGRHSIWRHTSQNTNKHVEVNFIEKFTTERYFCPNTRCSITINFLSWSPCGECSRAITEFLSR

YPHVTLFIYIARLYHHADPRNRQGLRDLISSGVTIQIMTEQESGYCWRNFVNYSPSNEAHWPRY

PHLVVVRLYVLELYCIILGLPPCLNILRRKQPQLTFFTIALQSCHYQRLPPHILWATGLKsggssggss gsetpgtsesatpessggssggSTQFEGFTNLYQVSKTLRFELIPQGKTLKHIQEQGFIEEDKARNDHYKE

LKPIIDRIYKTYADQCLQLVQLDWENLSAAIDSYRKEKTEETRNALIEEQATYRNAIHDYFIGRTDN

LTDAINKRHAEIYKGLFKAELFNGKVLKQLGTVTTTEHENALLRSFDKFTTYFSGFYRNRKNVFSA

EDISTAIPHRIVQDNFPKFKENCHIFTRLITAVPSLREHFENVKKAIGIFVSTSIEEVFSFPFYNQLLT

QTQIDLYNQLLGGISREAGTEKIKGLNEVLNLAIQKNDETAHIIASLPHRFIPLFKQILSDRNTLSFIL

EEFKSDEEVIQSFCKYKTLLRNENVLETAEALFNELNSIDLTHIFISHKKLETISSALCDHWDTLRNA

LYERRISELTGKITKSAKEKVQRSLKHEDINLQEIISAAGKELSEAFKQKTSEILSHAHAALDQPLPT

TLKKQEEKEILKSQLDSLLGLYHLLDWFAVDESNEVDPEFSARLTGIKLEMEPSLSFYNKARNYAT

KKPYSVEKFKLNFQMPTLARGWDVNREKNNGAILFVKNGLYYLGIMPKQKGRYKALSFEPTEKT

SEGFDKMYYDYFPDAAKMIPKCSTQLKAVTAHFQTHTTPILLSNNFIEPLEITKEIYDLNNPEKEPK

KFQTAYAKKTGDQKGYREALCKWIDFTRDFLSKYTKTTSIDLSSLRPSSQYKDLGEYYAELNPLL

YHISFQRIAEKEIMDAVETGKLYLFQIYNKDFAKGHHGKPNLHTLYVVTGLFSPENLAKTSIKLNGQ

AELFYRPKSRMKRMAHRLGEKMLNKKLKDQKTPIPDTLYQELYDYVNHRLSHDLSDEARALLPN

VITKEVSHEIIKDRRFTSDKFFFHVPITLNYQAANSPSKFNQRVNAYLKEHPETPIIGIARGERNLIYI

TVIDSTGKILEQRSLNTIQQFDYQKKLDNREKERVAARQAWSVVGTIKDLKQGYLSQVIHEIVDLM

IHYQAVVVLENLNFGFKSKRTGIAEKAVYQQFEKMLIDKLNCLVLKDYPAEKVGGVLNPYQLTDQ

FTSFAKMGTQSGFLFYVPAPYTSKIDPLTGFVDPFVWKTIKNHESRKHFLEGFDFLHYDVKTGDFI

LHFKMNRNLSFQRGLPGFMPAWDIVFEKNETQFDAKGTPFIAGKRIVPVIENHRFTGRYRDLYPA

NELIALLEEKGIVFRDGSNILPKLLENDDSHAIDTMVALIRSVLQMRNSNAATGEDYINSPVRDLNG

VCFDSRFQNPEWPMDADANGAYHIALKGQLLLNHLKESKDLKLQNGISNQDWLAYIQELRNkrpa atkkaggakkkkGSSGGSGGSGGS<u>TNLSDIIEKETGKQLVIQESILMLPEEVEEVIGNKPESDILVHTA</u>

<u>YDESTDENVMLLTSDAPEYKPWALVIQDSNGENKIKML</u>SGGSpkkkrkv
```

Example 1

Variants of AsCpf1 with Altered PAM Specificity

To attempt to alter the targeting range of Cpf1 nucleases, we first examined the available crystal structures of AsCpf1 and LbCpf1 (Dong, *Nature* 2016; Yamano, *Cell* 2016). Among other observations, these structures demonstrate that PAM specificity is mediated by a combination of electrostatic interactions and indirect base readout. We therefore hypothesized that certain combinations of amino acid substitutions at residues in close spatial proximity to the DNA bases of the PAM bases might yield variants with altered or relaxed PAM recognition preferences. To test this, we examined regions of AsCpf1 in the vicinity of the PAM that span residues G131-L137, S161-S181, N534-I555, Y595-T616, L628-F632, and S685-I693 (Table 1). We focused on amino acids in the reference AsCpf1 sequence whose three-dimensional position met at least one of the following criteria: 1) spatial proximity to PAM DNA bases (on either the target or non-target strand), 2) positioning within the DNA major or minor groove, and/or 3) residues positioned such that substitution of the existing amino acid with a positively charged alternative such as arginine, lysine, or histidine might be expected to increase proximity (and presumably interaction) of the side chain with the phosphodiester backbone. Because crystal structures that contain the crRNA and PAM-containing DNA are only available for AsCpf1, homologous positions in LbCpf1 and FnCpf1 were identified based on sequence alignment (Table 1) between the three orthologues.

TABLE 1

Comparison of candidate residues for mutation from AsCpf1 and LbCpf1 to create altered PAM recognition specificity variants. Alignments were performed with or without FnCpf1.

| | AsCpf1 | LbCpf1 | LbCpf1(+18) | FnCpf1 | alignment parameters |
|---|---|---|---|---|---|
| G131-L137 | G131 | S117* | S135* | G133** | * means LbCpf1 residues, from |
| | L132 | L118* | L136* | L142** | alignment with AsCpf1 only |
| | F133 | F119* | F137* | K143** | ** means FnCpf1 residues, from |
| | K134 | K120* | K138* | Q144** | alignment with AsCpf1 only |
| | A135 | K121* | K139* | S145** | black TEXT means residues from |
| | E136 | D122* | D140* | K146** | alignment with all 3 Cpf1 orthologs |
| | L137 | I123* | I141* | D147** | (AsCpf1 as reference) |
| S161-S181 | S161 | S143 | S161 | s171 | black TEXT means residues from |
| | F162 | F144 | F162 | F172 | alignment with all 3 Cpf1 orthologs |
| | D163 | N145 | N163 | K173 | |
| | K164 | G146 | G164 | G174 | |
| | F165 | F147 | F165 | W175 | |
| | T166 | T148 | T166 | T176 | |
| | T167 | T149 | T167 | T177 | |
| | Y168 | A150 | A168 | Y178 | |
| | F169 | F151 | F169 | F179 | |
| | S170 | T152 | T170 | K180 | |
| | G171 | G153 | G171 | G181 | |
| | F172 | F154 | F172 | F182 | |
| | Y173 | F155 | F173 | H183 | |
| | E174 | D156 | D174 | E184 | |
| | N175 | N157 | N175 | N185 | |
| | R176 | R158 | R176 | R186 | |
| | K177 | E159 | E177 | K187 | |
| | N178 | N160 | N178 | N188 | |
| | V179 | M161 | M179 | V189 | |
| | F180 | F162 | F180 | Y190 | |
| | S181 | S163 | S181 | S191 | |
| N534-I555 | N534 | Y524 | Y542 | N599 | black TEXT means residues from |
| | F535 | F525 | F543 | F600 | alignment with all 3 Cpf1 orthologs |
| | Q536 | Q526 | Q544 | E601 | |
| | M537 | N527 | N545 | N602 | |
| | P538 | P528 | P546 | S603 | |
| | T539 | Q529 | Q547 | T604 | |
| | L540 | F530 | F548 | L605 | |
| | A541 | M531 | M549 | A606 | |
| | S542 | G532 | G550 | N607 | |
| | G543 | G533 | G551 | G608 | |
| | W544 | W534 | W552 | W609 | |
| | D545 | D535 | D553 | D610 | |
| | V546 | K536 | K554 | K611 | |
| | N547 | D537 | D555 | N612 | |
| | K548 | K538 | K556 | K613 | |
| | E549 | E539 | E557 | E614 | |
| | K550 | T540 | T558 | P615 | |
| | N551 | D541 | D559 | D616 | |
| | N552 | Y542 | Y560 | N617 | |
| | G553 | R543 | R561 | T618 | |
| | A554 | A544 | A562 | A619 | |
| | I555 | T545 | T563 | I620 | |
| Y595-T616 | Y595 | Y583 | Y601 | Y659 | black TEXT means residues from |
| | D596 | K584 | K602 | K660 | alignment with all 3 Cpf1 orthologs |
| | Y597 | L585 | L603 | L661 | |
| | F598 | L586 | L604 | L662 | |
| | P599 | P587 | P605 | P663 | |

TABLE 1-continued

Comparison of candidate residues for mutation from AsCpf1 and LbCpf1 to create altered PAM recognition specificity variants. Alignments were performed with or without FnCpf1.

|  | AsCpf1 | LbCpf1 | LbCpf1(+18) | FnCpf1 | alignment parameters |
|---|---|---|---|---|---|
|  | D600 | G588 | G606 | G664 |  |
|  | A601 | P589 | P607 | A665 |  |
|  | A602 | N590 | N608 | N666 |  |
|  | K603 | K591 | K609 | K667 |  |
|  | M604 | M592 | M610 | M668 |  |
|  | I605 | L593 | L611 | L669 |  |
|  | P606 | P594 | P612 | P670 |  |
|  | K607 | K595 | K613 | K671 |  |
|  | C608 | V596 | V614 | V672 |  |
|  | S609 | F597 | F615 | F673 |  |
|  | T610 | F598 | F616 | F674 |  |
|  | Q611 | S599 | S617 | S675 |  |
|  | L612 | K600 | K618 | A676 |  |
|  | K613 | K601 | K619 | K677 |  |
|  | A614 | W602 | W620 | S678 |  |
|  | V615 | M603 | M621 | I679 |  |
|  | T616 | A604 | A622 | K680 |  |
| L628-F632 | L628 | F598* | F616* | R690** | * means LbCpf1 residues, from |
|  | S629 | S599* | S617* | I691** | alignment with AsCpf1 only |
|  | N630 | K600* | K618* | R692** | ** means FnCpf1 residues, from |
|  | N631 | K601* | K619* | N693** | alignment with AsCpf1 only |
|  | F632 | W602* | W620* | H694** | if alignment performed with AsCpf1, LbCpf1, and FnCpf1, both LbCpf1 and FnCpf1 don't align in this region with AsCpf1 |
| S685-I693 | S685 | S644 | S662 | S729 | black TEXT means residues from |
|  | K686 | R645 | R663 | K730 | alignment with all 3 Cpf1 orthologs |
|  | Y687 | Y646 | Y664 | H731 | ** means FnCpf1 residues, from |
|  | T688 | P647 | P665 | P732 | alignment with AsCpf1 only |
|  | K689 | K648 | K666 | E733 |  |
|  | T690 | W649 | W667 | W734 |  |
|  | T691 | S650 | S668 | K735 |  |
|  | S692 | N651 | N669 | D736 |  |
|  | I693 | A652 | A670 | F737** |  |

Figure 2:
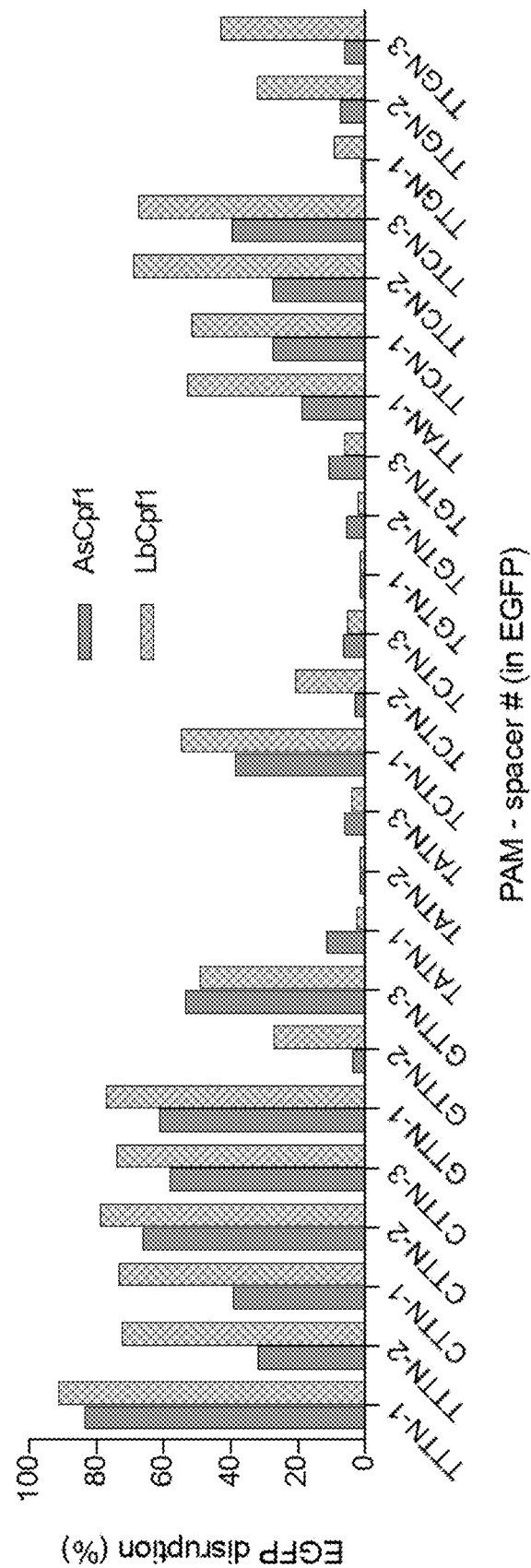
Figure 3:
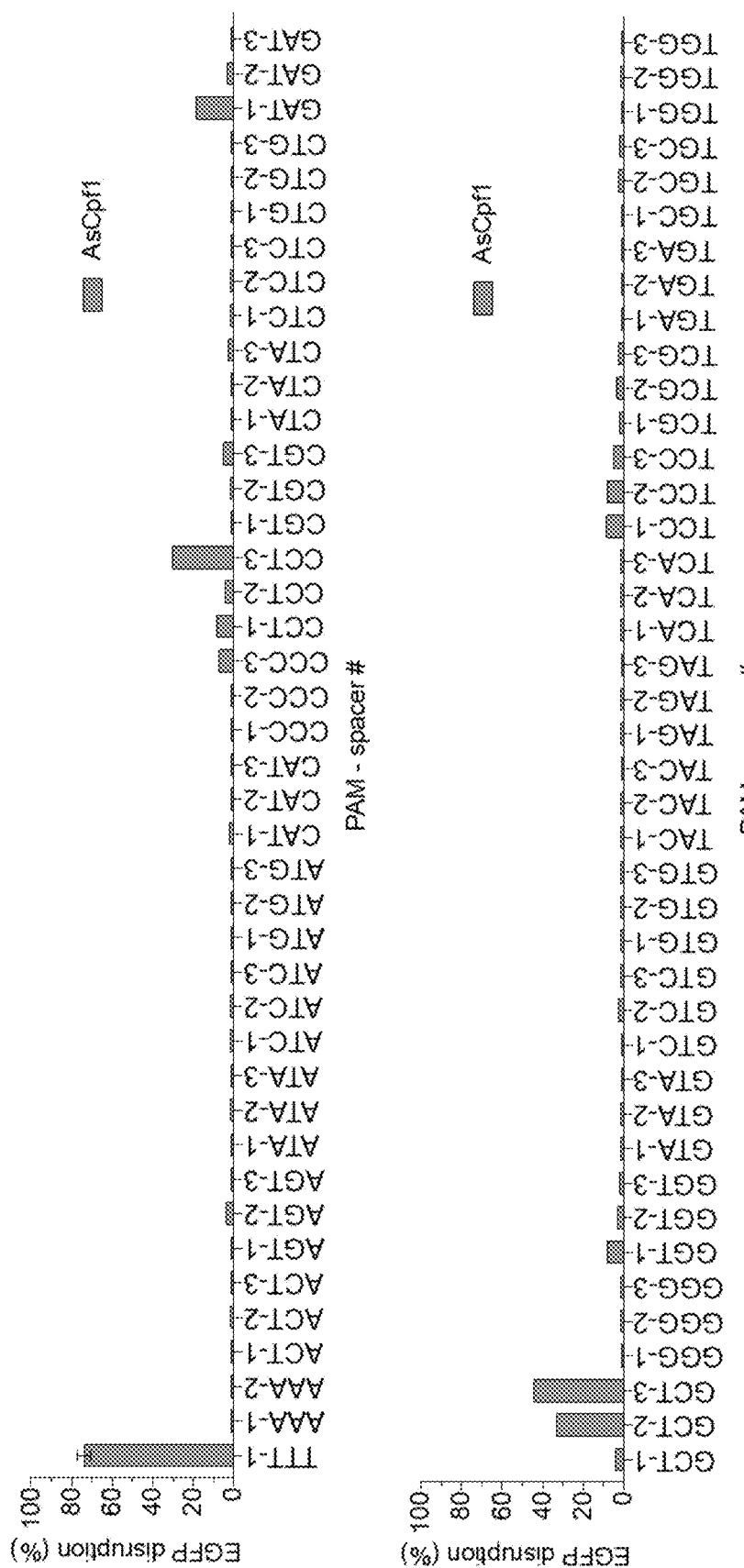

In initial experiments, we first sought to carefully define the PAM preferences of wild-type AsCpf1 and LbCpf1 by testing the activities of these nucleases in human cells against alternative PAM target sites that have base differences within the TTTN motif defined in initial characterization of these enzymes (Zetsche, Cell 2015). Using our well-established human cell-based EGFP disruption assay, we first tested the abilities of AsCpf1 and LbCpf1 to mutagenize various target sites harboring a canonical TTTN or non-canonical PAMs bearing a range of different single base mismatches within the TTT motif. We determined that although both AsCpf1 and LbCpf1 could tolerate non-canonical bases in the PAM, recognition by LbCpf1 was more promiscuous (FIG. 2). Both Cpf1 enzymes efficiently and consistently targeted sites in our EGFP disruption assay with alternative CTTN, GTTN, and TTCN PAMs. (The EGFP disruption assay measures loss of EGFP expression as a surrogate for targeting of sites within the EGFP sequence by genome-editing nucleases (Reyon, Nature Biotechnology 2012). We also examined the ability of AsCpf1 to recognize sites that contain more divergent PAM sequences in EGFP, with either two or three base differences in the TTT sequence of a TTTN PAM. With the exception of some slight and variable activity against sites containing CCCN, CCTN, GATN, GCTN, and TCCN PAMs, we found that the wild-type AsCpf1 nuclease did not efficiently target any of these alternative PAMs (FIG. 3).

Figure 4:
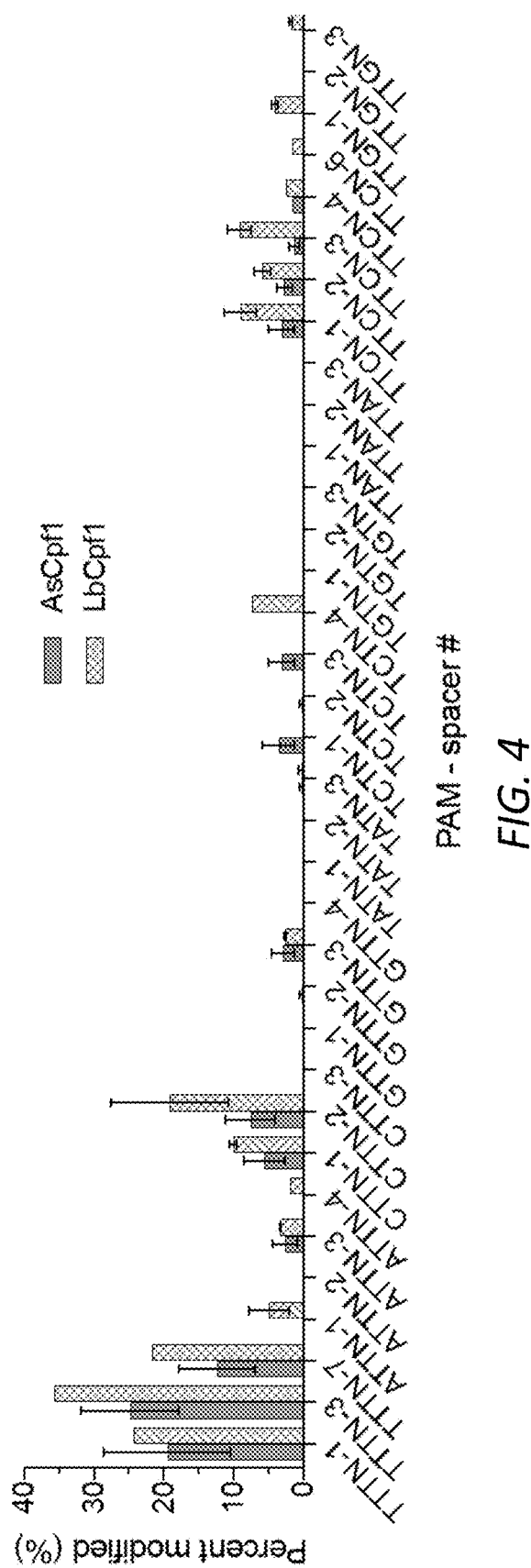

However, because activity observed in the EGFP disruption assay might represent a combination of nuclease mediated gene disruption and transcriptional repression mediated by DNA-binding (without cleavage), we tested the activities of AsCpf1 and LbCpf1 on endogenous human gene target sites that contain alternative PAM sequences with single base differences relative to the canonical PAM, because the read-out from this assay quantifies bona fide gene disruption events (FIG. 4). We found that even though modest activities were observed with AsCpf1 and LbCpf1 on sites harboring certain non-canonical PAM sites in our EGFP disruption assay, we did not observe comparable induction of indel mutations on endogenous gene sites bearing these alternative PAM sequences. This result suggests that although wild-type AsCpf1 and LbCpf1 nucleases may efficiently bind alternative PAM sequences with single base differences, in some cases they may not efficiently cleave these sites.

Given the limited capability of wild-type Cpf1 nucleases to cleave non-TTTN PAMs, we sought to engineer Cpf1 variants that could target and disrupt sites harboring such alternative PAMs. In initial experiments, we attempted to engineer Cpf1 nucleases with relaxed PAM recognition specificities. We used the EGFP disruption assay to rapidly identify and screen single amino acid substitutions in AsCpf1 that could alter PAM recognition, reasoning that we would need to ultimately validate any variants we identified for their abilities to cleave sites within actual endogenous genes in human cells given the limitations of the EGFP-based assay described above. To test the hypothesis of whether rational substitutions of AsCpf1 could alter PAM specificity, we focused on testing the effect of amino acid substitutions at positions: T167, S170, E174, T539, S542, K548, N551, N552, M604, and K607.

Note that the subsequent PAM numbering is based on the TTTN PAM being numbered T4T3T2N1, and only a small subset of all possible PAMs were examined for the initial tests of each AsCpf1 variant, with subsequent more extensive testing for combinations of variants.

Figure 5B:
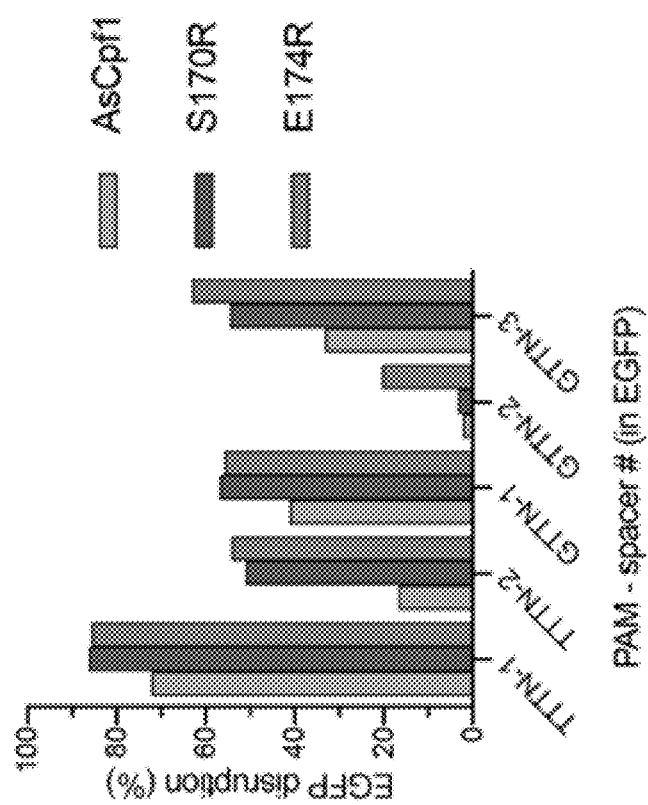
Figure 5A:
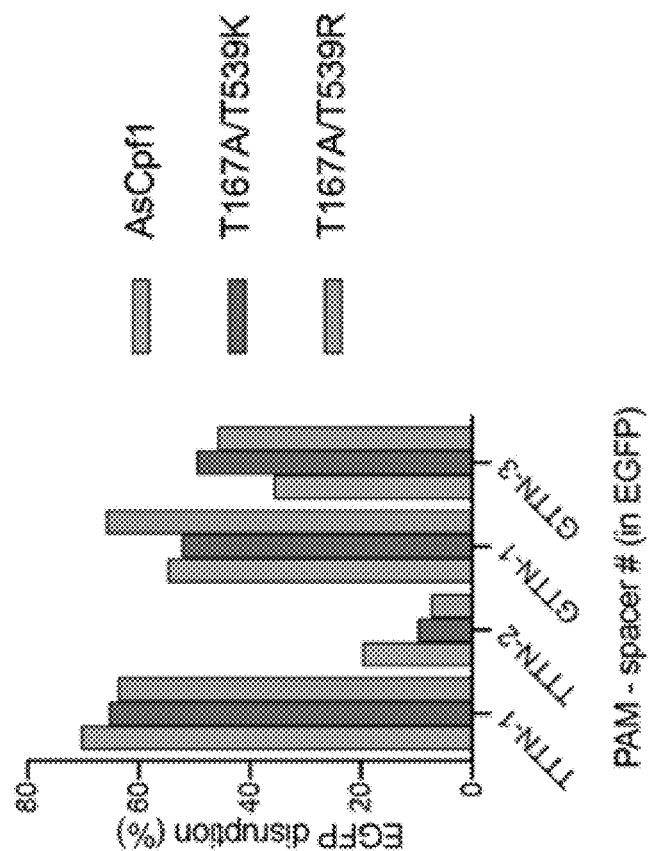

T167/T539: Based on the proximity of T539 to T4 of the PAM in the AsCpf1 co-crystal structure, we envisioned that concurrent substitutions of T539K/T167A or T539R/T167A might enable base specific recognition of a G at the fourth position of the PAM by: 1) the T539 substitution to K or R enabling base specific readout of a guanine, and/or 2) the T167A substitution alleviating other interfering or unfavorable contacts induced by alteration of the T539 residue. Relative to wild-type AsCpf1, both the T539K/T167A and T539R/T167A variants show improved activity in the EGFP disruption assay on sites harboring GTTN PAMs with minimal or only modest reductions in activity on sites harboring canonical TTTN PAMs (FIG. 5A).

S170/E174: Both residues lie within the DNA major groove with S170 near $T_2$ of the PAM and E174 positioned near the $T_2$ or $N_1$ position of the PAM and near the target strand DNA backbone. We envisioned that arginine substitutions at these positions might relax PAM specificity, enabling the creation of non-specific contacts to the DNA backbone or potentially establishing base specific recognition of TTGN or TTTG PAMs. Both the S170R and E174R variants increase activity at canonical TTTN PAMs in the EGFP disruption assay while also increasing activity on sites bearing GTTN PAMs (FIG. 5B). We also show that both the S170R and E174R variants confer an increased ability to target CTTN and TTCN PAM sites (FIG. 8C).

Figure 5C:
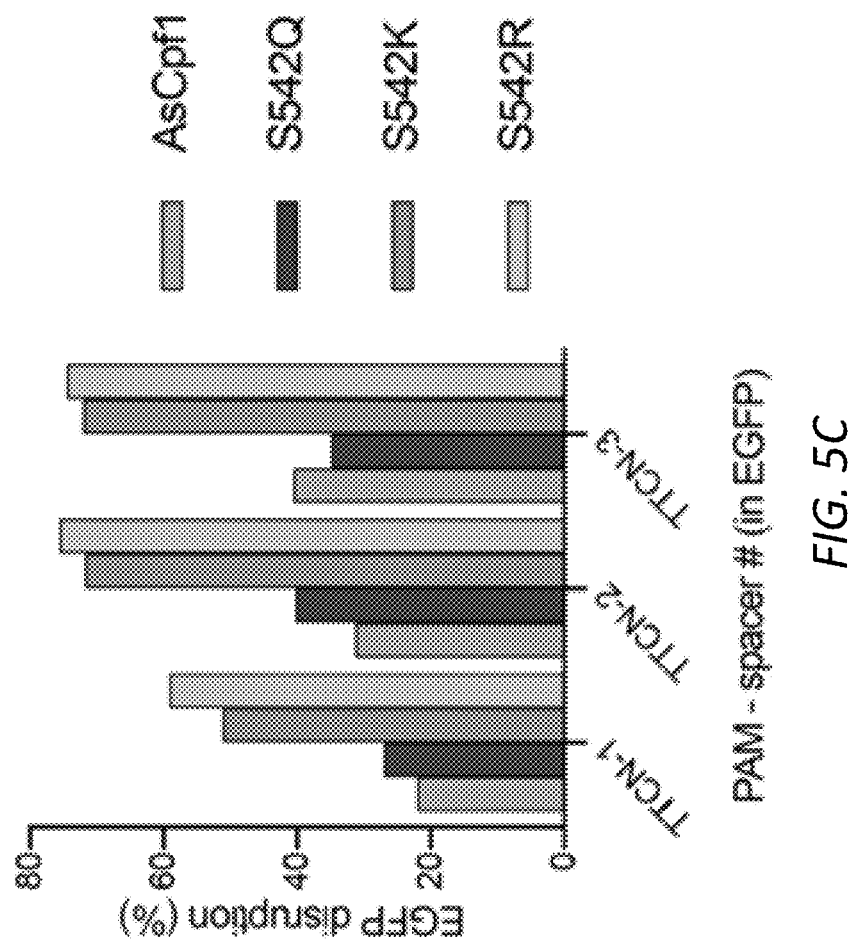
Figure 5E:
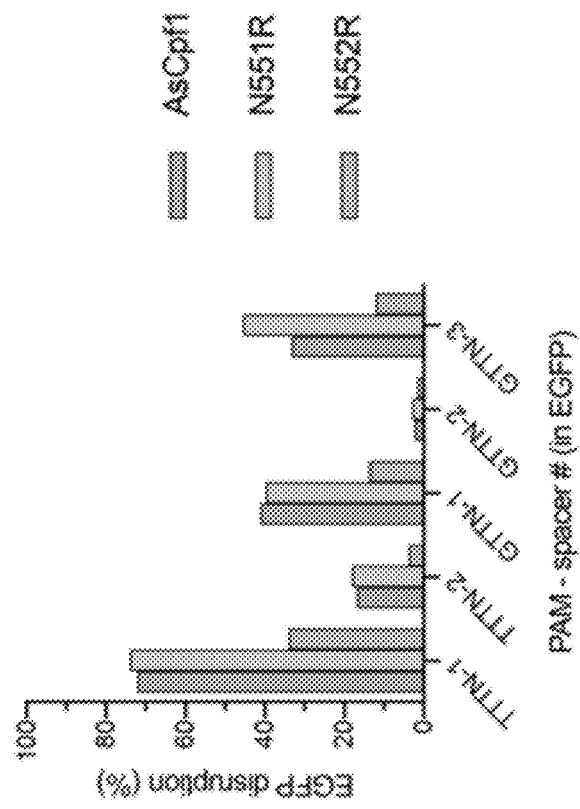
Figure 5D:
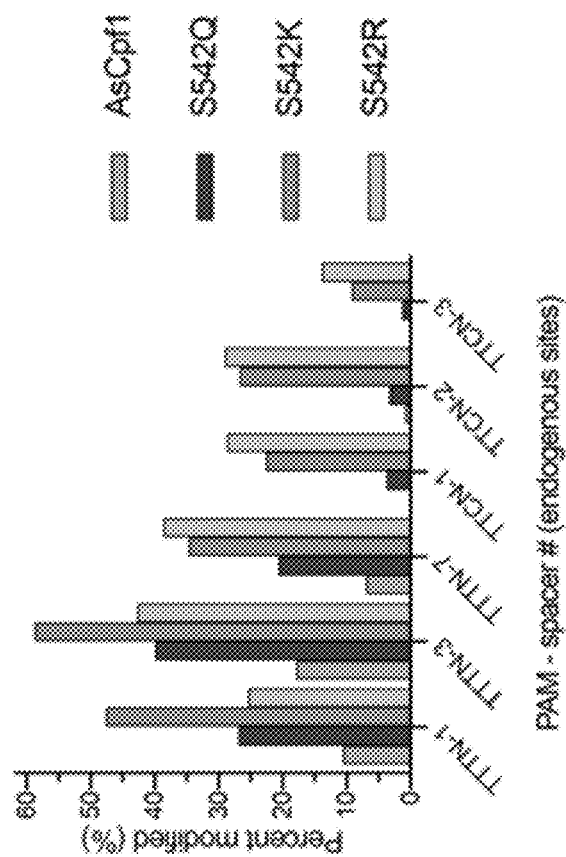

S542: This residue is positioned in the major groove in close proximity to the T3 and T2 bases of the PAM. Therefore, we hypothesized that S542K or S542R mutations might function to relax PAM specificity by: 1) providing additional non-specific energy in the PAM binding interface to accommodate non-canonical bases, and/or 2) creating a base-specific contact that might potentially recognize a $G_3$ or $G_2$ on the non-target strand, or perhaps a $G_3$ or $G_2$ on the target strand which would be a $C_3$ or $C_2$ on the non-target strand of the PAM. Our hypotheses would predict that variants bearing substitutions at S542 might be expected to enable recognition of sites harboring TGTN, TTGN, TCTN, or TTCN PAMs. Using the EGFP reporter assay, we found that AsCpf1 variants with either an S542K or an S542R substitution (but not with a S542Q substitution) exhibit increase activities on target sites with non-canonical TTCN PAMs (FIG. 5C). Interestingly, when tested for their abilities to cleave and mutagenize endogenous human gene targets, AsCpf1 variants bearing an S542Q, S542K, or S542R mutation all show increased abilities to induce indel mutations on target sites bearing TTTN PAMs (FIG. 5D) but only the S542K and S542R variants show increased activities on target sites bearing non-canonical TTCN PAMs (FIG. 5D). Recognition of additional non-canonical PAMs by these variants is also further examined in FIG. 7 (see below).

K548: This residue is positioned near $A_4$ and $A_3$ of the non-PAM DNA strand and near the backbone of the target strand DNA. We therefore hypothesized that substitutions at this position might potentially increase activity against target sites with non-canonical CTTN, TCTN, or CCTN PAMs. We found that introduction of a K548R mutation appears to confer no substantial alteration in PAM specificity on its own but does contribute to relaxing PAM recognition in the context of other substitutions at positions S542, N551, and N552 (see below in FIG. 9).

N551/N552: The residues N551 and N552 are both positioned in the major groove between the target and non-target DNA strand backbones, but N552 is also very near $A_3$ of the non-PAM DNA strand and near the target strand DNA backbone. Whereas an N551R substitution appears to have no detrimental effect or in one case perhaps slightly improve AsCpf1 activity on target sites with non-canonical GTTN PAM sequences (without impacting recognition of sites with canonical TTTN PAMs), an N552R substitution appears to abrogate activity on target sites with either TTTN or GTTN PAMs (FIG. 5E). We also explored the N551R and N552R substitutions in combination with the S542R mutation and other combinations of mutations (see FIG. 8B and FIG. 11 below)

Figure 5F:
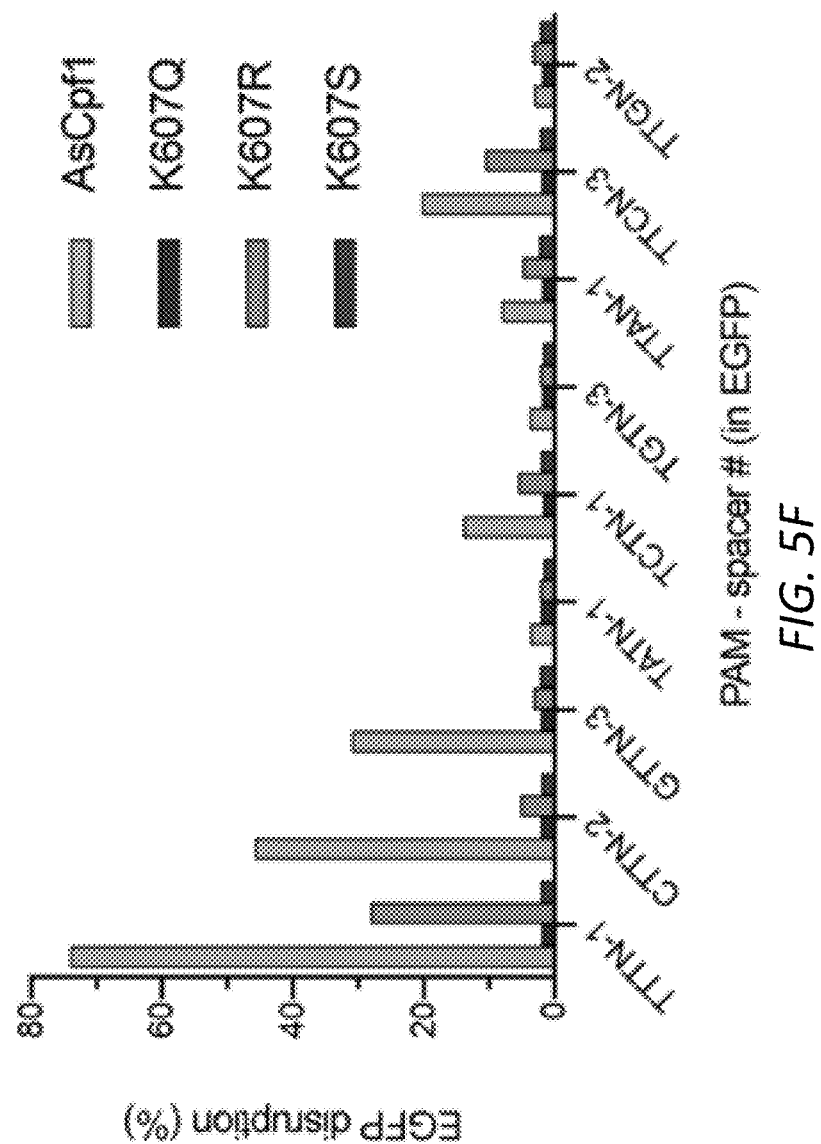

M604/K607: Residue M604 is positioned in the DNA minor groove near the $N_1$ position of the PAM and the $A_2$ nucleotide of the non-PAM target DNA strand. Residue K607 is also positioned in the minor groove and forms a network with $T_3$ and $T_2$ (of the PAM) and $A_3$ of the non-PAM DNA strand. Multiple different substitutions at K607 alone appear to negatively impact the activity of AsCpf1 (FIG. 5f), but combining a K607H substitution together with the S542R mutation leads to a variant with increased activity against sites harboring canonical TTTN or non-canonical TTCN PAMs (as judged by the EGFP disruption assay or by the mutagenesis of endogenous human gene target sites, in FIGS. 5g and 5h, respectively). Similarly, an M604A substitution combined with an S542R substitution improves activity against target sites harboring canonical TTTN or non-canonical TTCN PAMs when assayed using the EGFP disruption assay (FIG. 5g).

Figure 6A:
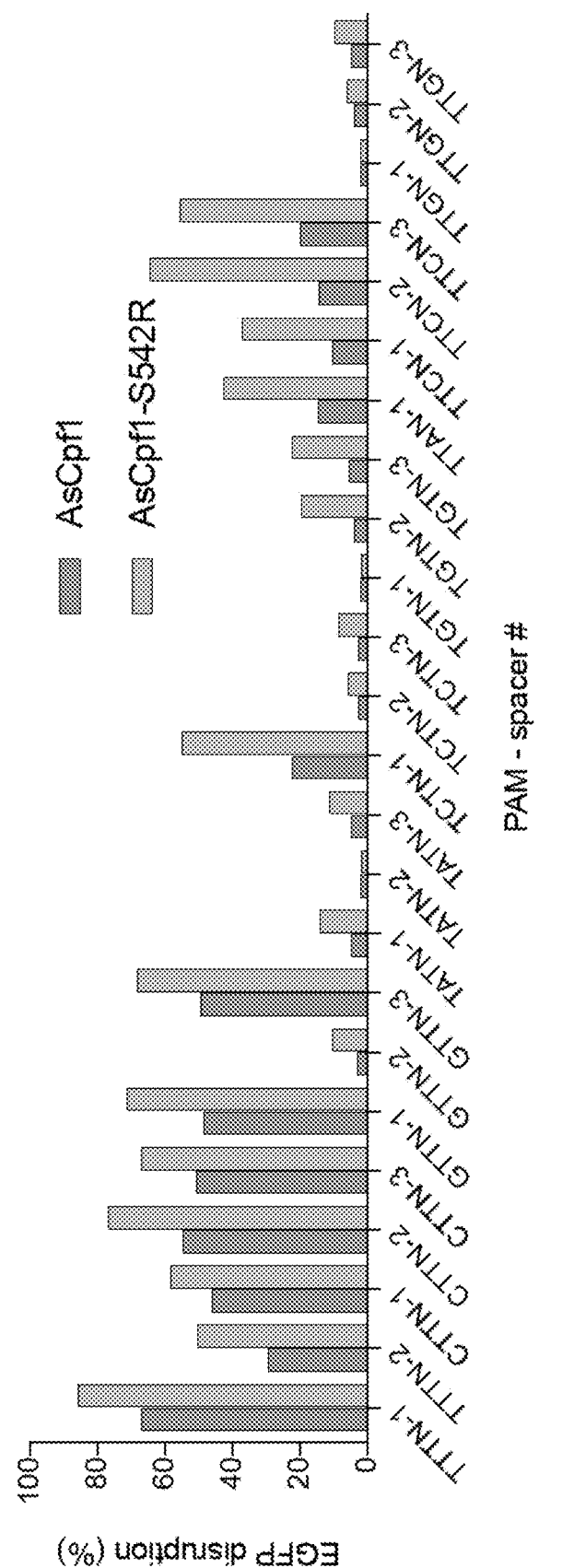
Figure 6B:
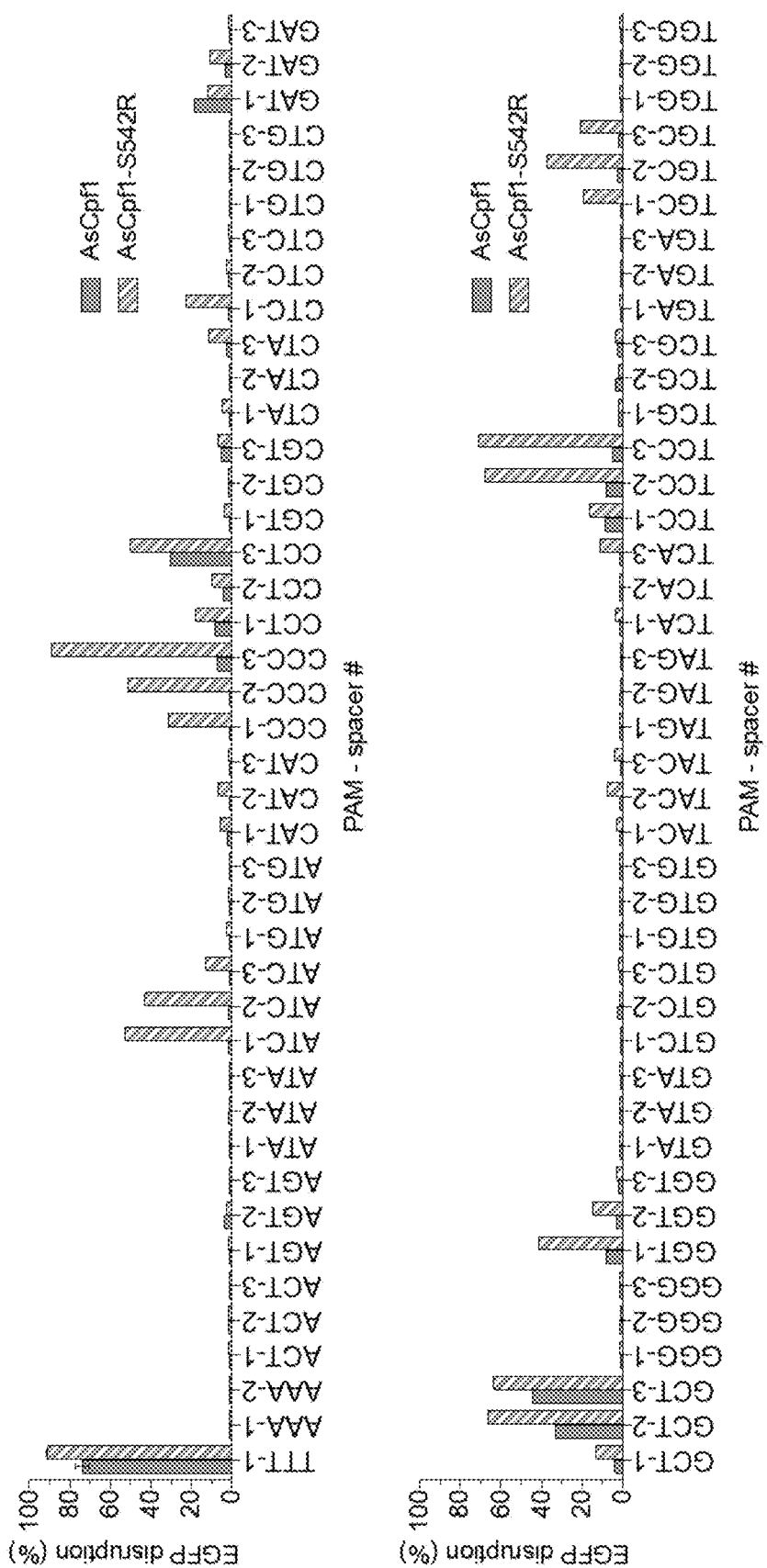

To further test the relaxed PAM specificity phenotype resulting from introduction of the S542R mutation, we compared the EGFP disruption activity of wild-type AsCpf1 with that of AsCpf1-S542R across target sites in EGFP that harbor a PAM with a single base difference relative to the canonical sequence (including the four non-canonical PAMs that we hypothesized might be recognized by the S542R variant) (FIG. 6A). In these experiments, we observed increased activities of the AsCpf1-S542R variant against target sites bearing multiple non-canonical PAM sites, including PAMs beyond the four hypothesized by our base-specific contact model (suggesting a general improvement in PAM binding affinity and a related relaxation in PAM specificity). To further examine the potential of the S542 mutant to expand AsCpf1 targeting range, we compared wild-type AsCpf1 to the S542R variant on a series of EGFP target sites with PAMs that harbor 2 or 3 base differences relative to the canonical site (FIG. 6B). The S542R mutant maintained at least the same level of activity observed with wild-type AsCpf1 at all sites, and dramatically improved activity (in some cases several fold) against many sites with PAMs harboring two or three substitutions (FIG. 6B). Our results with the EGFP disruption assay suggest that the AsCpf1-S542R variant can recognize sites harboring the following PAMs: TTTN, CTTN, GTTN, TCTN, TGTN, TTAN, TTCN, ATCN, CCCN, CCTN, GCTN, GGTN, TCCN, and TGCN. We next tested the S542R variant on endogenous human gene target sites bearing PAMs with one (FIG. 7A) and 2- or 3 base substitutions (FIG. 7B). These experiments again revealed that the S542R variant can cleave a wider range of mismatched PAM motifs but the spectrum of these sites was not as broad as what we observed in the EGFP disruption assay. Based on the results of our experiments with these endogenous human gene target sites, we conclude that the AsCpf1-S542R variant can cleave sites that harbor the following PAMs: TTTN, ATTN, CTTN, GTTN, TCTN, TTCN, CCCN, and TCCN.

The observation that a single substitution at S542 could expand the PAM recognition specificity of AsCpf1 suggested that it might be possible to further increase targeting range by adding single or multiple mutations to this variant. As shown in FIG. 5 and described in detail above, we found that amino acid substitutions at S170, E174, K548, N551, and K607 (alone or in combinations), resulted in somewhat altered PAM recognition specificities. Thus, we sought to explore whether various other combinations of substitutions at these positions together with the S542R mutation might further improve the targeting range of AsCpf1. First, we determined that combinations of substitutions that include S542R/K548R, S542R/N551R, and K548R/N551R could in most cases improve activity relative to the S542R substitution alone on target sites harboring canonical TTTN or non-canonical GTTN PAMs (FIG. 8A). Next, using the EGFP disruption assay, we determined across a larger number of target sites with more diverse PAM sequences that: 1) that variants harboring either the single S170R or E174R substitutions could for many target sites outperform the S542R substitution, 2) the E174R/S542R, S542R/K548R, and S542R/N551R variants perform as well or better than the S542R alone across a range of different target sites, and 3) that the E174R/S542R/K548R triple substitution variant conveyed the highest level of activity among a large series of AsCpf1 variants we tested against a range of target sites harboring canonical TTTN and non-canonical CTTN, GTTN, TATN, TCTN, TGTN, TTAN, TTCN, and TTGN PAM sites (FIGS. 8B And 8C).

Further comparison of the AsCpf1 E174R/S542R/K548R variant to wild-type AsCpf1 and the AsCpf1-S542R variant on EGFP target sites bearing PAMs with single base differences (FIG. 9A) revealed that the E174R/S542R/K548R variant had higher EGFP disruption activity than both wild-type AsCpf1 and S542 on nearly all target sites with various PAM sites tested. Furthermore, when the E174R/S542R/K548R variant was compared to wild-type AsCpf1 on a series of EGFP sites with PAMs bearing two or three mismatches, substantial increases in EGFP disruption were observed for many of these sites (FIG. 9B). The E174R/S542R/K548R triple substitution variant also showed generally higher activities and on a wider range of variant PAMs than the S542R variant (compare FIG. 9B to FIG. 6B), including efficient recognition of sites harboring the following PAMs: TTTN, CTTN, GTTN, TATN, TCTN, TGTN, TTAN, TTCN, TTGN, AGTN, ATCN, CATN, CCCN, CCTN, CGTN, CTAN, CTCN, GATN, GCTN, GGTN, GTCN, TACN, TCCN, and TGCN.

Because of the limitation of the EGFP disruption assay noted above for assessing Cpf1 nuclease activities, we next assessed the activity of our AsCpf1 E174R/S542R/K548R variant against a range of endogenous human gene target sites harboring PAMs with single base differences (FIG. 10A) or two or three base differences (FIG. 10B). These results demonstrate that AsCpf1 E174R/S542R/K548R can efficiently cleave sites bearing the following PAMs: TTTN, ATTN, CTTN, GTTN, TATN, TCTN, TGTN, TTCN, ATCN, CCCN, CCTN, CTCN, GCTN, GGTN, TCCN, and TGCN. It is important to note that AsCpf1-E174R/S542R/K548R was not tested on target sites with all possible PAMs. Significantly, target sites bearing most of these alternate PAMs could not be cleaved even with wild-type LbCpf1, which has a more relaxed PAM preference than wild-type AsCpf1 (FIGS. 2 and 4). Furthermore, for the variant PAM sites that could be cleaved by wild-type LbCpf1, we observed that the AsCpf1-E174R/S542R/K548R variant consistently outperformed wild-type LbCpf1 as judged by efficiency of indel mutation induction. Interestingly, the AsCpf1-E174R/S542R/K548R variant also displayed improved activity against canonical TTTN PAM sites, even demonstrating substantial activity against the TTTN-6 site previously untargetable with AsCpf1 or LbCpf1 (FIGS. 10A and 10B). The TTTN-6 site bears a T at the first position of the PAM (for a TTTT PAM), suggesting that the triple substitution AsCpf1 variant may improve activity against sites bearing a T in the first position of the PAM. Thus, the AsCpf1-E174R/S542R/K548R variant substantially improves the targeting range of the Cpf1 platform for sites with non-canonical PAMs relative to wild-type AsCpf1 and LbCpf1 nucleases and generally show improved activities on sites with canonical PAMs as well.

Next, to attempt to further relax the PAM specificity of our AsCpf1 PAM variants and/or improve the magnitude of activity at any given PAM, we added more amino acid substitutions to the E174R/S542R/K548R variant. First, we added the N551R or N552R substitution to generate quadruple substitution variants E174R/S542R/K548R/N551R and E174R/S542R/K548R/N552R, respectively. Comparison of these two quadruple substitution variants with wild-type AsCpf1 and the E174R/S542R/K548R variant revealed that the E174R/S542R/K548R/N551R variant could improve gene disruption activity at sites harboring various non-canonical PAMs bearing single, double, or triple differences as judged both by EGFP disruption assay or by their abilities to induce indel mutations in endogenous human gene target sites (FIGS. 11A and 11B, respectively). By contrast, the E174R/S542R/K548R/N552R quadruple substitution variant did not show improved activity in these same experiments and in many cases actually abrogated activity (FIGS. 11A and 11B). To further compare the PAM recognition specificities of the E174R/S542R/K548R and E174R/S542R/K548R/N551R variants, we examined their activities across an expanded larger number of endogenous human gene target sites that contained canonical or non-canonical (single base difference) PAMs. We observed comparable activity of both variants across the majority of sites, with a small number of cases in which one or the other variant exhibited slightly improved activity (FIG. 11C).

Example 1B

Further Characterization of AsCas12a Variants with Altered PAM Specificities and Improved On-Target Activities Prior characterizations of Cas12a orthologs in human cells revealed that As and LbCas12a were consistently more effective nucleases on sites with TTTV PAMs (Kim et al., Nat Biotechnol., 2016, 34:863-8), and that Fn and MbCas12a may possess relaxed PAM preferences of NTTN (Zetsche et al., Cell, 2015, 163:759-71). To more thoroughly assess the activities and PAM preferences of each ortholog, their genome editing activities using two sets of twelve crRNAs targeted to sites harboring TTTN or VTTN PAMs were examined in human cells (FIG. 19A). We observed similar gene disruption between the four orthologs on TTTN PAM sites, though target-specific differences were observed. Furthermore, Fn and Mb could more effectively target VTTN PAMs when compared to As and LbCas12a, but consistent with prior reports their mean activities on VTTN sites were too low to characterize these PAMs as bona fide targets (FIGS. 19A and 19B). These results support previous observations that Cas12a nucleases are mostly effective against sites harboring TTTV PAMs (Kim et al., Nat Biotechnol., 2016, 34:863-8), and that no naturally occurring Cas12a orthologs characterized to date have been shown to overcome this restrictive PAM requirement in human cells.

Figure 20A:
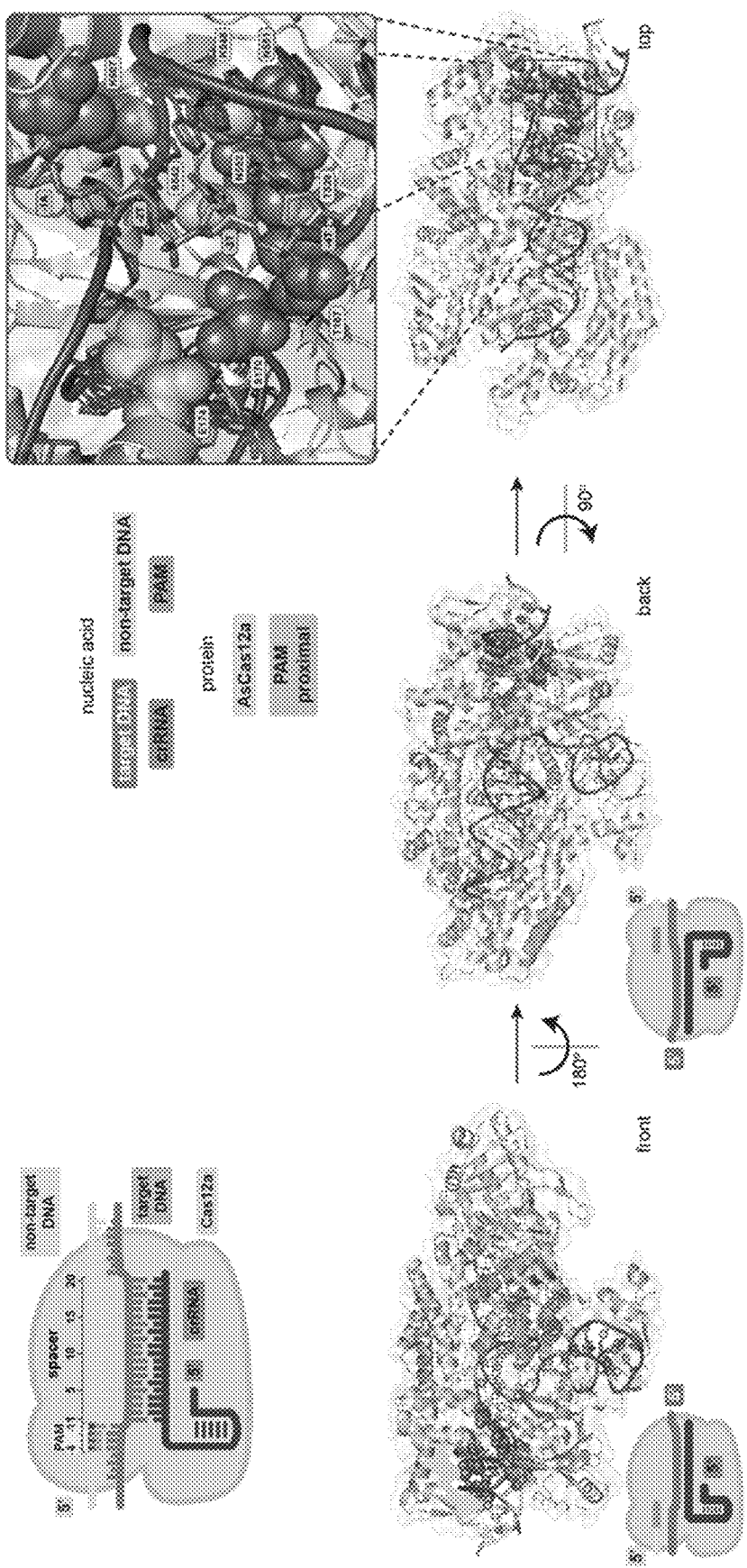
Figure 20B:
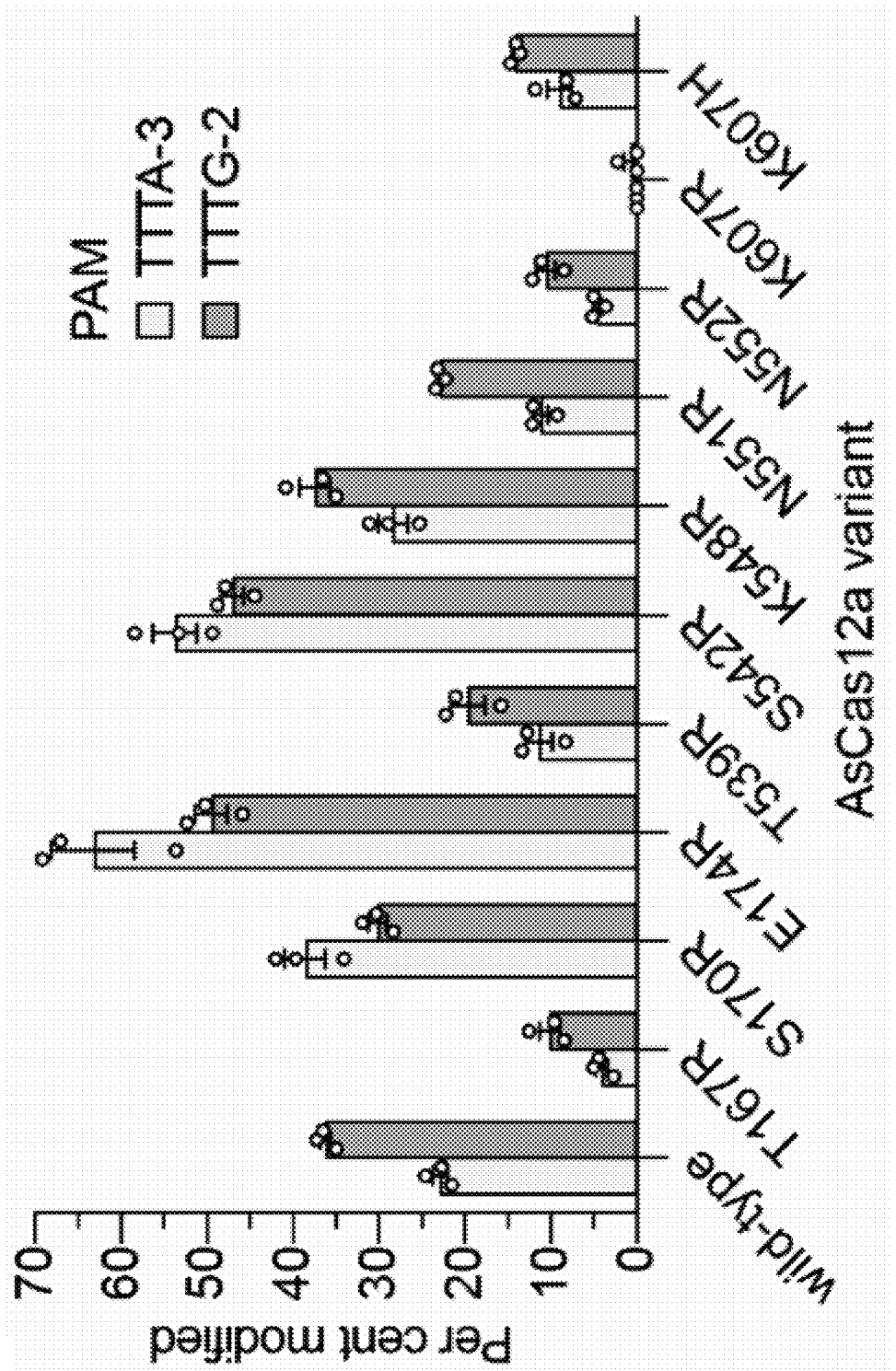
Figure 20C:
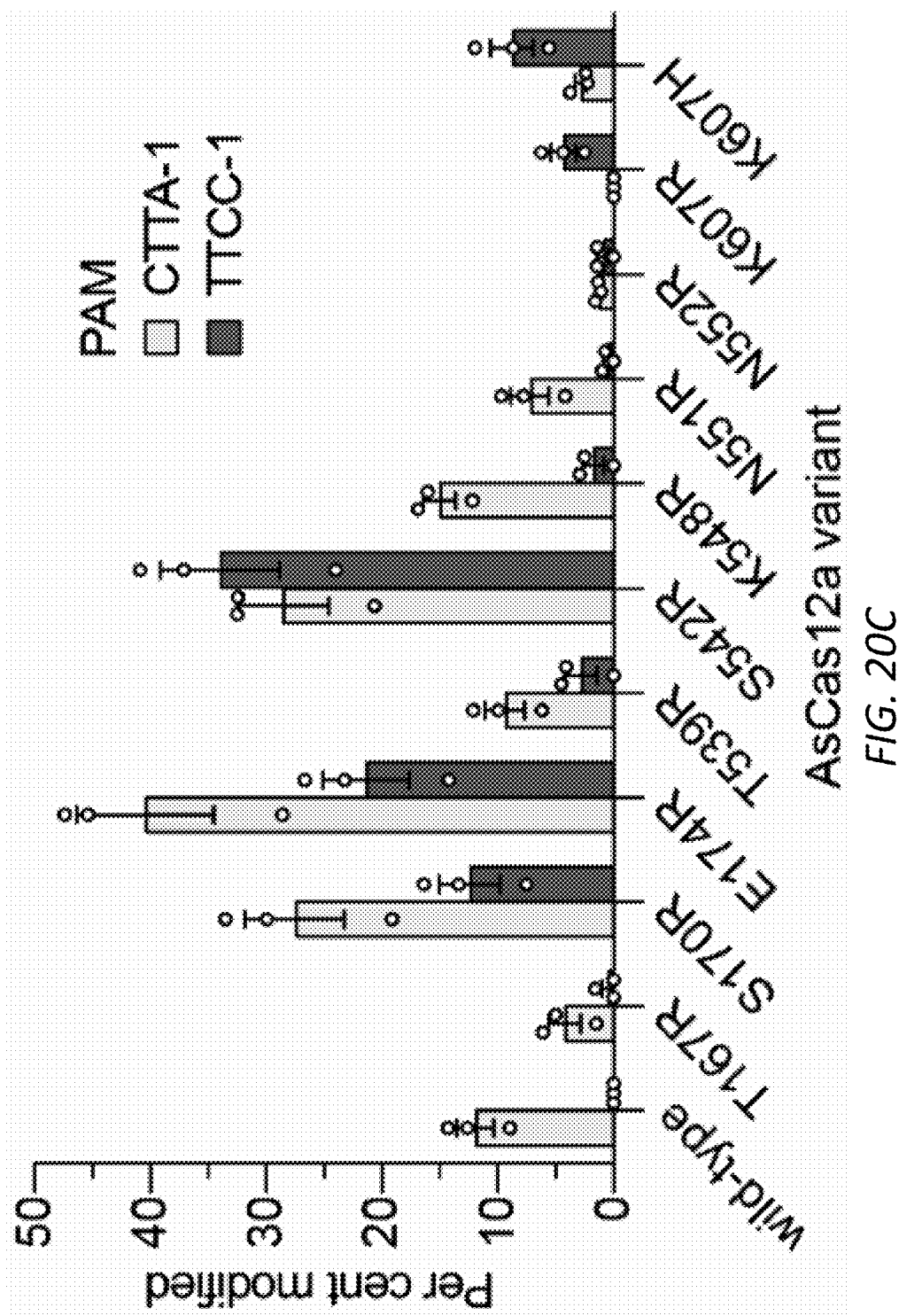

To expand the targeting range and broaden the utility of Cas12a nucleases, we leveraged structural studies of the AsCas12a ternary complex (Yamano et al., Cell. 2016 May 5; 165(4):949-62) to engineer a single variant capable of recognizing both canonical and non-canonical PAMs. Residues in close spatial proximity to the PAM DNA bases were identified (FIG. 20A), and we hypothesized that substitution of these residues could alter or relax PAM recognition by creating novel base- or non-specific interactions. We first tested the activities of variants encoding single substitutions at these positions in human cells against sites encoding canonical and non-canonical PAMs. Compared to wild-type AsCas12a, four single substitution variants (S170R, E174R, S542R, K548R) displayed superior activity on canonical TTTA or TTTC PAM sites, while also enabling more efficient targeting of sites with non-canonical CTTA or TTCC PAMs (FIGS. 20B and 20C, respectively).

Figure 15A:
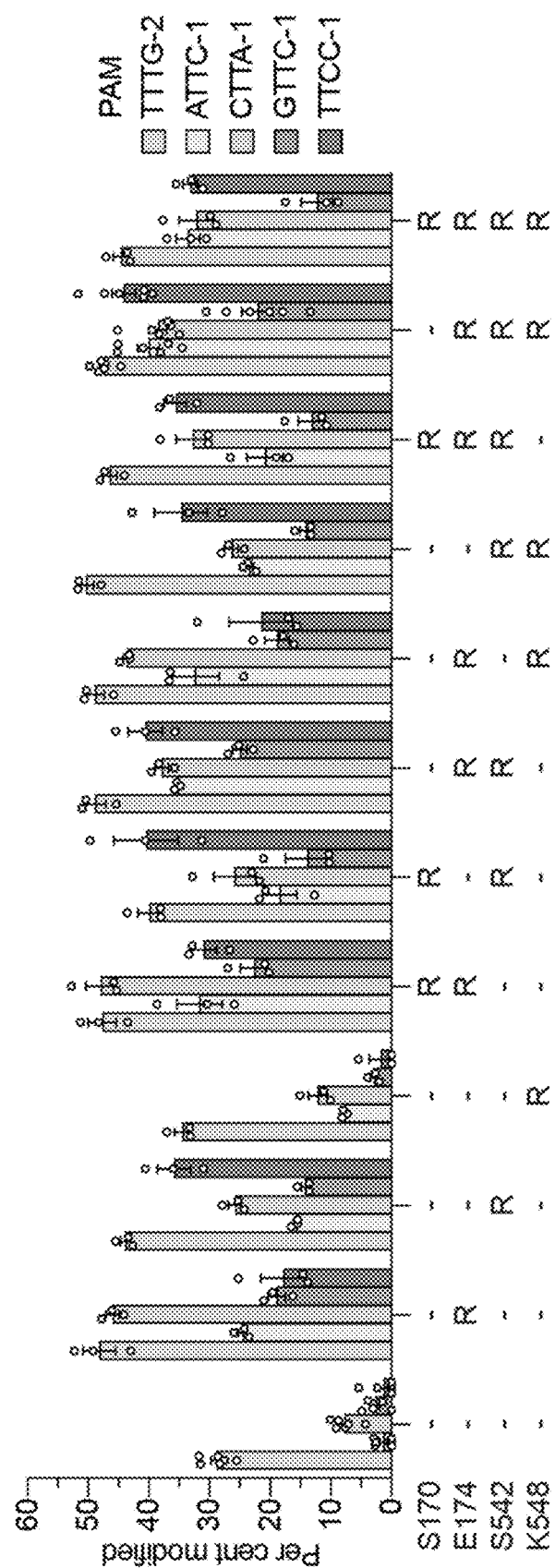
Figure 20D:
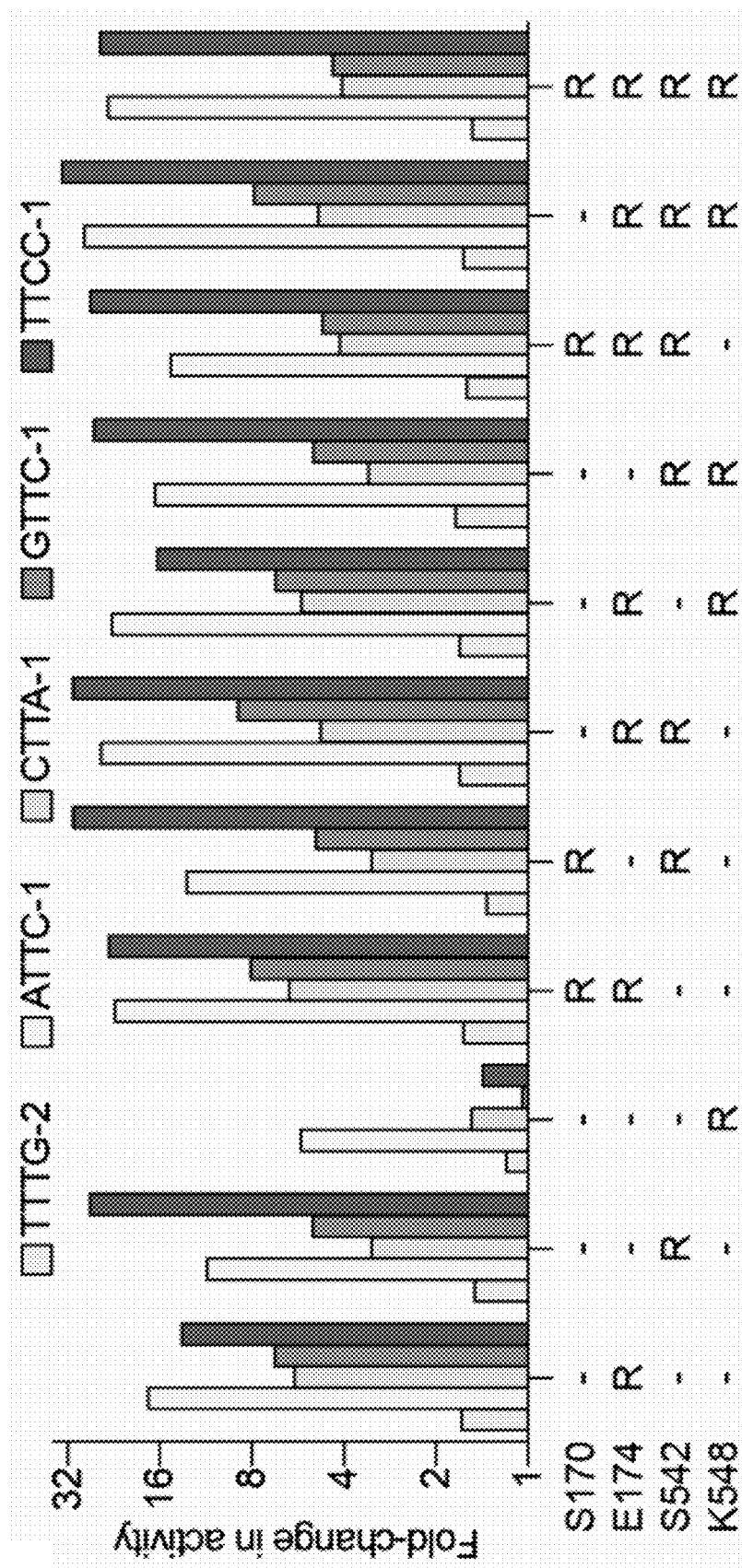

Combinatorial testing of these substitutions in human cells revealed substantial increases in activity compared to wild-type AsCas12a on four additional sites bearing non-canonical PAMs (ATTC, CTTA, GTTC, and TTCC), and recapitulated the observation of improved activity on a canonical TTTG PAM site (FIG. 15A). Some of the most prominent increases in activity and expansions in targeting range were observed when the E174R and S542R substitutions were combined, as E174R/S542R and E174R/S542R/K548R variants displayed between 4- and 32-fold improved activities on non-canonical PAM sites compared to AsCas12a, and nearly 2-fold enhanced activities on the canonical PAM site (FIG. 20D). Thus, we selected these two variants for further characterization.

To comprehensively profile the expanded PAM preferences of our AsCas12a variants, we optimized an unbiased in vitro high-throughput PAM determination assay (PAMDA; FIGS. 21A-21H). We first purified and assayed wild-type and E174R/S542R/K548R AsCas12a (FIG. 21A). The in vitro cleavage activities of these Cas12a nucleases were verified on plasmid substrates encoding two distinct spacer sequences with various targetable and non-targetable PAMs, corroborating previously observed improvements in activity in human cell assays (FIGS. 21B and 21C). We then adapted this workflow to perform the PAMDA by constructing two separate plasmid libraries encoding the same two spacer sequences, but now instead harboring a random 8-mer sequence in place of the PAM (FIG. 21D). Time-course cleavage reactions were performed on the two linearized plasmid libraries using AsCas12a/crRNA ribonucleoprotein (RNP) complexes, followed by PCR amplification and sequencing of the non-cleaved substrates to calculate the rates at which targetable PAMs are depleted (FIG. 21D). Strong correlations were observed between the PAM-specific rate constants (k; for depletion of the PAM from the population over time) on the most spacer proximal 4 nt PAM sequences between replicates and spacers across separate PAMDA experiments (FIGS. 21E and 21F, respectively). Binning of the count of $\log_{10}$ k values for each of the possible 256 4 nt PAMs for both wild-type and E174R/S542R/K548R AsCas12a suggested an approximate threshold for bona fide PAM recognition and targeting in the –2.25 $\log_{10}$ k range (FIG. 21G). Analysis of the depletion curves from the PAMDA data for the same PAM/spacer combinations used for optimization of the in vitro assay using static PAM substrates revealed consistent cleavage profiles (FIG. 21H).

Figure 15B:
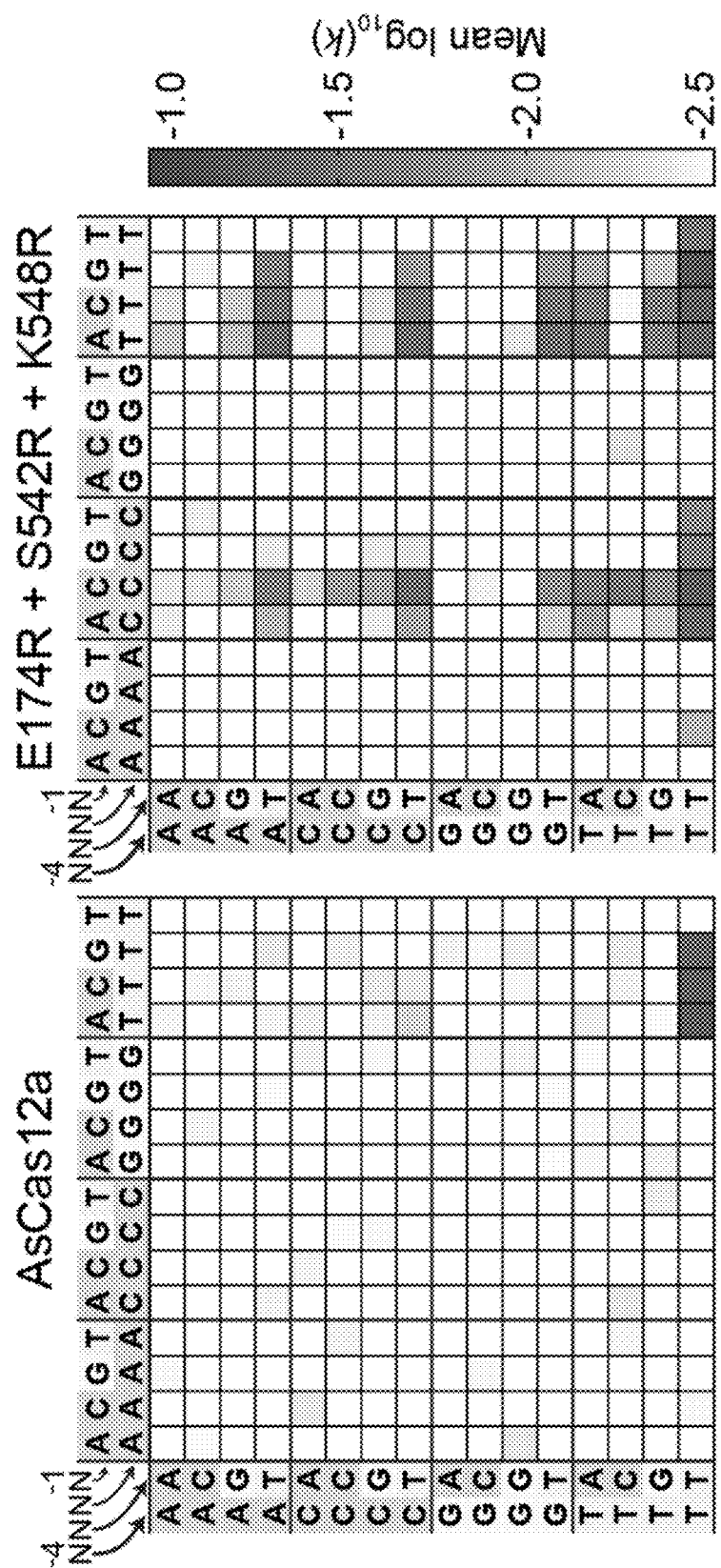

To perform the PAMDA, purified Cas12a nucleases are complexed with crRNAs to interrogate plasmid libraries harboring randomized 8 nt sequences in place of the PAM, enabling the calculation of in vitro rate constants (k) for depletion of targetable PAMs from the population. Plots of the mean $\log_{10}$ k values for wild-type AsCas12a on all possible 4 nt PAM sequences revealed that, as expected, targeting was only efficient on sites with TTTV PAMs (FIG. 15B). Conversely, the E174R/S542R/K548R variant displayed a dramatically broadened targeting of PAM classes that included TTTN and TTCN (TTYN); ATTV, CTTV, and GTTV (VTTV); TATV and TGTV (TRTV); and many additional PAMs (FIG. 15B). Importantly, this analysis also supported our observation that the variant maintains potent recognition of canonical TTTV PAMs.

Next, to gain a more complete understanding of the targeting range improvements conferred by each substitution, we deployed the PAMDA on the single and double substitution intermediate variants necessary to generate E174R/S542R/K548R (FIG. 22A). Consistent with our human cell assay data (FIG. 15A), this analysis revealed that the E174R/S542R variant also displayed improved activities across a broad range of PAMs. A comparison of the mean $\log_{10}$ k PAMDA values for E174R/S542R and E174R/S542R/K548R on NNYN PAMs demonstrated that both variants possess expanded targeting ranges (FIG. 22B), suggesting that the E174R and S542R substitutions are responsible for much of the broadened targeting range. Interestingly, the identities of these residues are not shared across Cas12a orthologs, but exist in regions where the flanking amino acids are strictly conserved (FIG. 22C)

Figure 15C:
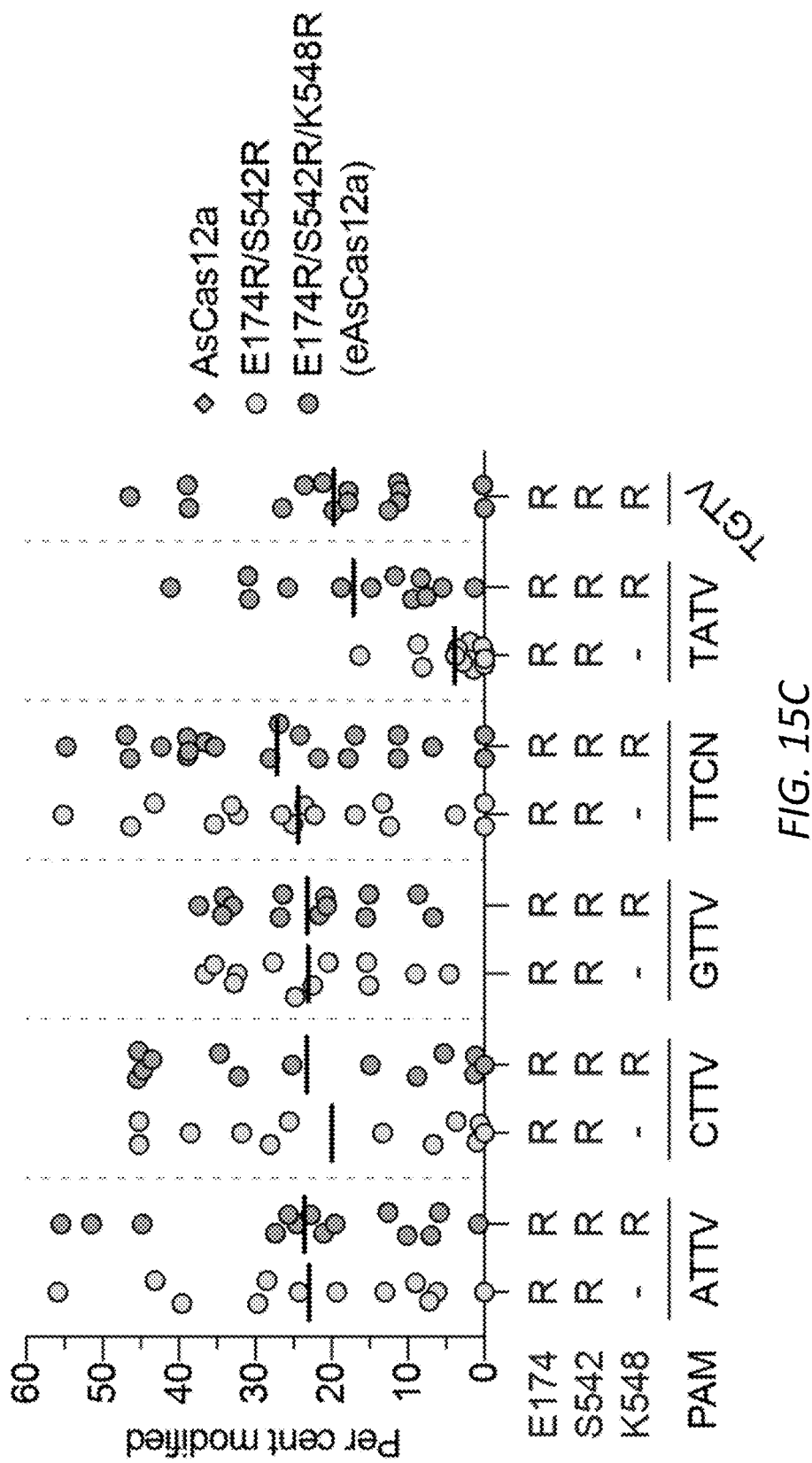
Figure 15E:
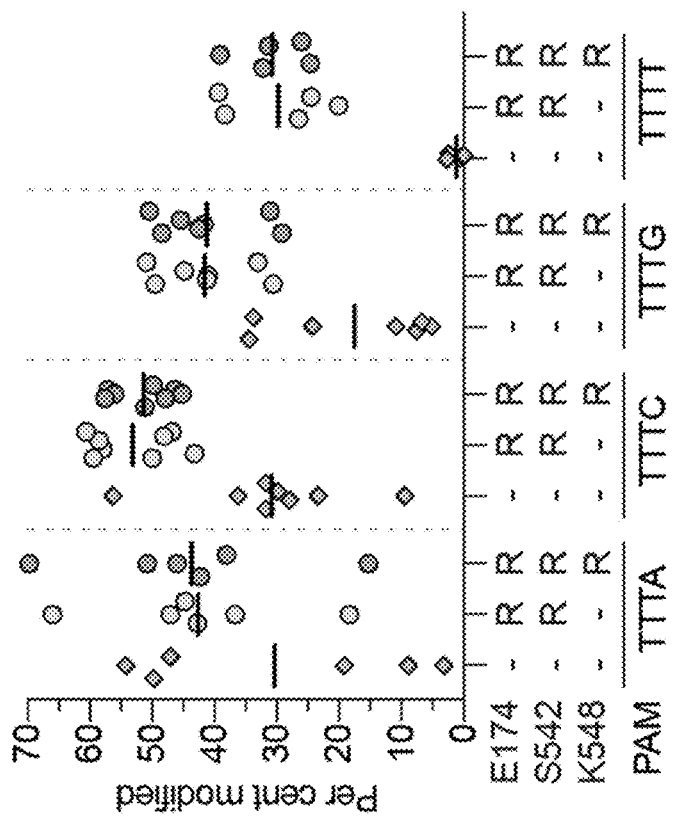
Figure 15D:
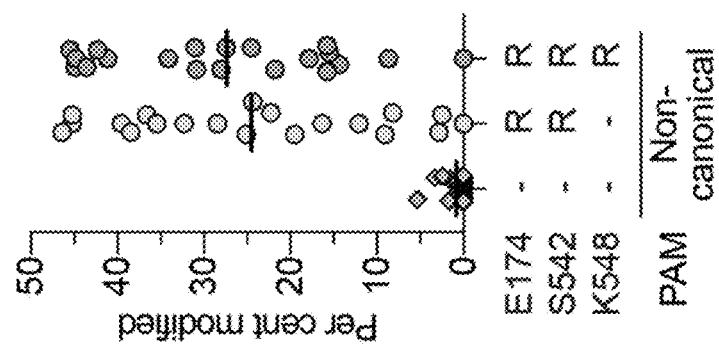
Figure 23A:
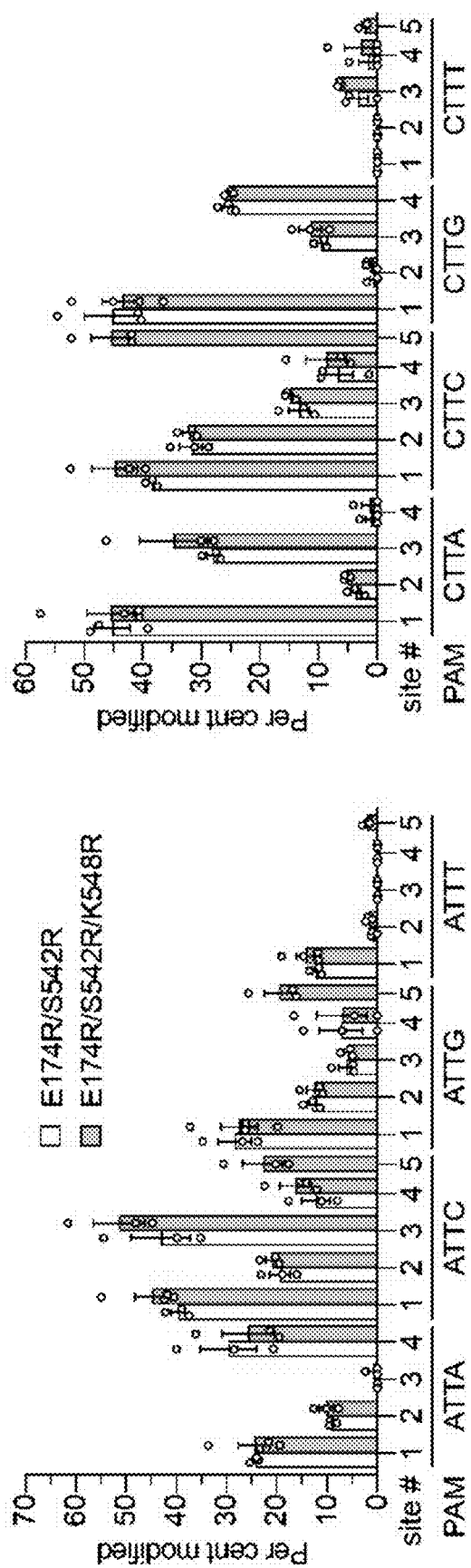
Figure 23A:
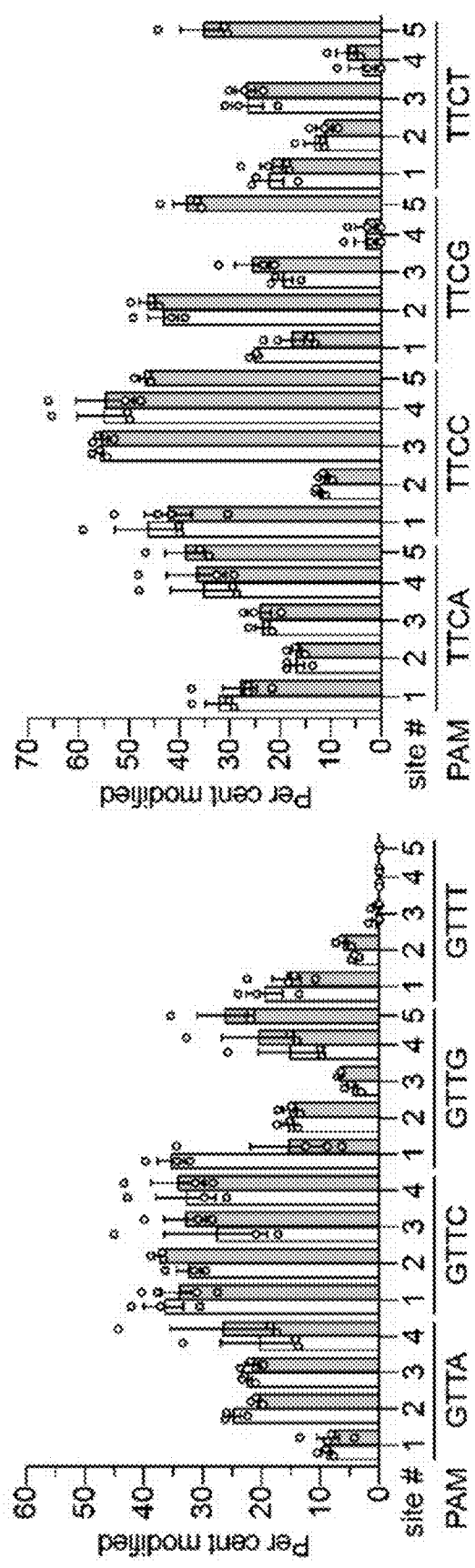
Figure 23F:
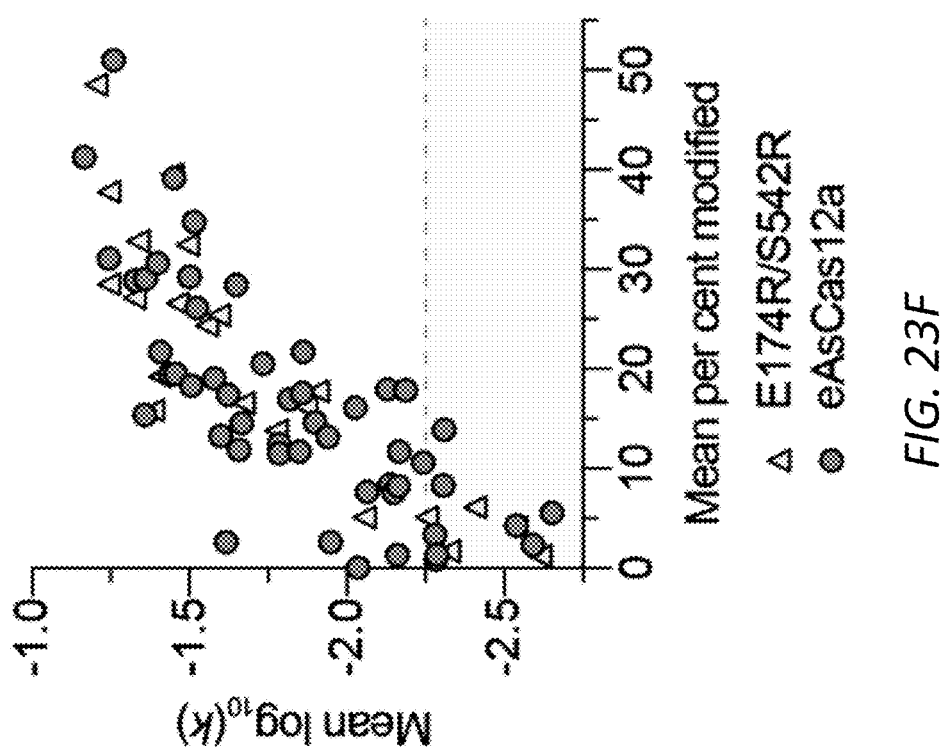

To further explore the targeting range improvements exhibited by the E174R/S542R and E174R/S542R/K548R variants in human cells, we characterized their activities on sites that the PAMDA identified as targetable or non-targetable, including 75 VTTN and TTCN sites harboring PAMs that should now mostly be accessible with either variant (VTTT as negative controls; FIG. 23A), and 17 sites with TATN PAMs where TATV sites should be effectively targeted only with E174R/S542R/K548R (FIG. 23B). As predicted by the PAMDA results for the variants, we observed consistent and robust targeting with E174R/S542R and E174R/S542R/K548R on sites with VTTV and TTCN PAMs, ineffective modification of VTTT sites, and only effective targeting of TATV sites with the E174R/S542R/K548R variant (FIGS. 15C, 23A and 23B). Importantly, both variants were far more effective at targeting these non-canonical PAM sites as compared to wild-type AsCas12a (FIGS. 15D, 19A, and 23C). Because the PAMDA results for the E174R/S542R/K548R variant indicated that it could also potentially recognize an expanded range of PAMs beyond those that we already tested, we examined 15 sites harboring TGTV PAMs and 83 other sites in human cells bearing alternate PAMs at or near a mean $\log_{10}$(k) PAMDA threshold of –2.25 (FIGS. 23D and 23E, respectively). We observed robust modification of many of the sites harboring these additional non-canonical PAMs, and also a strong correlation between the mean human cell activities and PAMDA ks for most PAMs (FIG. 23F).

One additional observation from the PAMDA was that the E174R/S542R and E174R/S542R/K548R variants could now target TTTT PAMs previously inaccessible with wild-type AsCas12a (FIG. 22A). To determine whether these variants could effectively target sites with non-canonical TTTT PAMs, while also maintaining activity on canonical TTTV PAMs, we compared their activities on 25 additional TTTN sites in human cells (FIG. 23G). Consistent with our earlier findings (FIG. 15A), we observed a roughly 2-fold increase in modification of sites bearing each TTTV PAM, as well as greatly improved targeting of sites encoding TTTT PAMs (FIG. 15E). These results suggest that variants bearing the combination of E174R and S542R not only dramatically improve targeting range, but can also surprisingly enhance targeting of sites with TTTN PAMs (FIG. 23H).

Figure 15F:
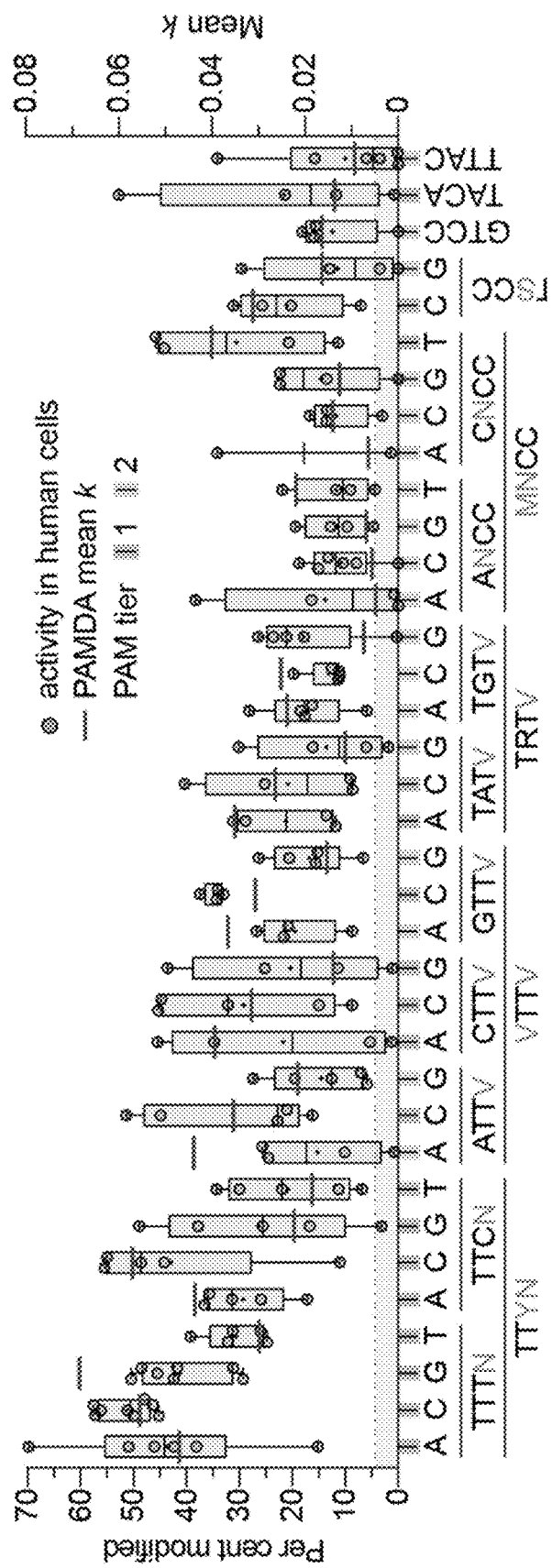

Overall, the E174R/S542R/K548R variant, henceforth referred to as enhanced AsCas12a (eAsCas12A), enables a dramatic expansion in targeting range and improvement of on-target activity. PAMs now accessible with eAsCas12a can be binned into confidence tiers based on consistency between PAMDA and human cell data (FIGS. 15F and 23I). We observed a strong correlation between the mean percent modification in human cells and the in vitro determined mean PAMDA ks (FIG. 23F), suggesting that the PAMDA is reasonably predictive of targetable and non-targetable PAMs in human cells. It is worth noting that the PAMDA data was generated from libraries encoding two separate spacer sequences, and it therefore possible that the PAM preference profiles observed from these libraries may not represent PAM rankings across all spacer sequences (though we did observe a good correlation between the two spacer libraries examined; FIG. 21F)

Figure 15G:
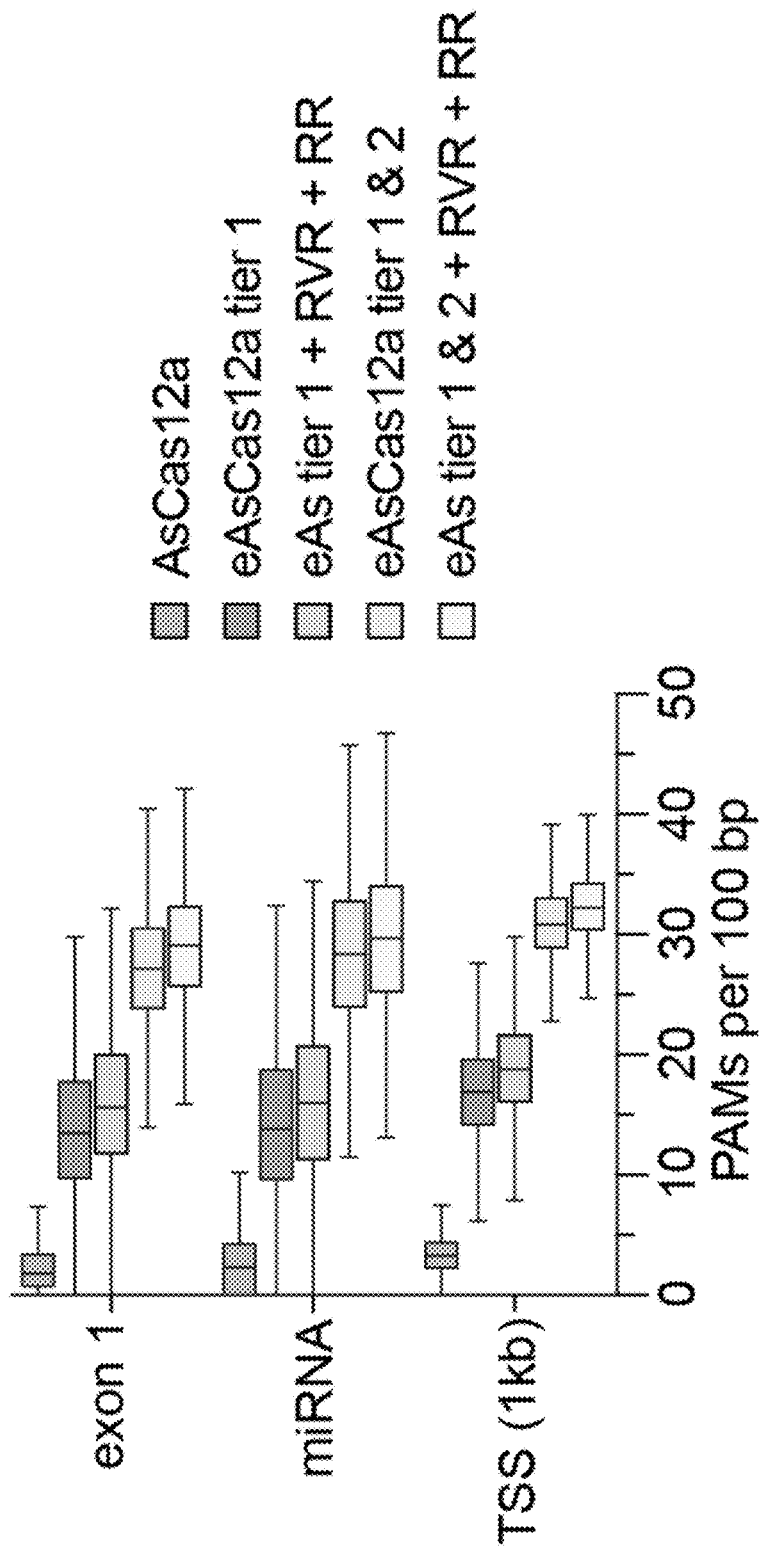

Thus, we classify PAMs that meet a stringent threshold of greater than 20% mean targeting in human cells across all sites examined and a PAMDA k greater than 0.01 as 'tier 1' PAMs (TTYN, CTTV, RTTC, TATM, CTCC, TCCC, and TACA), and PAMs that meet a medium targeting threshold of greater than 10% mean targeting in cells and a PAMDA k greater than 0.005 as 'tier 2' PAMs (RTTS, TATA, TGTV, ANCC, CVCC, TGCC, GTCC, TTAC) (FIG. 23I). Discrepant PAMs (poor correlation between human cell data and PAMDA data) and those with a mean modification in human cells of less than 10% are classified as 'tier 3' PAMs and are not recommended for most genome editing applications given our current data. For applications where targeting range may not be limiting and efficiency is the primary objective, we recommend prioritizing PAMs within tier 1 or 2 based on their PAMDA and human cell rankings (FIG. 23I). Taken together, eAsCas12a and other AsCas12a variants improve targeting by over 8-fold, enabling higher resolution targeting of coding and non-coding regions of the genome (FIG. 15G).

Improved On-Target Activity with eAsCas12a

Figure 16A:
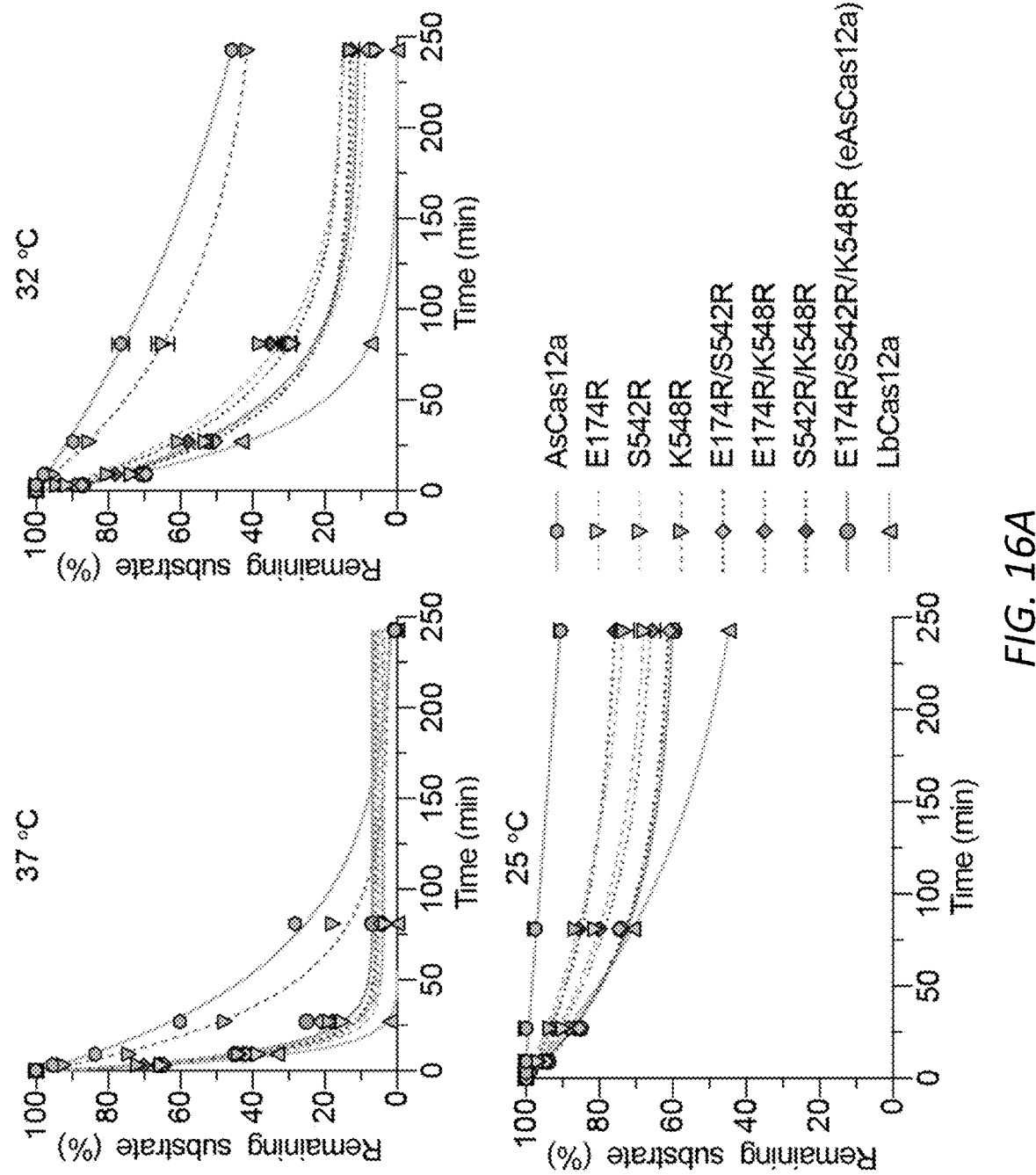

Beyond targeting range, another critical property of genome editing nucleases is potent on-target activity. We therefore sought to better understand which substitutions contribute to our observations of enhanced targeting efficiencies with eAsCas12a, as to the best of our knowledge, no amino acid substitutions have been described that increase the editing efficiencies of CRISPR nucleases. Thus, we first determined whether eAsCas12a or its derivative variants could revert DNA cleavage deficiencies at lower temperatures previously described for wild-type AsCas12a (Moreno-Mateos et al., Nat Commun., 2017, 8:2024). Comparative in vitro cleavage reactions at 37, 32, and 25° C. revealed that eAsCas12a nearly eliminates the temperature-dependent cleavage differences observed between AsCas12a and LbCas12a, and that the phenotypic recovery is largely attributable to the E174R and S542R substitutions (FIG. 16A).

A unique property of Cas12a nucleases is their ability to process individual crRNAs out of poly-crRNA transcripts (Fonfara et al., Nature, 2016, 532:517-21), simplifying multiplex targeting in cells (Zetsche et al., Nat Biotechnol., 2017, 35:31-34; Tak et al., Nat Methods, 2017, 14:1163-1166). To assess whether the enhanced activities of eAsCas12a could be extended to multiplex targeting, we compared the activities of As, eAs and LbCas12a when programmed with poly-crRNA arrays each encoding three crRNAs targeted to separate genes in human cells (FIGS. 18A-18C). In most cases, we observed superior targeting with eAsCas12a when poly-crRNA arrays were expressed from an RNA polymerase-III promoter, presumably due eAsCas12a's enhanced activity on sites with canonical PAMs (FIGS. 18A and 18B). This improvement of multiplex targeting was also observed when the poly-crRNA was expressed from an RNA polymerase-II promoter, expanding the scope of multiplex editing applications (FIG. 18C). We also designed multiplex arrays encoding two sets of proximally targeted crRNAs to generate small genomic deletions. Pairs of crRNAs were expressed from poly-crRNA transcripts or by instead transfecting pools of single crRNA plasmids into cells, and we again observed improved multiplex targeting with eAsCas12a (FIG. 18D).

Example 4 provides additional evidence to support the observation that the E174R substitution enhances on target activity.

Example 2

Variants of LbCpf1 with Altered PAM Specificity

Because AsCpf1 and LbCpf1 share a high degree of homology across the residues in the vicinity of the protein-DNA contacts surrounding the PAM (based on three-dimensional crystal structures and a primary sequence alignment, see Table 1), we made LbCpf1 PAM variants that would harbor residues at residues corresponding to the positions we mutated in AsCpf1. Single substitutions at positions T152, D156, G532, and K538 in LbCpf1 (that correspond to residues S170, E174, S542, and K548 in AsCpf1) revealed only modest increases in EGFP disruption activity against sites with non-canonical PAMs (FIG. 12A) when compared to their corresponding AsCpf1 variants (FIG. 5). However, the triple substitution LbCpf1-D156R/G532R/K538R variant (analogous to AsCpf1-E174R/S542R/K548R) exhibited a slightly more substantial increase in targeting of sites with non-canonical PAMs compared with wild-type LbCpf1 in the EGFP disruption assay (FIG. 12B).

Example 3

Variants of FnCpf1 with Altered PAM Specificity

Previous reports have suggested that FnCpf1 does not work, or has poor activity in human cells (Zetsche, Cell 2015; Kim, Nature Biotechnology 2016). Because AsCpf1 and FnCpf1 share a high degree of homology, we first sought to test whether wild-type FnCpf1 does indeed function in human cells, and then whether we could relax the previously reported PAM specificity of TTN (Zetsche, Cell 2015).

To examine the activity of FnCpf1 in human cells, we tested its activity in our human cell EGFP disruption assay against target sites that contain PAMs of the form NTTN, TNTN, and TTNN (FIG. 13A). Our results reveal that wild-type FnCpf1 can indeed mediate robust EGFP disruption in human cells against NTTN sites, with some detectable activity against TCTN and TTCN sites (FIG. 13A). Next, we compared the endogenous gene disruption activity of FnCpf1 to AsCpf1 and LbCpf1 at 10 different endogenous target sites bearing TTTN PAMs. In many cases, we observed comparable activity of FnCpf1 to AsCpf1 and LbCpf1, demonstrating that FnCpf1 does indeed function robustly in human cells (FIG. 13B).

Because FnCpf1 functions in human cells, we sought to determine whether we could generate FnCpf1 PAM variants by creating variants of FnCpf1 bearing substitutions at residues homologous to positions of AsCpf1 that led to altered PAM specificity (Table 1). Of the substitutions that we examined, single substitutions of K180R, N607R, and D616R led to increases in activity over wild-type AsCpf1 at TTTN, TNTN, and NTTN PAM sites (FIG. 13C). Additionally, a K671H mutation could increase activity against a TCTN PAM site. We also observed that variants bearing combinations of substitutions including N607R/K613R, N607R/K613V, N607R/K613V/D616R, or N607R/K613R/D616R improved activity over wild-type FnCpf1 at certain PAMs of the form TTTN, CTTN, GTTN, TATN, TCTN, TCTN, TTAN, of TTCN (FIG. 13C).

Example 4

Additional Variants of AsCpf1 with Altered PAM Specificities

Gao et al. recently published additional Cpf1 variants with altered PAM specificity (Gao et al., "Engineered Cpf1 Enzymes with Altered PAM Specificities," bioRxiv 091611; doi: https://doi.org/10.1101/091611). These variants, with their claimed activities on canonical and/or non-canonical PAMs are as follows:
1) AsCpf1-S542R/K548V/N552R—functions against TATV PAM sites
2) AsCpf1-S542R/K607R—functions optimally against TYCV PAM sites, but displays loss of activity against canonical TTTV sites.

To benchmark the triple and quadruple substitution AsCpf1 variants described herein (E174R/S542R/K548R and E174R/S542R/K548R/N551R, respectively) against the S542R/K548V/N552R variant, we compared the activity of these three variants using the EGFP disruption assay on target sites bearing canonical TTTN, TATN (reported to be recognized by the S542R/K548V/N552R variant), and PAMs with single or double base differences (FIG. 14A). For all sites tested, we observed that our triple and quadruple substitution variants outperformed the S542R/K548V/N552R variant at TTTV, TATN, and other non-canonical CTTN, GTTN, TCTN, TGTN, TTAN, TTCN, TTGN, and TCCN PAMs (FIG. 14A). Next, based on our previous observations that S170R or E174R substitutions can increase the activity of AsCpf1 variants when combined with other substitutions, we explored whether the addition of either of these substitutions to the S542R/K548V/N552R variant could also improve its activity. In comparing the S170R/S542R/K548V/N552R and E174R/S542R/K548V/N552R quadruple substitution variants to the parental S542R/K548V/N552R, we observed that the addition of the S170R or E174R substitutions substantially improved activity (with the effect of E174R being greater than S170R, yet the addition of S170R also produces improvements; FIG. 14A).

We also compared the activity of our triple and quadruple substitution AsCpf1 variants (E174R/S542R/K548R and E174R/S542R/K548R/N551R, respectively) against the S542R/K607R variant across a number of target sites in EGFP bearing the canonical TTTN PAM sequence or PAMs with a single base difference. For all of these sites, our triple and quadruple substitution variants (E174R/S542R/K548R and E174R/S542R/K548R/N551R) had roughly equal or higher levels of EGFP disruption activity when compared to the S542R/607R variant (FIG. 14B). S542R/K607R only outperformed our triple and quadruple variants on a target site with a TCCN PAM. Therefore, we added either the S170R or E174R substitutions to the S542R/K607R variant to create triple substitution S170R/S542R/K607R and E174R/S542R/K607R variants. These additional triple substitution variants performed as well or better than the S542R/K607R variant at all sites tested, notably working as well on sites with a TCCN PAM (FIG. 14B). Finally, we compared one of our triple substitution variants (E174R/S542R/K548R) with the S542R/K607R variant at a series of endogenous human gene target sites in U2OS cells bearing non-canonical PAMs (with 1, 2, or 3 base differences in the PAM). At all sites tested other than those bearing NCCC PAMs, our E174R/S542R/K548R variant performed as well as or better than the S542R/K607R variant (FIG. 14C). For the NCCC PAM sites where the S542R/K607R variant displayed higher gene disruption activity, we compared this variant to our S170R/S542R/K607R, E174R/S542R/K607R, and E174R/S542R/K607H variants and observed that in all cases, one of our triple substitution variants outperformed the S542R/K607H variant (FIG. 14C).

Example 4B

Improving the On-Target Activities of AsCas12a PAM Variants

Figure 16B:
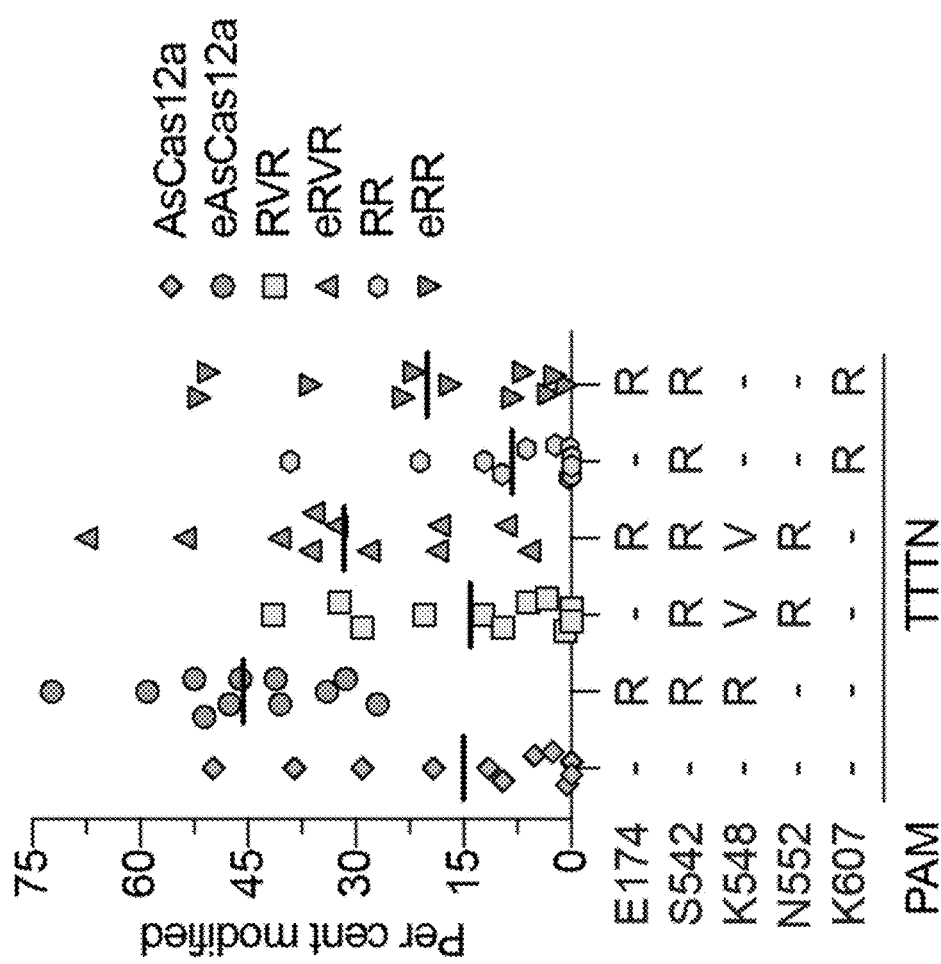

Since our results suggest that E174R and S542R lead to enhanced activities of eAsCas12a in human cells, we hypothesized that the inclusion of E174R in previously described AsCas12a variants that already encode S542R could also improve their activities. Thus, the E174R substitution was combined with the RVR (S542R/K548V/N552R) and RR (S542R/K607R) variants to create enhanced versions of these nucleases (eRVR and eRR, respectively). Comparison of the activities of the eAsCas12a, RVR, eRVR, RR, and eRR variants against 11 sites with TTTN PAMs in human cells (FIG. 24A) revealed that while the previously published RVR and RR variants have similar or weaker activities compared to wild-type AsCas12a, the addition of E174R to create the eRVR and eRR variants led to greater than 2-fold increases in their activities (albeit still lower than eAsCas12a; FIG. 16B). These results reinforce the observation that variants bearing the combination of E174R and S542R can improve on-target activity.

Next, because our PAMDA assessment of eAsCas12a revealed recognition of the primary PAMs previously reported as accessible by the RVR and RR variants (TATV and TYCV PAMs, respectively; FIG. 15B), we compared eAsCas12a to the published and enhanced versions of these nucleases at such sites in human cells. Across 12 TATN sites (FIG. 24B), we observed that eAsCas12a displayed roughly equivalent activity to the RVR variant (FIG. 16C). Interestingly, the addition of E174R to RVR led to a 2-fold improvement in activity, suggesting eRVR as the optimal variant for applications where targeting TATN sites is the primary objective (FIG. 16C). We then assessed eAsCas12a, RR, and eRR on 29 sites bearing TYCN PAMs in human cells (FIG. 24C). eAsCas12a exhibited higher modification compared to RR across the 18 TTCN sites, whereas the eRR variant containing E174R had comparable activity to eAsCas12a (FIG. 16D). Further comparison of these variants on 11 TCCN sites revealed that while the RR variant is a more effective nuclease compared to eAsCas12a on sites with TCCN PAMs, once again the E174R-containing eRR variant resulted in the most robust modification across all TCCN sites (FIG. 16D).

Figure 16E:
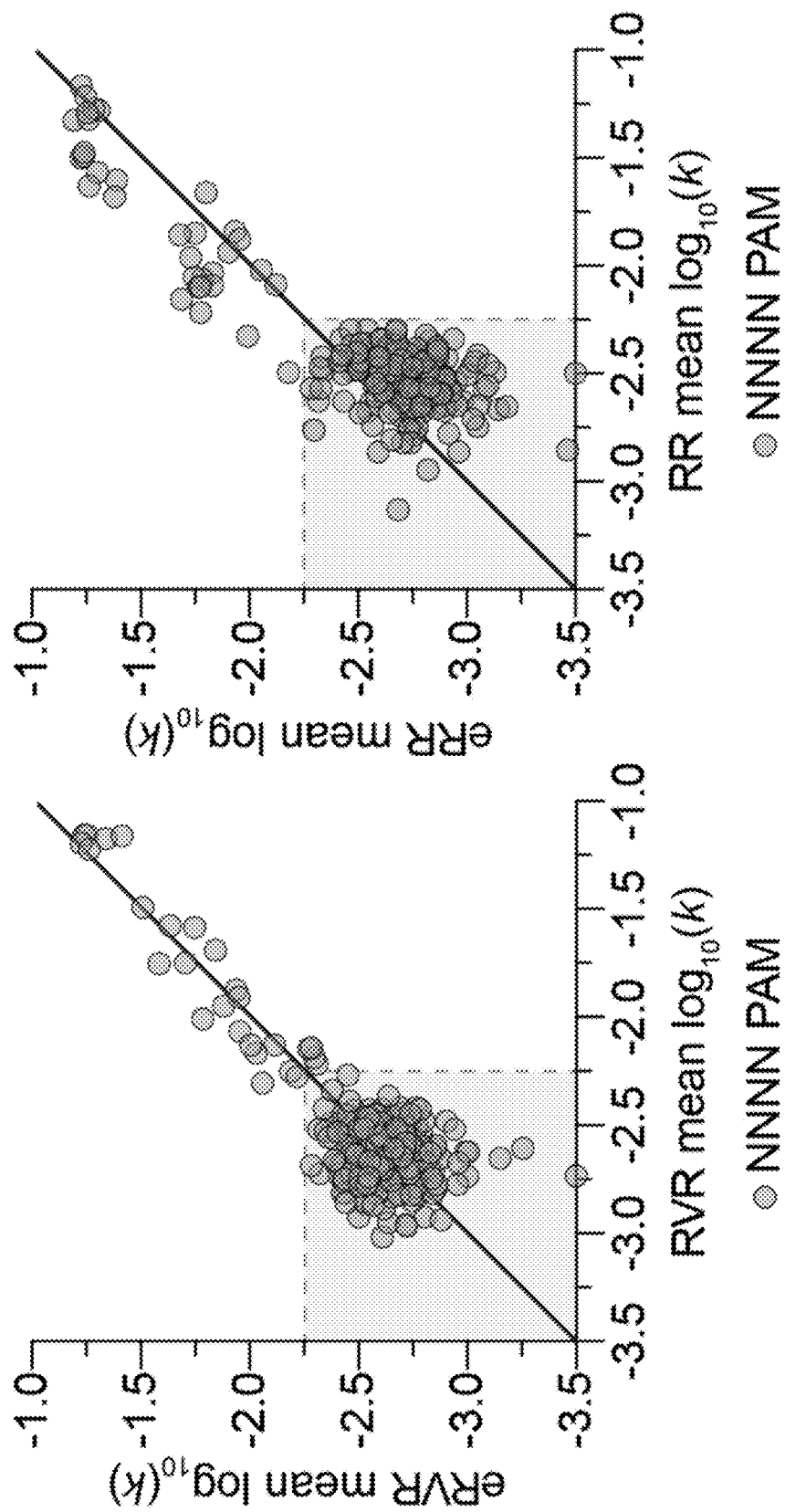
Figure 24D:
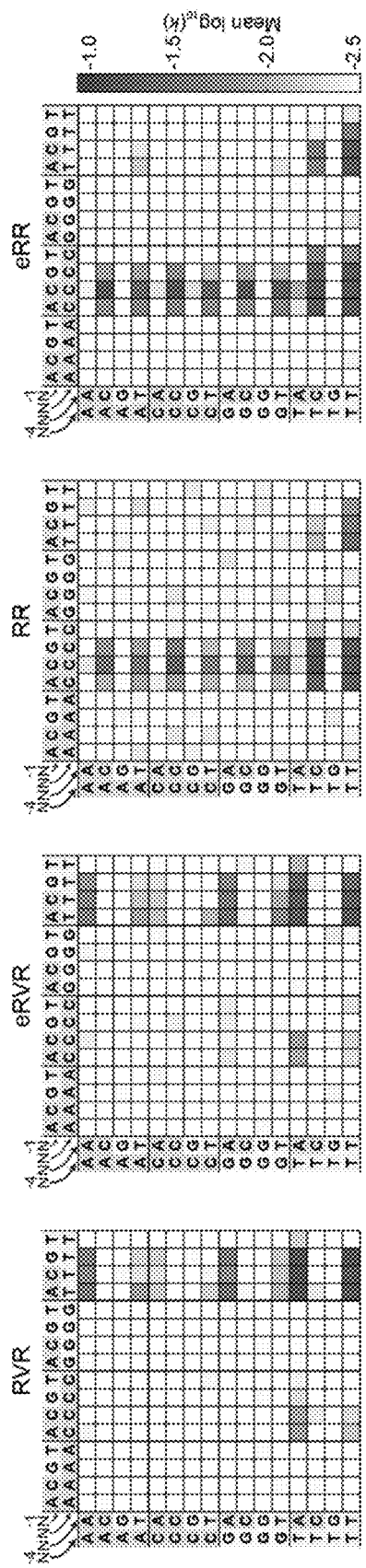
Figure 24E:
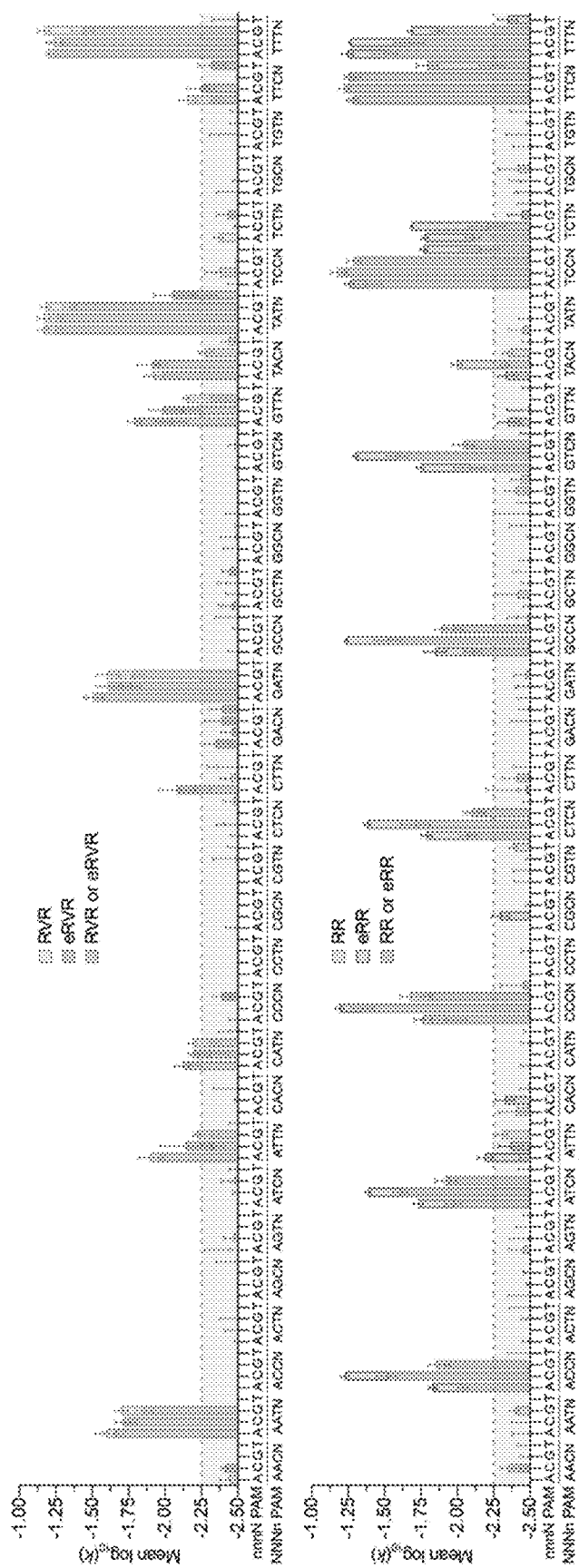

To determine whether the targeting range of the enhanced eRVR and eRR variants had been altered by the addition of E174R, we applied the PAMDA to the RVR, RR, and their E174R enhanced variants (FIG. 24D). Consistent with our human cell data, we observed that the eRVR and eRR nucleases had similar targeting range to their parental RVR and RR variants, but that their on-target potency was improved by the addition of the E174R substitution (FIGS. 16E and 24E). Taken together, these results demonstrate that the E174R and S542R substitutions not only improve targeting range, but that they can also improve the on-target activities of AsCas12a nucleases.

Example 5

Enhancing the Genome-Wide Specificity of eAsCas12a

Figure 17C:
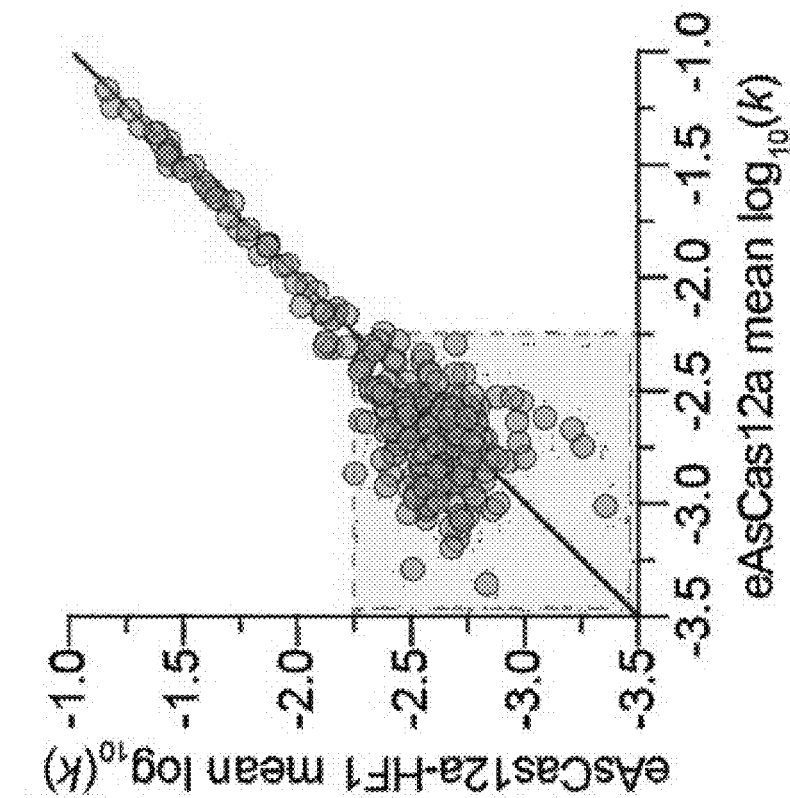
Figure 17B:
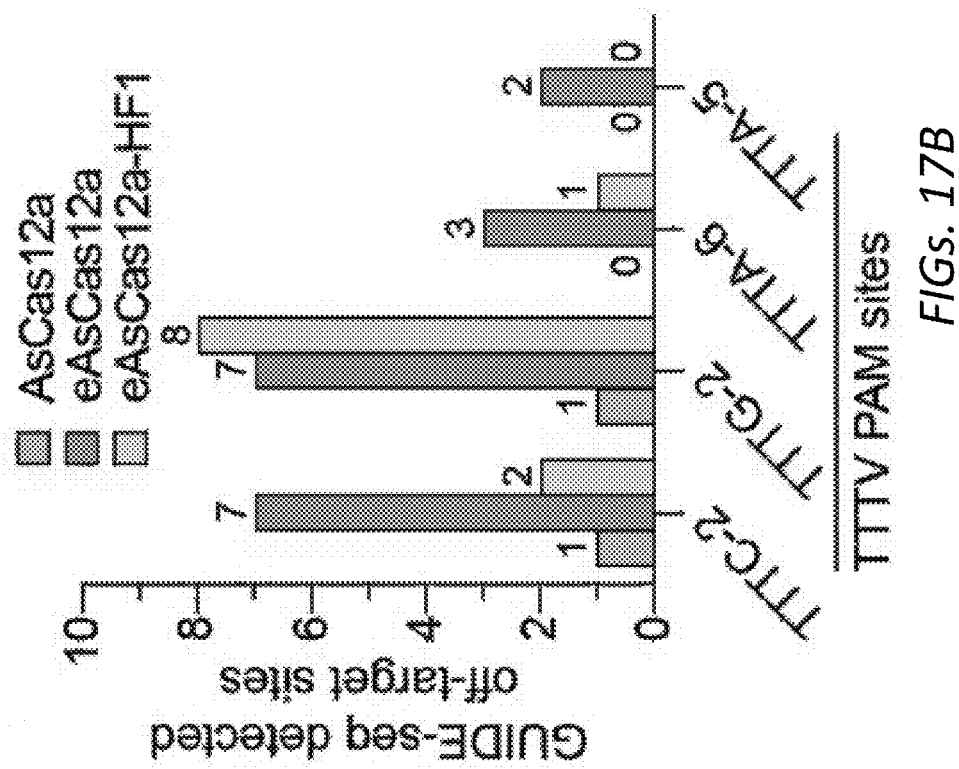
Figure 17D:
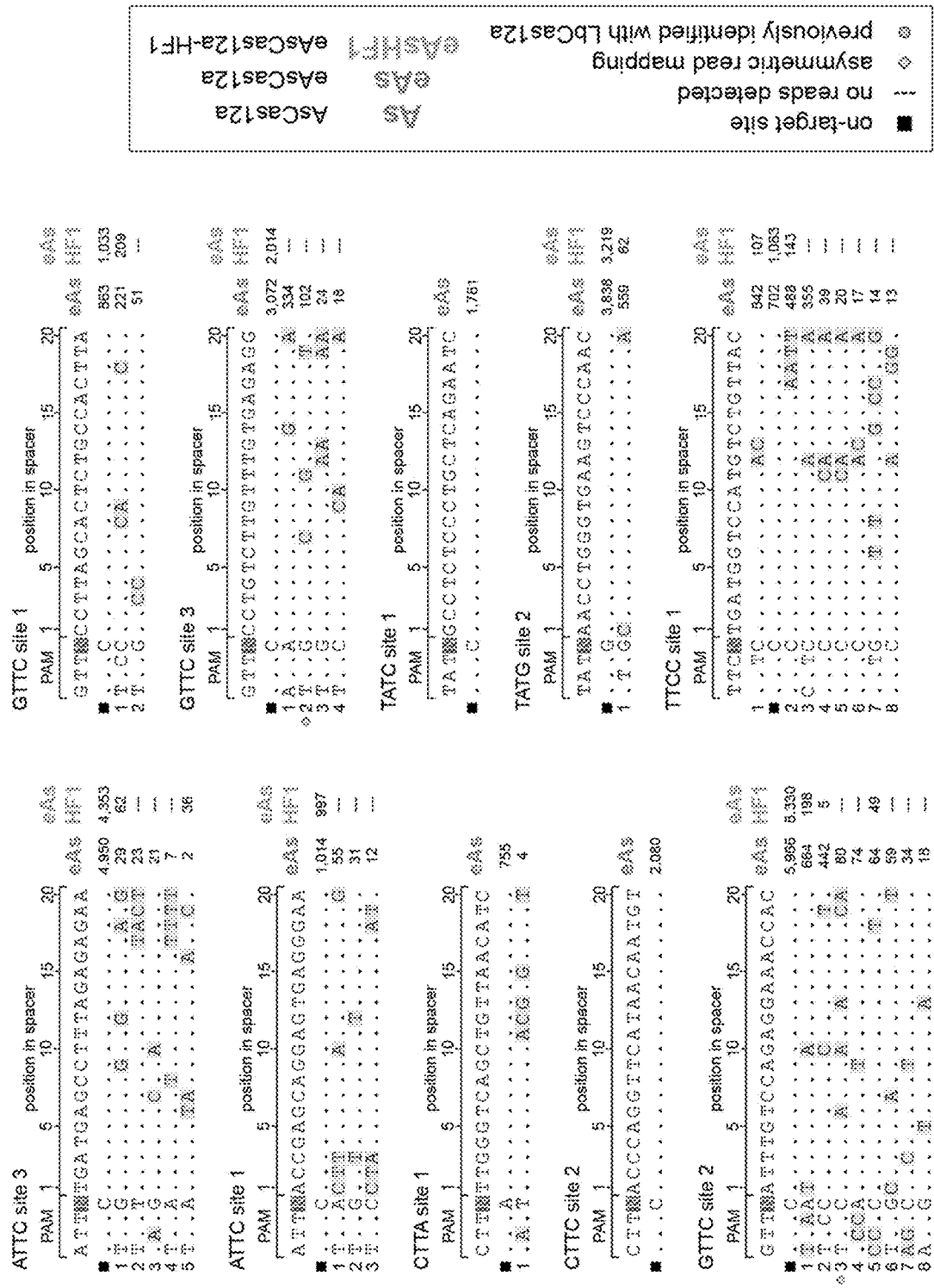

Given that eAsCas12a exhibits enhanced activity and relaxed PAM recognition compared to wild-type AsCas12a, we sought to compare the specificities of these nucleases as their ability to distinguish on- from off-target sites is critical for both research and therapeutic applications. In this regard, we and others have previously shown that wild-type Cas12a nucleases possess robust genome-wide specificities and are relatively intolerant of mismatched off-target sites that harbor single or double mismatches in the immediately PAM proximal, middle, and PAM distal regions of the spacer (Kleinstiver et al., Nat Biotechnol., 2016, 34:869-74; Kim et al., Nat Biotechnol., 2016, 34:863-8; WO2018/022634). Therefore, we used the genome-wide, unbiased identification of DSBs enabled by sequencing (GUIDE-seq) method (Tsai et al., Nat Biotechnol., 2015, 33:187-197) to compare the genome-wide specificities of As and eAsCas12a on four sites with TTTV PAMs (FIGS. 25A-25D). Few off-targets were detected by GUIDE-seq with wild-type AsCas12a, and we observed an increase in the number of off-targets for eAsCas12a (FIGS. 17A and 17B). Many of the off-targets observed for eAsCas12a were either previously identified in GUIDE-seq experiments with LbCas12a (Kleinstiver et al., Nat Biotechnol., 2016, 34:869-74), contained mismatches in positions known to be tolerant of nucleotide substitutions (Kleinstiver et al., Nat Biotechnol., 2016, 34:869-74; Kim et al., Nat Biotechnol., 2016, 34:863-8), or encoded now-targetable non-canonical PAMs (FIG. 17A).

Figure 25E:
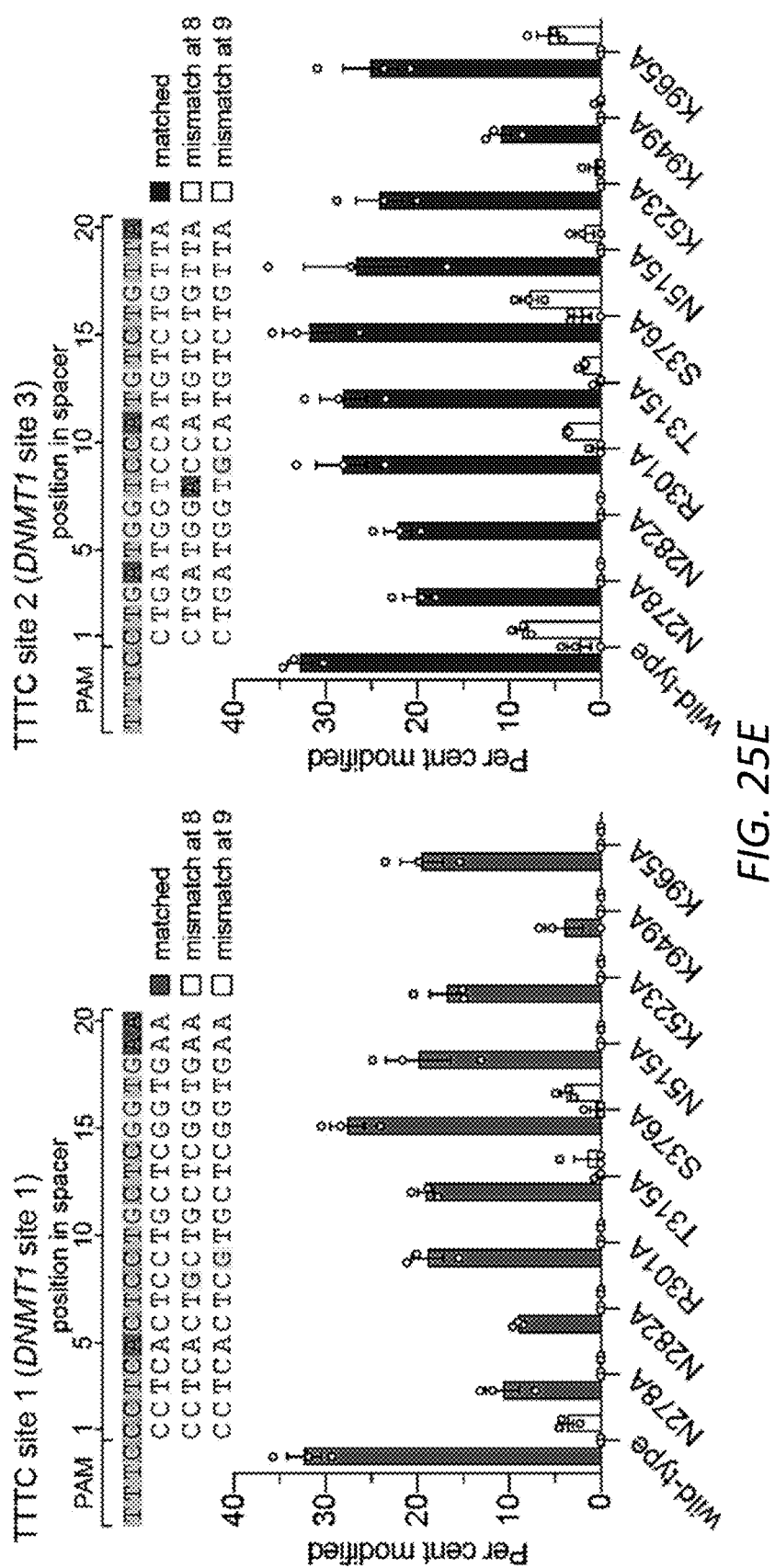
Figure 25F:
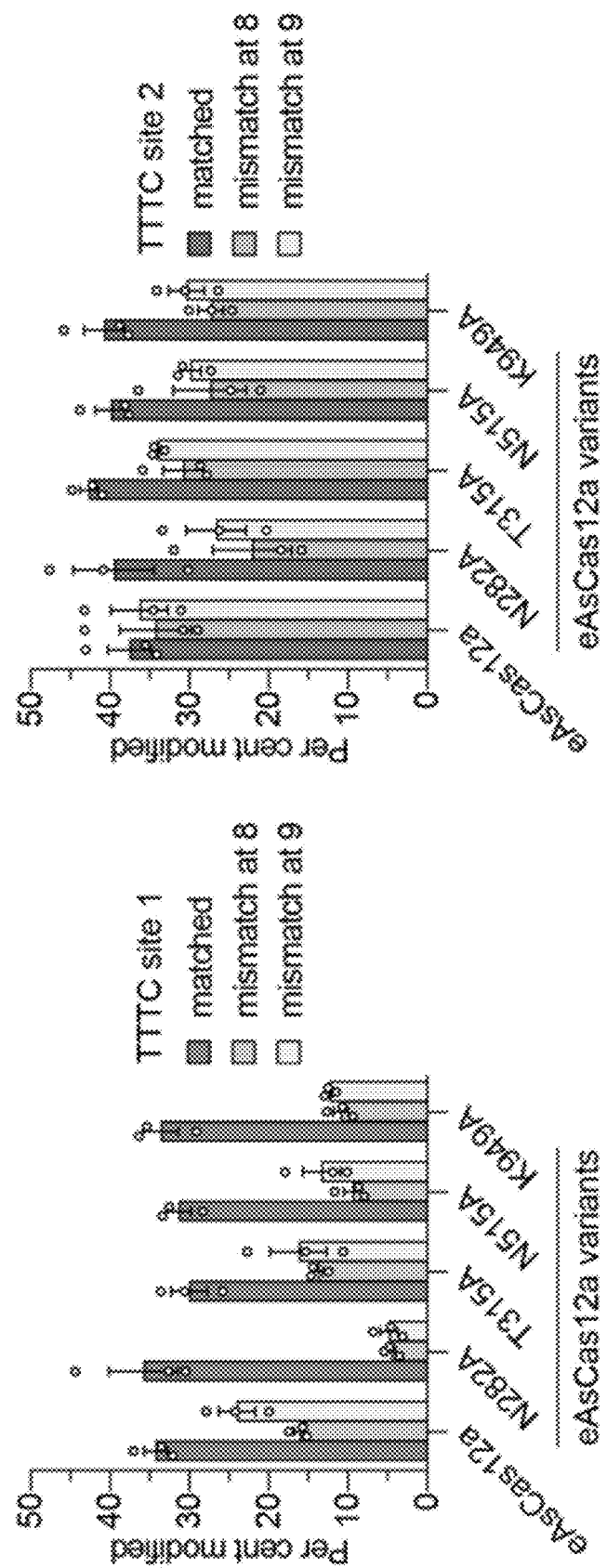
Figure 25G:
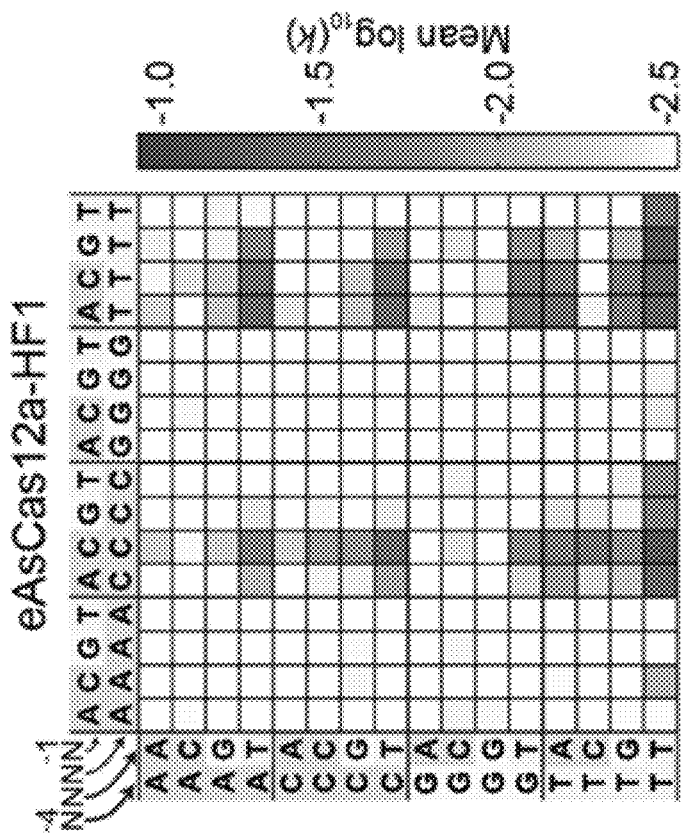
Figure 25G:
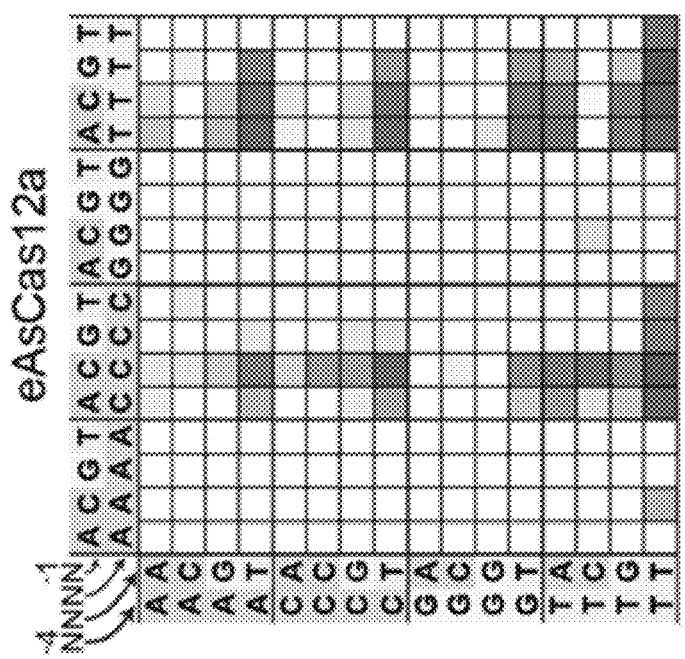
Figure 25H:
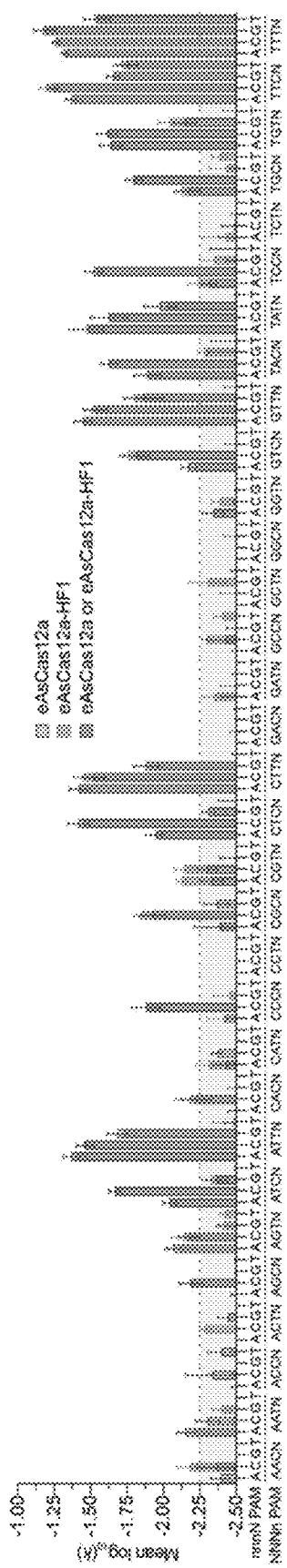
Figure 25I:
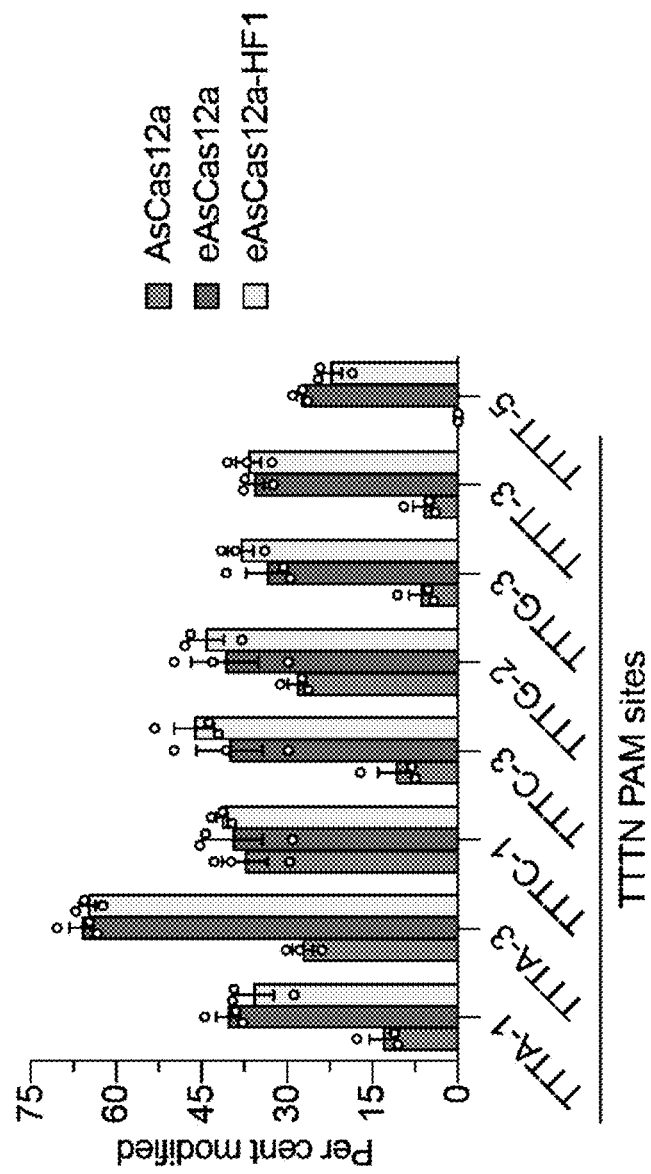
Figure 25J:
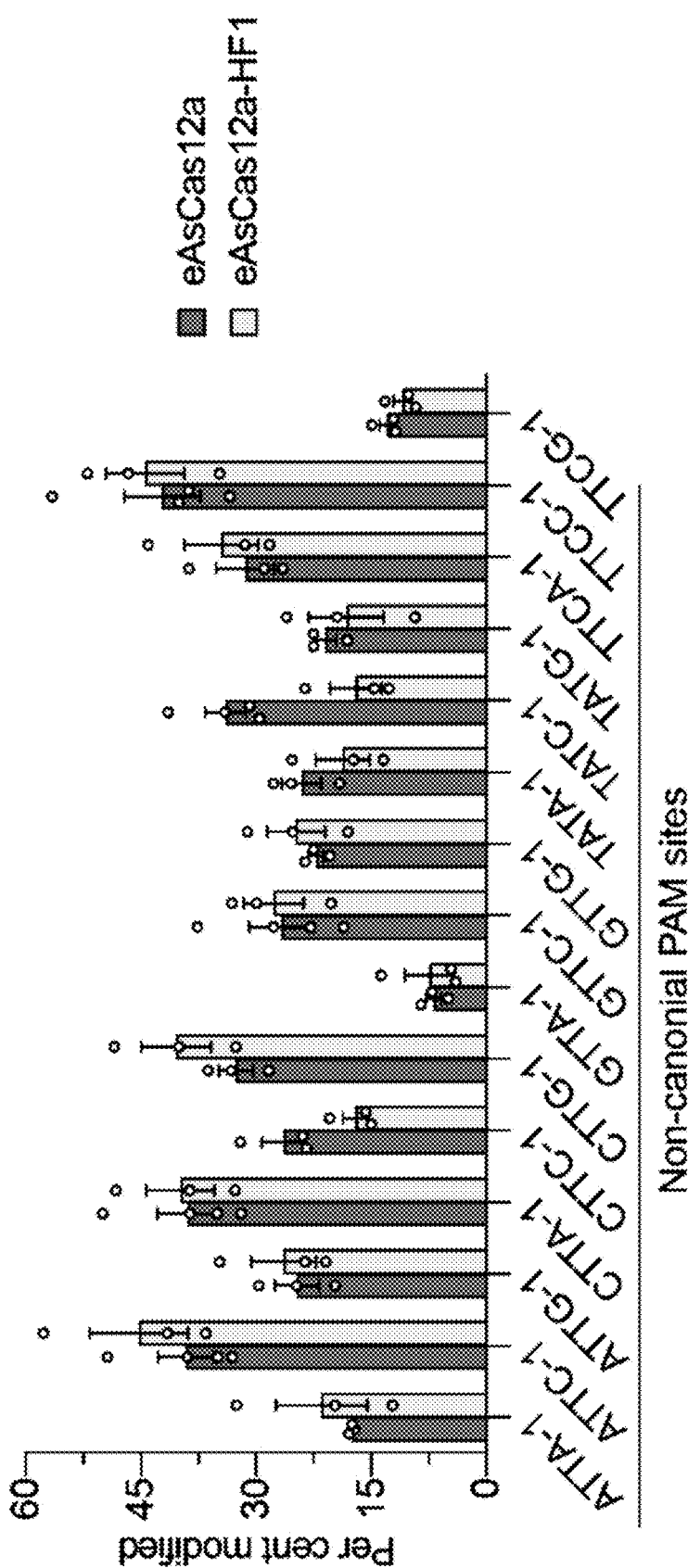

To explore whether a directed evolution method could be used to improve the fidelity of eAsCas12a, we examined the impact of amino acid substitutions at residues in AsCas12a predicted to make non-specific contacts to DNA. We assayed the single-mismatch tolerance of nine different putative high-fidelity (HF) substitutions (including the previously described K949A variant), and observed that while some substitutions improved the single mismatch tolerance profile of AsCas12a across two sites, many also reduced activity with the matched crRNA (FIG. 25E). We combined the most promising substitutions with eAsCas12a, and observed that the N282A version of eAsCas12a (named eAsCas12a-HF1) yielded the most desirable improvements in single mismatch intolerance and maintenance of on-target activity (FIG. 25F). Assessment of eAsCas12a and eAsCas12a-HF1 using the PAMDA revealed nearly identical PAM preference profiles (FIGS. 25G and 25H), suggesting that the N282A HF mutation does not alter PAM recognition or targeting range (FIG. 17C).

Next, to determine whether eAsCas12a-HF1 can improve genome-wide specificity, we performed GUIDE-seq using the same four previously examined TTTV PAM targeted crRNAs. Compared to eAsCas12a, we observed a reduction in both the number and frequency at which off-targets were detected with eAsCas12a-HF1 for 3 out of 4 crRNAs (FIGS. 17A and 17B), where their specificity profiles now more closely resembled that observed for wild-type AsCas12a. Additional GUIDE-seq experiments were performed to compare eAsCas12a and eAsCas12a-HF1 across sites with non-canonical PAMs (FIGS. 17D and 25B-25D), and we again observed reductions in the number and frequency of off-targets with eAsCas12a-HF1 compared to eAsCas12a (FIGS. 17E and 17F, respectively).

Figure 25K:
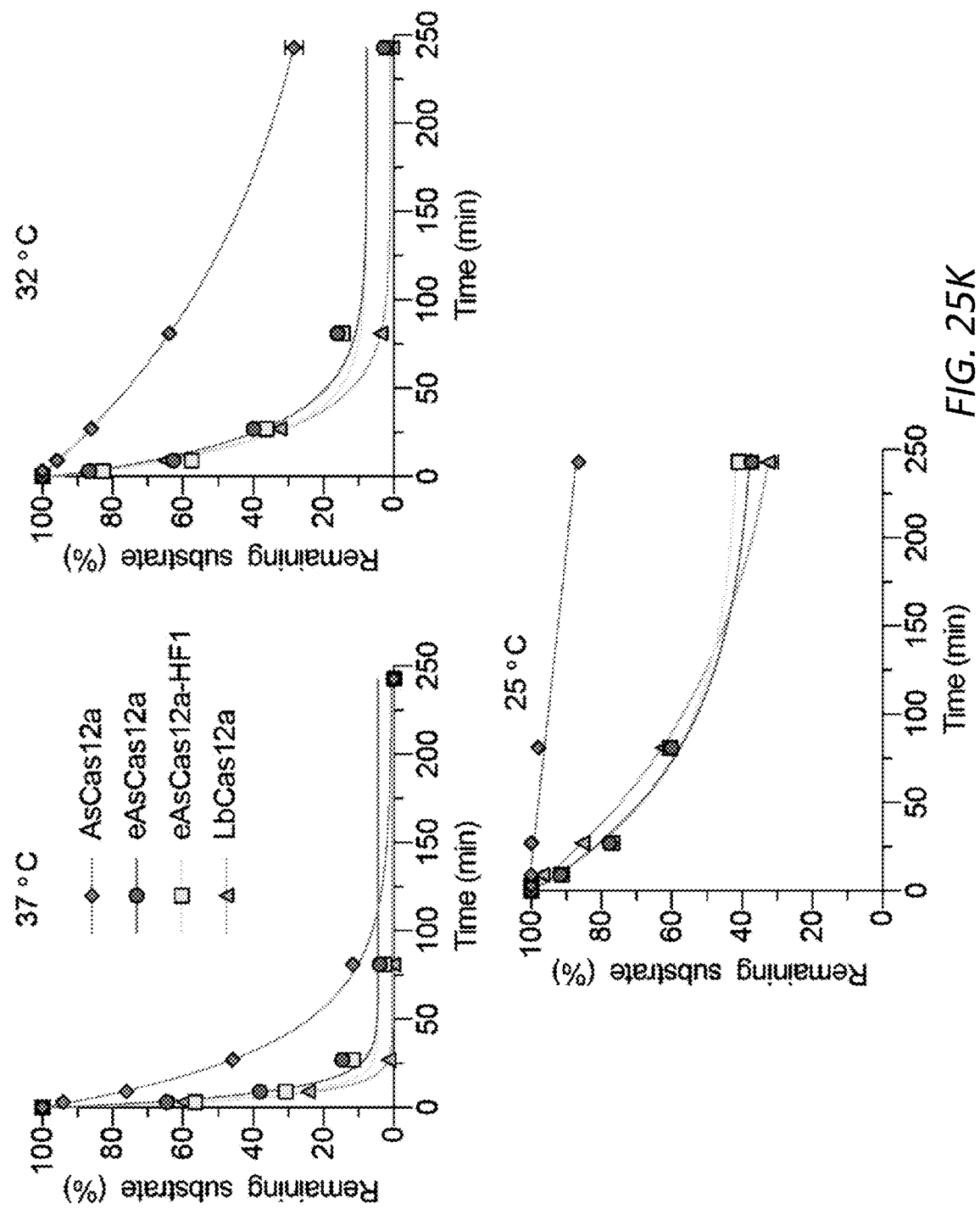

We then compared the on-target activities of eAsCas12a and eAsCas12a-HF1 across canonical and non-canonical PAM sites (FIGS. 25I and 25J, respectively) to examine whether the N282A substitution impacts targeting efficiency. We observed similar gene modification across 8 TTTN PAM sites (again with nearly 3-fold greater efficiency relative to wild-type AsCas12a; FIG. 17G), and comparable activities between eAsCas12a and eAsCas12a-HF1 on 15 sites bearing non-canonical PAMs (FIG. 17H). Moreover, in vitro cleavage assays to assess temperature tolerance revealed similar cleavage profiles between eAsCas12a, eAsCas12a-HF1, and LbCas12a at 37, 32, and 25° C. (FIG. 25K). Together, these results demonstrate that eAsCas12a-HF1 can improve genome-wide specificity while maintaining important targeting range, increased activity, and temperature tolerance properties.

Example 6

Figure 26A:
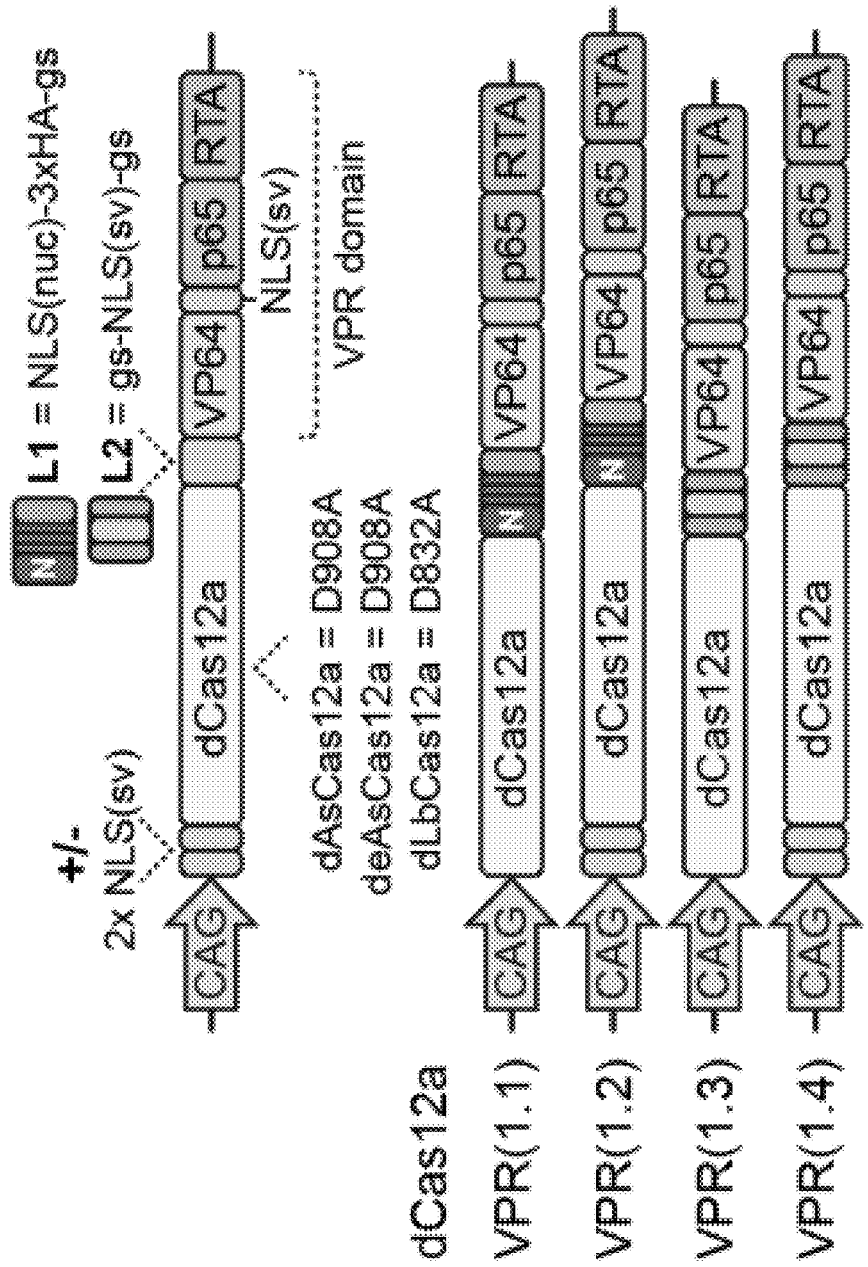
Figure 26E:
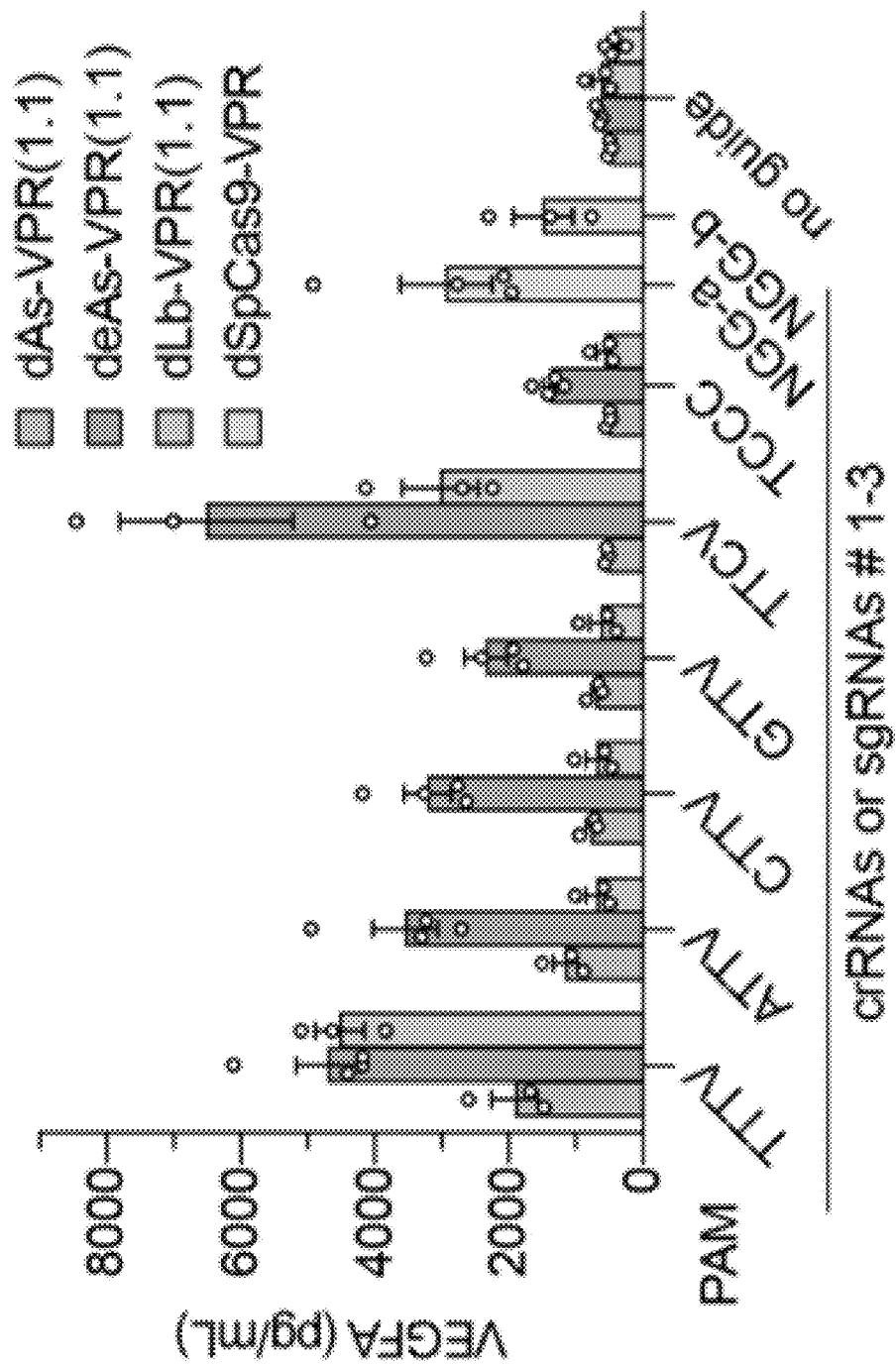
Figure 26F:
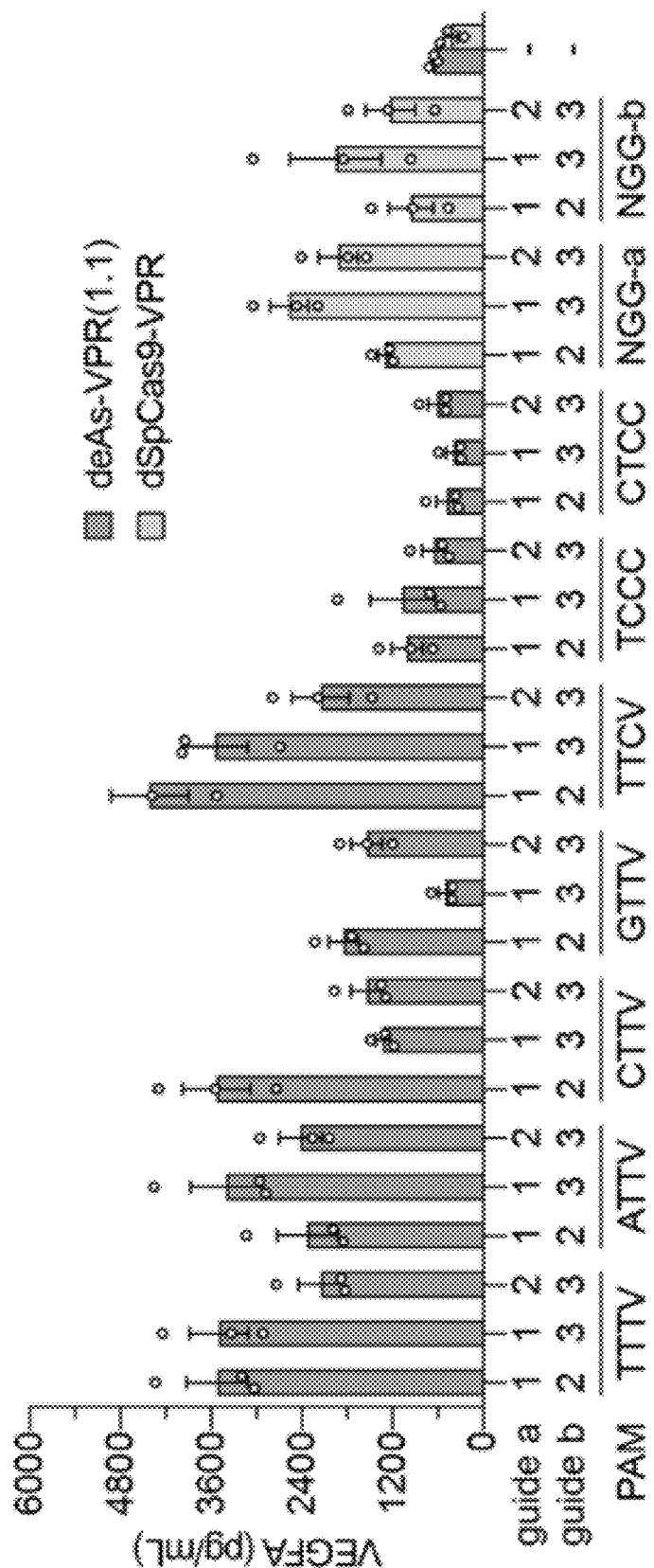

Leveraging the Enhanced Properties of eAsCas12a for Gene Activation and Epigenome Editing Applications Another prominent adaptation of CRISPR-Cas12a has been for epigenome editing, where fusions of DNase inactive Cas12a (dCas12a) to heterologous effectors have been shown to modulate gene expression. We previously demonstrated that dLbCas12a fusions to the synthetic VPR transactivation domain (a combination of VP64, p65, and Rta; Chavez et al., Nat Methods., 2015, 12:326-8) mediated more potent gene activation compared to equivalent dAsCas12a fusions in human cells (Tak et al., Nat Methods, 2017, 14:1163-1166). To explore whether eAsCas12a could improve epigenome editing compared to LbCas12a effectors, we first designed and tested different configurations of dAs, deAs, and dLbCas12a fusions to VPR (FIG. 26A). Comparisons of their activities on canonical TTTV and non-canonical TTCV PAM sites proximal to the VEGFA promoter established an optimal dCas12a-VPR fusion architecture (version 1.1; FIGS. 26B-26D, and also revealed that deAs-VPR effectors facilitated greater VEGFA production relative to dAs and dLbCas12a fusions when using crRNAs targeted to canonical or non-canonical sites (FIG. 26E). In experiments comparing deAs-VPR to the prototypical dSpCas9-VPR fusion (targeting separate but nearby sites), we observed comparable or better gene activation with deAs-VPR (FIGS. 26B-C and 26E-F).

Figure 18E:
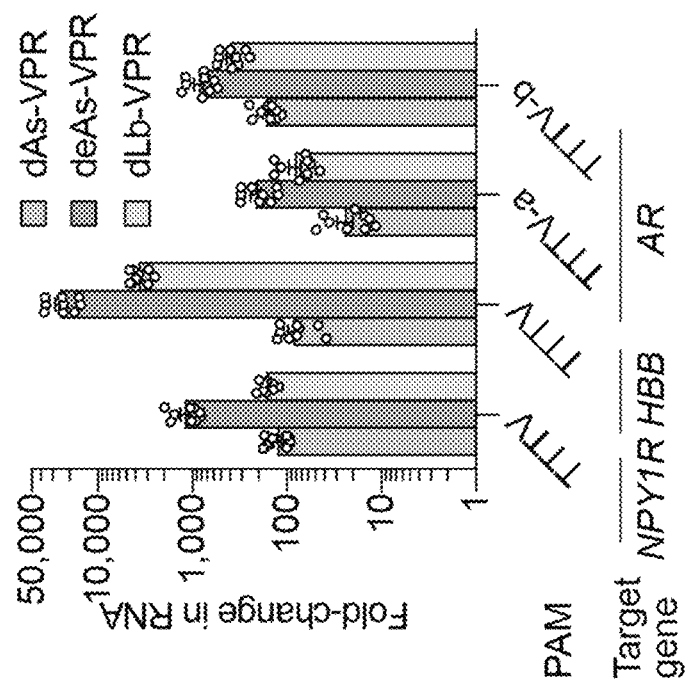

Additional experiments with dAs, deAs, and dLb-VPR fusions targeted to sites in the promoters of three additional endogenous genes (NPY1R, HBB, and AR) once again revealed the most potent gene activation with deAs-VPR when using pools of canonical PAM (FIG. 18E) or non-canonical PAM targeting crRNAs (FIGS. 18F and 18G). The deAs-VPR fusion achieved between 10 to 10,000-fold gene activation, frequently outperforming dAs or dLbCas12a-VPR by more than 10-100 fold.

Collectively, the deAsCas12a fusion to VPR can mediate robust gene activation at equivalent or greater efficiencies compared to published dLbCas12a-VPR fusions when targeted to canonical TTTV PAM sites, and also offers the novel capability to activate genes by targeting non-canonical PAM sites accessible only with this eAsCas12a variant. These results recapitulate the enhanced activity and improved targeting range properties of eAsCas12a, and provide potent and broadly targetable gene-activation technologies that may also be adaptable for other epigenome editing applications.

Example 7

Variants of AsCas12a and LbCas12a for Base Editing Applications

The ability to perform precise single base editing events has recently been demonstrated using engineered SpCas9 base editor (BE) constructs (see, e.g., Komor et al., Nature. 2016 May 19; 533(7603):420-4; Nishida et al., Science. 2016 Sep. 16; 353(6305); Kim et al., Nat Biotechnol. 2017 April; 35(4):371-376; Komor et al., Sci Adv. 2017 Aug. 30; 3(8):eaao4774; and Gaudelli et al., Nature. 2017 Nov. 23; 551(7681):464-471), which exploit the formation of SpCas9-gRNA formed R-loops that cause ssDNA accessibility of the non-target DNA strand. The fusion of heterologous cytidine or adenine deaminase enzymatic domains to SpCas9 can therefore act on the exposed ssDNA strand, leading to the efficient introduction of C to T, or A to G, respectively. Because cellular base-excision repair (BER) employs uracil DNA glycosylase (UDG; also known as uracil N-glycosylase, or UNG) to excise uracil bases, this endogenous process can effectively reverse edits generated by cytidine BEs because the deamination of cytidine leads to a uracil intermediate. Therefore, to improve the efficiency of cytidine BEs, heterologous effector domains such as uracil glycosylase inhibitor (UGI) can also be fused to SpCas9 to inhibit UDG, subverting the initiation of BER and increasing the effectiveness of cytidine BEs.

Figure 18H:
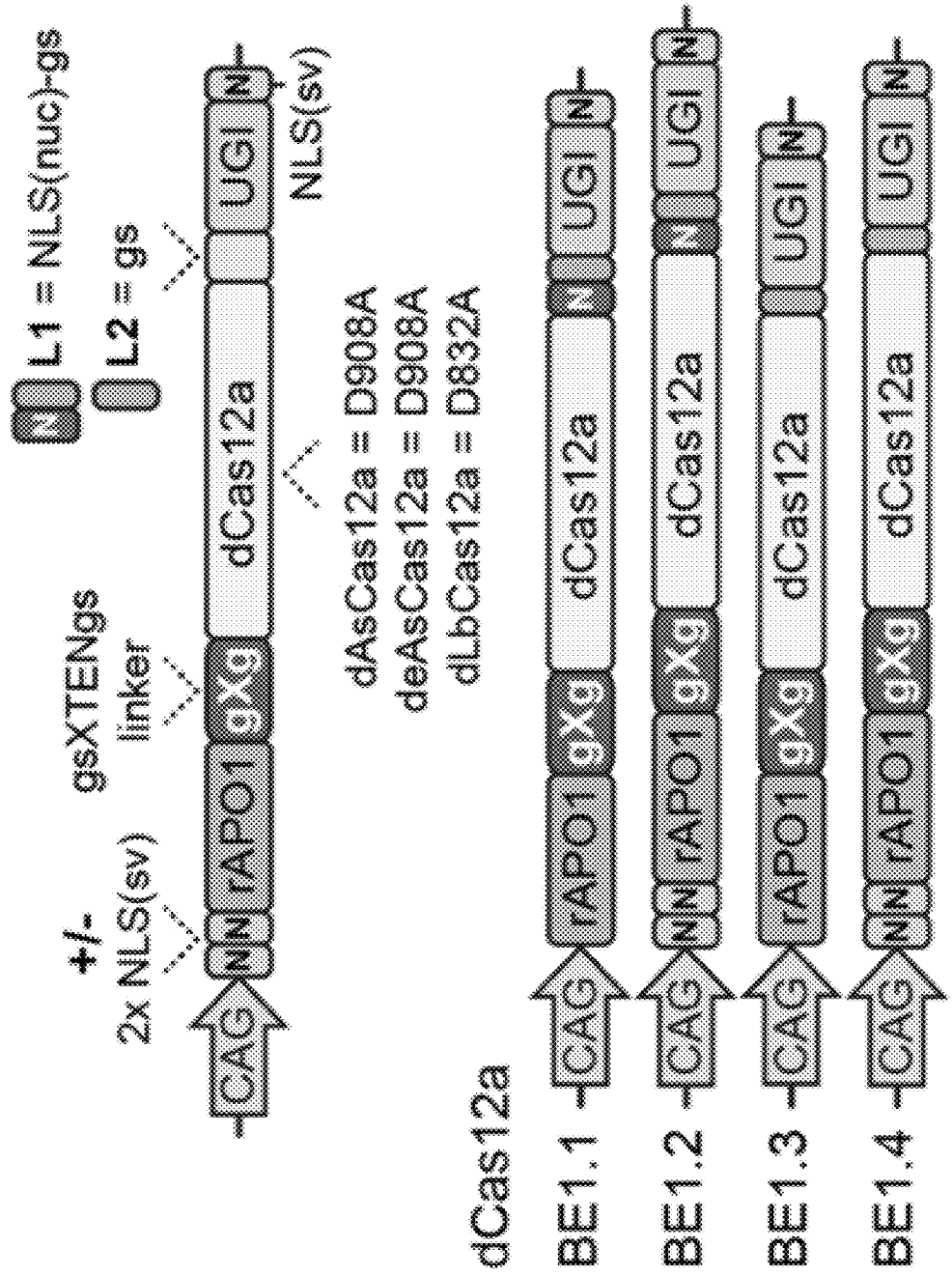
Figure 18I:
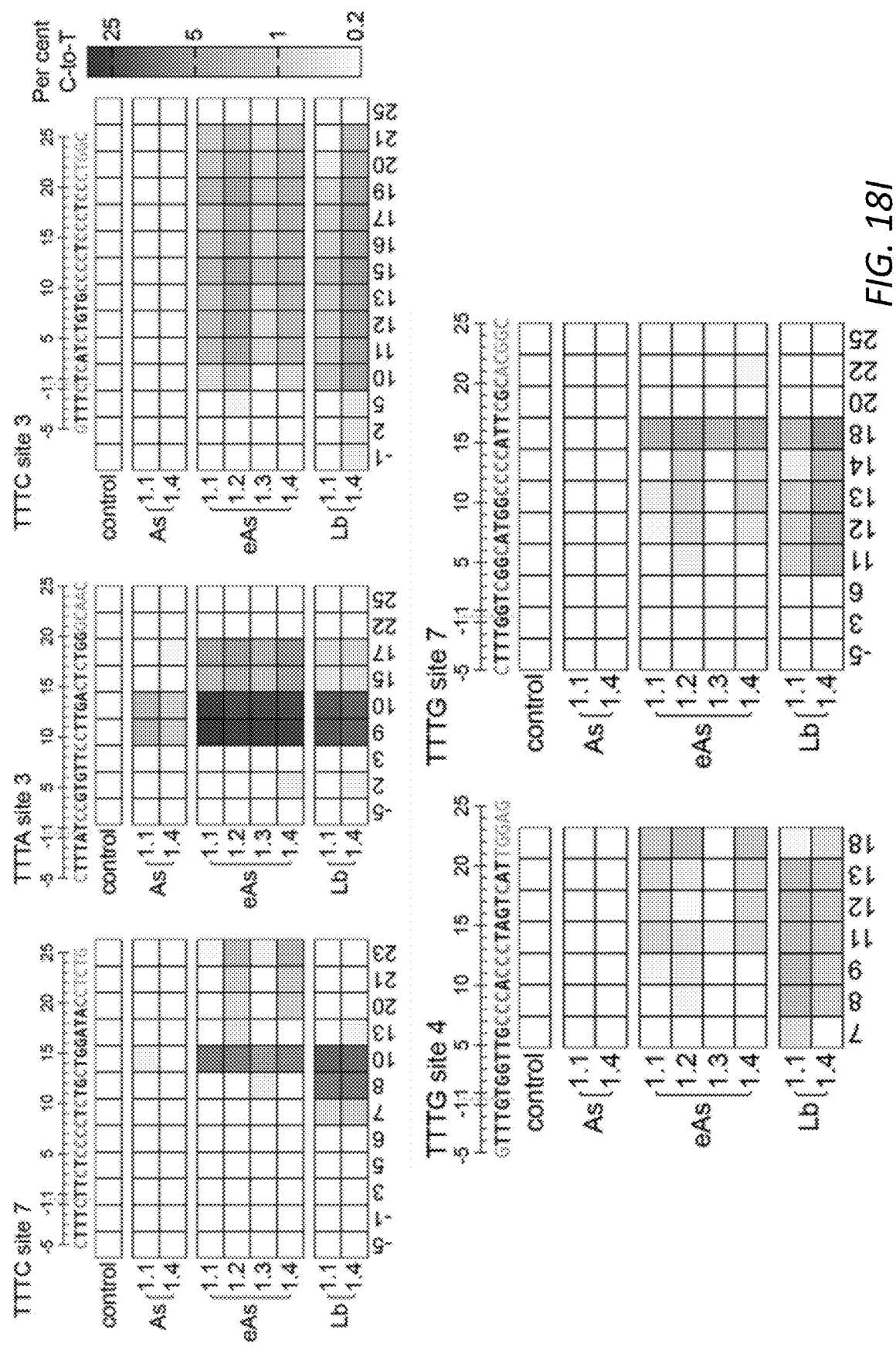
Figure 18I:
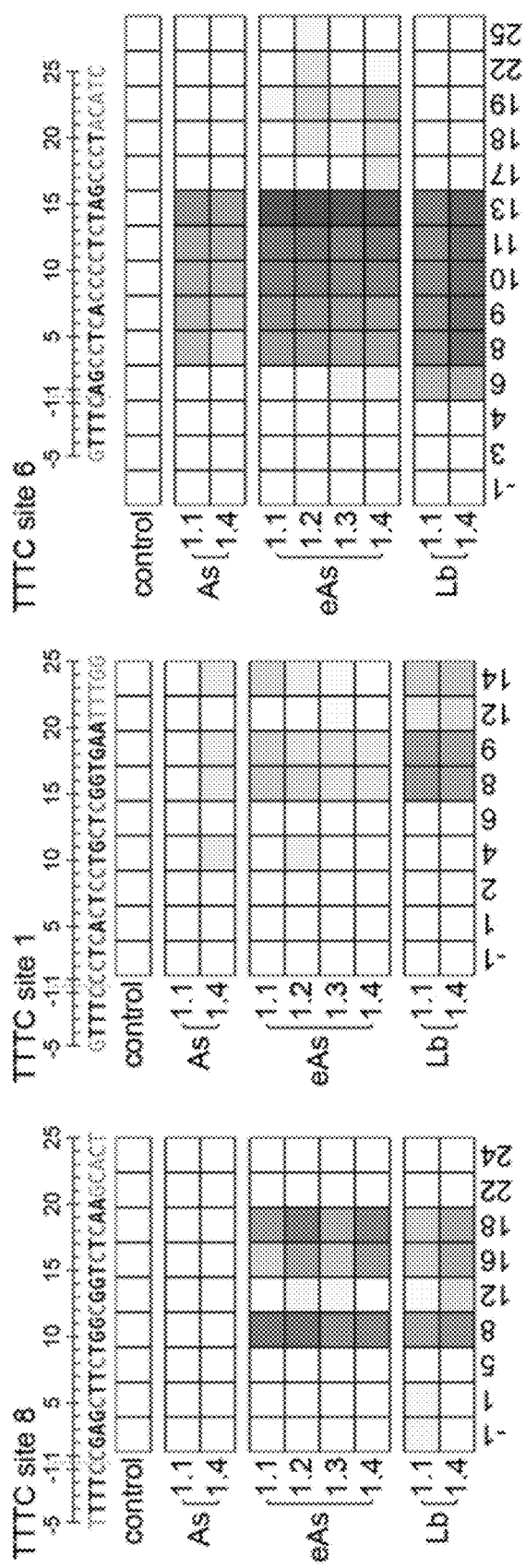
Figure 18J:
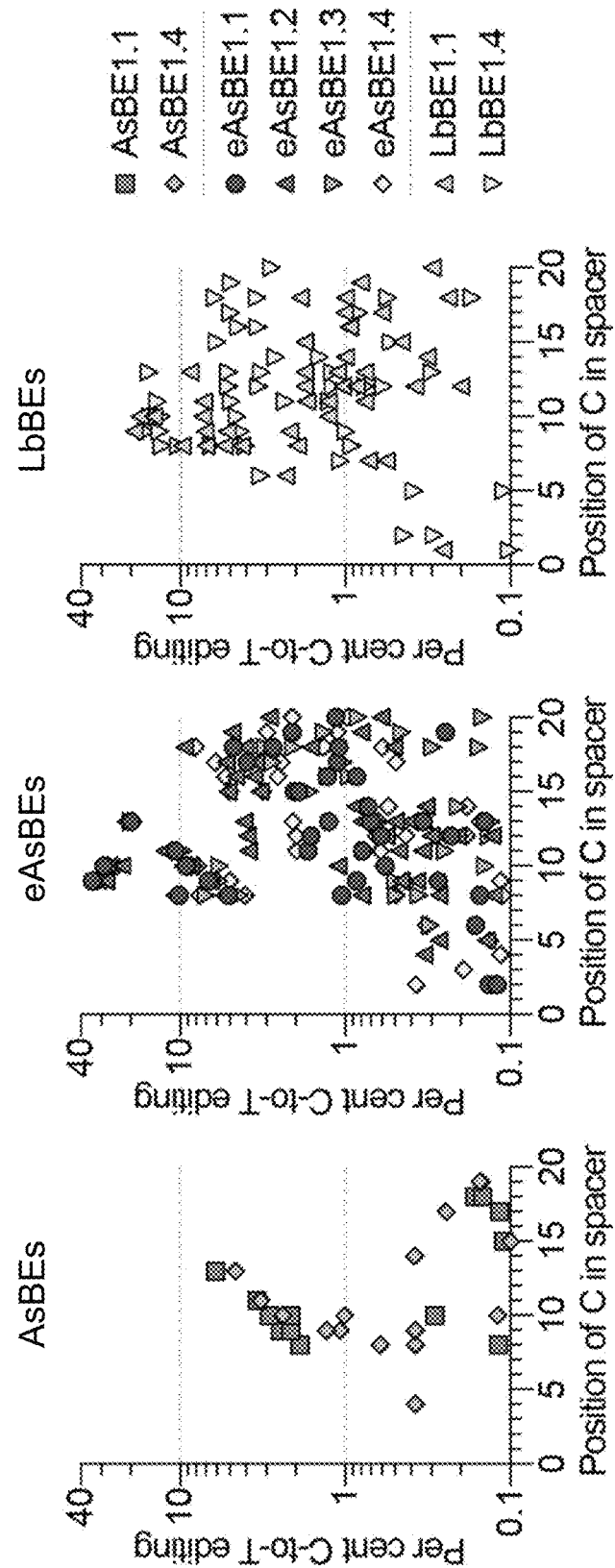
Figure 18K:
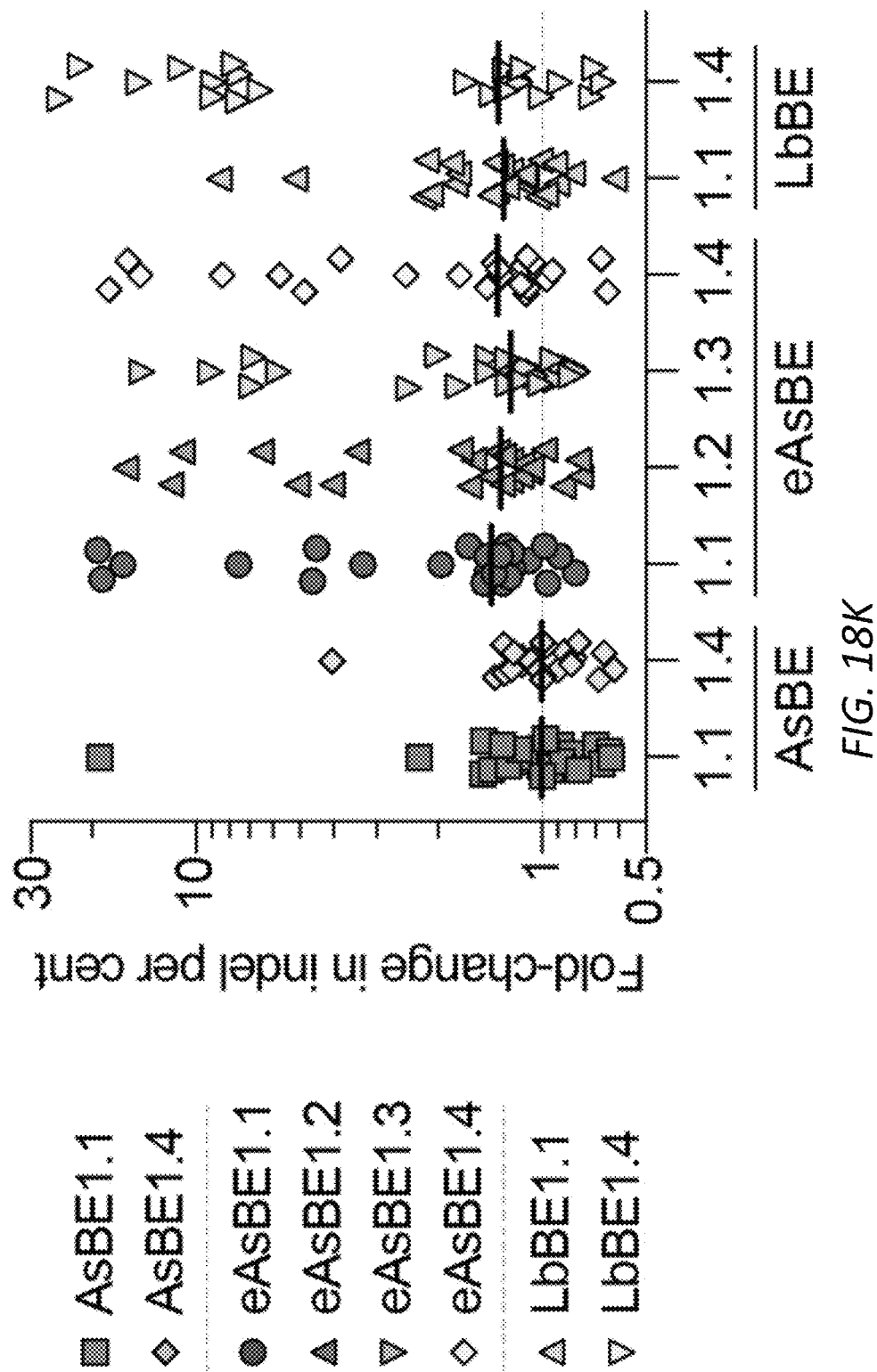
Figure 27A:
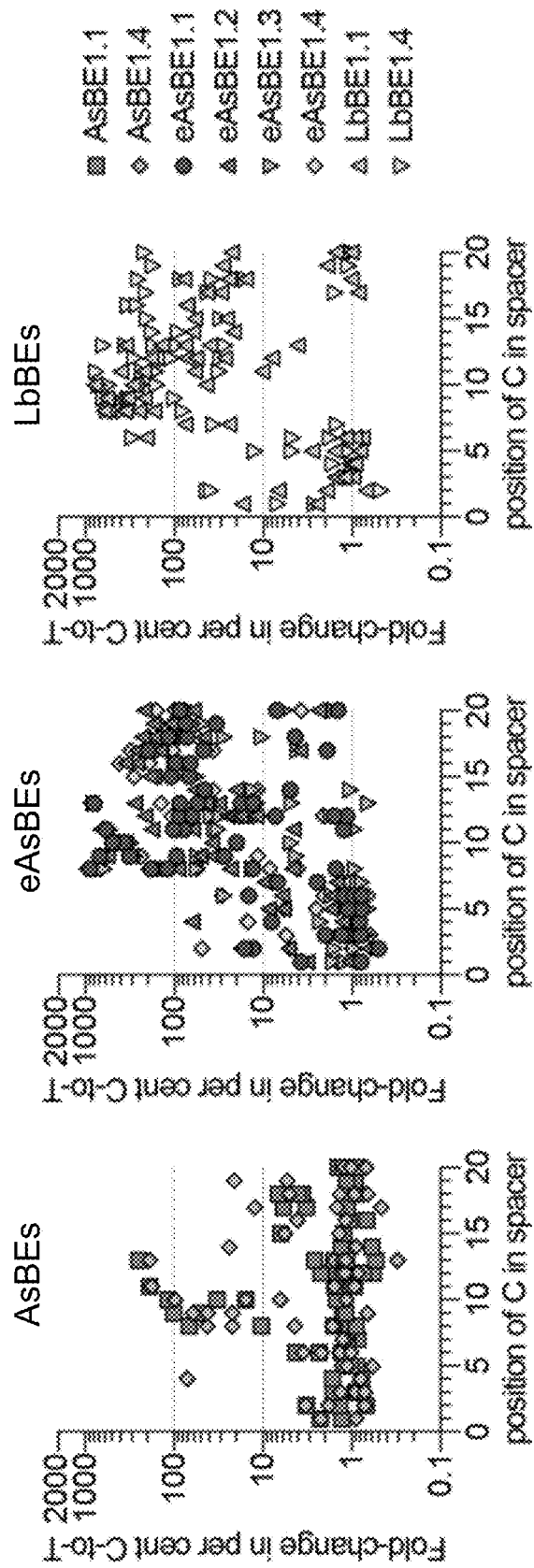
Figure 27B:
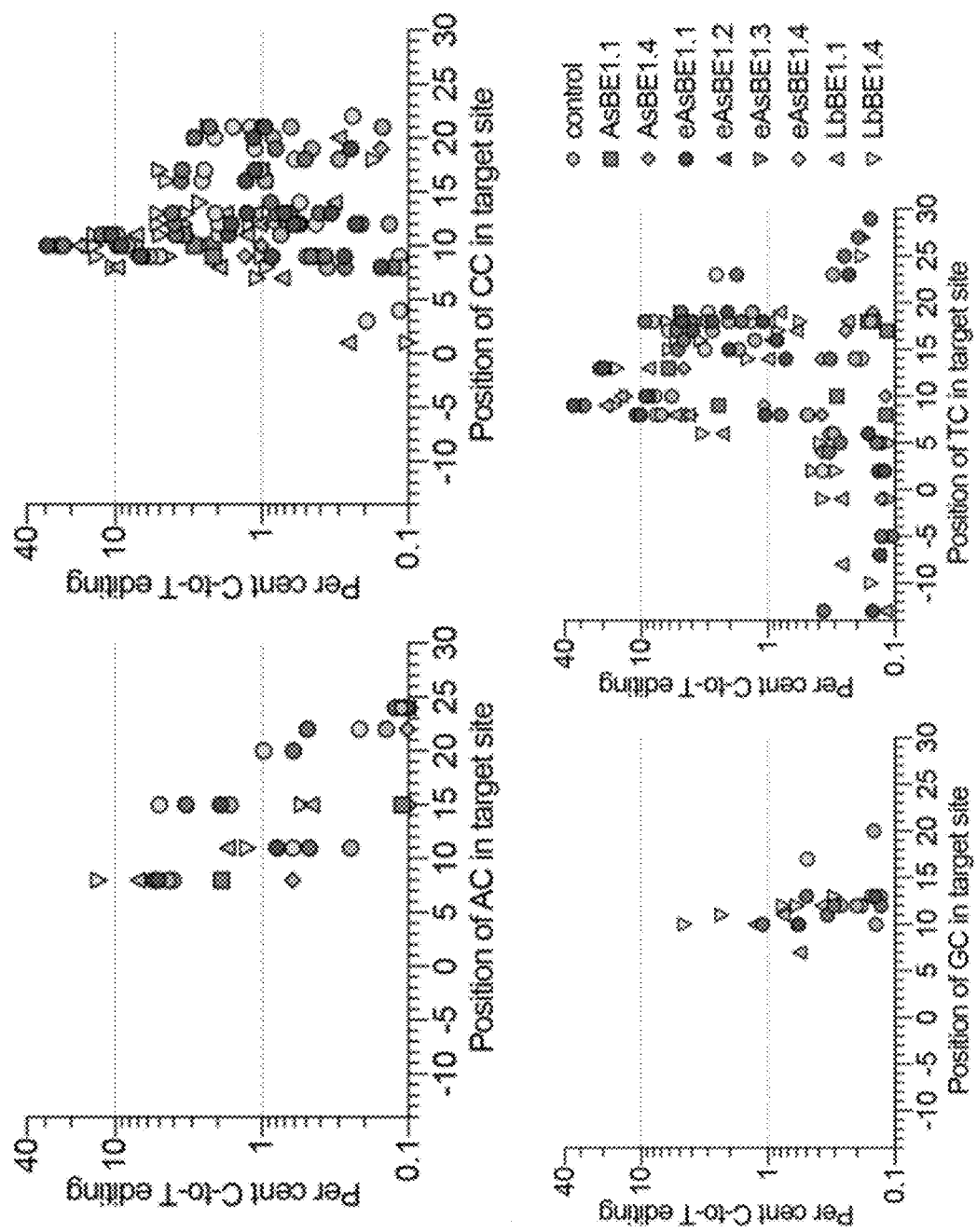
Figure 27C:
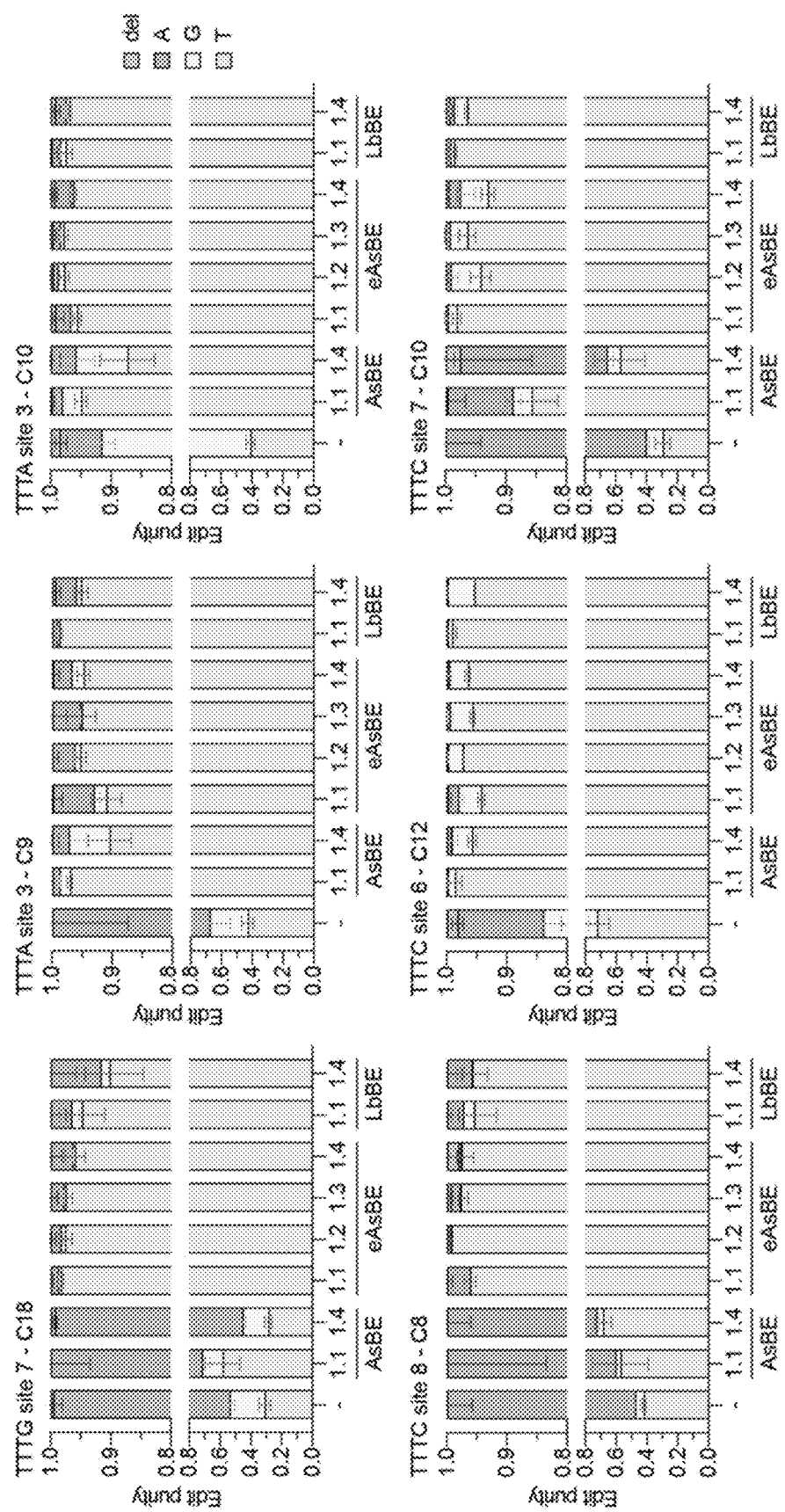
Figure 27D:
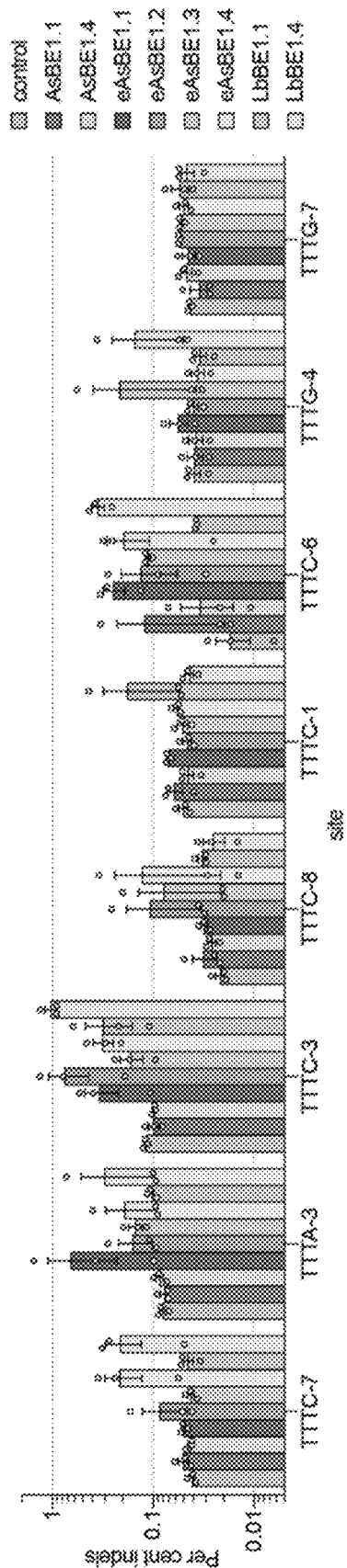

Because our prior observations suggested that eAsCas12a (E174R/S542R/K548R) possesses enhanced activity, we therefore wondered whether eAsCas12a could enable the development of putative AsCas12a base-editors (AsBEs). To test this hypothesis, we cloned four different DNase inactive eAsBE architectures (BE-1.1-1.4; FIG. 18H) that included an N-terminal fusion of rAPOBEC1, a D908A substitution to abrogate nuclease-mediated DNA hydrolysis activity, and a C-terminal fusion of UGI, and compared their activities to wild-type AsBE1.1 and 1.4 using eight different crRNAs. We observed minimal (<1%) C-to-T editing with AsBEs across all Cs for 7 of 8 sites (FIG. 18I). Interestingly, eAsBE fusions demonstrated far greater absolute levels of C-to-T conversion across the same eight sites (range of 2-34% editing; FIGS. 18I and 18J), dramatically improving editing relative to AsBEs (FIG. 27A). Assessment of two equivalent LbBE architectures (range of 2-19% C-to-T editing) revealed comparable levels of C-to-T editing relative to eAsBEs (FIGS. 18I and 18J). For all constructs, editing efficiencies varied by target site and BE architecture (FIG. 18I), and similar to observations with SpCas9BEs the presence of a G 5' of a C appeared to dampen C-to-T editing (FIG. 27B). Desirable edit purities (predominantly C-to-T as the major product) were observed with Cas12a-BEs for positions edited at high efficiencies (FIG. 27C). Low levels of indels were observed for Cas12a-BEs presumably due to the inactivation of their DNase activity (FIG. 18K and FIG. 27D). Taken together, these results demonstrate that the enhanced activities of eAsCas12a enable C-to-T editing at levels previously unachievable with AsBEs and at comparable efficacy to LbBEs, and expand the potential of CRISPR base-editing reagents.

Example 8

Variants of AsCas12a for DNA Detection

An additional recently described application of CRISPR-Cas12a nucleases is based on the observation that Cas12a molecules exhibit target-programmed non-specific DNase activity (Chen et al., Science, 2018, doi: 10.1126/science.aar6245), a property that has been leveraged for the sensitive detection specific DNA molecules in solution (Chen et al., Science, 2018, doi: 10.1126/science.aar6245; Gootenberg et al., Science, 2018, doi: 10.1126/science.aaq0179). When the Cas12a-crRNA complex is bound to a target DNA, the catalytic RuvC DNase active site adopts a hyper-active conformation that indiscriminately digests nearby DNA. A synthetic quenched fluorophore DNA-reporter molecule can be added to the solution, facilitating quantification of Cas12a-DNase activity that liberates the fluorescent reporter (East-Seletsky, Nature, 2016, 538:270-273). Thus, the expanded targeting range and improved activities of eAsCas12a could potentially improve DNA detection methodologies by enhancing sensitivity, facilitating detection of DNA molecules with non-canonical PAMs, or by enabling detection of variant alleles for diagnostic purposes.

Therefore, we sought to compare the collateral trans-DNase activities of wild-type AsCas12a and eAsCas12a to assess the compatibility of our engineered variant with DNA detection workflows. We assembled Cas12-crRNA complexes in vitro and programmed them with activating (matching the reporter molecule) or non-activating (control) DNA substrates prior to the addition of the reporter molecule. We also varied the PAM encoded on the activating DNA substrate to determine whether the expanded targeting range of eAsCas12a recapitulates in this in vitro assay. In experiments with wild-type AsCas12a, we observed robust detection in the presence of the matched substrate encoding a canonical TTTA PAM site, and greatly reduced activity when programmed with a substrate bearing a non-canonical ACCT PAM (FIG. 28A). Next, both eAsCas12a and eAsCas12a-HF1 exhibited comparable levels of detection to wild-type AsCas12a on the TTTA PAM substrate (FIG. 28B), but could also robustly detect a non-canonical CTTA PAM substrate (as expected given the expanded the PAM preference profile of eAsCas12a (FIG. 15B). Surprisingly, the eAsCas12a enzyme was also able to detect a DNA substrate bearing a non-targetable ACCT PAM (FIG. 28B), suggesting potential differences in PAM requirements for prototypical target DNA cleavage or for non-specific trans-DNase activities. These results demonstrate that both eAsCas12a and eAsCas12a-HF1 are potent engineered nucleases for DNA detection that offer targeting range and potentially specificity advantages over wild-type AsCas12a.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

<160> NUMBER OF SEQ ID NOS: 586

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: n is a, c, g, or t

<400> SEQUENCE: 1
tttngaccta ccgctcgaat agcgngg                                          27

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

```
Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
    610                 615                 620
```

```
Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035
```

Val Leu Asn Pro Tyr Gln Leu Thr Asp Gln Phe Thr Ser Phe Ala
    1040            1045            1050

Lys Met Gly Thr Gln Ser Gly Phe Leu Phe Tyr Val Pro Ala Pro
    1055            1060            1065

Tyr Thr Ser Lys Ile Asp Pro Leu Thr Gly Phe Val Asp Pro Phe
    1070            1075            1080

Val Trp Lys Thr Ile Lys Asn His Glu Ser Arg Lys His Phe Leu
    1085            1090            1095

Glu Gly Phe Asp Phe Leu His Tyr Asp Val Lys Thr Gly Asp Phe
    1100            1105            1110

Ile Leu His Phe Lys Met Asn Arg Asn Leu Ser Phe Gln Arg Gly
    1115            1120            1125

Leu Pro Gly Phe Met Pro Ala Trp Asp Ile Val Phe Glu Lys Asn
    1130            1135            1140

Glu Thr Gln Phe Asp Ala Lys Gly Thr Pro Phe Ile Ala Gly Lys
    1145            1150            1155

Arg Ile Val Pro Val Ile Glu Asn His Arg Phe Thr Gly Arg Tyr
    1160            1165            1170

Arg Asp Leu Tyr Pro Ala Asn Glu Leu Ile Ala Leu Leu Glu Glu
    1175            1180            1185

Lys Gly Ile Val Phe Arg Asp Gly Ser Asn Ile Leu Pro Lys Leu
    1190            1195            1200

Leu Glu Asn Asp Asp Ser His Ala Ile Asp Thr Met Val Ala Leu
    1205            1210            1215

Ile Arg Ser Val Leu Gln Met Arg Asn Ser Asn Ala Ala Thr Gly
    1220            1225            1230

Glu Asp Tyr Ile Asn Ser Pro Val Arg Asp Leu Asn Gly Val Cys
    1235            1240            1245

Phe Asp Ser Arg Phe Gln Asn Pro Glu Trp Pro Met Asp Ala Asp
    1250            1255            1260

Ala Asn Gly Ala Tyr His Ile Ala Leu Lys Gly Gln Leu Leu Leu
    1265            1270            1275

Asn His Leu Lys Glu Ser Lys Asp Leu Lys Leu Gln Asn Gly Ile
    1280            1285            1290

Ser Asn Gln Asp Trp Leu Ala Tyr Ile Gln Glu Leu Arg Asn
    1295            1300            1305

<210> SEQ ID NO 3
<211> LENGTH: 1246
<212> TYPE: PRT
<213> ORGANISM: Unknown
<220> FEATURE:
<223> OTHER INFORMATION: Lachnospiraceae bacterium

<400> SEQUENCE: 3

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
                20                  25                  30

Lys Thr Leu Arg Phe Lys Ala Ile Pro Val Gly Lys Thr Gln Glu Asn
            35                  40                  45

Ile Asp Asn Lys Arg Leu Leu Val Glu Asp Glu Lys Arg Ala Glu Asp
        50                  55                  60

Tyr Lys Gly Val Lys Lys Leu Leu Asp Arg Tyr Tyr Leu Ser Phe Ile
65                  70                  75                  80
Asn Asp Val Leu His Ser Ile Lys Leu Lys Asn Leu Asn Asn Tyr Ile

-continued

```
                85                  90                  95
Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
            115                 120                 125

Gly Asn Glu Gly Tyr Lys Ser Leu Phe Lys Lys Asp Ile Ile Glu Thr
130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
            165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
            195                 200                 205

Glu Lys Val Asp Ala Ile Phe Asp Lys His Glu Val Gln Glu Ile Lys
            210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
            245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
            290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
            325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
            355                 360                 365

Ile Phe Gly Glu Trp Asn Val Ile Arg Asp Lys Trp Asn Ala Glu Tyr
            370                 375                 380

Asp Asp Ile His Leu Lys Lys Ala Val Thr Glu Lys Tyr Glu
385                 390                 395                 400

Asp Asp Arg Arg Lys Ser Phe Lys Lys Ile Gly Ser Phe Ser Leu Glu
            405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
            435                 440                 445

Ser Ser Glu Lys Leu Phe Asp Ala Asp Phe Val Leu Glu Lys Ser Leu
            450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
            485                 490                 495

Glu Thr Asn Arg Asp Glu Ser Phe Tyr Gly Asp Phe Val Leu Ala Tyr
            500                 505                 510
```

```
Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
        530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925
```

```
Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser Phe Lys Ser Met Ser Thr Gln Asn
        995                 1000                1005

Gly Phe Ile Phe Tyr Ile Pro Ala Trp Leu Thr Ser Lys Ile Asp
    1010                1015                1020

Pro Ser Thr Gly Phe Val Asn Leu Leu Lys Thr Lys Tyr Thr Ser
    1025                1030                1035

Ile Ala Asp Ser Lys Lys Phe Ile Ser Ser Phe Asp Arg Ile Met
    1040                1045                1050

Tyr Val Pro Glu Glu Asp Leu Phe Glu Phe Ala Leu Asp Tyr Lys
    1055                1060                1065

Asn Phe Ser Arg Thr Asp Ala Asp Tyr Ile Lys Lys Trp Lys Leu
    1070                1075                1080

Tyr Ser Tyr Gly Asn Arg Ile Arg Ile Phe Arg Asn Pro Lys Lys
    1085                1090                1095

Asn Asn Val Phe Asp Trp Glu Glu Val Cys Leu Thr Ser Ala Tyr
    1100                1105                1110

Lys Glu Leu Phe Asn Lys Tyr Gly Ile Asn Tyr Gln Gln Gly Asp
    1115                1120                1125

Ile Arg Ala Leu Leu Cys Glu Gln Ser Asp Lys Ala Phe Tyr Ser
    1130                1135                1140

Ser Phe Met Ala Leu Met Ser Leu Met Leu Gln Met Arg Asn Ser
    1145                1150                1155

Ile Thr Gly Arg Thr Asp Val Asp Phe Leu Ile Ser Pro Val Lys
    1160                1165                1170

Asn Ser Asp Gly Ile Phe Tyr Asp Ser Arg Asn Tyr Glu Ala Gln
    1175                1180                1185

Glu Asn Ala Ile Leu Pro Lys Asn Ala Asp Ala Asn Gly Ala Tyr
    1190                1195                1200

Asn Ile Ala Arg Lys Val Leu Trp Ala Ile Gly Gln Phe Lys Lys
    1205                1210                1215

Ala Glu Asp Glu Lys Leu Asp Lys Val Lys Ile Ala Ile Ser Asn
    1220                1225                1230

Lys Glu Trp Leu Glu Tyr Ala Gln Thr Ser Val Lys His
    1235                1240                1245

<210> SEQ ID NO 4
<211> LENGTH: 1300
<212> TYPE: PRT
<213> ORGANISM: Francisella tularensis

<400> SEQUENCE: 4

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45
```

```
Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
 65                  70                  75                  80

Asp Val Tyr Phe Lys Leu Lys Ser Asp Asp Asn Leu Gln Lys
                85                  90                  95

Asp Phe Lys Ser Ala Lys Asp Thr Ile Lys Lys Gln Ile Ser Glu Tyr
                100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
        370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
        450                 455                 460
```

```
Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
            485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
            850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
```

-continued

```
                885                 890                 895
Asn Asp Glu Ile Asn Leu Leu Lys Glu Lys Ala Asn Asp Val His
                900                 905                 910
Ile Leu Ser Ile Asp Arg Gly Glu Arg His Leu Ala Tyr Tyr Thr Leu
                915                 920                 925
Val Asp Gly Lys Gly Asn Ile Ile Lys Gln Asp Thr Phe Asn Ile Ile
    930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
                980                 985                 990
Ala Lys Leu Val Ile Glu Tyr Asn Ala Ile Val Val Phe Glu Asp Leu
                995                1000                1005
Asn Phe Gly Phe Lys Arg Gly Arg Phe Lys Val Glu Lys Gln Val
            1010                1015                1020
Tyr Gln Lys Leu Glu Lys Met Leu Ile Glu Lys Leu Asn Tyr Leu
            1025                1030                1035
Val Phe Lys Asp Asn Glu Phe Asp Lys Thr Gly Gly Val Leu Arg
            1040                1045                1050
Ala Tyr Gln Leu Thr Ala Pro Phe Glu Thr Phe Lys Lys Met Gly
            1055                1060                1065
Lys Gln Thr Gly Ile Ile Tyr Tyr Val Pro Ala Gly Phe Thr Ser
            1070                1075                1080
Lys Ile Cys Pro Val Thr Gly Phe Val Asn Gln Leu Tyr Pro Lys
            1085                1090                1095
Tyr Glu Ser Val Ser Lys Ser Gln Glu Phe Phe Ser Lys Phe Asp
            1100                1105                1110
Lys Ile Cys Tyr Asn Leu Asp Lys Gly Tyr Phe Glu Phe Ser Phe
            1115                1120                1125
Asp Tyr Lys Asn Phe Gly Asp Lys Ala Ala Lys Gly Lys Trp Thr
            1130                1135                1140
Ile Ala Ser Phe Gly Ser Arg Leu Ile Asn Phe Arg Asn Ser Asp
            1145                1150                1155
Lys Asn His Asn Trp Asp Thr Arg Glu Val Tyr Pro Thr Lys Glu
            1160                1165                1170
Leu Glu Lys Leu Leu Lys Asp Tyr Ser Ile Glu Tyr Gly His Gly
            1175                1180                1185
Glu Cys Ile Lys Ala Ala Ile Cys Gly Glu Ser Asp Lys Lys Phe
            1190                1195                1200
Phe Ala Lys Leu Thr Ser Val Leu Asn Thr Ile Leu Gln Met Arg
            1205                1210                1215
Asn Ser Lys Thr Gly Thr Glu Leu Asp Tyr Leu Ile Ser Pro Val
            1220                1225                1230
Ala Asp Val Asn Gly Asn Phe Phe Asp Ser Arg Gln Ala Pro Lys
            1235                1240                1245
Asn Met Pro Gln Asp Ala Asp Ala Asn Gly Ala Tyr His Ile Gly
            1250                1255                1260
Leu Lys Gly Leu Met Leu Leu Gly Arg Ile Lys Asn Asn Gln Glu
            1265                1270                1275
Gly Lys Lys Leu Asn Leu Val Ile Lys Asn Glu Glu Tyr Phe Glu
            1280                1285                1290
```

```
Phe Val Gln Asn Arg Asn Asn
    1295            1300

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tacccatacg atgttccaga ttacgcttat ccctacgacg tgcctgatta tgcataccca      60
tatgatgtcc ccgactatgc c                                                81

<210> SEQ ID NO 6
<211> LENGTH: 4059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgacacagt tcgagggctt taccaacctg tatcaggtga gcaagacact gcggtttgag      60
ctgatcccac agggcaagac cctgaagcac atccaggagc agggcttcat cgaggaggac     120
aaggcccgca atgatcacta caaggagctg aagcccatca tcgatcggat ctacaagacc     180
tatgccgacc agtgcctgca gctggtgcag ctggattggg agaacctgag cgccgccatc     240
gactcctata gaaaggagaa aaccgaggag acaaggaacg ccctgatcga ggagcaggcc     300
acatatcgca tgccatcca cgactacttc atcggccgga cagacaacct gaccgatgcc     360
atcaataaga gacacgccga gatctacaag ggcctgttca aggccgagct gtttaatggc     420
aaggtgctga gcagctggg caccgtgacc acaaccgagc acgagaacgc cctgctgcgg     480
agcttcgaca gtttacaac ctacttctcc ggcttttatg agaacaggaa gaacgtgttc     540
agcgccgagg atatcagcac agccatccca caccgcatcg tgcaggacaa cttccccaag     600
tttaaggaga attgtcacat cttcacacgc ctgatcaccg ccgtgcccag cctgcgggag     660
cactttgaga cgtgaagaa ggccatcggc atcttcgtga gcacctccat cgaggaggtg     720
ttttccttcc cttttttataa ccagctgctg acacagaccc agatcgacct gtataaccag     780
ctgctgggag aatctctcg ggaggcaggc accgagaaga tcaagggcct gaacgaggtg     840
ctgaatctgg ccatccagaa gaatgatgag acagcccaca tcatcgcctc cctgccacac     900
agattcatcc cctgtttaa gcagatcctg tccgatagga cacccctgtc tttcatcctg     960
gaggagttta gagcgacga ggaagtgatc cagtccttct gcaagtacaa gacactgctg    1020
agaaacgaga cgtgctgga cagccgag gccctgttta cgagctgaa cagcatcgac    1080 ctgacacaca tcttcatcag ccacaagaag ctggagacaa tcagcagcgc cctgtgcgac    1140
cactgggata cactgaggaa tgccctgtat gagcggagaa tctccgagct gacaggcaag    1200
atcaccaagt ctgccaagga aaggtgcag cgcagcctga gcacgagga tatcaacctg    1260 caggagatca tctctgccgc aggcaaggag ctgagcgagg ccttcaagca gaaaaccagc    1320
gagatcctgt cccacgcaca cgccgccctg gatcagccac tgcctacaac cctgaagaag    1380
caggaggaga aggagatcct gaagtctcag ctggacagcc tgctgggcct gtaccacctg    1440
ctggactggt ttgccgtgga tgagtccaac gaggtggacc ccgagttctc tgcccggctg    1500
```

```
accggcatca agctggagat ggagccttct ctgagcttct acaacaaggc cagaaattat    1560
gccaccaaga agccctactc cgtggagaag ttcaagctga actttcagat gcctacactg    1620
gcctctggct gggacgtgaa taaggagaag aacaatggcg ccatcctgtt tgtgaagaac    1680
ggcctgtact atctgggcat catgccaaag cagaagggca ggtataaggc cctgagcttc    1740
gagcccacag agaaaaccag cgagggcttt gataagatgt actatgacta cttccctgat    1800
gccgccaaga tgatcccaaa gtgcagcacc cagctgaagg ccgtgacagc ccactttcag    1860
acccacacaa ccccccatcct gctgtccaac aatttcatcg agcctctgga gatcacaaag    1920
gagatctacg acctgaacaa tcctgagaag gagccaaaga gtttcagac agcctacgcc    1980 aagaaaaccg gcgaccagaa gggctacaga gaggccctgt gcaagtggat cgacttcaca    2040
agggattttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgtttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240 gacccccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840
```

```
ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg atcctaccc atacgatgtt ccagattacg cttatcccta cgacgtgcct     4020
gattatgcat acccatatga tgtccccgac tatgcctaa                           4059
```

```
<210> SEQ ID NO 7
<211> LENGTH: 16
<212> TYPE: PRT
<213> ORGANISM: Unknown
<220> FEATURE:
<223> OTHER INFORMATION: Description of Unknown: Nucleoplasmin NLS
      peptide

<400> SEQUENCE: 7
```

Lys Arg Pro Ala Ala Thr Lys Lys Ala Gly Gln Ala Lys Lys Lys Lys
1               5                   10                  15

```
<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25

```
<210> SEQ ID NO 9
<211> LENGTH: 1352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

```
Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
            210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
            245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
            325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
            405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
            485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
            565                 570                 575
```

-continued

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
```

| | | 995 | | | 1000 | | | 1005 | | |
|---|---|---|---|---|---|---|---|---|---|---|
| Lys | Ala | Val | Tyr | Gln | Gln | Phe | Glu | Lys | Met | Leu | Ile | Asp | Lys | Leu |
| | | 1010 | | | | 1015 | | | 1020 | |

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn Lys
    1295                1300                1305

Arg Pro Ala Ala Thr Lys Lys Ala Gly Gln Ala Lys Lys Lys Lys
    1310                1315                1320

Gly Ser Tyr Pro Tyr Asp Val Pro Asp Tyr Ala Tyr Pro Tyr Asp
    1325                1330                1335

Val Pro Asp Tyr Ala Tyr Pro Tyr Asp Val Pro Asp Tyr Ala
    1340                1345                1350

<210> SEQ ID NO 10
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgagcaagc tggagaagtt tacaaactgc tactccctgt ctaagaccct gaggttcaag      60
gccatccctg tgggcaagac ccaggagaac atcgacaata gcggctgct ggtggaggac      120
gagaagagag ccgaggatta aagggcgtg aagaagctgc tggatcgcta ctatctgtct      180
tttatcaacg acgtgctgca cagcatcaag ctgaagaatc tgaacaatta catcagcctg      240
ttccggaaga aaaccagaac cgagaaggag aataaggagc tggagaacct ggagatcaat      300
ctgcggaagg agatcgccaa ggccttcaag ggcaacgagg gctacaagtc cctgtttaag      360
aaggatatca tcgagacaat cctgccagag ttcctggacg ataaggacga gatcgccctg      420
gtgaacagct tcaatggctt taccacagcc ttcaccggct ctttgataa cagagagaat      480
atgttttccg aggaggccaa gagcacatcc atcgccttca ggtgtatcaa cgagaatctg      540
acccgctaca tctctaatat ggacatcttc gagaaggtgg acgccatctt tgataagcac      600
gaggtgcagg agatcaagga gaagatcctg aacagcgact atgatgtgga ggatttcttt      660
gagggcgagt tctttaactt tgtgctgaca caggagggca tcgacgtgta taacgccatc      720
atcgccggct tcgtgaccga gagcggcgag aagatcaagg gcctgaacga gtacatcaac      780
ctgtataatc agaaaaccaa gcagaagctg cctaagttta gccactgta taagcaggtg      840
ctgagcgatc gggagtctct gagcttctac ggcgagggca atacatccga tgaggaggtg      900
ctggaggtgt ttagaaacac cctgaacaag aacagcgaga tcttcagctc catcaagaag      960
ctggagaagc tgttcaagaa ttttgacgag tactctagcg ccggcatctt tgtgaagaac     1020
ggccccgcca tcagcacaat ctccaaggat atcttcggcg agtggaacgt gatccgggac     1080
aagtggaatg ccgagtatga cgatatccac ctgaagaaga aggccgtggt gaccgagaag     1140
tacgaggacg atcggagaaa gtccttcaag aagatcggct ccttttctct ggagcagctg     1200
caggagtacg ccgacgccga tctgtctgtg gtggagaagc tgaaggagat catcatccag     1260
aaggtggatg agatctacaa ggtgtatggc tcctctgaga gctgttcga cgccgatttt     1320
gtgctggaga gagcctgaa gaagaacgac gccgtggtgg ccatcatgaa ggacctgctg     1380
gattctgtga gagcttcga gaattacatc aaggccttct tggcgaggg caaggagaca     1440
aacagggacg agtccttcta tggcgatttt gtgctggcct acgacatcct gctgaaggtg     1500
gaccacatct acgatgccat ccgcaattat gtgacccaga gccctactc taaggataag     1560
ttcaagctgt attttcagaa ccctcagttc atgggcggct gggacaagga taaggagaca     1620
gactatcggg ccaccatcct gagatacggc tccaagtact atctggccat catggataag     1680
aagtacgcca agtgcctgca gaagatcgac aaggacgatg tgaacggcaa ttacgagaag     1740
atcaactata agctgctgcc cggccctaat aagatgctgc caaaggtgtt cttttctaag     1800
aagtggatgg cctactataa ccccagcgag gacatccaga gatctacaa gaatggcaca     1860
ttcaagaagg cgatatgtt taacctgaat gactgtcaca gctgatcga cttctttaag     1920
gatagcatct cccggtatcc aaagtggtcc aatgcctacg atttcaactt ttctgagaca     1980
gagaagtata aggacatcgc cggcttttac agagaggtgg aggagcaggg ctataaggtg     2040
agcttcgagt ctgccagcaa gaaggaggtg gataagctgg tggaggaggg caagctgtat     2100
atgttccaga tctataacaa ggacttttcc gataagtctc acggcacacc caatctgcac     2160
accatgtact tcaagctgct gtttgacgag aacaatcacg acagatcag gctgagcgga     2220
ggagcagagc tgttcatgag gcgcgcctcc ctgaagaagg aggagctggt ggtgcaccca     2280
```

```
gccaactccc ctatcgccaa caagaatcca gataatccca agaaaaccac aaccctgtcc    2340
tacgacgtgt ataaggataa gaggttttct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgataggg gcgagcgcaa tctgctgtat    2520
atcgtggtgg tggacggcaa gggcaacatc gtggagcagt attccctgaa cgagatcatc    2580
aacaacttca acggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc acccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga agctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagcctga tgctgcagat gcggaacagc    3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg cataccata tgatgtcccc gactatgcct aa                        3822
```

<210> SEQ ID NO 11
<211> LENGTH: 1273
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn

```
                    85                  90                  95
Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510
```

```
Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
        610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
        690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
        770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Asp Gly Lys Gly
                835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
        915                 920                 925
```

```
Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Lys Arg Pro Ala Ala
    1220                1225                1230

Thr Lys Lys Ala Gly Gln Ala Lys Lys Lys Lys Gly Ser Tyr Pro
    1235                1240                1245

Tyr Asp Val Pro Asp Tyr Ala Tyr Pro Tyr Asp Val Pro Asp Tyr
    1250                1255                1260

Ala Tyr Pro Tyr Asp Val Pro Asp Tyr Ala
    1265                1270

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Gly Gly Gly Ser
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser
1               5

<210> SEQ ID NO 14

<400> SEQUENCE: 14

000

<210> SEQ ID NO 15

<400> SEQUENCE: 15

000

<210> SEQ ID NO 16
<211> LENGTH: 7
<212> TYPE: PRT
<213> ORGANISM: Simian virus 40

<400> SEQUENCE: 16

Pro Lys Lys Lys Arg Arg Val
1               5

<210> SEQ ID NO 17
<211> LENGTH: 4038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgagcatct accaggagtt cgtcaacaag tattcactga gtaagacact gcggttcgag      60
ctgatcccac agggcaagac actggagaac atcaaggccc aggcctgat tctggacgat      120 gagaagcggg caaaagacta agaaagcc aagcagatca ttgataaata ccaccagttc      180
tttatcgagg aaattctgag ctccgtgtgc atcagtgagg atctgctgca gaattactca      240
gacgtgtact tcaagctgaa gaagagcgac gatgacaacc tgcagaagga cttcaagtcc      300
gccaaggaca ccatcaagaa acagattagc gagtacatca aggactccga aaagtttaaa      360
aatctgttca accagaatct gatcgatgct aagaaaggcc aggagtccga cctgatcctg      420
tggctgaaac agtctaagga caatgggatt gaactgttca aggctaactc cgatatcact      480
gatattgacg aggcactgga aatcatcaag agcttcaagg gatggaccac atactttaaa      540
ggcttccacg agaaccgcaa gaacgtgtac tccagcaacg acattcctac ctccatcatc      600
taccgaatcg tcgatgacaa tctgccaaag ttcctggaga acaaggccaa atatgaatct      660
ctgaaggaca agctcccga ggcaattaat tacgaacaga tcaagaaaga tctggctgag      720
gaactgacat tcgatatcga ctataagact agcgaggtga accagagggt cttttcctg     780
```

```
gacgaggtgt ttgaaatcgc caatttcaac aattacctga accagtccgg cattactaaa      840
ttcaatacca tcattggcgg gaagtttgtg aacggggaga ataccaagcg caagggaatt      900
aacgaataca tcaatctgta tagccagcag atcaacgaca aaactctgaa gaaatacaag      960
atgtctgtgc tgttcaaaca gatcctgagt gataccgagt ccaagtcttt tgtcattgat     1020
aaactggaag atgactcaga cgtggtcact accatgcaga gctttttatga gcagatcgcc     1080
gctttcaaga cagtggagga aaaatctatt aaggaaactc tgagtctgct gttcgatgac     1140
ctgaaagccc agaagctgga cctgagtaag atctacttca aaaacgataa gagtctgaca     1200
gacctgtcac agcaggtgtt tgatgactat tccgtgattg gaccgccgt cctggagtac      1260
attacacagc agatcgctcc aaagaacctg gataatccct ctaagaaaga gcaggaactg     1320
atcgctaaga aaaccgagaa ggcaaaatat ctgagtctgg aaacaattaa gctggcactg     1380
gaggagttca acaagcacag ggatattgac aaacagtgcc gctttgagga aatcctggcc     1440
aacttcgcag ccatcccat gattttttgat gagatcgccc agaacaaaga caatctggct     1500
cagatcagta ttaagtacca gaaccagggc aagaaagacc tgctgcaggc ttcagcagaa     1560
gatgacgtga agccatcaa ggatctgctg gaccagacca caatctgct gcacaagctg       1620
aaaatcttcc atattagtca gtcagaggat aaggctaata tcctggataa agacgaacac     1680
ttctacctgg tgttcgagga atgttacttc gagctggcaa acattgtccc cctgtataac     1740
aagattagga actacatcac acagaagcct tactctgacg agaagtttaa actgaacttc     1800
gaaaatagta ccctggccaa cgggtgggat aagaacaagg agcctgacaa cacagctatc     1860
ctgttcatca aggatgacaa gtactatctg ggagtgatga ataagaaaaa caataagatc     1920
ttcgatgaca aagccattaa ggagaacaaa ggggaaggat acaagaaaat cgtgtataag     1980
ctgctgcccg gcgcaaataa gatgctgcct aaggtgttct tcagcgccaa gagtatcaaa     2040
ttctacaacc catccgagga catcctgcgg attagaaatc actcaacaca tactaagaac     2100
gggagccccc agaagggata tgagaaattt gagttcaaca tcgaggattg caggaagttt     2160
attgacttct acaagcagag catctccaaa cacctgaat ggaaggatt tggcttccgg        2220
tttttccgaca cacagagata taactctatc gacgagttcc accgcgaggt ggaaaatcag     2280
gggtataagc tgactttga gaacatttct gaaagttaca tcgacagcgt ggtcaatcag       2340
ggaaagctgt acctgttcca gatctataac aaagattttt cagcatacag caagggcaga      2400
ccaaacctgc atacactgta ctggaaggcc ctgttcgatg agaggaatct gcaggacgtg      2460
gtctataaac tgaacggaga ggccgaactg ttttaccgga agcagtctat tcctaagaaa      2520
atcactcacc cagctaagga ggccatcgct aacaagaaca aggacaatcc taagaaagag      2580
agcgtgttcg aatacgatct gattaaggac aagcggttca ccgaagataa gttcttttc       2640
cattgtccaa tcaccattaa cttcaagtca gcggcgcta acaagttcaa cgacgagatc       2700
aatctgctgc tgaaggaaaa agcaaacgat gtgcacatcc tgagcattga ccgaggagag     2760
cggcatctgg cctactatac cctggtggat ggcaaaggga atatcattaa gcaggataca     2820
ttcaacatca ttggcaatga ccggatgaaa accaactacc acgataaact ggctgcaatc     2880
gagaaggata gagactcagc taggaaggac tggaagaaaa tcaacaacat taaggagatg     2940
aaggaaggct atctgagcca ggtggtccat gagattgcaa agctggtcat cgaatacaat     3000
gccattgtgg tgttcgagga tctgaacttc ggctttaaga gggggcgctt taaggtggaa     3060
aaacaggtct atcagaagct ggagaaaatg ctgatcgaaa agctgaatta cctggtgttt     3120
```

```
aaagataacg agttcgacaa gaccggaggc gtcctgagag cctaccagct gacagctccc   3180
tttgaaactt tcaagaaaat gggaaaacag acaggcatca tctactatgt gccagccgga   3240
ttcacttcca agatctgccc cgtgaccggc tttgtcaacc agctgtaccc taaatatgag   3300
tcagtgagca agtcccagga attttttcagc aagttcgata agatctgtta taatctggac   3360 aagggggtact tcgagttttc cttcgattac aagaacttcg gcgacaaggc cgctaagggg   3420
aaatggacca ttgcctcctt cggatctcgc ctgatcaact ttcgaaattc cgataaaaac   3480
cacaattggg acactaggga ggtgtaccca accaaggagc tggaaaagct gctgaaagac   3540
tactctatcg agtatggaca tggcgaatgc atcaaggcag ccatctgtgg cgagagtgat   3600
aagaaatttt tcgccaagct gacctcagtg ctgaatacaa tcctgcagat gcggaactca   3660
aagaccggga cagaactgga ctatctgatt agccccgtgg ctgatgtcaa cggaaacttc   3720
ttcgacagca gacaggcacc caaaaatatg cctcaggatg cagacgccaa cggggcctac   3780
cacatcgggc tgaagggact gatgctgctg ggccggatca agaacaatca ggagggggaag   3840 aagctgaacc tggtcattaa gaacgaggaa tacttcgagt ttgtccagaa tagaaataac   3900
aaaaggccgg cggccacgaa aaaggccggc caggcaaaaa agaaaaaggg atcctaccca   3960
tacgatgttc cagattacgc ttatccctac gacgtgcctg attatgcata cccatatgat   4020
gtccccgact atgcctaa                                                 4038
```

<210> SEQ ID NO 18
<211> LENGTH: 1345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190
```

```
Asn Asp Ile Pro Thr Ser Ile Ile Tyr Arg Ile Val Asp Asp Asn Leu
            195                 200                 205
Pro Lys Phe Leu Glu Asn Lys Ala Lys Tyr Glu Ser Leu Lys Asp Lys
210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
            420                 425                 430
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Asp Val Lys Ala Ile Lys Asp
        515                 520                 525
Leu Leu Asp Gln Thr Asn Asn Leu Leu His Lys Leu Lys Ile Phe His
530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
```

-continued

```
            610                 615                 620
Asp Asp Lys Tyr Tyr Leu Gly Val Met Asn Lys Asn Asn Lys Ile
625                 630                 635                 640

Phe Asp Asp Lys Ala Ile Lys Glu Asn Lys Gly Glu Gly Tyr Lys Lys
                    645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
                850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                 1000                1005

Asn Phe Gly Phe Lys Arg Gly Arg Phe Lys Val Glu Lys Gln Val
        1010                1015                1020

Tyr Gln Lys Leu Glu Lys Met Leu Ile Glu Lys Leu Asn Tyr Leu
        1025                1030                1035
```

```
Val Phe Lys Asp Asn Glu Phe Asp Lys Thr Gly Gly Val Leu Arg
    1040            1045                1050

Ala Tyr Gln Leu Thr Ala Pro Phe Glu Thr Phe Lys Lys Met Gly
    1055            1060                1065

Lys Gln Thr Gly Ile Ile Tyr Tyr Val Pro Ala Gly Phe Thr Ser
    1070            1075                1080

Lys Ile Cys Pro Val Thr Gly Phe Val Asn Gln Leu Tyr Pro Lys
    1085            1090                1095

Tyr Glu Ser Val Ser Lys Ser Gln Glu Phe Phe Ser Lys Phe Asp
    1100            1105                1110

Lys Ile Cys Tyr Asn Leu Asp Lys Gly Tyr Phe Glu Phe Ser Phe
    1115            1120                1125

Asp Tyr Lys Asn Phe Gly Asp Lys Ala Ala Lys Gly Lys Trp Thr
    1130            1135                1140

Ile Ala Ser Phe Gly Ser Arg Leu Ile Asn Phe Arg Asn Ser Asp
    1145            1150                1155

Lys Asn His Asn Trp Asp Thr Arg Glu Val Tyr Pro Thr Lys Glu
    1160            1165                1170

Leu Glu Lys Leu Leu Lys Asp Tyr Ser Ile Glu Tyr Gly His Gly
    1175            1180                1185

Glu Cys Ile Lys Ala Ala Ile Cys Gly Glu Ser Asp Lys Lys Phe
    1190            1195                1200

Phe Ala Lys Leu Thr Ser Val Leu Asn Thr Ile Leu Gln Met Arg
    1205            1210                1215

Asn Ser Lys Thr Gly Thr Glu Leu Asp Tyr Leu Ile Ser Pro Val
    1220            1225                1230

Ala Asp Val Asn Gly Asn Phe Phe Asp Ser Arg Gln Ala Pro Lys
    1235            1240                1245

Asn Met Pro Gln Asp Ala Asp Ala Asn Gly Ala Tyr His Ile Gly
    1250            1255                1260

Leu Lys Gly Leu Met Leu Leu Gly Arg Ile Lys Asn Asn Gln Glu
    1265            1270                1275

Gly Lys Lys Leu Asn Leu Val Ile Lys Asn Glu Glu Tyr Phe Glu
    1280            1285                1290

Phe Val Gln Asn Arg Asn Asn Lys Arg Pro Ala Ala Thr Lys Lys
    1295            1300                1305

Ala Gly Gln Ala Lys Lys Lys Lys Gly Ser Tyr Pro Tyr Asp Val
    1310            1315                1320

Pro Asp Tyr Ala Tyr Pro Tyr Asp Val Pro Asp Tyr Ala Tyr Pro
    1325            1330                1335

Tyr Asp Val Pro Asp Tyr Ala
    1340            1345

<210> SEQ ID NO 19
<211> LENGTH: 21
<212> TYPE: DNA
<213> ORGANISM: Simian virus 40

<400> SEQUENCE: 19
ccaaagaaaa agaggaaagt c                                              21

<210> SEQ ID NO 20
<211> LENGTH: 21
<212> TYPE: DNA
<213> ORGANISM: Simian virus 40
```

<400> SEQUENCE: 20
cctaaaaaga aacgaaaggt t                                                    21

<210> SEQ ID NO 21
<211> LENGTH: 48
<212> TYPE: DNA
<213> ORGANISM: Unknown
<220> FEATURE:
<223> OTHER INFORMATION: Description of Unknown: Nucleoplasmin NLS
      peptide

<400> SEQUENCE: 21
aaaaggccgg cggccacgaa aaaggccggc caggcaaaaa agaaaaag                        48

<210> SEQ ID NO 22
<211> LENGTH: 21
<212> TYPE: DNA
<213> ORGANISM: Simian virus 40

<400> SEQUENCE: 22
cccaagaaga agaggaaagt c                                                    21

<210> SEQ ID NO 23
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tctggtggtt cttctggtgg ttctagcggc agcgagactc ccgggacctc agagtccgcc          60
acacccgaaa gttccggagg gagtagcggc ggg                                       93

<210> SEQ ID NO 24
<211> LENGTH: 7
<212> TYPE: PRT
<213> ORGANISM: Simian virus 40

<400> SEQUENCE: 24

Pro Lys Lys Lys Arg Lys Val
1               5

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly
            20                  25                  30

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 26
aaccagtgga ggcaagaggg cggc                                          24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaccaagaca ggtcactgtt tcag                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaccacacct tcacctgggc cagg                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaccggtggc gcattgccac gaag                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatagcattg cagagaggcg tatc                                          24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aatatgctgt ctgaagccat cgct                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 32
aataagtggc agagtgctaa ggga                                            24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aatatggagc ctgctccagg tggg                                            24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aatcagtacg cagagagtcg ccgt                                            24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aatcctaact gagaccttac accg                                            24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aatgcgccac cggttgatgt gatg                                            24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
accccggctc tggctaaaga ggga                                            24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
```
accccctatt tctgacctcc caaa                                             24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acccagaggc tcaagtgagc agct                                             24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
accctagtca ttggaggtga catc                                             24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acccacgagg gcagagtgct gctt                                             24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
acccaataag tggcagagtg ctaa                                             24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agccgccctc ttgcctccac tggt                                             24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agccatcgct tcctcctgaa aatg                                              24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agcctcaccc ctctagccct acat                                              24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agcctgctcc aggtggggaa taag                                              24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agtaacagac atggaccatc agga                                              24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agtaccagat tctgagcagg gaga                                              24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agtctccgtg aacgttccct tagc                                              24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agtctgtcct gaacctgatg acac                                              24

```
<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atcaggaaac attaacgtac tgat                                          24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atcagaatcc tcttcgatgc catt                                          24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atcctcacag cagccccttg agaa                                          24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atccaatcaa ctctatacga aaat                                          24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atccccaaca tgcactgatg ttgt                                          24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atccatcggc gctttggtcg gcat                                          24
```

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
attaacgtac tgatgttaac agct                                          24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
attaacatta acaagaagca tttg                                          24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
attattcaag tggcgcagat ctag                                          24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
attagaagga gatgctcctg tctc                                          24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
attcaccgag caggagtgag ggaa                                          24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
attccccacc tggagcaggc tcca                                          24

```
<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
attctgatga gcctttagag agaa                                              24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
attccctctt tagccagagc cggg                                              24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
attcgcacgg ctctggagcg gcgg                                              24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
attgggtcag ctgttaacat cagt                                              24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
attgttatga acctgggtga agtc                                              24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
attggaatcc tggagtgacc cctg                                              24

<210> SEQ ID NO 69
```

<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
attggattga gaatagaatt cttc                                          24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
attggaacat ccgcgaaatg atac                                          24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atttggctca gcaggcacct gcct                                          24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atttgctttc cacccacctt tccc                                          24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atttctgacc tcccaaacag ctac                                          24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atttcttctt tctgcactaa attg                                          24

<210> SEQ ID NO 75
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atttcgcgga tgttccaatc agta                                              24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
caccgtgcgc cgggccttgc agtg                                              24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caccgaggca tctctgcacc gagg                                              24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccccgcccaa agccgccctc ttgc                                              24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ccccgccttc agaagagggt gcat                                              24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccccagaggg ttctagaccc agag                                              24

<210> SEQ ID NO 81
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 81
ccccagggcc agcccagcag ccaa                                          24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgcacggctc tggagcggcg gctg                                          24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgcattgcca cgaagcaggc caat                                          24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgccgctcca gagccgtgcg aatg                                          24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cgccaccggt tgatgtgatg ggag                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cgccacatcc atcggcgctt tggt                                          24

<210> SEQ ID NO 87
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 87
cgccgatgga tgtggcgcag gtag                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cgtcagcacc tgggaccccg ccac                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cgtctccaag gtgaaagcgg aagt                                          24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctcaaacggt ccccagaggg ttct                                          24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctcaaaactc atgggatgtg attc                                          24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctccgtgaac gttcccttag cact                                          24

<210> SEQ ID NO 93
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 93
ctccttctaa tgagaaacgg tgta                                              24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctccactggt tgtgcagccg ccgc                                              24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctccagagcc gtgcgaatgg ggcc                                              24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctctggggaa cacgcccggt gtca                                              24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cttattgggt cagctgttaa catc                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cttattcccc acctggagca ggct                                              24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
cttactaatc agatggaagc tctt                                          24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttacaccgt ttctcattag aagg                                          24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cttccgcttt caccttggag acgg                                          24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cttcacccag gttcataaca atgt                                          24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cttctccccg ctccaacgcc ctca                                          24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cttctaatga gaaacggtgt aagg                                          24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cttcgcgcac ctcatggaat ccct                                          24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cttgacaggc gagtaacaga catg                                          24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cttgttaatg ttaataactt gctt                                          24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cttggttaac tgagtgtgtc atca                                          24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cttggggagt cccagaggta tcca                                          24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctttggtcag gttggctgct gggc                                          24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 111
ctttccctgg cctacctcac tggc                                          24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ctttagccag agccggggtg tgca                                          24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctttagagag aaggctgtcc ttag                                          24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctttggtcgg catggcccca ttcg                                          24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcccggtgtc acgccacttg acag                                          24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gccccacgct tcaggcacga agga                                          24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
```

```
gtcacgccac ttgacaggcg agta                                              24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gtcatcaggt tcaggacaga ctgc                                              24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gtccccagag ggttctagac ccag                                              24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtccaggaga caggagcatc tcct                                              24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gtcccaggtg ctgacgtagg tagt                                              24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtcctcccca ttggcctgct tcgt                                              24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
```

```
gttactcgcc tgtcaagtgg cgtg                                              24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gttatgaacc tgggtgaagt ccca                                              24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gttaatgtta ataacttgct tcaa                                              24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gttaaccaag gtcagaacat tcac                                              24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gttcccttag cactctgcca ctta                                              24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gttcatttgt ccagaggaaa ccac                                              24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gttccctgtc ttgtttgtga gagg                                              24
```

```
<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gttcaggaca gactgcctcc ttcg                                              24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gttggggatt cctggtgcca gaaa                                              24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gttgggactt cacccaggtt cata                                              24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gttgagggcg ttggagcggg gaga                                              24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gttgattgga ttgagaatag aatt                                              24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gttgtgcagc cgccgctcca gagc                                              24
```

```
<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gtttcctgat ggtccatgtc tgtt                                          24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtttgacttg ggatagtgga atag                                          24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtttgggagg tcagaaatag gggg                                          24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtttctcatt agaaggagat gctc                                          24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtttcacctc ggtgcagaga tgcc                                          24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tacatctctc tttcttctcc cctc                                          24
```

```
<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tacaggcaaa gctgagcaaa agta                                            24

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tacaaacggc agaagctgga ggag                                            24

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tacaagacca gcatgtactc acct                                            24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tacccacgtt cgtggcccca tctt                                            24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
taccagattc tgagcaggga gagg                                            24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tacctcactg gccccacccc agag                                            24

<210> SEQ ID NO 148
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tacctgcgcc acatccatcg gcgc                                              24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tatagagttg attggattga gaat                                              24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tatattcaag aaggttatct caag                                              24

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tatatattca agaaggttat ctca                                              24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tatagacatg tcccatttgt ggga                                              24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tatcgcctct ccctgctcag aatc                                              24

<210> SEQ ID NO 154
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tatctcaaga aactggcttg gaaa                                           24

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tatccagttc agtcaagttt gcct                                           24

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tatcccaagt caaacttctc ttca                                           24

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tatgttcggg tgctgtgaac ttcc                                           24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tatgaacctg ggtgaagtcc caac                                           24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tatgtagctg tttgggaggt caga                                           24

<210> SEQ ID NO 160
<211> LENGTH: 24
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 160
tatgggacat tttcagaact ccaa                                          24

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tattgggtca gctgttaaca tcag                                          24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tatttctgac ctcccaaaca gcta                                          24

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tattctcaat ccaatcaact ctat                                          24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tattggtcga aatgcatgtc aatc                                          24

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tccatgtctg ttactcgcct gtca                                          24

<210> SEQ ID NO 166
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 166
tccaggagac aggagcatct cctt                                              24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tccagtccca aatatgtagc tgtt                                              24

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tccccagagg gttctagacc caga                                              24

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tccccaaact ctccagtctg ttta                                              24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tcccgtcacc cctgtttctg gcac                                              24

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tcccaggtgc tgacgtaggt agtg                                              24

<210> SEQ ID NO 172
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 172 tccctctttta gccagagccg gggt                                              24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tccgtgaacg ttcccttagc actc                                               24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tccgagcttc tggcggtctc aagc                                               24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tccgcacgta acctcacttt cctg                                               24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tcctgatggt ccatgtctgt tact                                               24

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tgcacacagc aggcctttgg tcag                                               24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 178
tgcagaaaga agaaattcaa tcct                                          24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tgccacttat tgggtcagct gtta                                          24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tgcctcgcat cagcgtgatc agca                                          24

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgcctccact ggttgtgcag ccgc                                          24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgccgaccaa agcgccgatg gatg                                          24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tgtaatgaaa tggcagcttg tttc                                          24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tgtactttgt cctccggttc tgga                                    24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tgtacctcac cactgacatt aatt                                    24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tgtaaccaca gtcaagtagt taat                                    24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgtaaggtct cagttaggat tgaa                                    24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tgtcaatctc ccagcgtctt tatc                                    24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tgtcttgttt gtgagaggaa ttca                                    24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tgtccagagg aaaccactgt tggg                                          24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgtctattcc actatcccaa gtca                                          24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tgtccctcac ccatctccct gtga                                          24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgtgcagccg ccgctccaga gccg                                          24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tgtgagagga attcaaactg aggc                                          24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tgtggcgcag gtagcgcgcc cact                                          24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196

```
tgtggttcca gaaccggagg acaa                                              24
```

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197

```
tgtgatggga gcccttcttc ttct                                              24
```

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198

```
ttacaggcaa agctgagcaa aagt                                              24
```

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199

```
ttactcatct ctgccagacc acct                                              24
```

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200

```
ttactgattc tggggtcaac atct                                              24
```

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201

```
ttacaaatga atggcatcga agag                                              24
```

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202

```
ttcaccgtt tctcattaga agga                                         24
```

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203

```
ttactagggc aataagcaac acct                                        24
```

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204

```
ttcagtctcc gtgaacgttc cctt                                        24
```

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205

```
ttcacccagg ttcataacaa tgtt                                        24
```

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

```
ttcacccagc ttccctgtgg tggc                                        24
```

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

```
ttcaatccta actgagacct taca                                        24
```

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208

```
ttcaccttgg agacggcgac tctc                                        24
```

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttcctgatgg tccatgtctg ttac                                          24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ttccctggcc tacctcactg gccc                                          24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ttccaaagcc cattccctct ttag                                          24

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ttccattgtg caaaagactc cctt                                          24

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ttccgagctt ctggcggtct caag                                          24

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ttcgtggccc catctttctc aagg                                          24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
ttcgagagtg aggacgtgtg tgtc                                        24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 216
ttcggagcga aaaccaagac aggt                                        24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 217
ttcgaccaat ttagtgcaga aaga                                        24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 218
ttcgcacggc tctggagcgg cggc                                        24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 219
ttctgccctc ccgtcacccc tgtt                                        24

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 220
ttctgccctt tactcatctc tgcc                                        24

```
<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ttctgacctc ccaaacagct acat                                              24

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ttctttcgac caatttagtg caga                                              24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ttctggcggt ctcaagcact acct                                              24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tttatttccc ttcagctaaa ataa                                              24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tttattttag ctgaagggaa ataa                                              24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tttatccgtg ttccttgact ctgg                                              24

<210> SEQ ID NO 227
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tttaccttcg gagcgaaaac caag                                            24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tttaggatgc cactaaaagg gaaa                                            24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tttagattga aggaaaagtt acaa                                            24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tttccctcac tcctgctcgg tgaa                                            24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tttcctgatg gtccatgtct gtta                                            24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tttctcatct gtgcccctcc ctcc                                            24

<210> SEQ ID NO 233
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tttcaccttg gagacggcga ctct                                              24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tttcgctccg aaggtaaaag aaat                                              24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tttcagcctc acccctctag ccct                                              24

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tttcttctcc cctctgctgg atac                                              24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tttccgagct tctggcggtc tcaa                                              24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tttgaggagt gttcagtctc cgtg                                              24

<210> SEQ ID NO 239
<211> LENGTH: 24
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 239
tttggctcag caggcacctg cctc                                          24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tttgtcctcc ggttctggaa ccac                                          24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tttgtggttg cccaccctag tcat                                          24

<210> SEQ ID NO 242
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tttgtacttt gtcctccggt tctg                                          24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tttgggcggg gtccagttcc ggga                                          24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tttggtcggc atggcccat tcgc                                           24

<210> SEQ ID NO 245
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 245
ttttatttcc cttcagctaa aata                                              24

<210> SEQ ID NO 246
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ttttcaggag gaagcgatgg cttc                                              24

<210> SEQ ID NO 247
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ttttccgagc ttctggcggt ctca                                              24

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ttttcgtata gagttgattg gatt                                              24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ttttgagcta aagtctggct gtag                                              24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tttgagagtc tggatgagaa atgc                                              24

<210> SEQ ID NO 251
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 251
tttctaccct cttctctgcc tttc                                              24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tttgctctag gaaccctcag cccc                                              24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tttctccaaa gccactaggc aggc                                              24

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tttaggaaag caggagctat tcag                                              24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tttggaacca aatttggtga gtgc                                              24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
attcaggaag cagggtcct ccag                                               24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 257
attgggcttt ggaaccaaat ttgg                                              24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
attccgtcat agggatagat cggg                                              24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cttgtttctc caaagccact aggc                                              24

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
cttcctgaat agctcctgct ttcc                                              24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cttatcagtc ctgaaaagaa cccc                                              24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gttgcatttg ctctccacct ccca                                              24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 263
gttagcgcgc ggtgagggga gggg                                              24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gttccaaagc ccaatctaaa aaac                                              24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ttcaggaagc agggtcctc cagg                                               24

<210> SEQ ID NO 266
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ttcctggagg ccagcactca ccaa                                              24

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ttcaggactg ataagagcgc gcag                                              24

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctccaaagcc actaggcagg cgtt                                              24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 269
ctccaggaaa tctggagccc tggc                                         24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ctccctccct cgcctccacc ctgt                                         24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tcccgccccc accgggccgg cctc                                         24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tcccctcacc gcgcgctaac gcct                                         24

<210> SEQ ID NO 273
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tccctcgcct ccaccctgtt ggtt                                         24

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tttgtactga tggtatgggg ccaa                                         24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tttgaagtcc aactcctaag ccag                                              24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tttgcaagtg tatttacgta atat                                              24

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
attggccaac cctagggtgt ggct                                              24

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
attgctacta aaacatcct cctt                                               24

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
attgggaaaa cgatcttcaa tatg                                              24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
cttagacctc accctgtgga gcca                                              24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281

```
cttaggagtt ggacttcaaa ccct                                        24
```

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282

```
cttaccaagc tgtgattcca aata                                        24
```

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283

```
tatgcccagc cctggctcct gccc                                        24
```

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284

```
tatctcttgg ccccatacca tcag                                        24
```

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285

```
tatcccaaag ctgaattatg gtag                                        24
```

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286

```
tgtcatcact tagacctcac cctg                                        24
```

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287

```
tgtactgatg gtatggggcc aaga                                        24
```

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgtagatgga tctcttcctg cgtc                                          24

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ttcaaaccct cagccctccc tcta                                          24

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ttccaaatat tacgtaaata cact                                          24

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ttcagctttg ggatatgtag atgg                                          24

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ctccctgctc ctgggagtag attg                                          24

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ctccctctaa gatatatctc ttgg                                          24

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ctccagaata tgcaaaatac ttac                                          24

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tacctgtcct tggctcttct ggca                                          24

<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
taccatcagt acaaattgct acta                                          24

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
taccataatt cagctttggg atat                                          24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tttcaagcct cgggaaactg ccct                                          24

<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tttctttgtt tgcaggtcag tgcc                                          24

```
<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
tttgggctgg cgctcgagct ctcc                                          24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
attcctggtt tgggctggcg ctcg                                          24

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
attagtgcca ttattgtggc gaat                                          24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
attctcggca ctggcgtgag agtt                                          24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
cttccccgga gtcgaggact gtgg                                          24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
cttcggccac aagatggcac tgac                                          24

<210> SEQ ID NO 306
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
cttataaagt gaggaaaaca aatt                                              24

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ttccccggag tcgaggactg tggg                                              24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ttcggccaca agatggcact gacc                                              24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ttcccagcga gccctttgat tcct                                              24

<210> SEQ ID NO 310
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ctccggggaa ggcagggcag tttc                                              24

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
ctccagccgg gtatgacttc ggcc                                              24

<210> SEQ ID NO 312
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ctcctttctt tggcccactg agaa                                         24

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tttcaggctg tgaaccttgg tggg                                         24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tttcctgctc cctcctcgcc aatg                                         24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tttgctagga atattgaagg gggc                                         24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
attgcggcgg gctgcgggcc aggc                                         24

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
attacccatc cgcccccgga aact                                         24

<210> SEQ ID NO 318
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 318
attcctagca aagagggaac ggct                                          24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
cttcccctcc attgcggcgg gctg                                          24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cttcccctcc attgcggcgg gctg                                          24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321 cttccctgc ccccttcaat attc                                           24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gttcacagcc tgaaaattac ccat                                          24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gttacgtgcg gacagggcct gaga                                          24

<210> SEQ ID NO 324
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 324
gttggagcgg ggagaaggcc aggg                                              24

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ttccacacgc ggctcgggcc cggg                                              24

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ttcaggctgt gaaccttggt gggg                                              24

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ttcctgctcc ctcctcgcca atgc                                              24

<210> SEQ ID NO 328
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ttccccttca ttgcggcggg ctgc                                              24

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ttcccctgcc cccttcaata ttcc                                              24

<210> SEQ ID NO 330
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 330
tccccttcat tgcggcgggc tgcg                                             24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tccctcctcg ccaatgcccc gcgg                                             24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tcccctgccc ccttcaatat tcct                                             24

<210> SEQ ID NO 333
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ctcctcgcca atgccccgcg ggcg                                             24

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ctccctcctc gccaatgccc cgcg                                             24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
ctccaggatt ccaatagatc tgtg                                             24

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 336
agggtgtgca gacggcagtc act                                              23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
agggagcagc gtcttcgaga gtg                                              23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tggggtgagt gagtgtgtgc gtg                                              23

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
aggggggcgg atgggtaatt ttc                                              23

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
aggggcattg gcgaggaggg agc                                              23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
agggcaaaga gggaacggct ctc                                              23

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 342
tttatccgtg ttccttgact ctgg                                          24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tttccctcac tcctgctcgg tgaa                                          24

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tttctcatct gtgcccctcc ctcc                                          24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tttcagcctc acccctctag ccct                                          24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tttcttctcc cctctgctgg atac                                          24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tttccgagct tctggcggtc tcaa                                          24

<210> SEQ ID NO 348
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 348
tttgtggttg cccaccctag tcat                                          24

<210> SEQ ID NO 349
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tttggtcggc atggccccat tcgc                                          24

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ccagaatgca caaagtactg cac                                           23

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
gccaaagccc gagagagtgc c                                             21

<210> SEQ ID NO 352
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gctgtgtctg taaactgatg gctaaca                                       27

<210> SEQ ID NO 353
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
ttgcattcta ctcaattgca ttctgtggg                                     29

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
ggagcagctg gtcagagggg                                              20

<210> SEQ ID NO 355
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
ccatagggaa gggggacact gg                                           22

<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
ctgcctccta ttcatacaca cttacggg                                     28

<210> SEQ ID NO 357
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
ctctgttggt ggaaactccc tgacc                                        25

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gggccgggaa agagttgctg                                              20

<210> SEQ ID NO 359
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
gccctacatc tgctctccct cc                                           22

<210> SEQ ID NO 360
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
ccagcacaac ttactcgcac ttgac                                        25

<210> SEQ ID NO 361
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
catcaccaac ccacagccaa gg                                           22

<210> SEQ ID NO 362
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
cagctccaca aacttggtgc caaattc                                      27

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
ccgcaatgaa ggggaagctc gac                                          23

<210> SEQ ID NO 364
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
cgctgttcag gtctctgcta gaagtagg                                     28

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
ccagaccaga gaccactggg aag                                          23

<210> SEQ ID NO 366
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
gacaaatgta tcatgctatt ataagatgtt gac                               33

<210> SEQ ID NO 367
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
ccatttactg agagtaatta taattgtgc                                    29

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
ccaaggacag gaatatctta taccctctgt                                   30

<210> SEQ ID NO 369
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
tgtcattgtc cttgtccttt agctaccg                                     28

<210> SEQ ID NO 370
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
caaaacagcc aagcttgcat gc                                           22

<210> SEQ ID NO 371
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
agctgccatc ggtatttcac accgcatacg tac                               33

<210> SEQ ID NO 372
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
agctggcaac ggtatttcac accgcatacg tac                               33

```
<210> SEQ ID NO 373
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
agctgatgcc ggtatttcac accgcatacg tac                                  33

<210> SEQ ID NO 374
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
agctggatgc ggtatttcac accgcatacg tac                                  33

<210> SEQ ID NO 375
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
agctgcgatc ggtatttcac accgcatacg tac                                  33

<210> SEQ ID NO 376
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: modified_base
<222> LOCATION: (18)..(27)
<223> OTHER INFORMATION: a, c, t, g, unknown or other
<220> FEATURE:
<221> NAME/KEY: misc_feature
<222> LOCATION: (18)..(27)
<223> OTHER INFORMATION: n is a, c, g, or t

<400> SEQUENCE: 376
agaccggaat tcnnngtnnn nnnnnnngga atcccttctg cagcacctgg gcgcaggtca     60
cgaggcatg                                                             69

<210> SEQ ID NO 377
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (13)..(15)
<223> OTHER INFORMATION: a, c, t, g, unknown or other
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: modified_base
<222> LOCATION: (18)..(27)
<223> OTHER INFORMATION: a, c, t, g, unknown or other
<220> FEATURE:
<221> NAME/KEY: misc_feature
<222> LOCATION: (18)..(27)
<223> OTHER INFORMATION: n is a, c, g, or t

<400> SEQUENCE: 377
agaccggaat tcnnngtnnn nnnnnnnctg atggtccatg tctgttactc gcgcaggtca    60
cgaggcatg                                                           69

<210> SEQ ID NO 378
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
cctcgtgacc tgcgc                                                    15

<210> SEQ ID NO 379
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
aattctttag gaatcccttc tgcagcacct gggcatg                            37

<210> SEQ ID NO 380
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
cccaggtgct gcagaaggga ttcctaaag                                     29

<210> SEQ ID NO 381
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
aattccttag gaatcccttc tgcagcacct gggcatg                            37

<210> SEQ ID NO 382
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 382
cccaggtgct gcagaaggga ttcctaagg                                       29

<210> SEQ ID NO 383
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
aattcacctg gaatcccttc tgcagcacct gggcatg                              37

<210> SEQ ID NO 384
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cccaggtgct gcagaaggga ttccaggtg                                       29

<210> SEQ ID NO 385
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aattctttac tgatggtcca tgtctgttac tcgcatg                              37

<210> SEQ ID NO 386
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
cgagtaacag acatggacca tcagtaaag                                       29

<210> SEQ ID NO 387
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
aattccttac tgatggtcca tgtctgttac tcgcatg                              37

<210> SEQ ID NO 388
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 388
cgagtaacag acatggacca tcagtaagg                                            29

<210> SEQ ID NO 389
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
aattcacctc tgatggtcca tgtctgttac tcgcatg                                   37

<210> SEQ ID NO 390
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
cgagtaacag acatggacca tcagaggtg                                            29

<210> SEQ ID NO 391
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
atggtgagca gagtgcccta tc                                                   22

<210> SEQ ID NO 392
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
atggtccctg gcagtctcca aa                                                   22

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ccatcggact ctcataggtt gtc                                                  23

<210> SEQ ID NO 394
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 394
gacctgtact tattgtctct catc                                          24

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
gcacgtggat cctgagaact                                               20

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
attggacagc aagaaagcga g                                             21

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
cattatgctg aggatttgga aagg                                          24

<210> SEQ ID NO 398
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
cttgagcaca cagagggcta ca                                            22

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
gctccagagc cgtgcgaatg g                                             21

<210> SEQ ID NO 400
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
gccctacatc tgctctccct cc                22

<210> SEQ ID NO 401
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
cagctgaccc aataagtggc agagtg            26

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
tcaggttggc tgctgggctg g                 21

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
ccccagtggc tgctctggg                    19

<210> SEQ ID NO 404
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
catcgatgtc ctccccattg gc                22

<210> SEQ ID NO 405
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
gctgtctgaa gccatcgctt cc                22

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
cagaggtatc cagcagaggg gag                                              23

<210> SEQ ID NO 407
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
ccttcggagc gaaaaccaag acag                                             24

<210> SEQ ID NO 408
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
caggcaggac gaatcacact gaatg                                            25

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
gctccagagc cgtgcgaatg g                                                21

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
gcacctcatg gaatcccttc tgc                                              23

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
gaagctggag gaggaagggc                                                  20

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412

```
cagcagcaag cagcactctg c                                              21

<210> SEQ ID NO 413
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
gccctcttgc ctccactggt tg                                             22

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
ccaatagcat tgcagagagg cgt                                            23

<210> SEQ ID NO 415
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccgt aatttctact cttgtagatg gagacgatta atgcgtctcc   360
ttttttt                                                             367

<210> SEQ ID NO 416
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccga atttctacta agtgtagatg gagacgatta atgcgtctcc   360
ttttttt                                                             367
```

<210> SEQ ID NO 417
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 417

```
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccga atttctactg ttgtagatgg agacgattaa tgcgtctcct   360
tttttt                                                              366
```

<210> SEQ ID NO 418
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 418

```
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccga atttctactg tttgtagatg gagacgatta atgcgtctcc   360
ttttttt                                                             367
```

<210> SEQ ID NO 419
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 419

```
taatacgact cactatagta atttctactc ttgtagatgg agacccatgc catagcgttg    60
ttcggaatat gaatttttga acagattcac caacacctag tggtctcctt taaaaagctt   120
```

<210> SEQ ID NO 420
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 420

```
taatacgact cactatagaa tttctactaa gtgtagatgg agacccatgc catagcgttg    60
ttcggaatat gaatttttga acagattcac caacacctag tggtctcctt taaaaagctt   120
```

<210> SEQ ID NO 421
<211> LENGTH: 4059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421

| | | | | | | |
|---|---|---|---|---|---|---|
| atgacacagt | tcgagggctt | taccaacctg | tatcaggtga | gcaagacact | gcggtttgag | 60 |
| ctgatcccac | agggcaagac | cctgaagcac | atccaggagc | agggcttcat | cgaggaggac | 120 |
| aaggcccgca | atgatcacta | caaggagctg | aagcccatca | tcgatcggat | ctacaagacc | 180 |
| tatgccgacc | agtgcctgca | gctggtgcag | ctggattggg | agaacctgag | cgccgccatc | 240 |
| gactcctata | gaaaggagaa | aaccgaggag | acaaggaacg | ccctgatcga | ggagcaggcc | 300 |
| acatatcgca | tgccatcca | cgactacttc | atcggccgga | cagacaacct | gaccgatgcc | 360 |
| atcaataaga | gacacgccga | gatctacaag | ggcctgttca | aggccgagct | gtttaatggc | 420 |
| aaggtgctga | gcagctggg | caccgtgacc | acaaccgagc | acgagaacgc | cctgctgcgg | 480 |
| agcttcgaca | gtttacaac | ctacttctcc | ggcttttatg | agaacaggaa | gaacgtgttc | 540 |
| agcgccgagg | atatcagcac | agccatccca | caccgcatcg | tgcaggacaa | cttccccaag | 600 |
| tttaaggaga | attgtcacat | cttcacacgc | ctgatcaccg | ccgtgcccag | cctgcgggag | 660 |
| cactttgaga | cgtgaagaa | ggccatcggc | atcttcgtga | gcacctccat | cgaggaggtg | 720 |
| tttttccttcc | ctttttataa | ccagctgctg | acacagaccc | agatcgacct | gtataaccag | 780 |
| ctgctgggag | gaatctctcg | ggaggcaggc | accgagaaga | tcaagggcct | gaacgaggtg | 840 |
| ctgaatctgg | ccatccagaa | gaatgatgag | acagcccaca | tcatcgcctc | cctgccacac | 900 |
| agattcatcc | ccctgtttaa | gcagatcctg | tccgataggg | acaccctgtc | tttcatcctg | 960 |
| gaggagttta | gagcgacga | ggaagtgatc | cagtccttct | gcaagtacaa | gacactgctg | 1020 |
| agaaacgaga | acgtgctgga | gacagccgag | gccctgttta | acgagctgaa | cagcatcgac | 1080 |
| ctgacacaca | tcttcatcag | ccacaagaag | ctggagacaa | tcagcagcgc | cctgtgcgac | 1140 |
| cactgggata | cactgaggaa | tgccctgtat | gagcggagaa | tctccgagct | gacaggcaag | 1200 |
| atcaccaagt | ctgccaagga | gaaggtgcag | cgcagcctga | gcacgagga | tatcaacctg | 1260 |
| caggagatca | tctctgccgc | aggcaaggag | ctgagcgagg | ccttcaagca | gaaaaccagc | 1320 |
| gagatcctgt | cccacgcaca | cgccgccctg | gatcagccac | tgcctacaac | cctgaagaag | 1380 |
| caggaggaga | aggagatcct | gaagtctcag | ctggacagcc | tgctgggcct | gtaccacctg | 1440 |
| ctggactggt | tgccgtgga | tgagtccaac | gaggtggacc | ccgagttctc | tgcccggctg | 1500 |
| accggcatca | agctggagat | ggagccttct | ctgagcttct | acaacaaggc | cagaaattat | 1560 |
| gccaccaaga | agccctactc | cgtggagaag | ttcaagctga | actttcagat | gcctacactg | 1620 |
| gcctctggct | gggacgtgaa | taaggagaag | aacaatggcg | ccatcctgtt | tgtgaagaac | 1680 |
| ggcctgtact | atctgggcat | catgccaaag | cagaagggca | ggtataaggc | cctgagcttc | 1740 |
| gagcccacag | agaaaaccag | cgagggcttt | gataagatgt | actatgacta | cttccctgat | 1800 |
| gccgccaaga | tgatcccaaa | gtgcagcacc | cagctgaagg | ccgtgacagc | ccactttcag | 1860 |
| acccacacaa | cccccatcct | gctgtccaac | aatttcatcg | agcctctgga | gatcacaaag | 1920 |
| gagatctacg | acctgaacaa | tcctgagaag | gagccaaaga | agtttcagac | agcctacgcc | 1980 |
| aagaaaaccg | gcgaccagaa | gggctacaga | gaggccctgt | gcaagtggat | cgacttcaca | 2040 |

```
agggatttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc aacgtgatc accaaggagg tgtctcacga gatcatcaag    2580
gataggcgct taccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240
gaccccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840
ctgaaggaga gcaaggatct gaagctgcag aacggcatct ccaatcagga ctggctggcc    3900
tacatccagg agctgcgcaa caaaaggccg gcggccacga aaaggccgg ccaggcaaaa    3960
aagaaaaagg atcctaccc atacgatgtt ccagattacg cttatcccta cgacgtgcct    4020
gattatgcat acccatatga tgtccccgac tatgcctaa                           4059
```

<210> SEQ ID NO 422
<211> LENGTH: 4059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 422

```
atgacacagt tcgagggctt taccaacctg tatcaggtga gcaagacact gcggtttgag    60
ctgatcccac agggcaagac cctgaagcac atccaggagc agggcttcat cgaggaggac   120
aaggcccgca atgatcacta caaggagctg aagcccatca tcgatcggat ctacaagacc   180
tatgccgacc agtgcctgca gctggtgcag ctggattggg agaacctgag cgccgccatc   240
gactcctata gaaaggagaa aaccgaggag acaaggaacg ccctgatcga ggagcaggcc   300
acatatcgca tgccatcca cgactacttc atcggccgga cagacaacct gaccgatgcc   360
atcaataaga gacacgccga gatctacaag ggcctgttca aggccgagct gtttaatggc   420
aaggtgctga agcagctggg caccgtgacc acaaccgagc acgagaacgc cctgctgcgg   480
agcttcgaca gtttacaac ctacttctcc ggcttttata gaaacaggaa gaacgtgttc   540
agcgccgagg atatcagcac agccatccca caccgcatcg tgcaggacaa cttccccaag   600
tttaaggaga attgtcacat cttcacacgc ctgatcaccg ccgtgcccag cctgcgggag   660
cactttgaga cgtgaagaa ggccatcggc atcttcgtga gcacctccat cgaggaggtg   720
ttttccttcc ctttttataa ccagctgctg acacagaccc agatcgacct gtataaccag   780
ctgctgggag gaatctctcg ggaggcaggc accgagaaga tcaagggcct gaacgaggtg   840
ctgaatctgg ccatccagaa gaatgatgag acagcccaca tcatcgcctc cctgccacac   900
agattcatcc ccctgtttaa gcagatcctg tccgatagga acaccctgtc tttcatcctg   960
gaggagttta gagcgacga ggaagtgatc cagtccttct gcaagtacaa gacactgctg  1020
agaaacgaga acgtgctgga gacagccgag gccctgttta cgagctgaa cagcatcgac  1080
ctgacacaca tcttcatcag ccacaagaag ctggagacaa tcagcagcgc cctgtgcgac  1140
cactgggata cactgaggaa tgccctgtat gagcggagaa tctccgagct gacaggcaag  1200
atcaccaagt ctgccaagga aaggtgcag cgcagcctga gcacgagga tatcaacctg  1260
caggagatca tctctgccgc aggcaaggag ctgagcgagg ccttcaagca gaaaaccagc  1320
gagatcctgt cccacgcaca cgccgccctg gatcagccac tgcctacaac cctgaagaag  1380
caggaggaga aggagatcct gaagtctcag ctggacagcc tgctgggcct gtaccacctg  1440
ctggactggt ttgccgtgga tgagtccaac gaggtggacc ccgagttctc tgcccggctg  1500
accggcatca gctggagat ggagccttct ctgagcttct acaacaaggc cagaaattat  1560
gccaccaaga agccctactc cgtggagaag ttcaagctga actttcagat gcctacactg  1620
gccagaggct gggacgtgaa taaggagaag aacaatggcg ccatcctgtt tgtgaagaac  1680
ggcctgtact atctgggcat catgccaaag cagaagggca ggtataaggc cctgagcttc  1740
gagcccacag agaaaaccag cgagggcttt gataagatgt actatgacta cttccctgat  1800
gccgccaaga tgatcccaaa gtgcagcacc cagctgaagg ccgtgacagc cactttcag  1860
acccacacaa cccccatcct gctgtccaac aatttcatcg agcctctgga tcacaaag  1920
gagatctacg acctgaacaa tcctgagaag gagccaaaga gtttcagac agcctacgcc  1980
aagaaaaccg gcgaccagaa gggctacaga gaggccctgt gcaagtggat cgacttcaca  2040
aggggattttc tgtccaagta taccaagaca acctctatcg atctgtctag cctgcggcca  2100
tcctctcagt ataaggacct gggcgagtac tatgccgagc tgaatcccct gctgtaccac  2160
atcagcttcc agagaatcgc cgagaaggag atcatggatg ccgtggagac aggcaagctg  2220
tacctgttcc agatctataa caaggacttt gccaagggcc accacggcaa gcctaatctg  2280
cacacactgt attggaccgg cctgtttttct ccagagaacc tggccaagac aagcatcaag  2340
```

| | | | | | |
|---|---|---|---|---|---|
| ctgaatggcc | aggccgagct | gttctaccgc | cctaagtcca | ggatgaagag | gatggcacac | 2400 |
| cggctgggag | agaagatgct | gaacaagaag | ctgaaggatc | agaaaacccc | aatccccgac | 2460 |
| accctgtacc | aggagctgta | cgactatgtg | aatcacagac | tgtcccacga | cctgtctgat | 2520 |
| gaggccaggg | ccctgctgcc | caacgtgatc | accaaggagg | tgtctcacga | gatcatcaag | 2580 |
| gataggcgct | ttaccagcga | caagttcttt | ttccacgtgc | ctatcacact | gaactatcag | 2640 |
| gccgccaatt | ccccatctaa | gttcaaccag | agggtgaatg | cctacctgaa | ggagcacccc | 2700 |
| gagacaccta | tcatcggcat | cgatcggggc | gagagaaacc | tgatctatat | cacagtgatc | 2760 |
| gactccaccg | gcaagatcct | ggagcagcgg | agcctgaaca | ccatccagca | gtttgattac | 2820 |
| cagaagaagc | tggacaacag | ggagaaggag | agggtggcag | caaggcaggc | ctggtctgtg | 2880 |
| gtgggcacaa | tcaaggatct | gaagcagggc | tatctgagcc | aggtcatcca | cgagatcgtg | 2940 |
| gacctgatga | tccactacca | ggccgtggtg | gtgctggaga | acctgaattt | cggctttaag | 3000 |
| agcaagagga | ccggcatcgc | cgagaaggcc | gtgtaccagc | agttcgagaa | gatgctgatc | 3060 |
| gataagctga | attgcctggt | gctgaaggac | tatccagcag | agaaagtggg | aggcgtgctg | 3120 |
| aacccatacc | agctgacaga | ccagttcacc | tcctttgcca | agatgggcac | ccagtctggc | 3180 |
| ttcctgtttt | acgtgcctgc | cccatataca | tctaagatcg | atcccctgac | cggcttcgtg | 3240 |
| gaccccttcg | tgtggaaaac | catcaagaat | cacgagagcc | gcaagcactt | cctggagggc | 3300 |
| ttcgactttc | tgcactacga | cgtgaaaacc | ggcgacttca | tcctgcactt | taagatgaac | 3360 |
| agaaatctgt | ccttccagag | gggcctgccc | ggctttatgc | ctgcatggga | tatcgtgttc | 3420 |
| gagaagaacg | agacacagtt | tgacgccaag | ggcacccctt | tcatcgccgg | caagagaatc | 3480 |
| gtgccagtga | tcgagaatca | cagattcacc | ggcagatacc | gggacctgta | tcctgccaac | 3540 |
| gagctgatcg | ccctgctgga | ggagaagggc | atcgtgttca | gggatggctc | caacatcctg | 3600 |
| ccaaagctgc | tggagaatga | cgattctcac | gccatcgaca | ccatggtggc | cctgatccgc | 3660 |
| agcgtgctgc | agatgcggaa | ctccaatgcc | gccacaggcg | aggactatat | caacagcccc | 3720 |
| gtgcgcgatc | tgaatggcgt | gtgcttcgac | tcccggtttc | agaacccaga | gtggcccatg | 3780 |
| gacgccgatg | ccaatggcgc | ctaccacatc | gccctgaagg | ccagctgct | gctgaatcac | 3840 |
| ctgaaggaga | gcaaggatct | gaagctgcag | aacggcatct | ccaatcagga | ctggctggcc | 3900 |
| tacatccagg | agctgcgcaa | caaaaggccg | gcggccacga | aaaaggccgg | ccaggcaaaa | 3960 |
| aagaaaaagg | gatcctaccc | atacgatgtt | ccagattacg | cttatcccta | cgacgtgcct | 4020 |
| gattatgcat | acccatatga | tgtccccgac | tatgcctaa | | | 4059 |

<210> SEQ ID NO 423
<211> LENGTH: 4059
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 423

| | | | | | |
|---|---|---|---|---|---|
| atgacacagt | tcgagggctt | taccaacctg | tatcaggtga | gcaagacact | gcggtttgag | 60 |
| ctgatcccac | agggcaagac | cctgaagcac | atccaggagc | agggcttcat | cgaggaggac | 120 |
| aaggcccgca | atgatcacta | caaggagctg | aagcccatca | tcgatcggat | ctacaagacc | 180 |
| tatgccgacc | agtgcctgca | gctggtgcag | ctggattggg | agaacctgag | cgccgccatc | 240 |
| gactcctata | gaaaggagaa | aaccgaggag | acaaggaacg | ccctgatcga | ggagcaggcc | 300 |

-continued

```
acatatcgca atgccatcca cgactacttc atcggccgga cagacaacct gaccgatgcc    360
atcaataaga gacacgccga gatctacaag ggcctgttca aggccgagct gtttaatggc    420
aaggtgctga agcagctggg caccgtgacc acaaccgagc acgagaacgc cctgctgcgg    480
agcttcgaca agtttacaac ctacttctcc ggcttttata gaaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720 tttttccttcc cttttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga cacccctgtc tttcatcctg    960
gaggagttta gagcgacga ggaagtgatc cagtccttct gcaagtacaa gacactgctg   1020
agaaacgaga acgtgctgga gacagccgag gccctgttta cgagctgaa cagcatcgac   1080 ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa ccccccatcct gctgtccaac aatttcatcg agcctctgga tcacaaaag   1920 gagatctacg acctgaacaa tcctgagaag gagccaaaga gtttcagac agcctacgcc   1980 aagaaaaccg cgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
```

```
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000 agcaaggagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atccctgac cggcttcgtg    3240 gaccccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840 ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg gatcctaccc atacgatgtt ccagattacg cttatcccta cgacgtgcct    4020
gattatgcat acccatatga tgtccccgac tatgcctaa                           4059
```

<210> SEQ ID NO 424
<211> LENGTH: 4059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424

```
atgacacagt tcgagggctt taccaacctg tatcaggtga gcaagacact gcggtttgag    60
ctgatcccac agggcaagac cctgaagcac atccaggagc agggcttcat cgaggaggac    120
aaggcccgca atgatcacta caaggagctg aagcccatca tcgatcggat ctacaagacc    180
tatgccgacc agtgcctgca gctggtgcag ctggattggg agaacctgag cgccgccatc    240
gactcctata gaaaggagaa aaccgaggag acaaggaacg ccctgatcga ggagcaggcc    300
acatatcgca atgccatcca cgactacttc atcggccgga cagacaacct gaccgatgcc    360
atcaataaga gacacgccga gatctacaag ggcctgttca aggccgagct gtttaatggc    420
aaggtgctga gcagctggg caccgtgacc acaaccgagc acgagaacgc cctgctgcgg    480
agcttcgaca gtttacaac ctacttctcc ggcttttata gaaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
```

```
cactttgaga acgtgaagaa ggccatcggc atcttcgtga gcacctccat cgaggaggtg    720
ttttccttcc cttttttataa ccagctgctg acacagaccc agatcgacct gtataaccag    780
ctgctgggag gaatctctcg ggaggcaggc accgagaaga tcaagggcct gaacgaggtg    840
ctggccctgg ccatccagaa gaatgatgag acagcccaca tcatcgcctc cctgccacac    900
agattcatcc ccctgtttaa gcagatcctg tccgatagga cacccctgtc tttcatcctg    960
gaggagttta gagcgacga ggaagtgatc cagtccttct gcaagtacaa gacactgctg   1020
agaaacgaga acgtgctgga cagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga gcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt tgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa ccccccatcct gctgtccaac aatttcatcg agcctctgga gatcacaaag   1920
gagatctacg acctgaacaa tcctgagaag gagccaaaga gtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttctt ttccacgtgc ctatcacact gaactatcag   2640
gccgccaatt ccccatctaa gttcaaccag agggtgaatg cctacctgaa ggagcacccc   2700
gagacaccta tcatcggcat cgatcgggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcaggc tatctgagcc aggtcatcca cgagatcgtg   2940
gacctgatga tccactacca ggccgtggtg gtgctggaga acctgaattt cggctttaag   3000
```

```
agcaagagga ccggcatcgc cgagaaggcc gtgtaccagc agttcgagaa gatgctgatc     3060
gataagctga attgcctggt gctgaaggac tatccagcag agaaagtggg aggcgtgctg     3120
aacccatacc agctgacaga ccagttcacc tcctttgcca agatgggcac ccagtctggc     3180
ttcctgtttt acgtgcctgc cccatataca tctaagatcg atcccctgac cggcttcgtg     3240
gaccccttcg tgtggaaaac catcaagaat cacgagagcc gcaagcactt cctggagggc     3300
ttcgactttc tgcactacga cgtgaaaacc ggcgacttca tcctgcactt taagatgaac     3360
agaaatctgt ccttccagag gggcctgccc ggctttatgc ctgcatggga tatcgtgttc     3420
gagaagaacg agacacagtt tgacgccaag ggcacccctt tcatcgccgg caagagaatc     3480
gtgccagtga tcgagaatca cagattcacc ggcagatacc gggacctgta tcctgccaac     3540
gagctgatcg ccctgctgga ggagaagggc atcgtgttca gggatggctc caacatcctg     3600
ccaaagctgc tggagaatga cgattctcac gccatcgaca ccatggtggc cctgatccgc     3660
agcgtgctgc agatgcggaa ctccaatgcc gccacaggcg aggactatat caacagcccc     3720
gtgcgcgatc tgaatggcgt gtgcttcgac tcccggtttc agaacccaga gtggcccatg     3780
gacgccgatg ccaatggcgc ctaccacatc gccctgaagg ccagctgct gctgaatcac     3840 ctgaaggaga gcaaggatct gaagctgcag aacggcatct ccaatcagga ctggctggcc     3900
tacatccagg agctgcgcaa caaaaggccg gcggccacga aaaaggccgg ccaggcaaaa     3960
aagaaaaagg gatcctaccc atacgatgtt ccagattacg cttatcccta cgacgtgcct     4020
gattatgcat acccatatga tgtccccgac tatgcctaa                            4059
```

<210> SEQ ID NO 425
<211> LENGTH: 4011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 425

```
atggggacac agttcgaggg ctttaccaac ctgtatcagg tgagcaagac actgcggttt       60
gagctgatcc cacagggcaa gaccctgaag cacatccagg agcagggctt catcgaggag      120
gacaaggccc gcaatgatca ctacaaggag ctgaagccca tcatcgatcg gatctacaag      180
acctatgccg accagtgcct gcagctggtg cagctggatt gggagaacct gagcgccgcc      240
atcgactcct atagaaagga gaaaaccgag gagacaagga acgccctgat cgaggagcag      300
gccacatatc gcaatgccat ccacgactac ttcatcggcc ggacagacaa cctgaccgat      360
gccatcaata gagacacgc cgagatctac aagggcctgt tcaaggccga gctgtttaat      420
ggcaaggtgc tgaagcagct gggcaccgtg accacaaccg agcacgagaa cgccctgctg      480
cggagcttcg acaagtttac aacctacttc tccggctttt atgagaacag gaagaacgtg      540
ttcagcgccg aggatatcag cacagccatc cacaccgca tcgtgcagga caacttcccc      600
aagtttaagg agaattgtca catcttcaca cgcctgatca ccgccgtgcc cagcctgcgg      660
gagcactttg agaacgtgaa gaaggccatc ggcatcttcg tgagcaccc catcgaggag      720 gtgttttcct tccctttta taaccagctg ctgacacaga cccagatcga cctgtataac      780
cagctgctgg gaggaatctc tcgggaggca ggcaccgaga agatcaaggg cctgaacgag      840
gtgctgaatc tggccatcca gaagaatgat gagacagccc acatcatcgc ctccctgcca      900
cacagattca tccccctgtt taagcagatc ctgtccgata ggaacaccct gtctttcatc      960
```

-continued

| | |
|---|---|
| ctggaggagt ttaagagcga cgaggaagtg atccagtcct tctgcaagta caagacactg | 1020 |
| ctgagaaacg agaacgtgct ggagacagcc gaggccctgt ttaacagct gaacagcatc | 1080 |
| gacctgacac acatcttcat cagccacaag aagctggaga caatcagcag cgccctgtgc | 1140 |
| gaccactggg atacactgag gaatgccctg tatgagcgga gaatctccga gctgacaggc | 1200 |
| aagatcacca gtctgccaa ggagaaggtg cagcgcagcc tgaagcacga ggatatcaac | 1260 |
| ctgcaggaga tcatctctgc cgcaggcaag gagctgagcg aggccttcaa gcagaaaacc | 1320 |
| agcgagatcc tgtcccacgc acacgccgcc ctggatcagc cactgcctac aaccctgaag | 1380 |
| aagcaggagg agaaggagat cctgaagtct cagctggaca gcctgctggg cctgtaccac | 1440 |
| ctgctggact ggtttgccgt ggatgagtcc aacgaggtgg accccgagtt ctctgcccgg | 1500 |
| ctgaccggca tcaagctgga gatggagcct tctctgagct tctacaacaa ggccagaaat | 1560 |
| tatgccacca agaagcccta ctccgtggag aagttcaagc tgaactttca gatgcctaca | 1620 |
| ctggcctctg gctgggacgt gaataaggag aagaacaatg gcgccatcct gtttgtgaag | 1680 |
| aacggcctgt actatctggg catcatgcca aagcagaagg gcaggtataa ggccctgagc | 1740 |
| ttcgagccca cagagaaaac cagcgagggc tttgataaga tgtactatga ctacttccct | 1800 |
| gatgccgcca agatgatccc aaagtgcagc acccagctga aggccgtgac agcccacttt | 1860 |
| cagacccaca caaccccat cctgctgtcc aacaatttca tcgagcctct ggagatcaca | 1920 |
| aaggagatct acgacctgaa caatcctgag aaggagccaa agaagtttca gacagcctac | 1980 |
| gccaagaaaa ccggcgacca gaagggctac agagaggccc tgtgcaagtg gatcgacttc | 2040 |
| acaagggatt ttctgtccaa gtataccaag acaacctcta tcgatctgtc tagcctgcgg | 2100 |
| ccatcctctc agtataagga cctgggcgag tactatgccg agctgaatcc cctgctgtac | 2160 |
| cacatcagct ccagagaat cgccgagaag gagatcatgg atgccgtgga cagaggcaag | 2220 |
| ctgtacctgt tccagatcta taacaaggac tttgccaagg ccaccacgg caagcctaat | 2280 |
| ctgcacacac tgtattggac cggcctgttt tctccagaga acctggccaa gacaagcatc | 2340 |
| aagctgaatg ccaggccga gctgttctac cgccctaagt ccaggatgaa gaggatggca | 2400 |
| caccggctgg gagagaagat gctgaacaag aagctgaagg atcagaaaac cccaatcccc | 2460 |
| gacaccctgt accaggagct gtacgactat gtgaatcaca gactgtccca cgacctgtct | 2520 |
| gatgaggcca gggccctgct gcccaacgtg atcaccaagg aggtgtctca cgagatcatc | 2580 |
| aaggataggc gctttaccag cgacaagttc ttttccacg tgcctatcac actgaactat | 2640 |
| caggccgcca attcccatc taagttcaac cagagggtga atgcctacct gaaggagcac | 2700 |
| cccgagacac ctatcatcgg catcgatcgg ggcgagagaa acctgatcta tatcacagtg | 2760 |
| atcgactcca ccggcaagat cctggagcag cggagcctga caccatcca gcagtttgat | 2820 |
| taccagaaga agctggacaa caggagaag gagagggtgg cagcaaggca ggcctggtct | 2880 |
| gtggtgggca caatcaagga tctgaagcag ggctatctga ccaggtcat ccacgagatc | 2940 |
| gtggacctga tgatccacta ccaggccgtg gtggtgctgg agaacctgaa tttcggcttt | 3000 |
| aagagcaaga ggaccggcat cgccgagaag gccgtgtacc agcagttcga gaagatgctg | 3060 |
| atcgataagc tgaattgcct ggtgctgaag gactatccag cagagaaagt gggaggcgtg | 3120 |
| ctgaacccat accagctgac agaccagttc acctcctttg ccaagatggg cacccagtct | 3180 |
| ggcttcctgt tttacgtgcc tgccccatat acatctaaga tcgatcccct gaccggcttc | 3240 |
| gtggacccct tcgtgtggaa aaccatcaag aatcacgaga gccgcaagca cttcctggag | 3300 |
| ggcttcgact ttctgcacta cgacgtgaaa accggcgact tcatcctgca ctttaagatg | 3360 |

```
aacagaaatc tgtccttcca gaggggcctg cccggcttta tgcctgcatg ggatatcgtg    3420
ttcgagaaga acgagacaca gtttgacgcc aagggcaccc ctttcatcgc cggcaagaga    3480
atcgtgccag tgatcgagaa tcacagattc accggcagat accgggacct gtatcctgcc    3540
aacgagctga tcgccctgct ggaggagaag ggcatcgtgt tcagggatgg ctccaacatc    3600
ctgccaaagc tgctggagaa tgacgattct cacgccatcg acacgatggt ggccctgatc    3660
cgcagcgtgc tgcagatgcg gaactccaat gccgccacag gcgaggacta tatcaacagc    3720
cccgtgcgcg atctgaatgg cgtgtgcttc gactcccggt tcagaaccc agagtggcca    3780 atggacgccg atgccaatgg cgcctaccac atcgccctga agggccagct gctgctgaat    3840
cacctgaagg agagcaagga tctgaagctg cagaacggca tctccaatca ggactggctg    3900
gcctacatcc aggagctgcg caacaaaagg ccggcggcca cgaaaaaggc cggccaggca    3960
aaaaagaaaa agggagcggc cgcactcgag caccaccacc accaccactg a            4011
```

<210> SEQ ID NO 426
<211> LENGTH: 3780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 426

```
atggggagca aactggaaaa atttacgaat tgttatagcc tgtccaagac cctgcgtttc      60
aaagccatcc ccgttggcaa aacccaggag aatattgata taaacgtct gctggttgag     120 gatgaaaaaa gagcagaaga ctataaggga gtcaaaaaac tgctggatcg gtactacctg     180
agctttataa atgacgtgct gcatagcatt aaactgaaaa atctgaataa ctatattagt     240
ctgttccgca agaaaacccg aacagagaaa gaaataaag agctggaaaa cctggagatc     300
aatctgcgta aagagatcgc aaaagctttt aaaggaaatg aaggttataa agcctgttc      360 aaaaaagaca ttattgaaac catcctgccg gaatttctgg atgataaaga cgagatagcg     420
ctcgtgaaca gcttcaacgg gttcacgacc gccttcacgg gcttttttga taacagggaa     480
aatatgtttt cagaggaagc caaaagcacc tcgatagcgt tccgttgcat taatgaaaat     540
ttgacaagat atatcagcaa catggatatt ttcgagaaag ttgatgcgat ctttgacaaa     600
catgaagtgc aggagattaa ggaaaaaatt ctgaacagcg attatgatgt tgaggatttt     660
ttcgaggggg aatttttaa ctttgtactg acacaggaag gtatagatgt gtataatgct     720
attatcggcg ggttcgttac cgaatccggc gagaaaatta agggtctgaa tgagtacatc     780
aatctgtata accaaaagac caaacagaaa ctgccaaaat tcaaaccgct gtacaagcaa     840
gtcctgagcg atcgggaaag cttgagcttt tacggtgaag gttataccag cgacgaggag     900
gtactggagg tctttcgcaa tacccctgaac aagaacagcg aaattttcag ctccattaaa     960
aagctggaga aactgtttaa gaattttgac gagtacagca cgcaggtat tttttgtgaag    1020 aacggacctg ccataagcac cattagcaag gatattttg gagagtggaa tgttatccgt    1080
gataaatgga cgcggaata tgatgacata cacctgaaaa agaaggctgt ggtaactgag    1140
aaatatgaag acgatcgccg caaaagcttt aaaaaaatcg gcagctttag cctggagcag    1200
ctgcaggaat atgcggacgc cgacctgagc gtggtcgaga aactgaagga aattattatc    1260
caaaaagtgg atgagattta caggtatat ggtagcagca aaaactgtt tgatgcggac    1320 ttcgttctgg aaaaaagcct gaaaaaaaat gatgctgttg ttgcgatcat gaaagacctg    1380
```

```
ctcgatagcg ttaagagctt tgaaaattac attaaagcat tctttggcga gggcaaagaa    1440
acaaacagag acgaaagctt ttatggcgac ttcgtcctgg cttatgacat cctgttgaag    1500
gtagatcata tatatgatgc aattcgtaat tacgtaaccc aaaagccgta cagcaaagat    1560
aagttcaaac tgtatttcca gaacccgcag tttatgggtg gctgggacaa agacaaggag    1620
acagactatc gcgccactat tctgcgttac ggcagcaagt actatctcgc catcatggac    1680
aaaaaatatg caaagtgtct gcagaaaatc gataaagacg acgtgaacgg aaattacgaa    1740
aagattaatt ataagctgct gccagggccc aacaagatgt taccgaaagt atttttttcc    1800
aaaaaatgga tggcatacta taacccgagc gaggatatac agaagattta caaaaatggg    1860
accttcaaaa aggggatat gttcaatctg aatgactgcc acaaactgat cgattttttt    1920
aaagatagca tcagccgtta tcctaaatgg tcaaacgcgt atgattttaa tttctccgaa    1980
acggagaaat ataaagacat tgctggtttc tatcgcgaag tcgaagaaca gggttataaa    2040
gttagctttg aatcggccag caagaaagag gttgataaac tggtggagga gggtaagctg    2100
tatatgtttc agatttataa caaagacttt agcgacaaaa gccacggtac tcctaatctg    2160
catacgatgt actttaaact gctgtttgat gagaataacc acggccaaat ccgtctctcc    2220
ggtggagcag aacttttat gcggcgtgcg agcctaaaaa aggaagaact ggtggtgcat    2280
cccgccaaca gcccgattgc taacaaaaat ccagataatc ctaagaagac caccacactg    2340
tcgtacgatg tctataagga taaacgtttc tcggaagacc agtatgaatt gcatataccg    2400
atagcaatta ataaatgccc aaaaaacatt ttcaaaatca acactgaagt tcgtgtgctg    2460
ctgaaacatg atgataatcc gtatgtgatc ggaattgacc gtgggggagag aaatctgctg    2520 tatattgtag tcgttgatgg caagggcaac atcgttgagc agtatagcct gaatgaaata    2580
attaataatt ttaacggtat acgtattaaa accgactatc atagcctgct ggataaaaag    2640
gagaaagagc gttttgaggc acgccaaaat tggacgagca tcgaaaacat caaggaactg    2700
aaggcaggat atatcagcca agtagtccat aaaatctgtg aactggtgga gaagtacgac    2760
gctgtcattg ccctggaaga cctcaatagc ggctttaaaa acagccgggt gaaggtggag    2820
aaacaggtat accaaaagtt tgaaaagatg ctcattgata agctgaacta tatggttgat    2880
aaaaagagca cccgtgcgc cactggcggt gcactgaaag ggtaccaaat taccaataaa    2940
tttgaaagct ttaaaagcat gagcacgcag aatgggttta ttttttatat accagcatgg    3000
ctgacgagca agattgaccc cagcactggt tttgtcaatc tgctgaaaac caaatacaca    3060
agcattgcgg atagcaaaaa atttatttcg agcttcgacc gtattatgta tgttccggag    3120
gaagatctgt ttgaatttgc cctggattat aaaaacttca gccgcaccga tgcagattat    3180
atcaaaaaat ggaagctgta cagttatggt aatcgtatac gtatcttccg taatccgaag    3240
aaaaacaatg tgttcgattg ggaagaggtc tgtctgacca gcgcgtataa agaactgttc    3300
aacaagtacg gaataaatta tcagcaaggt gacattcgcg cactgctgtg tgaacagtca    3360
gataaagcat tttatagcag ctttatggcg ctgatgagcc tgatgctcca gatgcgcaac    3420
agcataaccg gtcgcacaga tgttgacttt ctgatcagcc ctgtgaagaa tagcgacggc    3480
atcttctacg attccaggaa ctatgaagca caggaaaacg ctattctgcc taaaaatgcc    3540
gatgccaacg gcgcctataa tattgcacgg aaggttctgt gggcgattgg acagttcaag    3600
aaagcggaag atgagaagct ggataaggta aaaattgcta ttagcaataa ggaatggctg    3660
gagtacgcac agacatcggt taaacacggt agtaaaaggc cggcggccac gaaaaaggcc    3720
```

<210> SEQ ID NO 427
<211> LENGTH: 4011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 427

```
ggccaggcaa aaagaaaaa gggagcggcc gcactcgagc accaccacca ccaccactga      3780
atggggacac agttcgaggg ctttaccaac ctgtatcagg tgagcaagac actgcggttt      60
gagctgatcc cacagggcaa gaccctgaag cacatccagg agcagggctt catcgaggag     120
gacaaggccc gcaatgatca ctacaaggag ctgaagccca tcatcgatcg gatctacaag     180
acctatgccg accagtgcct gcagctggtg cagctggatt gggagaacct gagcgccgcc     240
atcgactcct atagaaagga gaaaaccgag agacaagga acgccctgat cgaggagcag     300
gccacatatc gcaatgccat ccacgactac ttcatcggcc ggacagacaa cctgaccgat     360
gccatcaata gagacacgc cgagatctac aagggcctgt tcaaggccga gctgtttaat     420
ggcaaggtgc tgaagcagct gggcaccgtg accacaaccg agcacgagaa cgccctgctg     480
cggagcttcg acaagtttac aacctacttc tccggctttt atagaaacag aagaacgtg     540
ttcagcgccg aggatatcag cacagccatc cacaccgca tcgtgcagga caacttcccc     600
aagtttaagg agaattgtca catcttcaca cgcctgatca ccgccgtgcc cagcctgcgg     660
gagcactttg agaacgtgaa gaaggccatc ggcatcttcg tgagcaccct catcgaggag     720
gtgttttcct tccctttta taaccagctg ctgacacaga cccagatcga cctgtataac     780
cagctgctgg gaggaatctc tcgggaggca ggcaccgaga gatcaagg cctgaacgag     840
gtgctgaatc tggccatcca gaagaatgat gagacagccc acatcatcgc ctccctgcca     900
cacagattca tccccctgtt taagcagatc ctgtccgata ggaacaccct gtctttcatc     960
ctggaggagt ttaagagcga cgaggaagtg atccagtcct ctgcaagta caagacactg    1020
ctgagaaacg agaacgtgct ggagacagcc gaggccctgt taacgagct gaacagcatc    1080
gacctgacac acatcttcat cagccacaag aagctggaga caatcagcag cgccctgtgc    1140
gaccactggg atacactgag gaatgccctg tatgagcgga aatctccga gctgacaggc    1200
aagatcacca gtctgccaa ggagaaggtg cagcgcagcc tgaagcacga ggatatcaac    1260
ctgcaggaga tcatctctgc cgcaggcaag gagctgagcg aggccttcaa gcagaaaacc    1320
agcgagatcc tgtcccacgc acacgccgcc tggatcagc cactgcctac aaccctgaag    1380
aagcaggagg agaaggagat cctgaagtct cagctggaca gcctgctggg cctgtaccac    1440
ctgctggact ggtttgccgt ggatgagtcc aacgaggtgg accccgagtt ctctgcccgg    1500
ctgaccggca tcaagctgga gatggagcct tctctgagct tctacaacaa ggccagaaat    1560
tatgccacca agaagcccta ctccgtggag aagttcaagc tgaactttca gatgccacac    1620
ctggccagag gctgggacgt gaatagagag aagaacaatg cgccatcct gtttgtgaag    1680
aacggcctgt actatctggg catcatgcca aagcagaagg caggtataa ggccctgagc    1740
ttcgagccca cagagaaaac cagcgagggc tttgataaga tgtactatga ctacttccct    1800
gatgccgcca agatgatccc aaagtgcagc acccagctga aggccgtgac agcccactt    1860
cagaccaca caaccccca tcctgctgtc aacaatttca tcgagcctct ggagatcaca    1920
aaggagatct acgacctgaa caatcctgag aaggagccaa agaagtttca gacagcctac    1980
```

```
gccaagaaaa ccggcgacca aagggctac agagaggccc tgtgcaagtg gatcgacttc    2040
acaagggatt ttctgtccaa gtataccaag acaacctcta tcgatctgtc tagcctgcgg    2100
ccatcctctc agtataagga cctgggcgag tactatgccg agctgaatcc cctgctgtac    2160
cacatcagct tccagagaat cgccgagaag gagatcatgg atgccgtgga gacaggcaag    2220
ctgtacctgt tccagatcta taacaaggac tttgccaagg ccaccacgg caagcctaat     2280
ctgcacacac tgtattggac cggcctgttt tctccagaga acctggccaa gacaagcatc    2340
aagctgaatg ccaggccga gctgttctac cgccctaagt ccaggatgaa gaggatggca    2400
caccggctgg gagagaagat gctgaacaag aagctgaagg atcagaaaac cccaatcccc    2460
gacaccctgt accaggagct gtacgactat gtgaatcaca gactgtccca cgacctgtct    2520
gatgaggcca gggccctgct gcccaacgtg atcaccaagg aggtgtctca cgagatcatc    2580
aaggataggc gctttaccag cgacaagttc tttttccacg tgcctatcac actgaactat    2640
caggccgcca ttccccatc taagttcaac cagagggtga atgcctacct gaaggagcac    2700
cccgagacac ctatcatcgg catcgatcgg ggcgagagaa acctgatcta tatcacagtg    2760
atcgactcca ccggcaagat cctggagcag cggagcctga acaccatcca gcagtttgat    2820
taccagaaga agctggacaa cagggagaag gagagggtgg cagcaaggca ggcctggtct    2880
gtggtgggca caatcaagga tctgaagcag ggctatctga ccaggtcat ccacgagatc     2940
gtggacctga tgatccacta ccaggccgtg gtggtgctgg agaacctgaa tttcggcttt    3000
aagagcaaga ggaccggcat cgccgagaag gccgtgtacc agcagttcga aagatgctg     3060
atcgataagc tgaattgcct ggtgctgaag gactatccag cagagaaagt gggaggcgtg    3120
ctgaacccat accagctgac agaccagttc acctcctttg ccaagatggg cacccagtct    3180
ggcttcctgt tttacgtgcc tgccccatat acatctaaga tcgatcccct gaccggcttc    3240
gtggacccct tcgtgtggaa aaccatcaag aatcacgaga ccgcaagca cttcctggag     3300
ggcttcgact ttctgcacta cgacgtgaaa accggcgact tcatcctgca ctttaagatg    3360
aacagaaatc tgtccttcca gagggcctg cccggcttta tgcctgcatg ggatatcgtg     3420
ttcgagaaga cgagacaca gtttgacgcc aagggcaccc cttttcatcg cggcaagaga     3480
atcgtgccag tgatcgagaa tcacagattc accggcagat accgggacct gtatcctgcc    3540
aacgagctga tcgccctgct ggaggagaag ggcatcgtgt tcagggatgg ctccaacatc    3600
ctgccaaagc tgctggagaa tgacgattct cacgccatcg acacgatggt ggccctgatc    3660
cgcagcgtgc tgcagatgcg gaactccaat gccgccacag gcgaggacta tcaacagc      3720
cccgtgcgcg atctgaatgg cgtgtgcttc gactcccggt tcagaaccc agagtggcca     3780
atggacgccg atgccaatgg cgcctaccac atcgccctga gggccagct gctgctgaat     3840
cacctgaagg agagcaagga tctgaagctg cagaacggca tctccaatca ggactggctg    3900
gcctacatcc aggagctgcg caacaaaagg ccggcggcca cgaaaaaggc cggccaggca    3960
aaaagaaaa agggagcggc cgcactcgag caccaccacc accaccactg a               4011
```

<210> SEQ ID NO 428
<211> LENGTH: 4011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 428

```
atgggacac agttcgaggg ctttaccaac ctgtatcagg tgagcaagac actgcggttt      60
gagctgatcc cacagggcaa gaccctgaag cacatccagg agcagggctt catcgaggag    120
gacaaggccc gcaatgatca ctacaaggag ctgaagccca tcatcgatcg gatctacaag    180
acctatgccg accagtgcct gcagctggtg cagctggatt gggagaacct gagcgccgcc    240
atcgactcct atagaaagga gaaaaccgag gagacaagga cgccctgat cgaggagcag     300
gccacatatc gcaatgccat ccacgactac ttcatcggcc ggacagacaa cctgaccgat    360
gccatcaata gagacacgc cgagatctac aagggcctgt tcaaggccga gctgtttaat     420
ggcaaggtgc tgaagcagct gggcaccgtg accacaaccg agcacgagaa cgccctgctg    480
cggagcttcg acaagtttac aacctacttc tccggctttt atagaaacag gaagaacgtg    540
ttcagcgccg aggatatcag cacagccatc ccacaccgca tcgtgcagga caacttcccc    600
aagtttaagg agaattgtca catcttcaca cgcctgatca ccgccgtgcc cagcctgcgg    660
gagcactttg agaacgtgaa gaaggccatc ggcatcttcg tgagcaccctc catcgaggag   720
gtgttttcct tccttttta taaccagctg ctgacacaga cccagatcga cctgtataac    780
cagctgctgg gaggaatctc tcgggaggca ggcaccgaga agatcaaggg cctgaacgag   840
gtgctgaatc tggccatcca agagaatgat gagacagccc acatcatcgc ctccctgcca    900
cacagattca tccccctgtt taagcagatc ctgtccgata ggaacaccct gtctttcatc    960
ctggaggagt ttaagagcga cgaggaagtg atccagtcct tctgcaagta caagacactg   1020
ctgagaaacg agaacgtgct ggagacagcc gaggccctgt taacgagct gaacagcatc    1080
gacctgcaca catcttcat cagccacaag aagctggaga caatcagcag cgccctgtgc    1140
gaccactggg atacactgag gaatgccctg tatgagcgga atctccga gctgacaggc    1200
aagatcacca gtctgccaa ggagaaggtg cagcgcagcc tgaagcacga ggatatcaac    1260
ctgcaggaga tcatctctgc cgcaggcaag gagctgagcg aggccttcaa gcagaaaacc    1320
agcgagatcc tgtcccacgc acacgccgcc tggatcagc cactgcctac aaccctgaag   1380
aagcaggagg agaaggagat cctgaagtct cagctggaca gcctgctggg cctgtaccac   1440
ctgctggact ggtttgccgt ggatgagtcc aacgaggtgg accccgagtt ctctgcccgg    1500
ctgaccggca tcaagctgga gatggagcct ctctgagct tctacaacaa ggccagaaat    1560
tatgccacca gaagcccta ctccgtggag aagttcaagc tgaactttca gatgcctaca    1620
ctggccagag ctgggacgt gaataaggag aagaacaatg gcgccatcct gtttgtgaag   1680
aacggcctgt actatctggg catcatgcca aagcagaagg gcaggtataa ggccctgagc   1740
ttcgagccca cagagaaaac cagcgagggc tttgataaga tgtactatga ctacttccct   1800
gatgccgcca agatgatccc aaaagtgcagc acccagctga aggccgtgac agcccacttt   1860
cagacccaca caaccccccat cctgctgtcc aacaatttca tcgagcctct ggagatcaca   1920
aaggagatct acgacctgaa caatcctgag aaggagccaa gaagtttca gacagcctac    1980
gccaagaaaa ccggcgacca agaagggctac agagaggccc tgtgcaagtg gatcgacttc   2040
acaagggatt ttctgtccaa gtataccaag acaacctcta tcgatctgtc tagcctgcgg    2100
ccatcctctc agtataagga cctgggcgag tactatgccg agctgaatcc cctgctgtac    2160
cacatcagct tccagagaat cgccgagaag gagatcatgg atgccgtgga gacaggcaag   2220
ctgtacctgt tccagatcta taacaaggac tttgccaagg gccaccacgg caagcctaat    2280
ctgcacacac tgtattggac cggcctgttt tctccagaga acctggccaa gacaagcatc    2340
aagctgaatg gccaggccga gctgttctac cgccctaagt ccaggatgaa gaggatggca    2400
```

-continued

```
caccggctgg gagagaagat gctgaacaag aagctgaagg atcagaaaac cccaatcccc    2460
gacaccctgt accaggagct gtacgactat gtgaatcaca gactgtccca cgacctgtct    2520
gatgaggcca gggccctgct gcccaacgtg atcaccaagg aggtgtctca cgagatcatc    2580
aaggataggc gctttaccag cgacaagttc tttttccacg tgcctatcac actgaactat    2640
caggccgcca attccccatc taagttcaac cagagggtga atgcctacct gaaggagcac    2700
cccgagacac ctatcatcgg catcgatcgg ggcgagagaa acctgatcta tatcacagtg    2760
atcgactcca ccggcaagat cctggagcag cggagcctga acaccatcca gcagtttgat    2820
taccagaaga agctggacaa cagggagaag gagagggtgg cagcaaggca ggcctggtct    2880
gtggtgggca aatcaagga tctgaagcag ggctatctga gccaggtcat ccacgagatc    2940
gtggacctga tgatccacta ccaggccgtg gtggtgctgg agaacctgaa tttcggcttt    3000
aagagcaaga ggaccggcat cgccgagaag gccgtgtacc agcagttcga aagatgctg    3060 atcgataagc tgaattgcct ggtgctgaag gactatccag cagagaaagt gggaggcgtg    3120
ctgaacccat accagctgac agaccagttc acctcctttg ccaagatggg caccagtct    3180 ggcttcctgt tttacgtgcc tgccccatat acatctaaga tcgatcccct gaccggcttc    3240
gtggacccct tcgtgtggaa aaccatcaag aatcacgaga gccgcaagca cttcctggag    3300
ggcttcgact tctgcactaa cgacgtgaaa accggcgact tcatcctgca ctttaagatg    3360
aacagaaatc tgtccttcca gaggggcctg cccggcttta tgcctgcatg ggatatcgtg    3420
ttcgagaaga cgagacaca gtttgacgcc aagggcaccc cttccatcgc cggcaagaga    3480
atcgtgccag tgatcgagaa tcacagattc accggcagat accgggacct gtatcctgcc    3540
aacgagctga tcgccctgct ggaggagaag ggcatcgtgt tcaggatgg ctccaacatc    3600 ctgccaaagc tgctggagaa tgacgattct cacgccatcg acacgatggt ggccctgatc    3660
cgcagcgtgc tgcagatgcg gaactccaat gccgccacag gcgaggacta tatcaacagc    3720
cccgtgcgcg atctgaatgg cgtgtgcttc gactcccggt tcagaaccc agagtggcca    3780 atggacgccg atgccaatgg cgcctaccac atcgccctga agggccagct gctgctgaat    3840
cacctgaagg agagcaagga tctgaagctg cagaacggca tctccaatca ggactggctg    3900
gcctacatcc aggagctgcg caacaaaagg ccggcggcca cgaaaaaggc cggccaggca    3960
aaaaagaaaa agggagcggc cgcactcgag caccaccacc accaccactg a             4011
```

<210> SEQ ID NO 429
<211> LENGTH: 4011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 429

```
atggggacac agttcgaggg ctttaccaac ctgtatcagg tgagcaagac actgcggttt      60
gagctgatcc cacagggcaa gaccctgaag cacatccagg agcagggctt catcgaggag     120
gacaaggccc gcaatgatca ctacaaggag ctgaagccca tcatcgatcg gatctacaag     180
acctatgccg accagtgcct gcagctggtg cagctggatt gggagaacct gagcgccgcc     240
atcgactcct atagaaagga gaaaccgag gagacaagga acgccctgat cgaggagcag     300
gccacatatc gcaatgccat ccacgactac ttcatcggcc ggacagacaa cctgaccgat     360
gccatcaata gagacacgc cgagatctac aagggcctgt tcaaggccga gctgtttaat     420
```

-continued

```
ggcaaggtgc tgaagcagct gggcaccgtg accacaaccg agcacgagaa cgccctgctg      480
cggagcttcg acaagtttac aacctacttc tccggctttt atagaaacag gaagaacgtg      540
ttcagcgccg aggatatcag cacagccatc ccacaccgca tcgtgcagga caacttcccc      600
aagtttaagg agaattgtca catcttcaca cgcctgatca ccgccgtgcc cagcctgcgg      660
gagcactttg agaacgtgaa gaaggccatc ggcatcttcg tgagcacctc catcgaggag      720
gtgttttcct tccttttta taaccagctg ctgacacaga cccagatcga cctgtataac      780
cagctgctgg aggaatctc tcgggaggca ggcaccgaga agatcaaggg cctgaacgag      840
gtgctggccc tggccatcca agaatgat gagacagccc acatcatcgc ctccctgcca      900
cacagattca tcccctgtt taagcagatc ctgtccgata ggaacaccct gtctttcatc      960
ctggaggagt ttaagagcga cgaggaagtg atccagtcct tctgcaagta caagacactg     1020
ctgagaaacg agaacgtgct ggagacagcc gaggccctgt taacgagct gaacagcatc     1080 gacctgacac acatcttcat cagccacaag aagctggaga caatcagcag cgccctgtgc     1140
gaccactggg atacactgag gaatgccctg tatgagcgga gaatctccga gctgacaggc     1200
aagatcacca gtctgccaa ggagaaggtg cagcgcagcc tgaagcacga ggatatcaac     1260
ctgcaggaga tcatctctgc cgcaggcaag gagctgagcg aggccttcaa gcagaaaacc     1320
agcgagatcc tgtcccacgc acacgccgcc tggatcagc cactgcctac aaccctgaag     1380
aagcaggagg agaaggagat cctgaagtct cagctggaca gcctgctggg cctgtaccac     1440
ctgctggact ggtttgccgt ggatgagtcc aacgaggtgg accccgagtt ctctgcccgg     1500
ctgaccggca tcaagctgga gatggagcct tctctgagct tctacaacaa ggccagaaat     1560
tatgccacca gaagcccta ctccgtggag aagttcaagc tgaacttca gatgcctaca     1620 ctggccagag gctgggacgt gaatagagag aagaacaatg cgccatcct gtttgtgaag     1680 aacggcctgt actatctggg catcatgcca aagcagaagg gcaggtataa ggccctgagc     1740
ttcgagccca cagagaaaac cagcgagggc tttgataaga tgtactatga ctacttccct     1800
gatgccgcca gatgatccc aaagtgcagc acccagctga aggccgtgac agcccacttt     1860
cagacccaca caacccccat cctgctgtcc aacaatttca tcgagcctct ggagatcaca     1920
aaggagatct acgacctgaa caatcctgag aaggagccaa agaagtttca gacagcctac     1980
gccaagaaaa ccggcgacca agggctac agagaggccc tgtgcaagtg gatcgacttc     2040
acaagggatt ttctgtccaa gtataccaag acaacctcta tcgatctgtc tagcctgcgg     2100
ccatcctctc agtataagga cctgggcgag tactatgccg agctgaatcc cctgctgtac     2160
cacatcagct tccagagaat cgccgagaag gagatcatgg atgccgtgga cacaggcaag     2220
ctgtacctgt tccagatcta taacaaggac tttgccaagg ccaccacgg caagcctaat     2280 ctgcacacac tgtattggac cggcctgttt tctccagaga acctggccaa gacaagcatc     2340
aagctgaatg ccaggccga gctgttctac cgccctaagt ccaggatgaa gaggatggca     2400
caccggctgg agagaagat gctgaacaag aagctgaagg atcagaaaac cccaatcccc     2460
gacaccctgt accaggagct gtacgactat gtgaatcaca gactgtccca cgacctgtct     2520
gatgaggcca gggccctgct gcccaacgtg atcaccaagg aggtgtctca cgagatcatc     2580 aaggatagc gctttaccag cgacaagttc ttttccacg tgcctatcac actgaactat     2640
caggccgcca attccccatc taagttcaac cagagggtga atgcctacct gaaggagcac     2700
cccgagacac ctatcatcgg catcgatcgg ggcgagagaa acctgatcta tatcacagtg     2760
```

| | |
|---|---:|
| atcgactcca ccggcaagat cctggagcag cggagcctga acaccatcca gcagtttgat | 2820 |
| taccagaaga agctggacaa cagggagaag gagagggtgg cagcaaggca ggcctggtct | 2880 |
| gtggtgggca caatcaagga tctgaagcag ggctatctga gccaggtcat ccacgagatc | 2940 |
| gtggacctga tgatccacta ccaggccgtg gtggtgctgg agaacctgaa tttcggcttt | 3000 |
| aagagcaaga ggaccggcat cgccgagaag gccgtgtacc agcagttcga gaagatgctg | 3060 |
| atcgataagc tgaattgcct ggtgctgaag gactatccag cagagaaagt gggaggcgtg | 3120 |
| ctgaacccat accagctgac agaccagttc acctcctttg ccaagatggg cacccagtct | 3180 |
| ggcttcctgt tttacgtgcc tgccccatat acatctaaga tcgatcccct gaccggcttc | 3240 |
| gtggacccct tcgtgtggaa aaccatcaag aatcacgaga gccgcaagca cttcctggag | 3300 |
| ggcttcgact ttctgcacta cgacgtgaaa accggcgact tcatcctgca ctttaagatg | 3360 |
| aacagaaatc tgtccttcca gaggggcctg cccggcttta tgcctgcatg ggatatcgtg | 3420 |
| ttcgagaaga cgagacaca gtttgacgcc aagggcaccc ctttcatcgc cggcaagaga | 3480 |
| atcgtgccag tgatcgagaa tcacagattc accggcagat accggaccct gtatcctgcc | 3540 |
| aacgagctga tcgccctgct ggaggagaag ggcatcgtgt tcagggatgg ctccaacatc | 3600 |
| ctgccaaagc tgctggagaa tgacgattct cacgccatcg acgatggt ggccctgatc | 3660 |
| cgcagcgtgc tgcagatgcg gaactccaat gccgccacag gcgaggacta tatcaacagc | 3720 |
| cccgtgcgcg atctgaatgg cgtgtgcttc gactcccggt ttcagaaccc agagtggcca | 3780 |
| atggacgccg atgccaatgg cgcctaccac atcgccctga agggccagct gctgctgaat | 3840 |
| cacctgaagg agagcaagga tctgaagctg cagaacggca tctccaatca ggactggctg | 3900 |
| gcctacatcc aggagctgcg caacaaaagg ccggcggcca cgaaaaaggc cggccaggca | 3960 |
| aaaaagaaaa agggagcggc cgcactcgag caccaccacc accaccactg a | 4011 |

<210> SEQ ID NO 430
<211> LENGTH: 4257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430

| | |
|---|---:|
| atgctgttcc aggactttac ccacctgtat ccactgtcca agacagtgag atttgagctg | 60 |
| aagcccatcg ataggaccct ggagcacatc cacgccaaga acttcctgtc tcaggacgag | 120 |
| acaatggccg atatgcacca gaaggtgaaa gtgatcctgg acgattacca ccgcgacttc | 180 |
| atcgccgata tgatgggcga ggtgaagctg accaagctgg ccgagttcta tgacgtgtac | 240 |
| ctgaagtttc ggaagaaccc aaaggacgat gagctgcaga gcagctgaa ggatctgcag | 300 |
| gccgtgctga gaaaggagat cgtgaagccc atcggcaatg cggcaagta taggccggc | 360 |
| tacgacaggc tgttcggcgc caagctgttt aaggacggca aggagctggg cgatctggcc | 420 |
| aagttcgtga tcgcacagga gggagagagc tccccaaagc tggcccacct ggcccacttc | 480 |
| gagaagtttt ccacctattt cacaggcttt cacgataacc ggaagaatat gtattctgac | 540 |
| gaggataagc acaccgccat cgcctaccgc ctgatccacg agaacctgcc ccggtttatc | 600 |
| gacaatctgc agatcctgac cacaatcaag cagaagcact tgccctgta cgatcagatc | 660 |
| atcaacgagc tgaccgccag cggcctggac gtgtctctgg ccagccacct ggatggctat | 720 |
| cacaagctgc tgacacagga gggcatcacc gcctacaata cactgctggg aggaatctcc | 780 |

```
ggagaggcag gctctcctaa gatccagggc atcaacgagc tgatcaattc tcaccacaac    840
cagcactgcc acaagagcga gagaatcgcc aagctgaggc cactgcacaa gcagatcctg    900
tccgacggca tgagcgtgtc cttcctgccc tctaagtttg ccgacgatag cgagatgtgc    960
caggccgtga acgagttcta tcgccactac gccgacgtgt tcgccaaggt gcagagcctg   1020
ttcgacggct ttgacgatca ccagaaggat ggcatctacg tggagcacaa gaacctgaat   1080
gagctgtcca gcaggccttt cggcgacttt gcactgctgg acgcgtgct ggacggatac    1140 tatgtggatg tggtgaatcc agagttcaac gagcggtttg ccaaggccaa gaccgacaat   1200
gccaaggcca agctgacaaa ggagaaggat aagttcatca agggcgtgca ctccctggcc   1260
tctctggagc aggccatcga gcactatacc gcaaggcacg acgatgagag cgtgcaggca   1320
ggcaagctgg acagtactt caagcacggc ctggccggag tggacaaccc catccagaag    1380
atccacaaca atcacagcac catcaagggc tttctggaga gggagcgccc tgcaggagag   1440
agagccctgc caaagatcaa gtccggcaag aatcctgaga tgacacagct gaggcagctg   1500
aaggagctgc tggataacgc cctgaatgtg gcccacttcg ccaagctgct gaccacaaag   1560
accacactgg acaatcagga tgcaacttc tatggcgagt ttggcgtgct gtacgacgag    1620
ctggccaaga tccccaccct gtataacaag gtgagagatt acctgagcca gaagcctttc   1680
tccaccgaga agtacaagct gaactttggc aatccaacac tgctgaatgg ctgggacctg   1740
aacaaggaga aggataattt cggcgtgatc ctgcagaagg acggctgcta ctatctggcc   1800
ctgctggaca aggcccacaa gaaggtgttt gataacgccc ctaatacagg caagagcatc   1860
tatcagaaga tgatctataa gtacctggag gtgaggaagc agttccccaa ggtgttcttt   1920
tccaaggagg ccatcgccat caactaccac ccttctaagg agctggtgga gatcaaggac   1980
aagggccggc agagatccga cgatgagcgc ctgaagctgt atcggtttat cctggagtgt   2040
ctgaagatcc accctaagta cgataagaag ttcgagggcg ccatcggcga catccagctg   2100
tttaagaagg ataagaaggg cagagaggtg ccaatcagcg agaaggacct gttcgataag   2160
atcaacggca tcttttctag caagcctaag ctggagatgg aggacttctt tatcggcgag   2220
ttcaagaggt ataacccaag ccaggacctg gtggatcagt ataatatcta caagaagatc   2280
gactccaacg ataatcgcaa gaaggagaat ttctacaaca atcaccccaa gtttaagaag   2340
gatctggtgc ggtactatta cgagtctatg tgcaagcacg aggagtggga ggagagcttc   2400
gagttttcca gaagctgca ggacatcggc tgttacgtgg atgtgaacga gctgtttacc    2460
gagatcgaga cacggagact gaattataag atctccttct gcaacatcaa tgccgactac   2520
atcgatgagc tggtggagca gggccagctg tatctgttcc agatctacaa caaggacttt   2580
tccccaaagg cccacggcaa gcccaatctg cacacacctgt acttcaaggc cctgttttct   2640
gaggacaacc tggccgatcc tatctataag ctgaatggcg aggcccagat cttctacaga   2700
aaggcctccc tggacatgaa cgagacaaca atccacaggg ccggcgaggt gctggagaac   2760
aagaatcccg ataatcctaa gaagagacag ttcgtgtacg acatcatcaa ggataagagg   2820
tacacacagg acaagttcat gctgcacgtg ccaatcacca tgaactttgg cgtgcagggc   2880
atgacaatca aggagttcaa taagaaggtg aaccagtcta tccagcagta tgacgaggtg   2940
aacgtgatcg gcatcgatcg gggcgagaga caccttgctgt acctgaccgt gatcaatagc   3000
aagggcgaga tcctggagca gtgttccctg aacgacatca ccacagcctc tgccaatggc   3060
acacagatga ccacacctta ccacaagatc ctggataaga gggagatcga gcgcctgaac   3120
gcccgggtgg gatgggcga gatcgagaca atcaaggagc tgaagtctgg ctatctgagc   3180
```

```
cacgtggtgc accagatcag ccagctgatg ctgaagtaca acgccatcgt ggtgctggag    3240
gacctgaatt tcggctttaa gaggggccgc tttaaggtgg agaagcagat ctatcagaac    3300
ttcgagaatg ccctgatcaa gaagctgaac cacctggtgc tgaaggacaa ggccgacgat    3360
gagatcggct cttacaagaa tgccctgcag ctgaccaaca atttcacaga tctgaagagc    3420
atcggcaagc agaccggctt cctgttttat gtgcccgcct ggaacacctc taagatcgac    3480
cctgagacag gctttgtgga tctgctgaag ccaagatacg agaacatcgc ccagagccag    3540
gccttctttg gcaagttcga caagatctgc tataatgccg acaaggatta cttcgagttt    3600
cacatcgact acgccaagtt taccgataag gccaagaata gccgccagat ctggacaatc    3660
tgttcccacg gcgacaagcg gtacgtgtac gataagacag ccaaccagaa taagggcgcc    3720
gccaagggca tcaacgtgaa tgatgagctg aagtccctgt tcgcccgcca ccacatcaac    3780
gagaagcagc ccaacctggt catggacatc tgccagaaca atgataagga gtttcacaag    3840
tctctgatgt acctgctgaa aaccctgctg gccctgcgt acagcaacgc ctcctctgac    3900
gaggatttca tcctgtcccc cgtggcaaac gacgagggcg tgttctttaa tagcgccctg    3960
gccgacgata cacagcctca gaatgccgat gccaacggcg cctaccacat cgccctgaag    4020
ggcctgtggc tgctgaatga gctgaagaac tccgacgatc tgaacaaggt gaagctggcc    4080
atcgacaatc agacctggct gaatttcgcc cagaacagga aaggccggc ggccacgaaa    4140 aaggccggcc aggcaaaaaa gaaaaaggga tcctacccat acgatgttcc agattacgct    4200
tatccctacg acgtgcctga ttatgcatac ccatatgatg tccccgacta tgcctaa      4257
```

<210> SEQ ID NO 431
<211> LENGTH: 5658
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 431

```
atgacacagt tcgagggctt taccaacctg tatcaggtga gcaagacact gcggtttgag     60
ctgatcccac agggcaagac cctgaagcac atccaggagc agggcttcat cgaggaggac    120
aaggcccgca atgatcacta caaggagctg aagcccatca tcgatcggat ctacaagacc    180
tatgccgacc agtgcctgca gctggtgcag ctggattggg agaacctgag cgccgccatc    240
gactcctata gaaaggagaa aaccgaggag acaaggaacg ccctgatcga ggagcaggcc    300
acatatcgca atgccatcca cgactacttc atcggccgga cagacaacct gaccgatgcc    360
atcaataaga gacacgccga gatctacaag ggcctgttca aggccgagct gtttaatggc    420
aaggtgctga gcagctggg caccgtgacc acaaccgagc acgagaacgc cctgctgcgg    480
agcttcgaca gtttacaac ctacttctcc ggcttttatg agaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc cttttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
```

```
gaggagttta agagcgacga ggaagtgatc cagtccttct gcaagtacaa gacactgctg    1020
agaaacgaga acgtgctgga gacagccgag gccctgttta cgagctgaa cagcatcgac     1080 ctgacacaca tcttcatcag ccacaagaag ctggagacaa tcagcagcgc cctgtgcgac    1140
cactgggata cactgaggaa tgccctgtat gagcggagaa tctccgagct gacaggcaag    1200
atcaccaagt ctgccaagga aaggtgcag cgcagcctga agcacgagga tatcaacctg     1260
caggagatca tctctgccgc aggcaaggag ctgagcgagg ccttcaagca gaaaaccagc    1320
gagatcctgt cccacgcaca cgccgccctg gatcagccac tgcctacaac cctgaagaag    1380
caggaggaga aggagatcct gaagtctcag ctggacagcc tgctgggcct gtaccacctg    1440
ctggactggt ttgccgtgga tgagtccaac gaggtggacc ccgagttctc tgcccggctg    1500
accggcatca agctggagat ggagccttct ctgagcttct acaacaaggc cagaaattat    1560
gccaccaaga agccctactc cgtggagaag ttcaagctga actttcagat gcctacactg    1620
gcctctggct gggacgtgaa taaggagaag aacaatggcg ccatcctgtt tgtgaagaac    1680
ggcctgtact atctgggcat catgccaaag cagaagggca ggtataaggc cctgagcttc    1740
gagcccacag agaaaaccag cgagggcttt gataagatgt actatgacta cttccctgat    1800
gccgccaaga tgatcccaaa gtgcagcacc cagctgaagg ccgtgacagc ccactttcag    1860
acccacacaa cccccatcct gctgtccaac aatttcatcg agcctctgga gatcacaaag    1920
gagatctacg acctgaacaa tcctgagaag gagccaaaga gtttcagac agcctacgcc     1980 aagaaaaccg cgaccagaa gggctacaga gaggccctgt gcaagtggat cgacttcaca    2040 agggatttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgtttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgccggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca gatgggcac ccagtctggc     3180 ttcctgtttt acgtgcctgc cccatataca tctaagatcg atcccctgac cggcttcgtg    3240
gaccccttcg tgtggaaaac catcaagaat cacgagagcc gcaagcactt cctggagggc    3300
```

-continued

```
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840
ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg gatcctaccc atacgatgtt ccagattacg cttatcccta cgacgtgcct    4020
gattatgcat acccatatga tgtccccgac tatgccggaa gcgaggccag cggttccgga    4080
cgggctgacg cattggacga ttttgatctg gatatgctgg gaagtgacgc cctcgatgat    4140
tttgaccttg acatgcttgg ttcggatgcc cttgatgact tgacctcga catgctcggc    4200
agtgacgccc ttgatgattt cgacctggac atgctgatta actctagaag ttccggatct    4260
ccgaaaaaga aacgcaaagt tggtagccag tacctgcccg acaccgacga ccggcaccgg    4320
atcgaggaaa agcggaagcg gacctacgag acattcaaga gcatcatgaa gaagtccccc    4380
ttcagcggcc ccaccgaccc tagacctcca cctagaagaa tcgccgtgcc cagcagatcc    4440
agcgccagcg tgccaaaacc tgcccccag ccttaccccct tcaccagcag cctgagcacc    4500
atcaactacg acgagttccc taccatggtg ttccccagcg gccagatctc tcaggcctct    4560
gctctggctc cagcccctcc tcaggtgctg cctcaggctc ctgctcctgc accagctcca    4620
gccatggtgt ctgcactggc tcaggcacca gcacccgtgc ctgtgctggc tcctggacct    4680
ccacaggctg tggctccacc agcccctaaa cctacacagg ccggcgaggg cacactgtct    4740
gaagctctgc tgcagctgca gttcgacgac gaggatctgg gagccctgct gggaaacagc    4800
accgatcctg ccgtgttcac cgacctggcc agcgtggaca cagcgagtt ccagcagctg    4860
ctgaaccagg gcatccctgt ggcccctcac accaccgagc ccatgctgat ggaataccc    4920
gaggccatca cccggctcgt gacaggcgct cagaggcctc ctgatccagc tcctgcccct    4980
ctgggagcac caggcctgcc taatggactg ctgtctggcg acgaggactt cagctctatc    5040
gccgatatgg atttctcagc cttgctgggc tctggcagcg gcagccggga ttccagggaa    5100
gggatgtttt tgccgaagcc tgaggccggc tccgctatta gtgacgtgtt tgagggccgc    5160
gaggtgtgcc agccaaaacg aatccggcca tttcatcctc caggaagtcc atgggccaac    5220
cgcccactcc ccgccagcct cgcaccaaca ccaaccggtc cagtacatga gccagtcggg    5280
tcactgaccc cggcaccagt ccctcagcca ctggatccag cgcccgcagt gactcccgag    5340
gccagtcacc tgttggagga tcccgatgaa gagacgagcc aggctgtcaa agcccttcgg    5400
gagatgccgc atactgtgat tccccagaag gaagaggctg caatctgtgg ccaaatggac    5460
cttccccatc cgccccaag gggccatctg gatgagctga caccacact tgagtccatg    5520
accgaggatc tgaacctgga ctcacccctg accccggaat tgaacgagat tctggataccc    5580
ttcctgaacg acgagtgcct cttgcatgcc atgcatatca gcacaggact gtccatcttc    5640
gacacatctc tgttttaa                                                 5658
```

<210> SEQ ID NO 432
<211> LENGTH: 1885
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 432

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
```

-continued

```
            355                 360                 365
Lys Lys Leu Glu Thr Ile Ser Ser Ala Leu Cys Asp His Trp Asp Thr
370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                405                 410                 415
Asp Ile Asn Leu Gln Glu Ile Ser Ala Ala Gly Lys Glu Leu Ser
            420                 425                 430
Glu Ala Phe Lys Gln Lys Thr Ser Glu Ile Leu Ser His Ala His Ala
        435                 440                 445
Ala Leu Asp Gln Pro Leu Pro Thr Thr Leu Lys Lys Gln Glu Glu Lys
    450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
                485                 490                 495
Ser Ala Arg Leu Thr Gly Ile Lys Leu Glu Met Glu Pro Ser Leu Ser
            500                 505                 510
Phe Tyr Asn Lys Ala Arg Asn Tyr Ala Thr Lys Lys Pro Tyr Ser Val
        515                 520                 525
Glu Lys Phe Lys Leu Asn Phe Gln Met Pro Thr Leu Ala Ser Gly Trp
    530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
        595                 600                 605
Ser Thr Gln Leu Lys Ala Val Thr Ala His Phe Gln Thr His Thr Thr
    610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
        675                 680                 685
Lys Thr Thr Ser Ile Asp Leu Ser Ser Leu Arg Pro Ser Ser Gln Tyr
    690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
        755                 760                 765
Phe Ser Pro Glu Asn Leu Ala Lys Thr Ser Ile Lys Leu Asn Gly Gln
    770                 775                 780
```

```
Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
        820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Ala Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185
```

| | | | | | | | | | | | |
|---|---|---|---|---|---|---|---|---|---|---|---|
| Lys | Gly 1190 | Ile | Val | Phe | Arg 1195 | Asp | Gly | Ser | Asn 1200 | Ile | Leu | Pro | Lys | Leu |
| Leu | Glu 1205 | Asn | Asp | Asp | Ser 1210 | His | Ala | Ile | Asp 1215 | Thr | Met | Val | Ala | Leu |
| Ile | Arg 1220 | Ser | Val | Leu | Gln 1225 | Met | Arg | Asn | Ser 1230 | Asn | Ala | Ala | Thr | Gly |
| Glu | Asp 1235 | Tyr | Ile | Asn | Ser 1240 | Pro | Val | Arg | Asp 1245 | Leu | Asn | Gly | Val | Cys |
| Phe | Asp 1250 | Ser | Arg | Phe | Gln 1255 | Asn | Pro | Glu | Trp 1260 | Pro | Met | Asp | Ala | Asp |
| Ala | Asn 1265 | Gly | Ala | Tyr | His 1270 | Ile | Ala | Leu | Lys 1275 | Gly | Gln | Leu | Leu | Leu |
| Asn | His 1280 | Leu | Lys | Glu | Ser 1285 | Lys | Asp | Leu | Lys 1290 | Leu | Gln | Asn | Gly | Ile |
| Ser | Asn 1295 | Gln | Asp | Trp | Leu 1300 | Ala | Tyr | Ile | Gln 1305 | Glu | Leu | Arg | Asn | Lys |
| Arg | Pro 1310 | Ala | Ala | Thr | Lys 1315 | Lys | Ala | Gly | Gln 1320 | Ala | Lys | Lys | Lys |
| Gly | Ser 1325 | Tyr | Pro | Tyr | Asp 1330 | Val | Pro | Asp | Tyr 1335 | Ala | Tyr | Pro | Tyr | Asp |
| Val | Pro 1340 | Asp | Tyr | Ala | Tyr 1345 | Pro | Tyr | Asp | Val 1350 | Pro | Asp | Tyr | Ala | Gly |
| Ser | Glu 1355 | Ala | Ser | Gly | Ser 1360 | Gly | Arg | Ala | Asp 1365 | Ala | Leu | Asp | Asp | Phe |
| Asp | Leu 1370 | Asp | Met | Leu | Gly 1375 | Ser | Asp | Ala | Leu 1380 | Asp | Asp | Phe | Asp | Leu |
| Asp | Met 1385 | Leu | Gly | Ser | Asp 1390 | Ala | Leu | Asp | Asp 1395 | Phe | Asp | Leu | Asp | Met |
| Leu | Gly 1400 | Ser | Asp | Ala | Leu 1405 | Asp | Asp | Phe | Asp 1410 | Leu | Asp | Met | Leu | Ile |
| Asn | Ser 1415 | Arg | Ser | Ser | Gly 1420 | Ser | Pro | Lys | Lys 1425 | Lys | Arg | Lys | Val | Gly |
| Ser | Gln 1430 | Tyr | Leu | Pro | Asp 1435 | Thr | Asp | Asp | Arg 1440 | His | Arg | Ile | Glu | Glu |
| Lys | Arg 1445 | Lys | Arg | Thr | Tyr 1450 | Glu | Thr | Phe | Lys 1455 | Ser | Ile | Met | Lys | Lys |
| Ser | Pro 1460 | Phe | Ser | Gly | Pro 1465 | Thr | Asp | Pro | Arg 1470 | Pro | Pro | Arg | Arg |
| Ile | Ala 1475 | Val | Pro | Ser | Arg 1480 | Ser | Ser | Ala | Ser 1485 | Val | Pro | Lys | Pro | Ala |
| Pro | Gln 1490 | Pro | Tyr | Pro | Phe 1495 | Thr | Ser | Ser | Leu 1500 | Ser | Thr | Ile | Asn | Tyr |
| Asp | Glu 1505 | Phe | Pro | Thr | Met 1510 | Val | Phe | Pro | Ser 1515 | Gly | Gln | Ile | Ser | Gln |
| Ala | Ser 1520 | Ala | Leu | Ala | Pro 1525 | Ala | Pro | Pro | Gln 1530 | Val | Leu | Pro | Gln | Ala |
| Pro | Ala 1535 | Pro | Ala | Pro | Ala 1540 | Pro | Ala | Met | Val 1545 | Ser | Ala | Leu | Ala | Gln |
| Ala | Pro 1550 | Ala | Pro | Val | Pro 1555 | Val | Leu | Ala | Pro 1560 | Gly | Pro | Pro | Gln | Ala |
| Val | Ala 1565 | Pro | Pro | Ala | Pro 1570 | Lys | Pro | Thr | Gln 1575 | Ala | Gly | Glu | Gly | Thr |
| Leu | Ser | Glu | Ala | Leu | Leu | Gln | Leu | Gln | Phe | Asp | Asp | Glu | Asp | Leu |

| | | | | | | | | | | |
|---|---|---|---|---|---|---|---|---|---|---|
| | | | | 1580 | | | | 1585 | | 1590 |

Gly Ala Leu Leu Gly Asn Ser Thr Asp Pro Ala Val Phe Thr Asp
            1595                1600                1605

Leu Ala Ser Val Asp Asn Ser Glu Phe Gln Gln Leu Leu Asn Gln
 1610                1615                1620

Gly Ile Pro Val Ala Pro His Thr Thr Glu Pro Met Leu Met Glu
 1625                1630                1635

Tyr Pro Glu Ala Ile Thr Arg Leu Val Thr Gly Ala Gln Arg Pro
 1640                1645                1650

Pro Asp Pro Ala Pro Ala Pro Leu Gly Ala Pro Gly Leu Pro Asn
 1655                1660                1665

Gly Leu Leu Ser Gly Asp Glu Asp Phe Ser Ser Ile Ala Asp Met
 1670                1675                1680

Asp Phe Ser Ala Leu Leu Gly Ser Gly Ser Gly Ser Arg Asp Ser
 1685                1690                1695

Arg Glu Gly Met Phe Leu Pro Lys Pro Glu Ala Gly Ser Ala Ile
 1700                1705                1710

Ser Asp Val Phe Glu Gly Arg Glu Val Cys Gln Pro Lys Arg Ile
 1715                1720                1725

Arg Pro Phe His Pro Pro Gly Ser Pro Trp Ala Asn Arg Pro Leu
 1730                1735                1740

Pro Ala Ser Leu Ala Pro Thr Pro Thr Gly Pro Val His Glu Pro
 1745                1750                1755

Val Gly Ser Leu Thr Pro Ala Pro Val Pro Gln Pro Leu Asp Pro
 1760                1765                1770

Ala Pro Ala Val Thr Pro Glu Ala Ser His Leu Leu Glu Asp Pro
 1775                1780                1785

Asp Glu Glu Thr Ser Gln Ala Val Lys Ala Leu Arg Glu Met Ala
 1790                1795                1800

Asp Thr Val Ile Pro Gln Lys Glu Glu Ala Ala Ile Cys Gly Gln
 1805                1810                1815

Met Asp Leu Ser His Pro Pro Pro Arg Gly His Leu Asp Glu Leu
 1820                1825                1830

Thr Thr Thr Leu Glu Ser Met Thr Glu Asp Leu Asn Leu Asp Ser
 1835                1840                1845

Pro Leu Thr Pro Glu Leu Asn Glu Ile Leu Asp Thr Phe Leu Asn
 1850                1855                1860

Asp Glu Cys Leu Leu His Ala Met His Ile Ser Thr Gly Leu Ser
 1865                1870                1875

Ile Phe Asp Thr Ser Leu Phe
 1880                1885

<210> SEQ ID NO 433
<211> LENGTH: 5655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433
atgacacagt tcgagggctt taccaacctg tatcaggtga gcaagacact gcggtttgag    60
ctgatcccac agggcaagac cctgaagcac atccaggagc agggcttcat cgaggaggac   120
aaggcccgca tgatcactaa caaggagctg aagcccatca tcgatcggat ctacaagacc   180

```
tatgccgacc agtgcctgca gctggtgcag ctggattggg agaacctgag cgccgccatc        240
gactcctata gaaaggagaa aaccgaggag acaaggaacg ccctgatcga ggagcaggcc        300
acatatcgca atgccatcca cgactacttc atcggccgga cagacaacct gaccgatgcc        360
atcaataaga gacacgccga gatctacaag ggcctgttca aggccgagct gtttaatggc        420
aaggtgctga agcagctggg caccgtgacc acaaccgagc acgagaacgc cctgctgcgg        480
agcttcgaca gtttacaac ctacttctcc ggcttttata gaaacaggaa gaacgtgttc         540
agcgccgagg atatcagcac agccatccca caccgcatcg tgcaggacaa cttccccaag        600
tttaaggaga attgtcacat cttcacacgc ctgatcaccg ccgtgcccag cctgcgggag        660
cactttgaga acgtgaagaa ggccatcggc atcttcgtga gcacctccat cgaggaggtg        720
ttttccttcc ctttttataa ccagctgctg acacagaccc agatcgacct gtataaccag        780
ctgctgggag gaatctctcg ggaggcaggc accgagaaga tcaagggcct gaacgaggtg        840
ctgaatctgg ccatccagaa gaatgatgag acagcccaca tcatcgcctc cctgccacac        900
agattcatcc ccctgtttaa gcagatcctg tccgatagga cacccctgtc tttcatcctg        960
gaggagttta gagcgacga ggaagtgatc cagtccttct gcaagtacaa gacactgctg        1020
agaaacgaga acgtgctgga gacagccgag gccctgttta cgagctgaaa cagcatcgac        1080
ctgacacaca tcttcatcag ccacaagaag ctggagacaa tcagcagcgc cctgtgcgac        1140
cactgggata cactgaggaa tgccctgtat gagcggagaa tctccgagct gacaggcaag        1200
atcaccaagt ctgccaagga gaaggtgcag cgcagcctga agcacgagga tatcaacctg        1260
caggagatca tctctgccgc aggcaaggag ctgagcgagg ccttcaagca gaaaaccagc        1320
gagatcctgt cccacgcaca cgccgccctg gatcagccac tgcctacaac cctgaagaag        1380
caggaggaga aggagatcct gaagtctcag ctggacagcc tgctgggcct gtaccacctg        1440
ctggactggt ttgccgtgga tgagtccaac gaggtggacc ccgagttctc tgcccggctg        1500
accggcatca agctggagat ggagccttct ctgagcttct acaacaaggc cagaaattat        1560
gccaccaaga agccctactc cgtggagaag ttcaagctga actttcagat gcctacactg        1620
gccagaggct gggacgtgaa tagagagaag aacaatggcg ccatcctgtt tgtgaagaac        1680
ggcctgtact atctgggcat catgccaaag cagaagggca ggtataaggc cctgagcttc        1740
gagcccacag agaaaaccag cgagggcttt gataagatgt actatgacta cttccctgat        1800
gccgccaaga tgatcccaaa gtgcagcacc cagctgaagg ccgtgacagc ccactttcag        1860
acccacacaa ccccccatcct gctgtccaac aatttcatcg agcctctgga tcacaaaag        1920 gagatctacg acctgaacaa tcctgagaag gagccaaaga agtttcagac agcctacgcc        1980
aagaaaaccg cgaccagaa gggctacaga gaggccctgt gcaagtggat cgacttcaca        2040
agggattttc tgtccaagta taccaagaca acctctatcg atctgtctag cctgcggcca        2100
tcctctcagt ataaggacct gggcgagtac tatgccgagc tgaatcccct gctgtaccac        2160
atcagcttcc agagaatcgc cgagaaggag atcatggatg ccgtggagac aggcaagctg        2220
tacctgttcc agatctataa caaggacttt gccaagggcc accacggcaa gcctaatctg        2280
cacacactgt attggaccgg cctgtttttct ccagagaacc tggccaagac aagcatcaag        2340
ctgaatggcc aggccgagct gttctaccgc cctaagtcca ggatgaagag gatggcacac        2400
cggctgggag agaagatgct gaacaagaag ctgaaggatc agaaaacccc aatccccgac        2460
accctgtacc aggagctgta cgactatgtg aatcacagac tgtcccacga cctgtctgat        2520
gaggccaggg ccctgctgcc caacgtgatc accaaggagg tgtctcacga gatcatcaag        2580
```

```
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgcccggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240
gacccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840
ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg gatcctaccc atacgatgtt ccagattacg cttatcccta cgacgtgcct    4020
gattatgcat acccatatga tgtccccgac tatgccggaa gcgaggccag cggttccgga    4080
cgggctgacg cattggacga ttttgatctg gatatgctgg gaagtgacgc cctcgatgat    4140
tttgaccttg acatgcttgg ttcggatgcc cttgatgact tgaccctcga catgctcggc    4200
agtgacgccc ttgatgattt cgacctggac atgctgatta actctagaag ttccggatct    4260
ccgaaaaaga aacgcaaagt tggtagccag tacctgcccg acaccgacga ccggcaccgg    4320
atcgaggaaa agcggaagcg gacctacgag acattcaaga gcatcatgaa gaagtccccc    4380
ttcagcggcc ccaccgaccc tagacctcca cctagaagaa tcgccgtgcc cagcagatcc    4440
agcgccagcg tgccaaaacc tgccccccag ccttacccct tcaccagcag cctgagcacc    4500
atcaactacg acgagttccc taccatggtg ttccccagcg ccagatctc tcaggcctct    4560
gctctggctc cagcccctcc tcaggtgctg cctcaggctc ctgctcctgc accagctcca    4620
gccatggtgt ctgcactggc tcaggcacca gcacccgtgc ctgtgctggc tcctggacct    4680
ccacaggctg tggctccacc agccccctaaa cctacacagg ccggcgaggg cacactgtct    4740
gaagctctgc tgcagctgca gttcgacgac gaggatctgg agccctgct gggaaacagc    4800
accgatcctg ccgtgttcac cgacctggcc agcgtggaca cagcgagtt ccagcagctg    4860
ctgaaccagg gcatccctgt ggcccctcac accaccgagc ccatgctgat ggaataccc    4920
```

```
gaggccatca cccggctcgt gacaggcgct cagaggcctc ctgatccagc tcctgcccct    4980
ctgggagcac caggcctgcc taatggactg ctgtctggcg acgaggactt cagctctatc    5040
gccgatatgg atttctcagc cttgctgggc tctggcagcg gcagccggga ttccagggaa    5100
gggatgtttt tgccgaagcc tgaggccggc tccgctatta gtgacgtgtt tgagggccgc    5160
gaggtgtgcc agccaaaacg aatccggcca tttcatcctc caggaagtcc atgggccaac    5220
cgcccactcc ccgccagcct cgcaccaaca ccaaccggtc cagtacatga gccagtcggg    5280
tcactgaccc cggcaccagt ccctcagcca ctggatccag cgcccgcagt gactcccgag    5340
gccagtcacc tgttggagga tcccgatgaa gagacgagcc aggctgtcaa agcccttcgg    5400
gagatggccg atactgtgat tccccagaag gaagaggctg caatctgtgg ccaaatggac    5460
ctttcccatc cgcccccaag gggccatctg gatgagctga caaccacact tgagtccatg    5520
accgaggatc tgaacctgga ctcaccctg accccggaat tgaacgagat tctggatacc    5580
ttcctgaacg acgagtgcct cttgcatgcc atgcatatca gcacaggact gtccatcttc    5640
gacacatctc tgttt                                                      5655
```

<210> SEQ ID NO 434
<211> LENGTH: 1885
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Arg Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

-continued

```
Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Arg Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
```

-continued

```
            645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
            675                 680                 685
Lys Thr Thr Ser Ile Asp Leu Ser Ser Leu Arg Pro Ser Ser Gln Tyr
            690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
            725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
            755                 760                 765
Phe Ser Pro Glu Asn Leu Ala Lys Thr Ser Ile Lys Leu Asn Gly Gln
            770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
            805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
            835                 840                 845
Val Ile Thr Lys Glu Val Ser His Glu Ile Ile Lys Asp Arg Arg Phe
850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
            885                 890                 895
Lys Glu His Pro Glu Thr Pro Ile Ile Gly Ile Ala Arg Gly Glu Arg
            900                 905                 910
Asn Leu Ile Tyr Ile Thr Val Ile Asp Ser Thr Gly Lys Ile Leu Glu
            915                 920                 925
Gln Arg Ser Leu Asn Thr Ile Gln Gln Phe Asp Tyr Gln Lys Lys Leu
            930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
            965                 970                 975
His Glu Ile Val Asp Leu Met Ile His Tyr Gln Ala Val Val Val Leu
            980                 985                 990
Glu Asn Leu Asn Phe Gly Phe Lys Ser Lys Arg Thr Gly Ile Ala Glu
            995                 1000                1005
Lys Ala Val Tyr Gln Gln Phe Glu Lys Met Leu Ile Asp Lys Leu
            1010                1015                1020
Asn Cys Leu Val Leu Lys Asp Tyr Pro Ala Glu Lys Val Gly Gly
            1025                1030                1035
Val Leu Asn Pro Tyr Gln Leu Thr Asp Gln Phe Thr Ser Phe Ala
            1040                1045                1050
Lys Met Gly Thr Gln Ser Gly Phe Leu Phe Tyr Val Pro Ala Pro
            1055                1060                1065
```

-continued

Tyr Thr Ser Lys Ile Asp Pro Leu Thr Gly Phe Val Asp Pro Phe
    1070            1075            1080

Val Trp Lys Thr Ile Lys Asn His Glu Ser Arg Lys His Phe Leu
    1085            1090            1095

Glu Gly Phe Asp Phe Leu His Tyr Asp Val Lys Thr Gly Asp Phe
    1100            1105            1110

Ile Leu His Phe Lys Met Asn Arg Asn Leu Ser Phe Gln Arg Gly
    1115            1120            1125

Leu Pro Gly Phe Met Pro Ala Trp Asp Ile Val Phe Glu Lys Asn
    1130            1135            1140

Glu Thr Gln Phe Asp Ala Lys Gly Thr Pro Phe Ile Ala Gly Lys
    1145            1150            1155

Arg Ile Val Pro Val Ile Glu Asn His Arg Phe Thr Gly Arg Tyr
    1160            1165            1170

Arg Asp Leu Tyr Pro Ala Asn Glu Leu Ile Ala Leu Leu Glu Glu
    1175            1180            1185

Lys Gly Ile Val Phe Arg Asp Gly Ser Asn Ile Leu Pro Lys Leu
    1190            1195            1200

Leu Glu Asn Asp Asp Ser His Ala Ile Asp Thr Met Val Ala Leu
    1205            1210            1215

Ile Arg Ser Val Leu Gln Met Arg Asn Ser Asn Ala Ala Thr Gly
    1220            1225            1230

Glu Asp Tyr Ile Asn Ser Pro Val Arg Asp Leu Asn Gly Val Cys
    1235            1240            1245

Phe Asp Ser Arg Phe Gln Asn Pro Glu Trp Pro Met Asp Ala Asp
    1250            1255            1260

Ala Asn Gly Ala Tyr His Ile Ala Leu Lys Gly Gln Leu Leu Leu
    1265            1270            1275

Asn His Leu Lys Glu Ser Lys Asp Leu Lys Leu Gln Asn Gly Ile
    1280            1285            1290

Ser Asn Gln Asp Trp Leu Ala Tyr Ile Gln Glu Leu Arg Asn Lys
    1295            1300            1305

Arg Pro Ala Ala Thr Lys Lys Ala Gly Gln Ala Lys Lys Lys Lys
    1310            1315            1320

Gly Ser Tyr Pro Tyr Asp Val Pro Asp Tyr Ala Tyr Pro Tyr Asp
    1325            1330            1335

Val Pro Asp Tyr Ala Tyr Pro Tyr Asp Val Pro Asp Tyr Ala Gly
    1340            1345            1350

Ser Glu Ala Ser Gly Ser Gly Arg Ala Asp Ala Leu Asp Asp Phe
    1355            1360            1365

Asp Leu Asp Met Leu Gly Ser Asp Ala Leu Asp Asp Phe Asp Leu
    1370            1375            1380

Asp Met Leu Gly Ser Asp Ala Leu Asp Asp Phe Asp Leu Asp Met
    1385            1390            1395

Leu Gly Ser Asp Ala Leu Asp Asp Phe Asp Leu Asp Met Leu Ile
    1400            1405            1410

Asn Ser Arg Ser Ser Gly Ser Pro Lys Lys Lys Arg Lys Val Gly
    1415            1420            1425

Ser Gln Tyr Leu Pro Asp Thr Asp Asp Arg His Arg Ile Glu Glu
    1430            1435            1440

Lys Arg Lys Arg Thr Tyr Glu Thr Phe Lys Ser Ile Met Lys Lys
    1445            1450            1455

```
Ser Pro Phe Ser Gly Pro Thr Asp Pro Arg Pro Pro Arg Arg
    1460                1465                1470

Ile Ala Val Pro Ser Arg Ser Ser Ala Ser Val Pro Lys Pro Ala
    1475                1480                1485

Pro Gln Pro Tyr Pro Phe Thr Ser Ser Leu Ser Thr Ile Asn Tyr
    1490                1495                1500

Asp Glu Phe Pro Thr Met Val Phe Pro Ser Gly Gln Ile Ser Gln
    1505                1510                1515

Ala Ser Ala Leu Ala Pro Ala Pro Pro Gln Val Leu Pro Gln Ala
    1520                1525                1530

Pro Ala Pro Ala Pro Ala Pro Ala Met Val Ser Ala Leu Ala Gln
    1535                1540                1545

Ala Pro Ala Pro Val Pro Val Leu Ala Pro Gly Pro Pro Gln Ala
    1550                1555                1560

Val Ala Pro Pro Ala Pro Lys Pro Thr Gln Ala Gly Glu Gly Thr
    1565                1570                1575

Leu Ser Glu Ala Leu Leu Gln Leu Gln Phe Asp Asp Glu Asp Leu
    1580                1585                1590

Gly Ala Leu Leu Gly Asn Ser Thr Asp Pro Ala Val Phe Thr Asp
    1595                1600                1605

Leu Ala Ser Val Asp Asn Ser Glu Phe Gln Gln Leu Leu Asn Gln
    1610                1615                1620

Gly Ile Pro Val Ala Pro His Thr Thr Glu Pro Met Leu Met Glu
    1625                1630                1635

Tyr Pro Glu Ala Ile Thr Arg Leu Val Thr Gly Ala Gln Arg Pro
    1640                1645                1650

Pro Asp Pro Ala Pro Ala Pro Leu Gly Ala Pro Gly Leu Pro Asn
    1655                1660                1665

Gly Leu Leu Ser Gly Asp Glu Asp Phe Ser Ser Ile Ala Asp Met
    1670                1675                1680

Asp Phe Ser Ala Leu Leu Gly Ser Gly Ser Gly Ser Arg Asp Ser
    1685                1690                1695

Arg Glu Gly Met Phe Leu Pro Lys Pro Glu Ala Gly Ser Ala Ile
    1700                1705                1710

Ser Asp Val Phe Glu Gly Arg Glu Val Cys Gln Pro Lys Arg Ile
    1715                1720                1725

Arg Pro Phe His Pro Pro Gly Ser Pro Trp Ala Asn Arg Pro Leu
    1730                1735                1740

Pro Ala Ser Leu Ala Pro Thr Pro Thr Gly Pro Val His Glu Pro
    1745                1750                1755

Val Gly Ser Leu Thr Pro Ala Pro Val Pro Gln Pro Leu Asp Pro
    1760                1765                1770

Ala Pro Ala Val Thr Pro Glu Ala Ser His Leu Leu Glu Asp Pro
    1775                1780                1785

Asp Glu Glu Thr Ser Gln Ala Val Lys Ala Leu Arg Glu Met Ala
    1790                1795                1800

Asp Thr Val Ile Pro Gln Lys Glu Glu Ala Ala Ile Cys Gly Gln
    1805                1810                1815

Met Asp Leu Ser His Pro Pro Arg Gly His Leu Asp Glu Leu
    1820                1825                1830

Thr Thr Thr Leu Glu Ser Met Thr Glu Asp Leu Asn Leu Asp Ser
    1835                1840                1845

Pro Leu Thr Pro Glu Leu Asn Glu Ile Leu Asp Thr Phe Leu Asn
```

Asp Glu Cys Leu Leu His Ala Met His Ile Ser Thr Gly Leu Ser
1865                1870                1875

Ile Phe Asp Thr Ser Leu Phe
1880                1885

<210> SEQ ID NO 435
<211> LENGTH: 5721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435

| | |
|---|---|
| atgggcccaa agaaaaagag gaaagtcggc agtggaccta aaaagaaacg aaaggttggg | 60 |
| tcaggtacac agttcgaggg ctttaccaac ctgtatcagg tgagcaagac actgcggttt | 120 |
| gagctgatcc cacagggcaa gaccctgaag cacatccagg agcagggctt catcgaggag | 180 |
| gacaaggccc gcaatgatca ctacaaggag ctgaagccca tcatcgatcg gatctacaag | 240 |
| acctatgccg accagtgcct gcagctggtg cagctggatt gggagaacct gagcgccgcc | 300 |
| atcgactcct atagaaagga gaaaaccgag agacaagga acgccctgat cgaggagcag | 360 |
| gccacatatc gcaatgccat ccacgactac ttcatcggcc ggacagacaa cctgaccgat | 420 |
| gccatcaata gagacacgc cgagatctac aagggcctgt tcaaggccga gctgtttaat | 480 |
| ggcaaggtgc tgaagcagct gggcaccgtg accacaaccg agcacgagaa cgccctgctg | 540 |
| cggagcttcg acaagtttac aacctacttc tccggctttt atagaaacag gaagaacgtg | 600 |
| ttcagcgccg aggatatcag cacagccatc ccacaccgca tcgtgcagga caacttcccc | 660 |
| aagtttaagg agaattgtca catcttcaca cgcctgatca ccgccgtgcc cagcctgcgg | 720 |
| gagcactttg agaacgtgaa gaaggccatc ggcatcttcg tgagccacct catcgaggag | 780 |
| gtgttttcct tccctttta taaccagctg ctgacacaga cccagatcga cctgtataac | 840 |
| cagctgctgg gaggaatctc tcgggaggca ggcaccgaga gatcaaggg cctgaacgag | 900 |
| gtgctgaatc tggccatcca gaagaatgat gagacagccc acatcatcgc ctccctgcca | 960 |
| cacagattca ccccctgtt taagcagatc ctgtccgata ggaacaccct gtctttcatc | 1020 |
| ctggaggagt ttaagagcga cgaggaagtg atccagtcct tctgcaagta caagacactg | 1080 |
| ctgagaaacg agaacgtgct ggagacagcc gaggccctgt taacgagct gaacagcatc | 1140 |
| gacctgacac acatcttcat cagccacaag aagctggaga caatcagcag cgccctgtgc | 1200 |
| gaccactggg atacactgag gaatgccctg tatgagcgga gaatctccga gctgacaggc | 1260 |
| aagatcacca gtctgccaa ggagaaggtg cagcgcagcc tgaagcacga ggatatcaac | 1320 |
| ctgcaggaga tcatctctgc cgcaggcaag gagctgagcg aggccttcaa gcagaaaacc | 1380 |
| agcgagatcc tgtcccacgc acacgccgcc tggatcagc cactgcctac aaccctgaag | 1440 |
| aagcaggagg agaaggagat cctgaagtct cagctggaca gcctgctggg cctgtaccac | 1500 |
| ctgctggact ggtttgccgt ggatgagtcc aacgaggtgg accccgagtt ctctgcccgg | 1560 |
| ctgaccggca tcaagctgga gatggagcct tctctgagct ctacaacaa ggccagaaat | 1620 |
| tatgccacca gaagccta ctccgtggag aagttcaagc tgaactttca gatgcctaca | 1680 |
| ctggccagag ctgggacgt gaatagagag aagaacaatg cgccatcct gtttgtgaag | 1740 |
| aacggcctgt actatctggg catcatgcca aagcagaagg gcaggtataa ggcccctgagc | 1800 |

```
ttcgagccca cagagaaaac cagcgagggc tttgataaga tgtactatga ctacttccct    1860
gatgccgcca agatgatccc aaagtgcagc acccagctga aggccgtgac agcccacttt    1920
cagacccaca caaccccat cctgctgtcc aacaatttca tcgagcctct ggagatcaca     1980
aaggagatct acgacctgaa caatcctgag aaggagccaa agaagtttca gacagcctac    2040
gccaagaaaa ccggcgacca aagggctac agagaggccc tgtgcaagtg gatcgacttc    2100
acaagggatt ttctgtccaa gtataccaag acaacctcta tcgatctgtc tagcctgcgg    2160
ccatcctctc agtataagga cctgggcgag tactatgccg agctgaatcc cctgctgtac    2220
cacatcagct tccagagaat cgccgagaag gagatcatgg atgccgtgga cacaggcaag    2280
ctgtacctgt tccagatcta taacaaggac tttgccaagg ccaccacgg caagcctaat     2340 ctgcacacac tgtattggac cggcctgttt tctccagaga acctggccaa gacaagcatc    2400
aagctgaatg ccaggccga gctgttctac cgccctaagt ccaggatgaa gaggatggca    2460
caccggctgg gagagaagat gctgaacaag aagctgaagg atcagaaaac cccaatcccc    2520
gacaccctgt accaggagct gtacgactat gtgaatcaca actgtcccca cgacctgtct    2580
gatgaggcca gggccctgct gcccaacgtg atcaccaagg aggtgtctca cgagatcatc    2640
aaggataggc gctttaccag cgacaagttc tttttccacg tgcctatcac actgaactat    2700
caggccgcca attccccatc taagttcaac cagagggtga atgcctacct gaaggagcac    2760
cccgagacac ctatcatcgg catcgcccgg ggcgagagaa acctgatcta tatcacagtg    2820
atcgactcca ccggcaagat cctggagcag cggagcctga acaccatcca gcagtttgat    2880
taccagaaga agctggacaa cagggagaag gagagggtgg cagcaaggca ggcctggtct    2940
gtggtgggca caatcaagga tctgaagcag ggctatctga gccaggtcat ccacgagatc    3000
gtggacctga tgatccacta ccaggccgtg gtggtgctgg agaacctgaa tttcggcttt    3060
aagagcaaga ggaccggcat cgccgagaag gccgtgtacc agcagttcga gaagatgctg    3120
atcgataagc tgaattgcct ggtgctgaag gactatccag cagagaaagt gggaggcgtg    3180
ctgaacccat accagctgac agaccagttc acctcctttg ccaagatggg cacccagtct    3240
ggcttcctgt tttacgtgcc tgccccatat acatctaaga tcgatcccct gaccggcttc    3300
gtggacccct tcgtgtggaa aaccatcaag aatcacgaga gccgcaagca cttcctggag    3360
ggcttcgact ttctgcacta cgacgtgaaa accggcgact tcatcctgca ctttaagatg    3420
aacagaaatc tgtccttcca gaggggcctg cccggcttta tgcctgcatg ggatatcgtg    3480
ttcgagaaga cgagacaca gtttgacgcc aagggcaccc cttctcatcgc cggcaagaga    3540 atcgtgccag tgatcgagaa tcacagattc accggcagat accggaccct gtatcctgcc    3600
aacgagctga tcgccctgct ggaggagaag ggcatcgtgt tcagggatgg ctccaacatc    3660
ctgccaaagc tgctggagaa tgacgattct cacgccatcg acacgatggt ggccctgatc    3720
cgcagcgtgc tgcagatgcg gaactccaat gccgccacag gcgaggacta tatcaacagc    3780
cccgtgcgcg atctgaatgg cgtgtgcttc gactcccggt tcagaacccc agagtggcca    3840
atggacgccg atgccaatgg cgcctaccac atcgccctga gggccagct gctgctgaat    3900 cacctgaagg agagcaagga tctgaagctg cagaacggca tctccaatca ggactggctg    3960
gcctacatcc aggagctgcg caacaaaagg ccggcggcca cgaaaaaggc cggccaggca    4020
aaaaagaaaa agggatccta cccatacgat gttccagatt acgcttatcc ctacgacgtg    4080
cctgattatg cataccccata tgatgtcccc gactatgccg gaagcgaggc cagcggttcc    4140
ggacgggctg acgcattgga cgattttgat ctggatatgc tgggaagtga cgccctcgat    4200
```

```
gattttgacc ttgacatgct tggttcggat gcccttgatg actttgacct cgacatgctc    4260
ggcagtgacg cccttgatga tttcgacctg gacatgctga ttaactctag aagttccgga    4320
tctccgaaaa agaaacgcaa agttggtagc cagtacctgc ccgacaccga cgaccggcac    4380
cggatcgagg aaaagcggaa gcggacctac gagacattca agagcatcat gaagaagtcc    4440
cccttcagcg gccccaccga ccctagacct ccacctagaa gaatcgccgt gcccagcaga    4500
tccagcgcca gcgtgccaaa acctgccccc agccttacc ccttcaccag cagcctgagc     4560
accatcaact acgacgagtt ccctaccatg gtgttcccca gcggccagat ctctcaggcc    4620
tctgctctgg ctccagcccc tcctcaggtg ctgcctcagg ctcctgctcc tgcaccagct    4680
ccagccatgg tgtctgcact ggctcaggca ccagcacccg tgcctgtgct ggctcctgga    4740
cctccacagg ctgtggctcc accagcccct aaacctacac aggccggcga gggcacactg    4800
tctgaagctc tgctgcagct gcagttcgac gacgaggatc tgggagccct gctgggaaac    4860
agcaccgatc ctgccgtgtt caccgacctg gccagcgtgg acaacagcga gttccagcag    4920
ctgctgaacc agggcatccc tgtggcccct cacaccaccg agcccatgct gatggaatac    4980
cccgaggcca tcacccggct cgtgacaggc gctcagaggc ctcctgatcc agctcctgcc    5040
cctctgggag caccaggcct gcctaatgga ctgctgtctg gcgacgagga cttcagctct    5100
atcgccgata tggatttctc agccttgctg ggctctggca gcggcagccg ggattccagg    5160
gaagggatgt ttttgccgaa gcctgaggcc ggctccgcta ttagtgacgt gtttgagggc    5220
cgcgaggtgt gccagccaaa acgaatccgg ccatttcatc ctccaggaag tccatgggcc    5280
aaccgcccac tccccgccag cctcgcacca acaccaaccg gtccagtaca tgagccagtc    5340
gggtcactga ccccggcacc agtccctcag ccactggatc cagcgcccgc agtgactccc    5400
gaggccagtc acctgttgga ggatcccgat gaagagacga gccaggctgt caaagccctt    5460
cgggagatgg ccgatactgt gattcccag aaggaagagg ctgcaatctg tggccaaatg     5520
gacctttccc atccgccccc aaggggccat ctggatgagc tgacaaccac acttgagtcc    5580
atgaccgagg atctgaacct ggactcaccc ctgaccccgg aattgaacga gattctggat    5640
accttcctga cgacgagtg cctccttgcat gccatgcata tcagcacagg actgtccatc     5700
ttcgacacat ctctgtttta a                                              5721
```

<210> SEQ ID NO 436
<211> LENGTH: 5574
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 436

```
atgacacagt tcgagggctt taccaacctg tatcaggtga gcaagacact gcggtttgag      60
ctgatcccac agggcaagac cctgaagcac atccaggagc agggcttcat cgaggaggac    120
aaggcccgca atgatcacta caaggagctg aagcccatca tcgatcggat ctacaagacc    180
tatgccgacc agtgcctgca gctggtgcag ctggattggg agaacctgag cgccgccatc    240
gactcctata gaaaggagaa aaccgaggag acaaggaacg ccctgatcga ggagcaggcc    300
acatatcgca atgccatcca cgactacttc atcggccgga cagacaacct gaccgatgcc    360
atcaataaga gacacgccga gatctacaag ggcctgttca aggccgagct gtttaatggc    420
aaggtgctga agcagctggg caccgtgacc acaaccgagc acgagaacgc cctgctgcgg    480
```

```
agcttcgaca agtttacaac ctacttctcc ggcttttata gaaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc cttttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga cacccctgtc tttcatcctg    960
gaggagttta gagcgacga ggaagtgatc cagtccttct gcaagtacaa gacactgctg   1020
agaaacgaga acgtgctgga gacagccgag gccctgttta cgagctgaa cagcatcgac   1080 ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga gcacgagga tatcaacctg   1260 caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca gctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg cgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgtttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460 acccctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgcccggggc gagagaaacc tgatctatat cacagtgatc   2760
gactccaccg gcaagatcct ggagcagcgg agcctgaaca ccatccagca gtttgattac   2820
```

```
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240
gacccctccg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcaccccct tcatcgccgg caagagaatc    3480
gtgccagtga tcgagaatca cagattcacc ggcagatacc gggacctgta cctgccaac    3540 gagctgatcg ccctgctgga ggagaagggc atcgtgttca gggatggctc caacatcctg    3600
ccaaagctgc tggagaatga cgattctcac gccatcgaca cgatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggccaatg    3780
gacgccgatg ccaatggcgc ctaccacatc gccctgaagg ccagctgct gctgaatcac    3840 ctgaaggaga gcaaggatct gaagctgcag aacggcatct ccaatcagga ctggctggcc    3900
tacatccagg agctgcgcaa cggtggaagc ggagggagtc ccaagaagaa gaggaaagtc    3960
gggggttccg gaggaagcga ggccagcggt tccggacggg ctgacgcatt ggacgatttt    4020
gatctggata tgctgggaag tgacgccctc gatgattttg accttgacat gcttggttcg    4080
gatgcccttg atgactttga cctcgacatg ctcggcagtg acgcccttga tgatttcgac    4140
ctggacatgc tgattaactc tagaagttcc ggatctccga aaaagaaacg caaagttggt    4200
agccagtacc tgcccgacac cgacgaccgg caccggatcg aggaaaagcg gaagcggacc    4260
tacgagacat tcaagagcat catgaagaag tccccttca gcggcccca cgaccctaga    4320 cctccaccta agaatcgc cgtgcccagc agatccagcg ccagcgtgcc aaaacctgcc    4380
ccccagcctt acccttcac cagcagcctg agcaccatca actacgacga gttccctacc    4440
atggtgttcc ccagcggcca gatctctcag gcctctgctc tggctccagc ccctcctcag    4500
gtgctgcctc aggctcctgc tcctgcacca gctccagcca tggtgtctgc actggctcag    4560
gcaccagcac ccgtgcctgt gctggctcct ggacctccac aggctgtggc tccaccagcc    4620
cctaaaccta cacaggccgg cgagggcaca ctgtctgaag ctctgctgca gctgcagttc    4680
gacgacgagg atctgggagc cctgctggga aacagcaccg atcctgccgt gttcaccgac    4740
ctggccagcg tggacaacag cgagttccag cagctgctga accagggcat ccctgtggcc    4800
cctcacacca ccgagcccat gctgatggaa taccccgagg ccatcacccg gctcgtgaca    4860
ggcgctcaga ggcctcctga tccagctcct gcccctctgg agcaccagg cctgcctaat    4920 ggactgctgt ctggcgacga ggacttcagc tctatcgccg atatggattt ctcagccttg    4980
ctgggctctg gcagcggcag ccgggattcc agggaaggga tgttttttgcc gaagcctgag    5040 gccggctccg ctattagtga cgtgtttgag ggccgcgagg tgtgccagcc aaaacgaatc    5100
cggccatttc atcctccagg aagtccatgg gccaaccgcc cactccccgc cagcctcgca    5160
ccaacaccaa ccggtccagt acatgagcca gtcgggtcac tgaccccggc accagtccct    5220
```

```
cagccactgg atccagcgcc cgcagtgact cccgaggcca gtcacctgtt ggaggatccc      5280
gatgaagaga cgagccaggc tgtcaaagcc cttcgggaga tggccgatac tgtgattccc      5340
cagaaggaag aggctgcaat ctgtggccaa atggaccttt cccatccgcc cccaaggggc      5400
catctggatg agctgacaac cacacttgag tccatgaccg aggatctgaa cctggactca      5460
cccctgaccc cggaattgaa cgagattctg gataccttcc tgaacgacga gtgcctcttg      5520
catgccatgc atatcagcac aggactgtcc atcttcgaca catctctgtt ttaa            5574
```

<210> SEQ ID NO 437
<211> LENGTH: 5637
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 437

```
atgggcccaa agaaaaagag gaaagtcggc agtggaccta aaagaaacg aaaggttggg       60 tcaggtacac agttcgaggg ctttaccaac ctgtatcagg tgagcaagac actgcggttt     120
gagctgatcc cacagggcaa gaccctgaag cacatccagg agcagggctt catcgaggag     180
gacaaggccc gcaatgatca ctacaaggag ctgaagccca tcatcgatcg gatctacaag     240
acctatgccg accagtgcct gcagctggtg cagctggatt gggagaacct gagcgccgcc     300
atcgactcct atagaaagga gaaaaccgag gagacaagga cgccctgat cgaggagcag      360 gccacatatc gcaatgccat ccacgactac ttcatcggcc ggacagacaa cctgaccgat     420
gccatcaata gagacacgc cgagatctac aagggcctgt tcaaggccga gctgtttaat     480
ggcaaggtgc tgaagcagct gggcaccgtg accacaaccg agcacgagaa cgccctgctg     540
cggagcttcg acaagtttac aacctacttc tccggctttt atagaaacag gaagaacgtg     600
ttcagcgccg aggatatcag cacagccatc ccacaccgca tcgtgcagga acttccccc     660 aagtttaagg agaattgtca catcttcaca cgcctgatca ccgccgtgcc cagcctgcgg     720
gagcactttg agaacgtgaa gaaggccatc ggcatcttcg tgagcacctc catcgaggag     780
gtgttttcct tcccttttta taaccagctg ctgacacaga cccagatcga cctgtataac     840
cagctgctgg gaggaatctc tcgggaggca ggcaccgaga gatcaaggg cctgaacgag     900 gtgctgaatc tggccatcca gaagaatgat gagacagccc acatcatcgc tccctgcca      960 cacagattca tccccctgtt taagcagatc ctgtccgata ggaacaccct gtctttcatc    1020
ctggaggagt ttaagagcga cgaggaagtg atccagtcct tctgcaagta caagacactg    1080
ctgagaaacg agaacgtgct ggagacagcc gaggccctgt taacgagct gaacagcatc     1140 gacctgacac acatcttcat cagccacaag aagctggaga caatcagcag cgccctgtgc    1200
gaccactggg atacactgag gaatgccctg tatgagcgga aatctccga gctgacaggc    1260 aagatcacca gtctgccaa ggagaaggtg cagcgcagcc tgaagcacga ggatatcaac    1320
ctgcaggaga tcatctctgc cgcaggcaag gagctgagcg aggccttcaa gcagaaaacc    1380
agcgagatcc tgtcccacgc acacgccgcc tggatcagc cactgcctac aaccctgaag    1440
aagcaggagg agaaggagat cctgaagtct cagctggaca gcctgctggg cctgtaccac    1500
ctgctggact ggtttgccgt ggatgagtcc aacgaggtgg accccgagtt ctctgcccgg    1560
ctgaccggca tcaagctgga gatggagcct tctctgagct ctacaacaa ggccagaaat    1620 tatgccacca gaagccccta ctccgtggag aagttcaagc tgaactttca gatgcctaca    1680
```

```
ctggccagag gctgggacgt gaatagagag aagaacaatg gcgccatcct gtttgtgaag   1740
aacggcctgt actatctggg catcatgcca agcagaagg gcaggtataa ggccctgagc    1800
ttcgagccca cagagaaaac cagcgagggc tttgataaga tgtactatga ctacttccct   1860
gatgccgcca agatgatccc aaagtgcagc acccagctga aggccgtgac agcccacttt   1920
cagacccaca caaccccccat cctgctgtcc aacaatttca tcgagcctct ggagatcaca   1980
aaggagatct acgacctgaa caatcctgag aaggagccaa agaagtttca gacagcctac   2040
gccaagaaaa ccggcgacca agggctac agagaggccc tgtgcaagtg gatcgacttc     2100
acaagggatt ttctgtccaa gtataccaag acaacctcta tcgatctgtc tagcctgcgg   2160
ccatcctctc agtataagga cctgggcgag tactatgccg agctgaatcc cctgctgtac   2220
cacatcagct tccagagaat cgccgagaag gagatcatgg atgccgtgga cacaggcaag   2280
ctgtacctgt tccagatcta taacaaggac tttgccaagg ccaccacgg caagcctaat    2340 ctgcacacac tgtattggac cggcctgttt tctccagaga acctggccaa gacaagcatc   2400
aagctgaatg ccaggccga gctgttctac cgccctaagt ccaggatgaa gaggatggca    2460
caccggctgg agagaagat gctgaacaag aagctgaagg atcagaaaac cccaatcccc    2520
gacaccctgt accaggagct gtacgactat gtgaatcaca gactgtccca cgacctgtct   2580
gatgaggcca gggccctgct gcccaacgtg atcaccaagg aggtgtctca cgagatcatc   2640
aaggataggc gctttaccag cgacaagttc tttttccacg tgcctatcac actgaactat   2700
caggccgcca attccccatc taagttcaac cagagggtga atgcctacct gaaggagcac   2760
cccgagacac ctatcatcgg catcgcccgg ggcgagagaa acctgatcta tatcacagtg   2820
atcgactcca ccggcaagat cctggagcag cggagcctga acaccatcca gcagtttgat   2880
taccagaaga agctggacaa cagggagaag gagagggtgg cagcaaggca ggcctggtct   2940
gtggtgggca caatcaagga tctgaagcag ggctatctga ccaggtcat ccacgagatc    3000 gtggacctga tgatccacta ccaggccgtg gtggtgctgg agaacctgaa tttcggcttt   3060
aagagcaaga ggaccggcat cgccgagaag gccgtgtacc agcagttcga aagatgctg    3120 atcgataagc tgaattgcct ggtgctgaag gactatccag cagagaaagt gggaggcgtg   3180
ctgaacccat accagctgac agaccagttc acctcctttg ccaagatggg cacccagtct   3240
ggcttcctgt tttacgtgcc tgcccccata acatctaaga tcgatcccct gaccggcttc   3300
gtggacccct tcgtgtggaa aaccatcaag aatcacgaga gccgcaagca cttcctggag   3360
ggcttcgact tctgcactac cgacgtgaaa accggcgact tcatcctgca ctttaagatg   3420
aacagaaatc tgtccttcca gaggggcctg cccggcttta tgcctgcatg ggatatcgtg   3480
ttcgagaaga cgagacaca gtttgacgcc aagggcaccc ctttcatcgc cggcaagaga    3540
atcgtgccag tgatcgagaa tcacagattc accggcagat accgggacct gtatcctgcc   3600
aacgagctga tcgccctgct ggaggagaag ggcatcgtgt tcagggatgg ctccaacatc   3660
ctgccaaagc tgctggagaa tgacgattct cacgccatcg acacgatggt ggccctgatc   3720
cgcagcgtgc tgcagatgcg gaactccaat gccgccacag gcgaggacta tatcaacagc   3780
cccgtgcgcg atctgaatgg cgtgtgcttc gactcccggt tcagaaccc agagtggcca    3840 atggacgccg atgccaatgg cgcctaccac atcgccctga agggccagct gctgctgaat   3900
cacctgaagg agagcaagga tctgaagctg cagaacggca tctccaatca ggactggctg   3960
gcctacatcc aggagctgcg caacggtgga agcggaggga gtcccaagaa gaagaggaaa   4020
```

```
gtcggggtt  ccggaggaag  cgaggccagc  ggttccggac  gggctgacgc  attggacgat     4080
tttgatctgg  atatgctggg  aagtgacgcc  ctcgatgatt  ttgaccttga  catgcttggt     4140
tcggatgccc  ttgatgactt  tgacctcgac  atgctcggca  gtgacgccct  tgatgatttc     4200
gacctggaca  tgctgattaa  ctctagaagt  tccggatctc  cgaaaaagaa  acgcaaagtt     4260
ggtagccagt  acctgcccga  caccgacgac  cggcaccgga  tcgaggaaaa  gcggaagcgg     4320
acctacgaga  cattcaagag  catcatgaag  aagtccccct  tcagcggccc  caccgaccct     4380
agacctccac  ctagaagaat  cgccgtgccc  agcagatcca  gcgccagcgt  gccaaaacct     4440 gcccccagc  cttacccctt  caccagcagc  ctgagcacca  tcaactacga  cgagttccct     4500
accatggtgt  tccccagcgg  ccagatctct  caggcctctg  ctctggctcc  agcccctcct     4560
caggtgctgc  tcaggctcc  tgctcctgca  ccagctccag  ccatggtgtc  tgcactggct     4620
caggcaccag  cacccgtgcc  tgtgctggct  cctggacctc  acaggctgt  ggctccacca     4680 gcccctaaac  ctacacaggc  cggcgagggc  acactgtctg  aagctctgct  gcagctgcag     4740
ttcgacgacg  aggatctggg  agccctgctg  ggaaacagca  ccgatcctgc  cgtgttcacc     4800
gacctggcca  gcgtggacaa  cagcgagttc  cagcagctgc  tgaaccaggg  catccctgtg     4860
gcccctcaca  ccaccgagcc  catgctgatg  gaataccccg  aggccatcac  ccggctcgtg     4920
acaggcgctc  agaggcctcc  tgatccagct  cctgccctc  tgggagcacc  aggcctgcct     4980
aatggactgc  tgtctggcga  cgaggacttc  agctctatcg  ccgatatgga  tttctcagcc     5040
ttgctgggct  ctggcagcgg  cagccgggat  tccagggaag  ggatgttttt  gccgaagcct     5100
gaggccggct  ccgctattag  tgacgtgttt  gagggccgcg  aggtgtgcca  gccaaaacga     5160
atccggccat  tcatcctcc  aggaagtcca  tgggccaacc  gcccactccc  cgccagcctc     5220
gcaccaacac  caaccggtcc  agtacatgag  ccagtcgggt  cactgacccc  ggcaccagtc     5280
cctcagccac  tggatccagc  gcccgcagtg  actcccgagg  ccagtcacct  gttggaggat     5340
cccgatgaag  agacgagcca  ggctgtcaaa  gcccttcggg  agatggccga  tactgtgatt     5400
ccccagaagg  aagaggctgc  aatctgtggc  caaatggacc  tttcccatcc  gcccccaagg     5460
ggccatctgg  atgagctgac  aaccacactt  gagtccatga  ccgaggatct  gaacctggac     5520 tcaccctga  ccccggaatt  gaacgagatt  ctggatacct  tcctgaacga  cgagtgcctc     5580
ttgcatgcca  tgcatatcag  cacaggactg  tccatcttcg  acacatctct  gttttaa     5637
```

<210> SEQ ID NO 438
<211> LENGTH: 5073
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 438

```
atgggcagct  cagagactgg  cccagtggct  gtggacccca  cattgagacg  gcggatcgag       60
ccccatgagt  ttgaggtatt  cttcgatccg  agagagctcc  gcaaggagac  ctgcctgctt      120
tacgaaatta  attgggggg  ccggcactcc  atttggcgac  atacatcaca  gaacactaac      180
aagcacgtcg  aagtcaactt  catcgagaag  ttcacgacag  aaagatattt  ctgtccgaac      240
acaaggtgca  gcattacctg  gtttctcagc  tggagcccat  gcggcgaatg  tagtagggcc      300
atcactgaat  tcctgtcaag  gtatcccac  gtcactctgt  ttatttacat  cgcaaggctg      360
taccaccacg  ctgaccccg  caatcgacaa  ggcctgcggg  atttgatctc  ttcaggtgtg      420
```

-continued

```
actatccaaa ttatgactga gcaggagtca ggatactgct ggagaaactt tgtgaattat      480
agcccgagta atgaagccca ctggcctagg tatccccatc tgtgggtacg actgtacgtt      540
cttgaactgt actgcatcat actgggcctg cctccttgtc tcaacattct gagaaggaag      600
cagccacagc tgacattctt taccatcgct cttcagtctt gtcattacca gcgactgccc      660
ccacacattc tctgggccac cgggttgaaa tctggtggtt cttctggtgg ttctagcggc      720
agcgagactc ccgggacctc agagtccgcc acacccgaaa gttccggagg gagtagcggc      780
gggtctacac agttcgaggg ctttaccaac ctgtatcagg tgagcaagac actgcggttt      840
gagctgatcc cacagggcaa gacccctgaa gcacatccagg agcagggctt catcgaggag      900
gacaaggccc gcaatgatca ctacaaggag ctgaagccca tcatcgatcg gatctacaag      960
acctatgccg accagtgcct gcagctggtg cagctggatt gggagaacct gagcgccgcc      1020
atcgactcct atagaaagga gaaaaccgag gagacaagga acgccctgat cgaggagcag      1080
gccacatatc gcaatgccat ccacgactac ttcatcggcc ggacagacaa cctgaccgat      1140
gccatcaata gagacacgc cgagatctac aagggcctgt tcaaggccga gctgtttaat      1200
ggcaaggtgc tgaagcagct gggcaccgtg accacaaccg agcacgagaa cgccctgctg      1260
cggagcttcg acaagtttac aacctacttc tccggctttt atgagaacag gaagaacgtg      1320
ttcagcgccg aggatatcag cacagccatc ccacaccgca tcgtgcagga caacttcccc      1380
aagtttaagg agaattgtca catcttcaca cgcctgatca ccgccgtgcc cagcctgcgg      1440
gagcactttg agaacgtgaa gaaggccatc ggcatcttcg tgagcaccctc catcgaggag      1500
gtgttttcct tccttttta taaccagctg ctgacacaga cccagatcga cctgtataac      1560
cagctgctgg gaggaatctc tcgggaggca ggcaccgaga agatcaaggg cctgaacgag      1620
gtgctgaatc tggccatcca gaagaatgat gagacagccc acatcatcgc ctccctgcca      1680
cacagattca tccccctgtt taagcagatc ctgtccgata ggaacaccct gtctttcatc      1740
ctggaggagt ttaagagcga cgaggaagtg atccagtcct tctgcaagta caagacactg      1800
ctgagaaacg agaacgtgct ggagacagcc gaggccctgt ttaacgagct gaacagcatc      1860
gacctgacac acatcttcat cagccacaag aagctggaga caatcagcag cgccctgtgc      1920
gaccactggg atacactgag gaatgccctg tatgagcgga aatctccga gctgacaggc      1980
aagatcacca gtctgccaa ggagaaggtg cagcgcagcc tgaagcacga ggatatcaac      2040
ctgcaggaga tcatctctgc cgcaggcaag gagctgagcg aggccttcaa gcagaaaacc      2100
agcgagatcc tgtcccacgc acacgccgcc tggatcagc cactgcctac aaccctgaag      2160
aagcaggagg agaaggagat cctgaagtct cagctggaca gcctgctggg cctgtaccac      2220
ctgctggact ggtttgccgt ggatgagtcc aacgaggtgg accccgagtt ctctgcccgg      2280
ctgaccggca tcaagctgga gatggagcct tctctgagct ctacaacaa ggccagaaat      2340
tatgccacca gaagcccta ctccgtggag aagttcaagc tgaactttca gatgcctaca      2400
ctggcctctg gctgggacgt gaataaggag aagaacaatg cgccatcct gtttgtgaag      2460
aacggcctgt actatctggg catcatgcca aagcagaagg gcaggtataa ggccctgagc      2520
ttcgagccca cagagaaaac cagcgagggc tttgataaga tgtactatga ctacttccct      2580
gatgccgcca agatgatccc aaagtgcagc acccagctga aggccgtgac agcccacttt      2640
cagacccaca caaccccat cctgctgtcc aacaatttca tcgagcctct ggagatcaca      2700
aaggagatct acgacctgaa caatcctgag aaggagccaa agaagtttca gacagcctac      2760
gccaagaaaa ccggcgacca gaagggctac agagaggccc tgtgcaagtg gatcgacttc      2820
```

```
acaagggatt ttctgtccaa gtataccaag acaacctcta tcgatctgtc tagcctgcgg    2880
ccatcctctc agtataagga cctgggcgag tactatgccg agctgaatcc cctgctgtac    2940
cacatcagct tccagagaat cgccgagaag gagatcatgg atgccgtgga gacaggcaag    3000
ctgtacctgt tccagatcta taacaaggac tttgccaagg ccaccacgg caagcctaat     3060
ctgcacacac tgtattggac cggcctgttt tctccagaga acctggccaa gacaagcatc    3120
aagctgaatg ccaggccga gctgttctac cgccctaagt ccaggatgaa gaggatggca     3180
caccggctgg gagagaagat gctgaacaag aagctgaagg atcagaaaac cccaatcccc    3240
gacaccctgt accaggagct gtacgactat gtgaatcaca gactgtccca cgacctgtct    3300
gatgaggcca gggccctgct gcccaacgtg atcaccaagg aggtgtctca cgagatcatc    3360
aaggataggc gctttaccag cgacaagttc ttttttccacg tgcctatcac actgaactat   3420
caggccgcca attccccatc taagttcaac cagagggtga atgcctacct gaaggagcac    3480
cccgagacac ctatcatcgg catcgcccgg ggcgagagaa acctgatcta tatcacagtg    3540
atcgactcca ccggcaagat cctggagcag cggagcctga acaccatcca gcagtttgat   3600
taccagaaga agctggacaa cagggagaag gagagggtgg cagcaaggca ggcctggtct    3660
gtggtgggca caatcaagga tctgaagcag ggctatctga gccaggtcat ccacgagatc    3720
gtggacctga tgatccacta ccaggccgtg gtggtgctgg agaacctgaa tttcggcttt    3780
aagagcaaga ggaccggcat cgccgagaag gccgtgtacc agcagttcga gaagatgctg    3840
atcgataagc tgaattgcct ggtgctgaag gactatccag cagagaaagt gggaggcgtg    3900
ctgaacccat accagctgac agaccagttc acctcctttg ccaagatggg cacccagtct    3960
ggcttcctgt tttacgtgcc tgccccatat acatctaaga tcgatcccct gaccggcttc    4020
gtggacccct tcgtgtggaa aaccatcaag aatcacgaga gccgcaagca cttcctggag    4080
ggcttcgact ttctgcacta cgacgtgaaa accggcgact tcatcctgca ctttaagatg    4140
aacagaaatc tgtccttcca gagggggctg cccggcttta tgcctgcatg ggatatcgtg    4200
ttcgagaaga cgagacaca gtttgacgcc aagggcaccc cttttcatcg cggcaagaga    4260
atcgtgccag tgatcgagaa tcacagattc accggcagat accggacct gtatcctgcc    4320
aacgagctga tcgccctgct ggaggagaag ggcatcgtgt tcagggatgg ctccaacatc    4380
ctgccaaagc tgctggagaa tgacgattct cacgccatcg acacgatggt ggccctgatc    4440
cgcagcgtgc tgcagatgcg gaactccaat gccgccacag gcgaggacta tatcaacagc    4500
cccgtgcgcg atctgaatgg cgtgtgcttc gactcccggt ttcagaaccc agagtggcca    4560
atggacgccg atgccaatgg cgcctaccac atcgccctga agggccagct gctgctgaat    4620
cacctgaagg agagcaagga tctgaagctg cagaacggca tctccaatca ggactggctg    4680
gcctacatcc aggagctgcg caacaaaagg ccggcggcca cgaaaaaggc cggccaggca    4740
aaaaagaaaa agggatcctc tggtggttct ggaggatctg gtggttctac taatctgtca    4800
gatattattg aaaaggagac cggtaagcaa ctggttatcc aggaatccat cctcatgctc    4860
ccagaggagg tggaagaagt cattgggaac aagccggaaa gcgatatact cgtgcacacc    4920
gcctacgacg agagcaccga cgagaatgtc atgcttctga ctagcgacgc ccctgaatac    4980
aagccttggg ctctggtcat acaggatagc aacggtgaga caagattaa gatgctctct    5040
ggtggttctc ccaagaagaa gaggaaagtc taa                                 5073
```

<210> SEQ ID NO 439

<211> LENGTH: 4836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 439

| | | | | | |
|---|---|---|---|---|---|
| atgggcagct | cagagactgg | cccagtggct | gtggaccca | cattgagacg | gcggatcgag | 60 |
| cccatgagt | ttgaggtatt | cttcgatccg | agagagctcc | gcaaggagac | ctgcctgctt | 120 |
| tacgaaatta | attggggggg | ccggcactcc | atttggcgac | atacatcaca | gaacactaac | 180 |
| aagcacgtcg | aagtcaactt | catcgagaag | ttcacgacag | aaagatattt | ctgtccgaac | 240 |
| acaaggtgca | gcattacctg | gtttctcagc | tggagcccat | gcggcgaatg | tagtagggcc | 300 |
| atcactgaat | tcctgtcaag | gtatccccac | gtcactctgt | ttatttacat | cgcaaggctg | 360 |
| taccaccacg | ctgaccccg | caatcgacaa | ggcctgcggg | atttgatctc | ttcaggtgtg | 420 |
| actatccaaa | ttatgactga | gcaggagtca | ggatactgct | ggagaaactt | tgtgaattat | 480 |
| agcccgagta | atgaagccca | ctggcctagg | tatccccatc | tgtgggtacg | actgtacgtt | 540 |
| cttgaactgt | actgcatcat | actgggcctg | cctccttgtc | tcaacattct | gagaaggaag | 600 |
| cagccacagc | tgacattctt | taccatcgct | cttcagtctt | gtcattacca | gcgactgccc | 660 |
| ccacacattc | tctgggccac | cgggttgaaa | tctggtggtt | cttctggtgg | ttctagcggc | 720 |
| agcgagactc | ccgggacctc | agagtccgcc | acacccgaaa | gttccggagg | gagtagcggc | 780 |
| gggtctagca | agctggagaa | gtttacaaac | tgctactccc | tgtctaagac | cctgaggttc | 840 |
| aaggccatcc | ctgtgggcaa | gacccaggag | aacatcgaca | taagcggct | gctggtggag | 900 |
| gacgagaaga | gagccgagga | ttataagggc | gtgaagaagc | tgctggatcg | ctactatctg | 960 |
| tcttttatca | cgacgtgct | gcacagcatc | aagctgaaga | atctgaacaa | ttacatcagc | 1020 |
| ctgttccgga | agaaaaccag | aaccgagaag | gagaataagg | agctggagaa | cctggagatc | 1080 |
| aatctgcgga | aggagatcgc | caaggccttc | aagggcaacg | agggctacaa | gtccctgttt | 1140 |
| aagaaggata | tcatcgagac | aatcctgcca | gagttcctgg | acgataagga | cgagatcgcc | 1200 |
| ctggtgaaca | gcttcaatgg | ctttaccaca | gccttcaccg | gcttctttga | taacagagag | 1260 |
| aatatgtttt | ccgaggaggc | caagagcaca | tccatcgcct | tcaggtgtat | caacgagaat | 1320 |
| ctgacccgct | acatctctaa | tatggacatc | ttcgagaagg | tggacgccat | cttttgataag | 1380 |
| cacgaggtgc | aggagatcaa | ggagaagatc | ctgaacagcg | actatgatgt | ggaggatttc | 1440 |
| tttgagggcg | agttctttaa | ctttgtgctg | acacaggagg | gcatcgacgt | gtataacgcc | 1500 |
| atcatcggcg | gcttcgtgac | cgagagcggc | gagaagatca | agggcctgaa | cgagtacatc | 1560 |
| aacctgtata | atcagaaaac | caagcagaag | ctgcctaagt | ttaagccact | gtataagcag | 1620 |
| gtgctgagcg | atcgggagtc | tctgagcttc | tacggcgagg | gctatacatc | cgatgaggag | 1680 |
| gtgctggagg | tgtttagaaa | caccctgaac | aagaacagcg | agatcttcag | ctccatcaag | 1740 |
| aagctggaga | agctgttcaa | gaattttgac | gagtactcta | gcgccggcat | ctttgtgaag | 1800 |
| aacggccccg | ccatcagcac | aatctccaag | gatatcttcg | gcgagtggaa | cgtgatccgg | 1860 |
| gacaagtgga | atgccgagta | tgacgatatc | cacctgaaga | gaaggccgt | ggtgaccgag | 1920 |
| aagtacgagg | acgatcggag | aaagtccttc | aagaagatcg | gctccttttc | tctggagcag | 1980 |
| ctgcaggagt | acgccgacgc | cgatctgtct | gtggtggaga | gctgaagga | gatcatcatc | 2040 |
| cagaaggtgg | atgagatcta | caaggtgtat | ggctcctctg | agaagctgtt | cgacgccgat | 2100 |

```
tttgtgctgg agaagagcct gaagaagaac gacgccgtgg tggccatcat gaaggacctg    2160
ctggattctg tgaagagctt cgagaattac atcaaggcct tctttggcga gggcaaggag    2220
acaaacaggg acgagtcctt ctatggcgat tttgtgctgg cctacgacat cctgctgaag    2280
gtggaccaca tctacgatgc catccgcaat tatgtgaccc agaagcccta ctctaaggat    2340
aagttcaagc tgtattttca gaaccctcag ttcatgggcg ctgggacaa ggataaggag     2400 acagactatc gggccaccat cctgagatac ggctccaagt actatctggc catcatggat    2460
aagaagtacg ccaagtgcct gcagaagatc gacaaggacg atgtgaacgg caattacgag    2520
aagatcaact ataagctgct gcccggccct aataagatgc tgccaaaggt gttctttct     2580 aagaagtgga tggcctacta accccagc gaggacatcc agaagatcta caagaatggc      2640
acattcaaga agggcgatat gtttaacctg aatgactgtc acaagctgat cgacttcttt    2700
aaggatagca tctcccggta tccaaagtgg tccaatgcct acgatttcaa cttttctgag    2760
acagagaagt ataaggacat cgccggcttt tacagagagg tggaggagca gggctataag    2820
gtgagcttcg agtctgccag caagaaggag gtggataagc tggtggagga gggcaagctg    2880
tatatgttcc agatctataa caaggacttt ccgataagt ctcacggcac acccaatctg     2940
cacaccatgt acttcaagct gctgtttgac gagaacaatc acggacagat caggctgagc    3000
ggaggagcag agctgttcat gaggcgcgcc tccctgaaga aggaggagct ggtggtgcac    3060
ccagccaact cccctatcgc caacaagaat ccagataatc ccaagaaaac cacaaccctg    3120
tcctacgacg tgtataagga taagaggttt ctgaggacc agtacgagct gcacatccca     3180
atcgccatca taagtgccc caagaacatc ttcaagatca atacagaggt gcgcgtgctg    3240
ctgaagcacg acgataaccc ctatgtgatc ggcatcgcca ggggcgagcg caatctgctg    3300
tatatcgtgt tggtggacgg caagggcaac atcgtggagc agtattccct gaacgagatc    3360
atcaacaact tcaacggcat caggatcaag acagattacc actctctgct ggacaagaag    3420
gagaaggaga ggttcgaggc ccgccagaac tggacctcca tcgagaatat caaggagctg    3480
aaggccggct atatctctca ggtggtgcac aagatctgcg agctggtgga agtacgat      3540 gccgtgatcg ccctggagga cctgaactct ggctttaaga atagccgcgt gaaggtggag    3600
aagcaggtgt atcagaagtt cgagaagatg ctgatcgata agctgaacta catggtggac    3660
aagaagtcta atccttgtgc aacaggcggc gccctgaagg ctatcagat caccaataag     3720 ttcgagagct ttaagtccat gtctacccag aacggcttca tcttttacat ccctgcctgg    3780
ctgacatcca gatcgatcc atctaccggc tttgtgaacc tgctgaaaac caagtatacc     3840
agcatcgccg attccaagaa gttcatcagc cctttgaca ggatcatgta cgtgcccgag     3900
gaggatctgt tcgagtttgc cctggactat aagaacttct ctcgcacaga cgccgattac    3960
atcaagaagt ggaagctgta ctcctacggc aaccggatca gaatcttccg gaatcctaag    4020
aagaacaacg tgttcgactg ggaggaggtg tgcctgacca cgccctataa ggagctgttc    4080
aacaagtacg gcatcaatta tcagcagggc gatatcagag ccctgctgtg cgagcagtcc    4140
gacaaggcct tctactctag ctttatggcc ctgatgagcc tgatgctgca gatgcggaac    4200
agcatcacag gccgcaccga cgtggatttt ctgatcagcc ctgtgaagaa ctccgacggc    4260
atcttctacg atagccggaa ctatgaggcc caggagaatg ccatcctgcc aaagaacgcc    4320
gacgccaatg gcgcctataa catcgccaga aaggtgctgt gggccatcgg ccagttcaag    4380
aaggccgagg acgagaagct ggataaggtg aagatcgcca tctctaacaa ggagtggctg    4440
gagtacgccc agaccagcgt gaagcacaaa aggccggcgg ccacgaaaaa ggccggccag    4500
```

```
gcaaaaaaga aaaagggatc ctctggtggt tctggaggat ctggtggttc tactaatctg   4560
tcagatatta ttgaaaagga gaccggtaag caactggtta tccaggaatc catcctcatg   4620
ctcccagagg aggtggaaga agtcattggg aacaagccgg aaagcgatat actcgtgcac   4680
accgcctacg acgagagcac cgacgagaat gtcatgcttc tgactagcga cgcccctgaa   4740
tacaagcctt gggctctggt catacaggat agcaacggtg agaacaagat taagatgctc   4800
tctggtggtt ctcccaagaa gaagaggaaa gtctaa                             4836
```

<210> SEQ ID NO 440
<211> LENGTH: 5073
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440

```
atgggcagct cagagactgg cccagtggct gtggacccca cattgagacg gcggatcgag     60
ccccatgagt ttgaggtatt cttcgatccg agagagctcc gcaaggagac ctgcctgctt    120
tacgaaatta ttgggggggg ccggcactcc atttggcgac atacatcaca gaacactaac    180
aagcacgtcg aagtcaactt catcgagaag ttcacgacag aaagatattt ctgtccgaac    240
acaaggtgca gcattacctg gtttctcagc tggagcccat cggcgaatg tagtagggcc    300 atcactgaat tcctgtcaag gtatccccac gtcactctgt ttatttacat cgcaaggctg    360
taccaccacg ctgaccccg caatcgacaa ggcctgcggg atttgatctc ttcaggtgtg    420
actatccaaa ttatgactga gcaggagtca ggatactgct ggagaaactt tgtgaattat    480
agcccgagta atgaagccca ctggcctagg tatccccatc tgtgggtacg actgtacgtt    540
cttgaactgt actgcatcat actgggcctg cctccttgtc tcaacattct gagaaggaag    600
cagccacagc tgacattctt taccatcgct cttcagtctt gtcattacca gcgactgccc    660
ccacacattc tctgggccac cgggttgaaa tctggtggtt cttctggtgg ttctagcggc    720
agcgagactc ccgggacctc agagtccgcc acacccgaaa gttccggagg gagtagcggc    780
gggtctacac agttcgaggg cttttaccaac ctgtatcagg tgagcaagac actgcggttt    840
gagctgatcc cacagggcaa gacccctgaag cacatccagg agcagggctt catcgaggag    900
gacaaggccc gcaatgatca ctacaaggag ctgaagccca tcatcgatcg gatctacaag    960
acctatgccg accagtgcct gcagctggtg cagctggatt gggagaacct gagcgccgcc   1020
atcgactcct atagaaagga gaaaaccgag gagacaagga acgccctgat cgaggagcag   1080
gccacatatc gcaatgccat ccacgactac ttcatcggcc ggacagacaa cctgaccgat   1140
gccatcaata gagacacgc cgagatctac aagggcctgt tcaaggccga gctgtttaat   1200
ggcaaggtgc tgaagcagct gggcaccgtg accacaaccg agcacgagaa cgccctgctg   1260
cggagcttcg acaagtttac aacctacttc tccggctttt atagaaacag gaagaacgtg   1320
ttcagcgccg aggatatcag cacagccatc ccacaccgca tcgtgcagga caacttcccc   1380
aagtttaagg agaattgtca catcttcaca cgcctgatca ccgccgtgcc cagcctgcgg   1440
gagcactttg agaacgtgaa gaaggccatc ggcatcttcg tgagcacctc catcgaggag   1500
gtgttttcct tccttttta taaccagctg ctgacacaga cccagatcga cctgtataac   1560
cagctgctgg gaggaatctc tcgggaggca ggcaccgaga gatcaaaggg cctgaacgag   1620
gtgctgaatc tggccatcca gaagaatgat gagacagccc acatcatcgc ctccctgcca   1680
```

```
cacagattca tccccctgtt taagcagatc ctgtccgata ggaacaccct gtctttcatc    1740
ctggaggagt ttaagagcga cgaggaagtg atccagtcct tctgcaagta caagacactg    1800
ctgagaaacg agaacgtgct ggagacagcc gaggccctgt ttaacgagct gaacagcatc    1860
gacctgacac acatcttcat cagccacaag aagctggaga caatcagcag cgccctgtgc    1920
gaccactggg atacactgag gaatgccctg tatgagcgga aatctccga gctgacaggc    1980 aagatcacca agtctgccaa ggagaaggtg cagcgcagcc tgaagcacga ggatatcaac    2040
ctgcaggaga tcatctctgc cgcaggcaag gagctgagcg aggccttcaa gcagaaaacc    2100
agcgagatcc tgtcccacgc acacgccgcc tggatcagc cactgcctac aaccctgaag    2160
aagcaggagg agaaggagat cctgaagtct cagctggaca gcctgctggg cctgtaccac    2220
ctgctggact ggtttgccgt ggatgagtcc aacgaggtgg accccgagtt ctctgcccgg    2280
ctgaccggca tcaagctgga gatggagcct tctctgagct tctacaacaa ggccagaaat    2340
tatgccacca gaagcccta ctccgtggag aagttcaagc tgaactttca gatgcctaca    2400
ctggccagag gctgggacgt gaatagagag aagaacaatg cgccatcct gtttgtgaag    2460 aacggcctgt actatctggg catcatgcca aagcagaagg gcaggtataa ggccctgagc    2520
ttcgagccca cagagaaaac cagcgagggc tttgataaga tgtactatga ctacttccct    2580
gatgccgcca agatgatccc aaagtgcagc acccagctga aggccgtgac agcccacttt    2640
cagacccaca caacccccat cctgctgtcc aacaatttca tcgagcctct ggagatcaca    2700
aaggagatct acgacctgaa caatcctgag aaggagccaa agaagtttca gacagcctac    2760
gccaagaaaa ccggcgacca aagggctac agagaggccc tgtgcaagtg gatcgacttc    2820
acaagggatt ttctgtccaa gtataccaag acaacctcta tcgatctgtc tagcctgcgg    2880
ccatcctctc agtataagga cctgggcgag tactatgccg agctgaatcc cctgctgtac    2940
cacatcagct tccagagaat cgccgagaag gagatcatgg atgccgtgga cacaggcaag    3000
ctgtacctgt tccagatcta taacaaggac tttgccaagg ccaccacgg caagcctaat    3060 ctgcacacac tgtattggac cggcctgttt tctccagaga acctggccaa gacaagcatc    3120
aagctgaatg ccaggccga gctgttctac cgccctaagt ccaggatgaa gaggatggca    3180
caccggctgg gagagaagat gctgaacaag aagctgaagg atcagaaaac cccaatcccc    3240
gacaccctgt accaggagct gtacgactat gtgaatcaca gactgtccca cgacctgtct    3300
gatgaggcca gggccctgct gcccaacgtg atcaccaagg aggtgtctca cgagatcatc    3360
aaggataggc gctttaccag cgacaagttc ttttccacg tgcctatcac actgaactat    3420
caggccgcca attccccatc taagttcaac cagagggtga atgcctacct gaaggagcac    3480
cccgagacac ctatcatcgg catcgcccgg ggcgagagaa acctgatcta tatcacagtg    3540
atcgactcca ccggcaagat cctggagcag cggagcctga caccatcca gcagtttgat    3600 taccagaaga agctggacaa cagggagaag gagagggtgg cagcaaggca ggcctggtct    3660
gtggtgggca caatcaagga tctgaagcag ggctatctga gccaggtcat ccacgagatc    3720
gtggacctga tgatccacta ccaggccgtg gtggtgctgg agaacctgaa tttcggcttt    3780
aagagcaaga ggaccggcat cgccgagaag gccgtgtacc agcagttcga gaagatgctg    3840
atcgataagc tgaattgcct ggtgctgaag gactatccag cagagaaagt gggaggcgtg    3900
ctgaacccat accagctgac agaccagttc acctcctttg ccaagatggg cacccagtct    3960
ggcttcctgt tttacgtgcc tgcccccatat acatctaaga tcgatcccct gaccggcttc    4020
```

```
gtggacccct tcgtgtggaa aaccatcaag aatcacgaga gccgcaagca cttcctggag    4080
ggcttcgact ttctgcacta cgacgtgaaa accggcgact tcatcctgca ctttaagatg    4140
aacagaaatc tgtccttcca gagggggcctg cccggcttta tgcctgcatg ggatatcgtg    4200
ttcgagaaga acgagacaca gtttgacgcc aagggcaccc ctttcatcgc cggcaagaga    4260
atcgtgccag tgatcgagaa tcacagattc accggcagat accgggacct gtatcctgcc    4320
aacgagctga tcgccctgct ggaggagaag ggcatcgtgt tcaggatgg ctccaacatc    4380 ctgccaaagc tgctggagaa tgacgattct cacgccatcg acacgatggt ggccctgatc    4440
cgcagcgtgc tgcagatgcg gaactccaat gccgccacag gcgaggacta tatcaacagc    4500
cccgtgcgcg atctgaatgg cgtgtgcttc gactcccggt tcagaaccc agagtggcca    4560 atggacgccg atgccaatgg cgcctaccac atcgccctga agggccagct gctgctgaat    4620
cacctgaagg agagcaagga tctgaagctg cagaacggca tctccaatca ggactggctg    4680
gcctacatcc aggagctgcg caacaaaagg ccggcggcca cgaaaaaggc cggccaggca    4740
aaaaagaaaa agggatcctc tggtggttct ggaggatctg gtggttctac taatctgtca    4800
gatattattg aaaaggagac cggtaagcaa ctggttatcc aggaatccat cctcatgctc    4860
ccagaggagg tggaagaagt cattgggaac aagccggaaa gcgatatact cgtgcacacc    4920
gcctacgacg agagcaccga cgagaatgtc atgcttctga ctagcgacgc ccctgaatac    4980
aagccttggg ctctggtcat acaggatagc aacggtgaga caagattaa gatgctctct    5040 ggtggttctc ccaagaagaa gaggaaagtc taa                                 5073

<210> SEQ ID NO 441
<211> LENGTH: 5133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 441
atgggcccaa agaaaaagag gaaagtcggc agtggaccta aaaagaaacg aaaggttggg     60
tcaggtagct cagagactgg cccagtggct gtggaccca cattgagacg gcggatcgag    120
ccccatgagt ttgaggtatt cttcgatccg agagagctcc gcaaggagac ctgcctgctt    180
tacgaaatta ttggggggg ccggcactcc atttggcgac atacatcaca gaacactaac    240
aagcacgtcg aagtcaactt catcgagaag ttcacgacag aaagatattt ctgtccgaac    300
acaaggtgca gcattacctg gtttctcagc tggagcccat gcggcgaatg tagtagggcc    360
atcactgaat tcctgtcaag gtatccccac gtcactctgt ttatttacat cgcaaggctg    420
taccaccact tgaccccccg caatcgacaa ggcctgcggg atttgatctc ttcaggtgtg    480
actatccaaa ttatgactga gcaggagtca ggatactgct ggagaaactt tgtgaattat    540
agcccgagta tgaagcccca ctggcctagg tatccccatc tgtgggtacg actgtacgtt    600
cttgaactgt actgcatcat actgggcctg cctccttgtc tcaacattct gagaaggaag    660
cagccacagc tgacattctt taccatcgct cttcagtctt gtcattacca gcgactgccc    720
ccacacattc tctgggccac cgggttgaaa tctggtggtt cttctggtgg ttctagcggc    780
agcgagactc ccgggacctc agagtccgcc acacccgaaa gttccggagg gagtagcggc    840
gggtctacac agttcgaggg cttttaccaac ctgtatcagg tgagcaagac actgcggttt    900
gagctgatcc cacagggcaa gaccctgaag cacatccagg agcagggctt catcgaggag    960
```

```
gacaaggccc gcaatgatca ctacaaggag ctgaagccca tcatcgatcg gatctacaag    1020
acctatgccg accagtgcct gcagctggtg cagctggatt gggagaacct gagcgccgcc    1080
atcgactcct atagaaagga gaaaaccgag gagacaagga acgccctgat cgaggagcag    1140
gccacatatc gcaatgccat ccacgactac ttcatcggcc ggacagacaa cctgaccgat    1200
gccatcaata agagacacgc cgagatctac aagggcctgt tcaaggccga gctgtttaat    1260
ggcaaggtgc tgaagcagct gggcaccgtg accacaaccg agcacgagaa cgccctgctg    1320
cggagcttcg acaagtttac aacctacttc tccggctttt atagaaacag gaagaacgtg    1380
ttcagcgccg aggatatcag cacagccatc ccacaccgca tcgtgcagga caacttcccc    1440
aagtttaagg agaattgtca catcttcaca cgcctgatca ccgccgtgcc cagcctgcgg    1500
gagcactttg agaacgtgaa gaaggccatc ggcatcttcg tgagcacctc catcgaggag    1560
gtgttttcct tcccttttta taaccagctg ctgacacaga cccagatcga cctgtataac    1620
cagctgctgg aggaatctc tcgggaggca ggcaccgaga agatcaaggg cctgaacgag    1680
gtgctgaatc tggccatcca agaggaatgat gagacagccc acatcatcgc ctccctgcca    1740
cacagattca tccccctgtt taagcagatc ctgtccgata ggaacacct gtctttcatc    1800
ctggaggagt ttaagagcga cgaggaagtg atccagtcct tctgcaagta caagacactg    1860
ctgagaaacg agaacgtgct ggagacagcc gaggccctgt ttaacgagct gaacagcatc    1920
gacctgacac acatcttcat cagccacaag aagctggaga caatcagcag cgccctgtgc    1980
gaccactggg atacactgag gaatgccctg tatgagcgga gaatctccga gctgacaggc    2040
aagatcacca gtctgccaa ggagaaggtg cagcgcagcc tgaagcacga ggatatcaac    2100
ctgcaggaga tcatctctgc cgcaggcaag gagctgagcg aggccttcaa gcagaaaacc    2160
agcgagatcc tgtcccacgc acacgccgcc tggatcagc cactgcctac aaccctgaag    2220
aagcaggagg agaaggagat cctgaagtct cagctggaca gcctgctggg cctgtaccac    2280
ctgctggact ggtttgccgt ggatgagtcc aacgaggtgg accccgagtt ctctgcccgg    2340
ctgaccggca tcaagctgga gatggagcct ctctctgagct tctacaacaa ggccagaaat    2400
tatgccacca gaagcccta ctccgtggag aagttcaagc tgaactttca gatgcctaca    2460
ctggccagag gctgggacgt gaatagagag aagaacaatg gcgccatcct gtttgtgaag    2520
aacggcctgt actatctggg catcatgcca aagcagaagg gcaggtataa ggccctgagc    2580
ttcgagccca cagagaaaac cagcgagggc tttgataaga tgtactatga ctacttccct    2640
gatgccgcca agatgatcc aaaagtgcagc acccagctga aggccgtgac agcccacttt    2700
cagacccaca caacccccat cctgctgtcc aacaattca tcgagcctct ggagatcaca    2760
aaggagatct acgacctgaa caatcctgag aaggagccaa agaagtttca gacagcctac    2820
gccaagaaaa ccggcgacca aagggctac agagaggccc tgtgcaagtg gatcgacttc    2880
acaagggatt ttctgtccaa gtataccaag acaacctcta tcgatctgtc tagcctgcgg    2940
ccatcctctc agtataagga cctgggcgag tactatgccg agctgaatcc cctgctgtac    3000
cacatcagct ccagagaat cgccgagaag gagatcatgg atgccgtgga cacaggcaag    3060
ctgtacctgt tccagatcta taacaaggac tttgccaagg ccaccacgg caagcctaat    3120
ctgcacacac tgtattggac cggcctgttt tctccagaga acctggccaa gacaagcatc    3180
aagctgaatg ccaggccga gctgttctac cgccctaagt ccaggatgaa gaggatggca    3240
caccggctgg gagagaagat gctgaacaag aagctgaagg atcagaaaac ccaatcccc    3300
gacaccctgt accaggagct gtacgactat gtgaatcaca gactgtccca cgacctgtct    3360
```

-continued

```
gatgaggcca gggccctgct gcccaacgtg atcaccaagg aggtgtctca cgagatcatc    3420
aaggataggc gctttaccag cgacaagttc tttttccacg tgcctatcac actgaactat    3480
caggccgcca attccccatc taagttcaac cagagggtga atgcctacct gaaggagcac    3540
cccgagacac ctatcatcgg catcgcccgg ggcgagagaa acctgatcta tatcacagtg    3600
atcgactcca ccggcaagat cctggagcag cggagcctga caccatcca gcagtttgat    3660 taccagaaga agctggacaa cagggagaag gagagggtgg cagcaaggca ggcctggtct    3720
gtggtgggca aatcaagga tctgaagcag ggctatctga gccaggtcat ccacgagatc    3780
gtggacctga tgatccacta ccaggccgtg gtggtgctgg agaacctgaa tttcggcttt    3840
aagagcaaga ggaccggcat cgccgagaag gccgtgtacc agcagttcga agatgctg     3900 atcgataagc tgaattgcct ggtgctgaag gactatccag cagagaaagt gggaggcgtg    3960
ctgaacccat accagctgac agaccagttc acctcctttg ccaagatggg cacccagtct    4020
ggcttcctgt tttacgtgcc tgccccatat acatctaaga tcgatcccct gaccggcttc    4080
gtggacccct tcgtgtggaa aaccatcaag aatcacgaga ccgcaagca cttcctggag    4140 ggcttcgact ttctgcacta cgacgtgaaa accggcgact tcatcctgca ctttaagatg    4200
aacagaaatc tgtccttcca gaggggcctg cccggcttta tgcctgcatg ggatatcgtg    4260
ttcgagaaga cgagacaca gtttgacgcc aagggcaccc ctttcatcgc cggcaagaga    4320
atcgtgccag tgatcgagaa tcacagattc accggcagat accgggacct gtatcctgcc    4380
aacgagctga tcgccctgct ggaggagaag ggcatcgtgt tcagggatgg ctccaacatc    4440
ctgccaaagc tgctggagaa tgacgattct cacgccatcg acacgatggt ggccctgatc    4500
cgcagcgtgc tgcagatgcg gaactccaat gccgccacag gcgaggacta tatcaacagc    4560
cccgtgcgcg atctgaatgg cgtgtgcttc gactcccggt tcagaaccc agagtggcca    4620 atggacgccg atgccaatgg cgcctaccac atcgccctga agggccagct gctgctgaat    4680
cacctgaagg agagcaagga tctgaagctg cagaacggca tctccaatca ggactggctg    4740
gcctacatcc aggagctgcg caacaaaagg ccggcggcca cgaaaaaggc cggccaggca    4800
aaaaagaaaa agggatcctc tggtggttct ggaggatctg gtggttctac taatctgtca    4860
gatattattg aaaaggagac cggtaagcaa ctggttatcc aggaatccat cctcatgctc    4920
ccagaggagg tggaagaagt cattgggaac aagccggaaa gcgatatact cgtgcacacc    4980
gcctacgacg agagcaccga cgagaatgtc atgcttctga ctagcgacgc ccctgaatac    5040
aagccttggg ctctggtcat acaggatagc aacggtgaga acaagattaa gatgctctct    5100
ggtggttctc ccaagaagaa gaggaaagtc taa                                 5133
```

<210> SEQ ID NO 442
<211> LENGTH: 5019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 442

```
atgggcagct cagagactgg cccagtggct gtggacccca cattgagacg gcggatcgag     60
ccccatgagt ttgaggtatt cttcgatccg agagagctcc gcaaggagac ctgcctgctt    120
tacgaaatta ttgggggggg ccggcactcc atttggcgac atacatcaca gaacactaac    180
aagcacgtcg aagtcaactt catcgagaag ttcacgacag aaagatattt ctgtccgaac    240
```

| | |
|---|---|
| acaaggtgca gcattacctg gtttctcagc tggagcccat gcggcgaatg tagtagggcc | 300 |
| atcactgaat tcctgtcaag gtatcccac gtcactctgt ttatttacat cgcaaggctg | 360 |
| taccaccacg ctgaccccg caatcgacaa ggcctgcggg atttgatctc ttcaggtgtg | 420 |
| actatccaaa ttatgactga gcaggagtca ggatactgct ggagaaactt tgtgaattat | 480 |
| agcccgagta atgaagccca ctggcctagg tatccccatc tgtgggtacg actgtacgtt | 540 |
| cttgaactgt actgcatcat actgggcctg cctccttgtc tcaacattct gagaaggaag | 600 |
| cagccacagc tgacattctt taccatcgct cttcagtctt gtcattacca gcgactgccc | 660 |
| ccacacattc tctgggccac cgggttgaaa tctggtggtt cttctggtgg ttctagcggc | 720 |
| agcgagactc ccgggaccctc agagtccgcc acacccgaaa gttccggagg gagtagcggc | 780 |
| gggtctacac agttcgaggg ctttaccaac ctgtatcagg tgagcaagac actgcggttt | 840 |
| gagctgatcc cacagggcaa gaccctgaag cacatccagg agcagggctt catcgaggag | 900 |
| gacaaggccc gcaatgatca ctacaaggag ctgaagccca tcatcgatcg gatctacaag | 960 |
| acctatgccg accagtgcct gcagctggtg cagctggatt gggagaacct gagcgccgcc | 1020 |
| atcgactcct atagaaagga gaaaaccgag gagacaagga cgccctgat cgaggagcag | 1080 |
| gccacatatc gcaatgccat ccacgactac ttcatcggcc ggacagacaa cctgaccgat | 1140 |
| gccatcaata gagacacgc cgagatctac aagggcctgt tcaaggccga gctgtttaat | 1200 |
| ggcaaggtgc tgaagcagct gggcaccgtg accacaaccg agcacgagaa cgccctgctg | 1260 |
| cggagcttcg acaagtttac aacctacttc tccggctttt atagaaacag gaagaacgtg | 1320 |
| ttcagcgccg aggatatcag cacagccatc ccacaccgca tcgtgcagga caacttcccc | 1380 |
| aagtttaagg agaattgtca catcttcaca cgcctgatca ccgccgtgcc cagcctgcgg | 1440 |
| gagcactttg agaacgtgaa gaaggccatc ggcatcttcg tgagcacctc catcgaggag | 1500 |
| gtgttttcct tccctttta taaccagctg ctgacacaga cccagatcga cctgtataac | 1560 |
| cagctgctgg aggaatctc tcgggaggca ggcaccgaga agatcaaggg cctgaacgag | 1620 |
| gtgctgaatc tggccatcca gaagaatgat gagacagccc acatcatcgc ctccctgcca | 1680 |
| cacagattca tcccctgtt taagcagatc ctgtccgata ggaacaccct gtctttcatc | 1740 |
| ctggaggagt ttaagagcga cgaggaagtg atccagtcct tctgcaagta caagacactg | 1800 |
| ctgagaaacg agaacgtgct ggagacagcc gaggccctgt taacgagct gaacagcatc | 1860 |
| gacctgacac acatcttcat cagccacaag aagctggaga caatcagcag cgccctgtgc | 1920 |
| gaccactggg atacactgag gaatgccctg tatgagcgga gaatctccga gctgacaggc | 1980 |
| aagatcacca gtctgccaa ggagaaggtg cagcgcagcc tgaagcacga ggatatcaac | 2040 |
| ctgcaggaga tcatctctgc cgcaggcaag gagctgagcg aggccttcaa gcagaaaacc | 2100 |
| agcgagatcc tgtcccacgc acacgccgcc ctggatcagc cactgcctac aaccctgaag | 2160 |
| aagcaggagg agaaggagat cctgaagtct cagctggaca gcctgctggg cctgtaccac | 2220 |
| ctgctggact ggtttgccgt ggatgagtcc aacgaggtgg accccgagtt ctctgcccgg | 2280 |
| ctgaccggca tcaagctgga gatggagcct tctctgagct ctacaacaa ggccagaaat | 2340 |
| tatgccacca agaagcccta ctccgtggag aagttcaagc tgaactttca gatgcctaca | 2400 |
| ctggccagag ctgggacgt gaatagagag aagaacaatg gcgccatcct gtttgtgaag | 2460 |
| aacggcctgt actatctggg catcatgcca aagcagaagg gcaggtataa ggccctgagc | 2520 |
| ttcgagccca cagagaaaac cagcgagggc tttgataaga tgtactatga ctacttccct | 2580 |

```
gatgccgcca agatgatccc aaagtgcagc acccagctga aggccgtgac agcccacttt    2640
cagacccaca caaccccat cctgctgtcc aacaatttca tcgagcctct ggagatcaca     2700
aaggagatct acgacctgaa caatcctgag aaggagccaa agaagtttca gacagcctac    2760
gccaagaaaa ccggcgacca gaagggctac agagaggccc tgtgcaagtg gatcgacttc    2820
acaagggatt ttctgtccaa gtataccaag acaacctcta tcgatctgtc tagcctgcgg    2880
ccatcctctc agtataagga cctgggcgag tactatgccg agctgaatcc cctgctgtac    2940
cacatcagct tccagagaat cgccgagaag gagatcatgg atgccgtgga cagggcaag    3000 ctgtacctgt tccagatcta taacaaggac tttgccaagg ccaccacggg caagcctaat    3060
ctgcacacac tgtattggac cggcctgttt tctccagaga acctggccaa gacaagcatc    3120
aagctgaatg ccaggccga gctgttctac cgccctaagt ccaggatgaa gaggatggca    3180
caccggctgg agagaagat gctgaacaag aagctgaagg atcagaaaac cccaatcccc    3240
gacaccctgt accaggagct gtacgactat gtgaatcaca gactgtccca cgacctgtct    3300
gatgaggcca gggccctgct gcccaacgtg atcaccaagg aggtgtctca cgagatcatc    3360
aaggataggc gctttaccag cgacaagttc tttttccacg tgcctatcac actgaactat    3420
caggccgcca attccccatc taagttcaac cagagggtga tgcctacct gaaggagcac    3480 cccgagacac ctatcatcgg catcgcccgg ggcgagagaa acctgatcta tcacagtg     3540 atcgactcca ccggcaagat cctggagcag cggagcctga acaccatcca gcagtttgat    3600
taccagaaga agctggacaa cagggagaag gagagggtgg cagcaaggca ggcctggtct    3660
gtggtgggca caatcaagga tctgaagcag ggctatctga gccaggtcat ccacgagatc    3720
gtggacctga tgatccacta ccaggccgtg gtggtgctgg agaacctgaa tttcggcttt    3780
aagagcaaga ggaccggcat cgccgagaag gccgtgtacc agcagttcga gaagatgctg    3840
atcgataagc tgaattgcct ggtgctgaag gactatccag cagagaaagt gggaggcgtg    3900
ctgaacccat accagctgac agaccagttc acctcctttg ccaagatggg cacccagtct    3960
ggcttcctgt tttacgtgcc tgccccatat acatctaaga tcgatcccct gaccggcttc    4020
gtggacccct tcgtgtggaa aaccatcaag aatcacgaga gccgcaagca cttcctggag    4080
ggcttcgact ttctgcacta cgacgtgaaa accggcgact tcatcctgca ctttaagatg    4140
aacagaaatc tgtccttcca gaggggcctg cccggcttta tgcctgcatg ggatatcgtg    4200
ttcgagaaga cgagacaca gtttgacgcc aagggcaccc ctttcatcgc cggcaagaga    4260
atcgtgccag tgatcgagaa tcacagattc accggcagat accgggacct gtatcctgcc    4320
aacgagctga tcgccctgct ggaggagaag ggcatcgtgt tcagggatgg ctccaacatc    4380
ctgccaaagc tgctggagaa tgacgattct cacgccatcg acacgatggt ggccctgatc    4440
cgcagcgtgc tgcagatgcg gaactccaat gccgccacag gcgaggacta tatcaacagc    4500
cccgtgcgcg atctgaatgg cgtgtgcttc gactcccggt tcagaaccc agagtggcca    4560 atggacgccg atgccaatgg cgcctaccac atcgccctga agggcagct gctgctgaat    4620 cacctgaagg agagcaagga tctgaagctg cagaacggca tctccaatca ggactggctg    4680
gcctacatcc aggagctgcg caactctggt ggttctggag atctggtgg ttctactaat    4740 ctgtcagata ttattgaaaa ggagaccggt aagcaactgg ttatccagga atccatcctc    4800
atgctcccag aggaggtgga agaagtcatt gggaacaagc cggaaagcga tatactcgtg    4860
cacaccgcct acgacgagag caccgacgag aatgtcatgc ttctgactag cgacgcccct    4920
gaatacaagc cttgggctct ggtcatacag gatagcaacg gtgagaacaa gattaagatg    4980
```
ctctctggtg gttctcccaa gaagaagagg aaagtctaa         5019

<210> SEQ ID NO 443
<211> LENGTH: 5421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 443

| | |
|---|---|
| atgagcaagc tggagaagtt tacaaactgc tactccctgt ctaagaccct gaggttcaag | 60 |
| gccatccctg tgggcaagac ccaggagaac atcgacaata agcggctgct ggtggaggac | 120 |
| gagaagagag ccgaggatta aagggcgtg aagaagctgc tggatcgcta ctatctgtct | 180 |
| tttatcaacg acgtgctgca cagcatcaag ctgaagaatc tgaacaatta catcagcctg | 240 |
| ttccggaaga aaaccagaac cgagaaggag aataaggagc tggagaacct ggagatcaat | 300 |
| ctgcggaagg agatcgccaa ggccttcaag ggcaacgagg gctacaagtc cctgtttaag | 360 |
| aaggatatca tcgagacaat cctgccagag ttcctggacg ataaggacga gatcgccctg | 420 |
| gtgaacagct tcaatggctt taccacagcc ttcaccggct tctttgataa cagagagaat | 480 |
| atgttttccg aggaggccaa gagcacatcc atcgccttca ggtgtatcaa cgagaatctg | 540 |
| acccgctaca tctctaatat ggacatcttc gagaaggtgg acgccatctt tgataagcac | 600 |
| gaggtgcagg atcaagga gaagatcctg aacagcgact atgatgtgga ggatttcttt | 660 |
| gagggcgagt tctttaactt tgtgctgaca caggagggca tcgacgtgta taacgccatc | 720 |
| atcggcggct tcgtgaccga gagcggcgag aagatcaagg gcctgaacga gtacatcaac | 780 |
| ctgtataatc agaaaaccaa gcagaagctg cctaagttta agccactgta taagcaggtg | 840 |
| ctgagcgatc gggagtctct gagcttctac ggcgagggct atacatccga tgaggaggtg | 900 |
| ctggaggtgt tagaaacac cctgaacaag aacagcgaga tcttcagctc catcaagaag | 960 |
| ctggagaagc tgttcaagaa ttttgacgag tactctagcg ccggcatctt tgtgaagaac | 1020 |
| ggccccgcca tcagcacaat ctccaaggat atcttcggcg agtggaacgt gatccgggac | 1080 |
| aagtggaatg ccgagtatga cgatatccac ctgaagaaga aggccgtggt gaccgagaag | 1140 |
| tacgaggaca tcggagaaaa gtccttcaag aagatcggcc cttttctct ggagcagctg | 1200 |
| caggagtacg ccgacgccga tctgtctgtg gtggagaagc tgaaggagat catcatccag | 1260 |
| aaggtggatg agatctacaa ggtgtatggc tcctctgaga gctgttcga cgccgatttt | 1320 |
| gtgctggaga agagcctgaa gaagaacgac gccgtggtgg ccatcatgaa ggacctgctg | 1380 |
| gattctgtga gagcttcga gaattacatc aaggccttct ttggcgaggg caaggagaca | 1440 |
| aacagggacg agtccttcta tggcgatttt gtgctggcct acgacatcct gctgaaggtg | 1500 |
| gaccacatct acgatgccat ccgcaattat gtgacccaga gccctactc taaggataag | 1560 |
| ttcaagctgt attttcagaa ccctcagttc atgggcggct gggacaagga taaggagaca | 1620 |
| gactatcggg ccaccatcct gagatacggc tccaagtact atctggccat catggataag | 1680 |
| aagtacgcca gtgcctgca gaagatcgac aaggacgatg tgaacggcaa ttacgagaag | 1740 |
| atcaactata gctgctgcc cggccctaat aagatgctgc caaggtgtt cttttctaag | 1800 |
| aagtggatgg cctactataa ccccagcgag gacatccaga gatctacaa gaatggcaca | 1860 |
| ttcaagaagg gcgatatgtt taacctgaat gactgtcaca gctgatcga cttctttaag | 1920 |
| gatagcatct cccggtatcc aaagtggtcc aatgcctacg atttcaactt ttctgagaca | 1980 |

```
gagaagtata aggacatcgc cggcttttac agagaggtgg aggagcaggg ctataaggtg    2040
agcttcgagt ctgccagcaa gaaggaggtg gataagctgg tggaggaggg caagctgtat    2100
atgttccaga tctataacaa ggacttttcc gataagtctc acggcacacc caatctgcac    2160
accatgtact tcaagctgct gtttgacgag aacaatcacg gacagatcag gctgagcgga    2220
ggagcagagc tgttcatgag gcgcgcctcc ctgaagaagg aggagctggt ggtgcaccca    2280
gccaactccc ctatcgccaa caagaatcca gataatccca agaaaaccac aaccctgtcc    2340
tacgacgtgt ataaggataa gaggtttcct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtgg tggacggcaa gggcaacatc gtggagcagt attccctgaa cgagatcatc    2580
aacaacttca acggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta agtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga gctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagcctga ctgcagat gcggaacagc    3420 atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct taacaagga gtggctggag    3660 tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg catacccata tgatgtcccc gactatgccg aagcgaggc cagcggttcc    3840 ggacgggctg acgcattgga cgattttgat ctggatatgc tgggaagtga cgccctcgat    3900
gattttgacc ttgacatgct tggttcggat gcccttgatg actttgacct cgacatgctc    3960
ggcagtgacg cccttgatga tttcgacctg gacatgctga ttaactctag aagttccgga    4020
tctccgaaaa agaaacgcaa agttggtagc cagtacctgc ccgacaccga cgaccggcac    4080
cggatcgagg aaaagcggaa gcggacctac gagacattca agagcatcat gaagaagtcc    4140
cccttcagcg gccccaccga ccctagacct ccacctagaa gaatcgccgt gcccagcaga    4200
tccagcgcca gcgtgccaaa acctgccccc cagccttacc ccttcaccag cagcctgagc    4260
accatcaact acgacgagtt ccctaccatg gtgttcccca gcggccagat ctctcaggcc    4320
```

```
tctgctctgg ctccagcccc tcctcaggtg ctgcctcagg ctcctgctcc tgcaccagct    4380
ccagccatgt gtctgcact ggctcaggca ccagcacccg tgcctgtgct ggctcctgga     4440
cctccacagg ctgtggctcc accagcccct aaacctacac aggccggcga gggcacactg    4500
tctgaagctc tgctgcagct gcagttcgac gacgaggatc tgggagccct gctgggaaac    4560
agcaccgatc ctgccgtgtt caccgacctg gccagcgtgg acaacagcga gttccagcag    4620
ctgctgaacc agggcatccc tgtggcccct cacaccaccg agcccatgct gatgaatac     4680
cccgaggcca tcacccggct cgtgacaggc gctcagaggc tcctgatcc agctcctgcc     4740
cctctgggag caccaggcct gcctaatgga ctgctgtctg cgacgagga cttcagctct    4800
atcgccgata tggatttctc agccttgctg ggctctggca gcggcagccg ggattccagg    4860
gaagggatgt ttttgccgaa gcctgaggcc ggctccgcta ttagtgacgt gtttgagggc    4920
cgcgaggtgt gccagccaaa acgaatccgg ccatttcatc ctccaggaag tccatgggcc    4980
aaccgcccac tccccgccag cctcgcacca acaccaaccg gtccagtaca tgagccagtc    5040
gggtcactga ccccggcacc agtccctcag ccactggatc cagcgcccgc agtgactccc    5100
gaggccagtc acctgttgga ggatcccgat gaagagacga gccaggctgt caaagcccctt    5160
cgggagatgg ccgatactgt gattccccag aaggaagagg ctgcaatctg tggccaaatg    5220
gacctttccc atccgccccc aaggggccat ctggatgagc tgacaaccac acttgagtcc    5280
atgaccgagg atctgaacct ggactcaccc ctgaccccgg aattgaacga gattctggat    5340
accttcctga cgacgagtg cctcttgcat gccatgcata tcagcacagg actgtccatc    5400
ttcgacacat ctctgtttta a                                              5421
```

<210> SEQ ID NO 444
<211> LENGTH: 1806
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 444

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160
```

```
Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
```

-continued

```
                580                 585                 590
Leu Pro Lys Val Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
                660                 665                 670
Val Glu Glu Gln Gly Tyr Lys Val Ser Phe Glu Ser Ala Ser Lys Lys
                675                 680                 685
Glu Val Asp Lys Leu Val Glu Glu Gly Lys Leu Tyr Met Phe Gln Ile
            690                 695                 700
Tyr Asn Lys Asp Phe Ser Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
                740                 745                 750
Lys Glu Glu Leu Val Val His Pro Ala Asn Ser Pro Ile Ala Asn Lys
            755                 760                 765
Asn Pro Asp Asn Pro Lys Lys Thr Thr Thr Leu Ser Tyr Asp Val Tyr
770                 775                 780
Lys Asp Lys Arg Phe Ser Glu Asp Gln Tyr Glu Leu His Ile Pro Ile
785                 790                 795                 800
Ala Ile Asn Lys Cys Pro Lys Asn Ile Phe Lys Ile Asn Thr Glu Val
                805                 810                 815
Arg Val Leu Leu Lys His Asp Asp Asn Pro Tyr Val Ile Gly Ile Ala
                820                 825                 830
Arg Gly Glu Arg Asn Leu Leu Tyr Ile Val Val Val Asp Gly Lys Gly
            835                 840                 845
Asn Ile Val Glu Gln Tyr Ser Leu Asn Glu Ile Ile Asn Asn Phe Asn
850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
            915                 920                 925
Ser Gly Phe Lys Asn Ser Arg Val Lys Val Glu Lys Gln Val Tyr Gln
            930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Gln Asn Gly Phe
                980                 985                 990
Ile Phe Tyr Ile Pro Ala Trp Leu Thr Ser Lys Ile Asp Pro Ser Thr
            995                 1000                1005
```

```
Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Lys Arg Pro Ala Ala
    1220                1225                1230

Thr Lys Lys Ala Gly Gln Ala Lys Lys Lys Lys Gly Ser Tyr Pro
    1235                1240                1245

Tyr Asp Val Pro Asp Tyr Ala Tyr Pro Tyr Asp Val Pro Asp Tyr
    1250                1255                1260

Ala Tyr Pro Tyr Asp Val Pro Asp Tyr Ala Gly Ser Glu Ala Ser
    1265                1270                1275

Gly Ser Gly Arg Ala Asp Ala Leu Asp Asp Phe Asp Leu Asp Met
    1280                1285                1290

Leu Gly Ser Asp Ala Leu Asp Asp Phe Asp Leu Asp Met Leu Gly
    1295                1300                1305

Ser Asp Ala Leu Asp Asp Phe Asp Leu Asp Met Leu Gly Ser Asp
    1310                1315                1320

Ala Leu Asp Asp Phe Asp Leu Asp Met Leu Ile Asn Ser Arg Ser
    1325                1330                1335

Ser Gly Ser Pro Lys Lys Lys Arg Lys Val Gly Ser Gln Tyr Leu
    1340                1345                1350

Pro Asp Thr Asp Asp Arg His Arg Ile Glu Glu Lys Arg Lys Arg
    1355                1360                1365

Thr Tyr Glu Thr Phe Lys Ser Ile Met Lys Lys Ser Pro Phe Ser
    1370                1375                1380

Gly Pro Thr Asp Pro Arg Pro Pro Pro Arg Arg Ile Ala Val Pro
    1385                1390                1395
```

```
Ser Arg Ser Ser Ala Ser Val Pro Lys Pro Ala Pro Gln Pro Tyr
    1400            1405                1410

Pro Phe Thr Ser Ser Leu Ser Thr Ile Asn Tyr Asp Glu Phe Pro
    1415            1420                1425

Thr Met Val Phe Pro Ser Gly Gln Ile Ser Gln Ala Ser Ala Leu
    1430            1435                1440

Ala Pro Ala Pro Pro Gln Val Leu Pro Gln Ala Pro Ala Pro Ala
    1445            1450                1455

Pro Ala Pro Ala Met Val Ser Ala Leu Ala Gln Ala Pro Ala Pro
    1460            1465                1470

Val Pro Val Leu Ala Pro Gly Pro Pro Gln Ala Val Ala Pro Pro
    1475            1480                1485

Ala Pro Lys Pro Thr Gln Ala Gly Glu Gly Thr Leu Ser Glu Ala
    1490            1495                1500

Leu Leu Gln Leu Gln Phe Asp Asp Glu Asp Leu Gly Ala Leu Leu
    1505            1510                1515

Gly Asn Ser Thr Asp Pro Ala Val Phe Thr Asp Leu Ala Ser Val
    1520            1525                1530

Asp Asn Ser Glu Phe Gln Gln Leu Leu Asn Gln Gly Ile Pro Val
    1535            1540                1545

Ala Pro His Thr Thr Glu Pro Met Leu Met Glu Tyr Pro Glu Ala
    1550            1555                1560

Ile Thr Arg Leu Val Thr Gly Ala Gln Arg Pro Pro Asp Pro Ala
    1565            1570                1575

Pro Ala Pro Leu Gly Ala Pro Gly Leu Pro Asn Gly Leu Leu Ser
    1580            1585                1590

Gly Asp Glu Asp Phe Ser Ser Ile Ala Asp Met Asp Phe Ser Ala
    1595            1600                1605

Leu Leu Gly Ser Gly Ser Gly Ser Arg Asp Ser Arg Glu Gly Met
    1610            1615                1620

Phe Leu Pro Lys Pro Glu Ala Gly Ser Ala Ile Ser Asp Val Phe
    1625            1630                1635

Glu Gly Arg Glu Val Cys Gln Pro Lys Arg Ile Arg Pro Phe His
    1640            1645                1650

Pro Pro Gly Ser Pro Trp Ala Asn Arg Pro Leu Pro Ala Ser Leu
    1655            1660                1665

Ala Pro Thr Pro Thr Gly Pro Val His Glu Pro Val Gly Ser Leu
    1670            1675                1680

Thr Pro Ala Pro Val Pro Gln Pro Leu Asp Pro Ala Pro Ala Val
    1685            1690                1695

Thr Pro Glu Ala Ser His Leu Leu Glu Asp Pro Asp Glu Glu Thr
    1700            1705                1710

Ser Gln Ala Val Lys Ala Leu Arg Glu Met Ala Asp Thr Val Ile
    1715            1720                1725

Pro Gln Lys Glu Glu Ala Ala Ile Cys Gly Gln Met Asp Leu Ser
    1730            1735                1740

His Pro Pro Pro Arg Gly His Leu Asp Glu Leu Thr Thr Thr Leu
    1745            1750                1755

Glu Ser Met Thr Glu Asp Leu Asn Leu Asp Ser Pro Leu Thr Pro
    1760            1765                1770

Glu Leu Asn Glu Ile Leu Asp Thr Phe Leu Asn Asp Glu Cys Leu
    1775            1780                1785

Leu His Ala Met His Ile Ser Thr Gly Leu Ser Ile Phe Asp Thr
```

```
                1790              1795              1800
Ser Leu Phe
    1805

<210> SEQ ID NO 445
<211> LENGTH: 5130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 445
atgggcccaa agaaaaagag gaaagtcggc agtggaccta aaagaaacg aaaggttggg       60 tcaggtagct cagagactgg cccagtggct gtggacccca cattgagacg gcggatcgag      120
ccccatgagt ttgaggtatt cttcgatccg agagagctcc gcaaggagac ctgcctgctt      180
tacgaaatta ttgggggg ccggcactcc atttggcgac atacatcaca gaacactaac        240
aagcacgtcg aagtcaactt catcgagaag ttcacgacaa aaagatattt ctgtccgaac      300
acaaggtgca gcattacctg gtttctcagc tggagcccat gcggcgaatg tagtagggcc      360
atcactgaat tcctgtcaag gtatccccac gtcactctgt ttatttacat cgcaaggctg      420
taccaccacg ctgaccccg caatcgacaa ggcctgcggg atttgatctc ttcaggtgtg       480
actatccaaa ttatgactga gcaggagtca ggatactgct ggagaaactt tgtgaattat      540
agcccgagta atgaagccca ctggcctagg tatccccatc tgtgggtacg actgtacgtt      600
cttgaactgt actgcatcat actgggcctg cctccttgtc tcaacattct gagaaggaag      660
cagccacagc tgacattctt taccatcgct cttcagtctt gtcattacca gcgactgccc      720
ccacacattc tctgggccac cgggttgaaa tctggtggtt cttctggtgg ttctagcggc      780
agcgagactc ccgggacctc agagtccgcc acacccgaaa gttccggagg gagtagcggc      840
gggtctacac agttcgaggg ctttaccaac ctgtatcagg tgagcaagac actgcggttt      900
gagctgatcc cacagggcaa gaccctgaag cacatccagg agcagggctt catcgaggag      960
gacaaggccc gcaatgatca ctacaaggag ctgaagccca tcatcgatcg gatctacaag     1020
acctatgccg accagtgcct gcagctggtg cagctggatt gggagaacct gagcgccgcc     1080
atcgactcct atagaaagga gaaaaccgag gagacaagga acgccctgat cgaggagcag     1140
gccacatatc gcaatgccat ccacgactac ttcatcggcc ggacagacaa cctgaccgat     1200
gccatcaata gagacacgc cgagatctac aagggcctgt tcaaggccga gctgtttaat      1260
ggcaaggtgc tgaagcagct gggcaccgtg accacaaccg agcacgagaa cgccctgctg     1320
cggagcttcg acaagtttac aacctacttc tccggctttt atgagaacag gaagaacgtg     1380
ttcagcgccg aggatatcag cacagccatc ccacaccgca tcgtgcagga caacttcccc     1440
aagtttaagg agaattgtca catcttcaca cgcctgatca cgccgtgcc cagcctgcgg     1500 gagcactttg agaacgtgaa gaaggccatc ggcatcttcg tgagccactc catcgaggag     1560
gtgttttcct tcccttttta taccagctg ctgacacaga cccagatcga cctgtataac      1620
cagctgctgg gaggaatctc tcgggaggca ggcaccgaga agatcaaggg cctgaacgag     1680
gtgctgaatc tggccatcca aagaatgat gagacagccc acatcatcgc ctccctgcca     1740
cacagattca tccccctgtt taagcagatc ctgtccgata ggaacacct gtctttcatc      1800 ctggaggagt ttaagagcga cgaggaagtg atccagtcct tctgcaagta caagacactg     1860
ctgagaaacg agaacgtgct ggagacagcc gaggccctgt taacgagct gaacagcatc      1920
```

```
gacctgacac acatcttcat cagccacaag aagctggaga caatcagcag cgccctgtgc    1980
gaccactggg atacactgag gaatgccctg tatgagcgga gaatctccga gctgacaggc    2040
aagatcacca agtctgccaa ggagaaggtg cagcgcagcc tgaagcacga ggatatcaac    2100
ctgcaggaga tcatctctgc cgcaggcaag gagctgagcg aggccttcaa gcagaaaacc    2160
agcgagatcc tgtcccacgc acacgccgcc ctggatcagc cactgcctac aaccctgaag    2220
aagcaggagg agaaggagat cctgaagtct cagctgaca gcctgctggg cctgtaccac    2280
ctgctggact ggtttgccgt ggatgagtcc aacgaggtgg accccgagtt ctctgcccgg    2340
ctgaccggca tcaagctgga gatggagcct tctctgagct tctacaacaa ggccagaaat    2400
tatgccacca agaagcccta ctccgtggag aagttcaagc tgaactttca gatgcctaca    2460
ctggcctctg gctgggacgt gaataaggag aagaacaatg cgccatcct gtttgtgaag    2520
aacggcctgt actatctggg catcatgcca aagcagaagg gcaggtataa ggccctgagc    2580
ttcgagccca cagagaaaac cagcgagggc tttgataaga tgtactatga ctacttccct    2640
gatgccgcca agatgatccc aaaagtgcagc acccagctga aggccgtgac agcccacttt    2700
cagacccaca caaccccccat cctgctgtcc aacaatttca tcgagcctct ggagatcaca    2760
aaggagatct acgacctgaa caatcctgag aaggagccaa agaagtttca gacagcctac    2820
gccaagaaaa ccggcgacca gaagggctac agagaggccc tgtgcaagtg gatcgacttc    2880
acaagggatt ttctgtccaa gtataccaag acaacctcta tcgatctgtc tagcctgcgg    2940
ccatcctctc agtataagga cctgggcgag tactatgccg agctgaatcc cctgctgtac    3000
cacatcagct tccagagaat cgccgagaag gagatcatgg atgccgtgga cacaggcaag    3060
ctgtacctgt tccagatcta taacaaggac tttgccaagg gccaccacgg caagcctaat    3120
ctgcacacac tgtattggac cggcctgttt tctccagaga acctggccaa gacaagcatc    3180
aagctgaatg gccaggccga gctgttctac cgccctaagt ccaggatgaa gaggatggca    3240
caccggctgg gagagaagat gctgaacaag aagctgaagg atcagaaaac cccaatcccc    3300
gacaccctgt accaggagct gtacgactat gtgaatcaca gactgtccca cgacctgtct    3360
gatgaggcca gggccctgct gcccaacgtg atcaccaagg aggtgtctca cgagatcatc    3420
aaggataggc gctttaccag cgacaagttc ttttttccacg tgcctatcac actgaactat    3480
caggccgcca ttcccccatc taagttcaac cagagggtga atgcctacct gaaggagcac    3540
cccgagacac ctatcatcgg catcgcccgg ggcgagagaa acctgatcta tatcacagtg    3600
atcgactcca ccgccaagat cctggagcag cggagcctga acaccatcca gcagtttgat    3660
taccagaaga gctggacaa cagggagaag gagagggtgg cagcaaggca ggcctggtct    3720
gtggtgggca aatcaaagga tctgaagcag ggctatctga ccaggtcat ccacgagatc    3780
gtggacctga tgatccacta ccaggccgtg gtggtgctgg agaacctgaa tttcggcttt    3840
aagagcaaga ggaccggcat cgccgagaag gccgtgtacc agcagttcga gaagatgctg    3900
atcgataagc tgaattgcct ggtgctgaag gactatccag cagagaaagt gggaggcgtg    3960
ctgaacccat accagctgac agaccagttc acctcctttg ccaagatggg caccccagtct   4020
ggcttcctgt tttacgtgcc tgccccatat acatctaaga tcgatcccct gaccggcttc    4080
gtggacccct tcgtgtggaa aaccatcaag aatcacgaga gccgcaagca cttcctggag    4140
ggcttcgact ttctgcacta cgacgtgaaa accggcgact tcatcctgca ctttaagatg    4200
aacagaaatc tgtccttcca gagggccctg cccggcttta tgcctgcatg ggatatcgtg    4260
```

-continued

```
ttcgagaaga acgagacaca gtttgacgcc aagggcaccc ctttcatcgc cggcaagaga    4320
atcgtgccag tgatcgagaa tcacagattc accggcagat accgggacct gtatcctgcc    4380
aacgagctga tcgccctgct ggaggagaag ggcatcgtgt tcagggatgg ctccaacatc    4440
ctgccaaagc tgctggagaa tgacgattct cacgccatcg acacgatggt ggccctgatc    4500
cgcagcgtgc tgcagatgcg gaactccaat gccgccacag gcgaggacta tatcaacagc    4560
cccgtgcgcg atctgaatgg cgtgtgcttc gactcccggt ttcagaaccc agagtggcca    4620
atggacgccg atgccaatgg cgcctaccac atcgccctga agggccagct gctgctgaat    4680
cacctgaagg agagcaagga tctgaagctg cagaacggca tctccaatca ggactggctg    4740
gcctacatcc aggagctgcg caacaaaagg ccggcggcca cgaaaaaggc cggccaggca    4800
aaaaagaaaa agggatcctc tggtggttct ggaggatctg gtggttctac taatctgtca    4860
gatattattg aaaaggagac cggtaagcaa ctggttatcc aggaatccat cctcatgctc    4920
ccagaggagt ggaagaagt cattgggaac aagccggaaa gcgatatact cgtgcacacc    4980
gcctacgacg agagcaccga cgagaatgtc atgcttctga ctagcgacgc ccctgaatac    5040
aagccttggg ctctggtcat acaggatagc aacggtgaga caagattaa gatgctctct    5100 ggtggttctc ccaagaagaa gaggaaagtc                                      5130
```

<210> SEQ ID NO 446
<211> LENGTH: 1710
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 446

```
Met Gly Pro Lys Lys Arg Lys Val Gly Ser Gly Pro Lys Lys Lys
1               5                   10                  15

Arg Lys Val Gly Ser Gly Ser Ser Glu Thr Gly Pro Val Ala Val Asp
            20                  25                  30

Pro Thr Leu Arg Arg Arg Ile Glu Pro His Glu Phe Glu Val Phe Phe
        35                  40                  45

Asp Pro Arg Glu Leu Arg Lys Glu Thr Cys Leu Leu Tyr Glu Ile Asn
    50                  55                  60

Trp Gly Gly Arg His Ser Ile Trp Arg His Thr Ser Gln Asn Thr Asn
65                  70                  75                  80

Lys His Val Glu Val Asn Phe Ile Glu Lys Phe Thr Thr Glu Arg Tyr
                85                  90                  95

Phe Cys Pro Asn Thr Arg Cys Ser Ile Thr Trp Phe Leu Ser Trp Ser
            100                 105                 110

Pro Cys Gly Glu Cys Ser Arg Ala Ile Thr Glu Phe Leu Ser Arg Tyr
        115                 120                 125

Pro His Val Thr Leu Phe Ile Tyr Ile Ala Arg Leu Tyr His His Ala
    130                 135                 140

Asp Pro Arg Asn Arg Gln Gly Leu Arg Asp Leu Ile Ser Ser Gly Val
145                 150                 155                 160

Thr Ile Gln Ile Met Thr Glu Gln Glu Ser Gly Tyr Cys Trp Arg Asn
                165                 170                 175

Phe Val Asn Tyr Ser Pro Ser Asn Glu Ala His Trp Pro Arg Tyr Pro
            180                 185                 190

His Leu Trp Val Arg Leu Tyr Val Leu Glu Leu Tyr Cys Ile Ile Leu
        195                 200                 205
```

```
Gly Leu Pro Pro Cys Leu Asn Ile Leu Arg Arg Lys Gln Pro Gln Leu
    210                 215                 220

Thr Phe Phe Thr Ile Ala Leu Gln Ser Cys His Tyr Gln Arg Leu Pro
225                 230                 235                 240

Pro His Ile Leu Trp Ala Thr Gly Leu Lys Ser Gly Gly Ser Ser Gly
                245                 250                 255

Gly Ser Ser Gly Ser Glu Thr Pro Gly Thr Ser Glu Ser Ala Thr Pro
        260                 265                 270

Glu Ser Ser Gly Gly Ser Ser Gly Gly Ser Thr Gln Phe Glu Gly Phe
    275                 280                 285

Thr Asn Leu Tyr Gln Val Ser Lys Thr Leu Arg Phe Glu Leu Ile Pro
290                 295                 300

Gln Gly Lys Thr Leu Lys His Ile Gln Glu Gln Gly Phe Ile Glu Glu
305                 310                 315                 320

Asp Lys Ala Arg Asn Asp His Tyr Lys Glu Leu Lys Pro Ile Ile Asp
                325                 330                 335

Arg Ile Tyr Lys Thr Tyr Ala Asp Gln Cys Leu Gln Leu Val Gln Leu
                340                 345                 350

Asp Trp Glu Asn Leu Ser Ala Ala Ile Asp Ser Tyr Arg Lys Glu Lys
            355                 360                 365

Thr Glu Glu Thr Arg Asn Ala Leu Ile Glu Glu Gln Ala Thr Tyr Arg
370                 375                 380

Asn Ala Ile His Asp Tyr Phe Ile Gly Arg Thr Asp Asn Leu Thr Asp
385                 390                 395                 400

Ala Ile Asn Lys Arg His Ala Glu Ile Tyr Lys Gly Leu Phe Lys Ala
                405                 410                 415

Glu Leu Phe Asn Gly Lys Val Leu Lys Gln Leu Gly Thr Val Thr Thr
                420                 425                 430

Thr Glu His Glu Asn Ala Leu Leu Arg Ser Phe Asp Lys Phe Thr Thr
            435                 440                 445

Tyr Phe Ser Gly Phe Tyr Glu Asn Arg Lys Asn Val Phe Ser Ala Glu
        450                 455                 460

Asp Ile Ser Thr Ala Ile Pro His Arg Ile Val Gln Asp Asn Phe Pro
465                 470                 475                 480

Lys Phe Lys Glu Asn Cys His Ile Phe Thr Arg Leu Ile Thr Ala Val
                485                 490                 495

Pro Ser Leu Arg Glu His Phe Glu Asn Val Lys Lys Ala Ile Gly Ile
                500                 505                 510

Phe Val Ser Thr Ser Ile Glu Glu Val Phe Ser Phe Pro Phe Tyr Asn
            515                 520                 525

Gln Leu Leu Thr Gln Thr Gln Ile Asp Leu Tyr Asn Gln Leu Leu Gly
        530                 535                 540

Gly Ile Ser Arg Glu Ala Gly Thr Glu Lys Ile Lys Gly Leu Asn Glu
545                 550                 555                 560

Val Leu Asn Leu Ala Ile Gln Lys Asn Asp Glu Thr Ala His Ile Ile
                565                 570                 575

Ala Ser Leu Pro His Arg Phe Ile Pro Leu Phe Lys Gln Ile Leu Ser
                580                 585                 590

Asp Arg Asn Thr Leu Ser Phe Ile Leu Glu Glu Phe Lys Ser Asp Glu
            595                 600                 605

Glu Val Ile Gln Ser Phe Cys Lys Tyr Lys Thr Leu Leu Arg Asn Glu
            610                 615                 620
```

```
Asn Val Leu Glu Thr Ala Glu Ala Leu Phe Asn Glu Leu Asn Ser Ile
625                 630                 635                 640

Asp Leu Thr His Ile Phe Ile Ser His Lys Lys Leu Glu Thr Ile Ser
            645                 650                 655

Ser Ala Leu Cys Asp His Trp Asp Thr Leu Arg Asn Ala Leu Tyr Glu
            660                 665                 670

Arg Arg Ile Ser Glu Leu Thr Gly Lys Ile Thr Lys Ser Ala Lys Glu
            675                 680                 685

Lys Val Gln Arg Ser Leu Lys His Glu Asp Ile Asn Leu Gln Glu Ile
    690                 695                 700

Ile Ser Ala Ala Gly Lys Glu Leu Ser Glu Ala Phe Lys Gln Lys Thr
705                 710                 715                 720

Ser Glu Ile Leu Ser His Ala His Ala Ala Leu Asp Gln Pro Leu Pro
                725                 730                 735

Thr Thr Leu Lys Lys Gln Glu Glu Lys Glu Ile Leu Lys Ser Gln Leu
            740                 745                 750

Asp Ser Leu Leu Gly Leu Tyr His Leu Leu Asp Trp Phe Ala Val Asp
            755                 760                 765

Glu Ser Asn Glu Val Asp Pro Glu Phe Ser Ala Arg Leu Thr Gly Ile
770                 775                 780

Lys Leu Glu Met Glu Pro Ser Leu Ser Phe Tyr Asn Lys Ala Arg Asn
785                 790                 795                 800

Tyr Ala Thr Lys Lys Pro Tyr Ser Val Glu Lys Phe Lys Leu Asn Phe
                805                 810                 815

Gln Met Pro Thr Leu Ala Ser Gly Trp Asp Val Asn Lys Glu Lys Asn
                820                 825                 830

Asn Gly Ala Ile Leu Phe Val Lys Asn Gly Leu Tyr Tyr Leu Gly Ile
            835                 840                 845

Met Pro Lys Gln Lys Gly Arg Tyr Lys Ala Leu Ser Phe Glu Pro Thr
850                 855                 860

Glu Lys Thr Ser Glu Gly Phe Asp Lys Met Tyr Tyr Asp Tyr Phe Pro
865                 870                 875                 880

Asp Ala Ala Lys Met Ile Pro Lys Cys Ser Thr Gln Leu Lys Ala Val
                885                 890                 895

Thr Ala His Phe Gln Thr His Thr Thr Pro Ile Leu Leu Ser Asn Asn
                900                 905                 910

Phe Ile Glu Pro Leu Glu Ile Thr Lys Glu Ile Tyr Asp Leu Asn Asn
            915                 920                 925

Pro Glu Lys Glu Pro Lys Lys Phe Gln Thr Ala Tyr Ala Lys Lys Thr
            930                 935                 940

Gly Asp Gln Lys Gly Tyr Arg Glu Ala Leu Cys Lys Trp Ile Asp Phe
945                 950                 955                 960

Thr Arg Asp Phe Leu Ser Lys Tyr Thr Lys Thr Thr Ser Ile Asp Leu
            965                 970                 975

Ser Ser Leu Arg Pro Ser Ser Gln Tyr Lys Asp Leu Gly Glu Tyr Tyr
            980                 985                 990

Ala Glu Leu Asn Pro Leu Leu Tyr His Ile Ser Phe Gln Arg Ile Ala
            995                 1000                1005

Glu Lys Glu Ile Met Asp Ala Val Glu Thr Gly Lys Leu Tyr Leu
    1010                1015                1020

Phe Gln Ile Tyr Asn Lys Asp Phe Ala Lys Gly His His Gly Lys
    1025                1030                1035

Pro Asn Leu His Thr Leu Tyr Trp Thr Gly Leu Phe Ser Pro Glu
```

-continued

```
                1040                1045                1050
Asn Leu Ala Lys Thr Ser Ile Lys Leu Asn Gly Gln Ala Glu Leu
    1055                1060                1065
Phe Tyr Arg Pro Lys Ser Arg Met Lys Arg Met Ala His Arg Leu
    1070                1075                1080
Gly Glu Lys Met Leu Asn Lys Lys Leu Lys Asp Gln Lys Thr Pro
    1085                1090                1095
Ile Pro Asp Thr Leu Tyr Gln Glu Leu Tyr Asp Tyr Val Asn His
    1100                1105                1110
Arg Leu Ser His Asp Leu Ser Asp Glu Ala Arg Ala Leu Leu Pro
    1115                1120                1125
Asn Val Ile Thr Lys Glu Val Ser His Glu Ile Ile Lys Asp Arg
    1130                1135                1140
Arg Phe Thr Ser Asp Lys Phe Phe Phe His Val Pro Ile Thr Leu
    1145                1150                1155
Asn Tyr Gln Ala Ala Asn Ser Pro Ser Lys Phe Asn Gln Arg Val
    1160                1165                1170
Asn Ala Tyr Leu Lys Glu His Pro Glu Thr Pro Ile Ile Gly Ile
    1175                1180                1185
Ala Arg Gly Glu Arg Asn Leu Ile Tyr Ile Thr Val Ile Asp Ser
    1190                1195                1200
Thr Gly Lys Ile Leu Glu Gln Arg Ser Leu Asn Thr Ile Gln Gln
    1205                1210                1215
Phe Asp Tyr Gln Lys Lys Leu Asp Asn Arg Glu Lys Glu Arg Val
    1220                1225                1230
Ala Ala Arg Gln Ala Trp Ser Val Val Gly Thr Ile Lys Asp Leu
    1235                1240                1245
Lys Gln Gly Tyr Leu Ser Gln Val Ile His Glu Ile Val Asp Leu
    1250                1255                1260
Met Ile His Tyr Gln Ala Val Val Val Leu Glu Asn Leu Asn Phe
    1265                1270                1275
Gly Phe Lys Ser Lys Arg Thr Gly Ile Ala Glu Lys Ala Val Tyr
    1280                1285                1290
Gln Gln Phe Glu Lys Met Leu Ile Asp Lys Leu Asn Cys Leu Val
    1295                1300                1305
Leu Lys Asp Tyr Pro Ala Glu Lys Val Gly Gly Val Leu Asn Pro
    1310                1315                1320
Tyr Gln Leu Thr Asp Gln Phe Thr Ser Phe Ala Lys Met Gly Thr
    1325                1330                1335
Gln Ser Gly Phe Leu Phe Tyr Val Pro Ala Pro Tyr Thr Ser Lys
    1340                1345                1350
Ile Asp Pro Leu Thr Gly Phe Val Asp Pro Phe Val Trp Lys Thr
    1355                1360                1365
Ile Lys Asn His Glu Ser Arg Lys His Phe Leu Glu Gly Phe Asp
    1370                1375                1380
Phe Leu His Tyr Asp Val Lys Thr Gly Asp Phe Ile Leu His Phe
    1385                1390                1395
Lys Met Asn Arg Asn Leu Ser Phe Gln Arg Gly Leu Pro Gly Phe
    1400                1405                1410
Met Pro Ala Trp Asp Ile Val Phe Glu Lys Asn Glu Thr Gln Phe
    1415                1420                1425
Asp Ala Lys Gly Thr Pro Phe Ile Ala Gly Lys Arg Ile Val Pro
    1430                1435                1440
```

-continued

| | | | | | | | | | | |
|---|---|---|---|---|---|---|---|---|---|---|
| Val | Ile | Glu | Asn | His | Arg | Phe | Thr | Gly | Arg | Tyr | Arg | Asp | Leu | Tyr |
| | 1445 | | | | 1450 | | | | 1455 | |

Val Ile Glu Asn His Arg Phe Thr Gly Arg Tyr Arg Asp Leu Tyr
   1445               1450              1455

Pro Ala Asn Glu Leu Ile Ala Leu Leu Glu Glu Lys Gly Ile Val
   1460               1465              1470

Phe Arg Asp Gly Ser Asn Ile Leu Pro Lys Leu Leu Glu Asn Asp
   1475               1480              1485

Asp Ser His Ala Ile Asp Thr Met Val Ala Leu Ile Arg Ser Val
   1490               1495              1500

Leu Gln Met Arg Asn Ser Asn Ala Ala Thr Gly Glu Asp Tyr Ile
   1505               1510              1515

Asn Ser Pro Val Arg Asp Leu Asn Gly Val Cys Phe Asp Ser Arg
   1520               1525              1530

Phe Gln Asn Pro Glu Trp Pro Met Asp Ala Asp Ala Asn Gly Ala
   1535               1540              1545

Tyr His Ile Ala Leu Lys Gly Gln Leu Leu Asn His Leu Lys
   1550               1555              1560

Glu Ser Lys Asp Leu Lys Leu Gln Asn Gly Ile Ser Asn Gln Asp
   1565               1570              1575

Trp Leu Ala Tyr Ile Gln Glu Leu Arg Asn Lys Arg Pro Ala Ala
   1580               1585              1590

Thr Lys Lys Ala Gly Gln Ala Lys Lys Lys Lys Gly Ser Ser Gly
   1595               1600              1605

Gly Ser Gly Gly Ser Gly Gly Ser Thr Asn Leu Ser Asp Ile Ile
   1610               1615              1620

Glu Lys Glu Thr Gly Lys Gln Leu Val Ile Gln Glu Ser Ile Leu
   1625               1630              1635

Met Leu Pro Glu Glu Val Glu Glu Val Ile Gly Asn Lys Pro Glu
   1640               1645              1650

Ser Asp Ile Leu Val His Thr Ala Tyr Asp Glu Ser Thr Asp Glu
   1655               1660              1665

Asn Val Met Leu Leu Thr Ser Asp Ala Pro Glu Tyr Lys Pro Trp
   1670               1675              1680

Ala Leu Val Ile Gln Asp Ser Asn Gly Glu Asn Lys Ile Lys Met
   1685               1690              1695

Leu Ser Gly Gly Ser Pro Lys Lys Lys Arg Lys Val
   1700               1705              1710

<210> SEQ ID NO 447
<211> LENGTH: 5130
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 447

| | |
|---|---|
| atgggcccaa agaaaaagag gaaagtcggc agtggaccta aaaagaaacg aaaggttggg | 60 |
| tcaggtagct cagagactgg cccagtggct gtggacccca cattgagacg gcggatcgag | 120 |
| ccccatgagt ttgaggtatt cttcgatccg agagagctcc gcaaggagac ctgcctgctt | 180 |
| tacgaaatta attgggggg ccggcactcc atttggcgac atacatcaca gaacactaac | 240 |
| aagcacgtcg aagtcaactt catcgagaag ttcacgacag aaagatattt ctgtccgaac | 300 |
| acaaggtgca gcattacctg gtttctcagc tggagcccat gcggcgaatg tagtagggcc | 360 |
| atcactgaat tcctgtcaag gtatccccac gtcactctgt ttatttacat cgcaaggctg | 420 |

-continued

```
taccaccacg ctgaccccg caatcgacaa ggcctgcggg atttgatctc ttcaggtgtg      480
actatccaaa ttatgactga gcaggagtca ggatactgct ggagaaactt tgtgaattat      540
agcccgagta atgaagccca ctggcctagg tatccccatc tgtgggtacg actgtacgtt      600
cttgaactgt actgcatcat actgggcctg cctccttgtc tcaacattct gagaaggaag      660
cagccacagc tgacattctt taccatcgct cttcagtctt gtcattacca gcgactgccc      720
ccacacattc tctgggccac cgggttgaaa tctggtggtt cttctggtgg ttctagcggc      780
agcgagactc ccgggacctc agagtccgcc acacccgaaa gttccggagg gagtagcggc      840
gggtctacac agttcgaggg ctttaccaac ctgtatcagg tgagcaagac actgcggttt      900
gagctgatcc cacagggcaa gaccctgaag cacatccagg agcagggctt catcgaggag      960
gacaaggccc gcaatgatca ctacaaggag ctgaagccca tcatcgatcg gatctacaag     1020
acctatgccg accagtgcct gcagctggtg cagctggatt gggagaacct gagcgccgcc     1080
atcgactcct atagaaagga gaaaccgag gagacaagga acgccctgat cgaggagcag     1140
gccacatatc gcaatgccat ccacgactac ttcatcggcc ggacagacaa cctgaccgat     1200
gccatcaata gagacacgc cgagatctac aagggcctgt tcaaggccga gctgtttaat     1260
ggcaaggtgc tgaagcagct gggcaccgtg accacaaccg agcacgagaa cgccctgctg     1320
cggagcttcg acaagtttac aacctacttc tccggctttt atgccaacag gaagaacgtg     1380
ttcagcgccg aggatatcag cacagccatc ccacaccgca tcgtgcagga caacttcccc     1440
aagtttaagg agaattgtca catcttcaca cgcctgatca ccgccgtgcc cagcctgcgg     1500
gagcactttg agaacgtgaa gaaggccatc ggcatcttcg tgagcacctc catcgaggag     1560 gtgtttcct tcccttttta taaccagctg ctgacacaga cccagatcga cctgtataac     1620
cagctgctgg aggaatctc tcgggaggca ggcaccgaga agatcaaggg cctgaacgag     1680
gtgctgaatc tggccatcca gaagaatgat gagacagccc acatcatcgc ctccctgcca     1740
cacagattca tcccctgtt taagcagatc ctgtccgata ggaacaccct gtctttcatc     1800
ctggaggagt ttaagagcga cgaggaagtg atccagtcct tctgcaagta caagacactg     1860
ctgagaaacg agaacgtgct ggagacagcc gaggccctgt taacgagct gaacagcatc     1920 gacctgacac acatcttcat cagccacaag aagctggaga caatcagcag cgccctgtgc     1980
gaccactggg atacactgag gaatgccctg tatgagcgga gaatctccga gctgacaggc     2040
aagatcacca gtctgccaa ggagaaggtg cagcgcagcc tgaagcacga ggatatcaac     2100
ctgcaggaga tcatctctgc cgcaggcaag gagctgagcg aggccttcaa gcagaaaacc     2160
agcgagatcc tgtcccacgc acacgccgcc ctggatcagc cactgcctac aaccctgaag     2220
aagcaggagg agaaggagat cctgaagtct cagctggaca gcctgctggg cctgtaccac     2280
ctgctggact ggtttgccgt ggatgagtcc aacgaggtgg accccgagtt ctctgcccgg     2340
ctgaccggca tcaagctgga gatggagcct ctctgagct tctacaacaa ggccagaaat     2400
tatgccacca gaagccccta ctccgtggag aagttcaagc tgaactttca gatgcctaca     2460
ctggccgccg gctgggacgt gaataaggcc aagaacaatg gcgccatcct gtttgtgaag     2520
aacggcctgt actatctggg catcatgcca aagcagaagg gcaggtataa ggccctgagc     2580
ttcgagccca cagagaaaac cagcgagggc tttgataaga tgtactatga ctacttccct     2640
gatgccgcca agatgatccc aaagtgcagc acccagctga aggccgtgac agcccacttt     2700
cagacccaca caacccccat cctgctgtcc aacaatttca tcgagcctct ggagatcaca     2760
```

-continued

```
aaggagatct cgacctgaa caatcctgag aaggagccaa agaagtttca gacagcctac    2820
gccaagaaaa ccggcgacca gaagggctac agagaggccc tgtgcaagtg gatcgacttc    2880
acaagggatt ttctgtccaa gtataccaag acaacctcta tcgatctgtc tagcctgcgg    2940
ccatcctctc agtataagga cctgggcgag tactatgccg agctgaatcc cctgctgtac    3000
cacatcagct tccagagaat cgccgagaag gagatcatgg atgccgtgga gacaggcaag    3060
ctgtacctgt tccagatcta taacaaggac tttgccaagg ccaccacgg caagcctaat     3120
ctgcacacac tgtattggac cggcctgttt tctccagaga acctggccaa gacaagcatc    3180
aagctgaatg ccaggccga gctgttctac cgccctaagt ccaggatgaa gaggatggca    3240
caccggctgg gagagaagat gctgaacaag aagctgaagg atcagaaaac cccaatcccc    3300
gacaccctgt accaggagct gtacgactat gtgaatcaca gactgtccca cgacctgtct    3360
gatgaggcca gggccctgct gcccaacgtg atcaccaagg aggtgtctca cgagatcatc    3420
aaggataggc gctttaccag cgacaagttc ttttttccacg tgcctatcac actgaactat    3480
caggccgcca attccccatc taagttcaac cagagggtga atgcctacct gaaggagcac    3540
cccgagacac ctatcatcgg catcgcccgg ggcgagagaa acctgatcta tcacagtg     3600
atcgactcca ccggcaagat cctggagcag cggagcctga acaccatcca gcagtttgat    3660
taccagaaga agctggacaa cagggagaag gagagggtgg cagcaaggca ggcctggtct    3720
gtggtgggca caatcaagga tctgaagcag ggctatctga ccaggtcat ccacgagatc     3780
gtggacctga tgatccacta ccaggccgtg gtggtgctgg agaacctgaa tttcggcttt    3840
aagagcaaga ggaccggcat cgccgagaag gccgtgtacc agcagttcga gaagatgctg    3900
atcgataagc tgaattgcct ggtgctgaag gactatccag cagagaaagt gggaggcgtg    3960
ctgaacccat accagctgac agaccagttc acctcctttg ccaagatggg cacccagtct    4020
ggcttcctgt tttacgtgcc tgccccatat acatctaaga tcgatcccct gaccggcttc    4080
gtggacccct tcgtgtggaa aaccatcaag aatcacgaga gccgcaagca cttcctggag    4140
ggcttcgact ttctgcacta cgacgtgaaa accggcgact tcatcctgca ctttaagatg    4200
aacagaaatc tgtccttcca gaggggcctg cccggcttta tgcctgcatg ggatatcgtg    4260
ttcgagaaga cgagacaca gtttgacgcc aagggcaccc ctttcatcgc cggcaagaga     4320
atcgtgccag tgatcgagaa tcacagattc accggcagat accggacct gtatcctgcc    4380
aacgagctga tcgccctgct ggaggagaag ggcatcgtgt tcagggatgg ctccaacatc    4440
ctgccaaagc tgctggagaa tgacgattct cacgccatcg acacgatggt ggccctgatc    4500
cgcagcgtgc tgcagatgcg gaactccaat gccgccacag gcgaggacta tatcaacagc    4560
cccgtgcgcg atctgaatgg cgtgtgcttc gactcccggt tcagaaaccc agagtggcca    4620
atggacgccg atgccaatgg cgcctaccac atcgccctga agggccagct gctgctgaat    4680
cacctgaagg agagcaagga tctgaagctg cagaacggca tctccaatca ggactggctg    4740
gcctacatcc aggagctgcg caacaaaagg ccggcggcca cgaaaaaggc cggccaggca    4800
aaaaagaaaa agggatcctc tggtggttct ggaggatctg tggttctac taatctgtca     4860
gatattattg aaaaggagac cggtaagcaa ctggttatcc aggaatccat cctcatgctc    4920
ccagaggagg tggaagaagt cattgggaac aagccggaaa gcgatatact cgtgcacacc    4980
gcctacgacg agagcaccga cgagaatgtc atgcttctga ctagcgacgc ccctgaatac    5040
aagccttggg ctctggtcat acaggatagc aacggtgaga acaagattaa gatgctctct    5100
ggtggttctc ccaagaagaa gaggaaagtc                                     5130
```

```
<210> SEQ ID NO 448
<211> LENGTH: 1710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448
```

Met Gly Pro Lys Lys Arg Lys Val Gly Ser Gly Pro Lys Lys Lys
1               5                   10                  15

Arg Lys Val Gly Ser Gly Ser Ser Glu Thr Gly Pro Val Ala Val Asp
            20                  25                  30

Pro Thr Leu Arg Arg Arg Ile Glu Pro His Glu Phe Glu Val Phe Phe
        35                  40                  45

Asp Pro Arg Glu Leu Arg Lys Glu Thr Cys Leu Leu Tyr Glu Ile Asn
50                  55                  60

Trp Gly Gly Arg His Ser Ile Trp Arg His Thr Ser Gln Asn Thr Asn
65                  70                  75                  80

Lys His Val Glu Val Asn Phe Ile Glu Lys Phe Thr Thr Glu Arg Tyr
                85                  90                  95

Phe Cys Pro Asn Thr Arg Cys Ser Ile Thr Trp Phe Leu Ser Trp Ser
            100                 105                 110

Pro Cys Gly Glu Cys Ser Arg Ala Ile Thr Glu Phe Leu Ser Arg Tyr
        115                 120                 125

Pro His Val Thr Leu Phe Ile Tyr Ile Ala Arg Leu Tyr His His Ala
    130                 135                 140

Asp Pro Arg Asn Arg Gln Gly Leu Arg Asp Leu Ile Ser Ser Gly Val
145                 150                 155                 160

Thr Ile Gln Ile Met Thr Glu Gln Glu Ser Gly Tyr Cys Trp Arg Asn
                165                 170                 175

Phe Val Asn Tyr Ser Pro Ser Asn Glu Ala His Trp Pro Arg Tyr Pro
            180                 185                 190

His Leu Trp Val Arg Leu Tyr Val Leu Glu Leu Tyr Cys Ile Ile Leu
        195                 200                 205

Gly Leu Pro Pro Cys Leu Asn Ile Leu Arg Arg Lys Gln Pro Gln Leu
    210                 215                 220

Thr Phe Phe Thr Ile Ala Leu Gln Ser Cys His Tyr Gln Arg Leu Pro
225                 230                 235                 240

Pro His Ile Leu Trp Ala Thr Gly Leu Lys Ser Gly Gly Ser Ser Gly
                245                 250                 255

Gly Ser Ser Gly Ser Glu Thr Pro Gly Thr Ser Glu Ser Ala Thr Pro
            260                 265                 270

Glu Ser Ser Gly Gly Ser Ser Gly Gly Ser Thr Gln Phe Glu Gly Phe
        275                 280                 285

Thr Asn Leu Tyr Gln Val Ser Lys Thr Leu Arg Phe Glu Leu Ile Pro
    290                 295                 300

Gln Gly Lys Thr Leu Lys His Ile Gln Glu Gln Gly Phe Ile Glu Glu
305                 310                 315                 320

Asp Lys Ala Arg Asn Asp His Tyr Lys Glu Leu Lys Pro Ile Ile Asp
                325                 330                 335

Arg Ile Tyr Lys Thr Tyr Ala Asp Gln Cys Leu Gln Leu Val Gln Leu
            340                 345                 350

Asp Trp Glu Asn Leu Ser Ala Ala Ile Asp Ser Tyr Arg Lys Glu Lys

```
                    355                 360                 365
Thr Glu Glu Thr Arg Asn Ala Leu Ile Glu Glu Gln Ala Thr Tyr Arg
    370                 375                 380
Asn Ala Ile His Asp Tyr Phe Ile Gly Arg Thr Asp Asn Leu Thr Asp
385                 390                 395                 400
Ala Ile Asn Lys Arg His Ala Glu Ile Tyr Lys Gly Leu Phe Lys Ala
                405                 410                 415
Glu Leu Phe Asn Gly Lys Val Leu Lys Gln Leu Gly Thr Val Thr Thr
                420                 425                 430
Thr Glu His Glu Asn Ala Leu Leu Arg Ser Phe Asp Lys Phe Thr Thr
                435                 440                 445
Tyr Phe Ser Gly Phe Tyr Arg Asn Arg Lys Asn Val Phe Ser Ala Glu
                450                 455                 460
Asp Ile Ser Thr Ala Ile Pro His Arg Ile Val Gln Asp Asn Phe Pro
465                 470                 475                 480
Lys Phe Lys Glu Asn Cys His Ile Phe Thr Arg Leu Ile Thr Ala Val
                485                 490                 495
Pro Ser Leu Arg Glu His Phe Glu Asn Val Lys Lys Ala Ile Gly Ile
                500                 505                 510
Phe Val Ser Thr Ser Ile Glu Glu Val Phe Ser Phe Pro Phe Tyr Asn
                515                 520                 525
Gln Leu Leu Thr Gln Thr Gln Ile Asp Leu Tyr Asn Gln Leu Leu Gly
                530                 535                 540
Gly Ile Ser Arg Glu Ala Gly Thr Glu Lys Ile Lys Gly Leu Asn Glu
545                 550                 555                 560
Val Leu Asn Leu Ala Ile Gln Lys Asn Asp Glu Thr Ala His Ile Ile
                565                 570                 575
Ala Ser Leu Pro His Arg Phe Ile Pro Leu Phe Lys Gln Ile Leu Ser
                580                 585                 590
Asp Arg Asn Thr Leu Ser Phe Ile Leu Glu Glu Phe Lys Ser Asp Glu
                595                 600                 605
Glu Val Ile Gln Ser Phe Cys Lys Tyr Lys Thr Leu Leu Arg Asn Glu
                610                 615                 620
Asn Val Leu Glu Thr Ala Glu Ala Leu Phe Asn Glu Leu Asn Ser Ile
625                 630                 635                 640
Asp Leu Thr His Ile Phe Ile Ser His Lys Lys Leu Glu Thr Ile Ser
                645                 650                 655
Ser Ala Leu Cys Asp His Trp Asp Thr Leu Arg Asn Ala Leu Tyr Glu
                660                 665                 670
Arg Arg Ile Ser Glu Leu Thr Gly Lys Ile Thr Lys Ser Ala Lys Glu
                675                 680                 685
Lys Val Gln Arg Ser Leu Lys His Glu Asp Ile Asn Leu Gln Glu Ile
                690                 695                 700
Ile Ser Ala Ala Gly Lys Glu Leu Ser Glu Ala Phe Lys Gln Lys Thr
705                 710                 715                 720
Ser Glu Ile Leu Ser His Ala His Ala Ala Leu Asp Gln Pro Leu Pro
                725                 730                 735
Thr Thr Leu Lys Lys Gln Glu Glu Lys Glu Ile Leu Lys Ser Gln Leu
                740                 745                 750
Asp Ser Leu Leu Gly Leu Tyr His Leu Leu Asp Trp Phe Ala Val Asp
                755                 760                 765
Glu Ser Asn Glu Val Asp Pro Glu Phe Ser Ala Arg Leu Thr Gly Ile
                770                 775                 780
```

```
Lys Leu Glu Met Glu Pro Ser Leu Ser Phe Tyr Asn Lys Ala Arg Asn
785                 790                 795                 800

Tyr Ala Thr Lys Lys Pro Tyr Ser Val Glu Lys Phe Lys Leu Asn Phe
            805                 810                 815

Gln Met Pro Thr Leu Ala Arg Gly Trp Asp Val Asn Arg Glu Lys Asn
                820                 825                 830

Asn Gly Ala Ile Leu Phe Val Lys Asn Gly Leu Tyr Tyr Leu Gly Ile
            835                 840                 845

Met Pro Lys Gln Lys Gly Arg Tyr Lys Ala Leu Ser Phe Glu Pro Thr
        850                 855                 860

Glu Lys Thr Ser Glu Gly Phe Asp Lys Met Tyr Tyr Asp Tyr Phe Pro
865                 870                 875                 880

Asp Ala Ala Lys Met Ile Pro Lys Cys Ser Thr Gln Leu Lys Ala Val
                885                 890                 895

Thr Ala His Phe Gln Thr His Thr Thr Pro Ile Leu Leu Ser Asn Asn
            900                 905                 910

Phe Ile Glu Pro Leu Glu Ile Thr Lys Glu Ile Tyr Asp Leu Asn Asn
        915                 920                 925

Pro Glu Lys Glu Pro Lys Lys Phe Gln Thr Ala Tyr Ala Lys Lys Thr
    930                 935                 940

Gly Asp Gln Lys Gly Tyr Arg Glu Ala Leu Cys Lys Trp Ile Asp Phe
945                 950                 955                 960

Thr Arg Asp Phe Leu Ser Lys Tyr Thr Lys Thr Thr Ser Ile Asp Leu
            965                 970                 975

Ser Ser Leu Arg Pro Ser Ser Gln Tyr Lys Asp Leu Gly Glu Tyr Tyr
        980                 985                 990

Ala Glu Leu Asn Pro Leu Leu Tyr His Ile Ser Phe Gln Arg Ile Ala
    995                 1000                1005

Glu Lys Glu Ile Met Asp Ala Val Glu Thr Gly Lys Leu Tyr Leu
    1010                1015                1020

Phe Gln Ile Tyr Asn Lys Asp Phe Ala Lys Gly His His Gly Lys
    1025                1030                1035

Pro Asn Leu His Thr Leu Tyr Trp Thr Gly Leu Phe Ser Pro Glu
    1040                1045                1050

Asn Leu Ala Lys Thr Ser Ile Lys Leu Asn Gly Gln Ala Glu Leu
    1055                1060                1065

Phe Tyr Arg Pro Lys Ser Arg Met Lys Arg Met Ala His Arg Leu
    1070                1075                1080

Gly Glu Lys Met Leu Asn Lys Lys Leu Lys Asp Gln Lys Thr Pro
    1085                1090                1095

Ile Pro Asp Thr Leu Tyr Gln Glu Leu Tyr Asp Tyr Val Asn His
    1100                1105                1110

Arg Leu Ser His Asp Leu Ser Asp Glu Ala Arg Ala Leu Leu Pro
    1115                1120                1125

Asn Val Ile Thr Lys Glu Val Ser His Glu Ile Ile Lys Asp Arg
    1130                1135                1140

Arg Phe Thr Ser Asp Lys Phe Phe Phe His Val Pro Ile Thr Leu
    1145                1150                1155

Asn Tyr Gln Ala Ala Asn Ser Pro Ser Lys Phe Asn Gln Arg Val
    1160                1165                1170

Asn Ala Tyr Leu Lys Glu His Pro Glu Thr Pro Ile Ile Gly Ile
    1175                1180                1185
```

```
Ala Arg Gly Glu Arg Asn  Leu Ile Tyr Ile Thr Val  Ile Asp Ser
1190           1195              1200

Thr Gly Lys Ile Leu Glu  Gln Arg Ser Leu Asn Thr  Ile Gln Gln
1205           1210              1215

Phe Asp Tyr Gln Lys Lys  Leu Asp Asn Arg Glu Lys  Glu Arg Val
1220           1225              1230

Ala Ala Arg Gln Ala Trp  Ser Val Val Gly Thr Ile  Lys Asp Leu
1235           1240              1245

Lys Gln Gly Tyr Leu Ser  Gln Val Ile His Glu Ile  Val Asp Leu
1250           1255              1260

Met Ile His Tyr Gln Ala  Val Val Leu Glu Asn  Leu Asn Phe
1265           1270              1275

Gly Phe Lys Ser Lys Arg  Thr Gly Ile Ala Glu Lys  Ala Val Tyr
1280           1285              1290

Gln Gln Phe Glu Lys Met  Leu Ile Asp Lys Leu Asn  Cys Leu Val
1295           1300              1305

Leu Lys Asp Tyr Pro Ala  Glu Lys Val Gly Gly Val  Leu Asn Pro
1310           1315              1320

Tyr Gln Leu Thr Asp Gln  Phe Thr Ser Phe Ala Lys  Met Gly Thr
1325           1330              1335

Gln Ser Gly Phe Leu Phe  Tyr Val Pro Ala Pro Tyr  Thr Ser Lys
1340           1345              1350

Ile Asp Pro Leu Thr Gly  Phe Val Asp Pro Phe Val  Trp Lys Thr
1355           1360              1365

Ile Lys Asn His Glu Ser  Arg Lys His Phe Leu Glu  Gly Phe Asp
1370           1375              1380

Phe Leu His Tyr Asp Val  Lys Thr Gly Asp Phe Ile  Leu His Phe
1385           1390              1395

Lys Met Asn Arg Asn Leu  Ser Phe Gln Arg Gly Leu  Pro Gly Phe
1400           1405              1410

Met Pro Ala Trp Asp Ile  Val Phe Glu Lys Asn Glu  Thr Gln Phe
1415           1420              1425

Asp Ala Lys Gly Thr Pro  Phe Ile Ala Gly Lys Arg  Ile Val Pro
1430           1435              1440

Val Ile Glu Asn His Arg  Phe Thr Gly Arg Tyr Arg  Asp Leu Tyr
1445           1450              1455

Pro Ala Asn Glu Leu Ile  Ala Leu Leu Glu Glu Lys  Gly Ile Val
1460           1465              1470

Phe Arg Asp Gly Ser Asn  Ile Leu Pro Lys Leu Leu  Glu Asn Asp
1475           1480              1485

Asp Ser His Ala Ile Asp  Thr Met Val Ala Leu Ile  Arg Ser Val
1490           1495              1500

Leu Gln Met Arg Asn Ser  Asn Ala Ala Thr Gly Glu  Asp Tyr Ile
1505           1510              1515

Asn Ser Pro Val Arg Asp  Leu Asn Gly Val Cys Phe  Asp Ser Arg
1520           1525              1530

Phe Gln Asn Pro Glu Trp  Pro Met Asp Ala Asp Ala  Asn Gly Ala
1535           1540              1545

Tyr His Ile Ala Leu Lys  Gly Gln Leu Leu Leu Asn  His Leu Lys
1550           1555              1560

Glu Ser Lys Asp Leu Lys  Leu Gln Asn Gly Ile Ser  Asn Gln Asp
1565           1570              1575

Trp Leu Ala Tyr Ile Gln  Glu Leu Arg Asn Lys Arg  Pro Ala Ala
```

```
                  1580                1585                1590

Thr Lys  Lys Ala Gly Gln Ala  Lys Lys Lys Lys Gly  Ser Ser Gly
    1595                1600                1605

Gly Ser  Gly Gly Ser Gly Gly  Ser Thr Asn Leu Ser  Asp Ile Ile
    1610                1615                1620

Glu Lys  Glu Thr Gly Lys Gln  Leu Val Ile Gln Glu  Ser Ile Leu
    1625                1630                1635

Met Leu  Pro Glu Glu Val Glu  Glu Val Ile Gly Asn  Lys Pro Glu
    1640                1645                1650

Ser Asp  Ile Leu Val His Thr  Ala Tyr Asp Glu Ser  Thr Asp Glu
    1655                1660                1665

Asn Val  Met Leu Leu Thr Ser  Asp Ala Pro Glu Tyr  Lys Pro Trp
    1670                1675                1680

Ala Leu  Val Ile Gln Asp Ser  Asn Gly Glu Asn Lys  Ile Lys Met
    1685                1690                1695

Leu Ser  Gly Gly Ser Pro Lys  Lys Lys Arg Lys Val
    1700                1705                1710

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 449
tttnctgatg gtccatgtct gtta                                           24

<210> SEQ ID NO 450
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
tttcctgatg gtccatgtct gaat                                           24

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
tttcctgatg gtccatgtct gtta                                           24

<210> SEQ ID NO 452
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 452
tttcctgatg gtccacatct gtta                                          24

<210> SEQ ID NO 453
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
tttcctgatg gtccatatct gtgg                                          24

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tttcctgatg gtccatacct gtta                                          24

<210> SEQ ID NO 455
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
tttcctgatg gtccacgcct gtta                                          24

<210> SEQ ID NO 456
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
gttcctgatg gtccacatct gtta                                          24

<210> SEQ ID NO 457
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ttttgtgatg tttcatgtgt ccta                                          24

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence: Synthetic

```
         oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 458
tttngctcag caggcacctg cctc                                          24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
cttagctcag caggcacctg ccca                                          24

<210> SEQ ID NO 460
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
tttggctcag caggcacctg cctc                                          24

<210> SEQ ID NO 461
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
agcagctcag caggcacctg cctt                                          24

<210> SEQ ID NO 462
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
aacagctcag cagacacctg ccaa                                          24

<210> SEQ ID NO 463
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tttagctcag ctgacacctg ccca                                          24
```

<210> SEQ ID NO 464
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tccagctcag cagacaccag cctc                                           24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
ttcccctcag cagacacctg ccat                                           24

<210> SEQ ID NO 466
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ttcccctcag cagacacctg ccat                                           24

<210> SEQ ID NO 467
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
ttcccctcag cagacacctg ccat                                           24

<210> SEQ ID NO 468
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
ttcccctcag cggacacctg ccat                                           24

<210> SEQ ID NO 469
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature

```
<222> LOCATION: (4)..(4)
<223> OTHER INFORMATION: n is a, c, g, or t

<400> SEQUENCE: 469
tttngattga aggaaaagtt acaa                                          24

<210> SEQ ID NO 470
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tttagattga aggaaaagtt acaa                                          24

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tttagattaa tggaaaagtt acaa                                          24

<210> SEQ ID NO 472
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tttagactta aagaaaagtt acaa                                          24

<210> SEQ ID NO 473
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
cttggattaa aggaaaagct acaa                                          24

<210> SEQ ID NO 474
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 474
tttnggatgc cactaaaagg gaaa                                          24
```

```
<210> SEQ ID NO 475
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tttaggatgc cactaaaagg gaaa                                              24

<210> SEQ ID NO 476
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tttagaatgc cactaaaaaa agag                                              24

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ttttgtatac cactaaaagg gaaa                                              24

<210> SEQ ID NO 478
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 478
attntgatga gcctttagag agaa                                              24

<210> SEQ ID NO 479
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
attctgatga gcctttagag agaa                                              24

<210> SEQ ID NO 480
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 480
tttgtgatga gcgttgagag aaag                                              24

<210> SEQ ID NO 481
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tttttgatga gcctttagag tact                                              24

<210> SEQ ID NO 482
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
aatgtgatga cccattagag agaa                                              24

<210> SEQ ID NO 483
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tttatgatga gtctttagag tttt                                              24

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
tttatgatgt acctttagaa agca                                              24

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 485
```
attnaccgag caggagtgag ggaa                                              24

<210> SEQ ID NO 486
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
attcaccgag caggagtgag ggaa                                              24

<210> SEQ ID NO 487
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tttacttgag cagaagtgag ggag                                              24

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
tttgactgag caggattgag ggaa                                              24

<210> SEQ ID NO 489
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tttcctagag caggagtgag gata                                              24

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 490
cttnttgggt cagctgttaa catc                                              24

<210> SEQ ID NO 491
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 491
cttattgggt cagctgttaa catc                                              24

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
cattttgggt cagcacgtga catt                                              24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 493
cttnacccag gttcataaca atgt                                              24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
cttcacccag gttcataaca atgt                                              24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 495
gttnatttgt ccagaggaaa ccac                                              24

<210> SEQ ID NO 496
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
gttcatttgt ccagaggaaa ccac                                          24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
ttaattttgt ccaaaggaaa ccac                                          24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
ttccatttgt ccacaggaaa cctc                                          24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
tttcatttga ccaaagaaaa ccca                                          24

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
gccaatttgt cctgaggaaa ccac                                          24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
cctcatttgt ccagaggaaa ctac                                          24

<210> SEQ ID NO 502
<211> LENGTH: 24
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
tttgctttgt acagaggaaa ccat                                           24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
agtcatctgt cctgaggaaa ccac                                           24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
attgattttt ccagagaaaa ccac                                           24

<210> SEQ ID NO 505
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
tttcattact ccagaagaaa ccac                                           24

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 506
gttnccttag cactctgcca ctta                                           24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gttcccttag cactctgcca ctta                                              24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ttccccttag ccatctgcca ccta                                              24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
tttgccccag cactctgcca ctta                                              24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 510
gttncctgtc ttgtttgtga gagg                                              24

<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
gttccctgtc ttgtttgtga gagg                                              24

<210> SEQ ID NO 512
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
attacctgtc ttgtttggga gaga                                              24

<210> SEQ ID NO 513

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
tttgcctgtc ctgtgtgtga gatg                                            24

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
tttgcctgtc ttgttaatga gaaa                                            24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
tttccctgtc ttcattgtga gaga                                            24

<210> SEQ ID NO 516
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 516
tatngcctct ccctgctcag aatc                                            24

<210> SEQ ID NO 517
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
tatcgcctct ccctgctcag aatc                                            24

<210> SEQ ID NO 518
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 518
tatnaacctg ggtgaagtcc caac                                              24

<210> SEQ ID NO 519
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tatgaacctg ggtgaagtcc caac                                              24

<210> SEQ ID NO 520
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
tttgcacctg ggtgaagtcc caaa                                              24

<210> SEQ ID NO 521
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 521
ttcntgatgg tccatgtctg ttac                                              24

<210> SEQ ID NO 522
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
tttctgatgg tccatacctg ttac                                              24

<210> SEQ ID NO 523
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 523
ttcctgatgg tccatgtctg ttac                                              24

<210> SEQ ID NO 524
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ttcctgatgg tccatgtctg aatt                                              24

<210> SEQ ID NO 525
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
cttctgatgg tccatatctg ttaa                                              24

<210> SEQ ID NO 526
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ttcctgatgg tccacatctg ttaa                                              24

<210> SEQ ID NO 527
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
ttcctgatgg tccacatctg ttaa                                              24

<210> SEQ ID NO 528
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
ttcctgatgg tccatacctg ttaa                                              24

<210> SEQ ID NO 529
<211> LENGTH: 24
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 529
tttgtgatgt ttcatgtgtc ctag                                              24

<210> SEQ ID NO 530
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ttcctgatgg tccatatctg tggc                                              24

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ctttcttctc ccctctgctg gatacctctg                                        30

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
ctttatccgt gttccttgac tctgggcaac                                        30

<210> SEQ ID NO 533
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gtttctcatc tgtgcccctc cctccctggc                                        30

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ttttccgagc ttctggcggt ctcaagcact                                        30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 535
gtttccctca ctcctgctcg gtgaatttgg                                     30

<210> SEQ ID NO 536
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
gtttcagcct cacccctcta gccctacatc                                     30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
gtttgtggtt gcccacccta gtcattggag                                     30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ctttggtcgg catggcccca ttcgcacggc                                     30

<210> SEQ ID NO 539
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ggaatccctt ctgcagcacc tgg                                            23

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ctgatggtcc atgtctgtta ctc                                            23

<210> SEQ ID NO 541
<211> LENGTH: 21
<212> TYPE: PRT
<213> ORGANISM: Acidaminococcus sp.

<400> SEQUENCE: 541

Ser Phe Asp Lys Phe Thr Thr Tyr Phe Ser Gly Phe Tyr Glu Asn Arg
```

```
                1               5                  10                 15

Lys Asn Val Phe Ser
            20

<210> SEQ ID NO 542
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 542

Ser Phe Asn Gly Phe Thr Thr Ala Phe Thr Gly Phe Phe Asp Asn Arg
1               5                  10                 15

Glu Asn Met Phe Ser
            20

<210> SEQ ID NO 543
<211> LENGTH: 21
<212> TYPE: PRT
<213> ORGANISM: Francisella tularensis

<400> SEQUENCE: 543

Ser Phe Lys Gly Trp Thr Thr Tyr Phe Lys Gly Phe His Glu Asn Arg
1               5

-continued

```
<211> LENGTH: 22
<212> TYPE: PRT
<213> ORGANISM: Acidaminococcus sp.

<400> SEQUENCE: 547

Asn Phe Gln Met Pro Thr Leu Ala Ser Gly Trp Asp Val Asn Lys Glu
1               5                   10                  15

Lys Asn Asn Gly Ala Ile
            20

<210> SEQ ID NO 548
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 548

Tyr Phe Gln Asn Pro Gln Phe Met Gly Gly Trp Asp Lys Asp Lys Glu
1               5                   10                  15

Thr Asp Tyr Arg Ala Thr
            20

<210> SEQ ID NO 549
<211> LENGTH: 22
<212> TYPE: PRT
<213> ORGANISM: Francisella tularensis

<400> SEQUENCE: 549

Asn Phe Glu Asn Ser Thr Leu Ala Asn Gly Trp Asp Lys Asn Lys Glu
1               5                   10                  15

Pro Asp Asn Thr Ala

```
                1               5                   10                  15
Lys Asp Asn Phe Gly Val
            20

<210> SEQ ID NO 553
<211> LENGTH: 24
<212> TYPE: DNA
<213> ORGANISM: Acidaminococcus sp.

<400> SEQUENCE: 553
tttccctcac tcctgctcgg tgaa                                              24

<210> SEQ ID NO 554
<211> LENGTH: 20
<212> TYPE: DNA
<213> ORGANISM: Acidaminococcus sp.

<400> SEQUENCE: 554
cctcactcct gctcggtgaa                                                   20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
cctcactgct gctcggtgaa                                                   20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
cctcactcgt gctcggtgaa                                                   20

<210> SEQ ID NO 557
<211> LENGTH: 24
<212> TYPE: DNA
<213> ORGANISM: Acidaminococcus sp.

<400> SEQUENCE: 557
tttcctgatg gtccatgtct gtta                                              24

<210> SEQ ID NO 558
<211> LENGTH: 20
<212> TYPE: DNA
<213> ORGANISM: Acidaminococcus sp.

<400> SEQUENCE: 558
ctgatggtcc atgtctgtta                                                   20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 559
ctgatggacc atgtctgtta                                              20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ctgatggtgc atgtctgtta                                              20

<210> SEQ ID NO 561
<211> LENGTH: 6
<212> TYPE: PRT
<213> ORGANISM: Unknown
<220> FEATURE:
<223> OTHER INFORMATION: Lachnospiraceae bacterium

<400> SEQUENCE: 561

Met Ser Lys Leu Glu Lys
1               5

<210> SEQ ID NO 562
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 562

His His His His His His
1               5

<210> SEQ ID NO 563
<211> LENGTH: 7
<212> TYPE: PRT
<213> ORGANISM: Acidaminococcus sp.

<400> SEQUENCE: 563

Gly Leu Phe Lys Ala Glu Leu
1               5

<210> SEQ ID NO 564
<211> LENGTH: 21
<212> TYPE: PRT
<213> ORGANISM: Acidaminococcus sp.

<400> SEQUENCE: 564

Ser Phe Asp Lys Phe Thr Thr Tyr Phe Ser Gly Phe Tyr Glu Asn Arg
1               5                   10                  15

Lys Asn Val Phe Ser
            20

<210> SEQ ID NO 565
<211> LENGTH: 22
<212> TYPE: PRT
<213> ORGANISM: Acidaminococcus sp.

<400> SEQUENCE: 565

Asn Phe Gln Met Pro Thr Leu Ala Ser Gly Trp Asp Val Asn Lys Glu
```

-continued

```
1               5                   10                  15

Lys Asn Asn Gly Ala Ile
            20

<210> SEQ ID NO 566
<211> LENGTH: 22
<212> TYPE: PRT
<213> ORGANISM: Acidaminococcus sp.

<400> SEQUENCE: 566

Tyr Asp Tyr Phe Pro Asp Ala Ala Lys Met Ile Pro Lys Cys Ser Thr
1               5                   10                  15

Gln Leu Lys Ala Val Thr
            20

<210> SEQ ID NO 567
<211> LENGTH: 5
<212> TYPE: PRT
<213> ORGANISM: Acidaminococcus sp.

<400> SEQUENCE: 567

Leu Ser Asn Asn Phe
1               5

<210> SEQ ID NO 568
<211> LENGTH: 9
<212> TYPE: PRT
<213> ORGANISM: Acidaminococcus sp.

<400> SEQUENCE: 568

Ser Lys Tyr Thr Lys Thr Thr Ser Ile
1               5

<210> SEQ ID NO 569
<211> LENGTH: 7
<212> TYPE: PRT
<213> ORGANISM: Unknown
<220> FEATURE:
<223> OTHER INFORMATION: Lachnospiraceae bacterium

<400> SEQUENCE: 569

Ser Leu Phe Lys Lys Asp Ile
1               5

<210> SEQ ID NO 570
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 570

Ser Phe Asn Gly Phe Thr Thr Ala Phe Thr Gly Phe Phe Asp Asn Arg
1               5                   10                  15

Glu Asn Met Phe Ser
            20

<210> SEQ ID NO 571
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 571
```

```
Tyr Phe Gln Asn Pro Gln Phe Met Gly Gly Trp Asp Lys Asp Lys Glu
1               5                   10                  15

Thr Asp Tyr Arg Ala Thr
            20

<210> SEQ ID NO 572
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 572

Tyr Lys Leu Leu Pro Gly Pro Asn Lys Met Leu Pro Lys Val Phe Phe
1               5                   10                  15

Ser Lys Lys Trp Met Ala
            20

<210> SEQ ID NO 573
<211> LENGTH: 5
<212> TYPE: PRT
<213> ORGANISM: Unknown
<220> FEATURE:
<223> OTHER INFORMATION: Lachnospiraceae bacterium

<400> SEQUENCE: 573

Phe Ser Lys Lys Trp
1               5

<210> SEQ ID NO 574
<211> LENGTH: 9
<212> TYPE: PRT
<213> ORGANISM: Unknown
<220> FEATURE:
<223> OTHER INFORMATION: Lachnospiraceae bacterium

<400> SEQUENCE: 574

Ser Arg Tyr Pro Lys Trp Ser Asn Ala
1               5

<210> SEQ ID NO 575
<211> LENGTH: 7
<212> TYPE: PRT
<213> ORGANISM: Unknown
<220> FEATURE:
<223> OTHER INFORMATION: Lachnospiraceae bacterium

<400> SEQUENCE: 575

Ser Leu Phe Lys Lys Asp Ile
1               5

<210> SEQ ID NO 576
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 576

Ser Phe Asn Gly Phe Thr Thr Ala Phe Thr Gly Phe Phe Asp Asn Arg
1               5                   10                  15

Glu Asn Met Phe Ser
            20
```

```
<210> SEQ ID NO 577
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 577

Tyr Phe Gln Asn Pro Gln Phe Met Gly Gly Trp Asp Lys Asp Lys Glu
1               5                   10                  15

Thr Asp Tyr Arg Ala Thr
            20

<210> SEQ ID NO 578
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 578

Tyr Lys Leu Leu Pro Gly Pro Asn Lys Met Leu Pro Lys Val Phe Phe
1               5                   10                  15

Ser Lys Lys Trp Met Ala
            20

<210> SEQ ID NO 579
<211> LENGTH: 5
<212> TYPE: PRT
<213> ORGANISM: Unknown
<220> FEATURE:
<223> OTHER INFORMATION: Lachnospiraceae bacterium

<400> SEQUENCE: 579

Phe Ser Lys Lys Trp
1               5

<210> SEQ ID NO 580
<211> LENGTH: 9
<212> TYPE: PRT
<213> ORGANISM: Unknown
<220> FEATURE:
<223> OTHER INFORMATION: Lachnospiraceae bacterium

<400> SEQUENCE: 580

Ser Arg Tyr Pro Lys Trp Ser Asn Ala
1               5

<210> SEQ ID NO 581
<211> LENGTH: 6
<212> TYPE: PRT
<213> ORGANISM: Francisella tularensis

<400> SEQUENCE: 581

Leu Lys Gln Ser Lys Asp
1               5

<210> SEQ ID NO 582
<211> LENGTH: 21
<212> TYPE: PRT
<213> ORGANISM: Francisella tularensis
```

```
<400> SEQUENCE: 582

Ser Phe Lys Gly Trp Thr Thr Tyr Phe Lys Gly Phe His Glu Asn Arg
1               5                   10                  15

Lys Asn Val Tyr Ser
            20

<210> SEQ ID NO 583
<211> LENGTH: 22
<212> TYPE: PRT
<213> ORGANISM: Francisella tularensis

<400> SEQUENCE: 583

Asn optional intervening linker, wherein the linker does not interfere with activity of the fusion protein.

9. The fusion protein of claim 8, wherein the heterologous functional domain is a transcriptional activation domain.

10. The fusion protein of claim 9, wherein the transcriptional activation domain is VP16, VP64, Rta, NF-κB p65, or a VPR fusion.

11. The fusion protein of claim 8, wherein the heterologous functional domain is a transcriptional silencer or transcriptional repression domain.

12. The fusion protein of claim 11, wherein the transcriptional repression domain is a Krueppel-associated box (KRAB) domain, ERF repressor domain (ERD), or mSin3A interaction domain (SID).

13. The fusion protein of claim 11, wherein the transcriptional silencer is Heterochromatin Protein 1 (HP1).

14. The fusion protein of claim 8, wherein the heterologous functional domain is an enzyme that modifies the methylation state of DNA.

15. The fusion protein of claim 14, wherein the enzyme that modifies the methylation state of DNA is a DNA methyltransferase (DNMT) or a TET protein.

16. The fusion protein of claim 15, wherein the TET protein is TET1.

17. The fusion protein of claim 8, wherein the heterologous functional domain is an enzyme that modifies a histone subunit.

18. The fusion protein of claim 17, wherein the enzyme that modifies a histone subunit is a histone acetyltransferase (HAT), histone deacetylase (HDAC), histone methyltransferase (HMT), or histone demethylase.

19. The fusion protein of claim 18, wherein the heterologous functional domain is a biological tether.

20. The fusion protein of claim 19, wherein the biological tether is MS2, Csy4 or lambda N protein.

21. The fusion protein of claim 8, wherein the heterologous functional domain is FokI.

22. The fusion protein of claim 8, wherein the heterologous functional domain is a deaminase.

23. The fusion protein of claim 22, wherein the heterologous functional domain is a cytidine deaminase.

24. The fusion protein of claim 22, wherein the heterologous functional domain is an adenosine deaminase.

25. The fusion protein of claim 8, wherein the heterologous functional domain is an enzyme, domain, or peptide that inhibits or enhances endogenous DNA repair or base excision repair (BER) pathways.

26. The fusion protein of claim 25, wherein the heterologous functional domain is uracil DNA glycosylase inhibitor (UGI) that inhibits uracil DNA glycosylase (UDG, also known as uracil N-glycosylase, or UNG); or Gam from the bacteriophage Mu.

27. An isolated nucleic acid encoding the protein of claim 1.

28. A vector comprising the isolated nucleic acid of claim 27.

29. The vector of claim 28, wherein the encoded protein further comprises a mutation at one or more of the amino acids S170, K548, N551, T167, T539, N552, M604, K607, and/or S542.

30. An isolated host cell comprising the nucleic acid of claim 27.

31. The isolated protein of claim 5, comprising the mutations E174R/S542R/K548R.

32. The isolated protein of claim 6, wherein the mutations are D908A, E993A, R1226A, D1235A, and/or D1263A.

33. The isolated protein of claim 7, wherein the mutations are D908A, E993A, R1226A, D1235A, and/or D1263A.

34. The fusion protein of claim 23, wherein the cytidine deaminase is selected from the group consisting of APOBEC1, APOBEC2, APOBEC3A, APOBEC3B, APOBEC3C, APOBEC3D/E, APOBEC3F, APOBEC3G, APOBEC3H, APOBEC4, activation-induced cytidine deaminase (AID), cytosine deaminase 1 (CDA1), CDA2, and cytosine deaminase acting on tRNA (CDAT).

35. The fusion protein of claim 24, wherein the adenosine deaminase is selected from the group consisting of adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA).

36. The isolated host cell of claim 30, wherein the host cell is a mammalian host cell.

* * * * *

UNITED STATES PATENT AND TRADEMARK OFFICE
CERTIFICATE OF CORRECTION

| | |
|---|---|
| PATENT NO. | : 11,591,589 B2 |
| APPLICATION NO. | : 15/960271 |
| DATED | : February 28, 2023 |
| INVENTOR(S) | : J. Keith Joung, Benjamin Kleinstiver and Alexander Sousa |

It is certified that error appears in the above-identified patent and that said Letters Patent is hereby corrected as shown below:

In the Claims

In Column 576, Line 62, Claim 7, after "activity" insert -- at amino acids --

In Column 576, Line 64, Claim 7, before "D908," delete "mutations at"

Signed and Sealed this
Ninth Day of May, 2023

Katherine Kelly Vidal
*Director of the United States Patent and Trademark Office*